United States Patent
Freier et al.

(10) Patent No.: US 11,530,410 B2
(45) Date of Patent: *Dec. 20, 2022

(54) METHODS FOR TREATING HYPERCHOLESTEROLEMIA

(71) Applicant: Ionis Pharmaceuticals, Inc., Carlsbad, CA (US)

(72) Inventors: Susan M. Freier, San Diego, CA (US); Rosanne M. Crooke, Carlsbad, CA (US); Mark J. Graham, San Clemente, CA (US); Kristina M. Lemonidis, Oceanside, CA (US); Diane Tribble, Ashbury, NJ (US); Sanjay Bhanot, Carlsbad, CA (US); Andrew T. Watt, San Diego, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/032,550

(22) Filed: Sep. 25, 2020

(65) Prior Publication Data

US 2021/0285003 A1    Sep. 16, 2021

Related U.S. Application Data

(63) Continuation of application No. 16/057,471, filed on Aug. 7, 2018, now Pat. No. 10,858,657, which is a
(Continued)

(51) Int. Cl.
*C12N 15/113* (2010.01)
*A61K 45/06* (2006.01)
*A61K 48/00* (2006.01)

(52) U.S. Cl.
CPC .......... *C12N 15/1137* (2013.01); *A61K 45/06* (2013.01); *A61K 48/00* (2013.01);
(Continued)

(58) Field of Classification Search
CPC ........ C12N 2310/3515; C12N 2310/11; C12N 2310/3231; C12N 2310/341;
(Continued)

(56) References Cited

U.S. PATENT DOCUMENTS 4,981,957 A    1/1991 Lebleu et al.
5,023,243 A    6/1991 Tullis
(Continued)

FOREIGN PATENT DOCUMENTS

JP    2007/215537    8/2007
WO    WO 94/17093    8/1994
(Continued)

OTHER PUBLICATIONS

Abifadel et al., "Mutations in PCSK9 cause autosomal dominant hypercholesterolemia" Nat. Genet. (2003) 34:154-156.
(Continued)

*Primary Examiner* — Terra C Gibbs

(57) ABSTRACT

Disclosed herein are antisense compounds and methods for decreasing LDL-C in an individual having elevated LDL-C. Additionally disclosed are antisense compounds and methods for treating, preventing, or ameliorating hypercholesterolemia and/or atherosclerosis. Further disclosed are antisense compounds and methods for decreasing coronary heart disease risk. Such methods include administering to an individual in need of treatment an antisense compound targeted to a PCSK9 nucleic acid. The antisense compounds administered include gapmer antisense oligonucleotides.

12 Claims, 29 Drawing Sheets

Specification includes a Sequence Listing.

Related U.S. Application Data continuation of application No. 15/483,992, filed on Apr. 10, 2017, now abandoned, which is a continuation of application No. 14/539,831, filed on Nov. 12, 2014, now Pat. No. 9,650,636, which is a continuation of application No. 14/152,825, filed on Jan. 10, 2014, now Pat. No. 8,912,160, which is a continuation of application No. 13/302,070, filed on Nov. 22, 2011, now Pat. No. 8,664,190, which is a continuation of application No. 12/478,488, filed on Jun. 4, 2009, now Pat. No. 8,093,222, which is a continuation-in-part of application No. 12/516,457, filed as application No. PCT/US2007/024369 on Nov. 27, 2007, now Pat. No. 8,084,437.

(60) Provisional application No. 60/867,395, filed on Nov. 27, 2006, provisional application No. 60/912,892, filed on Apr. 19, 2007, provisional application No. 60/986,286, filed on Nov. 7, 2007, provisional application No. 60/988,074, filed on Nov. 14, 2007, provisional application No. 61/058,707, filed on Jun. 4, 2008, provisional application No. 61/059,169, filed on Jun. 5, 2008.

(52) U.S. Cl.
CPC .... *C12N 2310/11* (2013.01); *C12N 2310/321* (2013.01); *C12N 2310/351* (2013.01); *C12N 2320/30* (2013.01)

(58) Field of Classification Search
CPC ...... C12N 2310/3521; C12N 2310/315; C12N 2310/31; C12N 15/113; C12N 15/1137; A61P 9/10; A61K 45/06
See application file for complete search history.

(56) References Cited

U.S. PATENT DOCUMENTS

| | | | |
|---|---|---|---|
| 5,118,800 A | 6/1992 | Smith et al. | |
| 5,319,080 A | 6/1994 | Leumann | |
| 5,359,044 A | 10/1994 | Cook et al. | |
| 5,393,878 A | 2/1995 | Leumann | |
| 5,446,137 A | 8/1995 | Maag et al. | |
| 5,457,187 A | 10/1995 | Gmeiner et al. | |
| 5,466,786 A | 11/1995 | Buhr et al. | |
| 5,514,785 A | 5/1996 | Van Ness et al. | |
| 5,519,134 A | 5/1996 | Acevedo et al. | |
| 5,567,811 A | 10/1996 | Misiura et al. | |
| 5,567,427 A | 11/1996 | Cook et al. | |
| 5,591,722 A | 1/1997 | Montgomery et al. | |
| 5,597,909 A | 1/1997 | Urdea et al. | |
| 5,610,300 A | 3/1997 | Altmann et al. | |
| 5,625,050 A | 4/1997 | Beaton et al. | |
| 5,627,053 A | 5/1997 | Usman et al. | |
| 5,633,360 A | 5/1997 | Bischofberger et al. | |
| 5,639,873 A | 6/1997 | Barascut et al. | |
| 5,646,265 A | 7/1997 | McGee | |
| 5,652,355 A | 7/1997 | Metelev et al. | |
| 5,658,873 A | 8/1997 | Bertsch-Frank et al. | |
| 5,663,312 A | 9/1997 | Chaturvedula | |
| 5,670,633 A | 9/1997 | Cook et al. | |
| 5,677,437 A | 10/1997 | Teng et al. | |
| 5,677,439 A | 10/1997 | Weis et al. | |
| 5,681,941 A | 10/1997 | Cook et al. | |
| 5,700,920 A | 12/1997 | Altmann et al. | |
| 5,792,747 A | 8/1998 | Schally et al. | |
| 5,801,154 A | 9/1998 | Baracchini et al. | |
| 5,830,653 A | 11/1998 | Froehler et al. | |
| 6,043,060 A | 3/2000 | Imanishi | |
| 6,268,490 B1 | 7/2001 | Imanishi et al. | |
| 6,426,220 B1 | 7/2002 | Bennett et al. | |
| 6,525,191 B1 | 2/2003 | Ramasamy | |
| 6,531,584 B1 | 3/2003 | Cook et al. | |
| 6,582,908 B2 | 6/2003 | Fodor et al. | |
| 6,600,032 B1 | 7/2003 | Manoharan et al. | |
| 6,670,461 B1 | 12/2003 | Wengel et al. | |
| 6,770,748 B2 | 8/2004 | Imanishi et al. | |
| 6,794,499 B2 | 9/2004 | Wengel et al. | |
| 7,034,133 B2 | 4/2006 | Wengel et al. | |
| 7,053,207 B2 | 5/2006 | Wengel | |
| 7,084,125 B2 | 8/2006 | Wengel | |
| 7,217,805 B2 | 5/2007 | Imanishi et al. | |
| 7,314,923 B2 | 1/2008 | Kaneko et al. | |
| 7,368,531 B2 | 5/2008 | Rosen et al. | |
| 7,399,845 B2 | 7/2008 | Seth et al. | |
| 7,407,943 B2 | 8/2008 | Crooke et al. | |
| 7,427,672 B2 | 9/2008 | Imanishi et al. | |
| 7,511,131 B2 | 3/2009 | Crooke et al. | |
| 7,605,251 B2 | 10/2009 | Tan et al. | |
| 7,655,785 B1 | 2/2010 | Bentwich | |
| 7,846,706 B2 | 12/2010 | Mintier et al. | |
| 8,084,437 B2* | 12/2011 | Freier .................. | A61P 9/00 514/44 R |
| 8,093,222 B2* | 1/2012 | Freier .................. | A61P 3/00 514/44 A |
| 8,664,190 B2 | 3/2014 | Freier et al. | |
| 8,912,160 B2* | 12/2014 | Freier .................. | A61P 9/00 514/44 A |
| 9,650,636 B2 | 5/2017 | Freier et al. | |
| 10,858,657 B2* | 12/2020 | Freier .................. | A61P 1/16 |
| 2001/0053519 A1 | 12/2001 | Fodor et al. | |
| 2003/0082807 A1 | 5/2003 | Wengel | |
| 2003/0087230 A1 | 5/2003 | Wengel | |
| 2003/0105309 A1 | 6/2003 | Imanishi et al. | |
| 2003/0199467 A1 | 10/2003 | Roberts et al. | |
| 2003/0224377 A1 | 12/2003 | Wengel et al. | |
| 2003/0228597 A1 | 12/2003 | Cowsert et al. | |
| 2004/0014959 A1 | 1/2004 | Sorensen et al. | |
| 2004/0096848 A1 | 5/2004 | Thrue et al. | |
| 2004/0102391 A1 | 5/2004 | Dean et al. | |
| 2004/0143114 A1 | 7/2004 | Imanishi et al. | |
| 2004/0171570 A1 | 9/2004 | Allerson et al. | |
| 2004/0192918 A1 | 9/2004 | Imanishi et al. | |
| 2004/0219565 A1 | 11/2004 | Kauppinen et al. | |
| 2006/0128646 A1 | 6/2006 | Christensen et al. | |
| 2007/0049542 A1 | 3/2007 | Geller et al. | |
| 2007/0173473 A1 | 7/2007 | Swiggen et al. | |
| 2008/0306015 A1 | 12/2008 | Khvorova et al. | |
| 2009/0306179 A1 | 12/2009 | Bhanot et al. | |
| 2009/0318536 A1 | 12/2009 | Freier et al. | |
| 2010/0105134 A1 | 4/2010 | Quay et al. | |

FOREIGN PATENT DOCUMENTS

| | | |
|---|---|---|
| WO | WO 94/22890 | 10/1994 |
| WO | WO 98/39352 | 9/1998 |
| WO | WO 99/14226 | 3/1999 |
| WO | WO 02/36743 | 5/2002 |
| WO | WO 2002/102994 | 12/2002 |
| WO | WO 2003/011887 | 2/2003 |
| WO | WO 2004/097047 | 11/2004 |
| WO | WO 2005/012372 | 2/2005 |
| WO | WO 2005/121371 | 12/2005 |
| WO | WO 2006/020676 | 2/2006 |
| WO | WO 2006/126040 | 11/2006 |
| WO | WO 2007/090071 | 8/2007 |
| WO | WO 2007/131237 | 11/2007 |
| WO | WO 2008/011431 | 1/2008 |
| WO | WO 2008/043561 | 4/2008 |
| WO | WO 2008/043753 | 4/2008 |
| WO | WO 2008/066776 | 6/2008 |
| WO | WO 2008/109472 | 9/2008 |
| WO | WO 2009/148605 | 12/2009 |

OTHER PUBLICATIONS

Agrawal, "Functionalization of Oligonucleotides with Amino Groups and Attachment of Amino Specific Reporter Groups" Methods in Molecular Biology (1994) 26:93-120.

(56) References Cited

OTHER PUBLICATIONS

Attie, "The Mystery of PCSK 9" Arterioscler. Thromb. Vasc. Biol. (2004) 24:1337-1339.
Beaucage et al., "Advances in the Synthesis of Oligonucleotides by the Phosphoramidite Approach" Tetrahedron (1992) 48(12):2223-2311.
Beaucage et al., "The Functionalization of Oligonucleotides Via Phosphoramidite Derivatives" Tetrahedron (1993) 49(10):1925-1963.
Belikova et al., "Synthesis of ribonucleosides and diribonucleoside phosphates containing 2-chloroethylamine and nitrogen mustard residues" Tetrahedron Lett. (1967) 37:3537-3562.
Berger et al., "Universal bases for hybridization, replication and chain termination" Nucleic Acids Res. (2000) 28:2911-2914.
Braasch et al., "Locked nucleic acid (LNA): fine-tuning the recognition of DNA and RNA" Chem. Biol. (2001) 8:1-7.
Branch et al., "A good antisense molecule is hard to find," TIBS (1998) 23:45-50.
Chiang et al., "Antisense Oligonucleotides Inhibit Intercellular Adhesion Molecule 1 Expression by Two Distinct Mechanisms" The Journal of Biological Chemistry (1991) 266(27):18162-18171.
Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.
Crooke et al., "Pharmacokinetic properties of several novel oligonucleotide analogs in mice" J. Pharmacol. Exp. Ther. (1996) 277(2):923-937.
Crooke et al., "Basic Principles of Antisense Therapeutics" Antisense Research and Application (1998) Chapter 1:1-50.
Elayadi et al., "Application of PNA and LNA oligomers to chemotherapy" Curr. Opinion Invest. Drugs (2001) 2:558-561.
Englisch et al., "Chemically Modified Oligonucleotides as Probes and Inhibitors" Angewandte Chemie (1991) 30(6):613-722.
Expert Panel on Detection, Evaluation, and Treatment of High Blood Cholesterol in Adults "Executive Summary of the Third Report of the National Choleseterol Education Program (NCEP) Expert Panel on Detection, Evaluation, and Treatment of High Blood Cholesterol in Adults (Adult Treatment Panel III)" JAMA (2001) 285:2486-2497.
Freier et al., "The ups and downs of nucleic acid duplex stability: structure-stability studies on chemically-modified DNA:RNA duplexes." Nucleic Acids Research (1997) 25(22):4429-4443.
Frieden et al., "Expanding the design horizon of antisense oligonucleotides with alpha-L-LNA" Nucleic Acids Research (2003) 31(21):6365-6372.
Gait et al., "Applications of Chemically synthesized RNA" RNA:Protein Interactions, Ed. Smith (1998) pp. 1-36.
Gallo et al., "2'-C-Methyluridine phosphoramidite: a new building block for the preparation of RNA analogues carrying the 2'-hydroxyl group" Tetrahedron (2001) 57(27):5707-5713.
Grundy et al., "Implications of recent clinical trials for the National Cholesterol Education Program Adult Treatment Panel III Guidelines" Circulation (2004) 110(2):227-239.
Graham et al., "Antisense Inhibition of Proprotein Convertase Subtilisin/Kexin Type 9 Reduces Serum LDL in Hyperlipidemic Mice" J. Lipid Research (2007) 48:763-767.
Graham et al., "Pharmacological Inhibition of PCSK9 in Hyperlipidemic Mice Significantly Reduces Semm LDL-C While Increasing Hepatic Low-Density Lipoprotein Receptor Protein Abundance" Arterioscler. Thromb. Vasc. Biol. (2007) 27(6):E36.
Kabanov et al., "A new class of antivirals: antisense oligonucleotides combined with a hydrophobic substituent effectively inhibit influenza virus reproduction and synthesis of virus-specific proteins in MDCK cells" FEBS Lett. (1990) 259(2):327-330.
Khatsenko et al., "Absorption of Antisense Oligonucleotides in Rat Intestine: Effect of Chemistry and Length" Antisense & Nucleic Acid Drug Development (2000) 10:35-44.
Koshkin et al., "LNA (Locked Nucleic Acids): Synthesis of the adenine, cytosine, guanine, 5-methylcytosine, thymine and uracil bicyclonucleoside monomers, oligomerisation, and unprecedented nucleic acid recognition" Tetrahedron (1998) 54(14):3607-3630.
Kroschwitz ed., "Concise Encyclopedia of Polymer Science and Engineering" John Wiley & Sons, NY, 1990, pp. 858-859.
Kumar et al., "The first analogues of LNA (locked nucleic acids): phosphorothioate-LNA and 2'-thio-LNA" Bioorg. Med. Chem. Lett. (1998) 8(16):2219-2222.
Kurreck, "Antisense Technologies—Improvement through novel chemical modifications" Eur. J. Biochem. (2003) 270:1628-1644.
Lalanne et al., "Wild-Type PCSK9 Inhibits LDL Clearance but Does Not Affect ApoB-Containing Lipoprotein Production in Mouse and Cultured Cells" Journal of Lipid Research (2005) 46:1312-1319.
Lambert et al., "PCSK9: un nouveau gene implique dans l'hypercholesterolemie familiale" Medicine/Science (2004) 20(12):1068-1070.
Lazowski et al., "Short, 12 mer fluorescently labeled methylphosphonated oligonucleotides to visualize beta-actin mRNA in vivo" J. Physiol. Pharmacol. (2003) 54(4):611-623.
Letsinger et al., "Cholesteryl-conjugated oligonucleotides: synthesis, properties, and activity as inhibitors of replication of human immunodeficiency virus in cell cultures" PNAS (1989) 86(17):6553-6556.
Manoharan et al., "Chemical modifications to improve uptake and bioavailability if antisense oligonucleotides" Ann. NY Acad. Sci. (1992) 660:306-309.
Manoharan et al., "Introduction of a lipophilic thioether tether in the minor groove of nucleic acids for antisense applications" Bioorg. Med. Chem. Lett. (1993) 3:2765-2770.
Manoharan et al., "Cholic acid-oligonucleotide conjugates for antisense applications" Bioorg. Med. Chem. Lett. (1994) 4(8):1054-1060.
Manoharan et al., "Lipidic nucleic acids" Tetrahedron Lett. (1995) 36(21):3651-3654.
Manoharan et al., "Oligonucleotide Conjugates: Alteration of the Pharmacokinetic Properties of Antisense Agents" Nucleosides & Nucleotides (1995) 14(3-5): 969-973.
Maxwell et al., "Proprotein convertase subtilisin kexin 9: the third locus implicated in autosomal dominant hypercholesterolemia" Current Opinion in Lipidology (2005) 16(2):167-172.
Mishra et al., "Improved leishmanicidal effect of phosphorothioate antisense oligonucleotides by LDL-mediated delivery" Biochim. Biophys. Acta (1995) 1264(2):229-237.
Monia et al., "Evaluation of 2'-Modifred Oligonucleotides Containing 2'-Deoxy Gaps as Antisense Inhibitors of Gene Expression" Journal of Biological Chemistry (1993) 268(19):14514-14522.
Monia et al., "Selective Inhibition of Mutant Ha-ras mRNA Expression by Antisense Oligonucleotides" J. Biol. Chem. (1992) 267(28):19954-19962.
Morita et al., "Synthesis and properties of 2'-O,4'-C-ethylene-bridged nucleic acids (ENA) as effective antisense oligonucleotides" Bioorganic Medicinal Chemistry (2003) 11(10):2211-2226.
New England Biolabs 1998/99 Catalog (cover page and pp. 121 and 284).
Oberhauser et al., "Effective incorporation of 2'-O-methyl-oligoribonucleotides into liposomes and enhanced cell association through modification and thiocholesterol." Nucl. Acids Res. (1992) 20(3):533-538.
Orum et al., "Locked nucleic acids: a promising molecular family for gene-functioning analysis and antisense drug development" Curr. Opinion Mol. Ther. (2001) 3(3):239-243.
Rashid et al., "Decreased Plasma Cholesterol and Hypersensitivity to Statins in Mice Lacking PCSK9" PNAS (2005) 102(15):5374-5379.
Reynolds et al., "Rational siRNA design for RNA interference" Nature Biotechnology (2004) 22(3):326-330.
Saison-Behmoaras et al., "Short modified antisense oligonucleotides directed against Ha-ras point mutation induce selective cleavage of the mRNA and inhibit T24 cells proliferation" EMBO J. (1991) 10(5):1111-1118.
Sanghvi et al., "Heterocyclic Base Modifications in Nucleic Acids and Their Applications in Antisense Oligonucleotides" Antisense Research and Applications (1993) pp. 273-288.

(56) References Cited

OTHER PUBLICATIONS

Scaringe, "RNA oligonucleotide synthesis via 5'-silyl-2'-orthoester chemistry" Methods (2001) 23(3):206-217.

Shea et al., "Synthesis, hybridization properties and antiviral activity of lipid-oligodeoxynucleotide conjugates" Nucleic Acids Res. (1990)18(13):3777-3783.

Singh et al., "Synthesis of 2'-Amino-LNA: A Novel Conformationally Restricted High-Affinity Oligonucleotide Analogue with a Handle" J. Org. Chem. (1998) 63(26):10035-10039.

Singh et al., "LNA (locked nucleic acids): synthesis and high-affinity nucleic acid recognition" Chem. Commun. (1998) 4:455-456.

Stein, "The experimental use of antisense oligonucleotides: a guide for the perplexed" J. Clinical Invest. (2001) 108(5):641-644.

Svinarchuk et al., "Inhibition of HIV proliferation in MT-4 cells by antisense oligonucleotide conjugated to lipophilic groups" Biochimie (1993) 75(1-2):49-54.

Swayze et al., "Antisense oligonucleotides containing locked nucleic acid improve potency but cause significant hepatotoxicity in animals" Nucleic Acids Research (2007) 35(2):687-700.

Thuong et al., "Oligonucleotides attached to intercalators, photoreactive and cleavage agents" In Oligonucleotides and Oligonucleotide Analogs: A Practical Approach, Eckstein, ed., Oxford University Press, 1990, Chapter 12, pp. 283-306.

Tuschl et al., "Targeted mRNA degradation by double-stranded RNA in vitro" Genes & Development (1999) 13:3191-3197.

Wahlestedt et al., "Potent and nontoxic antisense oligonucleotides containing locked nucleic acids" PNAS (2000) 97(10):5633-5638.

Zamecnik et al., "Inhibition of Rous sarcoma virus replication and cell transformation by a specific oligodeoxynucleotide" PNAS (1978) 75(1):280-284.

European Search Report dated Mar. 30, 2009 in application EP 07811874.2.

European Search Report dated May 28, 2010 in application EP 07811874.2.

European Search Report dated Aug. 13, 2012 in application EP 11192458.5.

Singapore Search Report and Written Opinion dated Oct. 13, 2010 in application No. 200903557-7.

International Search Report dated Mar. 13, 2008 in application No. PCT/US2007/068404.

International Search Report dated Jul. 28, 2008 in application No. PCT/US2007/024369.

International Search Report dated Nov. 9, 2009 in application No. PCT/US2009/003398.

International Search Report dated Feb. 15, 2010 in application No. PCT/US2009/003398.

International Preliminary Report on Patentability dated Dec. 6, 2010 in application No. PCT/US2009/003398.

\* cited by examiner

METHODS FOR TREATING HYPERCHOLESTEROLEMIA

SEQUENCE LISTING

The present application is being filed along with a Sequence Listing in electronic format. The Sequence Listing is provided as a file entitled BIOL0090USC6SEQ_ST25.txt, created on Sep. 22, 2020 which is 144 Kb in size. The information in the electronic format of the sequence listing is incorporated herein by reference in its entirety.

FIELD OF THE INVENTION

Methods are provided for lowering LDL-C levels in an individual having elevated LDL-C levels. Such methods are further useful to treat hypercholesterolemia, and to reduce the risk of coronary heart disease.

BACKGROUND

Atherosclerosis is a complex, polygenic disease of arterial degeneration that can lead to coronary heart disease (CHD). In Western societies, complications arising from atherosclerosis are the most common causes of death. Several risk factors for CHD have been well-established, and include elevated low density lipoprotein-cholesterol (LDL-C), low levels of high density lipoprotein cholesterol (HDL-C), cigarette smoking, hypertension, age, and family history of early CHD. Given the abundant clinical data and epidemiological studies indicating that lowering LDL-C is beneficial for the prevention of adverse coronary events, the primary target of pharmacological intervention in the treatment and prevention of CHD is lowered LDL-C.

In individuals with autosomal dominant hypercholesterolemia (ADH), elevated LDL-C levels have been linked to mutations in the genes encoding LDL-receptor (LDL-R), apolipoprotein B (apoB), or proprotein convertase subtilisin/kexin type 9 (PCSK9) (Abifadel et al., Nat. Genet., 2003, 34:154-156). The PCSK9 gene (also known as FH3; NARC1; NARC-1; and HCHOLA3) was mapped to Chromosome 1 at location 1p32.3. PCSK9 was identified as a third locus associated with ADH when gain-of-function mutations in PCSK9 were found to be linked to elevated LDL-C levels. ApoB-100 participates in the intracellular assembly and secretion of triglyceride-rich lipoproteins and is a ligand for the LDL-R. PCSK9 is proposed to reduce LDL-R expression levels in the liver. Reduced LDL-R expression results in reduced hepatic uptake of circulating apoB-100-containing lipoproteins, which in turn leads to elevated cholesterol.

Familial hypercholesterolemia (FH) is caused by hundreds of different mutations in the LDL-R, and is phenotypically characterized by elevated plasma LDL-C levels and deposits of LDL-C in tendons, skin and arteries, leading to premature cardiovascular disease. Homozygous and heterozygous mutations in the LDL-R are associated with FH. Likewise, heterozygous and homozygous mutations in the ligand-binding domain of PCSK9 are associated with the FH phenotype. Mutations in this gene have been associated with a third form of autosomal dominant FH.

In mice genetically deficient in PCSK9, a marked increase in LDL-R expression and increased plasma LDL clearance rate were observed. Conversely, overexpression in mice of wild-type PCSK9, or certain PCSK9 mutants, promotes decreased LDL-R expression and elevated LDL-C levels.

SUMMARY OF THE INVENTION

Provided herein are methods for the treatment of hypercholesterolemia and/or atherosclerosis, as well as methods for the reduction of elevated LDL-C levels and CHD risk. Methods for treating hypercholesterolemia comprise administering to an individual an antisense compound targeted to a PCSK9 nucleic acid. In such methods, an antisense compound targeted to a PCSK9 nucleic acid may be targeted to sequences as set forth in GENBANK® Accession No. NM_174936.2, nucleotides 25475000 to 25504000 of GENBANK® Accession No. NT_032977.8, or GENBANK® Accession No. AK124635.1.

Methods for treating and/or preventing atherosclerosis comprise administering to an individual an antisense compound targeted to a PCSK9 nucleic acid. Methods for reducing LDL-C levels comprise administering to an individual an antisense compound targeted to a PCSK9 nucleic acid. Methods for reducing CHD risk comprise administering to an individual an antisense compound targeted to a PCSK9 nucleic acid. Such methods may comprise the administration of a therapeutically effective amount of an antisense compound targeted to a PCSK9 nucleic acid.

Methods are provided for reducing LDL-C levels in an individual having elevated LDL-C levels, comprising administering to the individual a therapeutically effective amount of an antisense oligonucleotide targeted to a PCSK9 nucleic acid, thereby reducing LDL-C levels. Also provided are methods for reducing LDL-C levels in an individual comprising selecting an individual having elevated LDL-C levels, and administering to the individual a therapeutically effective amount of an antisense compound targeted to a PCSK9 nucleic acid, and additionally monitoring LDL-cholesterol levels. Further provided are methods for treating atherosclerosis in an individual, comprising selecting an individual diagnosed with atherosclerosis, administering to the individual a therapeutically effective amount of an antisense compound targeted to a PCSK9 nucleic acid, and monitoring atherosclerosis. Also provided are methods for reducing coronary heart disease risk, comprising selecting an individual having elevated LDL-C levels and one or more additional indicators of coronary heart disease, administering to the individual a therapeutically effective amount of an antisense compound targeted to a PCSK9 nucleic acid, and monitoring LDL-C levels. Additionally provided are methods for treating hypercholesterolemia, comprising administering to an individual diagnosed with hypercholesterolemia a therapeutically effective amount of an antisense oligonucleotide targeted to a PCSK9 nucleic acid, thereby reducing cholesterol levels.

Further provided is a use of an effective amount of one or more of the disclosed antisense compounds for treating atherosclerosis or hypercholesterolemia in an individual in need of such treatment. Also provided is a use of an effective amount of one or more of the disclosed antisense compounds for reducing LDL-C levels or reducing CHD risk in an individual in need of such treatment. Also provided is the use of one or more of the disclosed antisense compounds in the manufacture of a medicament for the treatment of atherosclerosis or hypercholesterolemia. Further provided is the use of one or more of the disclosed antisense compounds in the manufacture of a medicament for reducing LDL-C levels or for reducing CHD risk.

In any of the methods provided, a PCSK9 nucleic acid may be the sequence set forth in SEQ ID NO: 1. Thus, the antisense compound may be targeted to a PCSK9 nucleic acid as set forth in SEQ ID NO: 1.

Any of the methods provided herein may further comprise monitoring LDL-C levels.

An individual may be selected for administration of an antisense compound targeted to a PCSK9 nucleic acid when the individual exhibits an LDL-C level above 100 mg/dL, above 130 mg/dL, above 160 mg/dL, or above 190 mg/dL. Administration of an antisense compound targeted to a PCSK9 nucleic acid may result in an LDL-C level below 190 mg/dL, below 160 mg/dL, below 130 mg/dL, below 100 mg/dL, below 70 mg/dL, or below 50 mg/dL.

In any of the aforementioned methods, administration of the antisense compound may comprise parenteral administration. The parenteral administration may further comprise subcutaneous or intravenous administration.

In any of the methods provided herein, the antisense compound may have least 80%, at least 90%, or at least 95% complementarity to SEQ ID NO: 1. Alternatively, the antisense compound may have 100% complementarity to SEQ ID NO: 1.

The antisense compounds provided herein and employed in any of the described methods may be 8 to 80 subunits in length, 12 to 50 subunits in length, 12 to 30 subunits in length, 15 to 30 subunits in length, 18 to 24 subunits in length, 19 to 22 subunits in length, or 20 subunits in length. Further, the antisense compounds employed in any of the described methods may be antisense oligonucleotides 8 to 80 nucleotides in length, 12 to 50 nucleotides in length, 12 to 30 nucleotides in length 15 to 30 nucleotides in length, 18 to 24 nucleotides in length, 19 to 22 nucleotides in length, or 20 nucleotides in length.

In any of the methods provided, the antisense compound may be an antisense oligonucleotide. Moreover, the antisense oligonucleotide may be a gapmer antisense oligonucleotide. The gapmer antisense oligonucleotide may comprise a gap segment of ten 2'-deoxynucleotides positioned between wing segments of five 2'-MOE nucleotides. The gapmer antisense oligonucleotide may be a gap-widened antisense oligonucleotide, comprising a gap segment of fourteen 2'-deoxynucleotides positioned between wing segments of three 2'-MOE nucleotides.

In any of the methods provided, the antisense compounds may have at least one modified internucleoside linkage. Additionally, each internucleoside linkage may be a phosphorothioate internucleoside linkage. Each cytosine may be a 5-methyl cytosine.

Also provided herein are antisense compounds targeted to a PCSK9 nucleic acid. Further provided are antisense oligonucleotides targeted to a PCSK9 nucleic acid. The antisense compounds, including antisense oligonucleotides, may be targeted to PCSK9 nucleic acids, which include the sequences as set forth in GENBANK® Accession No. NM_174936.2, nucleotides 25475000 to 25504000 of GENBANK® Accession No. NT_032977.8, or GENBANK® Accession No. AK124635.1. The antisense compounds, including antisense oligonucleotides, may have at least 70%, at least 80%, at least 90%, or at least 95% complementarity to a PCSK9 nucleic acid. The antisense compounds, including antisense oligonucleotides, may have 99% complementarity to a PCSK9 nucleic acid. The antisense compounds, including antisense oligonucleotides, may have 100% complementarity to a PCSK9 nucleic acid. For any of the antisense compounds provided, including antisense oligonucleotides, the PCSK9 nucleic acid may be the sequence set forth in SEQ ID NO: 1.

Antisense compounds targeted to a PCSK9 nucleic acid may be 8 to 80 subunits in length, 12 to 50 subunits in length, 12 to 30 subunits in length, 15 to 30 subunits in length, 18 to 24 subunits in length, 19 to 22 subunits in length, or 20 subunits in length. Antisense oligonucleotides targeted to a PCSK9 nucleic acid may be 8 to 80 nucleotides in length, 12 to 50 nucleotides in length, 12 to 30 nucleotides in length, 15 to 30 nucleotides in length, 18 to 24 nucleotides in length, 19 to 22 nucleotides in length, or 20 nucleotides in length.

Moreover, the antisense compound may be a gapmer antisense oligonucleotide. The gapmer antisense oligonucleotide may comprise a gap segment of ten 2'-deoxynucleotides positioned between wing segments of five 2'-MOE nucleotides. The gapmer antisense oligonucleotide may be a gap-widened antisense oligonucleotide, comprising a gap segment of fourteen 2'-deoxynucleotides positioned between wing segments of three 2'-MOE nucleotides.

Antisense compounds, including antisense oligonucleotides, targeted to a PCSK9 nucleic acid may have at least one modified internucleoside linkage. Additionally, each internucleoside linkage may be a phosphorothioate internucleoside linkage. Each cytosine may be a 5-methyl cytosine.

Antisense compounds, including antisense oligonucleotides, targeted to a PCSK9 nucleic acid may have at least one modified nucleoside. In certain embodiments, a modified nucleoside is a sugar-modified nucleoside. In certain such embodiments, the sugar-modified nucleosides can further comprise a natural or modified heterocyclic base moiety and/or a natural or modified internucleoside linkage and may include further modifications independent from the sugar modification. In certain embodiments, a sugar modified nucleoside is a 2'-modified nucleoside, wherein the sugar ring is modified at the 2' carbon from natural ribose or 2'-deoxy-ribose.

In certain embodiments, a 2' modified nucleoside has a 2'-F, 2'-OCH$_2$ (2'-OMe) or a 2'-O(CH$_2$)$_2$—OCH$_3$ (2'-O-methoxyethyl or 2'-MOE) substituent group In certain embodiments, a 2'-modified nucleoside has a bicyclic sugar moiety. In certain such embodiments, the bicyclic sugar moiety is a D sugar in the alpha configuration. In certain such embodiments, the bicyclic sugar moiety is a D sugar in the beta configuration. In certain such embodiments, the bicyclic sugar moiety is an L sugar in the alpha configuration. In certain such embodiments, the bicyclic sugar moiety is an L sugar in the beta configuration.

In certain embodiments, the bicyclic sugar moiety comprises a bridge group between the 2' and the 4'-carbon atoms. In certain such embodiments, the bridge group comprises from 1 to 8 linked biradical groups. In certain embodiments, the bicyclic sugar moiety comprises from 1 to 4 linked biradical groups. In certain embodiments, the bicyclic sugar moiety comprises 2 or 3 linked biradical groups. In certain embodiments, the bicyclic sugar moiety comprises 2 linked biradical groups. In certain embodiments, a linked biradical group is selected from —O—, —S—, —N(R1)-, —C(R1)(R2)-, —C(R1)=C(R1)-, —C(R1)=N—, —C(=NR1)-, —Si(R1)(R2)-, —S(=O)2-, —S(=O)—, —C(=O)— and —C(=S)—; where each R1 and R2 is, independently, H, hydroxyl, C1-C12 alkyl, substituted C1-C12 alkyl, C2-C12 alkenyl, substituted C2-C12 alkenyl, C2-C12 alkynyl, substituted C2-C12 alkynyl, C5-C20 aryl, substituted C5-C20 aryl, a heterocycle radical, a substituted hetero-cycle radical, heteroaryl, substituted heteroaryl, C5-C7 alicyclic radical, substituted C5-C7 alicyclic radical, halogen, substituted oxy (—O—), amino, substituted amino, azido, carboxyl, substituted carboxyl, acyl, substituted acyl, CN, thiol, substituted thiol, sulfonyl (S(=O)2-H), substituted sulfonyl, sulfoxyl (S(=O)—H) or substituted sulfoxyl; and each substituent group is, independently, halogen, C1-C12 alkyl, substituted C1-C12 alkyl, C2-C12 alkenyl, substituted C2-C12 alkenyl, C2-C12 alkynyl, substituted C2-C12 alkynyl, amino, substituted amino, acyl, substituted acyl, C1-C12 aminoalkyl, C1-C12 aminoalkoxy, substituted C1-C12 aminoalkyl, substituted C1-C12 aminoalkoxy or a protecting group.

In some embodiments, the bicyclic sugar moiety is bridged between the 2' and 4' carbon atoms with a biradical group selected from —O—(CH2)p-, —O—CH2-, —O—CH2CH2-, —O—CH(alkyl)-, —NH—(CH2)p-, —N(alkyl)-(CH2)p-, —O—CH(alkyl)-, —(CH(alkyl))-(CH2)p-, —NH—O—(CH2)p-, —N(alkyl)-O—(CH2)p-, or —O—N(alkyl)-(CH2)p-, wherein p is 1, 2, 3, 4 or 5 and each alkyl group can be further substituted. In certain embodiments, p is 1, 2 or 3.

In one aspect, each of said bridges is, independently, —[C(R1)(R2)]n-, —[C(R1)(R2)]n-O—, —C(R1R2)-N(R1)-O— or —C(R1R2)-O—N(R1)-. In another aspect, each of said bridges is, independently, 4'-(CH2)3-2', 4'-(CH2)2-2', 4'-CH2-O-2', 4'-(CH2)2-O-2', 4'-CH2-O—N(R1)-2' and 4'-CH2-N(R1)-O-2'- wherein each R1 is, independently, H, a protecting group or C1-C12 alkyl.

The present disclosure further discloses subsets of the antisense compounds above that show superior properties relating to pharmacodynamics and/or pharmacokinetics, among other properties. Exemplary antisense compounds reduce PCSK9 expression in a cultured cell model system, e.g., Hep3B cells, cynomolgus monkey hepatocytes, or human primary hepatocytes. In particular embodiments, antisense compounds reduce PCSK9 expression in a dose-dependent manner in a cell culture system, where the antisense compounds have an $IC_{50}$ in the nanomolar range.

Exemplary antisense compounds also reduce the expression of a PCSK9 nucleic acid in an animal model, such as a transgenic mouse that expresses a human PCSK9 nucleic acid (HuPCSK9Tg mice). In particular embodiments, antisense compounds include those that reduce PCSK9 express in an animal model with a physiology that correlates closely with humans, such as monkey, e.g., the cynomolgus monkey.

Exemplary antisense compounds display minimal side effects. Side effects include responses to the administration of the antisense compound unrelated to the targeting of a PCSK9 nucleic acid, such as an inflammatory response in the host individual. Exemplary antisense compounds are well tolerated by the host individual. Tolerability may be determined though histological analysis of various cell types, and includes examination of such markers as cytoplasmic swelling from multifocal apoptosis in liver cells, follicular hyperplasia in spleen cells, macrophage infiltration, and the like. In particular embodiments, antisense compounds produce minimal signs of host intolerance.

Exemplary antisense compounds further display favorable pharmacokinetics. In particular embodiments, antisense compounds accumulate at a relatively high ratio in the liver versus other sensitive organs, such as kidneys. In particular embodiments, antisense compounds exhibit relatively high half-lives in relevant biological fluids or tissues, e.g., liver tissue, reflecting higher stability and resistance to nucleases, for example.

In particular embodiments, antisense compounds target identical sequences in human and animal PCSK9 sequences. In other embodiments, antisense compounds target PCSK9 sequences without a known single nucleotide polymorphism (SNP), have a high relative G-content, have minimal secondary structure, have greatly reduced effects on the host's serum chemistry, body weight, or histopathology, compared to other antisense compounds, and/or induce a minimal adverse immunohistocompatibility reaction.

In a particular embodiment, the antisense compound is selected from the group of Isis 405881, Isis 399819, Isis 395165, Isis 405879, Isis 406008, Isis 405891, Isis 395186, Isis 405988, Isis 405994, Isis 406023, Isis 395187, Isis 395185, Isis 406033, Isis 405923, Isis 399900, Isis 405995, Isis 405991, Isis 406005, Isis 399793, and Isis 395152. The aforementioned antisense compounds effectively repress PCSK9 expression in a Hep3B cell culture system. In another embodiment, antisense compounds effectively inhibit PCSK9 expression with a low $IC_{50}$ in a battery of cell culture systems. Exemplary antisense compounds include those selected from the group of Isis 395165, Isis 395185, Isis 395186, Isis 395187, Isis 405879, Isis 405881, Isis 405891, Isis 405988, Isis 405994, and Isis 406008. In yet another embodiment, antisense compounds exhibit minimal or no adverse histopathological effects when administered at particularly high doses to an individual. Exemplary antisense compounds include those selected from the group consisting of Isis 395185, Isis 395186, Isis 395187, Isis 405879, Isis 405891, and Isis 405988. In yet another embodiment, antisense compounds affect therapeutic endpoints, e.g., reduction of plasma LDL-C, liver TG, or liver PCSK9 mRNA, in an animal model. Exemplary antisense compounds include Isis 405879. In yet another embodiment, antisense compounds display combinations of the characteristics above and reduce liver PCSK9 mRNA expression in an animal model with high efficiency, e.g., Isis 405879.

Definitions

Unless defined otherwise, all technical and scientific terms used herein have the same meaning as is commonly understood by on of skill in the art to which the invention(s) belong. Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, chemical analysis, pharmaceutical preparation, formulation and delivery, and treatment of subjects. Certain such techniques and procedures may be found for example in "Antisense Drug Technology: Principles, Strategies, and Applications." by Stanley Crooke, Boca Raton: Taylor & Francis Group, 2008; "Carbohydrate Modifications in Antisense Research" Edited by Sangvi and Cook, American Chemical Society, Washington D.C., 1994; and "Remington's Pharmaceutical Sciences," Mack Publishing Co., Easton, Pa., 18th edition, 1990; and which is hereby incorporated by reference for any purpose. Where permitted, all patents, patent applications, published applications and publications, GENBANK sequences, websites and other published materials referred to throughout the entire disclosure herein, unless noted otherwise, are incorporated by reference in their entirety. All of the GENBANK® Accession Nos. along with their associated sequence and structural data pertaining to such sequences including gene organization and structural elements and SNP information that may be found in sequence databases such as the National Center for Biotechnology Information (NCBI) are incorporated herein by reference in their entirety. In the event that there is a plurality of definitions for terms herein, those in this section prevail. Where reference is made to a URL or other such identifier or address, it is understood that such identifiers can change and particular information on the internet can come and go, but equivalent information can be found by searching the internet. Reference thereto evidences the availability and public dissemination of such information.

A "pharmaceutical composition" means a mixture of substances suitable for administering to an individual. For example, a pharmaceutical composition may comprise an antisense oligonucleotide and a sterile aqueous solution.

"Administering" means providing a pharmaceutical agent to an individual, and includes, but is not limited to administering by a medical professional and self-administering.

"Individual" means a human or non-human animal selected for treatment or therapy.

"Duration" means the period of time during which an activity or event continues. In certain embodiments, the duration of treatment is the period of time during which doses of a pharmaceutical agent are administered.

"Parenteral administration," means administration through injection or infusion. Parenteral administration includes, but is not limited to, subcutaneous administration, intravenous administration, or intramuscular administration.

"Subcutaneous administration" means administration just below the skin. "Intravenous administration" means administration into a vein.

"Dose" means a specified quantity of a pharmaceutical agent provided in a single administration. In certain embodiments, a dose may be administered in two or more boluses, tablets, or injections. For example, in certain embodiments, where subcutaneous administration is desired, the desired dose requires a volume not easily accommodated by a single injection. In such embodiments, two or more injections may be used to achieve the desired dose. In certain embodiments, a dose may be administered in two or more injections to minimize injection site reaction in a individual.

"Dosage unit" means a form in which a pharmaceutical agent is provided. In certain embodiments, a dosage unit is a vial containing lyophilized antisense oligonucleotide. In certain embodiments, a dosage unit is a vial containing reconstituted antisense oligonucleotide.

"Pharmaceutical agent" means a substance provides a therapeutic benefit when administered to a individual. For example, in certain embodiments, an antisense oligonucleotide targeted to PCSK9 is pharmaceutical agent.

"Diluent" means an ingredient in a composition that lacks pharmacological activity, but is pharmaceutically necessary or desirable. For example, in drugs that are injected the diluent may be a liquid, e.g., saline solution.

"Active pharmaceutical ingredient" means the substance in a pharmaceutical composition that provides a desired effect.

"Pharmaceutically acceptable carrier" means a medium or diluent that does not interfere with the structure of the oligonucleotide. Certain of such carriers enable pharmaceutical compositions to be formulated as, for example, tablets, pills, dragees, capsules, liquids, gels, syrups, slurries, suspension and lozenges for the oral ingestion by a subject.

"Therapeutically effective amount" means an amount of a pharmaceutical agent that provides a therapeutic benefit to an individual. In certain embodiments, a therapeutically effective amount of antisense compound targeted to a PCSK9 nucleic acid is an amount that decreases LDL-C in the individual.

"Hypercholesterolemia" means a condition characterized by elevated serum cholesterol.

"Hyperlipidemia" means a condition characterized by elevated serum lipids.

"Hypertriglyceridemia" means a condition characterized by elevated serum triglyceride levels.

"Non-familial hypercholesterolemia" means a condition characterized by elevated serum cholesterol that is not the result of a single gene mutation.

"Polygenic hypercholesterolemia" means a condition characterized by elevated cholesterol that results from the influence of a variety of genetic factors. In certain embodiments, polygenic hypercholesterolemia may be exacerbated by dietary intake of lipids.

"Familial hypercholesterolemia (FH)" means an autosomal dominant metabolic disorder characterized by a mutation in the LDL-receptor (LDL-R) gene, markedly elevated LDL-C and premature onset of atherosclerosis. A diagnosis of familial hypercholesterolemia is made when an individual meets one or more of the following criteria: genetic testing confirming 2 mutated LDL-receptor genes; genetic testing confirming one mutated LDL-receptor gene; document history of untreated serum LDL-cholesterol greater than 500 mg/dL; tendinous and/or cutaneous xanthoma prior to age 10 years; or, both parents have documented elevated serum LDL-cholesterol prior to lipid-lowering therapy consistent with heterozygous familial hypercholesterolemia.

"Homozygous familial hypercholesterolemia" or "HoFH" means a condition characterized by a mutation in both maternal and paternal LDL-R genes.

"Heterozygous familial hypercholesterolemia" or "HeFH" means a condition characterized by a mutation in either the maternal or paternal LDL-R gene.

"Mixed dyslipidemia" means a condition characterized by elevated serum cholesterol and elevated serum triglycerides.

"Diabetic dyslipidemia" or "Type II diabetes with dyslipidemia" means a condition characterized by Type II diabetes, reduced HDL-C, elevated serum triglycerides, and elevated small, dense LDL particles.

"CHD risk equivalents," means indicators of clinical atherosclerotic disease that confer a high risk for coronary heart disease, and include clinical coronary heart disease, symptomatic carotid artery disease, peripheral arterial disease, and/or abdominal aortic aneurysm.

"Metabolic syndrome" means a condition characterized by a clustering of lipid and non-lipid cardiovascular risk factors of metabolic origin. In certain embodiments, metabolic syndrome is identified by the presence of any 3 of the following factors: waist circumference of greater than 102 cm in men or greater than 88 cm in women; serum triglyceride of at least 150 mg/dL; HDL-C less than 40 mg/dL in men or less than 50 mg/dL in women; blood pressure of at least 130/85 mmHg; and fasting glucose of at least 110 mg/dL.

"Non-alcoholic fatty liver disease (NAFLD)" means a condition characterized by fatty inflammation of the liver that is not due to excessive alcohol use (for example, alcohol consumption of over 20 g/day). In certain embodiments, NAFLD is related to insulin resistance and the metabolic syndrome.

"Non-alcoholic steatohepatitis (NASH)" means a condition characterized by inflammation and the accumulation of fat and fibrous tissue in the liver, that is not due to excessive alcohol use. NASH is an extreme form of NAFLD.

"Major risk factors" mean factors that contribute to a high risk for coronary heart disease, and include without limitation cigarette smoking, hypertension, low HDL-C, family history of coronary heart disease, and age.

"CHD risk factors" mean CHD risk equivalents and major risk factors.

"Coronary heart disease (CHD)" means a narrowing of the small blood vessels that supply blood and oxygen to the heart, which is often a result of atherosclerosis.

"Reduced coronary heart disease risk" means a reduction in the likelihood that an individual will develop coronary heart disease. In certain embodiments, a reduction in coronary heart disease risk is measured by an improvement in one or more CHD risk factors, for example, a decrease in LDL-C levels.

"Atherosclerosis" means a hardening of the arteries affecting large and medium-sized arteries and is characterized by the presence of fatty deposits. The fatty deposits are called "atheromas" or "plaques," which consist mainly of cholesterol and other fats, calcium and scar tissue, and damage the lining of arteries.

"History of coronary heart disease" means the occurrence of clinically evident coronary heart disease in the medical history of an individual or a individual's family member.

"Early onset coronary heart disease" means a diagnosis of coronary heart disease prior to age 50.

"Statin intolerant individual" means an individual who as a result of statin therapy experiences one or more of creatine kinase increases, liver function test abnormalities, muscle aches, or central nervous system side effects.

"Efficacy" means the ability to produce a desired effect. For example, efficacy of a lipid-lowering therapy may be reduction in the concentration of one or more of LDL-C, VLDL-C, IDL-C, non-HDL-C, ApoB, lipoprotein(a), or triglycerides.

"Acceptable safety profile" means a pattern of side effects that is within clinically acceptable limits.

"Side effects" means physiological responses attributable to a treatment other than desired effects. In certain embodiments, side effects include, without limitation, injection site reactions, liver function test abnormalities, renal function abnormalities, liver toxicity, renal toxicity, central nervous system abnormalities, and myopathies. For example, increased aminotransferase levels in serum may indicate liver toxicity or liver function abnormality. For example, increased bilirubin may indicate liver toxicity or liver function abnormality.

"Injection site reaction" means inflammation or abnormal redness of skin at a site of injection in an individual.

"Individual compliance" means adherence to a recommended or prescribed therapy by an individual.

"Lipid-lowering therapy" means a therapeutic regimen provided to an individual to reduce one or more lipids in a individual. In certain embodiments, a lipid-lowering therapy is provide to reduce one or more of ApoB, total cholesterol, LDL-C, VLDL-C, IDL-C, non-HDL-C, triglycerides, small dense LDL particles, and Lp(a) in a individual.

"Lipid-lowering agent" means a pharmaceutical agent provided to an individual to achieve a lowering of lipids in the individual. For example, in certain embodiments, a lipid-lowering agent is provided to an individual to reduce one or more of ApoB, LDL-C, total cholesterol, and triglycerides.

"LDL-C target" means an LDL-C level that is desired following lipid-lowering therapy.

"Comply" means the adherence with a recommended therapy by a individual.

"Recommended therapy" means a therapeutic regimen recommended by a medical professional for the treatment, amelioration, or prevention of a disease.

"Low LDL-receptor activity" means LDL-receptor activity that is not sufficiently high to maintain clinically acceptable levels of LDL-C in the bloodstream.

"Cardiovascular outcome" means the occurrence of major adverse cardiovascular events.

"Improved cardiovascular outcome" means a reduction in the occurrence of major adverse cardiovascular events, or the risk thereof. Examples of major adverse cardiovascular events include, without limitation, death, reinfarction, stroke, cardiogenic shock, pulmonary edema, cardiac arrest, and atrial dysrhythmia.

"Surrogate markers of cardiovascular outcome" means indirect indicators of cardiovascular events, or the risk thereof. For example, surrogate markers of cardiovascular outcome include carotid intimal media thickness (CIMT). Another example of a surrogate marker of cardiovascular outcome includes atheroma size. Atheroma size may be determined by intravascular ultrasound (IVUS). Surrogate markers also include increased HDL-cholesterol, or any combination of the markers above.

"Increased HDL-C" means an increase in serum HDL-C in an individual over time.

"Lipid-lowering" means a reduction in one or more serum lipids in an individual over time.

"Co-administration" means administration of two or more pharmaceutical agents to a individual. The two or more pharmaceutical agents may be in a single pharmaceutical composition, or may be in separate pharmaceutical compositions. Each of the two or more pharmaceutical agents may be administered through the same or different routes of administration. Co-administration encompasses administration in parallel or sequentially.

"Administered concomitantly" refers to the administration of two agents at the same therapeutic time frame, in any manner in which the pharmacological effects of both are manifest in the patient at the same time. Concomitant administration does not require that both agents be administered in a single pharmaceutical composition, in the same dosage form, or by the same route of administration.

"Therapeutic lifestyle change" means dietary and lifestyle changes intended to lower cholesterol and reduce the risk of developing heart disease, and includes recommendations for dietary intake of total daily calories, total fat, saturated fat, polyunsaturated fat, monounsaturated fat, carbohydrate, protein, cholesterol, insoluble fiber, as well as recommendations for physical activity.

"Statin" means a pharmaceutical agent that inhibits the activity of HMG-CoA reductase.

"HMG-CoA reductase inhibitor" means a pharmaceutical agent that acts through the inhibition of the enzyme HMG-CoA reductase.

"Cholesterol absorption inhibitor" means a pharmaceutical agent that inhibits the absorption of exogenous cholesterol obtained from diet.

"LDL apheresis" means a form of apheresis by which LDL-C is removed from blood. Typically, a individual's blood is removed from a vein, and separated into red cells and plasma. LDL-C is filtered out of the plasma prior to return of the plasma and red blood cells to the individual.

"MTP inhibitor" means a pharmaceutical agent that inhibits the enzyme microsomal triglyceride transfer protein.

"Low density lipoprotein-cholesterol (LDL-C)" means cholesterol carried in low density lipoprotein particles. Concentration of LDL-C in serum (or plasma) is typically quantified in mg/dL or nmol/L. "Serum LDL-C" and "plasma LDL-C" mean LDL-C in the serum and plasma, respectively.

"Very low density lipoprotein-cholesterol (VLDL-C)" means cholesterol associated with very low density lipoprotein particles. Concentration of VLDL-C in serum (or plasma) is typically quantified in mg/dL or nmol/L. "Serum VLDL-C" and "plasma VLDL-C" mean VLDL-C in the serum or plasma, respectively.

"Intermediate low density lipoprotein-cholesterol (IDL-C)" means cholesterol associated with intermediate density lipoprotein. Concentration of IDL-C in serum (or plasma) is typically quantified in mg/dL or nmol/L. "Serum IDL-C" and "plasma IDL-C" mean IDL-C in the serum or plasma, respectively.

"Non-high density lipoprotein-cholesterol (Non-HDL-C)" means cholesterol associated with lipoproteins other than high density lipoproteins, and includes, without limitation, LDL-C, VLDL-C, and IDL-C.

"High density lipoprotein-C(HDL-C)" means cholesterol associated with high density lipoprotein particles. Concentration of HDL-C in serum (or plasma) is typically quantified in mg/dL or nmol/L. "Serum HDL-C" and "plasma HDL-C" mean HDL-C in the serum and plasma, respectively.

"Total cholesterol" means all types of cholesterol, including, but not limited to, LDL-C, HDL-C, IDL-C and VLDL-C. Concentration of total cholesterol in serum (or plasma) is typically quantified in mg/dL or nmol/L.

"Lipoprotein(a)" or "Lp(a)" means a lipoprotein particle that is comprised of LDL-C, an apolipoprotein(a) particle, and an apolipoprotein B-100 particle.

"ApoA1" means apolipoprotein-A1 protein in serum. Concentration of ApoA1 in serum is typically quantified in mg/dL or nmol/L.

"ApoB:ApoA1 ratio" means the ratio of ApoB concentration to ApoA1 concentration.

"ApoB-containing lipoprotein" means any lipoprotein that has apolipoprotein B as its protein component, and is understood to include LDL, VLDL, IDL, and lipoprotein(a).

"Small LDL particle" means a subclass of LDL particles characterized by a smaller, denser size compared to other LDL particles. In certain embodiments, large LDL particles are 23-27 nm in diameter. In certain embodiments, intermediate LDL particles are 21.2-23 nm in diameter. In certain embodiments, small LDL particles are 18-21.2 nm in diameter. In certain embodiments, particle size is measured by nuclear magnetic resonance analysis.

"Small VLDL particle" means a subclass of VLDL particles characterized by a smaller, denser size compared to other VLDL particles. In certain embodiments, large VLDL particles are greater than 60 nm in diameter. In certain embodiments, medium VLDL particles are 35-60 nm in diameter. In certain embodiments, small VLDL particles are 27-35 nm in diameter. In certain embodiments, particle size is measured by nuclear magnetic resonance analysis.

"Triglycerides" means lipids that are the triesters of glycerol. "Serum triglycerides" mean triglycerides present in serum. "Liver triglycerides" mean triglycerides present in liver tissue.

"Serum lipids" mean cholesterol and triglycerides in the serum.

"Elevated total cholesterol" means total cholesterol at a concentration in an individual at which lipid-lowering therapy is recommended, and includes, without limitation, elevated LDL-C", "elevated VLDL-C," "elevated IDL-C," and "elevated non-HDL-C." In certain embodiments, total cholesterol concentrations of less than 200 mg/dL, 200-239 mg/dL, and greater than 240 mg/dL are considered desirable, borderline high, and high, respectively. In certain embodiments, LDL-C concentrations of 100 mg/dL, 100-129 mg/dL, 130-159 mg/dL, 160-189 mg/dL, and greater than 190 mg/dL are considered optimal, near optimal/above optimal, borderline high, high, and very high, respectively.

"Elevated triglyceride" means concentrations of triglyceride in the serum or liver at which lipid-lowering therapy is recommended, and includes "elevated serum triglyceride" and "elevated liver triglyceride." In certain embodiments, serum triglyceride concentration of 150-199 mg/dL, 200-499 mg/dL, and greater than or equal to 500 mg/dL is considered borderline high, high, and very high, respectively.

"Elevated small LDL particles" means a concentration of small LDL particles in an individual at which lipid-lowering therapy is recommended.

"Elevated small VLDL particles" means a concentration of small VLDL particles in an individual at which lipid-lowering therapy is recommended.

"Elevated lipoprotein(a)" means a concentration of lipoprotein(a) in an individual at which lipid-lowering therapy is recommended.

"Low HDL-C" means a concentration of HDL-C in an individual at which lipid-lowering therapy is recommended. In certain embodiments lipid-lowering therapy is recommended when low HDL-C is accompanied by elevations in non-HDL-C and/or elevations in triglyceride. In certain embodiments, HDL-C concentrations of less than 40 mg/dL are considered low. In certain embodiments, HDL-C concentrations of less than 50 mg/dL are considered low.

"ApoB" means apolipoprotein B-100 protein. Concentration of ApoB in serum (or plasma) is typically quantified in mg/dL or nmol/L. "Serum ApoB" and "plasma ApoB" mean ApoB in the serum and plasma, respectively.

"LDL/HDL ratio" means the ratio of LDL-C to HDL-C.

"Oxidized-LDL" or "Ox-LDL-C" means LDL-C that is oxidized following exposure to free radicals.

"Individual having elevated LDL-C levels" means an individual who has been identified by a medical professional (e.g., a physician) as having LDL-C levels near or above the level at which therapeutic intervention is recommended, according to guidelines recognized by medical professionals. Such an individual may also be considered "in need of treatment" to decrease LDL-C levels.

"Individual having elevated apoB-100 levels" means an individual who has been identified as having apoB-100 levels near or above the level at which therapeutic intervention is recommended, according to guidelines recognized by medical professionals. Such an individual may also be considered "in need of treatment" to decrease apoB-100 levels.

"Treatment of elevated LDL-C levels" means administration of an antisense compound targeted to a PCSK9 nucleic acid to an individual having elevated LDL-C levels.

"Treatment of atherosclerosis" means administration of an antisense compound targeted to a PCSK9 nucleic acid to an individual who, based upon a physician's assessment, has or is likely to have atherosclerosis. "Prevention of atherosclerosis" means administration of an antisense compound targeted to a PCSK9 nucleic acid to an individual who, based upon a physician's assessment, is susceptible to atherosclerosis.

"Ameliorate" means to make better or improve a detrimental condition in an individual.

"Target nucleic acid," "target RNA," "target RNA transcript" and "nucleic acid target" all mean any nucleic acid capable of being targeted by antisense compounds.

"PCSK9 nucleic acid" means any nucleic acid encoding PCSK9. For example, in certain embodiments, a PCSK9 nucleic acid includes, without limitation, a DNA sequence encoding PCSK9, an RNA sequence transcribed from DNA encoding PCSK9, and an mRNA sequence encoding PCSK9. "PCSK9 mRNA" means an mRNA encoding a PCSK9 protein.

"Targeting" means the process of design and selection of an antisense compound that will specifically hybridize to a target nucleic acid and induce a desired effect.

"Targeted" means having a nucleobase sequence that will allow specific hybridization of an antisense compound to a target nucleic acid to induce a desired effect. In certain embodiments, a desired effect is reduction of a target nucleic acid. In certain such embodiments, a desired effect is reduction of PCSK9 mRNA.

"Antisense inhibition" means reduction of a target nucleic acid levels in the presence of an antisense compound complementary to a target nucleic acid compared to target nucleic acid levels in the absence of the antisense compound.

"Target region" means a fragment of a target nucleic acid to which one or more antisense compounds is targeted.

"Target segment" means the sequence of nucleotides of a target nucleic acid to which an antisense compound is targeted. "5' target site" refers to the 5'-most nucleotide of a target segment. "3' target site" refers to the 3'-most nucleotide of a target segment.

"Active target region" means a target region to which one or more active antisense compounds is targeted. "Active antisense compounds" means antisense compounds that reduce target nucleic acid levels.

"Hybridization" means the annealing of complementary nucleic acid molecules. In certain embodiments, complementary nucleic acid molecules include, but are not limited to, an antisense compound and a nucleic acid target. In certain such embodiments, complementary nucleic acid molecules include, but are not limited to, an antisense oligonucleotide and a nucleic acid target "Stringent hybridization conditions" means conditions under which a nucleic acid molecule, such as an antisense compound, will hybridize to a target nucleic acid sequence, but to a minimal number of other sequences.

"Specifically hybridizable" means an antisense compound that hybridizes to a target nucleic acid to induce a desired effect, while exhibiting minimal or no effects on non-target nucleic acids.

"Complementarity" means the capacity for pairing between nucleobases of a first nucleic acid and a second nucleic acid.

"Fully complementary" means each nucleobase of a first nucleic acid is capable of pairing with each nucleobase of a second nucleic acid. In certain embodiments, a first nucleic acid is an antisense compound and a target nucleic acid is a second nucleic acid. In certain such embodiments, an antisense oligonucleotide is a first nucleic acid and a target nucleic acid is a second nucleic acid.

"Non-complementary nucleobase" means a nucleobase of first nucleic acid that is not capable of pairing with the corresponding nucleobase of a target nucleic acid. "Mismatch" a nucleobase of first nucleic acid that is not capable of pairing with the corresponding nucleobase of a target nucleic acid.

"Portion" means a defined number of contiguous (i.e., linked) nucleobases. In certain embodiments, a portion is a defined number of contiguous nucleobases of a target nucleic acid. In certain embodiments, a portion is a defined number of contiguous nucleobases of an antisense compound.

"Oligomeric compound" means a polymer of linked monomeric subunits which is capable of hybridizing to at least a region of an RNA molecule.

"Antisense compound" means an oligomeric compound that is capable of undergoing hybridization to a target nucleic acid through hydrogen bonding.

"Oligonucleotide" means a polymer of linked nucleosides each of which can be modified or unmodified, independent one from another.

"Oligonucleoside" means an oligonucleotide in which the internucleoside linkages do not contain a phosphorus atom.

"Unmodified nucleotide" means a nucleotide composed of naturally occurring nucleobases, sugar moieties and internucleoside linkages. In certain embodiments, an unmodified nucleotide is an RNA nucleotide (i.e., β-D-ribonucleosides) or a DNA nucleotide (i.e., β-D-deoxyribonucleoside).

"Antisense oligonucleotide" means a single-stranded oligonucleotide having a nucleobase sequence that permits hybridization to a corresponding region of a target nucleic acid.

"Motif" means the pattern of unmodified and modified nucleosides in an antisense compound.

"Chimeric antisense compound" means an antisense compound that has at least 2 chemically distinct regions, each region having a plurality of subunits.

A "gapmer" means an antisense compound in which an internal position having a plurality of nucleotides that supports RNaseH cleavage is positioned between external regions having one or more nucleotides that are chemically distinct from the nucleosides of the internal region.

A "gap segment" means the plurality of nucleotides that make up the internal region of a gapmer.

A "wing segment" means the external region of a gapmer.

"Gap-widened" means an antisense compound has a gap segment of 12 or more contiguous 2'-deoxyribonucleotides positioned between 5' and 3' wing segments having from one to six nucleotides having modified sugar moieties.

"Nucleoside" means a nucleobase linked to a sugar.

"Nucleobase" means a heterocyclic base moiety capable of pairing with a base of another nucleic acid.

"Nucleotide" means a nucleoside having a phosphate group covalently linked to the sugar portion of the nucleoside.

"Nucleobase sequence" means the order of contiguous nucleobases independent of any sugar, linkage, and/or nucleobase modification.

"Modified nucleotide" means a nucleotide having, independently, a modified sugar moiety, modified internucleoside linkage, or modified nucleobase.

"Modified nucleoside" means a nucleotide having, independently, a modified sugar moiety or modified nucleobase.

"Contiguous nucleobases" means nucleobases immediately adjacent to each other.

"Modified oligonucleotide" means an oligonucleotide comprising a modified internucleoside linkage, a modified sugar, and/or a modified nucleobase.

"Single-stranded modified oligonucleotide" means a modified oligonucleotide which is not hybridized to a complementary strand.

"Internucleoside linkage" refers to the chemical bond between nucleosides.

"Linked nucleoside" means adjacent nucleosides which are bonded together.

"Linked deoxynucleoside" means a nucleic acid base (A, G, C, T, U) substituted by deoxyribose linked by a phosphate ester to form a nucleotide.

"Naturally occurring internucleoside linkage" means a 3' to 5' phosphodiester linkage.

"Modified internucleoside linkage" means substitution and/or any change from a naturally occurring internucleoside bond. In certain instances, the modified internucleoside linkage refers to a phosphodiester internucleoside bond.

"Phosphorothioate linkage" means a linkage between nucleosides where the phosphodiester bond is modified by replacing one of the non-bridging oxygen atoms with a sulfur atom. A phosphorothioate linkage is a modified internucleoside linkage.

"Modified sugar moiety" means substitution and/or any change from a natural sugar moiety. For the purposes of this disclosure, a "natural sugar moiety" is a sugar moiety found in DNA (2'-H) or RNA (2'-OH).

"Modified sugar" refers to a substitution and/or any change from a natural sugar.

"Bicyclic sugar" means a furosyl ring modified by the bridging of the two non-geminal ring atoms. A bicyclic sugar is a modified sugar.

"Modified nucleobase" means any nucleobase other than adenine, cytosine, guanine, thymidine, or uracil. An "unmodified nucleobase" means the purine bases adenine (A) and guanine (G), and the pyrimidine bases thymine (T), cytosine (C) and uracil (U).

"Modified sugar moiety" means a sugar moiety having a substitution and/or any change from a natural sugar moiety.

"Natural sugar moiety" means a sugar moiety found in DNA (2'-H) or RNA (2'-OH).

"2'-O-methoxyethyl sugar moiety" means a 2'-substituted furosyl ring having a 2'-O(CH2)$_2$-OCH$_3$ (2'-O-methoxyethyl or 2'-MOE) substituent group.

"2'-O-methoxyethyl nucleotide" means a nucleotide comprising a 2'-O-methoxyethyl modified sugar moiety.

"2'-O-methoxyethyl" refers to an O-methoxy-ethyl modification of the 2' position of a furosyl ring. A 2'-O-methoxyethyl modified sugar is a modified sugar.

"Bicyclic nucleic acid sugar moiety" means a furosyl ring modified by the bridging of two non-geminal ring atoms.

"5-methylcytosine" means a cytosine modified with a methyl group attached to the 5' position. A 5-methylcytosine is a modified nucleobase.

"Prodrug" means a therapeutic agent that is prepared in an inactive form that is converted to an active form (i.e., drug) within the body or cells thereof by the action of endogenous enzymes or other chemicals and/or conditions.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Salts" refers to physiologically and pharmaceutically acceptable salts of antisense compounds, i.e., salts that retain the desired biological activity of the parent oligonucleotide and do not impart undesired toxicological effects thereto.

"Cures" means a method or course that restores health or a prescribed treatment for an illness.

"Slows progression" means decrease in the development of the said disease.

"Cap structure" or "terminal cap moiety" means chemical modifications, which have been incorporated at either terminus of an antisense compound.

"ISIS 301012" means a lipid-lowering agent that is an antisense oligonucleotide having the sequence "GCCTCAGTCTGCTTCGCACC" (SEQ ID NO: 457), where each internucleoside linkage is a phosphorothioate internucleoside linkage, each cytosine is a 5-methylcytosine, nucleotides 6-15 are 2'-deoxynucleotides, and nucleotides 1-5 and 16-20 are 2'-O-methoxyethyl nucleotides. ISIS 301012 does not target PCSK9. It is used herein as a non-PCSK9 control.

BRIEF DESCRIPTION OF THE FIGURES

FIG. 5, Panel B, depicts inhibition of liver TG (mg/gram) in mice administered Isis 394816 at 20 mg/kg/wk or 50 mg/kg/wk.

DETAILED DESCRIPTION

Overview

Figure 1:
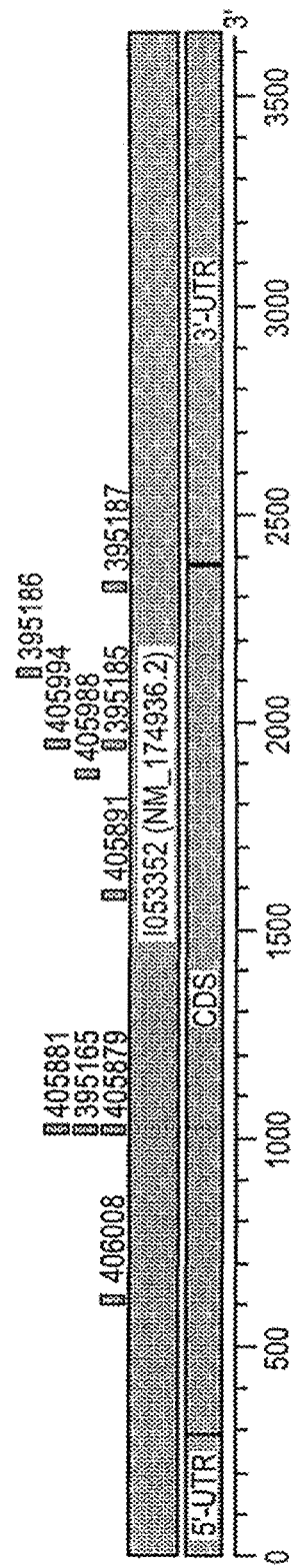
FIG. 1 depicts the location of PCSK9 mRNA target sequences of exemplary antisense compounds.

Elevated levels of LDL-cholesterol (HDL-C) are recognized as a major independent risk factor for coronary heart disease (CHD). Even in individuals undergoing aggressive treatment with currently available cholesterol-lowering agents to reduce LDL-cholesterol (LDL-C) levels, coronary events still occur, and elevated LDL-C levels remain a major risk factor for coronary heart disease in these individuals. Furthermore, many individuals undergoing LDL-lowering therapy do not reach their target LDL-C levels, and thus remain at risk for CHD. Accordingly, there is a need for additional LDL-C lowering agents.

The antisense compounds and methods provided herein are useful for the treatment of hypercholesterolemia. Treatment of hypercholesterolemia encompasses a therapeutic regimen that results in a clinically desirable outcome. For example, the antisense compounds and methods provided herein are useful for the treatment of elevated cholesterol, such as elevated LDL-C. In addition, the antisense compounds and methods provided herein may be used to reduce the risk of CHD, in individuals exhibiting one or more risk factors for CHD. Furthermore, the antisense compounds and methods provided herein may be used to treat and/or prevent atherosclerosis.

As illustrated herein, administration of an antisense oligonucleotide targeted to PCSK9 to animals fed a high-fat diet (an experimental model of hyperlipidemia) resulted in antisense inhibition of PCSK9, upregulation of the LDL-R, reduction of LDL-C levels, and reduction of liver triglycerides. Thus, it is demonstrated that in an experimental model of hyperlipidemia, antisense inhibition of PCSK9 results in lowering LDL-C levels. Accordingly, provided herein are methods for the treatment of reducing LDL-C levels through the administration of an antisense compound targeted to a PCSK9 nucleic acid. Increased LDL-C levels are considered a risk factor for CHD, and are also linked to atherosclerosis. Accordingly, also provided herein are methods for the reduction of CHD risk, and for the prevention and/or treatment of atherosclerosis. Also provided herein are methods for the treatment of conditions characterized by elevated liver triglycerides, such as hepatic steatosis.

In a particular embodiment, methods comprise the use of antisense compounds targeted to particularly advantageous sequences within a PCSK9 nucleic acid. The PCSK9 target sequences are selected on the basis of superior results shown in one or more selection criteria. The presently disclosed antisense compounds all exhibit high in vitro efficacy, determined using a battery of cell models to measure antisense regulation of PCSK9 expression. Further, preferred antisense compounds exhibit relatively high in vivo efficacy, determined using a transgenic mouse model that expresses human PCSK9 or a cynomolgus ("cyno") monkey model. The antisense compound ISIS 405879 (SEQ ID NO: 248) displays superior results in suppressing PCSK9 mRNA expression in the liver of a host individual.

The present antisense compounds are tolerated to different extents when administered to a host individual. Increased tolerability can depend on a number of factors, including, but not limited to, the nucleotide sequence of the antisense compound, chemical modifications to the nucleotides, the particular motif of unmodified and modified nucleosides in the antisense compound, or combinations thereof. Antisense compounds that exhibit increased or superior tolerability are particularly preferred in the present methods. The present antisense compounds also can show different pharmacokinetic properties, depending on their nucleotide sequence, chemical modifications, motifs, or combinations thereof. Particularly preferred antisense compounds also exhibit favorable pharmacokinetics when administered to a host individual.

Certain Indications

In certain embodiments, the invention provides methods of treating an individual comprising administering one or more pharmaceutical compositions of the present invention. In certain embodiments, the individual has hypercholesterolemia, mixed dyslipidemia, atherosclerosis, a risk of developing atherosclerosis, coronary heart disease, a history of coronary heart disease, early onset coronary heart disease, acute coronary syndrome, one or more risk factors for coronary heart disease, type II diabetes, type II diabetes with dyslipidemia, dyslipidemia, hypertriglyceridemia, hyperlipidemia, hyperfattyacidemia, hepatic steatosis, non-alcoholic steatohepatitis, or non-alcoholic fatty liver disease.

Guidelines for lipid-lowering therapy were established in 2001 by Adult Treatment Panel III (ATP III) of the National Cholesterol Education Program (NCEP), and updated in 2004 (Grundy et al., Circulation, 2004, 110, 227-239). The guidelines include obtaining a complete lipoprotein profile, typically after a 9 to 12 hour fast, for determination of LDL-C, total cholesterol, and HDL-C levels. According to the most recently established guidelines, LDL-C levels of 130-159 mg/dL, 160-189 mg/dL, and greater than or equal to 190 mg/dL are considered borderline high, high, and very high, respectively. Total cholesterol levels of 200-239 and greater than or equal to 240 mg/dL are considered borderline high and high, respectively. HDL-C levels of less than 40 mg/dL are considered low.

In certain embodiments, the individual has been identified as in need of lipid-lowering therapy. In certain such embodiments, the individual has been identified as in need of lipid-lowering therapy according to the guidelines established in 2001 by Adult Treatment Panel III (ATP III) of the National Cholesterol Education Program (NCEP), and updated in 2004 (Grundy et al., Circulation, 2004, 110, 227-239). In certain such embodiments, the individual in need of lipid-lowering therapy has LDL-C above 190 mg/dL. In certain such embodiments, the individual in need of lipid-lowering therapy has LDL-C above 160 mg/dL. In certain such embodiments, the individual in need of lipid-lowering therapy has LDL-C above 130 mg/dL. In certain such embodiments, the individual in need of lipid-lowering therapy has LDL-C above 100 mg/dL. In certain such embodiments, the individual in need of lipid-lowering therapy should maintain LDL-C below 160 mg/dL. In certain such embodiments, the individual in need of lipid-lowering therapy should maintain LDL-C below 130 mg/dL. In certain such embodiments, the individual in need of lipid-lowering therapy should maintain LDL-C below 100 mg/dL. In certain such embodiments, the individual should maintain LDL-C below 70 mg/dL or even below 50 mg/dL.

In certain embodiments, the invention provides methods for reducing ApoB in an individual. In certain embodiments, the invention provides methods for reducing ApoB-containing lipoprotein in an individual. In certain embodiments, the invention provides methods for reducing LDL-C in an individual. In certain embodiments, the invention provides methods for reducing VLDL-C in an individual. In certain embodiments, the invention provides methods for reducing IDL-C in an individual. In certain embodiments, the invention provides methods for reducing non-HDL-C in an individual. In certain embodiments the invention provides methods for reducing Lp(a) in an individual. In certain embodiments, the invention provides methods for reducing serum triglyceride in an individual. In certain embodiments, the invention provides methods for reducing liver triglyceride in an individual. In certain embodiments, the invention provides methods for reducing Ox-LDL-C in an individual. In certain embodiments, the invention provides methods for reducing small LDL particles in an individual. In certain embodiments, the invention provides methods for reducing small VLDL particles in an individual. In certain embodiments, the invention provides methods for reducing phospholipids in an individual. In certain embodiments, the invention provides methods for reducing oxidized phospholipids in an individual.

In certain embodiments, the methods provided by the present invention do not lower HDL-C. In certain embodiments, the methods provided by the present invention do not result in accumulation of lipids in the liver.

In one embodiment are methods for decreasing LDL-C levels, or alternatively methods for treating hypercholesterolemia, by administering to an individual suffering from elevated LDL-C levels a therapeutically effective amount of an antisense compound targeted to a PCSK9 nucleic acid. In another embodiment, a method of decreasing LDL-C levels comprises selecting an individual in need of a decrease in LDL-C levels, and administering to the individual a therapeutically effective amount of an antisense compound targeted to a PCSK9 nucleic acid. In a further embodiment, a method of reducing coronary heart disease risk includes selecting an individual having elevated LDL-C levels and one or more additional indicators of coronary heart disease risk, and administering to the individual a therapeutically effective amount of an antisense compound targeted to a PCSK9 nucleic acid.

In other embodiments, the LDL-C level is from 100-129 mg/dL, from 130 to 159 mg/dL, from 160-189 mg/dL, or greater than or equal to 190 mg/dL.

In one embodiment, administration of a therapeutically effective amount of an antisense compound targeted to a PCSK9 nucleic acid is accompanied by monitoring of LDL-C levels in the serum of an individual, to determine an individual's response to administration of the antisense compound. An individual's response to administration of the antisense compound is used by a physician to determine the amount and duration of therapeutic intervention.

In one embodiment, administration of an antisense compound targeted to a PCSK9 nucleic acid results in LDL-C levels below 190 mg/dL, below 160 mg/dL, below 130 mg/dL, below 100 mg/dL, below 70 mg/dL, or below 50 mg/dL. In another embodiment, administration of an antisense compound targeted to a PCSK9 nucleic acid decreases LDL-C by at least 15%, by at least 25%, by at least 50%, by at least 60%, by at least 70%, by at least 75%, by at least 80%, by at least 85%, by at least 90%, or by at least 95%.

An individual having elevated LDL-C levels may also exhibit reduced HDL-C levels and/or elevated total cholesterol levels. Accordingly, in one embodiment a therapeutically effective amount of an antisense compound targeted to a PCSK9 nucleic acid is administered to an individual having elevated LDL-C levels, who also has reduced HDL-C levels and/or elevated total cholesterol levels.

Individuals having elevated LDL-C levels may also exhibit elevated triglyceride levels. Accordingly, in one embodiment a therapeutically effective amount of an antisense compound targeted to a PCSK9 nucleic acid is administered to an individual having elevated LDL-C levels, and also having elevated triglyceride levels.

Atherosclerosis can lead to coronary heart disease, stroke, or peripheral vascular disease. Elevated LDL-C levels are considered a risk factor in the development and progression of atherosclerosis. Accordingly, in one embodiment, a therapeutically effective amount of an antisense compound targeted to a PCSK9 nucleic acid is administered to an individual having atherosclerosis. In a further embodiment, a therapeutically effective amount of antisense compound targeted to a PCSK9 nucleic acid is administered to an individual susceptible to atherosclerosis. Atherosclerosis is assessed directly through routine imaging techniques such as, for example, ultrasound imaging techniques that reveal carotid intimomedial thickness. Accordingly, treatment and/or prevention of atherosclerosis further include monitoring atherosclerosis through routine imaging techniques. In one embodiment, administration of an antisense compound targeted to a PCSK9 nucleic acid leads to a lessening of the severity of atherosclerosis, as indicated by, for example, a reduction of carotid intimomedial thickness in arteries.

Measurements of cholesterol, lipoproteins and triglycerides are obtained using serum or plasma collected from an individual. Methods of obtaining serum or plasma samples are routine, as are methods of preparation of the serum samples for analysis of cholesterol, triglycerides, and other serum markers.

A physician may determine the need for therapeutic intervention for individuals in cases where more or less aggressive LDL-lowering therapy is needed. The practice of the methods herein may be applied to any altered guidelines provided by the NCEP, or other entities that establish guidelines for physicians used in treating any of the diseases or conditions listed herein, for determining coronary heart disease risk and diagnosing metabolic syndrome.

In one embodiment, administration of an antisense compound targeted to a PCSK9 nucleic acid is parenteral administration. Parenteral administration may be intravenous or subcutaneous administration. Accordingly, in another embodiment, administration of an antisense compound targeted to a PCSK9 nucleic acid is intravenous or subcutaneous administration. Administration may include multiple doses of an antisense compound targeted to a PCSK9 nucleic acid.

In certain embodiments, a pharmaceutical composition comprising an antisense compound targeted to PCSK9 is for use in therapy. In certain embodiments, the therapy is the reduction of LDL-C, ApoB, VLDL-C, IDL-C, non-HDL-C, Lp(a), serum triglyceride, liver triglyceride, Ox-LDL-C, small LDL particles, small VLDL, phospholipids, or oxidized phospholipids in an individual. In certain embodiments, the therapy is the treatment of hypercholesterolemia, mixed dyslipidemia, atherosclerosis, a risk of developing atherosclerosis, coronary heart disease, acute coronary syndrome, a history of coronary heart disease, early onset coronary heart disease, one or more risk factors for coronary heart disease, type II diabetes, type II diabetes with dyslipidemia, dyslipidemia, hypertriglyceridemia, hyperlipidemia, hyperfattyacidemia, hepatic steatosis, non-alcoholic steatohepatitis, or non-alcoholic fatty liver disease. In additional embodiments, the therapy is the reduction of CHD risk. In certain aspects, the therapy is prevention of atherosclerosis. In certain embodiments, the therapy is the prevention of coronary heart disease.

In certain embodiments, a pharmaceutical composition comprising an antisense compound targeted to PCSK9 is used for the preparation of a medicament for reducing LDL-C, ApoB, VLDL-C, IDL-C, non-HDL-C, Lp(a), serum triglyceride, liver triglyceride, Ox-LDL-C, small LDL particles, small VLDL, phospholipids, or oxidized phospholipids in an individual. In certain embodiments pharmaceutical composition comprising an antisense compound targeted to PCKS9 is used for the preparation of a medicament for reducing coronary heart disease risk. In certain embodiments, an antisense compound targeted to PCSK9 is used for the preparation of a medicament for the treatment of hypercholesterolemia, mixed dyslipidemia, atherosclerosis, a risk of developing atherosclerosis, coronary heart disease, a history of coronary heart disease, early onset coronary heart disease, one or more risk factors for coronary heart disease, type II diabetes, type II diabetes with dyslipidemia, dyslipidemia, hypertriglyceridemia, hyperlipidemia, hyperfattyacidemia, hepatic steatosis, non-alcoholic steatohepatitis, or non-alcoholic fatty liver disease.

Certain Combination Therapies

In certain embodiments, one or more pharmaceutical compositions of the present invention are co-administered with one or more other pharmaceutical agents. In certain embodiments, such one or more other pharmaceutical agents are designed to treat the same disease or condition as the one or more pharmaceutical compositions of the present invention. In certain embodiments, such one or more other pharmaceutical agents are designed to treat a different disease or condition as the one or more pharmaceutical compositions of the present invention. In certain embodiments, such one or more other pharmaceutical agents are designed to treat an undesired effect of one or more pharmaceutical compositions of the present invention. In certain embodiments, one or more pharmaceutical compositions of the present invention are co-administered with another pharmaceutical agent to treat an undesired effect of that other pharmaceutical agent. In certain embodiments, one or more pharmaceutical compositions of the present invention and one or more other pharmaceutical agents are administered at the same time. In certain embodiments, one or more pharmaceutical compositions of the present invention and one or more other pharmaceutical agents are administered at different times. In certain embodiments, one or more pharmaceutical compositions of the present invention and one or more other pharmaceutical agents are prepared together in a single formulation. In certain embodiments, one or more pharmaceutical compositions of the present invention and one or more other pharmaceutical agents are prepared separately. For example, a composition may comprise a pharmaceutical agent for separate, sequential, or simultaneous administration with an antisense compound.

In certain embodiments, pharmaceutical agents that may be co-administered with a pharmaceutical composition of the present invention include lipid-lowering agents or LXR agonists. In certain such embodiments, pharmaceutical agents that may be co-administered with a pharmaceutical composition of the present invention include, but are not limited to atorvastatin, simvastatin, rosuvastatin, and ezetimibe. In certain such embodiments, the lipid-lowering agent is administered prior to administration of a pharmaceutical composition of the present invention. In certain such embodiments, the lipid-lowering agent is administered following administration of a pharmaceutical composition of the present invention. In certain such embodiments the lipid-lowering agent is administered at the same time as a pharmaceutical composition of the present invention. In certain such embodiments the dose of a co-administered lipid-lowering agent is the same as the dose that would be administered if the lipid-lowering agent was administered alone. In certain such embodiments the dose of a co-administered lipid-lowering agent is lower than the dose that would be administered if the lipid-lowering agent was administered alone. In certain such embodiments the dose of a co-administered lipid-lowering agent is greater than the dose that would be administered if the lipid-lowering agent was administered alone.

In certain embodiments, a co-administered lipid-lowering agent is a HMG-CoA reductase inhibitor. In certain such embodiments the HMG-CoA reductase inhibitor is a statin. In certain such embodiments, the statin is selected from, for example, atorvastatin, simvastatin, pravastatin, fluvastatin, and rosuvastatin.

In certain embodiments, a co-administered lipid-lowering agent is a cholesterol absorption inhibitor. In certain such embodiments, cholesterol absorption inhibitor is ezetimibe.

In certain embodiments, a co-administered lipid-lowering agent is a co-formulated HMG-CoA reductase inhibitor and cholesterol absorption inhibitor. In certain such embodiments the co-formulated lipid-lowering agent is ezetimibe/simvastatin.

In certain embodiments, a co-administered lipid-lowering agent is a microsomal triglyceride transfer protein inhibitor (MTP inhibitor).

In certain embodiments, a co-administered lipid-lowering agent is an oligonucleotide targeted to ApoB.

In certain embodiments, a co-administered pharmaceutical agent is a bile acid sequestrant. In certain such embodiments, the bile acid sequestrant is selected from cholestyramine, colestipol, and colesevelam.

In certain embodiments, a co-administered pharmaceutical agent is a nicotinic acid. In certain such embodiments, the nicotinic acid is selected from immediate release nicotinic acid, extended release nicotinic acid, and sustained release nicotinic acid.

In certain embodiments, a co-administered pharmaceutical agent is a fibric acid. In certain such embodiments, a fibric acid is selected from gemfibrozil, fenofibrate, clofibrate, bezafibrate, and ciprofibrate.

Further examples of pharmaceutical agents that may be co-administered with a pharmaceutical composition of the present invention include, but are not limited to, corticosteroids, including but not limited to prednisone; LXR agonists; immunoglobulins, including, but not limited to intravenous immunoglobulin (IVIg); analgesics (e.g., acetaminophen); anti-inflammatory agents, including, but not limited to non-steroidal anti-inflammatory drugs (e.g., ibuprofen, COX-1 inhibitors, and COX-2, inhibitors); salicylates; antibiotics; antivirals; antifungal agents; antidiabetic agents (e.g., biguanides, glucosidase inhibitors, insulins, sulfonylureas, and thiazolidenediones); adrenergic modifiers; diuretics; hormones (e.g., anabolic steroids, androgen, estrogen, calcitonin, progestin, somatostan, and thyroid hormones); immunomodulators; muscle relaxants; antihistamines; osteoporosis agents (e.g., biphosphonates, calcitonin, and estrogens); prostaglandins, antineoplastic agents; psychotherapeutic agents; sedatives; poison oak or poison sumac products; antibodies; and vaccines.

In certain embodiments, the pharmaceutical compositions of the present invention may be administered in conjunction with a lipid-lowering therapy. In certain such embodiments, a lipid-lowering therapy is therapeutic lifestyle change. In certain such embodiments, a lipid-lowering therapy is LDL apheresis.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound may be "antisense" to a target nucleic acid, meaning that is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to a PCSK9 nucleic acid is 8 to 80, 12 to 50, 12 to 30 or 15 to 30 subunits in length. In other words, antisense compounds are from 8 to 80, 12 to 50, 12 to 30 or 15 to 30 linked subunits. In certain such embodiments, the antisense compounds are 12, 13, 14, 15, 16, 17, 18, 19, 20, 21, 22, 23, 24, 25, 26, 27, 28, 29, or 30 subunits in length.

In certain embodiments, an antisense oligonucleotide targeted to a PCSK9 nucleic acid is 12 to 30 nucleotides in length. In certain such embodiments, an antisense oligonucleotide targeted to a PCSK9 nucleic acid is 12, 13, 14, 15, 16, 17, 18, 19, 20, 21, 22, 23, 24, 25, 26, 27, 28, 29, or 30 nucleotides in length.

In certain embodiment, an antisense compound targeted to a PCSK9 nucleic acid is 15 to 30 subunits in length. In other words, antisense compounds are from 15 to 30 linked subunits. In certain such embodiments, the antisense compounds are 15, 16, 17, 18, 19, 20, 21, 22, 23, 24, 25, 26, 27, 28, 29, or 30 subunits in length.

In certain embodiments, an antisense oligonucleotide targeted to a PCSK9 nucleic acid is 15 to 30 nucleotides in length. In certain such embodiments, an antisense oligonucleotide targeted to a PCSK9 nucleic acid is 15, 16, 17, 18, 19, 20, 21, 22, 23, 24, 25, 26, 27, 28, 29, or 30 nucleotides in length.

In certain embodiments, an antisense compound targeted to a PCSK9 nucleic acid is 18 to 24 subunits in length. In other words, antisense compounds are from 18 to 24 linked subunits. In one embodiment, the antisense compounds are 18, 19, 20, 21, 22, 23, or 24 subunits in length.

In certain embodiments, an antisense oligonucleotide targeted to a PCSK9 nucleic acid is 18 to 24 nucleotides in length. In certain such embodiments, an antisense oligonucleotide targeted to a PCSK9 nucleic acid is 18, 19, 20, 21, 22, 23, or 24 nucleotides in length.

In certain embodiments, an antisense compound targeted to a PCSK9 nucleic acid is 19 to 22 subunits in length. In other words, antisense compounds are from 19 to 22 linked subunits. This embodies antisense compounds of 19, 20, 21, or 22 subunits in length.

In certain embodiments, an antisense oligonucleotide targeted to a PCSK9 nucleic acid is 19 to 22 nucleotides in length. In certain such embodiments, an antisense oligonucleotide targeted to a PCSK9 nucleic acid is 19, 20, 21, or 22 nucleotides in length.

In certain embodiments, an antisense compound targeted to a PCSK9 nucleic acid is 20 subunits in length. In certain such embodiments, antisense compounds are 20 linked subunits in length.

In certain embodiments, an antisense oligonucleotide targeted to a PCSK9 nucleic acid is 20 nucleotides in length. In certain such embodiments, an antisense oligonucleotide targeted to an PCSK9 nucleic acid is 20 linked nucleotides in length.

In certain embodiments, antisense compounds target a range of a PCSK9 nucleic acid. In certain embodiment, such compounds contain at least an 8 nucleotide core sequence in common. In certain embodiments, such compounds sharing at least an 8 nucleotide core sequence target a region identified herein.

In certain embodiments, an antisense compound targeted to a PCSK9 nucleic acid may target the following nucleotide regions of SEQ ID NO: 1: 294-317, 406-440, 406-526, 410-436, 410-499, 446-526, 545-581, 591-619, 591-704, 591-743, 595-622, 600-626, 600-639, 600-670, 601-628, 602-628, 603-630, 611-636, 620-647, 638-665, 648-674, 657-684, 705-743, 782-810, 821-859, 835-859, 835-917, 835-942, 860-887, 860-899, 860-909, 860-917, 869-895, 878-905, 888-909, 923-952, 960-1034, 960-1173, 960-986, 967-991, 970-1023, 970-1064, 970-1117, 970-996, 977-1004, 985-1011, 989-1016, 992-1019, 997-1024, 997-1024, 998-1025, 999-1026, 1000-1027, 1001-1028, 1002-1029, 1003-1029, 1004-1029, 1005-1029, 1006-1029, 1007-1034, 1036-1061, 1045-1072, 1076-1096, 1088-1115, 1098-1123, 1200-1251, 1210-1237, 1219-1245, 1228-1251, 1273-1444, 1295-1316, 1318-1345, 1328-1354, 1337-1361, 1344-1371, 1354-1377, 1380-1406, 1389-1416, 1400-1426, 1409-1434, 1465-1491, 1465-1602, 1474-1499, 1482-1519, 1513-1540, 1523-1549, 1526-1602, 1526-1624, 1532-1558, 1541-1568, 1552-1579, 1560-1587, 1561-1589, 1564-1591, 1565-1592, 1566-1592, 1567-1592, 1570-1597, 1571-1599, 1605-1706, 1628-1706, 1640-1666, 1672-1698, 1681-1706, 1735-1761, 1735-1765, 1740-1765, 1849-1876, 1849-1879, 1850-1877, 1851-1877, 1852-1878, 1852-1879, 1853-1879, 1854-1879, 1905-1955, 1915-1942, 1916-1943, 1917-1944, 1918-1945, 1919-1946, 1920-1939, 1920-1947, 1921-1948, 1922-1949, 1923-1950, 1924-1951, 1925-1952, 1926-1952, 1927-1952, 1928-1955, 1962-2059, 2040-2126, 2100-2126, 2100-2139, 2100-2206, 2101-2126, 2305-2332, 2305-2354, 2306-2333, 2307-2334, 2308-2334, 2309-2334, 2310-2334, 2410-2434, 2504-2528, 2509-2528, 2582-2625, 2606-2668, 2828-2855, 2832-2851, 2900-2927, 2900-2929, 2902-2927, 2983-3007, 2983-3013, 3227-3252, 3227-3456, 3472-3496, or 3543-3569.

In certain embodiments, antisense compounds target a range of a PCSK9 nucleic acid. In certain embodiment, such compounds contain at least an 8 nucleotide core sequence in common. In certain embodiments, such compounds sharing at least an 8 nucleotide core sequence targets the following nucleotide regions of SEQ ID NO: 1: 294-317, 406-440, 406-526, 410-436, 410-499, 446-526, 545-581, 591-619, 591-704, 591-743, 595-622, 600-626, 600-639, 600-670, 601-628, 602-628, 603-630, 611-636, 620-647, 638-665, 648-674, 657-684, 705-743, 782-810, 821-859, 835-859, 835-917, 835-942, 860-887, 860-899, 860-909, 860-917, 869-895, 878-905, 888-909, 923-952, 960-1034, 960-1173, 960-986, 967-991, 970-1023, 970-1064, 970-1117, 970-996, 977-1004, 985-1011, 989-1016, 992-1019, 997-1024, 997-1024, 998-1025, 999-1026, 1000-1027, 1001-1028, 1002-1021, 1002-1029, 1003-1029, 1004-1029, 1005-1029, 1006-1029, 1007-1034, 1036-1061, 1045-1072, 1076-1096, 1088-1115, 1098-1123, 1200-1251, 1210-1237, 1219-1245, 1228-1251, 1273-1444, 1295-1316, 1318-1345, 1328-1354, 1337-1361, 1344-1371, 1354-1377, 1380-1406, 1389-1416, 1400-1426, 1409-1434, 1465-1491, 1465-1602, 1474-1499, 1482-1519, 1513-1540, 1523-1549, 1526-1602, 1526-1624, 1532-1558, 1541-1568, 1552-1579, 1560-1587, 1561-1589, 1564-1591, 1565-1592, 1566-1592, 1567-1592, 1570-1597, 1571-1599, 1605-1706, 1628-1706, 1640-1666, 1672-1698, 1681-1706, 1735-1761, 1735-1765, 1740-1765, 1849-1876, 1849-1879, 1850-1877, 1851-1877, 1852-1878, 1852-1879, 1853-1879, 1854-1879, 1905-1955, 1915-1942, 1916-1943, 1917-1944, 1918-1945, 1919-1946, 1920-1939, 1920-1947, 1921-1948, 1922-1949, 1923-1950, 1924-1951, 1925-1952, 1926-1952, 1927-1952, 1928-1955, 1962-2059, 2040-2126, 2100-2126, 2100-2139, 2100-2206, 2101-2126, 2305-2332, 2305-2354, 2306-2333, 2307-2334, 2308-2334, 2309-2334, 2310-2334, 2410-2434, 2504-2528, 2509-2528, 2582-2625, 2606-2668, 2828-2855, 2832-2851, 2900-2927, 2900-2929, 2902-2927, 2983-3007, 2983-3013, 3227-3252, 3227-3456, 3472-3496, or 3543-3569.

In certain embodiments, an antisense compound targeted to a PCSK9 nucleic acid may target the following nucleotide regions of SEQ ID NO: 2: 2274-2400, 2274-2575, 2433-2570, 2433-2579, 2549-2575, 2552-2579, 2585-2638, 2605-2638, 3056-3075, 4150-5159, 4306-4325, 5590-5618, 5667-5686, 6444-6463, 6482-6518, 6492-6518, 6528-6555, 6528-6623, 6534-6561, 6535-6562, 6536-6563, 6537-6563, 6538-6565, 6539-6565, 6540-6567, 6541-6567, 6542-6569, 6546-6573, 6557-6584, 6575-6602, 6585-6611, 6594-6621, 6596-6623, 6652-6671, 7099-7118, 7556-7584, 8836-8855, 8948-8967, 9099-9118, 9099-9168, 9130-9168, 9207-9233, 9207-9235, 9209-9235, 10252-10271, 10633-10652, 11308-11491, 12715-12734, 12928-12947, 13681-13700, 13746-13779, 13816-13847, 13903-13945, 13977-14141, 14179-14198, 14267-14286, 14397-14423, 14441-14460, 14494-14513, 14494-14543, 14524-14543, 14601-14650, 14670-14700, 14675-14700, 14801-14828, 14877-14912, 14877-14915, 14877-14973, 14916-14943, 14916-14973, 14925-14951, 14934-14963, 14946-14973, 14979-14998, 15254-15280, 15254-15328, 15264-15290, 15279-15305, 15291-15318, 15292-15319, 15293-15320, 15294-15321, 15294-15321, 15295-15322, 15296-15323, 15297-15323, 15298-15323, 15299-15323, 15300-15323, 15301-15328, 15330-15355, 15330-15490, 15339-15366, 15358-15490, 16134-16153, 16668-16687, 17267-17286, 18377-18427, 18561-18580, 18591-18618, 18591-18646, 18591-18668, 18695-18746, 18705-18730, 18709-18736, 18719-18746, 19203-20080, 19931-19952, 19954-19981, 19964-19990, 19973-19999, 19982-20009, 19992-20016, 20016-20042, 20025-20052, 20036-20062, 20045-20070, 20100-20119, 20188-20207, 20624-20650, 20624-20759, 20629-20804, 20633-20660, 20635-20781, 20643-20662, 20657-20676, 20670-20697, 20680-20706, 20683-20781, 20689-20715, 20698-20725, 20709-20736, 20717-20744, 20718-20745, 20719-20746, 20720-20747, 20721-20748, 20722-20749, 20727-20752, 20735-20759, 20762-21014, 20785-21014, 21082-21107, 21082-21152, 21091-21114, 21118-21144, 21127-21152, 21181-21209, 21181-21211, 21183-21211, 21481-21500, 21589-21608, 21692-21719, 22000-22227, 22096-22115, 22096-22223, 22096-22311, 22133-22160, 22133-22163, 22134-22161, 22135-22162, 22136-22163, 22137-22163, 22138-22163, 22189-22239, 22199-22226, 22199-22227, 22200-22227, 22201-22228, 22202-22229, 22203-22230, 22204-22231, 22205-22232, 22206-22233, 22207-22234, 22208-22235, 22209-22236, 22210-22236, 22210-22239, 22211-22236, 22212-22239, 22292-22311, 23985-24054, 24035-24134, 24095-24121, 24858-24877, 24907-24926, 25413-25432, 25994-26013, 26112-26139, 26112-26161, 26112-27303, 26113-26140, 26114-26141, 26115-26141, 26116-26141, 26117-26141, 26117-26475, 26118-26141, 26120-26141, 26132-26151, 26142-26161, 26217-26241, 26311-26335, 26389-26432, 26456-26576, 26635-26662, 26707-26734, 26707-26736, 26790-26820, 27034-27263, 27279-27303, or 27350-27376.

In certain embodiments, antisense compounds target a range of a PCSK9 nucleic acid. In certain embodiment, such compounds contain at least an 8 nucleotide core sequence in common. In certain embodiments, such compounds sharing at least an 8 nucleotide core sequence targets the following nucleotide regions of SEQ ID NO: 2: 2274-2400, 2274-2575, 2433-2570, 2433-2579, 2549-2575, 2552-2579, 2585-2638, 2605-2638, 3056-3075, 4150-5159, 4306-4325, 5590-5618, 5667-5686, 6444-6463, 6482-6518, 6492-6518, 6528-6555, 6528-6623, 6534-6561, 6535-6562, 6536-6563, 6537-6563, 6538-6565, 6539-6565, 6540-6567, 6541-6567, 6542-6569, 6546-6573, 6557-6584, 6575-6602, 6585-6611, 6594-6621, 6596-6623, 6652-6671, 7099-7118, 7556-7584, 8836-8855, 8948-8967, 9099-9118, 9099-9168, 9130-9168, 9207-9233, 9207-9235, 9209-9235, 10252-10271, 10633-10652, 11308-11491, 12715-12734, 12928-12947, 13681-13700, 13746-13779, 13816-13847, 13903-13945, 13977-14141, 14179-14198, 14267-14286, 14397-14423, 14441-14460, 14494-14513, 14494-14543, 14524-14543, 14601-14650, 14670-14700, 14675-14700, 14801-14828, 14877-14912, 14877-14915, 14877-14973, 14916-14943, 14916-14973, 14925-14951, 14934-14963, 14946-14973, 14979-14998, 15254-15280, 15254-15328, 15264-15290, 15279-15305, 15291-15318, 15292-15319, 15293-15320, 15294-15321, 15294-15321, 15295-15322, 15296-15323, 15297-15323, 15298-15323, 15299-15323, 15300-15323, 15301-15328, 15330-15355, 15330-15490, 15339-15366, 15358-15490, 16134-16153, 16668-16687, 17267-17286, 18377-18427, 18561-18580, 18591-18618, 18591-18646, 18591-18668, 18695-18746, 18705-18730, 18709-18736, 18719-18746, 19203-20080, 19931-19952, 19954-19981, 19964-19990, 19973-19999, 19982-20009, 19992-20016, 20016-20042, 20025-20052, 20036-20062, 20045-20070, 20100-20119, 20188-20207, 20624-20650, 20624-20759, 20629-20804, 20633-20660, 20635-20781, 20643-20662, 20657-20676, 20670-20697, 20680-20706, 20683-20781, 20689-20715, 20698-20725, 20709-20736, 20717-20744, 20718-20745, 20719-20746, 20720-20747, 20721-20748, 20722-20749, 20727-20752, 20735-20759, 20762-21014, 20785-21014, 21082-21107, 21082-21152, 21091-21114, 21118-21144, 21127-21152, 21181-21209, 21181-21211, 21183-21211, 21481-21500, 21589-21608, 21692-21719, 22000-22227, 22096-22115, 22096-22223, 22096-22311, 22133-22160, 22133-22163, 22134-22161, 22135-22162, 22136-22163, 22137-22163, 22138-22163, 22189-22239, 22199-22226, 22199-22227, 22200-22227, 22201-22228, 22202-22229, 22203-22230, 22204-22231, 22205-22232, 22206-22233, 22207-22234, 22208-22235, 22209-22236, 22210-22236, 22210-22239, 22211-22236, 22212-22239, 22292-22311, 23985-24054, 24035-24134, 24095-24121, 24858-24877, 24907-24926, 25413-25432, 25994-26013, 26112-26139, 26112-26161, 26112-27303, 26113-26140, 26114-26141, 26115-26141, 26116-26141, 26117-26141, 26117-26475, 26118-26141, 26120-26141, 26132-26151, 26142-26161, 26217-26241, 26311-26335, 26389-26432, 26456-26576, 26635-26662, 26707-26734, 26707-26736, 26790-26820, 27034-27263, 27279-27303, or 27350-27376.

In certain embodiments, an antisense compound targeted to a PCSK9 nucleic acid may target the following nucleotide regions of SEQ ID NO: 3: 220-253, 290-321, 377-419, 451-615, 653-672, 741-760, 871-897, 915-934, 968-1017, 1075-1124, 1075-1174, 1144-1174, 1275-1302, 1315-1341, 1351-1389, 1351-1447, 1365-1439, 1390-1417, 1390-1429, 1390-1439, 1399-1425, 1408-1435, 1420-1447, 1453-1482, 1490-1516, 1490-1564, 1500-1526, 1515-1541, 1527-1553, 1527-1554, 1528-1554, 1529-1555, 1529-1556, 1530-1556, 1530-1557, 1531-1557, 1532-1558, 1533-1559, 1534-1559, 1535-1559, 1536-1559, 1537-1564, 1566-1602, 1566-1681, 1606-1626, 1618-1645, 1626-1653, 1684-1703, 1730-1781, 1740-1767, 1749-1775, 1758-1781, 1820-1847, 1820-1877, 1822-2198, 1830-1856, 1839-1865, 1840-1867, 1898-1924, 1898-2035, 1903-2127, 1907-1934, 1911-1938, 1946-1971, 1954-1980, 1959-2035, 1959-2057, 1963-1988, 1967-2035, 1972-1999, 1982-2008, 1991-2018, 1993-2019, 1995-2022, 1996-2023, 1997-2024, 1998-2025, 1999-2025, 2000-2025, 2009-2035, 2038-2139, 2061-2139, 2073-2099, 2078-2104, 2105-2131, 2112-2139, 2168-2198, 2170-2177, 2245-2284, 2295-2394, 2355-2381, 2355-2394, 2405-2461, 2560-2587, 2560-2609, 2561-2588, 2562-2589, 2563-2589, 2564-2589, 2565-2589, 2566-2589, 2567-2589, 2568-2589, 2665-2689, 2759-2783, 2837-2880, 2904-2923, 3005-3024, 3005-3174, 3083-3110, 3155-3184, 3238-3268, 3482-3711, 3727-3751, or 3798-3824.

In certain embodiments, an antisense compound targeted to a PCSK9 nucleic acid may target the following nucleotide regions of SEQ ID NO: 1: 320-405, 441-445, 527-544, 582-590, 744-781, 811-820, 918-922, 953-959, 1034-1036, 1152-1153, 1174-1199, 1251-1272, 1445-1464, 1603-1604, 1625-1627, 1707-1734, 1766-1811, 1832-1848, 1880-1904, 1956-1961, 1982-1939, 2030-2039, 2060-2099, 2140-2149, 2170-2186, 2207-2304, 2355-2409, 2435-2503, 2529-2581, 2626-2648, 2669-2749, 2770-2827, 2856-2876, 2891-2899, 2930-2982, 3014-3226, 3253-3436, 3457-3471, or 3497-3542.

In certain embodiments, antisense compounds target a range of a PCSK9 nucleic acid. In certain embodiment, such compounds contain at least an 8 nucleotide core sequence in common. In certain embodiments, such compounds sharing at least an 8 nucleotide core sequence targets the following nucleotide regions of SEQ ID NO: 1: 320-405, 441-445, 527-544, 582-590, 744-781, 811-820, 918-922, 953-959, 1034-1036, 1152-1153, 1174-1199, 1251-1272, 1445-1464, 1603-1604, 1625-1627, 1707-1734, 1766-1811, 1832-1848, 1880-1904, 1956-1961, 1982-1939, 2030-2039, 2060-2099, 2140-2149, 2170-2186, 2207-2304, 2355-2409, 2435-2503, 2529-2581, 2626-2648, 2669-2749, 2770-2827, 2856-2876, 2891-2899, 2930-2982, 3014-3226, 3253-3436, 3457-3471, or 3497-3542.

In certain embodiments, a shortened or truncated antisense compound targeted to a PCSK9 nucleic acid has a single subunit deleted from the 5' end (5' truncation), or alternatively from the 3' end (3' truncation). A shortened or truncated antisense compound targeted to a PCSK9 nucleic acid may have two subunits deleted from the 5' end, or alternatively may have two subunits deleted from the 3' end, of the antisense compound. Alternatively, the deleted nucleosides may be dispersed throughout the antisense compound, for example, in an antisense compound having one nucleoside deleted from the 5' end and one nucleoside deleted from the 3' end.

When a single additional subunit is present in a lengthened antisense compound, the additional subunit may be located at the 5' or 3' end of the antisense compound. When two or more additional subunits are present, the added subunits may be adjacent to each other, for example, in an antisense compound having two subunits added to the 5' end (5' addition), or alternatively to the 3' end (3' addition), of the antisense compound. Alternatively, the added subunits may be dispersed throughout the antisense compound, for example, in an antisense compound having one subunit added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

PCT/US2007/068404 describes incorporation of chemically-modified high-affinity nucleotides into short antisense compounds about 8-16 nucleobases in length and that such compounds are useful in the reduction of target RNAs in animals with increased potency and improved therapeutic index.

In certain embodiments, antisense compounds targeted to a PCSK9 nucleic acid are short antisense compounds. In certain embodiments, such short antisense compounds are oligonucleotide compounds. In certain embodiments, such short antisense compounds are about 8 to 16, preferably 9 to 15, more preferably 9 to 14, more preferably 10 to 14 nucleotides in length and comprises a gap region flanked on each side by a wing, wherein each wing independently consists of 1 to 3 nucleotides. Preferred motifs include but are not limited to wing-deoxy gap-wing motifs selected from 3-10-3, 2-10-3, 2-10-2, 1-10-1, 2-8-2, 1-8-1, 3-6-3 or 1-6-1.

Antisense compounds targeted to a PCSK9 nucleic acid are synthesized in vitro and do not include antisense compositions of biological origin, or genetic vector constructs designed to direct the in vivo synthesis of antisense molecules.

In certain embodiments, an antisense compound is targeted to a region of a PCSK9 nucleic acid that does not contain a single nucleotide polymorphism (SNPs). In certain embodiments, an antisense compound is targeted to a region of a PCSK9 nucleic acid that does contain a single nucleotide polymorph (SNPs). A single nucleotide polymorphism refers to polymorphisms that are the result of a single nucleotide alteration or the existence of two or more alternative sequences which can be, for example, different allelic forms of a gene. A polymorphism may comprise one or more base changes including, for example, an insertion, a repeat, or a deletion. In certain embodiments, an antisense oligonucleotide targeted to a PCSK9 nucleic acid overlaps with a SNP at the following positions: 428, 432, 449, 996, 1011, 1044, 1317, 1565, 1617, 1618, 1671, 1711, 1722, 1836, 1911. In certain embodiments, the compounds provided herein that target a region of a PCSK9 nucleic acid that contains one or more SNPs will contain the appropriate base substitution, insertion, repeat or deletion such that the compound is fully complementary to the altered PCSK9 nucleic acid sequence.

A subgroup of these antisense compounds were selected for further characterization, based on the ability of the selected antisense compounds to inhibit PCSK9 expression selectively and effectively in cell culture assays, set forth in the Examples. The antisense compounds selected for further evaluation are listed in Table 1. The 5' and 3' boundaries of the PCSK9 target sequence are shown for each antisense compound, with reference to the nucleotide positions of SEQ ID NO: 1.

"Motif" in Table 1 refers to the use of chemically modified nucleosides at the 5' and 3' ends of the antisense compounds. In a "5-10-5" motif, for example, five chemical modified nucleosides at both the 5' and 3' ends flank ten unmodified nucleosides in the center of the antisense compound. As disclosed in more detail below, modified nucleosides may make the antisense compounds more resistant to nucleases, among other things, which generally improves the pharmacodynamic and pharmacokinetic properties of the antisense compounds when administered to an individual.

Table 1 further discloses the nucleobase sequence of the antisense compounds. In certain embodiments, an antisense compound has a nucleobase sequence that, when written in the 5' to 3' direction, comprises the reverse complement of the target segment of a target nucleic acid to which it is targeted.

TABLE 1

| Isis No. | 5' Target Site | 3' Target Site | Sequence 5'-3' | Motif | SEQ ID NO |
|---|---|---|---|---|---|
| 405881 | 1005 | 1024 | CACCCTTGGCCACGCCGGCA | 5-10-5 | 250 |
| 399819 | 2509 | 2528 | CCCACTCAAGGGCCAGGCCA | 5-10-5 | 65 |
| 395165 | 1004 | 1023 | ACCCTTGGCCACGCCGGCAT | 5-10-5 | 28 |
| 405879 | 1002 | 1021 | CCTTGGCCACGCCGGCATCC | 5-10-5 | 248 |
| 406008 | 602 | 621 | CTTGGTGAGGTATCCCCGGC | 5-10-5 | 188 |
| 405891 | 1567 | 1586 | TCCTCAGGGAACCAGGCCTC | 5-10-5 | 352 |
| 395186 | 2100 | 2119 | CTTTGCATTCCAGACCTGGG | 5-10-5 | 60 |
| 405988 | 1854 | 1873 | GGCAGCACCTGGCAATGGCG | 5-10-5 | 381 |
| 405994 | 1928 | 1947 | GCAGTGGACACGGGTCCCCA | 5-10-5 | 400 |
| 406023 | 787 | 806 | TGGTATTCATCCGCCCGGTA | 5-10-5 | 212 |

TABLE 1-continued

| Isis No. | 5' Target Site | 3' Target Site | Sequence 5'-3' | Motif | SEQ ID NO |
|---|---|---|---|---|---|
| 395187 | 2310 | 2329 | GGCAGCAGATGGCAACGGCT | 5-10-5 | 62 |
| 395185 | 1920 | 1939 | CACGGGTCCCCATGCTGGCC | 5-10-5 | 59 |
| 406033 | 967 | 986 | CCTGCCAGGTGGGTGCCATG | 5-10-5 | 237 |
| 405923 | 1295 | 1314 | GGCATTGGTGGCCCCAACTG | 5-10-5 | 288 |
| 399900 | 1569 | 1588 | GGTCCTCAGGGAACCAGGCC | 3-14-3 | 50 |
| 405995 | 1930 | 1949 | TGGCAGTGGACACGGGTCCC | 5-10-5 | 402 |
| 405991 | 1922 | 1941 | GACACGGGTCCCCATGCTGG | 5-10-5 | 394 |
| 406005 | 559 | 578 | CGGGCAGTGCGCTCTGACTG | 5-10-5 | 180 |
| 399793 | 417 | 436 | CCTCGGAACGCAAGGCTAGC | 5-10-5 | 8 |
| 395152 | 410 | 429 | ACGCAAGGCTAGCACCAGCT | 5-10-5 | 7 |

Antisense Compound Motifs

In certain embodiments, antisense compounds targeted to a PCSK9 nucleic acid have chemically modified subunits arranged in patterns, or motifs, to confer to the antisense compounds properties such as enhanced the inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may serve as a substrate for the cellular endonuclease RNase H, which cleaves the RNA strand of an RNA:DNA duplex.

Antisense compounds having a gapmer motif are considered chimeric antisense compounds. In a gapmer an internal position having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. The regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE, and 2'-O—CH$_3$, among others), and bicyclic sugar modified nucleosides (such bicyclic sugar modified nucleosides may include those having a 4'-(CH2)n-O-2' bridge, where n=1 or n=2). In general, each distinct region comprises uniform sugar moieties. The wing-gap-wing motif is frequently described as "X-Y-Z", where "X" represents the length of the 5' wing region, "Y" represents the length of the gap region, and "Z" represents the length of the 3' wing region.

In some embodiments, an antisense compound targeted to a PCSK9 nucleic acid has a gap-widened motif. In other embodiments, an antisense oligonucleotide targeted to a PCSK9 nucleic acid has a gap-widened motif.

The gap-widened oligonucleotides described herein may have various wing-gap-wing motifs selected from: 1-16-1, 2-15-1, 1-15-2, 1-14-3, 3-14-1, 2-14-2, 1-13-4, 4-13-1, 2-13-3, 3-13-2, 1-12-5, 5-12-1, 2-12-4, 4-12-2, 3-12-3, 1-11-6, 6-11-1, 2-11-5, 5-11-2, 3-11-4, 4-11-3, 1-17-1, 2-16-1, 1-16-2, 1-15-3, 3-15-1, 2-15-2, 1-14-4, 4-14-1, 2-14-3, 3-14-2, 1-13-5, 5-13-1, 2-13-4, 4-13-2, 3-13-3, 1-12-6, 6-12-1, 2-12-5, 5-12-2, 3-12-4, 4-12-3, 1-11-7, 7-11-1, 2-11-6, 6-11-2, 3-11-5, 5-11-3, 4-11-4, 1-18-1, 1-17-2, 2-17-1, 1-16-3, 1-16-3, 2-16-2, 1-15-4, 4-15-1, 2-15-3, 3-15-2, 1-14-5, 5-14-1, 2-14-4, 4-14-2, 3-14-3, 1-13-6, 6-13-1, 2-13-5, 5-13-2, 3-13-4, 4-13-3, 1-12-7, 7-12-1, 2-12-6, 6-12-2, 3-12-5, 5-12-3, 4-12-4, 1-11-8, 8-11-1, 2-11-7, 7-11-2, 3-11-6, 6-11-3, 4-11-5, 5-11-4, 1-18-1, 1-17-2, 2-17-1, 1-16-3, 3-16-1, 2-16-2, 1-15-4, 4-15-1, 2-15-3, 3-15-2, 1-14-5, 2-14-4, 4-14-2, 3-14-3, 1-13-6, 6-13-1, 2-13-5, 5-13-2, 3-13-4, 4-13-3, 1-12-7, 7-12-1, 2-12-6, 6-12-2, 3-12-5, 5-12-3, 4-12-4, 1-11-8, 8-11-1, 2-11-7, 7-11-2, 3-11-6, 6-11-3, 4-11-5, 5-11-4, 1-19-1, 1-18-2, 2-18-1, 1-17-3, 3-17-1, 2-17-2, 1-16-4, 4-16-1, 2-16-3, 3-16-2, 1-15-5, 2-15-4, 4-15-2, 3-15-3, 1-14-6, 6-14-1, 2-14-5, 5-14-2, 3-14-4, 4-14-3, 1-13-7, 7-13-1, 2-13-6, 6-13-2, 3-13-5, 5-13-3, 4-13-4, 1-12-8, 8-12-1, 2-12-7, 7-12-2, 3-12-6, 6-12-3, 4-12-5, 5-12-4, 2-11-8, 8-11-2, 3-11-7, 7-11-3, 4-11-6, 6-11-4, 5-11-5, 1-20-1, 1-19-2, 2-19-1, 1-18-3, 3-18-1, 2-18-2, 1-17-4, 4-17-1, 2-17-3, 3-17-2, 1-16-5, 2-16-4, 4-16-2, 3-16-3, 1-15-6, 6-15-1, 2-15-5, 5-15-2, 3-15-4, 4-15-3, 1-14-7, 7-14-1, 2-14-6, 6-14-2, 3-14-5, 5-14-3, 4-14-4, 1-13-8, 8-13-1, 2-13-7, 7-13-2, 3-13-6, 6-13-3, 4-13-5, 5-13-4, 2-12-8, 8-12-2, 3-12-7, 7-12-3, 4-12-6, 6-12-4, 5-12-5, 3-11-8, 8-11-3, 4-11-7, 7-11-4, 5-11-6, 6-11-5, 1-21-1, 1-20-2, 2-20-1, 1-20-3, 3-19-1, 2-19-2, 1-18-4, 4-18-1, 2-18-3, 3-18-2, 1-17-5, 2-17-4, 4-17-2, 3-17-3, 1-16-6, 6-16-1, 2-16-5, 5-16-2, 3-16-4, 4-16-3, 1-15-7, 7-15-1, 2-15-6, 6-15-2, 3-15-5, 5-15-3, 4-15-4, 1-14-8, 8-14-1, 2-14-7, 7-14-2, 3-14-6, 6-14-3, 4-14-5, 5-14-4, 2-13-8, 8-13-2, 3-13-7, 7-13-3, 4-13-6, 6-13-4, 5-13-5, 1-12-10, 10-12-1, 2-12-9, 9-12-2, 3-12-8, 8-12-3, 4-12-7, 7-12-4, 5-12-6, 6-12-5, 4-11-8, 8-11-4, 5-11-7, 7-11-5, 6-11-6, 1-22-1, 1-21-2, 2-21-1, 1-21-3, 3-20-1, 2-20-2, 1-19-4, 4-19-1, 2-19-3, 3-19-2, 1-18-5, 2-18-4, 4-18-2, 3-18-3, 1-17-6, 6-17-1, 2-17-5, 5-17-2, 3-17-4, 4-17-3, 1-16-7, 7-16-1, 2-16-6, 6-16-2, 3-16-5, 5-16-3, 4-16-4, 1-15-8, 8-15-1, 2-15-7, 7-15-2, 3-15-6, 6-15-3, 4-15-5, 5-15-4, 2-14-8, 8-14-2, 3-14-7, 7-14-3, 4-14-6, 6-14-4, 5-14-5, 3-13-8, 8-13-3, 4-13-7, 7-13-4, 5-13-6, 6-13-5, 4-12-8, 8-12-4, 5-12-7, 7-12-5, 6-12-6, 5-11-8, 8-11-5, 6-11-7, or 7-11-6. In certain preferred embodiments, a gap-widened motif includes, but is not limited to, 2-13-5, 3-14-3, 3-14-4 gapmer motif.

In one embodiment, a gap-widened antisense oligonucleotide targeted to a PCSK9 nucleic acid has a gap segment of fourteen 2'-deoxyribonucleotides positioned between wing segments of three chemically modified nucleosides. In one embodiment, the chemical modification comprises a 2'-sugar modification. In another embodiment, the chemical modification comprises a 2'-MOE sugar modification.

In one embodiment, antisense compounds targeted to a PCSK9 nucleic acid possess a 5-10-5 gapmer motif.

Target Nucleic Acids, Target Regions and Nucleotide Sequences

Nucleotide sequences that encode PCSK9 include, without limitation, the following: GENBANK® Accession No. NM_174936.2, first deposited with GENBANK® on Jun. 1, 2003, and incorporated herein as SEQ ID NO: 1; nucleotides 25475000 to 25504000 of GENBANK® Accession No. NT_032977.8, first deposited with GENBANK® on Feb. 26, 2006, and incorporated herein as SEQ ID NO: 2; and GENBANK® Accession No. AK124635.1, first deposited with GENBANK® on Sep. 8, 2003, and incorporated herein as SEQ ID NO: 3.

It is noted that some portions of these nucleotide sequences share identical sequence. For example, portions of SEQ ID NO: 1 are identical to portions of SEQ ID NO: 2; portions of SEQ ID NO: 1 are identical to portions of SEQ ID NO: 3; and portions of SEQ ID NO: 2 are identical to portions of SEQ ID NO: 3. Accordingly, antisense compounds targeted to SEQ ID NO: 1 may also target SEQ ID NO: 2 and/or SEQ ID NO: 3; antisense compounds targeted to SEQ ID NO: 2 may also target SEQ ID NO: 1 and/or SEQ ID NO: 3; and antisense compounds targeted to SEQ ID NO: 3 may also target SEQ ID NO: 1 and/or SEQ ID NO: 2. Examples of such antisense compounds are shown in the following tables.

In certain embodiments, antisense compounds target a PCSK9 nucleic acid having the sequence of GENBANK® Accession No. NM_174936.2, first deposited with GENBANK® on Jun. 1, 2003, and incorporated herein as SEQ ID NO: 1. In certain such embodiments, an antisense oligonucleotide targets SEQ ID NO: 1. In certain such embodiments, an antisense oligonucleotide that is targeted to SEQ ID NO: 1 is at least 90% complementary to SEQ ID NO: 1. In certain such embodiments, an antisense oligonucleotide that is targeted to SEQ ID NO: 1 is at least 95% complementary to SEQ ID NO: 1. In certain such embodiments, an antisense oligonucleotide that is targeted to SEQ ID NO: 1 is 100% complementary to SEQ ID NO: 1. In certain embodiments, an antisense oligonucleotide targeted to SEQ ID NO: 1 comprises a nucleotide sequence selected from the nucleotide sequences set forth in Table 2.

TABLE 2

Nucleotide sequences targeted to NM_174936.2 (SEQ ID NO: 1)

| SEQ ID NO | 5' Target Site on SEQ ID NO: 1 | 3' Target Site on SEQ ID NO: 1 | Sequence (5'-3') |
| --- | --- | --- | --- |
| 4 | 135 | 154 | GCGCGGAATCCTGGCTGGGA |
| 5 | 242 | 261 | GAGGAGACCTAGAGGCCGTG |
| 159 | 294 | 313 | GCCTGGAGCTGACGGTGCCC |
| 160 | 298 | 317 | GACCGCCTGGAGCTGACGGT |
| 6 | 300 | 319 | AGGACCGCCTGGAGCTGACG |
| 162 | 406 | 425 | AAGGCTAGCACCAGCTCCTC |
| 163 | 407 | 426 | CAAGGCTAGCACCAGCTCCT |
| 164 | 408 | 427 | GCAAGGCTAGCACCAGCTCC |
| 165 | 409 | 428 | CGCAAGGCTAGCACCAGCTC |
| 7 | 410 | 429 | ACGCAAGGCTAGCACCAGCT |
| 166 | 411 | 430 | AACGCAAGGCTAGCACCAGC |
| 167 | 412 | 431 | GAACGCAAGGCTAGCACCAG |
| 168 | 413 | 432 | GGAACGCAAGGCTAGCACCA |
| 169 | 414 | 433 | CGGAACGCAAGGCTAGCACC |
| 8 | 417 | 436 | CCTCGGAACGCAAGGCTAGC |
| 170 | 421 | 440 | TCCTCCTCGGAACGCAAGGC |
| 171 | 446 | 465 | GTGCTCGGGTGCTTCGGCCA |
| 172 | 466 | 485 | TGGAAGGTGGCTGTGGTTCC |
| 9 | 480 | 499 | CCTTGGCGCAGCGGTGGAAG |
| 173 | 482 | 501 | ATCCTTGGCGCAGCGGTGGA |
| 174 | 484 | 503 | GGATCCTTGGCGCAGCGGTG |
| 175 | 488 | 507 | CCACGGATCCTTGGCGCAGC |
| 176 | 507 | 526 | CGTAGGTGCCAGGCAACCTC |
| 177 | 545 | 564 | TGACTGCGAGAGGTGGGTCT |
| 178 | 555 | 574 | CAGTGCGCTCTGACTGCGAG |
| 179 | 557 | 576 | GGCAGTGCGCTCTGACTGCG |
| 180 | 559 | 578 | CGGGCAGTGCGCTCTGACTG |
| 10 | 561 | 580 | GGCGGGCAGTGCGCTCTGAC |
| 181 | 562 | 581 | CGGCGGGCAGTGCGCTCTGA |
| 182 | 591 | 610 | ATCCCCGGCGGGCAGCCTGG |
| 183 | 595 | 614 | AGGTATCCCCGGCGGGCAGC |
| 184 | 597 | 616 | TGAGGTATCCCCGGCGGGCA |
| 185 | 598 | 617 | GTGAGGTATCCCCGGCGGGC |
| 186 | 599 | 618 | GGTGAGGTATCCCCGGCGGG |
| 11 | 600 | 619 | TGGTGAGGTATCCCCGGCGG |
| 187 | 601 | 620 | TTGGTGAGGTATCCCCGGCG |
| 188 | 602 | 621 | CTTGGTGAGGTATCCCCGGC |
| 189 | 603 | 622 | TCTTGGTGAGGTATCCCCGG |
| 190 | 604 | 623 | ATCTTGGTGAGGTATCCCCG |
| 191 | 605 | 624 | GATCTTGGTGAGGTATCCCC |
| 12 | 606 | 625 | GGATCTTGGTGAGGTATCCC |
| 192 | 607 | 626 | AGGATCTTGGTGAGGTATCC |
| 193 | 609 | 628 | GCAGGATCTTGGTGAGGTAT |
| 194 | 611 | 630 | ATGCAGGATCTTGGTGAGGT |
| 195 | 613 | 632 | ACATGCAGGATCTTGGTGAG |
| 13 | 615 | 634 | AGACATGCAGGATCTTGGTG |
| 196 | 617 | 636 | GAAGACATGCAGGATCTTGG |
| 14 | 620 | 639 | ATGGAAGACATGCAGGATCT |
| 197 | 628 | 647 | AGAAGGCCATGGAAGACATG |
| 198 | 638 | 657 | GAAGCCAGGAAGAAGGCCAT |
| 15 | 646 | 665 | TTCACCAGGAAGCCAGGAAG |
| 199 | 648 | 667 | TCTTCACCAGGAAGCCAGGA |

TABLE 2-continued

Nucleotide sequences targeted to NM_174936.2 (SEQ ID NO: 1)

| SEQ ID NO | 5' Target Site on SEQ ID NO: 1 | 3' Target Site on SEQ ID NO: 1 | Sequence (5'-3') |
|---|---|---|---|
| 16 | 651 | 670 | TCATCTTCACCAGGAAGCCA |
| 200 | 653 | 672 | ACTCATCTTCACCAGGAAGC |
| 201 | 655 | 674 | CCACTCATCTTCACCAGGAA |
| 202 | 657 | 676 | CGCCACTCATCTTCACCAGG |
| 203 | 659 | 678 | GTCGCCACTCATCTTCACCA |
| 204 | 661 | 680 | AGGTCGCCACTCATCTTCAC |
| 205 | 663 | 682 | GCAGGTCGCCACTCATCTTC |
| 206 | 665 | 684 | CAGCAGGTCGCCACTCATCT |
| 207 | 667 | 686 | TCCAGCAGGTCGCCACTCAT |
| 208 | 685 | 704 | GGCAACTTCAAGGCCAGCTC |
| 17 | 705 | 724 | CCTCGATGTAGTCGACATGG |
| 209 | 724 | 743 | GCAAAGACAGAGGAGTCCTC |
| 210 | 782 | 801 | TTCATCCGCCCGGTACCGTG |
| 211 | 784 | 803 | TATTCATCCGCCCGGTACCG |
| 18 | 785 | 804 | GTATTCATCCGCCCGGTACC |
| 212 | 787 | 806 | TGGTATTCATCCGCCCGGTA |
| 213 | 789 | 808 | GCTGGTATTCATCCGCCCGG |
| 214 | 791 | 810 | GGGCTGGTATTCATCCGCCC |
| 215 | 821 | 840 | ATACACCTCCACCAGGCTGC |
| 216 | 832 | 851 | GTGTCTAGGAGATACACCTC |
| 19 | 835 | 854 | CTGGTGTCTAGGAGATACAC |
| 217 | 837 | 856 | TGCTGGTGTCTAGGAGATAC |
| 20 | 840 | 859 | GTATGCTGGTGTCTAGGAGA |
| 21 | 860 | 879 | GATTTCCCGGTGGTCACTCT |
| 218 | 862 | 881 | TCGATTTCCCGGTGGTCACT |
| 219 | 863 | 882 | CTCGATTTCCCGGTGGTCAC |
| 220 | 864 | 883 | CCTCGATTTCCCGGTGGTCA |
| 221 | 865 | 884 | CCCTCGATTTCCCGGTGGTC |
| 22 | 866 | 885 | GCCCTCGATTTCCCGGTGGT |
| 222 | 867 | 886 | TGCCCTCGATTTCCCGGTGG |
| 223 | 868 | 887 | CTGCCCTCGATTTCCCGGTG |
| 224 | 869 | 888 | CCTGCCCTCGATTTCCCGGT |
| 225 | 870 | 889 | CCCTGCCCTCGATTTCCCGG |
| 226 | 874 | 893 | ATGACCCTGCCCTCGATTTC |
| 227 | 876 | 895 | CCATGACCCTGCCCTCGATT |
| 228 | 878 | 897 | GACCATGACCCTGCCCTCGA |
| 23 | 880 | 899 | GTGACCATGACCCTGCCCTC |
| 229 | 882 | 901 | CGGTGACCATGACCCTGCCC |
| 230 | 884 | 903 | GTCGGTGACCATGACCCTGC |
| 231 | 886 | 905 | AAGTCGGTGACCATGACCCT |
| 232 | 888 | 907 | CGAAGTCGGTGACCATGACC |
| 24 | 890 | 909 | CTCGAAGTCGGTGACCATGA |
| 233 | 898 | 917 | GGCACATTCTCGAAGTCGGT |
| 25 | 923 | 942 | GTGGAAGCGGGTCCCGTCCT |
| 234 | 933 | 952 | TGGCCTGTCTGTGGAAGCGG |
| 235 | 960 | 979 | GGTGGGTGCCATGACTGTCA |
| 236 | 963 | 982 | CCAGGTGGGTGCCATGACTG |
| 237 | 967 | 986 | CCTGCCAGGTGGGTGCCATG |
| 26 | 970 | 989 | ACCCCTGCCAGGTGGGTGCC |
| 238 | 972 | 991 | CCACCCCTGCCAGGTGGGTG |
| 27 | 975 | 994 | TGACCACCCCTGCCAGGTGG |
| 239 | 977 | 996 | GCTGACCACCCCTGCCAGGT |
| 240 | 985 | 1004 | TCCCGGCCGCTGACCACCCC |
| 241 | 989 | 1008 | GGCATCCCGGCCGCTGACCA |
| 242 | 992 | 1011 | GCCGGCATCCCGGCCGCTGA |
| 243 | 997 | 1016 | GCCACGCCGGCATCCCGGCC |
| 244 | 998 | 1017 | GGCCACGCCGGCATCCCGGC |
| 245 | 999 | 1018 | TGGCCACGCCGGCATCCCGG |
| 246 | 1000 | 1019 | TTGGCCACGCCGGCATCCCG |
| 247 | 1001 | 1020 | CTTGGCCACGCCGGCATCCC |
| 248 | 1002 | 1021 | CCTTGGCCACGCCGGCATCC |
| 249 | 1003 | 1022 | CCCTTGGCCACGCCGGCATC |
| 28 | 1004 | 1023 | ACCCTTGGCCACGCCGGCAT |
| 447 | 1004 | 1023 | ACCCTTGGTCACGCGGCAT |
| 250 | 1005 | 1024 | CACCCTTGGCCACGCCGGCA |
| 251 | 1006 | 1025 | GCACCCTTGGCCACGCCGGC |
| 252 | 1007 | 1026 | GGCACCCTTGGCCACGCCGG |
| 253 | 1008 | 1027 | TGGCACCCTTGGCCACGCCG |
| 254 | 1009 | 1028 | CTGGCACCCTTGGCCACGCC |
| 255 | 1010 | 1029 | GCTGGCACCCTTGGCCACGC |
| 256 | 1015 | 1034 | CGCATGCTGGCACCCTTGGC |
| 257 | 1036 | 1055 | CAGTTGAGCACGCGCAGGCT |

TABLE 2-continued

Nucleotide sequences targeted to NM_174936.2 (SEQ ID NO: 1)

| SEQ ID NO | 5' Target Site on SEQ ID NO: 1 | 3' Target Site on SEQ ID NO: 1 | Sequence (5'-3') |
| --- | --- | --- | --- |
| 258 | 1038 | 1057 | GGCAGTTGAGCACGCGCAGG |
| 29 | 1040 | 1059 | TTGGCAGTTGAGCACGCGCA |
| 259 | 1042 | 1061 | CCTTGGCAGTTGAGCACGCG |
| 30 | 1045 | 1064 | TTCCCTTGGCAGTTGAGCAC |
| 260 | 1047 | 1066 | CCTTCCCTTGGCAGTTGAGC |
| 261 | 1051 | 1070 | GTGCCCTTCCCTTGGCAGTT |
| 262 | 1053 | 1072 | CCGTGCCCTTCCCTTGGCAG |
| 263 | 1064 | 1083 | GGTGCCGCTAACCGTGCCCT |
| 264 | 1076 | 1095 | CAGGCCTATGAGGGTGCCGC |
| 31 | 1077 | 1096 | CCAGGCCTATGAGGGTGCCG |
| 458 | 1079 | 1092 | GCCTATGAGGGTGC |
| 459 | 1084 | 1097 | TCCAGGCCTATGAG |
| 265 | 1088 | 1107 | CCGAATAAACTCCAGGCCTA |
| 266 | 1096 | 1115 | TGGCTTTTCCGAATAAACTC |
| 32 | 1098 | 1117 | GCTGGCTTTTCCGAATAAAC |
| 267 | 1100 | 1119 | CAGCTGGCTTTTCCGAATAA |
| 268 | 1102 | 1121 | ACCAGCTGGCTTTTCCGAAT |
| 269 | 1104 | 1123 | GGACCAGCTGGCTTTTCCGA |
| 270 | 1108 | 1127 | GGCTGGACCAGCTGGCTTTT |
| 271 | 1119 | 1138 | GTGGCCCCACAGGCTGGACC |
| 272 | 1132 | 1151 | AGCAGCACCACCAGTGGCCC |
| 273 | 1154 | 1173 | GCTGTACCCACCCGCCAGGG |
| 274 | 1200 | 1219 | CGACCCCAGCCCTCGCCAGG |
| 33 | 1210 | 1229 | GTGACCAGCACGACCCCAGC |
| 275 | 1212 | 1231 | CGGTGACCAGCACGACCCCA |
| 276 | 1214 | 1233 | AGCGGTGACCAGCACGACCC |
| 277 | 1216 | 1235 | GCAGCGGTGACCAGCACGAC |
| 278 | 1218 | 1237 | CGGCAGCGGTGACCAGCACG |
| 279 | 1219 | 1238 | CCGGCAGCGGTGACCAGCAC |
| 280 | 1222 | 1241 | TTGCCGGCAGCGGTGACCAG |
| 281 | 1224 | 1243 | AGTTGCCGGCAGCGGTGACC |
| 282 | 1226 | 1245 | GAAGTTGCCGGCAGCGGTGA |
| 283 | 1228 | 1247 | CGGAAGTTGCCGGCAGCGGT |
| 284 | 1230 | 1249 | CCCGGAAGTTGCCGGCAGCG |
| 285 | 1232 | 1251 | GTCCCGGAAGTTGCCGGCAG |
| 286 | 1273 | 1292 | ATGACCTCGGGAGCTGAGGC |
| 287 | 1283 | 1302 | CCCAACTGTGATGACCTCGG |
| 288 | 1295 | 1314 | GGCATTGGTGGCCCCAACTG |
| 149 | 1297 | 1316 | TGGGCATTGGTGGCCCCAAC |
| 289 | 1305 | 1324 | GCTGGTCTTGGGCATTGGTG |
| 290 | 1318 | 1337 | CCCAGGGTCACCGGCTGGTC |
| 291 | 1320 | 1339 | TCCCCAGGGTCACCGGCTGG |
| 292 | 1322 | 1341 | AGTCCCCAGGGTCACCGGCT |
| 293 | 1324 | 1343 | AAAGTCCCCAGGGTCACCGG |
| 34 | 1326 | 1345 | CCAAAGTCCCCAGGGTCACC |
| 294 | 1328 | 1347 | CCCCAAAGTCCCCAGGGTCA |
| 128 | 1330 | 1349 | GTCCCCAAAGTCCCCAGGGT |
| 295 | 1333 | 1352 | TTGGTCCCCAAAGTCCCCAG |
| 35 | 1335 | 1354 | AGTTGGTCCCCAAAGTCCCC |
| 296 | 1337 | 1356 | AAAGTTGGTCCCCAAAGTCC |
| 36 | 1340 | 1359 | GCCAAAGTTGGTCCCCAAAG |
| 297 | 1342 | 1361 | CGGCCAAAGTTGGTCCCCAA |
| 298 | 1344 | 1363 | AGCGGCCAAAGTTGGTCCCC |
| 299 | 1346 | 1365 | ACAGCGGCCAAAGTTGGTCC |
| 300 | 1348 | 1367 | ACACAGCGGCCAAAGTTGGT |
| 301 | 1350 | 1369 | CCACACAGCGGCCAAAGTTG |
| 37 | 1352 | 1371 | GTCCACACAGCGGCCAAAGT |
| 302 | 1354 | 1373 | AGGTCCACACAGCGGCCAAA |
| 303 | 1356 | 1375 | AGAGGTCCACACAGCGGCCA |
| 304 | 1358 | 1377 | AAAGAGGTCCACACAGCGGC |
| 38 | 1361 | 1380 | GGCAAAGAGGTCCACACAGC |
| 305 | 1380 | 1399 | CAATGATGTCCTCCCCTGGG |
| 306 | 1387 | 1406 | GAGGCACCAATGATGTCCTC |
| 39 | 1389 | 1408 | TGGAGGCACCAATGATGTCC |
| 307 | 1391 | 1410 | GCTGGAGGCACCAATGATGT |
| 308 | 1393 | 1412 | TCGCTGGAGGCACCAATGAT |
| 309 | 1395 | 1414 | AGTCGCTGGAGGCACCAATG |
| 310 | 1397 | 1416 | GCAGTCGCTGGAGGCACCAA |
| 40 | 1400 | 1419 | GCTGCAGTCGCTGGAGGCAC |
| 311 | 1402 | 1421 | GTGCTGCAGTCGCTGGAGGC |
| 312 | 1404 | 1423 | AGGTGCTGCAGTCGCTGGAG |
| 313 | 1406 | 1425 | GCAGGTGCTGCAGTCGCTGG |

TABLE 2-continued

Nucleotide sequences targeted to NM_174936.2 (SEQ ID NO: 1)

| SEQ ID NO | 5' Target Site on SEQ ID NO: 1 | 3' Target Site on SEQ ID NO: 1 | Sequence (5'-3') |
|---|---|---|---|
| 314 | 1407 | 1426 | AGCAGGTGCTGCAGTCGCTG |
| 315 | 1409 | 1428 | AAAGCAGGTGCTGCAGTCGC |
| 41 | 1411 | 1430 | ACAAAGCAGGTGCTGCAGTC |
| 316 | 1413 | 1432 | ACACAAAGCAGGTGCTGCAG |
| 317 | 1415 | 1434 | TGACACAAAGCAGGTGCTGC |
| 318 | 1425 | 1444 | TCCCACTCTGTGACACAAAG |
| 101 | 1465 | 1484 | ATGGCTGCAATGCCAGCCAC |
| 319 | 1467 | 1486 | TCATGGCTGCAATGCCAGCC |
| 42 | 1470 | 1489 | GCATCATGGCTGCAATGCCA |
| 320 | 1472 | 1491 | CAGCATCATGGCTGCAATGC |
| 321 | 1474 | 1493 | GACAGCATCATGGCTGCAAT |
| 322 | 1476 | 1495 | CAGACAGCATCATGGCTGCA |
| 43 | 1478 | 1497 | GGCAGACAGCATCATGGCTG |
| 323 | 1480 | 1499 | TCGGCAGACAGCATCATGGC |
| 324 | 1482 | 1501 | GCTCGGCAGACAGCATCATG |
| 325 | 1484 | 1503 | CGGCTCGGCAGACAGCATCA |
| 326 | 1486 | 1505 | TCCGGCTCGGCAGACAGCAT |
| 327 | 1500 | 1519 | CGGCCAGGGTGAGCTCCGGC |
| 328 | 1513 | 1532 | CTCTGCCTCAACTCGGCCAG |
| 329 | 1515 | 1534 | GTCTCTGCCTCAACTCGGCC |
| 330 | 1517 | 1536 | CAGTCTCTGCCTCAACTCGG |
| 331 | 1519 | 1538 | ATCAGTCTCTGCCTCAACTC |
| 332 | 1521 | 1540 | GGATCAGTCTCTGCCTCAAC |
| 333 | 1523 | 1542 | GTGGATCAGTCTCTGCCTCA |
| 334 | 1525 | 1544 | AAGTGGATCAGTCTCTGCCT |
| 44 | 1526 | 1545 | GAAGTGGATCAGTCTCTGCC |
| 335 | 1528 | 1547 | GAGAAGTGGATCAGTCTCTG |
| 336 | 1530 | 1549 | CAGAGAAGTGGATCAGTCTC |
| 337 | 1532 | 1551 | GGCAGAGAAGTGGATCAGTC |
| 45 | 1534 | 1553 | TTGGCAGAGAAGTGGATCAG |
| 338 | 1536 | 1555 | CTTTGGCAGAGAAGTGGATC |
| 46 | 1539 | 1558 | CATCTTTGGCAGAGAAGTGG |
| 339 | 1541 | 1560 | GACATCTTTGGCAGAGAAGT |
| 340 | 1543 | 1562 | ATGACATCTTTGGCAGAGAA |
| 47 | 1545 | 1564 | TGATGACATCTTTGGCAGAG |
| 341 | 1547 | 1566 | ATTGATGACATCTTTGGCAG |
| 342 | 1549 | 1568 | TCATTGATGACATCTTTGGC |
| 48 | 1552 | 1571 | GCCTCATTGATGACATCTTT |
| 343 | 1554 | 1573 | AGGCCTCATTGATGACATCT |
| 344 | 1556 | 1575 | CCAGGCCTCATTGATGACAT |
| 345 | 1558 | 1577 | AACCAGGCCTCATTGATGAC |
| 346 | 1560 | 1579 | GGAACCAGGCCTCATTGATG |
| 347 | 1561 | 1580 | GGGAACCAGGCCTCATTGAT |
| 348 | 1562 | 1581 | AGGGAACCAGGCCTCATTGA |
| 349 | 1563 | 1582 | CAGGGAACCAGGCCTCATTG |
| 49 | 1564 | 1583 | TCAGGGAACCAGGCCTCATT |
| 49 | 1564 | 1583 | TCAGGGAACCAGGCCTCATT |
| 350 | 1565 | 1584 | CTCAGGGAACCAGGCCTCAT |
| 351 | 1566 | 1585 | CCTCAGGGAACCAGGCCTCA |
| 352 | 1567 | 1586 | TCCTCAGGGAACCAGGCCTC |
| 353 | 1568 | 1587 | GTCCTCAGGGAACCAGGCCT |
| 50 | 1569 | 1588 | GGTCCTCAGGGAACCAGGCC |
| 354 | 1570 | 1589 | TGGTCCTCAGGGAACCAGGC |
| 355 | 1571 | 1590 | CTGGTCCTCAGGGAACCAGG |
| 356 | 1572 | 1591 | GCTGGTCCTCAGGGAACCAG |
| 357 | 1573 | 1592 | CGCTGGTCCTCAGGGAACCA |
| 87 | 1576 | 1595 | ACCCGCTGGTCCTCAGGGAA |
| 358 | 1578 | 1597 | GTACCCGCTGGTCCTCAGGG |
| 359 | 1580 | 1599 | CAGTACCCGCTGGTCCTCAG |
| 51 | 1583 | 1602 | GGTCAGTACCCGCTGGTCCT |
| 119 | 1605 | 1624 | GCAGGGCGGCCACCAGGTTG |
| 360 | 1628 | 1647 | ACCTGCCCCATGGGTGCTGG |
| 52 | 1640 | 1659 | AAACAGCTGCCAACCTGCCC |
| 361 | 1642 | 1661 | CAAAACAGCTGCCAACCTGC |
| 53 | 1645 | 1664 | CTGCAAAACAGCTGCCAACC |
| 362 | 1647 | 1666 | TCCTGCAAAACAGCTGCCAA |
| 363 | 1649 | 1668 | AGTCCTGCAAAACAGCTGCC |
| 364 | 1660 | 1679 | GCTGACCATACAGTCCTGCA |
| 365 | 1672 | 1691 | GGCCCGAGTGTGCTGACCA |
| 54 | 1675 | 1694 | GTAGGCCCGAGTGTGCTGA |
| 366 | 1677 | 1696 | GTGTAGGCCCGAGTGTGCT |
| 367 | 1679 | 1698 | CCGTGTAGGCCCGAGTGTG |

TABLE 2-continued

Nucleotide sequences targeted to NM_174936.2 (SEQ ID NO: 1)

| SEQ ID NO | 5' Target Site on SEQ ID NO: 1 | 3' Target Site on SEQ ID NO: 1 | Sequence (5'-3') |
| --- | --- | --- | --- |
| 368 | 1681 | 1700 | ATCCGTGTAGGCCCCGAGTG |
| 369 | 1683 | 1702 | CCATCCGTGTAGGCCCCGAG |
| 370 | 1685 | 1704 | GGCCATCCGTGTAGGCCCCG |
| 371 | 1687 | 1706 | GTGGCCATCCGTGTAGGCCC |
| 372 | 1735 | 1754 | CTGGAGCAGCTCAGCAGCTC |
| 460 | 1735 | 1748 | CAGCTCAGCAGCTC |
| 373 | 1737 | 1756 | AACTGGAGCAGCTCAGCAGC |
| 55 | 1740 | 1759 | AGAAACTGGAGCAGCTCAGC |
| 374 | 1742 | 1761 | GGAGAAACTGGAGCAGCTCA |
| 375 | 1744 | 1763 | CTGGAGAAACTGGAGCAGCT |
| 56 | 1746 | 1765 | TCCTGGAGAAACTGGAGCAG |
| 57 | 1812 | 1831 | CGTTGTGGGCCCGGCAGACC |
| 376 | 1849 | 1868 | CACCTGGCAATGGCGTAGAC |
| 377 | 1850 | 1869 | GCACCTGGCAATGGCGTAGA |
| 378 | 1851 | 1870 | AGCACCTGGCAATGGCGTAG |
| 379 | 1852 | 1871 | CAGCACCTGGCAATGGCGTA |
| 380 | 1853 | 1872 | GCAGCACCTGGCAATGGCGT |
| 381 | 1854 | 1873 | GGCAGCACCTGGCAATGGCG |
| 382 | 1855 | 1874 | AGGCAGCACCTGGCAATGGC |
| 383 | 1856 | 1875 | CAGGCAGCACCTGGCAATGG |
| 384 | 1857 | 1876 | GCAGGCAGCACCTGGCAATG |
| 58 | 1858 | 1877 | AGCAGGCAGCACCTGGCAAT |
| 385 | 1859 | 1878 | TAGCAGGCAGCACCTGGCAA |
| 386 | 1860 | 1879 | GTAGCAGGCAGCACCTGGCA |
| 387 | 1905 | 1924 | TGGCCTCAGCTGGTGGAGCT |
| 388 | 1915 | 1934 | GTCCCCATGCTGGCCTCAGC |
| 389 | 1916 | 1935 | GGTCCCCATGCTGGCCTCAG |
| 390 | 1917 | 1936 | GGGTCCCCATGCTGGCCTCA |
| 391 | 1918 | 1937 | CGGGTCCCCATGCTGGCCTC |
| 392 | 1919 | 1938 | ACGGGTCCCCATGCTGGCCT |
| 59 | 1920 | 1939 | CACGGGTCCCCATGCTGGCC |
| 59 | 1920 | 1939 | CACGGGTCCCCATGCTGGCC |
| 393 | 1921 | 1940 | ACACGGGTCCCCATGCTGGC |
| 394 | 1922 | 1941 | GACACGGGTCCCCATGCTGG |
| 395 | 1923 | 1942 | GGACACGGGTCCCCATGCTG |
| 396 | 1924 | 1943 | TGGACACGGGTCCCCATGCT |
| 397 | 1925 | 1944 | GTGGACACGGGTCCCCATGC |
| 398 | 1926 | 1945 | AGTGGACACGGGTCCCCATG |
| 399 | 1927 | 1946 | CAGTGGACACGGGTCCCCAT |
| 400 | 1928 | 1947 | GCAGTGGACACGGGTCCCCA |
| 401 | 1929 | 1948 | GGCAGTGGACACGGGTCCCC |
| 402 | 1930 | 1949 | TGGCAGTGGACACGGGTCCC |
| 403 | 1931 | 1950 | GTGGCAGTGGACACGGGTCC |
| 404 | 1932 | 1951 | GGTGGCAGTGGACACGGGTC |
| 405 | 1933 | 1952 | TGGTGGCAGTGGACACGGGT |
| 406 | 1936 | 1955 | TGTTGGTGGCAGTGGACACG |
| 407 | 1962 | 1981 | AGCTGCAGCCTGTGAGGACG |
| 408 | 1990 | 2009 | GTGCCAAGGTCCTCCACCTC |
| 409 | 2010 | 2029 | TCAGCACAGGCGGCTTGTGG |
| 410 | 2040 | 2059 | CCACGCACTGGTTGGGCTGA |
| 60 | 2100 | 2119 | CTTTGCATTCCAGACCTGGG |
| 411 | 2101 | 2120 | ACTTTGCATTCCAGACCTGG |
| 412 | 2102 | 2121 | GACTTTGCATTCCAGACCTG |
| 413 | 2103 | 2122 | TGACTTTGCATTCCAGACCT |
| 414 | 2104 | 2123 | TTGACTTTGCATTCCAGACC |
| 61 | 2105 | 2124 | CTTGACTTTGCATTCCAGAC |
| 415 | 2107 | 2126 | TCCTTGACTTTGCATTCCAG |
| 416 | 2120 | 2139 | CGGGATTCCATGCTCCTTGA |
| 417 | 2150 | 2169 | GCAGGCCACGGTCACCTGCT |
| 418 | 2187 | 2206 | GGAGGGCACTGCAGCCAGTC |
| 419 | 2305 | 2324 | CAGATGGCAACGGCTGTCAC |
| 420 | 2306 | 2325 | GCAGATGGCAACGGCTGTCA |
| 421 | 2307 | 2326 | AGCAGATGGCAACGGCTGTC |
| 422 | 2308 | 2327 | CAGCAGATGGCAACGGCTGT |
| 423 | 2309 | 2328 | GCAGCAGATGGCAACGGCTG |
| 62 | 2310 | 2329 | GGCAGCAGATGGCAACGGCT |
| 424 | 2311 | 2330 | CGGCAGCAGATGGCAACGGC |
| 425 | 2312 | 2331 | CCGGCAGCAGATGGCAACGG |
| 426 | 2313 | 2332 | TCCGGCAGCAGATGGCAACG |
| 427 | 2314 | 2333 | CTCCGGCAGCAGATGGCAAC |
| 428 | 2315 | 2334 | GCTCCGGCAGCAGATGGCAA |
| 429 | 2325 | 2344 | CCAGGTGCCGGCTCCGGCAG |

TABLE 2-continued

Nucleotide sequences targeted to NM_174936.2 (SEQ ID NO: 1)

| SEQ ID NO | 5' Target Site on SEQ ID NO: 1 | 3' Target Site on SEQ ID NO: 1 | Sequence (5'-3') |
|---|---|---|---|
| 430 | 2335 | 2354 | GAGGCCTGCGCCAGGTGCCG |
| 154 | 2410 | 2429 | TTTTAAAGCTCAGCCCCAGC |
| 63 | 2415 | 2434 | AACCATTTTAAAGCTCAGCC |
| 64 | 2504 | 2523 | TCAAGGGCCAGGCCAGCAGC |
| 65 | 2509 | 2528 | CCCACTCAAGGGCCAGGCCA |
| 122 | 2582 | 2601 | GGAGGGAGCTTCCTGGCACC |
| 66 | 2597 | 2616 | ATGCCCCACAGTGAGGGAGG |
| 67 | 2606 | 2625 | AATGGTGAAATGCCCCACAG |
| 153 | 2649 | 2668 | TTGGGAGCAGCTGGCAGCAC |
| 68 | 2750 | 2769 | CATGGGAAGAATCCTGCCTC |
| 431 | 2828 | 2847 | ATGAGGGCCATCAGCACCTT |
| 432 | 2829 | 2848 | GATGAGGGCCATCAGCACCT |
| 433 | 2830 | 2849 | AGATGAGGGCCATCAGCACC |
| 434 | 2831 | 2850 | GAGATGAGGGCCATCAGCAC |
| 69 | 2832 | 2851 | GGAGATGAGGGCCATCAGCA |
| 435 | 2833 | 2852 | TGGAGATGAGGGCCATCAGC |
| 436 | 2834 | 2853 | CTGGAGATGAGGGCCATCAG |
| 437 | 2835 | 2854 | GCTGGAGATGAGGGCCATCA |
| 438 | 2836 | 2855 | AGCTGGAGATGAGGGCCATC |
| 461 | 2877 | 2890 | TTAATCAGGGAGCC |
| 70 | 2900 | 2919 | TAGATGCCATCCAGAAAGCT |
| 439 | 2902 | 2921 | GCTAGATGCCATCCAGAAAG |
| 440 | 2903 | 2922 | GGCTAGATGCCATCCAGAAA |
| 441 | 2904 | 2923 | TGGCTAGATGCCATCCAGAA |
| 442 | 2905 | 2924 | CTGGCTAGATGCCATCCAGA |
| 71 | 2906 | 2925 | TCTGGCTAGATGCCATCCAG |
| 443 | 2907 | 2926 | CTCTGGCTAGATGCCATCCA |
| 444 | 2908 | 2927 | CCTCTGGCTAGATGCCATCC |
| 445 | 2909 | 2928 | GCCTCTGGCTAGATGCCATC |
| 446 | 2910 | 2929 | AGCCTCTGGCTAGATGCCAT |
| 72 | 2983 | 3002 | GGCATAGAGCAGAGTAAAGG |
| 73 | 2988 | 3007 | AGCCTGGCATAGAGCAGAGT |
| 135 | 2994 | 3013 | TAGCACAGCCTGGCATAGAG |
| 112 | 3227 | 3246 | GAAGAGGCTTGGCTTCAGAG |
| 74 | 3233 | 3252 | AAGTAAGAAGAGGCTTGGCT |
| 75 | 3437 | 3456 | GCTCAAGGAGGGACAGTTGT |
| 76 | 3472 | 3491 | AAAGATAAATGTCTGCTTGC |
| 77 | 3477 | 3496 | ACCCAAAAGATAAATGTCTG |
| 78 | 3543 | 3562 | TCTTCAAGTTACAAAAGCAA |
| 99 | 3550 | 3569 | ATAAATATCTTCAAGTTACA |

In certain embodiments, gapmer antisense compounds are targeted to a PCSK9 nucleic acid. In certain such embodiments, gapmer antisense compounds are targeted to SEQ ID NO: 1. In certain such embodiments, the nucleotide sequences illustrated in Table 2 have a 5-10-5 gapmer motif. Table 3 illustrates gapmer antisense compounds targeted to SEQ ID NO: 1, having a 5-10-5 motif, where the gap segment comprises 2'-deoxynucleotides and each wing segment comprises nucleotides comprising a 2'-O-methoxyethyl sugar modification. Internucleoside linkages are phosphorthioate, and cytidines are 5-methylcytidines.

TABLE 3

Gapmer antisense compounds having a 5-10-5 motif targeted to SEQ ID NO: 1

| Isis No | Motif | SEQ ID NO | 5' Target Site on SEQ ID NO: 1 | 3' Target Site on SEQ ID NO: 1 | Mismatches | Sequence (5'-3') |
|---|---|---|---|---|---|---|
| 395149 | 5-10-5 | 4 | 135 | 154 | 0 | GCGCGGAATCCTGGCTGGGA |
| 395150 | 5-10-5 | 5 | 242 | 261 | 0 | GAGGAGACCTAGAGGCCGTG |
| 395151 | 5-10-5 | 6 | 300 | 319 | 0 | AGGACCGCCTGGAGCTGACG |
| 395152 | 5-10-5 | 7 | 410 | 429 | 0 | ACGCAAGGCTAGCACCAGCT |
| 399793 | 5-10-5 | 8 | 417 | 436 | 0 | CCTCGGAACGCAAGGCTAGC |
| 395153 | 5-10-5 | 9 | 480 | 499 | 0 | CCTTGGCGCAGCGGTGGAAG |

TABLE 3-continued

Gapmer antisense compounds having a 5-10-5 motif targeted to SEQ ID NO: 1

| Isis No | Motif | SEQ ID NO | 5' Target Site on SEQ ID NO: 1 | 3' Target Site on SEQ ID NO: 1 | Mismatches | Sequence (5'-3') |
|---------|-------|-----------|-------------------------------|-------------------------------|------------|------------------|
| 395154 | 5-10-5 | 10 | 561 | 580 | 0 | GGCGGGCAGTGCGCTCTGAC |
| 395155 | 5-10-5 | 11 | 600 | 619 | 0 | TGGTGAGGTATCCCCGGCGG |
| 399794 | 5-10-5 | 12 | 606 | 625 | 0 | GGATCTTGGTGAGGTATCCC |
| 399795 | 5-10-5 | 13 | 615 | 634 | 0 | AGACATGCAGGATCTTGGTG |
| 395156 | 5-10-5 | 14 | 620 | 639 | 0 | ATGGAAGACATGCAGGATCT |
| 395157 | 5-10-5 | 15 | 646 | 665 | 0 | TTCACCAGGAAGCCAGGAAG |
| 399796 | 5-10-5 | 16 | 651 | 670 | 0 | TCATCTTCACCAGGAAGCCA |
| 395158 | 5-10-5 | 17 | 705 | 724 | 0 | CCTCGATGTAGTCGACATGG |
| 395159 | 5-10-5 | 18 | 785 | 804 | 0 | GTATTCATCCGCCCGGTACC |
| 395160 | 5-10-5 | 19 | 835 | 854 | 0 | CTGGTGTCTAGGAGATACAC |
| 399797 | 5-10-5 | 20 | 840 | 859 | 0 | GTATGCTGGTGTCTAGGAGA |
| 395161 | 5-10-5 | 21 | 860 | 879 | 0 | GATTTCCCGGTGGTCACTCT |
| 399798 | 5-10-5 | 22 | 866 | 885 | 0 | GCCCTCGATTTCCCGGTGGT |
| 399799 | 5-10-5 | 23 | 880 | 899 | 0 | GTGACCATGACCCTGCCCTC |
| 395162 | 5-10-5 | 24 | 890 | 909 | 0 | CTCGAAGTCGGTGACCATGA |
| 395163 | 5-10-5 | 25 | 923 | 942 | 0 | GTGGAAGCGGGTCCCGTCCT |
| 395164 | 5-10-5 | 26 | 970 | 989 | 0 | ACCCCTGCCAGGTGGGTGCC |
| 399800 | 5-10-5 | 27 | 975 | 994 | 0 | TGACCACCCTGCCAGGTGG |
| 395165 | 5-10-5 | 28 | 1004 | 1023 | 0 | ACCCTTGGCCACGCCGGCAT |
| 395166 | 5-10-5 | 29 | 1040 | 1059 | 0 | TTGGCAGTTGAGCACGCGCA |
| 399801 | 5-10-5 | 30 | 1045 | 1064 | 0 | TTCCCTTGGCAGTTGAGCAC |
| 395167 | 5-10-5 | 31 | 1077 | 1096 | 0 | CCAGGCCTATGAGGGTGCCG |
| 395168 | 5-10-5 | 32 | 1098 | 1117 | 0 | GCTGGCTTTTCCGAATAAAC |
| 395169 | 5-10-5 | 33 | 1210 | 1229 | 0 | GTGACCAGCACGACCCCAGC |
| 395170 | 5-10-5 | 149 | 1297 | 1316 | 0 | TGGGCATTGGTGGCCCCAAC |
| 395171 | 5-10-5 | 34 | 1326 | 1345 | 0 | CCAAAGTCCCCAGGGTCACC |
| 395172 | 5-10-5 | 128 | 1330 | 1349 | 0 | GTCCCCAAAGTCCCCAGGGT |
| 399802 | 5-10-5 | 35 | 1335 | 1354 | 0 | AGTTGGTCCCCAAAGTCCCC |
| 395173 | 5-10-5 | 36 | 1340 | 1359 | 0 | GCCAAAGTTGGTCCCCAAAG |
| 399803 | 5-10-5 | 37 | 1352 | 1371 | 0 | GTCCACACAGCGGCCAAAGT |
| 395174 | 5-10-5 | 38 | 1361 | 1380 | 0 | GGCAAAGAGGTCCACACAGC |
| 395175 | 5-10-5 | 39 | 1389 | 1408 | 0 | TGGAGGCACCAATGATGTCC |
| 399804 | 5-10-5 | 40 | 1400 | 1419 | 0 | GCTGCAGTCGCTGGAGGCAC |
| 399805 | 5-10-5 | 41 | 1411 | 1430 | 0 | ACAAAGCAGGTGCTGCAGTC |
| 395176 | 5-10-5 | 101 | 1465 | 1484 | 0 | ATGGCTGCAATGCCAGCCAC |
| 399806 | 5-10-5 | 42 | 1470 | 1489 | 0 | GCATCATGGCTGCAATGCCA |

TABLE 3-continued

Gapmer antisense compounds having a 5-10-5 motif targeted to SEQ ID NO: 1

| Isis No | Motif | SEQ ID NO | 5' Target Site on SEQ ID NO: 1 | 3' Target Site on SEQ ID NO: 1 | Mismatches | Sequence (5'-3') |
|---|---|---|---|---|---|---|
| 399807 | 5-10-5 | 43 | 1478 | 1497 | 0 | GGCAGACAGCATCATGGCTG |
| 399808 | 5-10-5 | 44 | 1526 | 1545 | 0 | GAAGTGGATCAGTCTCTGCC |
| 395177 | 5-10-5 | 45 | 1534 | 1553 | 0 | TTGGCAGAGAAGTGGATCAG |
| 399809 | 5-10-5 | 46 | 1539 | 1558 | 0 | CATCTTTGGCAGAGAAGTGG |
| 399810 | 5-10-5 | 47 | 1545 | 1564 | 0 | TGATGACATCTTTGGCAGAG |
| 399811 | 5-10-5 | 48 | 1552 | 1571 | 0 | GCCTCATTGATGACATCTTT |
| 399812 | 5-10-5 | 49 | 1564 | 1583 | 0 | TCAGGGAACCAGGCCTCATT |
| 395178 | 5-10-5 | 50 | 1569 | 1588 | 0 | GGTCCTCAGGGAACCAGGCC |
| 395179 | 5-10-5 | 87 | 1576 | 1595 | 0 | ACCCGCTGGTCCTCAGGGAA |
| 399813 | 5-10-5 | 51 | 1583 | 1602 | 0 | GGTCAGTACCCGCTGGTCCT |
| 395180 | 5-10-5 | 119 | 1605 | 1624 | 0 | GCAGGGCGGCCACCAGGTTG |
| 395181 | 5-10-5 | 52 | 1640 | 1659 | 0 | AAACAGCTGCCAACCTGCCC |
| 399814 | 5-10-5 | 53 | 1645 | 1664 | 0 | CTGCAAAACAGCTGCCAACC |
| 395182 | 5-10-5 | 54 | 1675 | 1694 | 0 | GTAGGCCCCGAGTGTGCTGA |
| 399815 | 5-10-5 | 55 | 1740 | 1759 | 0 | AGAAACTGGAGCAGCTCAGC |
| 399816 | 5-10-5 | 56 | 1746 | 1765 | 0 | TCCTGGAGAAACTGGAGCAG |
| 395183 | 5-10-5 | 57 | 1812 | 1831 | 0 | CGTTGTGGGCCCGGCAGACC |
| 395184 | 5-10-5 | 58 | 1858 | 1877 | 0 | AGCAGGCAGCACCTGGCAAT |
| 395185 | 5-10-5 | 59 | 1920 | 1939 | 0 | CACGGGTCCCCATGCTGGCC |
| 395186 | 5-10-5 | 60 | 2100 | 2119 | 0 | CTTTGCATTCCAGACCTGGG |
| 399817 | 5-10-5 | 61 | 2105 | 2124 | 0 | CTTGACTTTGCATTCCAGAC |
| 395187 | 5-10-5 | 62 | 2310 | 2329 | 0 | GGCAGCAGATGGCAACGGCT |
| 395188 | 5-10-5 | 154 | 2410 | 2429 | 0 | TTTTAAAGCTCAGCCCCAGC |
| 399818 | 5-10-5 | 63 | 2415 | 2434 | 0 | AACCATTTTAAAGCTCAGCC |
| 395189 | 5-10-5 | 64 | 2504 | 2523 | 0 | TCAAGGGCCAGGCCAGCAGC |
| 399819 | 5-10-5 | 65 | 2509 | 2528 | 0 | CCCACTCAAGGGCCAGGCCA |
| 399820 | 5-10-5 | 122 | 2582 | 2601 | 0 | GGAGGGAGCTTCCTGGCACC |
| 395190 | 5-10-5 | 66 | 2597 | 2616 | 0 | ATGCCCCACAGTGAGGGAGG |
| 395191 | 5-10-5 | 67 | 2606 | 2625 | 0 | AATGGTGAAATGCCCCACAG |
| 395192 | 5-10-5 | 153 | 2649 | 2668 | 0 | TTGGGAGCAGCTGGCAGCAC |
| 395193 | 5-10-5 | 68 | 2750 | 2769 | 0 | CATGGGAAGAATCCTGCCTC |
| 395194 | 5-10-5 | 69 | 2832 | 2851 | 0 | GGAGATGAGGGCCATCAGCA |
| 395195 | 5-10-5 | 70 | 2900 | 2919 | 0 | TAGATGCCATCCAGAAAGCT |
| 399821 | 5-10-5 | 71 | 2906 | 2925 | 0 | TCTGGCTAGATGCCATCCAG |
| 395196 | 5-10-5 | 72 | 2983 | 3002 | 0 | GGCATAGAGCAGAGTAAAGG |
| 399822 | 5-10-5 | 73 | 2988 | 3007 | 0 | AGCCTGGCATAGAGCAGAGT |

TABLE 3-continued

Gapmer antisense compounds having a 5-10-5 motif targeted to SEQ ID NO: 1

| Isis No | Motif | SEQ ID NO | 5' Target Site on SEQ ID NO: 1 | 3' Target Site on SEQ ID NO: 1 | Mismatches | Sequence (5'-3') |
|---|---|---|---|---|---|---|
| 399823 | 5-10-5 | 135 | 2994 | 3013 | 0 | TAGCACAGCCTGGCATAGAG |
| 395197 | 5-10-5 | 112 | 3227 | 3246 | 0 | GAAGAGGCTTGGCTTCAGAG |
| 399824 | 5-10-5 | 74 | 3233 | 3252 | 0 | AAGTAAGAAGAGGCTTGGCT |
| 395198 | 5-10-5 | 75 | 3437 | 3456 | 0 | GCTCAAGGAGGGACAGTTGT |
| 395199 | 5-10-5 | 76 | 3472 | 3491 | 0 | AAAGATAAATGTCTGCTTGC |
| 399825 | 5-10-5 | 77 | 3477 | 3496 | 0 | ACCCAAAAGATAAATGTCTG |
| 395200 | 5-10-5 | 78 | 3543 | 3562 | 0 | TCTTCAAGTTACAAAAGCAA |
| 399826 | 5-10-5 | 99 | 3550 | 3569 | 0 | ATAAATATCTTCAAGTTACA |
| 405861 | 5-10-5 | 162 | 406 | 425 | 0 | AAGGCTAGCACCAGCTCCTC |
| 405862 | 5-10-5 | 163 | 407 | 426 | 0 | CAAGGCTAGCACCAGCTCCT |
| 405863 | 5-10-5 | 164 | 408 | 427 | 0 | GCAAGGCTAGCACCAGCTCC |
| 405864 | 5-10-5 | 165 | 409 | 428 | 0 | CGCAAGGCTAGCACCAGCTC |
| 405865 | 5-10-5 | 166 | 411 | 430 | 0 | AACGCAAGGCTAGCACCAGC |
| 405866 | 5-10-5 | 167 | 412 | 431 | 0 | GAACGCAAGGCTAGCACCAG |
| 405867 | 5-10-5 | 168 | 413 | 432 | 0 | GGAACGCAAGGCTAGCACCA |
| 405868 | 5-10-5 | 169 | 414 | 433 | 0 | CGGAACGCAAGGCTAGCACC |
| 405869 | 5-10-5 | 218 | 862 | 881 | 0 | TCGATTTCCCGGTGGTCACT |
| 405870 | 5-10-5 | 219 | 863 | 882 | 0 | CTCGATTTCCCGGTGGTCAC |
| 405871 | 5-10-5 | 220 | 864 | 883 | 0 | CCTCGATTTCCCGGTGGTCA |
| 405872 | 5-10-5 | 221 | 865 | 884 | 0 | CCCTCGATTTCCCGGTGGTC |
| 405873 | 5-10-5 | 222 | 867 | 886 | 0 | TGCCCTCGATTTCCCGGTGG |
| 405874 | 5-10-5 | 223 | 868 | 887 | 0 | CTGCCCTCGATTTCCCGGTG |
| 405875 | 5-10-5 | 224 | 869 | 888 | 0 | CCTGCCCTCGATTTCCCGGT |
| 405876 | 5-10-5 | 225 | 870 | 889 | 0 | CCCTGCCCTCGATTTCCCGG |
| 405877 | 5-10-5 | 246 | 1000 | 1019 | 0 | TTGGCCACGCCGGCATCCCG |
| 405878 | 5-10-5 | 247 | 1001 | 1020 | 0 | CTTGGCCACGCCGGCATCCC |
| 405879 | 5-10-5 | 248 | 1002 | 1021 | 0 | CCTTGGCCACGCCGGCATCC |
| 405880 | 5-10-5 | 249 | 1003 | 1022 | 0 | CCCTTGGCCACGCCGGCATC |
| 405881 | 5-10-5 | 250 | 1005 | 1024 | 0 | CACCCTTGGCCACGCCGGCA |
| 405882 | 5-10-5 | 251 | 1006 | 1025 | 0 | GCACCCTTGGCCACGCCGGC |
| 405883 | 5-10-5 | 252 | 1007 | 1026 | 0 | GGCACCCTTGGCCACGCCGG |
| 405884 | 5-10-5 | 253 | 1008 | 1027 | 0 | TGGCACCCTTGGCCACGCCG |
| 405885 | 5-10-5 | 346 | 1560 | 1579 | 0 | GGAACCAGGCCTCATTGATG |
| 405886 | 5-10-5 | 347 | 1561 | 1580 | 0 | GGGAACCAGGCCTCATTGAT |
| 405887 | 5-10-5 | 348 | 1562 | 1581 | 0 | AGGGAACCAGGCCTCATTGA |
| 405888 | 5-10-5 | 349 | 1563 | 1582 | 0 | CAGGGAACCAGGCCTCATTG |

TABLE 3-continued

Gapmer antisense compounds having a 5-10-5 motif targeted to SEQ ID NO: 1

| Isis No | Motif | SEQ ID NO | 5' Target Site on SEQ ID NO: 1 | 3' Target Site on SEQ ID NO: 1 | Mismatches | Sequence (5'-3') |
|---|---|---|---|---|---|---|
| 405889 | 5-10-5 | 350 | 1565 | 1584 | 0 | CTCAGGGAACCAGGCCTCAT |
| 405890 | 5-10-5 | 351 | 1566 | 1585 | 0 | CCTCAGGGAACCAGGCCTCA |
| 405891 | 5-10-5 | 352 | 1567 | 1586 | 0 | TCCTCAGGGAACCAGGCCTC |
| 405892 | 5-10-5 | 353 | 1568 | 1587 | 0 | GTCCTCAGGGAACCAGGCCT |
| 405893 | 5-10-5 | 431 | 2828 | 2847 | 0 | ATGAGGGCCATCAGCACCTT |
| 405894 | 5-10-5 | 432 | 2829 | 2848 | 0 | GATGAGGGCCATCAGCACCT |
| 405895 | 5-10-5 | 433 | 2830 | 2849 | 0 | AGATGAGGGCCATCAGCACC |
| 405896 | 5-10-5 | 434 | 2831 | 2850 | 0 | GAGATGAGGGCCATCAGCAC |
| 405897 | 5-10-5 | 435 | 2833 | 2852 | 0 | TGGAGATGAGGGCCATCAGC |
| 405898 | 5-10-5 | 436 | 2834 | 2853 | 0 | CTGGAGATGAGGGCCATCAG |
| 405899 | 5-10-5 | 437 | 2835 | 2854 | 0 | GCTGGAGATGAGGGCCATCA |
| 405900 | 5-10-5 | 438 | 2836 | 2855 | 0 | AGCTGGAGATGAGGGCCATC |
| 405901 | 5-10-5 | 439 | 2902 | 2921 | 0 | GCTAGATGCCATCCAGAAAG |
| 405902 | 5-10-5 | 440 | 2903 | 2922 | 0 | GGCTAGATGCCATCCAGAAA |
| 405903 | 5-10-5 | 441 | 2904 | 2923 | 0 | TGGCTAGATGCCATCCAGAA |
| 405904 | 5-10-5 | 442 | 2905 | 2924 | 0 | CTGGCTAGATGCCATCCAGA |
| 405905 | 5-10-5 | 443 | 2907 | 2926 | 0 | CTCTGGCTAGATGCCATCCA |
| 405906 | 5-10-5 | 444 | 2908 | 2927 | 0 | CCTCTGGCTAGATGCCATCC |
| 405907 | 5-10-5 | 445 | 2909 | 2928 | 0 | GCCTCTGGCTAGATGCCATC |
| 405908 | 5-10-5 | 446 | 2910 | 2929 | 0 | AGCCTCTGGCTAGATGCCAT |
| 405909 | 5-10-5 | 267 | 1100 | 1119 | 0 | CAGCTGGCTTTTCCGAATAA |
| 405910 | 5-10-5 | 268 | 1102 | 1121 | 0 | ACCAGCTGGCTTTTCCGAAT |
| 405911 | 5-10-5 | 269 | 1104 | 1123 | 0 | GGACCAGCTGGCTTTTCCGA |
| 405912 | 5-10-5 | 270 | 1108 | 1127 | 0 | GGCTGGACCAGCTGGCTTTT |
| 405913 | 5-10-5 | 275 | 1212 | 1231 | 0 | CGGTGACCAGCACGACCCCA |
| 405914 | 5-10-5 | 276 | 1214 | 1233 | 0 | AGCGGTGACCAGCACGACCC |
| 405915 | 5-10-5 | 277 | 1216 | 1235 | 0 | GCAGCGGTGACCAGCACGAC |
| 405916 | 5-10-5 | 278 | 1218 | 1237 | 0 | CGGCAGCGGTGACCAGCACG |
| 405917 | 5-10-5 | 280 | 1222 | 1241 | 0 | TTGCCGGCAGCGGTGACCAG |
| 405918 | 5-10-5 | 281 | 1224 | 1243 | 0 | AGTTGCCGGCAGCGGTGACC |
| 405919 | 5-10-5 | 282 | 1226 | 1245 | 0 | GAAGTTGCCGGCAGCGGTGA |
| 405920 | 5-10-5 | 283 | 1228 | 1247 | 0 | CGGAAGTTGCCGGCAGCGGT |
| 405921 | 5-10-5 | 284 | 1230 | 1249 | 0 | CCCGGAAGTTGCCGGCAGCG |
| 405922 | 5-10-5 | 285 | 1232 | 1251 | 0 | GTCCCGGAAGTTGCCGGCAG |
| 405923 | 5-10-5 | 288 | 1295 | 1314 | 0 | GGCATTGGTGGCCCCAACTG |
| 405924 | 5-10-5 | 290 | 1318 | 1337 | 0 | CCCAGGGTCACCGGCTGGTC |

TABLE 3-continued

Gapmer antisense compounds having a 5-10-5 motif targeted to SEQ ID NO: 1

| Isis No | Motif | SEQ ID NO | 5' Target Site on SEQ ID NO: 1 | 3' Target Site on SEQ ID NO: 1 | Mismatches | Sequence (5'-3') |
|---|---|---|---|---|---|---|
| 405925 | 5-10-5 | 292 | 1322 | 1341 | 0 | AGTCCCCAGGGTCACCGGCT |
| 405926 | 5-10-5 | 293 | 1324 | 1343 | 0 | AAAGTCCCCAGGGTCACCGG |
| 405927 | 5-10-5 | 294 | 1328 | 1347 | 0 | CCCCAAAGTCCCCAGGGTCA |
| 405928 | 5-10-5 | 295 | 1333 | 1352 | 0 | TTGGTCCCCAAAGTCCCCAG |
| 405929 | 5-10-5 | 296 | 1337 | 1356 | 0 | AAAGTTGGTCCCCAAAGTCC |
| 405930 | 5-10-5 | 297 | 1342 | 1361 | 0 | CGGCCAAAGTTGGTCCCCAA |
| 405931 | 5-10-5 | 298 | 1344 | 1363 | 0 | AGCGGCCAAAGTTGGTCCCC |
| 405932 | 5-10-5 | 299 | 1346 | 1365 | 0 | ACAGCGGCCAAAGTTGGTCC |
| 405933 | 5-10-5 | 300 | 1348 | 1367 | 0 | ACACAGCGGCCAAAGTTGGT |
| 405934 | 5-10-5 | 301 | 1350 | 1369 | 0 | CCACACAGCGGCCAAAGTTG |
| 405935 | 5-10-5 | 302 | 1354 | 1373 | 0 | AGGTCCACACAGCGGCCAAA |
| 405936 | 5-10-5 | 304 | 1358 | 1377 | 0 | AAAGAGGTCCACACAGCGGC |
| 405937 | 5-10-5 | 306 | 1387 | 1406 | 0 | GAGGCACCAATGATGTCCTC |
| 405938 | 5-10-5 | 307 | 1391 | 1410 | 0 | GCTGGAGGCACCAATGATGT |
| 405939 | 5-10-5 | 308 | 1393 | 1412 | 0 | TCGCTGGAGGCACCAATGAT |
| 405940 | 5-10-5 | 309 | 1395 | 1414 | 0 | AGTCGCTGGAGGCACCAATG |
| 405941 | 5-10-5 | 310 | 1397 | 1416 | 0 | GCAGTCGCTGGAGGCACCAA |
| 405942 | 5-10-5 | 311 | 1402 | 1421 | 0 | GTGCTGCAGTCGCTGGAGGC |
| 405943 | 5-10-5 | 312 | 1404 | 1423 | 0 | AGGTGCTGCAGTCGCTGGAG |
| 405944 | 5-10-5 | 314 | 1407 | 1426 | 0 | AGCAGGTGCTGCAGTCGCTG |
| 405945 | 5-10-5 | 315 | 1409 | 1428 | 0 | AAAGCAGGTGCTGCAGTCGC |
| 405946 | 5-10-5 | 316 | 1413 | 1432 | 0 | ACACAAAGCAGGTGCTGCAG |
| 405947 | 5-10-5 | 317 | 1415 | 1434 | 0 | TGACACAAAGCAGGTGCTGC |
| 405948 | 5-10-5 | 319 | 1467 | 1486 | 0 | TCATGGCTGCAATGCCAGCC |
| 405949 | 5-10-5 | 320 | 1472 | 1491 | 0 | CAGCATCATGGCTGCAATGC |
| 405950 | 5-10-5 | 321 | 1474 | 1493 | 0 | GACAGCATCATGGCTGCAAT |
| 405951 | 5-10-5 | 322 | 1476 | 1495 | 0 | CAGACAGCATCATGGCTGCA |
| 405952 | 5-10-5 | 323 | 1480 | 1499 | 0 | TCGGCAGACAGCATCATGGC |
| 405953 | 5-10-5 | 325 | 1484 | 1503 | 0 | CGGCTCGGCAGACAGCATCA |
| 405954 | 5-10-5 | 326 | 1486 | 1505 | 0 | TCCGGCTCGGCAGACAGCAT |
| 405955 | 5-10-5 | 328 | 1513 | 1532 | 0 | CTCTGCCTCAACTCGGCCAG |
| 405956 | 5-10-5 | 329 | 1515 | 1534 | 0 | GTCTCTGCCTCAACTCGGCC |
| 405957 | 5-10-5 | 330 | 1517 | 1536 | 0 | CAGTCTCTGCCTCAACTCGG |
| 405958 | 5-10-5 | 331 | 1519 | 1538 | 0 | ATCAGTCTCTGCCTCAACTC |
| 405959 | 5-10-5 | 332 | 1521 | 1540 | 0 | GGATCAGTCTCTGCCTCAAC |
| 405960 | 5-10-5 | 333 | 1523 | 1542 | 0 | GTGGATCAGTCTCTGCCTCA |

TABLE 3-continued

Gapmer antisense compounds having a 5-10-5 motif targeted to SEQ ID NO: 1

| Isis No | Motif | SEQ ID NO | 5' Target Site on SEQ ID NO: 1 | 3' Target Site on SEQ ID NO: 1 | Mismatches | Sequence (5'-3') |
|---|---|---|---|---|---|---|
| 405961 | 5-10-5 | 334 | 1525 | 1544 | 0 | AAGTGGATCAGTCTCTGCCT |
| 405962 | 5-10-5 | 335 | 1528 | 1547 | 0 | GAGAAGTGGATCAGTCTCTG |
| 405963 | 5-10-5 | 337 | 1532 | 1551 | 0 | GGCAGAGAAGTGGATCAGTC |
| 405964 | 5-10-5 | 338 | 1536 | 1555 | 0 | CTTTGGCAGAGAAGTGGATC |
| 405965 | 5-10-5 | 339 | 1541 | 1560 | 0 | GACATCTTTGGCAGAGAAGT |
| 405966 | 5-10-5 | 340 | 1543 | 1562 | 0 | ATGACATCTTTGGCAGAGAA |
| 405967 | 5-10-5 | 341 | 1547 | 1566 | 0 | ATTGATGACATCTTTGGCAG |
| 405968 | 5-10-5 | 342 | 1549 | 1568 | 0 | TCATTGATGACATCTTTGGC |
| 405969 | 5-10-5 | 343 | 1554 | 1573 | 0 | AGGCCTCATTGATGACATCT |
| 405970 | 5-10-5 | 344 | 1556 | 1575 | 0 | CCAGGCCTCATTGATGACAT |
| 405971 | 5-10-5 | 355 | 1571 | 1590 | 0 | CTGGTCCTCAGGGAACCAGG |
| 405972 | 5-10-5 | 357 | 1573 | 1592 | 0 | CGCTGGTCCTCAGGGAACCA |
| 405973 | 5-10-5 | 358 | 1578 | 1597 | 0 | GTACCCGCTGGTCCTCAGGG |
| 405974 | 5-10-5 | 359 | 1580 | 1599 | 0 | CAGTACCCGCTGGTCCTCAG |
| 405975 | 5-10-5 | 361 | 1642 | 1661 | 0 | CAAAACAGCTGCCAACCTGC |
| 405976 | 5-10-5 | 362 | 1647 | 1666 | 0 | TCCTGCAAAACAGCTGCCAA |
| 405977 | 5-10-5 | 363 | 1649 | 1668 | 0 | AGTCCTGCAAAACAGCTGCC |
| 405978 | 5-10-5 | 365 | 1672 | 1691 | 0 | GGCCCCGAGTGTGCTGACCA |
| 405979 | 5-10-5 | 366 | 1677 | 1696 | 0 | GTGTAGGCCCCGAGTGTGCT |
| 405980 | 5-10-5 | 367 | 1679 | 1698 | 0 | CCGTGTAGGCCCCGAGTGTG |
| 405981 | 5-10-5 | 368 | 1681 | 1700 | 0 | ATCCGTGTAGGCCCCGAGTG |
| 405982 | 5-10-5 | 370 | 1685 | 1704 | 0 | GGCCATCCGTGTAGGCCCCG |
| 405983 | 5-10-5 | 371 | 1687 | 1706 | 0 | GTGGCCATCCGTGTAGGCCC |
| 405984 | 5-10-5 | 372 | 1735 | 1754 | 0 | CTGGAGCAGCTCAGCAGCTC |
| 405985 | 5-10-5 | 373 | 1737 | 1756 | 0 | AACTGGAGCAGCTCAGCAGC |
| 405986 | 5-10-5 | 374 | 1742 | 1761 | 0 | GGAGAAACTGGAGCAGCTCA |
| 405987 | 5-10-5 | 375 | 1744 | 1763 | 0 | CTGGAGAAACTGGAGCAGCT |
| 405988 | 5-10-5 | 381 | 1854 | 1873 | 0 | GGCAGCACCTGGCAATGGCG |
| 405989 | 5-10-5 | 383 | 1856 | 1875 | 0 | CAGGCAGCACCTGGCAATGG |
| 405990 | 5-10-5 | 386 | 1860 | 1879 | 0 | GTAGCAGGCAGCACCTGGCA |
| 405991 | 5-10-5 | 394 | 1922 | 1941 | 0 | GACACGGGTCCCCATGCTGG |
| 405992 | 5-10-5 | 396 | 1924 | 1943 | 0 | TGGACACGGGTCCCCATGCT |
| 405993 | 5-10-5 | 398 | 1926 | 1945 | 0 | AGTGGACACGGGTCCCCATG |
| 405994 | 5-10-5 | 400 | 1928 | 1947 | 0 | GCAGTGGACACGGGTCCCCA |
| 405995 | 5-10-5 | 402 | 1930 | 1949 | 0 | TGGCAGTGGACACGGGTCCC |
| 405996 | 5-10-5 | 412 | 2102 | 2121 | 0 | GACTTTGCATTCCAGACCTG |

TABLE 3-continued

Gapmer antisense compounds having a 5-10-5 motif targeted to SEQ ID NO: 1

| Isis No | Motif | SEQ ID NO | 5' Target Site on SEQ ID NO: 1 | 3' Target Site on SEQ ID NO: 1 | Mismatches | Sequence (5'-3') |
|---|---|---|---|---|---|---|
| 405997 | 5-10-5 | 415 | 2107 | 2126 | 0 | TCCTTGACTTTGCATTCCAG |
| 405998 | 5-10-5 | 426 | 2313 | 2332 | 0 | TCCGGCAGCAGATGGCAACG |
| 405999 | 5-10-5 | 160 | 298 | 317 | 0 | GACCGCCTGGAGCTGACGGT |
| 406000 | 5-10-5 | 173 | 482 | 501 | 0 | ATCCTTGGCGCAGCGGTGGA |
| 406001 | 5-10-5 | 174 | 484 | 503 | 0 | GGATCCTTGGCGCAGCGGTG |
| 406002 | 5-10-5 | 175 | 488 | 507 | 0 | CCACGGATCCTTGGCGCAGC |
| 406003 | 5-10-5 | 178 | 555 | 574 | 0 | CAGTGCGCTCTGACTGCGAG |
| 406004 | 5-10-5 | 179 | 557 | 576 | 0 | GGCAGTGCGCTCTGACTGCG |
| 406005 | 5-10-5 | 180 | 559 | 578 | 0 | CGGGCAGTGCGCTCTGACTG |
| 406006 | 5-10-5 | 181 | 562 | 581 | 0 | CGGCGGGCAGTGCGCTCTGA |
| 406007 | 5-10-5 | 183 | 595 | 614 | 0 | AGGTATCCCCGGCGGGCAGC |
| 406008 | 5-10-5 | 188 | 602 | 621 | 0 | CTTGGTGAGGTATCCCCGGC |
| 406009 | 5-10-5 | 190 | 604 | 623 | 0 | ATCTTGGTGAGGTATCCCCG |
| 406010 | 5-10-5 | 193 | 609 | 628 | 0 | GCAGGATCTTGGTGAGGTAT |
| 406011 | 5-10-5 | 194 | 611 | 630 | 0 | ATGCAGGATCTTGGTGAGGT |
| 406012 | 5-10-5 | 195 | 613 | 632 | 0 | ACATGCAGGATCTTGGTGAG |
| 406013 | 5-10-5 | 196 | 617 | 636 | 0 | GAAGACATGCAGGATCTTGG |
| 406014 | 5-10-5 | 199 | 648 | 667 | 0 | TCTTCACCAGGAAGCCAGGA |
| 406015 | 5-10-5 | 200 | 653 | 672 | 0 | ACTCATCTTCACCAGGAAGC |
| 406016 | 5-10-5 | 201 | 655 | 674 | 0 | CCACTCATCTTCACCAGGAA |
| 406017 | 5-10-5 | 203 | 659 | 678 | 0 | GTCGCCACTCATCTTCACCA |
| 406018 | 5-10-5 | 204 | 661 | 680 | 0 | AGGTCGCCACTCATCTTCAC |
| 406019 | 5-10-5 | 205 | 663 | 682 | 0 | GCAGGTCGCCACTCATCTTC |
| 406020 | 5-10-5 | 206 | 665 | 684 | 0 | CAGCAGGTCGCCACTCATCT |
| 406021 | 5-10-5 | 210 | 782 | 801 | 0 | TTCATCCGCCCGGTACCGTG |
| 406022 | 5-10-5 | 211 | 784 | 803 | 0 | TATTCATCCGCCCGGTACCG |
| 406023 | 5-10-5 | 212 | 787 | 806 | 0 | TGGTATTCATCCGCCCGGTA |
| 406024 | 5-10-5 | 213 | 789 | 808 | 0 | GCTGGTATTCATCCGCCCGG |
| 406025 | 5-10-5 | 216 | 832 | 851 | 0 | GTGTCTAGGAGATACACCTC |
| 406026 | 5-10-5 | 217 | 837 | 856 | 0 | TGCTGGTGTCTAGGAGATAC |
| 406027 | 5-10-5 | 226 | 874 | 893 | 0 | ATGACCCTGCCCTCGATTTC |
| 406028 | 5-10-5 | 227 | 876 | 895 | 0 | CCATGACCCTGCCCTCGATT |
| 406029 | 5-10-5 | 228 | 878 | 897 | 0 | GACCATGACCCTGCCCTCGA |
| 406030 | 5-10-5 | 229 | 882 | 901 | 0 | CGGTGACCATGACCCTGCCC |
| 406031 | 5-10-5 | 230 | 884 | 903 | 0 | GTCGGTGACCATGACCCTGC |
| 406032 | 5-10-5 | 232 | 888 | 907 | 0 | CGAAGTCGGTGACCATGACC |

TABLE 3-continued

Gapmer antisense compounds having a 5-10-5 motif targeted to SEQ ID NO: 1

| Isis No | Motif | SEQ ID NO | 5' Target Site on SEQ ID NO: 1 | 3' Target Site on SEQ ID NO: 1 | Mismatches | Sequence (5'-3') |
|---|---|---|---|---|---|---|
| 406033 | 5-10-5 | 237 | 967 | 986 | 0 | CCTGCCAGGTGGGTGCCATG |
| 406034 | 5-10-5 | 238 | 972 | 991 | 0 | CCACCCCTGCCAGGTGGGTG |
| 406035 | 5-10-5 | 239 | 977 | 996 | 0 | GCTGACCACCCCTGCCAGGT |
| 406036 | 5-10-5 | 241 | 989 | 1008 | 0 | GGCATCCCGGCCGCTGACCA |
| 406037 | 5-10-5 | 242 | 992 | 1011 | 0 | GCCGGCATCCCGGCCGCTGA |
| 406038 | 5-10-5 | 245 | 999 | 1018 | 0 | TGGCCACGCCGGCATCCCGG |
| 406039 | 5-10-5 | 257 | 1036 | 1055 | 0 | CAGTTGAGCACGCGCAGGCT |
| 406040 | 5-10-5 | 258 | 1038 | 1057 | 0 | GGCAGTTGAGCACGCGCAGG |
| 406041 | 5-10-5 | 259 | 1042 | 1061 | 0 | CCTTGGCAGTTGAGCACGCG |
| 406042 | 5-10-5 | 260 | 1047 | 1066 | 0 | CCTTCCCTTGGCAGTTGAGC |
| 406043 | 5-10-5 | 261 | 1051 | 1070 | 0 | GTGCCCTTCCCTTGGCAGTT |
| 406044 | 5-10-5 | 262 | 1053 | 1072 | 0 | CCGTGCCCTTCCCTTGGCAG |
| 406045 | 5-10-5 | 266 | 1096 | 1115 | 0 | TGGCTTTTCCGAATAAACTC |
| 408642 | 5-10-5 | 264 | 1076 | 1095 | 0 | CAGGCCTATGAGGGTGCCGC |
| 408653 | 5-10-5 | 354 | 1570 | 1589 | 0 | TGGTCCTCAGGGAACCAGGC |
| 409126 | 5-10-5 | 447 | 1004 | 1023 | 1 | ACCCTTGGTCACGCCGGCAT |
| 410529 | 5-10-5 | 184 | 597 | 616 | 0 | TGAGGTATCCCCGGCGGGCA |
| 410530 | 5-10-5 | 185 | 598 | 617 | 0 | GTGAGGTATCCCCGGCGGGC |
| 410531 | 5-10-5 | 186 | 599 | 618 | 0 | GGTGAGGTATCCCCGGCGGG |
| 410532 | 5-10-5 | 187 | 601 | 620 | 0 | TTGGTGAGGTATCCCCGGCG |
| 410533 | 5-10-5 | 189 | 603 | 622 | 0 | TCTTGGTGAGGTATCCCCGG |
| 410534 | 5-10-5 | 191 | 605 | 624 | 0 | GATCTTGGTGAGGTATCCCC |
| 410535 | 5-10-5 | 192 | 607 | 626 | 0 | AGGATCTTGGTGAGGTATCC |
| 410536 | 5-10-5 | 243 | 997 | 1016 | 0 | GCCACGCCGGCATCCCGGCC |
| 410537 | 5-10-5 | 244 | 998 | 1017 | 0 | GGCCACGCCGGCATCCCGGC |
| 410538 | 5-10-5 | 254 | 1009 | 1028 | 0 | CTGGCACCCTTGGCCACGCC |
| 410539 | 5-10-5 | 255 | 1010 | 1029 | 0 | GCTGGCACCCTTGGCCACGC |
| 410540 | 5-10-5 | 356 | 1572 | 1591 | 0 | GCTGGTCCTCAGGGAACCAG |
| 410541 | 5-10-5 | 376 | 1849 | 1868 | 0 | CACCTGGCAATGGCGTAGAC |
| 410542 | 5-10-5 | 377 | 1850 | 1869 | 0 | GCACCTGGCAATGGCGTAGA |
| 410543 | 5-10-5 | 378 | 1851 | 1870 | 0 | AGCACCTGGCAATGGCGTAG |
| 410544 | 5-10-5 | 379 | 1852 | 1871 | 0 | CAGCACCTGGCAATGGCGTA |
| 410545 | 5-10-5 | 380 | 1853 | 1872 | 0 | GCAGCACCTGGCAATGGCGT |
| 410546 | 5-10-5 | 382 | 1855 | 1874 | 0 | AGGCAGCACCTGGCAATGGC |
| 410547 | 5-10-5 | 384 | 1857 | 1876 | 0 | GCAGGCAGCACCTGGCAATG |
| 410548 | 5-10-5 | 385 | 1859 | 1878 | 0 | TAGCAGGCAGCACCTGGCAA |

TABLE 3-continued

Gapmer antisense compounds having a 5-10-5 motif targeted to SEQ ID NO: 1

| Isis No | Motif | SEQ ID NO | 5' Target Site on SEQ ID NO: 1 | 3' Target Site on SEQ ID NO: 1 | Mismatches | Sequence (5'-3') |
|---|---|---|---|---|---|---|
| 410549 | 5-10-5 | 388 | 1915 | 1934 | 0 | GTCCCCATGCTGGCCTCAGC |
| 410550 | 5-10-5 | 389 | 1916 | 1935 | 0 | GGTCCCCATGCTGGCCTCAG |
| 410551 | 5-10-5 | 390 | 1917 | 1936 | 0 | GGGTCCCCATGCTGGCCTCA |
| 410552 | 5-10-5 | 391 | 1918 | 1937 | 0 | CGGGTCCCCATGCTGGCCTC |
| 410553 | 5-10-5 | 392 | 1919 | 1938 | 0 | ACGGGTCCCCATGCTGGCCT |
| 410554 | 5-10-5 | 393 | 1921 | 1940 | 0 | ACACGGGTCCCCATGCTGGC |
| 410555 | 5-10-5 | 395 | 1923 | 1942 | 0 | GGACACGGGTCCCCATGCTG |
| 410556 | 5-10-5 | 397 | 1925 | 1944 | 0 | GTGGACACGGGTCCCCATGC |
| 410557 | 5-10-5 | 399 | 1927 | 1946 | 0 | CAGTGGACACGGGTCCCCAT |
| 410558 | 5-10-5 | 401 | 1929 | 1948 | 0 | GGCAGTGGACACGGGTCCCC |
| 410559 | 5-10-5 | 403 | 1931 | 1950 | 0 | GTGGCAGTGGACACGGGTCC |
| 410560 | 5-10-5 | 404 | 1932 | 1951 | 0 | GGTGGCAGTGGACACGGGTC |
| 410561 | 5-10-5 | 405 | 1933 | 1952 | 0 | TGGTGGCAGTGGACACGGGT |
| 410562 | 5-10-5 | 411 | 2101 | 2120 | 0 | ACTTTGCATTCCAGACCTGG |
| 410563 | 5-10-5 | 413 | 2103 | 2122 | 0 | TGACTTTGCATTCCAGACCT |
| 410564 | 5-10-5 | 414 | 2104 | 2123 | 0 | TTGACTTTGCATTCCAGACC |
| 410565 | 5-10-5 | 419 | 2305 | 2324 | 0 | CAGATGGCAACGGCTGTCAC |
| 410566 | 5-10-5 | 420 | 2306 | 2325 | 0 | GCAGATGGCAACGGCTGTCA |
| 410567 | 5-10-5 | 421 | 2307 | 2326 | 0 | AGCAGATGGCAACGGCTGTC |
| 410568 | 5-10-5 | 422 | 2308 | 2327 | 0 | CAGCAGATGGCAACGGCTGT |
| 410569 | 5-10-5 | 423 | 2309 | 2328 | 0 | GCAGCAGATGGCAACGGCTG |
| 410570 | 5-10-5 | 424 | 2311 | 2330 | 0 | CGGCAGCAGATGGCAACGGC |
| 410571 | 5-10-5 | 425 | 2312 | 2331 | 0 | CCGGCAGCAGATGGCAACGG |
| 410572 | 5-10-5 | 427 | 2314 | 2333 | 0 | CTCCGGCAGCAGATGGCAAC |
| 410573 | 5-10-5 | 428 | 2315 | 2334 | 0 | GCTCCGGCAGCAGATGGCAA |
| 410730 | 5-10-5 | 202 | 657 | 676 | 0 | CGCCACTCATCTTCACCAGG |
| 410731 | 5-10-5 | 207 | 667 | 686 | 0 | TCCAGCAGGTCGCCACTCAT |
| 410732 | 5-10-5 | 214 | 791 | 810 | 0 | GGGCTGGTATTCATCCGCCC |
| 410733 | 5-10-5 | 231 | 886 | 905 | 0 | AAGTCGGTGACCATGACCCT |
| 410734 | 5-10-5 | 279 | 1219 | 1238 | 0 | CCGGCAGCGGTGACCAGCAC |
| 410735 | 5-10-5 | 291 | 1320 | 1339 | 0 | TCCCCAGGGTCACCGGCTGG |
| 410736 | 5-10-5 | 303 | 1356 | 1375 | 0 | AGAGGTCCACACAGCGGCCA |
| 410737 | 5-10-5 | 313 | 1406 | 1425 | 0 | GCAGGTGCTGCAGTCGCTGG |
| 410738 | 5-10-5 | 324 | 1482 | 1501 | 0 | GCTCGGCAGACAGCATCATG |
| 410739 | 5-10-5 | 336 | 1530 | 1549 | 0 | CAGAGAAGTGGATCAGTCTC |
| 410740 | 5-10-5 | 345 | 1558 | 1577 | 0 | AACCAGGCCTCATTGATGAC |

TABLE 3-continued

Gapmer antisense compounds having a 5-10-5 motif targeted to SEQ ID NO: 1

| Isis No | Motif | SEQ ID NO | 5' Target Site on SEQ ID NO: 1 | 3' Target Site on SEQ ID NO: 1 | Mismatches | Sequence (5'-3') |
|---|---|---|---|---|---|---|
| 410741 | 5-10-5 | 369 | 1683 | 1702 | 0 | CCATCCGTGTAGGCCCCGAG |
| 410742 | 5-10-5 | 159 | 294 | 313 | 0 | GCCTGGAGCTGACGGTGCCC |
| 410743 | 5-10-5 | 170 | 421 | 440 | 0 | TCCTCCTCGGAACGCAAGGC |
| 410744 | 5-10-5 | 171 | 446 | 465 | 0 | GTGCTCGGGTGCTTCGGCCA |
| 410745 | 5-10-5 | 172 | 466 | 485 | 0 | TGGAAGGTGGCTGTGGTTCC |
| 410746 | 5-10-5 | 176 | 507 | 526 | 0 | CGTAGGTGCCAGGCAACCTC |
| 410747 | 5-10-5 | 177 | 545 | 564 | 0 | TGACTGCGAGAGGTGGGTCT |
| 410748 | 5-10-5 | 182 | 591 | 610 | 0 | ATCCCCGGCGGGCAGCCTGG |
| 410749 | 5-10-5 | 197 | 628 | 647 | 0 | AGAAGGCCATGGAAGACATG |
| 410750 | 5-10-5 | 198 | 638 | 657 | 0 | GAAGCCAGGAAGAAGGCCAT |
| 410751 | 5-10-5 | 208 | 685 | 704 | 0 | GGCAACTTCAAGGCCAGCTC |
| 410752 | 5-10-5 | 209 | 724 | 743 | 0 | GCAAAGACAGAGGAGTCCTC |
| 410753 | 5-10-5 | 215 | 821 | 840 | 0 | ATACACCTCCACCAGGCTGC |
| 410754 | 5-10-5 | 233 | 898 | 917 | 0 | GGCACATTCTCGAAGTCGGT |
| 410755 | 5-10-5 | 234 | 933 | 952 | 0 | TGGCCTGTCTGTGGAAGCGG |
| 410756 | 5-10-5 | 235 | 960 | 979 | 0 | GGTGGGTGCCATGACTGTCA |
| 410757 | 5-10-5 | 240 | 985 | 1004 | 0 | TCCCGGCCGCTGACCACCCC |
| 410758 | 5-10-5 | 256 | 1015 | 1034 | 0 | CGCATGCTGGCACCCTTGGC |
| 410759 | 5-10-5 | 263 | 1064 | 1083 | 0 | GGTGCCGCTAACCGTGCCCT |
| 410760 | 5-10-5 | 265 | 1088 | 1107 | 0 | CCGAATAAACTCCAGGCCTA |
| 410761 | 5-10-5 | 271 | 1119 | 1138 | 0 | GTGGCCCCACAGGCTGGACC |
| 410762 | 5-10-5 | 272 | 1132 | 1151 | 0 | AGCAGCACCACCAGTGGCCC |
| 410763 | 5-10-5 | 273 | 1154 | 1173 | 0 | GCTGTACCCACCCGCCAGGG |
| 410764 | 5-10-5 | 274 | 1200 | 1219 | 0 | CGACCCCAGCCCTCGCCAGG |
| 410765 | 5-10-5 | 286 | 1273 | 1292 | 0 | ATGACCTCGGGAGCTGAGGC |
| 410766 | 5-10-5 | 287 | 1283 | 1302 | 0 | CCCAACTGTGATGACCTCGG |
| 410767 | 5-10-5 | 289 | 1305 | 1324 | 0 | GCTGGTCTTGGGCATTGGTG |
| 410768 | 5-10-5 | 305 | 1380 | 1399 | 0 | CAATGATGTCCTCCCCTGGG |
| 410769 | 5-10-5 | 318 | 1425 | 1444 | 0 | TCCCACTCTGTGACACAAAG |
| 410770 | 5-10-5 | 327 | 1500 | 1519 | 0 | CGGCCAGGGTGAGCTCCGGC |
| 410771 | 5-10-5 | 360 | 1628 | 1647 | 0 | ACCTGCCCCATGGGTGCTGG |
| 410772 | 5-10-5 | 364 | 1660 | 1679 | 0 | GCTGACCATACAGTCCTGCA |
| 410773 | 5-10-5 | 387 | 1905 | 1924 | 0 | TGGCCTCAGCTGGTGGAGCT |
| 410774 | 5-10-5 | 406 | 1936 | 1955 | 0 | TGTTGGTGGCAGTGGACACG |
| 410775 | 5-10-5 | 407 | 1962 | 1981 | 0 | AGCTGCAGCCTGTGAGGACG |
| 410776 | 5-10-5 | 408 | 1990 | 2009 | 0 | GTGCCAAGGTCCTCCACCTC |

TABLE 3-continued

Gapmer antisense compounds having a 5-10-5 motif targeted to SEQ ID NO: 1

| Isis No | Motif | SEQ ID NO | 5' Target Site on SEQ ID NO: 1 | 3' Target Site on SEQ ID NO: 1 | Mismatches | Sequence (5'-3') |
|---|---|---|---|---|---|---|
| 410777 | 5-10-5 | 409 | 2010 | 2029 | 0 | TCAGCACAGGCGGCTTGTGG |
| 410778 | 5-10-5 | 410 | 2040 | 2059 | 0 | CCACGCACTGGTTGGGCTGA |
| 410779 | 5-10-5 | 416 | 2120 | 2139 | 0 | CGGGATTCCATGCTCCTTGA |
| 410780 | 5-10-5 | 417 | 2150 | 2169 | 0 | GCAGGCCACGGTCACCTGCT |
| 410781 | 5-10-5 | 418 | 2187 | 2206 | 0 | GGAGGGCACTGCAGCCAGTC |
| 410782 | 5-10-5 | 429 | 2325 | 2344 | 0 | CCAGGTGCCGGCTCCGGCAG |
| 410783 | 5-10-5 | 430 | 2335 | 2354 | 0 | GAGGCCTGCGCCAGGTGCCG |

In certain embodiments, gap-widened antisense compounds are targeted to a PCSK9 nucleic acid. In certain such embodiments, gap-widened antisense compounds are targeted to SEQ ID NO: 1. In certain such embodiments, the nucleotide sequences illustrated in Table 2 have a 3-14-3 gap-widened motif. Table 4 illustrates gap-widened antisense compounds targeted to SEQ ID NO: 1, having a 3-14-3 motif, where the gap segment comprises 2'-deoxynucleotides and each wing segment comprises nucleotides comprising a 2'-O-methoxyethyl sugar modification. Internucleoside linkages are phosphorthioate, and cytidines are 5-methylcytidines.

TABLE 4

Gapmer antisense compounds having a 3-14-3 motif targeted to SEQ ID NO: 1

| Isis No | Motif | SEQ ID NO | 5' Target Site on SEQ ID NO: 1 | 3' Target Site on SEQ ID NO: 1 | Mismatches | Sequence (5'-3') |
|---|---|---|---|---|---|---|
| 399871 | 3-14-3 | 4 | 135 | 154 | 0 | GCGCGGAATCCTGGCTGGGA |
| 399872 | 3-14-3 | 5 | 242 | 261 | 0 | GAGGAGACCTAGAGGCCGTG |
| 399873 | 3-14-3 | 6 | 300 | 319 | 0 | AGGACCGCCTGGAGCTGACG |
| 399874 | 3-14-3 | 7 | 410 | 429 | 0 | ACGCAAGGCTAGCACCAGCT |
| 399949 | 3-14-3 | 8 | 417 | 436 | 0 | CCTCGGAACGCAAGGCTAGC |
| 399875 | 3-14-3 | 9 | 480 | 499 | 0 | CCTTGGCGCAGCGGTGGAAG |
| 399876 | 3-14-3 | 10 | 561 | 580 | 0 | GGCGGGCAGTGCGCTCTGAC |
| 399877 | 3-14-3 | 11 | 600 | 619 | 0 | TGGTGAGGTATCCCCGGCGG |
| 399950 | 3-14-3 | 12 | 606 | 625 | 0 | GGATCTTGGTGAGGTATCCC |
| 399951 | 3-14-3 | 13 | 615 | 634 | 0 | AGACATGCAGGATCTTGGTG |
| 399878 | 3-14-3 | 14 | 620 | 639 | 0 | ATGGAAGACATGCAGGATCT |
| 399879 | 3-14-3 | 15 | 646 | 665 | 0 | TTCACCAGGAAGCCAGGAAG |
| 399952 | 3-14-3 | 16 | 651 | 670 | 0 | TCATCTTCACCAGGAAGCCA |
| 399880 | 3-14-3 | 17 | 705 | 724 | 0 | CCTCGATGTAGTCGACATGG |
| 399881 | 3-14-3 | 18 | 785 | 804 | 0 | GTATTCATCCGCCCGGTACC |
| 399882 | 3-14-3 | 19 | 835 | 854 | 0 | CTGGTGTCTAGGAGATACAC |
| 399953 | 3-14-3 | 20 | 840 | 859 | 0 | GTATGCTGGTGTCTAGGAGA |
| 399883 | 3-14-3 | 21 | 860 | 879 | 0 | GATTTCCCGGTGGTCACTCT |
| 399954 | 3-14-3 | 22 | 866 | 885 | 0 | GCCCTCGATTTCCCGGTGGT |

TABLE 4-continued

Gapmer antisense compounds having a 3-14-3 motif targeted to SEQ ID NO: 1

| Isis No | Motif | SEQ ID NO | 5' Target Site on SEQ ID NO: 1 | 3' Target Site on SEQ ID NO: 1 | Mismatches | Sequence (5'-3') |
|---|---|---|---|---|---|---|
| 399955 | 3-14-3 | 23 | 880 | 899 | 0 | GTGACCATGACCCTGCCCTC |
| 399884 | 3-14-3 | 24 | 890 | 909 | 0 | CTCGAAGTCGGTGACCATGA |
| 399885 | 3-14-3 | 25 | 923 | 942 | 0 | GTGGAAGCGGGTCCCGTCCT |
| 399886 | 3-14-3 | 26 | 970 | 989 | 0 | ACCCCTGCCAGGTGGGTGCC |
| 399956 | 3-14-3 | 27 | 975 | 994 | 0 | TGACCACCCTGCCAGGTGG |
| 399887 | 3-14-3 | 28 | 1004 | 1023 | 0 | ACCCTTGGCCACGCCGGCAT |
| 399888 | 3-14-3 | 29 | 1040 | 1059 | 0 | TTGGCAGTTGAGCACGCGCA |
| 399957 | 3-14-3 | 30 | 1045 | 1064 | 0 | TTCCCTTGGCAGTTGAGCAC |
| 399889 | 3-14-3 | 31 | 1077 | 1096 | 0 | CCAGGCCTATGAGGGTGCCG |
| 399890 | 3-14-3 | 32 | 1098 | 1117 | 0 | GCTGGCTTTTCCGAATAAAC |
| 399891 | 3-14-3 | 33 | 1210 | 1229 | 0 | GTGACCAGCACGACCCCAGC |
| 399892 | 3-14-3 | 149 | 1297 | 1316 | 0 | TGGGCATTGGTGGCCCCAAC |
| 399893 | 3-14-3 | 34 | 1326 | 1345 | 0 | CCAAAGTCCCCAGGGTCACC |
| 399894 | 3-14-3 | 128 | 1330 | 1349 | 0 | GTCCCCAAAGTCCCCAGGGT |
| 399958 | 3-14-3 | 35 | 1335 | 1354 | 0 | AGTTGGTCCCCAAAGTCCCC |
| 399895 | 3-14-3 | 36 | 1340 | 1359 | 0 | GCCAAAGTTGGTCCCCAAAG |
| 399959 | 3-14-3 | 37 | 1352 | 1371 | 0 | GTCCACACAGCGGCCAAAGT |
| 399896 | 3-14-3 | 38 | 1361 | 1380 | 0 | GGCAAAGAGGTCCACACAGC |
| 399897 | 3-14-3 | 39 | 1389 | 1408 | 0 | TGGAGGCACCAATGATGTCC |
| 399960 | 3-14-3 | 40 | 1400 | 1419 | 0 | GCTGCAGTCGCTGGAGGCAC |
| 399961 | 3-14-3 | 41 | 1411 | 1430 | 0 | ACAAAGCAGGTGCTGCAGTC |
| 399898 | 3-14-3 | 101 | 1465 | 1484 | 0 | ATGGCTGCAATGCCAGCCAC |
| 399962 | 3-14-3 | 42 | 1470 | 1489 | 0 | GCATCATGGCTGCAATGCCA |
| 399963 | 3-14-3 | 43 | 1478 | 1497 | 0 | GGCAGACAGCATCATGGCTG |
| 399964 | 3-14-3 | 44 | 1526 | 1545 | 0 | GAAGTGGATCAGTCTCTGCC |
| 399899 | 3-14-3 | 45 | 1534 | 1553 | 0 | TTGGCAGAGAAGTGGATCAG |
| 399965 | 3-14-3 | 46 | 1539 | 1558 | 0 | CATCTTTGGCAGAGAAGTGG |
| 399966 | 3-14-3 | 47 | 1545 | 1564 | 0 | TGATGACATCTTTGGCAGAG |
| 399967 | 3-14-3 | 48 | 1552 | 1571 | 0 | GCCTCATTGATGACATCTTT |
| 399968 | 3-14-3 | 49 | 1564 | 1583 | 0 | TCAGGGAACCAGGCCTCATT |
| 399900 | 3-14-3 | 50 | 1569 | 1588 | 0 | GGTCCTCAGGGAACCAGGCC |
| 399901 | 3-14-3 | 87 | 1576 | 1595 | 0 | ACCCGCTGGTCCTCAGGGAA |
| 399969 | 3-14-3 | 51 | 1583 | 1602 | 0 | GGTCAGTACCCGCTGGTCCT |
| 399902 | 3-14-3 | 119 | 1605 | 1624 | 0 | GCAGGGCGGCCACCAGGTTG |
| 399903 | 3-14-3 | 52 | 1640 | 1659 | 0 | AAACAGCTGCCAACCTGCCC |
| 399970 | 3-14-3 | 53 | 1645 | 1664 | 0 | CTGCAAAACAGCTGCCAACC |
| 399904 | 3-14-3 | 54 | 1675 | 1694 | 0 | GTAGGCCCCGAGTGTGCTGA |

TABLE 4-continued

Gapmer antisense compounds having a 3-14-3 motif targeted to SEQ ID NO: 1

| Isis No | Motif | SEQ ID NO | 5' Target Site on SEQ ID NO: 1 | 3' Target Site on SEQ ID NO: 1 | Mismatches | Sequence (5'-3') |
|---|---|---|---|---|---|---|
| 399971 | 3-14-3 | 55 | 1740 | 1759 | 0 | AGAAACTGGAGCAGCTCAGC |
| 399972 | 3-14-3 | 56 | 1746 | 1765 | 0 | TCCTGGAGAAACTGGAGCAG |
| 399905 | 3-14-3 | 57 | 1812 | 1831 | 0 | CGTTGTGGGCCCGGCAGACC |
| 399906 | 3-14-3 | 58 | 1858 | 1877 | 0 | AGCAGGCAGCACCTGGCAAT |
| 399907 | 3-14-3 | 59 | 1920 | 1939 | 0 | CACGGGTCCCCATGCTGGCC |
| 399908 | 3-14-3 | 60 | 2100 | 2119 | 0 | CTTTGCATTCCAGACCTGGG |
| 399973 | 3-14-3 | 61 | 2105 | 2124 | 0 | CTTGACTTTGCATTCCAGAC |
| 399909 | 3-14-3 | 62 | 2310 | 2329 | 0 | GGCAGCAGATGGCAACGGCT |
| 399910 | 3-14-3 | 154 | 2410 | 2429 | 0 | TTTTAAAGCTCAGCCCCAGC |
| 399974 | 3-14-3 | 63 | 2415 | 2434 | 0 | AACCATTTTAAAGCTCAGCC |
| 399911 | 3-14-3 | 64 | 2504 | 2523 | 0 | TCAAGGGCCAGGCCAGCAGC |
| 399975 | 3-14-3 | 65 | 2509 | 2528 | 0 | CCCACTCAAGGGCCAGGCCA |
| 399976 | 3-14-3 | 122 | 2582 | 2601 | 0 | GGAGGGAGCTTCCTGGCACC |
| 399912 | 3-14-3 | 66 | 2597 | 2616 | 0 | ATGCCCCACAGTGAGGGAGG |
| 399913 | 3-14-3 | 67 | 2606 | 2625 | 0 | AATGGTGAAATGCCCCACAG |
| 399914 | 3-14-3 | 153 | 2649 | 2668 | 0 | TTGGGAGCAGCTGGCAGCAC |
| 399915 | 3-14-3 | 68 | 2750 | 2769 | 0 | CATGGGAAGAATCCTGCCTC |
| 399916 | 3-14-3 | 69 | 2832 | 2851 | 0 | GGAGATGAGGGCCATCAGCA |
| 399917 | 3-14-3 | 70 | 2900 | 2919 | 0 | TAGATGCCATCCAGAAAGCT |
| 399977 | 3-14-3 | 71 | 2906 | 2925 | 0 | TCTGGCTAGATGCCATCCAG |
| 399918 | 3-14-3 | 72 | 2983 | 3002 | 0 | GGCATAGAGCAGAGTAAAGG |
| 399978 | 3-14-3 | 73 | 2988 | 3007 | 0 | AGCCTGGCATAGAGCAGAGT |
| 399979 | 3-14-3 | 135 | 2994 | 3013 | 0 | TAGCACAGCCTGGCATAGAG |
| 399919 | 3-14-3 | 112 | 3227 | 3246 | 0 | GAAGAGGCTTGGCTTCAGAG |
| 399980 | 3-14-3 | 74 | 3233 | 3252 | 0 | AAGTAAGAAGAGGCTTGGCT |
| 399920 | 3-14-3 | 75 | 3437 | 3456 | 0 | GCTCAAGGAGGGACAGTTGT |
| 399921 | 3-14-3 | 76 | 3472 | 3491 | 0 | AAAGATAAATGTCTGCTTGC |
| 399981 | 3-14-3 | 77 | 3477 | 3496 | 0 | ACCCAAAAGATAAATGTCTG |
| 399922 | 3-14-3 | 78 | 3543 | 3562 | 0 | TCTTCAAGTTACAAAAGCAA |
| 399982 | 3-14-3 | 99 | 3550 | 3569 | 0 | ATAAATATCTTCAAGTTACA |
| 410574 | 3-14-3 | 184 | 597 | 616 | 0 | TGAGGTATCCCCGGCGGGCA |
| 410575 | 3-14-3 | 185 | 598 | 617 | 0 | GTGAGGTATCCCCGGCGGGC |
| 410576 | 3-14-3 | 186 | 599 | 618 | 0 | GGTGAGGTATCCCCGGCGGG |
| 410577 | 3-14-3 | 187 | 601 | 620 | 0 | TTGGTGAGGTATCCCCGGCG |
| 410578 | 3-14-3 | 188 | 602 | 621 | 0 | CTTGGTGAGGTATCCCCGGC |
| 410579 | 3-14-3 | 189 | 603 | 622 | 0 | TCTTGGTGAGGTATCCCCGG |

TABLE 4-continued

Gapmer antisense compounds having a 3-14-3 motif targeted to SEQ ID NO: 1

| Isis No | Motif | SEQ ID NO | 5' Target Site on SEQ ID NO: 1 | 3' Target Site on SEQ ID NO: 1 | Mismatches | Sequence (5'-3') |
|---|---|---|---|---|---|---|
| 410580 | 3-14-3 | 190 | 604 | 623 | 0 | ATCTTGGTGAGGTATCCCCG |
| 410581 | 3-14-3 | 191 | 605 | 624 | 0 | GATCTTGGTGAGGTATCCCC |
| 410582 | 3-14-3 | 192 | 607 | 626 | 0 | AGGATCTTGGTGAGGTATCC |
| 405604 | 3-14-3 | 236 | 963 | 982 | 0 | CCAGGTGGGTGCCATGACTG |
| 410583 | 3-14-3 | 243 | 997 | 1016 | 0 | GCCACGCCGGCATCCCGGCC |
| 410584 | 3-14-3 | 244 | 998 | 1017 | 0 | GGCCACGCCGGCATCCCGGC |
| 410585 | 3-14-3 | 245 | 999 | 1018 | 0 | TGGCCACGCCGGCATCCCGG |
| 410586 | 3-14-3 | 246 | 1000 | 1019 | 0 | TTGGCCACGCCGGCATCCCG |
| 410587 | 3-14-3 | 247 | 1001 | 1020 | 0 | CTTGGCCACGCCGGCATCCC |
| 410588 | 3-14-3 | 248 | 1002 | 1021 | 0 | CCTTGGCCACGCCGGCATCC |
| 410589 | 3-14-3 | 249 | 1003 | 1022 | 0 | CCCTTGGCCACGCCGGCATC |
| 410590 | 3-14-3 | 250 | 1005 | 1024 | 0 | CACCCTTGGCCACGCCGGCA |
| 410591 | 3-14-3 | 251 | 1006 | 1025 | 0 | GCACCCTTGGCCACGCCGGC |
| 410592 | 3-14-3 | 252 | 1007 | 1026 | 0 | GGCACCCTTGGCCACGCCGG |
| 410593 | 3-14-3 | 253 | 1008 | 1027 | 0 | TGGCACCCTTGGCCACGCCG |
| 410594 | 3-14-3 | 254 | 1009 | 1028 | 0 | CTGGCACCCTTGGCCACGCC |
| 410595 | 3-14-3 | 255 | 1010 | 1029 | 0 | GCTGGCACCCTTGGCCACGC |
| 410596 | 3-14-3 | 348 | 1562 | 1581 | 0 | AGGGAACCAGGCCTCATTGA |
| 410597 | 3-14-3 | 349 | 1563 | 1582 | 0 | CAGGGAACCAGGCCTCATTG |
| 410598 | 3-14-3 | 350 | 1565 | 1584 | 0 | CTCAGGGAACCAGGCCTCAT |
| 410599 | 3-14-3 | 351 | 1566 | 1585 | 0 | CCTCAGGGAACCAGGCCTCA |
| 410600 | 3-14-3 | 352 | 1567 | 1586 | 0 | TCCTCAGGGAACCAGGCCTC |
| 410601 | 3-14-3 | 353 | 1568 | 1587 | 0 | GTCCTCAGGGAACCAGGCCT |
| 410602 | 3-14-3 | 354 | 1570 | 1589 | 0 | TGGTCCTCAGGGAACCAGGC |
| 410603 | 3-14-3 | 355 | 1571 | 1590 | 0 | CTGGTCCTCAGGGAACCAGG |
| 410604 | 3-14-3 | 356 | 1572 | 1591 | 0 | GCTGGTCCTCAGGGAACCAG |
| 405641 | 3-14-3 | 373 | 1737 | 1756 | 0 | AACTGGAGCAGCTCAGCAGC |
| 410605 | 3-14-3 | 376 | 1849 | 1868 | 0 | CACCTGGCAATGGCGTAGAC |
| 410606 | 3-14-3 | 377 | 1850 | 1869 | 0 | GCACCTGGCAATGGCGTAGA |
| 410607 | 3-14-3 | 378 | 1851 | 1870 | 0 | AGCACCTGGCAATGGCGTAG |
| 410608 | 3-14-3 | 379 | 1852 | 1871 | 0 | CAGCACCTGGCAATGGCGTA |
| 410609 | 3-14-3 | 380 | 1853 | 1872 | 0 | GCAGCACCTGGCAATGGCGT |
| 410610 | 3-14-3 | 381 | 1854 | 1873 | 0 | GGCAGCACCTGGCAATGGCG |
| 410611 | 3-14-3 | 382 | 1855 | 1874 | 0 | AGGCAGCACCTGGCAATGGC |
| 410612 | 3-14-3 | 383 | 1856 | 1875 | 0 | CAGGCAGCACCTGGCAATGG |
| 410613 | 3-14-3 | 384 | 1857 | 1876 | 0 | GCAGGCAGCACCTGGCAATG |
| 410614 | 3-14-3 | 385 | 1859 | 1878 | 0 | TAGCAGGCAGCACCTGGCAA |

TABLE 4-continued

Gapmer antisense compounds having a 3-14-3 motif targeted to SEQ ID NO: 1

| Isis No | Motif | SEQ ID NO | 5' Target Site on SEQ ID NO: 1 | 3' Target Site on SEQ ID NO: 1 | Mismatches | Sequence (5'-3') |
|---|---|---|---|---|---|---|
| 410615 | 3-14-3 | 388 | 1915 | 1934 | 0 | GTCCCCATGCTGGCCTCAGC |
| 410616 | 3-14-3 | 389 | 1916 | 1935 | 0 | GGTCCCCATGCTGGCCTCAG |
| 410617 | 3-14-3 | 390 | 1917 | 1936 | 0 | GGGTCCCCATGCTGGCCTCA |
| 410618 | 3-14-3 | 391 | 1918 | 1937 | 0 | CGGGTCCCCATGCTGGCCTC |
| 410619 | 3-14-3 | 392 | 1919 | 1938 | 0 | ACGGGTCCCCATGCTGGCCT |
| 410620 | 3-14-3 | 393 | 1921 | 1940 | 0 | ACACGGGTCCCCATGCTGGC |
| 410621 | 3-14-3 | 394 | 1922 | 1941 | 0 | GACACGGGTCCCCATGCTGG |
| 410622 | 3-14-3 | 395 | 1923 | 1942 | 0 | GGACACGGGTCCCCATGCTG |
| 410623 | 3-14-3 | 396 | 1924 | 1943 | 0 | TGGACACGGGTCCCCATGCT |
| 410624 | 3-14-3 | 397 | 1925 | 1944 | 0 | GTGGACACGGGTCCCCATGC |
| 410625 | 3-14-3 | 398 | 1926 | 1945 | 0 | AGTGGACACGGGTCCCCATG |
| 410626 | 3-14-3 | 399 | 1927 | 1946 | 0 | CAGTGGACACGGGTCCCCAT |
| 410627 | 3-14-3 | 400 | 1928 | 1947 | 0 | GCAGTGGACACGGGTCCCCA |
| 410628 | 3-14-3 | 401 | 1929 | 1948 | 0 | GGCAGTGGACACGGGTCCCC |
| 410629 | 3-14-3 | 402 | 1930 | 1949 | 0 | TGGCAGTGGACACGGGTCCC |
| 410630 | 3-14-3 | 403 | 1931 | 1950 | 0 | GTGGCAGTGGACACGGGTCC |
| 410631 | 3-14-3 | 404 | 1932 | 1951 | 0 | GGTGGCAGTGGACACGGGTC |
| 410632 | 3-14-3 | 405 | 1933 | 1952 | 0 | TGGTGGCAGTGGACACGGGT |
| 410633 | 3-14-3 | 411 | 2101 | 2120 | 0 | ACTTTGCATTCCAGACCTGG |
| 410634 | 3-14-3 | 412 | 2102 | 2121 | 0 | GACTTTGCATTCCAGACCTG |
| 410635 | 3-14-3 | 413 | 2103 | 2122 | 0 | TGACTTTGCATTCCAGACCT |
| 410636 | 3-14-3 | 414 | 2104 | 2123 | 0 | TTGACTTTGCATTCCAGACC |
| 410637 | 3-14-3 | 419 | 2305 | 2324 | 0 | CAGATGGCAACGGCTGTCAC |
| 410638 | 3-14-3 | 420 | 2306 | 2325 | 0 | GCAGATGGCAACGGCTGTCA |
| 410639 | 3-14-3 | 421 | 2307 | 2326 | 0 | AGCAGATGGCAACGGCTGTC |
| 410640 | 3-14-3 | 422 | 2308 | 2327 | 0 | CAGCAGATGGCAACGGCTGT |
| 410641 | 3-14-3 | 423 | 2309 | 2328 | 0 | GCAGCAGATGGCAACGGCTG |
| 410642 | 3-14-3 | 424 | 2311 | 2330 | 0 | CGGCAGCAGATGGCAACGGC |
| 410643 | 3-14-3 | 425 | 2312 | 2331 | 0 | CCGGCAGCAGATGGCAACGG |
| 410644 | 3-14-3 | 426 | 2313 | 2332 | 0 | TCCGGCAGCAGATGGCAACG |
| 410645 | 3-14-3 | 427 | 2314 | 2333 | 0 | CTCCGGCAGCAGATGGCAAC |
| 410646 | 3-14-3 | 428 | 2315 | 2334 | 0 | GCTCCGGCAGCAGATGGCAA |

In certain embodiments, gap-widened antisense compounds are targeted to a PCSK9 nucleic acid. In certain such embodiments, gap-widened antisense compounds are targeted to SEQ ID NO: 1. In certain such embodiments, the nucleotide sequences illustrated in Table 2 have a 2-13-5 gap-widened motif. Table 5 illustrates gap-widened antisense compounds targeted to SEQ ID NO: 1, having a 2-13-5 motif, where the gap segment comprises 2'-deoxynucleotides and each wing segment comprises nucleotides comprising a 2'-O-methoxyethyl sugar modification. Internucleoside linkages are phosphorthioate, and cytidines are 5-methylcytidines.

TABLE 5

Gapmer antisense compounds having a 2-13-5 motif targeted to SEQ ID NO: 1

| Isis No | Motif | SEQ ID NO | 5' Target Site on SEQ ID NO: 1 | 3' Target Site on SEQ ID NO: 1 | Mismatches | Sequence (5'-3') |
|---|---|---|---|---|---|---|
| 410647 | 2-13-5 | 184 | 597 | 616 | 0 | TGAGGTATCCCCGGCGGGCA |
| 410648 | 2-13-5 | 185 | 598 | 617 | 0 | GTGAGGTATCCCCGGCGGGC |
| 410649 | 2-13-5 | 186 | 599 | 618 | 0 | GGTGAGGTATCCCCGGCGGG |
| 410650 | 2-13-5 | 11 | 600 | 619 | 0 | TGGTGAGGTATCCCCGGCGG |
| 410651 | 2-13-5 | 187 | 601 | 620 | 0 | TTGGTGAGGTATCCCCGGCG |
| 410652 | 2-13-5 | 188 | 602 | 621 | 0 | CTTGGTGAGGTATCCCCGGC |
| 410653 | 2-13-5 | 189 | 603 | 622 | 0 | TCTTGGTGAGGTATCCCCGG |
| 410654 | 2-13-5 | 190 | 604 | 623 | 0 | ATCTTGGTGAGGTATCCCCG |
| 410655 | 2-13-5 | 191 | 605 | 624 | 0 | GATCTTGGTGAGGTATCCCC |
| 410656 | 2-13-5 | 12 | 606 | 625 | 0 | GGATCTTGGTGAGGTATCCC |
| 410657 | 2-13-5 | 192 | 607 | 626 | 0 | AGGATCTTGGTGAGGTATCC |
| 410658 | 2-13-5 | 243 | 997 | 1016 | 0 | GCCACGCCGGCATCCCGGCC |
| 410659 | 2-13-5 | 244 | 998 | 1017 | 0 | GGCCACGCCGGCATCCCGGC |
| 410660 | 2-13-5 | 245 | 999 | 1018 | 0 | TGGCCACGCCGGCATCCCGG |
| 410661 | 2-13-5 | 246 | 1000 | 1019 | 0 | TTGGCCACGCCGGCATCCCG |
| 410662 | 2-13-5 | 247 | 1001 | 1020 | 0 | CTTGGCCACGCCGGCATCCC |
| 410663 | 2-13-5 | 248 | 1002 | 1021 | 0 | CCTTGGCCACGCCGGCATCC |
| 410664 | 2-13-5 | 249 | 1003 | 1022 | 0 | CCCTTGGCCACGCCGGCATC |
| 410665 | 2-13-5 | 28 | 1004 | 1023 | 0 | ACCCTTGGCCACGCCGGCAT |
| 410666 | 2-13-5 | 250 | 1005 | 1024 | 0 | CACCCTTGGCCACGCCGGCA |
| 410667 | 2-13-5 | 251 | 1006 | 1025 | 0 | GCACCCTTGGCCACGCCGGC |
| 410668 | 2-13-5 | 252 | 1007 | 1026 | 0 | GGCACCCTTGGCCACGCCGG |
| 410669 | 2-13-5 | 253 | 1008 | 1027 | 0 | TGGCACCCTTGGCCACGCCG |
| 410670 | 2-13-5 | 254 | 1009 | 1028 | 0 | CTGGCACCCTTGGCCACGCC |
| 410671 | 2-13-5 | 255 | 1010 | 1029 | 0 | GCTGGCACCCTTGGCCACGC |
| 410672 | 2-13-5 | 348 | 1562 | 1581 | 0 | AGGGAACCAGGCCTCATTGA |
| 410673 | 2-13-5 | 349 | 1563 | 1582 | 0 | CAGGGAACCAGGCCTCATTG |
| 410674 | 2-13-5 | 49 | 1564 | 1583 | 0 | TCAGGGAACCAGGCCTCATT |
| 410675 | 2-13-5 | 350 | 1565 | 1584 | 0 | CTCAGGGAACCAGGCCTCAT |
| 410676 | 2-13-5 | 351 | 1566 | 1585 | 0 | CCTCAGGGAACCAGGCCTCA |
| 410677 | 2-13-5 | 352 | 1567 | 1586 | 0 | TCCTCAGGGAACCAGGCCTC |
| 410678 | 2-13-5 | 353 | 1568 | 1587 | 0 | GTCCTCAGGGAACCAGGCCT |
| 410679 | 2-13-5 | 50 | 1569 | 1588 | 0 | GGTCCTCAGGGAACCAGGCC |
| 410680 | 2-13-5 | 354 | 1570 | 1589 | 0 | TGGTCCTCAGGGAACCAGGC |
| 410681 | 2-13-5 | 355 | 1571 | 1590 | 0 | CTGGTCCTCAGGGAACCAGG |
| 410682 | 2-13-5 | 356 | 1572 | 1591 | 0 | GCTGGTCCTCAGGGAACCAG |
| 410683 | 2-13-5 | 376 | 1849 | 1868 | 0 | CACCTGGCAATGGCGTAGAC |

TABLE 5-continued

Gapmer antisense compounds having a 2-13-5 motif targeted to SEQ ID NO: 1

| Isis No | Motif | SEQ ID NO | 5' Target Site on SEQ ID NO: 1 | 3' Target Site on SEQ ID NO: 1 | Mismatches | Sequence (5'-3') |
|---|---|---|---|---|---|---|
| 410684 | 2-13-5 | 377 | 1850 | 1869 | 0 | GCACCTGGCAATGGCGTAGA |
| 410685 | 2-13-5 | 378 | 1851 | 1870 | 0 | AGCACCTGGCAATGGCGTAG |
| 410686 | 2-13-5 | 379 | 1852 | 1871 | 0 | CAGCACCTGGCAATGGCGTA |
| 410687 | 2-13-5 | 380 | 1853 | 1872 | 0 | GCAGCACCTGGCAATGGCGT |
| 410688 | 2-13-5 | 381 | 1854 | 1873 | 0 | GGCAGCACCTGGCAATGGCG |
| 410689 | 2-13-5 | 382 | 1855 | 1874 | 0 | AGGCAGCACCTGGCAATGGC |
| 410690 | 2-13-5 | 383 | 1856 | 1875 | 0 | CAGGCAGCACCTGGCAATGG |
| 410691 | 2-13-5 | 384 | 1857 | 1876 | 0 | GCAGGCAGCACCTGGCAATG |
| 410692 | 2-13-5 | 58 | 1858 | 1877 | 0 | AGCAGGCAGCACCTGGCAAT |
| 410693 | 2-13-5 | 385 | 1859 | 1878 | 0 | TAGCAGGCAGCACCTGGCAA |
| 410694 | 2-13-5 | 388 | 1915 | 1934 | 0 | GTCCCCATGCTGGCCTCAGC |
| 410695 | 2-13-5 | 389 | 1916 | 1935 | 0 | GGTCCCCATGCTGGCCTCAG |
| 410696 | 2-13-5 | 390 | 1917 | 1936 | 0 | GGGTCCCCATGCTGGCCTCA |
| 410697 | 2-13-5 | 391 | 1918 | 1937 | 0 | CGGGTCCCCATGCTGGCCTC |
| 410698 | 2-13-5 | 392 | 1919 | 1938 | 0 | ACGGGTCCCCATGCTGGCCT |
| 410699 | 2-13-5 | 59 | 1920 | 1939 | 0 | CACGGGTCCCCATGCTGGCC |
| 410700 | 2-13-5 | 393 | 1921 | 1940 | 0 | ACACGGGTCCCCATGCTGGC |
| 410701 | 2-13-5 | 394 | 1922 | 1941 | 0 | DACACGGGTCCCCATGCTGG |
| 410702 | 2-13-5 | 395 | 1923 | 1942 | 0 | GGACACGGGTCCCCATGCTG |
| 410703 | 2-13-5 | 396 | 1924 | 1943 | 0 | TGGACACGGGTCCCCATGCT |
| 410704 | 2-13-5 | 397 | 1925 | 1944 | 0 | GTGGACACGGGTCCCCATGC |
| 410705 | 2-13-5 | 398 | 1926 | 1945 | 0 | AGTGGACACGGGTCCCCATG |
| 410706 | 2-13-5 | 399 | 1927 | 1946 | 0 | CAGTGGACACGGGTCCCCAT |
| 410707 | 2-13-5 | 400 | 1928 | 1947 | 0 | GCAGTGGACACGGGTCCCCA |
| 410708 | 2-13-5 | 401 | 1929 | 1948 | 0 | GGCAGTGGACACGGGTCCCC |
| 410709 | 2-13-5 | 402 | 1930 | 1949 | 0 | TGGCAGTGGACACGGGTCCC |
| 410710 | 2-13-5 | 403 | 1931 | 1950 | 0 | GTGGCAGTGGACACGGGTCC |
| 410711 | 2-13-5 | 404 | 1932 | 1951 | 0 | GGTGGCAGTGGACACGGGTC |
| 410712 | 2-13-5 | 405 | 1933 | 1952 | 0 | TGGTGGCAGTGGACACGGGT |
| 410713 | 2-13-5 | 60 | 2100 | 2119 | 0 | CTTTGCATTCCAGACCTGGG |
| 410714 | 2-13-5 | 411 | 2101 | 2120 | 0 | ACTTTGCATTCCAGACCTGG |
| 410715 | 2-13-5 | 412 | 2102 | 2121 | 0 | GACTTTGCATTCCAGACCTG |
| 410716 | 2-13-5 | 413 | 2103 | 2122 | 0 | TGACTTTGCATTCCAGACCT |
| 410717 | 2-13-5 | 414 | 2104 | 2123 | 0 | TTGACTTTGCATTCCAGACC |
| 410718 | 2-13-5 | 61 | 2105 | 2124 | 0 | CTTGACTTTGCATTCCAGAC |
| 410719 | 2-13-5 | 419 | 2305 | 2324 | 0 | CAGATGGCAACGGCTGTCAC |

TABLE 5-continued

Gapmer antisense compounds having a 2-13-5 motif targeted to SEQ ID NO: 1

| Isis No | Motif | SEQ ID NO | 5' Target Site on SEQ ID NO: 1 | 3' Target Site on SEQ ID NO: 1 | Mismatches | Sequence (5'-3') |
|---|---|---|---|---|---|---|
| 410720 | 2-13-5 | 420 | 2306 | 2325 | 0 | GCAGATGGCAACGGCTGTCA |
| 410721 | 2-13-5 | 421 | 2307 | 2326 | 0 | AGCAGATGGCAACGGCTGTC |
| 410722 | 2-13-5 | 422 | 2308 | 2327 | 0 | CAGCAGATGGCAACGGCTGT |
| 410723 | 2-13-5 | 423 | 2309 | 2328 | 0 | GCAGCAGATGGCAACGGCTG |
| 410724 | 2-13-5 | 62 | 2310 | 2329 | 0 | GGCAGCAGATGGCAACGGCT |
| 410725 | 2-13-5 | 424 | 2311 | 2330 | 0 | CGGCAGCAGATGGCAACGGC |
| 410726 | 2-13-5 | 425 | 2312 | 2331 | 0 | CCGGCAGCAGATGGCAACGG |
| 410727 | 2-13-5 | 426 | 2313 | 2332 | 0 | TCCGGCAGCAGATGGCAACG |
| 410728 | 2-13-5 | 427 | 2314 | 2333 | 0 | CTCCGGCAGCAGATGGCAAC |
| 410729 | 2-13-5 | 428 | 2315 | 2334 | 0 | GCTCCGGCAGCAGATGGCAA |

In certain embodiments, gap-widened antisense compounds are targeted to a PCSK9 nucleic acid. In certain such embodiments, gap-widened antisense compounds are targeted to SEQ ID NO: 1. In certain such embodiments, the nucleotide sequences illustrated in Table 2 have a 3-13-4 gap-widened motif. Table 6 illustrates gap-widened antisense compounds targeted to SEQ ID NO: 1, having a 3-13-4 motif, where the gap segment comprises 2'-deoxynucleotides and each wing segment comprises nucleotides comprising a 2'-O-methoxyethyl sugar modification. Internucleoside linkages are phosphorthioate, and cytidines are 5-methylcytidines.

TABLE 6

Gapmer antisense compounds having a 3-13-4 motif targeted to SEQ ID NO: 1

| Oligo | Motif | SEQ ID NO: | 5' start site | 3' Start Site | Mismatches | OligoSeq |
|---|---|---|---|---|---|---|
| 405526 | 3-13-4 | 236 | 963 | 982 | 0 | CCAGGTGGGTGCCATGACTG |
| 405557 | 3-13-4 | 50 | 1569 | 1588 | 0 | GGTCCTCAGGGAACCAGGCC |
| 405564 | 3-13-4 | 373 | 1737 | 1756 | 0 | AACTGGAGCAGCTCAGCAGC |

The following embodiments set forth target regions of PCSK9 nucleic acids. Also illustrated are examples of antisense compounds targeted to the target regions. It is understood that the sequence set forth in each SEQ ID NO is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

In certain embodiments, antisense compounds target a range of a PCSK9 nucleic acid. In certain embodiment, such compounds contain at least an 8 nucleotide core sequence in common. In certain embodiments, such compounds sharing at least an 8 nucleotide core sequence targets the following nucleotide regions of SEQ ID NO: 1: 294-317, 406-440, 406-526, 410-436, 410-499, 446-526, 545-581, 591-619, 591-704, 591-743, 595-622, 600-626, 600-639, 600-670, 601-628, 602-628, 603-630, 611-636, 620-647, 638-665, 648-674, 657-684, 705-743, 782-810, 821-859, 835-859, 835-917, 835-942, 860-887, 860-899, 860-909, 860-917, 869-895, 878-905, 888-909, 923-952, 960-1034, 960-1173, 960-986, 967-991, 970-1023, 970-1064, 970-1117, 970-996, 977-1004, 985-1011, 989-1016, 992-1019, 997-1024, 997-1024, 998-1025, 999-1026, 1000-1027, 1001-1028, 1002-1021, 1002-1029, 1003-1029, 1004-1029, 1005-1029, 1006-1029, 1007-1034, 1036-1061, 1045-1072, 1076-1096, 1088-1115, 1098-1123, 1200-1251, 1210-1237, 1219-1245, 1228-1251, 1273-1444, 1295-1316, 1318-1345, 1328-1354, 1337-1361, 1344-1371, 1354-1377, 1380-1406, 1389-1416, 1400-1426, 1409-1434, 1465-1491, 1465-1602, 1474-1499, 1482-1519, 1513-1540, 1523-1549, 1526-1602, 1526-1624, 1532-1558, 1541-1568, 1552-1579, 1560-1587, 1561-1589, 1564-1591, 1565-1592, 1566-1592, 1567-1592, 1570-1597, 1571-1599, 1605-1706, 1628-1706, 1640-1666, 1672-1698, 1681-1706, 1735-1761, 1735-1765, 1740-1765, 1849-1876, 1849-1879, 1850-1877, 1851-1877, 1852-1878, 1852-1879, 1853-1879, 1854-1879, 1905-1955, 1915-1942, 1916-1943, 1917-1944, 1918-1945, 1919-1946, 1920-1939, 1920-1947, 1921-1948, 1922-1949, 1923-1950, 1924-1951, 1925-1952, 1926-1952, 1927-1952, 1928-1955, 1962-2059, 2040-2126, 2100-2126, 2100-2139, 2100-2206, 2101-2126, 2305-2332, 2305-2354, 2306-2333, 2307-2334, 2308-2334, 2309-2334, 2310-2334, 2410-2434, 2504-2528, 2509-2528, 2582-2625, 2606-2668, 2828-2855, 2832-2851, 2900-2927, 2900-2929, 2902-2927, 2983-3007, 2983-3013, 3227-3252, 3227-3456, 3472-3496, or 3543-3569.

In certain embodiments, a target region is nucleotides 294-317 of SEQ ID NO: 1. In certain embodiments, an antisense compound is targeted to nucleotides 294-317 of SEQ ID NO: 1. In certain embodiments, an antisense compound targeted to a PCSK9 nucleic acid comprises a nucleotide sequence selected from SEQ ID NOs: 159 or 160. In certain such embodiments, an antisense compound targeted to nucleotides 294-317 of SEQ ID NO: 1 is selected from ISIS NOs: 410742 or 405999.

In certain embodiments, a target region is nucleotides 406-440 of SEQ ID NO: 1. In certain embodiments, an antisense compound is targeted to nucleotides 406-440 of SEQ ID NO: 1. In certain embodiments, an antisense compound targeted to a PCSK9 nucleic acid comprises a nucleotide sequence selected from SEQ ID NOs: 7, 8, 162, 163, 164, 165, 166, 167, 168, 169 or 170. In certain such embodiments, an antisense compound targeted to nucleotides 406-440 of SEQ ID NO: 1 is selected from ISIS NOs: 405861, 405862, 405863, 405864, 395152, 399874, 405865, 405866, 405867, 405868, 399793, 399949, or 410743.

In certain embodiments, a target region is nucleotides 406-526 of SEQ ID NO: 1. In certain embodiments, an antisense compound is targeted to nucleotides 406-526 of SEQ ID NO: 1. In certain embodiments, an antisense compound targeted to a PCSK9 nucleic acid comprises a nucleotide sequence selected from SEQ ID NOs: 7, 8, 9, 162, 163, 164, 165, 166, 167, 168, 169, 170, 171, 172, 173, 174, 175, or 176. In certain such embodiments, an antisense compound targeted to nucleotides 406-526 of SEQ ID NO: 1 is selected from ISIS NOs: 405861, 405862, 405863, 405864, 395152, 399874, 405865, 405866, 405867, 405868, 399793, 399950, 410743, 410744, 410745, 395153, 399875, 406000, 406001, 406002 or 410746.

In certain embodiments, a target region is nucleotides 410-436 of SEQ ID NO: 1. In certain embodiments, an antisense compound is targeted to nucleotides 410-436 of SEQ ID NO: 1. In certain embodiments, an antisense compound targeted to a PCSK9 nucleic acid comprises a nucleotide sequence selected from SEQ ID NOs: 7, 8, 166, 167, 168, 169 or 169. In certain such embodiments, an antisense compound targeted to nucleotides 410-436 of SEQ ID NO: 1 is selected from ISIS NOs: 395152, 399874, 405865, 405866, 405867, 405868, or 399793.

In certain embodiments, a target region is nucleotides 410-499 of SEQ ID NO: 1. In certain embodiments, an antisense compound is targeted to nucleotides 410-499 of SEQ ID NO: 1. In certain embodiments, an antisense compound targeted to a PCSK9 nucleic acid comprises a nucleotide sequence selected from SEQ ID NOs: 7, 8, 9, 166, 167, 169, 170, 171 or 172. In certain such embodiments, an antisense compound targeted to nucleotides 410-499 of SEQ ID NO: 1 is selected from ISIS NOs: 395152, 399874, 405865, 405866, 405867, 405868, 399793, 399949, 410743, 410744, 410745, 395153, or 399875.

In certain embodiments, a target region is nucleotides 446-526 of SEQ ID NO: 1. In certain embodiments, an antisense compound is targeted to nucleotides 446-526 of SEQ ID NO: 1. In certain embodiments, an antisense compound targeted to a PCSK9 nucleic acid comprises a nucleotide sequence selected from SEQ ID NOs: 9, 171, 172, 173, 174, 175 or 176. In certain such embodiments, an antisense compound targeted to nucleotides 446-526 of SEQ ID NO: 1 is selected from ISIS NOs: 410744, 410745, 395153, 399875, 406000, 406001, 406002, or 410746.

In certain embodiments, a target region is nucleotides 545-581 of SEQ ID NO: 1. In certain embodiments, an antisense compound is targeted to nucleotides 545-581 of SEQ ID NO: 1. In certain embodiments, an antisense compound targeted to a PCSK9 nucleic acid comprises a nucleotide sequence selected from SEQ ID NOs: 10, 177, 178, 179, 180 or 181. In certain such embodiments, an antisense compound targeted to nucleotides 545-581 of SEQ ID NO: 1 is selected from ISIS NOs: 410747, 406003, 406004, 406005, 395154, 399876, or 406006.

In certain embodiments, a target region is nucleotides 591-619 of SEQ ID NO: 1. In certain embodiments, an antisense compound is targeted to nucleotides 591-619 of SEQ ID NO: 1. In certain embodiments, an antisense compound targeted to a PCSK9 nucleic acid comprises a nucleotide sequence selected from SEQ ID NOs: 11, 182, 183, 184, 185 or 186. In certain such embodiments, an antisense compound targeted to nucleotides 591-619 of SEQ ID NO: 1 is selected from ISIS NOs: 410748, 406007, 410529, 410574, 410647, 410530, 410575, 410648, 410531, 410576, 410649, 395155, 399877, or 410650.

In certain embodiments, a target region is nucleotides 591-704 of SEQ ID NO: 1. In certain embodiments, an antisense compound is targeted to nucleotides 591-704 of SEQ ID NO: 1. In certain embodiments, an antisense compound targeted to a PCSK9 nucleic acid comprises a nucleotide sequence selected from SEQ ID NOs: 11, 12, 13, 14, 15, 16, 182, 183, 184, 185, 186, 187, 188, 189, 190, 191, 192, 193, 194, 195, 196, 197, 198, 199, 200, 201, 202, 203, 204, 205, 206, 207, or 208. In certain such embodiments, an antisense compound targeted to nucleotides 591-704 of SEQ ID NO: 1 is selected from ISIS NOs: 410748, 406007, 410529, 410574, 410647, 410530, 410575, 410648, 410531, 410576, 410649, 395155, 399877, 410650, 410532, 410577, 410651, 406008, 410578, 410652, 410533, 410579, 410653, 406009, 410580, 410654, 410534, 410581, 410655, 399794, 399950, 410656, or 410751.

In certain embodiments, a target region is nucleotides 591-743 of SEQ ID NO: 1. In certain embodiments, an antisense compound is targeted to nucleotides 591-743 of SEQ ID NO: 1. In certain embodiments, an antisense compound targeted to a PCSK9 nucleic acid comprises a nucleotide sequence selected from SEQ ID NOs: 11, 12, 13, 14, 15, 16, 17, 182, 183, 184, 185, 186, 187, 188, 189, 190, 191, 192, 193, 194, 195, 196, 197, 198, 199, 200, 201, 202, 203, 204, 205, 206, 207, 208, or 209. In certain such embodiments, an antisense compound targeted to nucleotides 591-743 of SEQ ID NO: 1 is selected from ISIS NOs: 410748, 406007, 410529, 410574, 410647, 410530, 410575, 410648, 410531, 410576, 410649, 395155, 399877, 410650, 410532, 410577, 410651, 406008, 410578, 410652, 410533, 410579, 410653, 406009, 410580, 410654, 410534, 410581, 410655, 399794, 399950, 410656, or 410752.

In certain embodiments, a target region is nucleotides 595-622 of SEQ ID NO: 1. In certain embodiments, an antisense compound is targeted to nucleotides 595-622 of SEQ ID NO: 1. In certain embodiments, an antisense compound targeted to a PCSK9 nucleic acid comprises a nucleotide sequence selected from SEQ ID NOs: 11, 183, 184, 185, 186, 187, 188, or 189. In certain such embodiments, an antisense compound targeted to nucleotides 595-622 of SEQ ID NO: 1 is selected from ISIS NOs: 406007, 410529, 410574, 410647, 410530, 410575, 410648, 410531, 410576, 410649, 395155, 399877, 410650, 410532, 410577, 410651, 406008, 410578, 410652, 410533, 410579, or 410653.

In certain embodiments, a target region is nucleotides 600-626 of SEQ ID NO: 1. In certain embodiments, an antisense compound is targeted to nucleotides 600-626 of SEQ ID NO: 1. In certain embodiments, an antisense compound targeted to a PCSK9 nucleic acid comprises a nucleotide sequence selected from SEQ ID NOs: 11, 12, 87, 188, 189, 190, 191, or 192. In certain such embodiments, an antisense compound targeted to nucleotides 600-626 of SEQ ID NO: 1 is selected from ISIS NOs: 395155, 399877, 410650, 410532, 410577, 410651, 406008, 410578, 410652, 410533, 410579, 410653, 406009, 410580, 410654, 410534, 410581, 410655, 399794, 399950, 410656, 410535, 410582, or 410657.

In certain embodiments, a target region is nucleotides 600-639 of SEQ ID NO: 1. In certain embodiments, an antisense compound is targeted to nucleotides 600-639 of SEQ ID NO: 1. In certain embodiments, an antisense compound targeted to a PCSK9 nucleic acid comprises a nucleotide sequence selected from SEQ ID NOs: 11, 12, 13, 14, 187, 188, 189, 190, 191, 192, 193, 194, 195, or 196. In certain such embodiments, an antisense compound targeted to nucleotides 600-639 of SEQ ID NO: 1 is selected from ISIS NOs: 395155, 399877, 410650, 410532, 410577, 410651, 406008, 410578, 410652, 410533, 410579, 410653, 406009, 410580, 410654, 410534, 410581, 410655, 399794, 399950, 410656, 410535, 410582, 410657, 406010, 406011, 406012, 399795, 399951, 406013, 395156, or 399878.

In certain embodiments, a target region is nucleotides 600-670 of SEQ ID NO: 1. In certain embodiments, an antisense compound is targeted to nucleotides 600-670 of SEQ ID NO: 1. In certain embodiments, an antisense compound targeted to a PCSK9 nucleic acid comprises a nucleotide sequence selected from SEQ ID NOs: 11, 12, 13, 14, 15, 16, 187, 188, 189, 190, 191, 192, 193, 194, 195, 196, 197, 198, or 199. In certain such embodiments, an antisense compound targeted to nucleotides 600-670 of SEQ ID NO: 1 is selected from ISIS NOs: 395155, 399877, 410650, 410532, 410577, 410651, 406008, 410578, 410652, 410533, 410579, 410653, 406009, 410580, 410654, 410534, 410581, 410655, 399794, 399950, 410656, 410535, 410582, 410657, 406010, 406011, 406012, 399795, 399951, 406013, 395156, 399878, or 399952.

In certain embodiments, a target region is nucleotides 601-628 of SEQ ID NO: 1. In certain embodiments, an antisense compound is targeted to nucleotides 601-628 of SEQ ID NO: 1. In certain embodiments, an antisense compound targeted to a PCSK9 nucleic acid comprises a nucleotide sequence selected from SEQ ID NOs: 12, 187, 188, 189, 190, 191, 192 or 193. In certain such embodiments, an antisense compound targeted to nucleotides 601-628 of SEQ ID NO: 1 is selected from ISIS NOs: 410532, 410577, 410651, 406008, 410578, 410652, 410533, 410579, 410653, 406009, 410580, 410654, 410534, 410581, 410655, 399794, 399950, 410656, 410535, 410582, 410657, or 406010.

In certain embodiments, a target region is nucleotides 602-628 of SEQ ID NO: 1. In certain embodiments, an antisense compound is targeted to nucleotides 602-628 of SEQ ID NO: 1. In certain embodiments, an antisense compound targeted to a PCSK9 nucleic acid comprises a nucleotide sequence selected from SEQ ID NOs: 12, 188, 189, 190, 191, 192 or 193. In certain such embodiments, an antisense compound targeted to nucleotides 602-628 of SEQ ID NO: 1 is selected from ISIS NOs: 406008, 410578, 410652, 410533, 410579, 410653, 406009, 410580, 410654, 410534, 410581, 410655, 399794, 399950, 410656, 410535, 410582, 410657, or 406010.

In certain embodiments, a target region is nucleotides 603-630 of SEQ ID NO: 1. In certain embodiments, an antisense compound is targeted to nucleotides 603-630 of SEQ ID NO: 1. In certain embodiments, an antisense compound targeted to a PCSK9 nucleic acid comprises a nucleotide sequence selected from SEQ ID NOs: 12, 189, 190, 191, 192, 193 or 194. In certain such embodiments, an antisense compound targeted to nucleotides 603-630 of SEQ ID NO: 1 is selected from ISIS NOs: 410533, 410579, 410653, 406009, 410580, 410654, 410534, 410581, 410655, 399794, 399950, 410656, 410535, 410582, 410657, 406010, or 406011.

In certain embodiments, a target region is nucleotides 611-636 of SEQ ID NO: 1. In certain embodiments, an antisense compound is targeted to nucleotides 611-636 of SEQ ID NO: 1. In certain embodiments, an antisense compound targeted to a PCSK9 nucleic acid comprises a nucleotide sequence selected from SEQ ID NOs: 13, 194, 195 or 196. In certain such embodiments, an antisense compound targeted to nucleotides 611-636 of SEQ ID NO: 1 is selected from ISIS NOs: 406011, 406012, 399795, 399951, or 406013.

In certain embodiments, a target region is nucleotides 620-647 of SEQ ID NO: 1. In certain embodiments, an antisense compound is targeted to nucleotides 620-647 of SEQ ID NO: 1. In certain embodiments, an antisense compound targeted to a PCSK9 nucleic acid comprises a nucleotide sequence selected from SEQ ID NOs: 14 or 197. In certain such embodiments, an antisense compound targeted to nucleotides 620-647 of SEQ ID NO: 1 is selected from ISIS NOs: 395156, 399878, or 410749.

In certain embodiments, a target region is nucleotides 638-665 of SEQ ID NO: 1. In certain embodiments, an antisense compound is targeted to nucleotides 638-665 of SEQ ID NO: 1. In certain embodiments, an antisense compound targeted to a PCSK9 nucleic acid comprises a nucleotide sequence selected from SEQ ID NOs: 15 or 198. In certain such embodiments, an antisense compound targeted to nucleotides 638-665 of SEQ ID NO: 1 is selected from ISIS NOs: 410750, 395157, or 399879.

In certain embodiments, a target region is nucleotides 648-674 of SEQ ID NO: 1. In certain embodiments, an antisense compound is targeted to nucleotides 648-674 of SEQ ID NO: 1. In certain embodiments, an antisense compound targeted to a PCSK9 nucleic acid comprises a nucleotide sequence selected from SEQ ID NOs: 16, 199, 200, or 201. In certain such embodiments, an antisense compound targeted to nucleotides 648-674 of SEQ ID NO: 1 is selected from ISIS NOs: 406014, 399796, 399952, 406015, or 406016.

In certain embodiments, a target region is nucleotides 657-684 of SEQ ID NO: 1. In certain embodiments, an antisense compound is targeted to nucleotides 657-684 of SEQ ID NO: 1. In certain embodiments, an antisense compound targeted to a PCSK9 nucleic acid comprises a nucleotide sequence selected from SEQ ID NOs: 202, 203, 204, 205, or 206. In certain such embodiments, an antisense compound targeted to nucleotides 657-684 of SEQ ID NO: 1 is selected from ISIS NOs: 410730, 406017, 406018, 406019, or 406020.

In certain embodiments, a target region is nucleotides 705-743 of SEQ ID NO: 1. In certain embodiments, an antisense compound is targeted to nucleotides 705-743 of SEQ ID NO: 1. In certain embodiments, an antisense compound targeted to a PCSK9 nucleic acid comprises a nucleotide sequence selected from SEQ ID NOs: 17 or 209. In certain such embodiments, an antisense compound targeted to nucleotides 705-743 of SEQ ID NO: 1 is selected from ISIS NOs: 395158, 399880, or 410752.

In certain embodiments, a target region is nucleotides 782-810 of SEQ ID NO: 1. In certain embodiments, an antisense compound is targeted to nucleotides 782-810 of SEQ ID NO: 1. In certain embodiments, an antisense compound targeted to a PCSK9 nucleic acid comprises a nucleotide sequence selected from SEQ ID NOs: 18, 210, 211, 212, 213, or 214. In certain such embodiments, an antisense compound targeted to nucleotides 782-810 of SEQ ID NO: 1 is selected from ISIS NOs: 406021, 406022, 395159, 399881, 406023, 406024, or 410732.

In certain embodiments, a target region is nucleotides 821-859 of SEQ ID NO: 1. In certain embodiments, an antisense compound is targeted to nucleotides 821-859 of SEQ ID NO: 1. In certain embodiments, an antisense compound targeted to a PCSK9 nucleic acid comprises a nucleotide sequence selected from SEQ ID NOs: 19, 20, 215, 216 or 217. In certain such embodiments, an antisense compound targeted to nucleotides 821-859 of SEQ ID NO: 1 is selected from ISIS NOs: 410753, 406025, 395160, 399882, 406026, 399797, or 399953.

In certain embodiments, a target region is nucleotides 835-859 of SEQ ID NO: 1. In certain embodiments, an antisense compound is targeted to nucleotides 835-859 of SEQ ID NO: 1. In certain embodiments, an antisense compound targeted to a PCSK9 nucleic acid comprises a nucleotide sequence selected from SEQ ID NOs: 19, 20 or 217. In certain such embodiments, an antisense compound targeted to nucleotides 835-859 of SEQ ID NO: 1 is selected from ISIS NOs: 395160, 399882, 406026, 399797, or 399953.

In certain embodiments, a target region is nucleotides 835-917 of SEQ ID NO: 1. In certain embodiments, an antisense compound is targeted to nucleotides 835-917 of SEQ ID NO: 1. In certain embodiments, an antisense compound targeted to a PCSK9 nucleic acid comprises a nucleotide sequence selected from SEQ ID NOs: 19, 20, 21, 22, 23, 24, 217, 218, 219, 220, 221, 222, 223, 224, 225, 226, 227, 228, 229, 230, 231, 232 or 233. In certain such embodiments, an antisense compound targeted to nucleotides 835-917 of SEQ ID NO: 1 is selected from ISIS NOs: 395160, 399882, 406026, 399797, 399953, 395161, 399883, 405869, 405870, 405871, 405872, 399798, 399954, 405873, 405874, 405875, 405876, 406027, 406028, 406029, 399799, 399955, 406030, 406031, 410733, 406032, 395162, 399884, or 410754.

In certain embodiments, a target region is nucleotides 835-942 of SEQ ID NO: 1. In certain embodiments, an antisense compound is targeted to nucleotides 835-942 of SEQ ID NO: 1. In certain embodiments, an antisense compound targeted to a PCSK9 nucleic acid comprises a nucleotide sequence selected from SEQ ID NOs: 19, 20, 21, 22, 23, 24, 25, 217, 218, 219, 220, 221, 222, 223, 224, 225, 226, 227, 228, 229, 230, 231, 232, or 233. In certain such embodiments, an antisense compound targeted to nucleotides 835-942 of SEQ ID NO: 1 is selected from ISIS NOs: 395160, 399882, 406026, 399797, 399953, 395161, 399883, 405869, 405870, 405871, 405872, 399798, 399954, 405873, 405874, 405875, 405876, 406027, 406028, 406029, 399799, 399955, 406030, 406031, 410733, 406032, 395162, 399884, 410754, 395163, or 399885.

In certain embodiments, a target region is nucleotides 860-887 of SEQ ID NO: 1. In certain embodiments, an antisense compound is targeted to nucleotides 860-887 of SEQ ID NO: 1. In certain embodiments, an antisense compound targeted to a PCSK9 nucleic acid comprises a nucleotide sequence selected from SEQ ID NOs: 21, 22, 218, 219, 220, 221, 222 or 223. In certain such embodiments, an antisense compound targeted to nucleotides 860-887 of SEQ ID NO: 1 is selected from ISIS NOs: 395161, 399883, 405869, 405870, 405871, 405872, 399798, 399954, 405874, or 405874.

In certain embodiments, a target region is nucleotides 860-899 of SEQ ID NO: 1. In certain embodiments, an antisense compound is targeted to nucleotides 860-899 of SEQ ID NO: 1. In certain embodiments, an antisense compound targeted to a PCSK9 nucleic acid comprises a nucleotide sequence selected from SEQ ID NOs: 21, 22, 23, 218, 219, 220, 221, 222, 223, 224, 225, 226, 227 or 228. In certain such embodiments, an antisense compound targeted to nucleotides 860-899 of SEQ ID NO: 1 is selected from ISIS NOs: 395161, 399883, 405869, 405870, 405871, 405872, 399798, 399954, 405873, 405874, 405875, 405876, 406027, 406028, 406029, 399799, or 399955.

In certain embodiments, a target region is nucleotides 860-909 of SEQ ID NO: 1. In certain embodiments, an antisense compound is targeted to nucleotides 860-909 of SEQ ID NO: 1. In certain embodiments, an antisense compound targeted to a PCSK9 nucleic acid comprises a nucleotide sequence selected from SEQ ID NOs: 21, 22, 23, 24, 218, 219, 220, 221, 222, 223, 224, 225, 226, 227, 228, 229, 230, 231 or 232. In certain such embodiments, an antisense compound targeted to nucleotides 860-909 of SEQ ID NO: 1 is selected from ISIS NOs: 395161, 399883, 405869, 405870, 405871, 405872, 399798, 399954, 405873, 405874, 405875, 405876, 406027, 406028, 406029, 399799, 399955, 406030, 406031, 410733, 406032, 395162, or 399884.

In certain embodiments, a target region is nucleotides 860-917 of SEQ ID NO: 1. In certain embodiments, an antisense compound is targeted to nucleotides 860-917 of SEQ ID NO: 1. In certain embodiments, an antisense compound targeted to a PCSK9 nucleic acid comprises a nucleotide sequence selected from SEQ ID NOs: 21, 22, 23, 24, 218, 219, 220, 221, 222, 223, 224, 225, 226, 227, 228, 229, 230, 231, 232, or 233. In certain such embodiments, an antisense compound targeted to nucleotides 860-917 of SEQ ID NO: 1 is selected from ISIS NOs: 395161, 399883, 405869, 405870, 405871, 405872, 399798, 399954, 405873, 405874, 405875, 405876, 406027, 406028, 406029, 399799, 399955, 406030, 406031, 410733, 406032, 395162, 399884, or 410754.

In certain embodiments, a target region is nucleotides 869-895 of SEQ ID NO: 1. In certain embodiments, an antisense compound is targeted to nucleotides 869-895 of SEQ ID NO: 1. In certain embodiments, an antisense compound targeted to a PCSK9 nucleic acid comprises a nucleotide sequence selected from SEQ ID NOs: 224, 225, 226, or 227. In certain such embodiments, an antisense compound targeted to nucleotides 869-895 of SEQ ID NO: 1 is selected from ISIS NOs: 405875, 405876, 406027, or 406028.

In certain embodiments, a target region is nucleotides 878-905 of SEQ ID NO: 1. In certain embodiments, an antisense compound is targeted to nucleotides 878-905 of SEQ ID NO: 1. In certain embodiments, an antisense compound targeted to a PCSK9 nucleic acid comprises a nucleotide sequence selected from SEQ ID NOs: 23, 228, 229, 230, or 231. In certain such embodiments, an antisense compound targeted to nucleotides 878-905 of SEQ ID NO: 1 is selected from ISIS NOs: 406029, 399799, 399955, 406030, 406031, or 410733.

In certain embodiments, a target region is nucleotides 888-909 of SEQ ID NO: 1. In certain embodiments, an antisense compound is targeted to nucleotides 888-909 of SEQ ID NO: 1. In certain embodiments, an antisense compound targeted to a PCSK9 nucleic acid comprises a nucleotide sequence selected from SEQ ID NOs: 24 or 232. In certain such embodiments, an antisense compound targeted to nucleotides 888-909 of SEQ ID NO: 1 is selected from ISIS NOs: 406032, 395162, or 399884.

In certain embodiments, a target region is nucleotides 923-952 of SEQ ID NO: 1. In certain embodiments, an antisense compound is targeted to nucleotides 923-952 of SEQ ID NO: 1. In certain embodiments, an antisense compound targeted to a PCSK9 nucleic acid comprises a nucleotide sequence selected from SEQ ID NOs: 25 or 234. In certain such embodiments, an antisense compound targeted to nucleotides 923-952 of SEQ ID NO: 1 is selected from ISIS NOs: 395163, 399885, or 410755.

In certain embodiments, a target region is nucleotides 960-1034 of SEQ ID NO: 1. In certain embodiments, an antisense compound is targeted to nucleotides 960-1034 of SEQ ID NO: 1. In certain embodiments, an antisense compound targeted to a PCSK9 nucleic acid comprises a nucleotide sequence selected from SEQ ID NOs: 26, 27, 28, 235, 236, 237, 238, 239, 240, 241, 242, 243, 244, 245, 246, 247, 248, 249, 250, 251, 252, 253, 254, 255, or 256. In certain such embodiments, an antisense compound targeted to nucleotides 960-1034 of SEQ ID NO: 1 is selected from ISIS NOs: 410756, 405526, 405604, 406033, 395164, 399886, 406034, 399800, 399956, 406035, 410757, 406036, 406037, 410536, 410583, 410658, 410537, 410584, 410659, 406038, 410585, 410660, 405877, 410586, 410661, 405878, 410587, 410662, 405879, 410588, 410663, 405880, or 410758.

In certain embodiments, a target region is nucleotides 960-1173 of SEQ ID NO: 1. In certain embodiments, an antisense compound is targeted to nucleotides 960-1173 of SEQ ID NO: 1. In certain embodiments, an antisense compound targeted to a PCSK9 nucleic acid comprises a nucleotide sequence selected from SEQ ID NOs: 26, 27, 28, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, or 273. In certain such embodiments, an antisense compound targeted to nucleotides 960-1173 of SEQ ID NO: 1 is selected from ISIS NOs: 410756, 405526, 405604, 406033, 395164, 399886, 406034, 399800, 399956, 406035, 410757, 406036, 406037, 410536, 410583, 410658, 410537, 410584, 410659, 406038, 410585, 410660, 405877, 410586, 410661, 405878, 410587, 410662, 405879, 410588, 410663, 405880, or 410763.

In certain embodiments, a target region is nucleotides 960-986 of SEQ ID NO: 1. In certain embodiments, an antisense compound is targeted to nucleotides 960-986 of SEQ ID NO: 1. In certain embodiments, an antisense compound targeted to a PCSK9 nucleic acid comprises a nucleotide sequence selected from SEQ ID NOs: 235, 236, or 237. In certain such embodiments, an antisense compound targeted to nucleotides 960-986 of SEQ ID NO: 1 is selected from ISIS NOs: 410756, 405526, 405604, or 406033.

In certain embodiments, a target region is nucleotides 967-991 of SEQ ID NO: 1. In certain embodiments, an antisense compound is targeted to nucleotides 967-991 of SEQ ID NO: 1. In certain embodiments, an antisense compound targeted to a PCSK9 nucleic acid comprises a nucleotide sequence selected from SEQ ID NOs: 237 or 238. In certain such embodiments, an antisense compound targeted to nucleotides 967-991 of SEQ ID NO: 1 is selected from ISIS NOs: 406033 or 406034.

In certain embodiments, a target region is nucleotides 970-1023 of SEQ ID NO: 1. In certain embodiments, an antisense compound is targeted to nucleotides 970-1023 of SEQ ID NO: 1. In certain embodiments, an antisense compound targeted to a PCSK9 nucleic acid comprises a nucleotide sequence selected from SEQ ID NOs: 26, 27, 28, 238, 239, 240, 241, 242, 243, 244, 245, 246, 247, 248, or 249. In certain such embodiments, an antisense compound targeted to nucleotides 970-1023 of SEQ ID NO: 1 is selected from ISIS NOs: 395164, 399886, 406034, 399800, 399956, 406035, 410757, 406036, 406037, 410536, 410583, 410658, 410537, 410584, 410659, 406038, 410585, 410660, 405877, 410586, 410661, 405878, 410587, 410662, 405879, 410588, 410663, 405880, 410589, 410664, 395165, 399887, or 410665.

In certain embodiments, a target region is nucleotides 970-1064 of SEQ ID NO: 1. In certain embodiments, an antisense compound is targeted to nucleotides 970-1064 of SEQ ID NO: 1. In certain embodiments, an antisense compound targeted to a PCSK9 nucleic acid comprises a nucleotide sequence selected from SEQ ID NOs: 26, 27, 28, 29, 30, 238, 239, 240, 241, 242, 243, 244, 245, 246, 247, 248, 149, 250, 251, 252, 253, 254, 255, 256, 257, 258, 259, 260, 261, 262, or 263. In certain such embodiments, an antisense compound targeted to nucleotides 970-1064 of SEQ ID NO: 1 is selected from ISIS NOs: 395164, 399886, 406034, 399800, 399956, 406035, 410757, 406036, 406037, 410536, 410583, 410658, 410537, 410584, 410659, 406038, 410585, 410660, 405877, 410586, 410661, 405878, 410587, 410662, 405879, 410588, 410663, 405880, 410589, 410664, 395165, 399887, or 399957.

In certain embodiments, a target region is nucleotides 970-1117 of SEQ ID NO: 1. In certain embodiments, an antisense compound is targeted to nucleotides 970-1117 of SEQ ID NO: 1. In certain embodiments, an antisense compound targeted to a PCSK9 nucleic acid comprises a nucleotide sequence selected from SEQ ID NOs: 26, 27, 28, 29, 30, 31, 32, 238, 239, 240, 241, 242, 243, 244, 245, 246, 247, 248, 149, 250, 251, 252, 253, 254, 255, 256, 257, 258, 259, 260, 261, 262, 263, 264, 265, or 266. In certain such embodiments, an antisense compound targeted to nucleotides 970-1117 of SEQ ID NO: 1 is selected from ISIS NOs: 395164, 399886, 406034, 399800, 399956, 406035, 410757, 406036, 406037, 410536, 410583, 410658, 410537, 410584, 410659, 406038, 410585, 410660, 405877, 410586, 410661, 405878, 410587, 410662, 405879, 410588, 410663, 405880, 410589, 410664, 395165, 399887, or 399890.

In certain embodiments, a target region is nucleotides 970-996 of SEQ ID NO: 1. In certain embodiments, an antisense compound is targeted to nucleotides 970-996 of SEQ ID NO: 1. In certain embodiments, an antisense compound targeted to a PCSK9 nucleic acid comprises a nucleotide sequence selected from SEQ ID NOs: 26, 27, or 238. In certain such embodiments, an antisense compound targeted to nucleotides 970-996 of SEQ ID NO: 1 is selected from ISIS NOs: 395164, 399886, 406034, 399800, 399956, or 406035.

In certain embodiments, a target region is nucleotides 977-1004 of SEQ ID NO: 1. In certain embodiments, an antisense compound is targeted to nucleotides 977-1004 of SEQ ID NO: 1. In certain embodiments, an antisense compound targeted to a PCSK9 nucleic acid comprises a nucleotide sequence selected from SEQ ID NOs: 239 or 240. In certain such embodiments, an antisense compound targeted to nucleotides 977-1004 of SEQ ID NO: 1 is selected from ISIS NOs: 406035 or 410757.

In certain embodiments, a target region is nucleotides 985-1011 of SEQ ID NO: 1. In certain embodiments, an antisense compound is targeted to nucleotides 985-1011 of SEQ ID NO: 1. In certain embodiments, an antisense compound targeted to a PCSK9 nucleic acid comprises a nucleotide sequence selected from SEQ ID NOs: 240, 241, or 242. In certain such embodiments, an antisense compound targeted to nucleotides 985-1011 of SEQ ID NO: 1 is selected from ISIS NOs: 410757, 406036, or 406037.

In certain embodiments, a target region is nucleotides 989-1016 of SEQ ID NO: 1. In certain embodiments, an antisense compound is targeted to nucleotides 989-1016 of SEQ ID NO: 1. In certain embodiments, an antisense compound targeted to a PCSK9 nucleic acid comprises a nucleotide sequence selected from SEQ ID NOs: 241, 242, or 243. In certain such embodiments, an antisense compound targeted to nucleotides 989-1016 of SEQ ID NO: 1 is selected from ISIS NOs: 406036, 406037, 410536, 410583, or 410658.

In certain embodiments, a target region is nucleotides 992-1019 of SEQ ID NO: 1. In certain embodiments, an antisense compound is targeted to nucleotides 992-1019 of SEQ ID NO: 1. In certain embodiments, an antisense compound targeted to a PCSK9 nucleic acid comprises a nucleotide sequence selected from SEQ ID NOs: 242, 243, 244, 245, or 246. In certain such embodiments, an antisense compound targeted to nucleotides 992-1019 of SEQ ID NO: 1 is selected from ISIS NOs: 406037, 410536, 410583, 410658, 410537, 410584, 410659, 406038, 410585, 410660, 405877, 410586, or 410661.

In certain embodiments, a target region is nucleotides 997-1024 of SEQ ID NO: 1. In certain embodiments, an antisense compound is targeted to nucleotides 997-1024 of SEQ ID NO: 1. In certain embodiments, an antisense compound targeted to a PCSK9 nucleic acid comprises a nucleotide sequence selected from SEQ ID NOs: 243, 244, 245, 246, 247, 248, 249, or 250. In certain such embodiments, an antisense compound targeted to nucleotides 997-1024 of SEQ ID NO: 1 is selected from ISIS NOs: 410536, 410583, 410658, 410537, 410584, 410659, 406038, 410585, 410660, 405877, 410586, 410661, 405878, 410587, 410662, 405879, 410588, 410663, 405880, 410589, 410664, 395165, 399887, 409126, 410665, 405881, 410590, or 410666.

In certain embodiments, a target region is nucleotides 997-1024 of SEQ ID NO: 1. In certain embodiments, an antisense compound is targeted to nucleotides 997-1024 of SEQ ID NO: 1. In certain embodiments, an antisense compound targeted to a PCSK9 nucleic acid comprises a nucleotide sequence selected from SEQ ID NOs: 243, 244, 245, 246, 247, 248, 249, or 250. In certain such embodiments, an antisense compound targeted to nucleotides 997-1024 of SEQ ID NO: 1 is selected from ISIS NOs: 410536, 410583, 410658, 410537, 410584, 410659, 406038, 410585, 410660, 405877, 410586, 410661, 405878, 410587, 410662, 405879, 410588, 410663, 405880, 410589, 410664, 395165, 399887, 409126, 410665, 405881, 410590, or 410666.

In certain embodiments, a target region is nucleotides 998-1025 of SEQ ID NO: 1. In certain embodiments, an antisense compound is targeted to nucleotides 998-1025 of SEQ ID NO: 1. In certain embodiments, an antisense compound targeted to a PCSK9 nucleic acid comprises a nucleotide sequence selected from SEQ ID NOs: 28, 244, 245, 246, 247, 248, 249, 250, or 251. In certain such embodiments, an antisense compound targeted to nucleotides 998-1025 of SEQ ID NO: 1 is selected from ISIS NOs: 410537, 410584, 410659, 406038, 410585, 410660, 405877, 410586, 410661, 405878, 410587, 410662, 405879, 410588, 410663, 405880, 410589, 410664, 395165, 399887, 410665, 405881, 410590, 410666, 405882, 410591, or 410667.

In certain embodiments, a target region is nucleotides 999-1026 of SEQ ID NO: 1. In certain embodiments, an antisense compound is targeted to nucleotides 999-1026 of SEQ ID NO: 1. In certain embodiments, an antisense compound targeted to a PCSK9 nucleic acid comprises a nucleotide sequence selected from SEQ ID NOs: 28, 245, 246, 247, 248, 249, 250, 251, or 252. In certain such embodiments, an antisense compound targeted to nucleotides 999-1026 of SEQ ID NO: 1 is selected from ISIS NOs: 406038, 410585, 410660, 405877, 410586, 410661, 405878, 410587, 410662, 405879, 410588, 410663, 405880, 410589, 410664, 395165, 399887, 410665, 405881, 410590, 410666, 405882, 410591, 410667, 405833, 410592, or 410668.

In certain embodiments, a target region is nucleotides 1000-1027 of SEQ ID NO: 1. In certain embodiments, an antisense compound is targeted to nucleotides 1000-1027 of SEQ ID NO: 1. In certain embodiments, an antisense compound targeted to a PCSK9 nucleic acid comprises a nucleotide sequence selected from SEQ ID NOs: 28, 246, 247, 248, 249, 250, 251, 252, or 253. In certain such embodiments, an antisense compound targeted to nucleotides 1000-1027 of SEQ ID NO: 1 is selected from ISIS NOs: 405877, 410586, 410661, 405878, 410587, 410662, 405879, 410588, 410663, 405880, 410589, 410664, 395165, 399887, 410665, 405881, 410590, 410666, 405882, 410591, 410667, 405833, 410592, 410668, 405884, 410593, or 410669.

In certain embodiments, a target region is nucleotides 1001-1028 of SEQ ID NO: 1. In certain embodiments, an antisense compound is targeted to nucleotides 1001-1028 of SEQ ID NO: 1. In certain embodiments, an antisense compound targeted to a PCSK9 nucleic acid comprises a nucleotide sequence selected from SEQ ID NOs: 28, 247, 248, 249, 250, 251, 252, 253, or 254. In certain such embodiments, an antisense compound targeted to nucleotides 1001-1028 of SEQ ID NO: 1 is selected from ISIS NOs: 405878, 410587, 410662, 405879, 410588, 410663, 405880, 410589, 410664, 395165, 399887, 410665, 405881, 410590, 410666, 405882, 410591, 410667, 405833, 410592, 410668, 405884, 410593, 410669, 410538, 410594, or 410670.

In certain embodiments, a target region is nucleotides 1002-1021 of SEQ ID NO: 1. In certain embodiments, an antisense compound is targeted to nucleotides 1002-1021 of SEQ ID NO: 1. In one such embodiment, an antisense compound targeted to nucleotides 1002-1021 of SEQ ID NO: 1 is ISIS NO: 405879.

In certain embodiments, a target region is nucleotides 1002-1029 of SEQ ID NO: 1. In certain embodiments, an antisense compound is targeted to nucleotides 1002-1029 of SEQ ID NO: 1. In certain embodiments, an antisense compound targeted to a PCSK9 nucleic acid comprises a nucleotide sequence selected from SEQ ID NOs: 28, 248, 249, 250, 251, 252, 253, 254, or 255. In certain such embodiments, an antisense compound targeted to nucleotides 1002-1029 of SEQ ID NO: 1 is selected from ISIS NOs: 405879, 410588, 410663, 405880, 410589, 410664, 395165, 399887, 410665, 405881, 410590, 410666, 405882, 410591, 410667, 405833, 410592, 410668, 405884, 410593, 410669, 410538, 410594, 410670, 410539, 410595, or 410671.

In certain embodiments, a target region is nucleotides 1003-1029 of SEQ ID NO: 1. In certain embodiments, an antisense compound is targeted to nucleotides 1003-1029 of SEQ ID NO: 1. In certain embodiments, an antisense compound targeted to a PCSK9 nucleic acid comprises a nucleotide sequence selected from SEQ ID NOs: 28, 249, 250, 251, 252, 253, 254, or 255. In certain such embodiments, an antisense compound targeted to nucleotides 1003-1029 of SEQ ID NO: 1 is selected from ISIS NOs: 405880, 410589, 410664, 395165, 399887, 409126, 410665, 405881, 410590, 410666, 405882, 410591, 410667, 405883, 410592, 410668, 405884, 410593, 410669, 410538, 410594, 410670, 410539, 410595, or 410671.

In certain embodiments, a target region is nucleotides 1004-1029 of SEQ ID NO: 1. In certain embodiments, an antisense compound is targeted to nucleotides 1004-1029 of SEQ ID NO: 1. In certain embodiments, an antisense compound targeted to a PCSK9 nucleic acid comprises a nucleotide sequence selected from SEQ ID NOs: 28, 250, 251, 252, 253, 254, or 255. In certain such embodiments, an antisense compound targeted to nucleotides 1004-1029 of SEQ ID NO: 1 is selected from ISIS NOs: 395165, 399887, 409126, 410665, 405881, 410590, 410666, 405882, 410591, 410667, 405883, 410592, 410668, 405884, 410593, 410669, 410538, 410594, 410670, 410539, 410595, or 410671.

In certain embodiments, a target region is nucleotides 1005-1029 of SEQ ID NO: 1. In certain embodiments, an antisense compound is targeted to nucleotides 1005-1029 of SEQ ID NO: 1. In certain embodiments, an antisense compound targeted to a PCSK9 nucleic acid comprises a nucleotide sequence selected from SEQ ID NOs: 250, 251, 252, 253, 254, or 255. In certain such embodiments, an antisense compound targeted to nucleotides 1005-1029 of SEQ ID NO: 1 is selected from ISIS NOs: 410665, 405881, 410590, 410666, 405882, 410591, 410667, 405883, 410592, 410668, 405884, 410593, 410669, 410538, 410594, 410670, 410539, 410595, or 410671.

In certain embodiments, a target region is nucleotides 1006-1029 of SEQ ID NO: 1. In certain embodiments, an antisense compound is targeted to nucleotides 1006-1029 of SEQ ID NO: 1. In certain embodiments, an antisense compound targeted to a PCSK9 nucleic acid comprises a nucleotide sequence selected from SEQ ID NOs: 251, 252, 253, 254, or 255. In certain such embodiments, an antisense compound targeted to nucleotides 1006-1029 of SEQ ID NO: 1 is selected from ISIS NOs: 405882, 410591, 410667, 405883, 410592, 410668, 405884, 410593, 410669, 410538, 410594, 410670, 410539, 410595, or 410671.

In certain embodiments, a target region is nucleotides 1007-1034 of SEQ ID NO: 1. In certain embodiments, an antisense compound is targeted to nucleotides 1007-1034 of SEQ ID NO: 1. In certain embodiments, an antisense compound targeted to a PCSK9 nucleic acid comprises a nucleotide sequence selected from SEQ ID NOs: 252, 253, 254, 255, or 256. In certain such embodiments, an antisense compound targeted to nucleotides 1007-1034 of SEQ ID NO: 1 is selected from ISIS NOs: 405883, 410592, 410668, 405884, 410593, 410669, 410538, 410594, 410670, 410539, 410595, 410671, or 410758.

In certain embodiments, a target region is nucleotides 1036-1061 of SEQ ID NO: 1. In certain embodiments, an antisense compound is targeted to nucleotides 1036-1061 of SEQ ID NO: 1. In certain embodiments, an antisense compound targeted to a PCSK9 nucleic acid comprises a nucleotide sequence selected from SEQ ID NOs: 29, 257, 258, or 259. In certain such embodiments, an antisense compound targeted to nucleotides 1036-1061 of SEQ ID NO: 1 is selected from ISIS NOs: 406039, 406040, 395166, 399888, or 406041.

In certain embodiments, a target region is nucleotides 1045-1072 of SEQ ID NO: 1. In certain embodiments, an antisense compound is targeted to nucleotides 1045-1072 of SEQ ID NO: 1. In certain embodiments, an antisense compound targeted to a PCSK9 nucleic acid comprises a nucleotide sequence selected from SEQ ID NOs: 30, 260, 261, or 262. In certain such embodiments, an antisense compound targeted to nucleotides 1045-1072 of SEQ ID NO: 1 is selected from ISIS NOs: 399801, 399957, 406042, 406043, or 406044.

In certain embodiments, a target region is nucleotides 1076-1096 of SEQ ID NO: 1. In certain embodiments, an antisense compound is targeted to nucleotides 1076-1096 of SEQ ID NO: 1. In certain embodiments, an antisense compound targeted to a PCSK9 nucleic acid comprises a nucleotide sequence selected from SEQ ID NOs: 31 or 264. In certain such embodiments, an antisense compound targeted to nucleotides 1076-1096 of SEQ ID NO: 1 is selected from ISIS NOs: 408642, 395167, or 399889.

In certain embodiments, a target region is nucleotides 1088-1115 of SEQ ID NO: 1. In certain embodiments, an antisense compound is targeted to nucleotides 1088-1115 of SEQ ID NO: 1. In certain embodiments, an antisense compound targeted to a PCSK9 nucleic acid comprises a nucleotide sequence selected from SEQ ID NOs: 265 or 266. In certain such embodiments, an antisense compound targeted to nucleotides 1088-1115 of SEQ ID NO: 1 is selected from ISIS NOs: 410760 or 406045.

In certain embodiments, a target region is nucleotides 1098-1123 of SEQ ID NO: 1. In certain embodiments, an antisense compound is targeted to nucleotides 1098-1123 of SEQ ID NO: 1. In certain embodiments, an antisense compound targeted to a PCSK9 nucleic acid comprises a nucleotide sequence selected from SEQ ID NOs: 32, 267, 268, or 269. In certain such embodiments, an antisense compound targeted to nucleotides 1098-1123 of SEQ ID NO: 1 is selected from ISIS NOs: 395168, 399890, 405909, 405910, or 405911.

In certain embodiments, a target region is nucleotides 1200-1251 of SEQ ID NO: 1. In certain embodiments, an antisense compound is targeted to nucleotides 1200-1251 of SEQ ID NO: 1. In certain embodiments, an antisense compound targeted to a PCSK9 nucleic acid comprises a nucleotide sequence selected from SEQ ID NOs: 33, 274, 275, 276, 277, 278, 279, 280, 281, 282, 283, 284, or 285. In certain such embodiments, an antisense compound targeted to nucleotides 1200-1251 of SEQ ID NO: 1 is selected from ISIS NOs: 410764, 395169, 399891, 405913, 405914, 405915, 405916, 410734, 405917, 405918, 405919, 405920, 405921, or 405922.

In certain embodiments, a target region is nucleotides 1210-1237 of SEQ ID NO: 1. In certain embodiments, an antisense compound is targeted to nucleotides 1210-1237 of SEQ ID NO: 1. In certain embodiments, an antisense compound targeted to a PCSK9 nucleic acid comprises a nucleotide sequence selected from SEQ ID NOs: 33, 275, 276, 277, or 278. In certain such embodiments, an antisense compound targeted to nucleotides 1210-1237 of SEQ ID NO: 1 is selected from ISIS NOs: 395169, 399891, 405913, 405914, 405915, or 405916.

In certain embodiments, a target region is nucleotides 1219-1245 of SEQ ID NO: 1. In certain embodiments, an antisense compound is targeted to nucleotides 1219-1245 of SEQ ID NO: 1. In certain embodiments, an antisense compound targeted to a PCSK9 nucleic acid comprises a nucleotide sequence selected from SEQ ID NOs: 279, 280, 281 or 282. In certain such embodiments, an antisense compound targeted to nucleotides 1219-1245 of SEQ ID NO: 1 is selected from ISIS NOs: 410734, 405917, 405918, or 405919.

In certain embodiments, a target region is nucleotides 1228-1251 of SEQ ID NO: 1. In certain embodiments, an antisense compound is targeted to nucleotides 1228-1251 of SEQ ID NO: 1. In certain embodiments, an antisense compound targeted to a PCSK9 nucleic acid comprises a nucleotide sequence selected from SEQ ID NOs: 283, 284, or 285. In certain such embodiments, an antisense compound targeted to nucleotides 1228-1251 of SEQ ID NO: 1 is selected from ISIS NOs: 405920, 405921, or 405922.

In certain embodiments, a target region is nucleotides 1273-1444 of SEQ ID NO: 1. In certain embodiments, an antisense compound is targeted to nucleotides 1273-1444 of SEQ ID NO: 1. In certain embodiments, an antisense compound targeted to a PCSK9 nucleic acid comprises a nucleotide sequence selected from SEQ ID NOs: 34, 35, 36, 37, 38, 39, 40, 41, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 316, and 318. In certain such embodiments, an antisense compound targeted to nucleotides 1273-1444 of SEQ ID NO: 1 is selected from ISIS NOs: 410765, 410766, 405923, 395170, 399892, 410767, 405924, 410735, 405925, 405926, 395171, 399893, 405927, 395172, 399894, 405928, 399802, 399958, 405929, 395173, 399895, 405930, 405931, 405932, 405933, 405934, 399803, 399959, 405935, 410736, 405936, 395174, or 410769.

In certain embodiments, a target region is nucleotides 1295-1316 of SEQ ID NO: 1. In certain embodiments, an antisense compound is targeted to nucleotides 1295-1316 of SEQ ID NO: 1. In certain embodiments, an antisense compound targeted to a PCSK9 nucleic acid comprises a nucleotide sequence selected from SEQ ID NOs: 149 or 288. In certain such embodiments, an antisense compound targeted to nucleotides 1295-1316 of SEQ ID NO: 1 is selected from ISIS NOs: 405923, 395170, or 399892.

In certain embodiments, a target region is nucleotides 1318-1345 of SEQ ID NO: 1. In certain embodiments, an antisense compound is targeted to nucleotides 1318-1345 of SEQ ID NO: 1. In certain embodiments, an antisense compound targeted to a PCSK9 nucleic acid comprises a nucleotide sequence selected from SEQ ID NOs: 34, 290, 291, 292 or 293. In certain such embodiments, an antisense compound targeted to nucleotides 1318-1345 of SEQ ID NO: 1 is selected from ISIS NOs: 405924, 410735, 405925, 405926, 395171, or 399893.

In certain embodiments, a target region is nucleotides 1328-1354 of SEQ ID NO: 1. In certain embodiments, an antisense compound is targeted to nucleotides 1328-1354 of SEQ ID NO: 1. In certain embodiments, an antisense compound targeted to a PCSK9 nucleic acid comprises a nucleotide sequence selected from SEQ ID NOs: 35, 128, 294 or 295. In certain such embodiments, an antisense compound targeted to nucleotides 1328-1354 of SEQ ID NO: 1 is selected from ISIS NOs: 405927, 395172, 399894, 405928, 399802, or 399958.

In certain embodiments, a target region is nucleotides 1337-1361 of SEQ ID NO: 1. In certain embodiments, an antisense compound is targeted to nucleotides 1337-1361 of SEQ ID NO: 1. In certain embodiments, an antisense compound targeted to a PCSK9 nucleic acid comprises a nucleotide sequence selected from SEQ ID NOs: 36, 296, or 297. In certain such embodiments, an antisense compound targeted to nucleotides 1337-1361 of SEQ ID NO: 1 is selected from ISIS NOs: 405929, 395173, 399895, or 405930.

In certain embodiments, a target region is nucleotides 1344-1371 of SEQ ID NO: 1. In certain embodiments, an antisense compound is targeted to nucleotides 1344-1371 of SEQ ID NO: 1. In certain embodiments, an antisense compound targeted to a PCSK9 nucleic acid comprises a nucleotide sequence selected from SEQ ID NOs: 37, 298, 299, 300, or 301. In certain such embodiments, an antisense compound targeted to nucleotides 1344-1371 of SEQ ID NO: 1 is selected from ISIS NOs: 405931, 405932, 405933, 405934, 399803, or 399959.

In certain embodiments, a target region is nucleotides 1354-1377 of SEQ ID NO: 1. In certain embodiments, an antisense compound is targeted to nucleotides 1354-1377 of SEQ ID NO: 1. In certain embodiments, an antisense compound targeted to a PCSK9 nucleic acid comprises a nucleotide sequence selected from SEQ ID NOs: 302, 303, or 304. In certain such embodiments, an antisense compound targeted to nucleotides 1354-1377 of SEQ ID NO: 1 is selected from ISIS NOs: 405935, 410736, or 405936.

In certain embodiments, a target region is nucleotides 1380-1406 of SEQ ID NO: 1. In certain embodiments, an antisense compound is targeted to nucleotides 1380-1406 of SEQ ID NO: 1. In certain embodiments, an antisense compound targeted to a PCSK9 nucleic acid comprises a nucleotide sequence selected from SEQ ID NOs: 305 or 306. In certain such embodiments, an antisense compound targeted to nucleotides 1380-1406 of SEQ ID NO: 1 is selected from ISIS NOs: 410768 or 405937.

In certain embodiments, a target region is nucleotides 1389-1416 of SEQ ID NO: 1. In certain embodiments, an antisense compound is targeted to nucleotides 1389-1416 of SEQ ID NO: 1. In certain embodiments, an antisense compound targeted to a PCSK9 nucleic acid comprises a nucleotide sequence selected from SEQ ID NOs: 39, 307, 308, 309 or 310. In certain such embodiments, an antisense compound targeted to nucleotides 1389-1416 of SEQ ID NO: 1 is selected from ISIS NOs: 395175, 399897, 405938, 405939, 405940, or 405941.

In certain embodiments, a target region is nucleotides 1400-1426 of SEQ ID NO: 1. In certain embodiments, an antisense compound is targeted to nucleotides 1400-1426 of SEQ ID NO: 1. In certain embodiments, an antisense compound targeted to a PCSK9 nucleic acid comprises a nucleotide sequence selected from SEQ ID NOs: 40, 311, 312, 313, or 314. In certain such embodiments, an antisense compound targeted to nucleotides 1400-1426 of SEQ ID NO: 1 is selected from ISIS NOs: 399804, 399960, 405942, 405943, 410737, or 405944.

In certain embodiments, a target region is nucleotides 1409-1434 of SEQ ID NO: 1. In certain embodiments, an antisense compound is targeted to nucleotides 1409-1434 of SEQ ID NO: 1. In certain embodiments, an antisense compound targeted to a PCSK9 nucleic acid comprises a nucleotide sequence selected from SEQ ID NOs: 41, 315, 316, or 317. In certain such embodiments, an antisense compound targeted to nucleotides 1409-1434 of SEQ ID NO: 1 is selected from ISIS NOs: 405945, 399805, 399961, 405946, or 405947.

In certain embodiments, a target region is nucleotides 1465-1491 of SEQ ID NO: 1. In certain embodiments, an antisense compound is targeted to nucleotides 1465-1491 of SEQ ID NO: 1. In certain embodiments, an antisense compound targeted to a PCSK9 nucleic acid comprises a nucleotide sequence selected from SEQ ID NOs: 42, 101, 319, or 320. In certain such embodiments, an antisense compound targeted to nucleotides 1465-1491 of SEQ ID NO: 1 is selected from ISIS NOs: 395176, 399898, 405948, 399806, 399962, or 405949.

In certain embodiments, a target region is nucleotides 1465-1602 of SEQ ID NO: 1. In certain embodiments, an antisense compound is targeted to nucleotides 1465-1602 of SEQ ID NO: 1. In certain embodiments, an antisense compound targeted to a PCSK9 nucleic acid comprises a nucleotide sequence selected from SEQ ID NOs: 42, 43, 44, 45, 46, 47, 48, 49, 50, 51, 87, 101, 319, 320, 321, 322, 323, 324, 325, 326, 327, 328, 329, 330, 331, 332, 333, 334, 335, 336, 337, 338, 339, 340, 341, 342, 343, 345, 346, 347, 348, 349, 350, 351, 352, 353, 354, 355, 356, 357, 358, or 359. In certain such embodiments, an antisense compound targeted to nucleotides 1465-1602 of SEQ ID NO: 1 is selected from ISIS NOs: 395176, 399898, 405948, 399806, 399962, 405949, 405950, 405951, 399807, 399963, 405952, 410738, 405953, 405954, 410770, 405955, 405956, 405957, 405958, 405959, 405960, 405961, 399808, 399964, 405962, 410739, 405963, 395177, 399899, 405964, 399809, 399965, or 399969.

In certain embodiments, a target region is nucleotides 1474-1499 of SEQ ID NO: 1. In certain embodiments, an antisense compound is targeted to nucleotides 1474-1499 of SEQ ID NO: 1. In certain embodiments, an antisense compound targeted to a PCSK9 nucleic acid comprises a nucleotide sequence selected from SEQ ID NOs: 43, 321, 322, or 323. In certain such embodiments, an antisense compound targeted to nucleotides 1474-1499 of SEQ ID NO: 1 is selected from ISIS NOs: 405950, 405951, 399807, 399963, or 405952.

In certain embodiments, a target region is nucleotides 1482-1519 of SEQ ID NO: 1. In certain embodiments, an antisense compound is targeted to nucleotides 1482-1519 of SEQ ID NO: 1. In certain embodiments, an antisense compound targeted to a PCSK9 nucleic acid comprises a nucleotide sequence selected from SEQ ID NOs: 324, 325, 326, or 327. In certain such embodiments, an antisense compound targeted to nucleotides 1482-1519 of SEQ ID NO: 1 is selected from ISIS NOs: 410738, 405953, 405954, or 410770.

In certain embodiments, a target region is nucleotides 1513-1540 of SEQ ID NO: 1. In certain embodiments, an antisense compound is targeted to nucleotides 1513-1540 of SEQ ID NO: 1. In certain embodiments, an antisense compound targeted to a PCSK9 nucleic acid comprises a nucleotide sequence selected from SEQ ID NOs: 328, 329, 330, 331, or 332. In certain such embodiments, an antisense compound targeted to nucleotides 1513-1540 of SEQ ID NO: 1 is selected from ISIS NOs: 405955, 405956, 405957, 405958, or 405959.

In certain embodiments, a target region is nucleotides 1523-1549 of SEQ ID NO: 1. In certain embodiments, an antisense compound is targeted to nucleotides 1523-1549 of SEQ ID NO: 1. In certain embodiments, an antisense compound targeted to a PCSK9 nucleic acid comprises a nucleotide sequence selected from SEQ ID NOs: 44, 333, 334, 335, or 336. In certain such embodiments, an antisense compound targeted to nucleotides 1523-1549 of SEQ ID NO: 1 is selected from ISIS NOs: 405960, 405961, 399808, 399964, 405962, or 410739.

In certain embodiments, a target region is nucleotides 1526-1602 of SEQ ID NO: 1. In certain embodiments, an antisense compound is targeted to nucleotides 1526-1602 of SEQ ID NO: 1. In certain embodiments, an antisense compound targeted to a PCSK9 nucleic acid comprises a nucleotide sequence selected from SEQ ID NOs: 44, 45, 46, 47, 48, 49, 50, 51, 87, 335, 336, 337, 338, 339, 340, 341, 342, 343, 345, 346, 347, 348, 349, 350, 351, 352, 353, 354, 355, 356, 357, 358, or 359. In certain such embodiments, an antisense compound targeted to nucleotides 1526-1602 of SEQ ID NO: 1 is selected from ISIS NOs: 399808, 399964, 405962, 410739, 405963, 395177, 399899, 405964, 399809, 399965, 405965, 405966, 399810, 399966, 405967, 405968, 399811, 399967, 405969, 405970, 410740, 405885, 405886, 405887, 410596, 410672, 405888, 410597, 410673, 399812, 399968, 410674, or 399969.

In certain embodiments, a target region is nucleotides 1526-1624 of SEQ ID NO: 1. In certain embodiments, an antisense compound is targeted to nucleotides 1526-1624 of SEQ ID NO: 1. In certain embodiments, an antisense compound targeted to a PCSK9 nucleic acid comprises a nucleotide sequence selected from SEQ ID NOs: 44, 45, 46, 47, 48, 49, 50, 51, 87, 119, 335, 336, 337, 338, 339, 340, 341, 342, 343, 345, 346, 347, 348, 349, 350, 351, 352, 353, 354, 355, 356, 357, 358, or 359. In certain such embodiments, an antisense compound targeted to nucleotides 1526-1624 of SEQ ID NO: 1 is selected from ISIS NOs: 399808, 399964, 405962, 410739, 405963, 395177, 399899, 405964, 399809, 399965, 405965, 405966, 399810, 399966, 405967, 405968, 399811, 399967, 405969, 405970, 410740, 405885, 405886, 405887, 410596, 410672, 405888, 410597, 410673, 399812, 399968, 410674, or 399902.

In certain embodiments, a target region is nucleotides 1532-1558 of SEQ ID NO: 1. In certain embodiments, an antisense compound is targeted to nucleotides 1532-1558 of SEQ ID NO: 1. In certain embodiments, an antisense compound targeted to a PCSK9 nucleic acid comprises a nucleotide sequence selected from SEQ ID NOs: 45, 46, 337, or 338. In certain such embodiments, an antisense compound targeted to nucleotides 1532-1558 of SEQ ID NO: 1 is selected from ISIS NOs: 405963, 395177, 399899, 405964, 399809, or 399965.

In certain embodiments, a target region is nucleotides 1541-1568 of SEQ ID NO: 1. In certain embodiments, an antisense compound is targeted to nucleotides 1541-1568 of SEQ ID NO: 1. In certain embodiments, an antisense compound targeted to a PCSK9 nucleic acid comprises a nucleotide sequence selected from SEQ ID NOs: 47, 340, 341, or 342. In certain such embodiments, an antisense compound targeted to nucleotides 1541-1568 of SEQ ID NO: 1 is selected from ISIS NOs: 405965, 405966, 399810, 399966, 405967, or 405968.

In certain embodiments, a target region is nucleotides 1552-1579 of SEQ ID NO: 1. In certain embodiments, an antisense compound is targeted to nucleotides 1552-1579 of SEQ ID NO: 1. In certain embodiments, an antisense compound targeted to a PCSK9 nucleic acid comprises a nucleotide sequence selected from SEQ ID NOs: 48, 343, 344, 345, or 346. In certain such embodiments, an antisense compound targeted to nucleotides 1552-1579 of SEQ ID NO: 1 is selected from ISIS NOs: 399811, 399967, 405969, 405970, 410740, or 405885.

In certain embodiments, a target region is nucleotides 1560-1587 of SEQ ID NO: 1. In certain embodiments, an antisense compound is targeted to nucleotides 1560-1587 of SEQ ID NO: 1. In certain embodiments, an antisense compound targeted to a PCSK9 nucleic acid comprises a nucleotide sequence selected from SEQ ID NOs: 49, 346, 347, 348, 349, 350, 351, 352, or 353. In certain such embodiments, an antisense compound targeted to nucleotides 1560-1587 of SEQ ID NO: 1 is selected from ISIS NOs: 405885, 405886, 405887, 410596, 410672, 405888, 410597, 410673, 399812, 399968, 410674, 405889, 410598, 410675, 405890, 410599, 410676, 405891, 410600, 410677, 405892, 410601, or 410678.

In certain embodiments, a target region is nucleotides 1561-1589 of SEQ ID NO: 1. In certain embodiments, an antisense compound is targeted to nucleotides 1561-1589 of SEQ ID NO: 1. In certain embodiments, an antisense compound targeted to a PCSK9 nucleic acid comprises a nucleotide sequence selected from SEQ ID NOs: 49, 50, 346, 347, 348, 349, 350, 351, 352, 353, or 354. In certain such embodiments, an antisense compound targeted to nucleotides 1561-1589 of SEQ ID NO: 1 is selected from ISIS NOs: 405886, 405887, 410596, 410672, 405888, 410597, 410673, 399812, 399968, 410674, 405889, 410598, 410675, 405890, 410599, 410676, 405891, 410600, 410677, 405892, 410601, 410678, 395178, 399900, 405557, 410679, 408653, 410602, or 410680.

In certain embodiments, a target region is nucleotides 1564-1591 of SEQ ID NO: 1. In certain embodiments, an antisense compound is targeted to nucleotides 1564-1591 of SEQ ID NO: 1. In certain embodiments, an antisense compound targeted to a PCSK9 nucleic acid comprises a nucleotide sequence selected from SEQ ID NOs: 49, 50, 350, 351, 352, 353, 354, 355, or 356. In certain such embodiments, an antisense compound targeted to nucleotides 1564-1591 of SEQ ID NO: 1 is selected from ISIS NOs: 399812, 399968, 410674, 405889, 410598, 410675, 405890, 410599, 410676, 405891, 410600, 410677, 405892, 410601, 410678, 395178, 399900, 405557, 410679, 408653, 410602, 410680, 405971, 410603, 410681, 410540, 410604, or 410682.

In certain embodiments, a target region is nucleotides 1565-1592 of SEQ ID NO: 1. In certain embodiments, an antisense compound is targeted to nucleotides 1565-1592 of SEQ ID NO: 1. In certain embodiments, an antisense compound targeted to a PCSK9 nucleic acid comprises a nucleotide sequence selected from SEQ ID NOs: 50, 350, 351, 352, 353, 354, 355, 356, or 357. In certain such embodiments, an antisense compound targeted to nucleotides 1565-1592 of SEQ ID NO: 1 is selected from ISIS NOs: 405889, 410598, 410675, 405890, 410599, 410676, 405891, 410600, 410677, 405892, 410601, 410678, 395178, 399900, 405557, 410679, 408653, 410602, 410680, 405971, 410603, 410681, 410540, 410604, 410682, or 405972.

In certain embodiments, a target region is nucleotides 1566-1592 of SEQ ID NO: 1. In certain embodiments, an antisense compound is targeted to nucleotides 1566-1592 of SEQ ID NO: 1. In certain embodiments, an antisense compound targeted to a PCSK9 nucleic acid comprises a nucleotide sequence selected from SEQ ID NOs: 50, 351, 352, 353, 354, 355, 356, or 357. In certain such embodiments, an antisense compound targeted to nucleotides 1566-1592 of SEQ ID NO: 1 is selected from ISIS NOs: 405890, 410599, 410676, 405891, 410600, 410677, 405892, 410601, 410678, 395178, 399900, 405557, 410679, 408653, 410602, 410680, 405971, 410603, 410681, 410540, 410604, 410682, or 405972.

In certain embodiments, a target region is nucleotides 1567-1592 of SEQ ID NO: 1. In certain embodiments, an antisense compound is targeted to nucleotides 1567-1592 of SEQ ID NO: 1. In certain embodiments, an antisense compound targeted to a PCSK9 nucleic acid comprises a nucleotide sequence selected from SEQ ID NOs: 50, 352, 353, 354, 355, 356, or 357. In certain such embodiments, an antisense compound targeted to nucleotides 1567-1592 of SEQ ID NO: 1 is selected from ISIS NOs: 405891, 410600, 410677, 405892, 410601, 410678, 395178, 399900, 405557, 410679, 408653, 410602, 410680, 405971, 410603, 410681, 410540, 410604, 410682, or 405972.

In certain embodiments, a target region is nucleotides 1570-1597 of SEQ ID NO: 1. In certain embodiments, an antisense compound is targeted to nucleotides 1570-1597 of SEQ ID NO: 1. In certain embodiments, an antisense compound targeted to a PCSK9 nucleic acid comprises a nucleotide sequence selected from SEQ ID NOs: 354, 355, 356, 357 or 358. In certain such embodiments, an antisense compound targeted to nucleotides 1570-1597 of SEQ ID NO: 1 is selected from ISIS NOs: 408653, 410602, 410680, 405971, 410603, 410681, 410540, 410604, 410682, 405972 or 405973.

In certain embodiments, a target region is nucleotides 1571-1599 of SEQ ID NO: 1. In certain embodiments, an antisense compound is targeted to nucleotides 1571-1599 of SEQ ID NO: 1. In certain embodiments, an antisense compound targeted to a PCSK9 nucleic acid comprises a nucleotide sequence selected from SEQ ID NOs: 87, 356, 357, 358, or 359. In certain such embodiments, an antisense compound targeted to nucleotides 1571-1599 of SEQ ID NO: 1 is selected from ISIS NOs: 405971, 410603, 410681, 410540, 410604, 410682, 405972, 395179, 399901, 405973, or 405974.

In certain embodiments, a target region is nucleotides 1605-1706 of SEQ ID NO: 1. In certain embodiments, an antisense compound is targeted to nucleotides 1605-1706 of SEQ ID NO: 1. In certain embodiments, an antisense compound targeted to a PCSK9 nucleic acid comprises a nucleotide sequence selected from SEQ ID NOs: 52, 53, 54, 119, 360, 361, 362, 363, 364, 365, 366, 367, 368, 369, 370, or 371. In certain such embodiments, an antisense compound targeted to nucleotides 1605-1706 of SEQ ID NO: 1 is selected from ISIS NOs: 395180, 399902, 410771, 395181, 399903, 405975, 399814, 399970, 405976, 405977, 410772, 405978, 395182, 399904, 405979, 405980, 405981, 410741, 405982, or 405983.

In certain embodiments, a target region is nucleotides 1628-1706 of SEQ ID NO: 1. In certain embodiments, an antisense compound is targeted to nucleotides 1628-1706 of SEQ ID NO: 1. In certain embodiments, an antisense compound targeted to a PCSK9 nucleic acid comprises a nucleotide sequence selected from SEQ ID NOs: 52, 53, 54, 360, 361, 362, 363, 364, 365, 366, 367, 368, 369, 370, or 371. In certain such embodiments, an antisense compound targeted to nucleotides 1628-1706 of SEQ ID NO: 1 is selected from ISIS NOs: 410771, 395181, 399903, 405975, 399814, 399970, 405976, 405977, 410772, 405978, 395182, 399904, 405979, 405980, 405981, 410741, 405982, or 405983.

In certain embodiments, a target region is nucleotides 1640-1666 of SEQ ID NO: 1. In certain embodiments, an antisense compound is targeted to nucleotides 1640-1666 of SEQ ID NO: 1. In certain embodiments, an antisense compound targeted to a PCSK9 nucleic acid comprises a nucleotide sequence selected from SEQ ID NOs: 52, 53, 361, or 362. In certain such embodiments, an antisense compound targeted to nucleotides 1640-1666 of SEQ ID NO: 1 is selected from ISIS NOs: 395181, 399903, 405975, 399814, 399970, or 405976.

In certain embodiments, a target region is nucleotides 1672-1698 of SEQ ID NO: 1. In certain embodiments, an antisense compound is targeted to nucleotides 1672-1698 of SEQ ID NO: 1. In certain embodiments, an antisense compound targeted to a PCSK9 nucleic acid comprises a nucleotide sequence selected from SEQ ID NOs: 54, 365, 366, or 367. In certain such embodiments, an antisense compound targeted to nucleotides 1672-1698 of SEQ ID NO: 1 is selected from ISIS NOs: 405978, 395182, 399904, 405979, or 405980.

In certain embodiments, a target region is nucleotides 1681-1706 of SEQ ID NO: 1. In certain embodiments, an antisense compound is targeted to nucleotides 1681-1706 of SEQ ID NO: 1. In certain embodiments, an antisense compound targeted to a PCSK9 nucleic acid comprises a nucleotide sequence selected from SEQ ID NOs: 368, 369, 370, or 371. In certain such embodiments, an antisense compound targeted to nucleotides 1681-1706 of SEQ ID NO: 1 is selected from ISIS NOs: 405981, 410741, 405982, or 405983.

In certain embodiments, a target region is nucleotides 1735-1761 of SEQ ID NO: 1. In certain embodiments, an antisense compound is targeted to nucleotides 1735-1761 of SEQ ID NO: 1. In certain embodiments, an antisense compound targeted to a PCSK9 nucleic acid comprises a nucleotide sequence selected from SEQ ID NOs: 55, 372, 373, or 374. In certain such embodiments, an antisense compound targeted to nucleotides 1735-1761 of SEQ ID NO: 1 is selected from ISIS NOs: 405984, 405564, 405641, 405985, 399815, 399971, or 405986.

In certain embodiments, a target region is nucleotides 1735-1765 of SEQ ID NO: 1. In certain embodiments, an antisense compound is targeted to nucleotides 1735-1765 of SEQ ID NO: 1. In certain embodiments, an antisense compound targeted to a PCSK9 nucleic acid comprises a nucleotide sequence selected from SEQ ID NOs: 55, 56, 372, 373, 374, or 375. In certain such embodiments, an antisense compound targeted to nucleotides 1735-1765 of SEQ ID NO: 1 is selected from ISIS NOs: 405984, 405564, 405641, 405985, 399815, 399971, 405986, 405987, 399816 or 399972.

In certain embodiments, a target region is nucleotides 1740-1765 of SEQ ID NO: 1. In certain embodiments, an antisense compound is targeted to nucleotides 1740-1765 of SEQ ID NO: 1. In certain embodiments, an antisense compound targeted to a PCSK9 nucleic acid comprises a nucleotide sequence selected from SEQ ID NOs: 55, 56, 374, or 375. In certain such embodiments, an antisense compound targeted to nucleotides 1740-1765 of SEQ ID NO: 1 is selected from ISIS NOs: 399815, 399971, 405986, 405987, 399816, or 399972.

In certain embodiments, a target region is nucleotides 1849-1876 of SEQ ID NO: 1. In certain embodiments, an antisense compound is targeted to nucleotides 1849-1876 of SEQ ID NO: 1. In certain embodiments, an antisense compound targeted to a PCSK9 nucleic acid comprises a nucleotide sequence selected from SEQ ID NOs: 376, 377, 378, 379, 380, 381, 382, 383, or 384. In certain such embodiments, an antisense compound targeted to nucleotides 1849-1876 of SEQ ID NO: 1 is selected from ISIS NOs: 410541, 410605, 410683, 410542, 410606, 410684, 410543, 410607, 410685, 410544, 410608, 410686, 410545, 410609, 410687, 405988, 410610, 410688, 410546, 410611, 410689, 405989, 410612, 410690, 410547, 410613, or 410691.

In certain embodiments, a target region is nucleotides 1849-1879 of SEQ ID NO: 1. In certain embodiments, an antisense compound is targeted to nucleotides 1849-1879 of SEQ ID NO: 1. In certain embodiments, an antisense compound targeted to a PCSK9 nucleic acid comprises a nucleotide sequence selected from SEQ ID NOs: 58, 376, 377, 378, 379, 380, 381, 382, 383, 384, 385, or 386. In certain such embodiments, an antisense compound targeted to nucleotides 1849-1879 of SEQ ID NO: 1 is selected from ISIS NOs: 410541, 410605, 410683, 410542, 410606, 410684, 410543, 410607, 410685, 410544, 410608, 410686, 410545, 410609, 410687, 405988, 410610, 410688, 410546, 410611, 410689, 405989, 410612, 410690, 410547, 410613, 395184, 410691, 399906, 410692, 410548, 410614, or 405990.

In certain embodiments, a target region is nucleotides 1850-1877 of SEQ ID NO: 1. In certain embodiments, an antisense compound is targeted to nucleotides 1850-1877 of SEQ ID NO: 1. In certain embodiments, an antisense compound targeted to a PCSK9 nucleic acid comprises a nucleotide sequence selected from SEQ ID NOs: 58, 377, 378, 379, 380, 381, 382, 383 or 384. In certain such embodiments, an antisense compound targeted to nucleotides 1850-1877 of SEQ ID NO: 1 is selected from ISIS NOs: 410542, 410606, 410684, 410543, 410607, 410685, 410544, 410608, 410686, 410545, 410609, 410687, 405988, 410610, 410688, 410546, 410611, 410689, 405989, 410612, 410690, 410547, 410613, 395184, 410691, 399906, or 410692.

In certain embodiments, a target region is nucleotides 1851-1877 of SEQ ID NO: 1. In certain embodiments, an antisense compound is targeted to nucleotides 1851-1877 of SEQ ID NO: 1. In certain embodiments, an antisense compound targeted to a PCSK9 nucleic acid comprises a nucleotide sequence selected from SEQ ID NOs: 58, 378, 379, 380, 381, 382, 383, or 384. In certain such embodiments, an antisense compound targeted to nucleotides 1851-1877 of SEQ ID NO: 1 is selected from ISIS NOs: 410543, 410607, 410685, 410544, 410608, 410686, 410545, 410609, 410687, 405988, 410610, 410688, 410546, 410611, 410689, 405989, 410612, 410690, 410547, 410613, 395184, 410691, 399906, or 410692.

In certain embodiments, a target region is nucleotides 1852-1878 of SEQ ID NO: 1. In certain embodiments, an antisense compound is targeted to nucleotides 1852-1878 of SEQ ID NO: 1. In certain embodiments, an antisense compound targeted to a PCSK9 nucleic acid comprises a nucleotide sequence selected from SEQ ID NOs: 58, 379, 380, 381, 382, 383, 384, or 385. In certain such embodiments, an antisense compound targeted to nucleotides 1852-1878 of SEQ ID NO: 1 is selected from ISIS NOs: 410544, 410608, 410686, 410545, 410609, 410687, 405988, 410610, 410688, 410546, 410611, 410689, 405989, 410612, 410690, 410547, 410613, 395184, 410691, 399906, 410692, 410548, 410614, or 410693.

In certain embodiments, a target region is nucleotides 1852-1879 of SEQ ID NO: 1. In certain embodiments, an antisense compound is targeted to nucleotides 1852-1879 of SEQ ID NO: 1. In certain embodiments, an antisense compound targeted to a PCSK9 nucleic acid comprises a nucleotide sequence selected from SEQ ID NOs: 58, 379, 380, 381, 382, 383, 384, 385, or 386. In certain such embodiments, an antisense compound targeted to nucleotides 1852-1879 of SEQ ID NO: 1 is selected from ISIS NOs: 410544, 410608, 410686, 410545, 410609, 410687, 405988, 410610, 410688, 410546, 410611, 410689, 405989, 410612, 410690, 410547, 410613, 395184, 410691, 399906, 410692, 410548, 410614, 410693, or 405990.

In certain embodiments, a target region is nucleotides 1853-1879 of SEQ ID NO: 1. In certain embodiments, an antisense compound is targeted to nucleotides 1853-1879 of SEQ ID NO: 1. In certain embodiments, an antisense compound targeted to a PCSK9 nucleic acid comprises a nucleotide sequence selected from SEQ ID NOs: 58, 380, 381, 382, 383, 384, 385 or 386. In certain such embodiments, an antisense compound targeted to nucleotides 1853-1879 of SEQ ID NO: 1 is selected from ISIS NOs: 410545, 410609, 410687, 405988, 410610, 410688, 410546, 410611, 410689, 405989, 410612, 410690, 410547, 410613, 395184, 410691, 399906, 410692, 410548, 410614, 410693, or 405990.

In certain embodiments, a target region is nucleotides 1854-1879 of SEQ ID NO: 1. In certain embodiments, an antisense compound is targeted to nucleotides 1854-1879 of SEQ ID NO: 1. In certain embodiments, an antisense compound targeted to a PCSK9 nucleic acid comprises a nucleotide sequence selected from SEQ ID NOs: 58, 381, 382, 383, 384, 385, or 386. In certain such embodiments, an antisense compound targeted to nucleotides 1854-1879 of SEQ ID NO: 1 is selected from ISIS NOs: 405988, 410610, 410688, 410546, 410611, 410689, 405989, 410612, 410690, 410547, 410613, 395184, 410691, 399906, 410692, 410548, 410614, 410693, or 405990.

In certain embodiments, a target region is nucleotides 1905-1955 of SEQ ID NO: 1. In certain embodiments, an antisense compound is targeted to nucleotides 1905-1955 of SEQ ID NO: 1. In certain embodiments, an antisense compound targeted to a PCSK9 nucleic acid comprises a nucleotide sequence selected from SEQ ID NOs: 59, 387, 388, 389, 390, 391, 392, 393, 394, 395, 396, 397, 398, 399, 400, 401, 402, 403, 404, 405, or 406. In certain such embodiments, an antisense compound targeted to nucleotides 1905-1955 of SEQ ID NO: 1 is selected from ISIS NOs: 410773, 410549, 410615, 410694, 410550, 410616, 410695, 410551, 410617, 410696, 410552, 410618, 410697, 410553, 410619, 410698, 395185, 399907, 410699, 410554, 410620, 410700, 405991, 410621, 410701, 410555, 410622, 410702, 405992, 410623, 410703, 410556, or 410774.

In certain embodiments, a target region is nucleotides 1915-1942 of SEQ ID NO: 1. In certain embodiments, an antisense compound is targeted to nucleotides 1915-1942 of SEQ ID NO: 1. In certain embodiments, an antisense compound targeted to a PCSK9 nucleic acid comprises a nucleotide sequence selected from SEQ ID NOs: 59, 388, 389, 390, 391, 392, 393, 394, or 395. In certain such embodiments, an antisense compound targeted to nucleotides 1915-1942 of SEQ ID NO: 1 is selected from ISIS NOs: 410549, 410615, 410694, 410550, 410616, 410695, 410551, 410617, 410696, 410552, 410618, 410697, 410553, 410619, 410698, 395185, 399907, 410699, 410554, 410620, 410700, 405991, 410621, 410701, 410555, 410622, or 410702.

In certain embodiments, a target region is nucleotides 1916-1943 of SEQ ID NO: 1. In certain embodiments, an antisense compound is targeted to nucleotides 1916-1943 of SEQ ID NO: 1. In certain embodiments, an antisense compound targeted to a PCSK9 nucleic acid comprises a nucleotide sequence selected from SEQ ID NOs: 59, 389, 390, 391, 392, 393, 394, 395, or 396. In certain such embodiments, an antisense compound targeted to nucleotides 1916-1943 of SEQ ID NO: 1 is selected from ISIS NOs: 410550, 410616, 410695, 410551, 410617, 410696, 410552, 410618, 410697, 410553, 410619, 410698, 395185, 399907, 410699, 410554, 410620, 410700, 405991, 410621, 410701, 410555, 410622, 410702, 405992, 410623, or 410703.

In certain embodiments, a target region is nucleotides 1917-1944 of SEQ ID NO: 1. In certain embodiments, an antisense compound is targeted to nucleotides 1917-1944 of SEQ ID NO: 1. In certain embodiments, an antisense compound targeted to a PCSK9 nucleic acid comprises a nucleotide sequence selected from SEQ ID NOs: 59, 390, 391, 392, 393, 394, 395, 396, or 397. In certain such embodiments, an antisense compound targeted to nucleotides 1917-1944 of SEQ ID NO: 1 is selected from ISIS NOs: 410551, 410617, 410696, 410552, 410618, 410697, 410553, 410619, 410698, 395185, 399907, 410699, 410554, 410620, 410700, 405991, 410621, 410701, 410555, 410622, 410702, 405992, 410623, 410703, 410556, 410624, or 410704.

In certain embodiments, a target region is nucleotides 1918-1945 of SEQ ID NO: 1. In certain embodiments, an antisense compound is targeted to nucleotides 1918-1945 of SEQ ID NO: 1. In certain embodiments, an antisense compound targeted to a PCSK9 nucleic acid comprises a nucleotide sequence selected from SEQ ID NOs: 59, 391, 392, 393, 394, 395, 396, 397, or 398. In certain such embodiments, an antisense compound targeted to nucleotides 1918-1945 of SEQ ID NO: 1 is selected from ISIS NOs: 410552, 410618, 410697, 410553, 410619, 410698, 395185, 399907, 410699, 410554, 410620, 410700, 405991, 410621, 410701, 410555, 410622, 410702, 405992, 410623, 410703, 410556, 410624, 410704, 405993, 410625, or 410705.

In certain embodiments, a target region is nucleotides 1919-1946 of SEQ ID NO: 1. In certain embodiments, an antisense compound is targeted to nucleotides 1919-1946 of SEQ ID NO: 1. In certain embodiments, an antisense compound targeted to a PCSK9 nucleic acid comprises a nucleotide sequence selected from SEQ ID NOs: 59, 392, 393, 394, 395, 396, 397, or 399. In certain such embodiments, an antisense compound targeted to nucleotides 1919-1946 of SEQ ID NO: 1 is selected from ISIS NOs: 410553, 410619, 410698, 395185, 399907, 410699, 410554, 410620, 410700, 405991, 410621, 410701, 410555, 410622, 410702, 405992, 410623, 410703, 410556, 410624, 410704, 405993, 410625, 410705, 410557, 410626, or 410706.

In certain embodiments, a target region is nucleotides 1920-1939 of SEQ ID NO: 1. In certain embodiments, an antisense compound is targeted to nucleotides 1920-1939 of SEQ ID NO: 1. In certain embodiments, an antisense compound targeted to a PCSK9 nucleic acid comprises a nucleotide sequence selected from SEQ ID NOs: 59. In certain such embodiments, an antisense compound targeted to nucleotides 1920-1939 of SEQ ID NO: 1 is selected from ISIS NOs: 395185, 399907, or 410699.

In certain embodiments, a target region is nucleotides 1920-1947 of SEQ ID NO: 1. In certain embodiments, an antisense compound is targeted to nucleotides 1920-1947 of SEQ ID NO: 1. In certain embodiments, an antisense compound targeted to a PCSK9 nucleic acid comprises a nucleotide sequence selected from SEQ ID NOs: 59, 393, 394, 395, 396, 397, 398, 399, or 400. In certain such embodiments, an antisense compound targeted to nucleotides 1920-1947 of SEQ ID NO: 1 is selected from ISIS NOs: 395185, 399907, 410699, 410554, 410620, 410700, 405991, 410621, 410701, 410555, 410622, 410702, 405992, 410623, 410703, 410556, 410624, 410704, 405993, 410625, 410705, 410557, 410626, 410706, 405944, 410627, or 410707.

In certain embodiments, a target region is nucleotides 1921-1948 of SEQ ID NO: 1. In certain embodiments, an antisense compound is targeted to nucleotides 1921-1948 of SEQ ID NO: 1. In certain embodiments, an antisense compound targeted to a PCSK9 nucleic acid comprises a nucleotide sequence selected from SEQ ID NOs: 393, 394, 395, 396, 397, 398, 399, 400, or 401. In certain such embodiments, an antisense compound targeted to nucleotides 1921-1948 of SEQ ID NO: 1 is selected from ISIS NOs: 410554, 410620, 410700, 405991, 410621, 410701, 410555, 410622, 410702, 405992, 410623, 410703, 410556, 410624, 410704, 405993, 410625, 410705, 410557, 410626, 410706, 405944, 410627, 410707, 410558, 410628, or 410708.

In certain embodiments, a target region is nucleotides 1922-1949 of SEQ ID NO: 1. In certain embodiments, an antisense compound is targeted to nucleotides 1922-1949 of SEQ ID NO: 1. In certain embodiments, an antisense compound targeted to a PCSK9 nucleic acid comprises a nucleotide sequence selected from SEQ ID NOs: 394, 395, 396, 397, 398, 399, 400, 401, or 402. In certain such embodiments, an antisense compound targeted to nucleotides 1922-1949 of SEQ ID NO: 1 is selected from ISIS NOs: 405991, 410621, 410701, 410555, 410622, 410702, 405992, 410623, 410703, 410556, 410624, 410704, 405993, 410625, 410705, 410557, 410626, 410706, 405944, 410627, 410707, 410558, 410628, 410708, 405995, 410629, or 410709.

In certain embodiments, a target region is nucleotides 1923-1950 of SEQ ID NO: 1. In certain embodiments, an antisense compound is targeted to nucleotides 1923-1950 of SEQ ID NO: 1. In certain embodiments, an antisense compound targeted to a PCSK9 nucleic acid comprises a nucleotide sequence selected from SEQ ID NOs: 395, 396, 397, 398, 399, 400, 401, 402, or 403. In certain such embodiments, an antisense compound targeted to nucleotides 1923-1950 of SEQ ID NO: 1 is selected from ISIS NOs: 410555, 410622, 410702, 405992, 410623, 410703, 410556, 410624, 410704, 405993, 410625, 410705, 410557, 410626, 410706, 405944, 410627, 410707, 410558, 410628, 410708, 405995, 410629, 410709, 410559, 410630, or 410710.

In certain embodiments, a target region is nucleotides 1924-1951 of SEQ ID NO: 1. In certain embodiments, an antisense compound is targeted to nucleotides 1924-1951 of SEQ ID NO: 1. In certain embodiments, an antisense compound targeted to a PCSK9 nucleic acid comprises a nucleotide sequence selected from SEQ ID NOs: 396, 397, 398, 399, 400, 401, 402, 403, or 404. In certain such embodiments, an antisense compound targeted to nucleotides 1924-1951 of SEQ ID NO: 1 is selected from ISIS NOs: 405992, 410623, 410703, 410556, 410624, 410704, 405993, 410625, 410705, 410557, 410626, 410706, 405994, 410627, 410707, 410558, 410628, 410708, 405995, 410629, 410709, 410559, 410630, 410710, 410560, 410631, or 410711.

In certain embodiments, a target region is nucleotides 1925-1952 of SEQ ID NO: 1. In certain embodiments, an antisense compound is targeted to nucleotides 1925-1952 of SEQ ID NO: 1. In certain embodiments, an antisense compound targeted to a PCSK9 nucleic acid comprises a nucleotide sequence selected from SEQ ID NOs: 397, 398, 399, 400, 401, 402, 403, 404, or 405. In certain such embodiments, an antisense compound targeted to nucleotides 1925-1952 of SEQ ID NO: 1 is selected from ISIS NOs: 410556, 410624, 410704, 405993, 410625, 410705, 410557, 410626, 410706, 405994, 410627, 410707, 410558, 410628, 410708, 405995, 410629, 410709, 410559, 410630, 410710, 410560, 410631, 410711, 410561, 410632, or 410712.

In certain embodiments, a target region is nucleotides 1926-1952 of SEQ ID NO: 1. In certain embodiments, an antisense compound is targeted to nucleotides 1926-1952 of SEQ ID NO: 1. In certain embodiments, an antisense compound targeted to a PCSK9 nucleic acid comprises a nucleotide sequence selected from SEQ ID NOs: 398, 399, 400, 401, 402, 403, 404, or 405. In certain such embodiments, an antisense compound targeted to nucleotides 1926-1952 of SEQ ID NO: 1 is selected from ISIS NOs: 405993, 410625, 410705, 410557, 410626, 410706, 405994, 410627, 410707, 410558, 410628, 410708, 405995, 410629, 410709, 410559, 410630, 410710, 410560, 410631, 410711, 410561, 410632, or 410712.

In certain embodiments, a target region is nucleotides 1927-1952 of SEQ ID NO: 1. In certain embodiments, an antisense compound is targeted to nucleotides 1927-1952 of SEQ ID NO: 1. In certain embodiments, an antisense compound targeted to a PCSK9 nucleic acid comprises a nucleotide sequence selected from SEQ ID NOs: 399, 400, 401, 402, 403, 404, or 405. In certain such embodiments, an antisense compound targeted to nucleotides 1927-1952 of SEQ ID NO: 1 is selected from ISIS NOs: 410557, 410626, 410706, 405994, 410627, 410707, 410558, 410628, 410708, 405995, 410629, 410709, 410559, 410630, 410710, 410560, 410631, 410711, 410561, 410632, or 410712.

In certain embodiments, a target region is nucleotides 1928-1955 of SEQ ID NO: 1. In certain embodiments, an antisense compound is targeted to nucleotides 1928-1955 of SEQ ID NO: 1. In certain embodiments, an antisense compound targeted to a PCSK9 nucleic acid comprises a nucleotide sequence selected from SEQ ID NOs: 400, 401, 402, 403, 404, 405, or 406. In certain such embodiments, an antisense compound targeted to nucleotides 1928-1955 of SEQ ID NO: 1 is selected from ISIS NOs: 405994, 410627, 410707, 410558, 410628, 410708, 405995, 410629, 410709, 410559, 410630, 410710, 410560, 410631, 410711, 410561, 410632, 410712, or 410774.

In certain embodiments, a target region is nucleotides 1962-2059 of SEQ ID NO: 1. In certain embodiments, an antisense compound is targeted to nucleotides 1962-2059 of SEQ ID NO: 1. In certain embodiments, an antisense compound targeted to a PCSK9 nucleic acid comprises a nucleotide sequence selected from SEQ ID NOs: 407, 408, 409, or 410. In certain such embodiments, an antisense compound targeted to nucleotides 1962-2059 of SEQ ID NO: 1 is selected from ISIS NOs: 410775, 410776, 410777, or 410778.

In certain embodiments, a target region is nucleotides 2040-2126 of SEQ ID NO: 1. In certain embodiments, an antisense compound is targeted to nucleotides 2040-2126 of SEQ ID NO: 1. In certain embodiments, an antisense compound targeted to a PCSK9 nucleic acid comprises a nucleotide sequence selected from SEQ ID NOs: 60, 61, 410, 411, 412, 413, 414, or 415. In certain such embodiments, an antisense compound targeted to nucleotides 2040-2126 of SEQ ID NO: 1 is selected from ISIS NOs: 410778, 395186, 399908, 410713, 410562, 410633, 410714, 405996, 410634, 410715, 410563, 410635, 410716, 410564, 410636, 410717, 399817, 399973, 410718, or 405997.

In certain embodiments, a target region is nucleotides 2100-2126 of SEQ ID NO: 1. In certain embodiments, an antisense compound is targeted to nucleotides 2100-2126 of SEQ ID NO: 1. In certain embodiments, an antisense compound targeted to a PCSK9 nucleic acid comprises a nucleotide sequence selected from SEQ ID NOs: 60, 61, 411, 412, 413, 414, or 415. In certain such embodiments, an antisense compound targeted to nucleotides 2100-2126 of SEQ ID NO: 1 is selected from ISIS NOs: 395186, 399908, 410713, 410562, 410633, 410714, 405996, 410634, 410715, 410563, 410635, 410716, 410564, 410636, 410717, 399817, 399973, 410718 or 405997.

In certain embodiments, a target region is nucleotides 2100-2139 of SEQ ID NO: 1. In certain embodiments, an antisense compound is targeted to nucleotides 2100-2139 of SEQ ID NO: 1. In certain embodiments, an antisense compound targeted to a PCSK9 nucleic acid comprises a nucleotide sequence selected from SEQ ID NOs: 60, 61, 411, 412, 413, 414, 415, or 416. In certain such embodiments, an antisense compound targeted to nucleotides 2100-2139 of SEQ ID NO: 1 is selected from ISIS NOs: 395186, 399908, 410713, 410562, 410633, 410714, 405996, 410634, 410715, 410563, 410635, 410716, 410564, 410636, 410717, 399817, 399973, 410718, 405997 or 410779.

In certain embodiments, a target region is nucleotides 2100-2206 of SEQ ID NO: 1. In certain embodiments, an antisense compound is targeted to nucleotides 2100-2206 of SEQ ID NO: 1. In certain embodiments, an antisense compound targeted to a PCSK9 nucleic acid comprises a nucleotide sequence selected from SEQ ID NOs: 60, 61, 411, 412, 413, 414, 415, 416, 417, or 418. In certain such embodiments, an antisense compound targeted to nucleotides 2100-2206 of SEQ ID NO: 1 is selected from ISIS NOs: 395186, 399908, 410713, 410562, 410633, 410714, 405996, 410634, 410715, 410563, 410635, 410716, 410564, 410636, 410717, 399817, 399973, 410718, 405997, 405997, 410780, or 410781.

In certain embodiments, a target region is nucleotides 2101-2126 of SEQ ID NO: 1. In certain embodiments, an antisense compound is targeted to nucleotides 2101-2126 of SEQ ID NO: 1. In certain embodiments, an antisense compound targeted to a PCSK9 nucleic acid comprises a nucleotide sequence selected from SEQ ID NOs: 61, 411, 412, 413, 414, or 415. In certain such embodiments, an antisense compound targeted to nucleotides 2101-2126 of SEQ ID NO: 1 is selected from ISIS NOs: 410562, 410633, 410714, 405996, 410634, 410715, 410563, 410635, 410716, 410564, 410636, 410717, 399817, 399973, 410718, or 405997.

In certain embodiments, a target region is nucleotides 2305-2332 of SEQ ID NO: 1. In certain embodiments, an antisense compound is targeted to nucleotides 2305-2332 of SEQ ID NO: 1. In certain embodiments, an antisense compound targeted to a PCSK9 nucleic acid comprises a nucleotide sequence selected from SEQ ID NOs: 62, 419, 420, 421, 422, 423, 424, 425, or 426. In certain such embodiments, an antisense compound targeted to nucleotides 2305-2332 of SEQ ID NO: 1 is selected from ISIS NOs: 410565, 410637, 410719, 410566, 410638, 410720, 410567, 410639, 410721, 410568, 410640, 410722, 410569, 410641, 410723, 395187, 399909, 410724, 410570, 410642, 410725, 410571, 410643, 410726, 405998, 410644, or 410727.

In certain embodiments, a target region is nucleotides 2305-2354 of SEQ ID NO: 1. In certain embodiments, an antisense compound is targeted to nucleotides 2305-2354 of SEQ ID NO: 1. In certain embodiments, an antisense compound targeted to a PCSK9 nucleic acid comprises a nucleotide sequence selected from SEQ ID NOs: 62, 419, 420, 421, 422, 423, 424, 425, 426, 427, 428, 429, or 430. In certain such embodiments, an antisense compound targeted to nucleotides 2305-2354 of SEQ ID NO: 1 is selected from ISIS NOs: 410565, 410637, 410719, 410566, 410638, 410720, 410567, 410639, 410721, 410568, 410640, 410722, 410569, 410641, 410723, 395187, 399909, 410724, 410570, 410642, 410725, 410571, 410643, 410726, 405998, 410644, 410727, 410572, 410645, 410728, 410573, 410646, or 410783.

In certain embodiments, a target region is nucleotides 2306-2333 of SEQ ID NO: 1. In certain embodiments, an antisense compound is targeted to nucleotides 2306-2333 of SEQ ID NO: 1. In certain embodiments, an antisense compound targeted to a PCSK9 nucleic acid comprises a nucleotide sequence selected from SEQ ID NOs: 62, 420, 421, 422, 423, 424, 425, 426, or 427. In certain such embodiments, an antisense compound targeted to nucleotides 2306-2333 of SEQ ID NO: 1 is selected from ISIS NOs: 410566, 410638, 410720, 410567, 410639, 410721, 410568, 410640, 410722, 410569, 410641, 410723, 395187, 399909, 410724, 410570, 410642, 410725, 410571, 410643, 410726, 405998, 410644, 410727, 410572, 410645, or 410728.

In certain embodiments, a target region is nucleotides 2307-2334 of SEQ ID NO: 1. In certain embodiments, an antisense compound is targeted to nucleotides 2307-2334 of SEQ ID NO: 1. In certain embodiments, an antisense compound targeted to a PCSK9 nucleic acid comprises a nucleotide sequence selected from SEQ ID NOs: 62, 421, 422, 423, 424, 425, 426, 427, or 428. In certain such embodiments, an antisense compound targeted to nucleotides 2307-2334 of SEQ ID NO: 1 is selected from ISIS NOs: 410567, 410639, 410721, 410568, 410640, 410722, 410569, 410641, 410723, 395187, 399909, 410724, 410570, 410642, 410725, 410571, 410643, 410726, 405998, 410644, 410727, 410572, 410645, 410728, 410573, 410646, or 410729.

In certain embodiments, a target region is nucleotides 2308-2334 of SEQ ID NO: 1. In certain embodiments, an antisense compound is targeted to nucleotides 2308-2334 of SEQ ID NO: 1. In certain embodiments, an antisense compound targeted to a PCSK9 nucleic acid comprises a nucleotide sequence selected from SEQ ID NOs: 62, 422, 423, 424, 425, 426, 427, or 428. In certain such embodiments, an antisense compound targeted to nucleotides 2308-2334 of SEQ ID NO: 1 is selected from ISIS NOs: 410568, 410640, 410722, 410569, 410641, 410723, 395187, 399909, 410724, 410570, 410642, 410725, 410571, 410643, 410726, 405998, 410644, 410727, 410572, 410645, 410728, 410573, 410646, or 410729.

In certain embodiments, a target region is nucleotides 2309-2334 of SEQ ID NO: 1. In certain embodiments, an antisense compound is targeted to nucleotides 2309-2334 of SEQ ID NO: 1. In certain embodiments, an antisense compound targeted to a PCSK9 nucleic acid comprises a nucleotide sequence selected from SEQ ID NOs: 62, 423, 424, 425, 426, 427, or 428. In certain such embodiments, an antisense compound targeted to nucleotides 2309-2334 of SEQ ID NO: 1 is selected from ISIS NOs: 410569, 410641, 410723, 395187, 399909, 410724, 410570, 410642, 410725, 410571, 410643, 410726, 405998, 410644, 410727, 410572, 410645, 410728, 410573, 410646, or 410729.

In certain embodiments, a target region is nucleotides 2310-2334 of SEQ ID NO: 1. In certain embodiments, an antisense compound is targeted to nucleotides 2310-2334 of SEQ ID NO: 1. In certain embodiments, an antisense compound targeted to a PCSK9 nucleic acid comprises a nucleotide sequence selected from SEQ ID NOs: 62, 424, 425, 426, 427, or 428. In certain such embodiments, an antisense compound targeted to nucleotides 2310-2334 of SEQ ID NO: 1 is selected from ISIS NOs: 395187, 399909, 410724, 410570, 410642, 410725, 410571, 410643, 410726, 405998, 410644, 410727, 410572, 410645, 410728, 410573, 410646, or 410729.

In certain embodiments, a target region is nucleotides 2410-2434 of SEQ ID NO: 1. In certain embodiments, an antisense compound is targeted to nucleotides 2410-2434 of SEQ ID NO: 1. In certain embodiments, an antisense compound targeted to a PCSK9 nucleic acid comprises a nucleotide sequence selected from SEQ ID NOs: 63 or 154. In certain such embodiments, an antisense compound targeted to nucleotides 2410-2434 of SEQ ID NO: 1 is selected from ISIS NOs: 395188, 399910, 399818, or 399974.

In certain embodiments, a target region is nucleotides 2504-2528 of SEQ ID NO: 1. In certain embodiments, an antisense compound is targeted to nucleotides 2504-2528 of SEQ ID NO: 1. In certain embodiments, an antisense compound targeted to a PCSK9 nucleic acid comprises a nucleotide sequence selected from SEQ ID NOs: 64 or 65. In certain such embodiments, an antisense compound targeted to nucleotides 2504-2528 of SEQ ID NO: 1 is selected from ISIS NOs: 395189, 399911, 399819, or 399975.

In certain embodiments, a target region is nucleotides 2509-2528 of SEQ ID NO: 1. In certain embodiments, an antisense compound is targeted to nucleotides 2509-2528 of SEQ ID NO: 1. In certain embodiments, an antisense compound targeted to a PCSK9 nucleic acid comprises a nucleotide sequence selected from SEQ ID NOs: 65. In certain such embodiments, an antisense compound targeted to nucleotides 2509-2528 of SEQ ID NO: 1 is selected from ISIS NOs: 399819 or 399975.

In certain embodiments, a target region is nucleotides 2582-2625 of SEQ ID NO: 1. In certain embodiments, an antisense compound is targeted to nucleotides 2582-2625 of SEQ ID NO: 1. In certain embodiments, an antisense compound targeted to a PCSK9 nucleic acid comprises a nucleotide sequence selected from SEQ ID NOs: 66, 67 or 122. In certain such embodiments, an antisense compound targeted to nucleotides 2582-2625 of SEQ ID NO: 1 is selected from ISIS NOs: 399820, 399976, 395190, 399912, 395191, or 399913.

In certain embodiments, a target region is nucleotides 2606-2668 of SEQ ID NO: 1. In certain embodiments, an antisense compound is targeted to nucleotides 2606-2668 of SEQ ID NO: 1. In certain embodiments, an antisense compound targeted to a PCSK9 nucleic acid comprises a nucleotide sequence selected from SEQ ID NOs: 67 or 153. In certain such embodiments, an antisense compound targeted to nucleotides 2606-2668 of SEQ ID NO: 1 is selected from ISIS NOs: 395191, 399913, 395192, or 399914.

In certain embodiments, a target region is nucleotides 2828-2855 of SEQ ID NO: 1. In certain embodiments, an antisense compound is targeted to nucleotides 2828-2855 of SEQ ID NO: 1. In certain embodiments, an antisense compound targeted to a PCSK9 nucleic acid comprises a nucleotide sequence selected from SEQ ID NOs: 69, 431, 432, 433, 434, 435, 436, 437 or 438. In certain such embodiments, an antisense compound targeted to nucleotides 2828-2855 of SEQ ID NO: 1 is selected from ISIS NOs: 405893, 405894, 405895, 405896, 395194, 399916, 405897, 405898, 405899, or 405900.

In certain embodiments, a target region is nucleotides 2832-2851 of SEQ ID NO: 1. In certain embodiments, an antisense compound is targeted to nucleotides 2832-2851 of SEQ ID NO: 1. In certain embodiments, an antisense compound targeted to a PCSK9 nucleic acid comprises a nucleotide sequence selected from SEQ ID NOs: 69. In certain such embodiments, an antisense compound targeted to nucleotides 2832-2851 of SEQ ID NO: 1 is selected from ISIS NOs: 395194, or 399916.

In certain embodiments, a target region is nucleotides 2900-2927 of SEQ ID NO: 1. In certain embodiments, an antisense compound is targeted to nucleotides 2900-2927 of SEQ ID NO: 1. In certain embodiments, an antisense compound targeted to a PCSK9 nucleic acid comprises a nucleotide sequence selected from SEQ ID NOs: 70, 71, 439, 440, 441, 442, 443 or 444. In certain such embodiments, an antisense compound targeted to nucleotides 2900-2927 of SEQ ID NO: 1 is selected from ISIS NOs: 395195, 399917, 405901, 405902, 405903, 405904, 399821, 399977, 405905, or 405906.

In certain embodiments, a target region is nucleotides 2900-2929 of SEQ ID NO: 1. In certain embodiments, an antisense compound is targeted to nucleotides 2900-2929 of SEQ ID NO: 1. In certain embodiments, an antisense compound targeted to a PCSK9 nucleic acid comprises a nucleotide sequence selected from SEQ ID NOs: 70, 71, 439, 440, 441, 442, 443, 444, 446 or 446. In certain such embodiments, an antisense compound targeted to nucleotides 2900-2929 of SEQ ID NO: 1 is selected from ISIS NOs: 395195, 399917, 405901, 405902, 405903, 405904, 399821, 399977, 405905, 405906, 405907, or 405908.

In certain embodiments, a target region is nucleotides 2902-2927 of SEQ ID NO: 1. In certain embodiments, an antisense compound is targeted to nucleotides 2902-2927 of SEQ ID NO: 1. In certain embodiments, an antisense compound targeted to a PCSK9 nucleic acid comprises a nucleotide sequence selected from SEQ ID NOs: 71, 439, 440, 441, 442, 443 or 444. In certain such embodiments, an antisense compound targeted to nucleotides 2902-2927 of SEQ ID NO: 1 is selected from ISIS NOs: 405901, 405902, 405903, 405904, 399821, 399977, 405905, or 405906.

In certain embodiments, a target region is nucleotides 2983-3007 of SEQ ID NO: 1. In certain embodiments, an antisense compound is targeted to nucleotides 2983-3007 of SEQ ID NO: 1. In certain embodiments, an antisense compound targeted to a PCSK9 nucleic acid comprises a nucleotide sequence selected from SEQ ID NOs: 72 or 73. In certain such embodiments, an antisense compound targeted to nucleotides 2983-3007 of SEQ ID NO: 1 is selected from ISIS NOs: 395196, 399918, 399822, or 399978.

In certain embodiments, a target region is nucleotides 2983-3013 of SEQ ID NO: 1. In certain embodiments, an antisense compound is targeted to nucleotides 2983-3013 of SEQ ID NO: 1. In certain embodiments, an antisense compound targeted to a PCSK9 nucleic acid comprises a nucleotide sequence selected from SEQ ID NOs: 72, 73 or 135. In certain such embodiments, an antisense compound targeted to nucleotides 2983-3013 of SEQ ID NO: 1 is selected from ISIS NOs: 395196, 399918, 399822, 399978, 399823, or 399979.

In certain embodiments, a target region is nucleotides 3227-3252 of SEQ ID NO: 1. In certain embodiments, an antisense compound is targeted to nucleotides 3227-3252 of SEQ ID NO: 1. In certain embodiments, an antisense compound targeted to a PCSK9 nucleic acid comprises a nucleotide sequence selected from SEQ ID NOs: 74 or 112. In certain such embodiments, an antisense compound targeted to nucleotides 3227-3252 of SEQ ID NO: 1 is selected from ISIS NOs: 395197, 399919, 399824, or 399980.

In certain embodiments, a target region is nucleotides 3227-3456 of SEQ ID NO: 1. In certain embodiments, an antisense compound is targeted to nucleotides 3227-3456 of SEQ ID NO: 1. In certain embodiments, an antisense compound targeted to a PCSK9 nucleic acid comprises a nucleotide sequence selected from SEQ ID NOs: 74, 75 or 112. In certain such embodiments, an antisense compound targeted to nucleotides 3227-3456 of SEQ ID NO: 1 is selected from ISIS NOs: 395197, 399919, 399824, 399980, 395198, or 399920.

In certain embodiments, a target region is nucleotides 3472-3496 of SEQ ID NO: 1. In certain embodiments, an antisense compound is targeted to nucleotides 3472-3496 of SEQ ID NO: 1. In certain embodiments, an antisense compound targeted to a PCSK9 nucleic acid comprises a nucleotide sequence selected from SEQ ID NOs: 76 or 77. In certain such embodiments, an antisense compound targeted to nucleotides 3472-3496 of SEQ ID NO: 1 is selected from ISIS NOs: 395199, 399921, 399825 or 399981.

In certain embodiments, a target region is nucleotides 3543-3569 of SEQ ID NO: 1. In certain embodiments, an antisense compound is targeted to nucleotides 3543-3569 of SEQ ID NO: 1. In certain embodiments, an antisense compound targeted to a PCSK9 nucleic acid comprises a nucleotide sequence selected from SEQ ID NOs: 78 or 99. In certain such embodiments, an antisense compound targeted to nucleotides 3543-3569 of SEQ ID NO: 1 is selected from ISIS NOs: 395200, 399922, 399826 or 399982.

In certain embodiments, antisense compound target a PCSK9 nucleic acid having the sequence of nucleotides 25475000 to 25504000 of GENBANK® Accession No. NT_032977.8, first deposited with GENBANK® on Feb. 26, 2006, and incorporated herein as SEQ ID NO: 2. In certain such embodiments, an antisense oligonucleotide is targeted to SEQ ID NO: 2. In certain such embodiments, an antisense oligonucleotide that is targeted to SEQ ID NO: 2 is at least 90% complementary to SEQ ID NO: 2. In certain such embodiments, an antisense oligonucleotide that is targeted to SEQ ID NO: 2 is at least 95% complementary to SEQ ID NO: 2. In certain such embodiments, an antisense oligonucleotide that is targeted to SEQ ID NO: 1 is 100% complementary to SEQ ID NO: 1. In certain such embodiments, an antisense oligonucleotide comprises a nucleotide sequence selected from a nucleotide sequence set forth in Table 7.

TABLE 7

Antisense sequences targeted to NT_032977.8 (SEQ ID NO: 2)

| SEQ ID NO | 5' Start Site to SEQ ID NO: 2 | 3' Start Site to SEQ ID NO: 2 | Sequence (5' to 3') |
|---|---|---|---|
| 4 | 2274 | 2293 | GCGCGGAATCCTGGCTGGGA |
| 5 | 2381 | 2400 | GAGGAGACCTAGAGGCCGTG |
| 159 | 2433 | 2452 | GCCTGGAGCTGACGGTGCCC |
| 160 | 2437 | 2456 | GACCGCCTGGAGCTGACGGT |
| 6 | 2439 | 2458 | AGGACCGCCTGGAGCTGACG |
| 162 | 2545 | 2564 | AAGGCTAGCACCAGCTCCTC |
| 163 | 2546 | 2565 | CAAGGCTAGCACCAGCTCCT |
| 164 | 2547 | 2566 | GCAAGGCTAGCACCAGCTCC |
| 165 | 2548 | 2567 | CGCAAGGCTAGCACCAGCTC |
| 7 | 2549 | 2568 | ACGCAAGGCTAGCACCAGCT |
| 166 | 2550 | 2569 | AACGCAAGGCTAGCACCAGC |
| 167 | 2551 | 2570 | GAACGCAAGGCTAGCACCAG |
| 168 | 2552 | 2571 | GGAACGCAAGGCTAGCACCA |
| 169 | 2553 | 2572 | CGGAACGCAAGGCTAGCACC |
| 8 | 2556 | 2575 | CCTCGGAACGCAAGGCTAGC |
| 170 | 2560 | 2579 | TCCTCCTCGGAACGCAAGGC |
| 171 | 2585 | 2604 | GTGCTCGGGTGCTTCGGCCA |
| 172 | 2605 | 2624 | TGGAAGGTGGCTGTGGTTCC |
| 9 | 2619 | 2638 | CCTTGGCGCAGCGGTGGAAG |
| 107 | 3056 | 3075 | CCCACTATAATGGCAAGCCC |
| 80 | 4306 | 4325 | AACCCAGTTCTAATGCACCT |
| 106 | 5140 | 5159 | CCAGTCAGAGTAGAACAGAG |
| 102 | 5590 | 5609 | ATGTGCAGAGATCAATCACA |
| 121 | 5599 | 5618 | GGAGCCTACATGTGCAGAGA |
| 94 | 5667 | 5686 | AGCATGGCACCAGCATCTGC |
| 176 | 6444 | 6463 | CGTAGGTGCCAGGCAACCTC |
| 177 | 6482 | 6501 | TGACTGCGAGAGGTGGGTCT |
| 178 | 6492 | 6511 | CAGTGCGCTCTGACTGCGAG |
| 179 | 6494 | 6513 | GGCAGTGCGCTCTGACTGCG |
| 180 | 6496 | 6515 | CGGGCAGTGCGCTCTGACTG |
| 10 | 6498 | 6517 | GGCGGGCAGTGCGCTCTGAC |
| 181 | 6499 | 6518 | CGGCGGGCAGTGCGCTCTGA |
| 182 | 6528 | 6547 | ATCCCCGGCGGGCAGCCTGG |
| 183 | 6532 | 6551 | AGGTATCCCCGGCGGGCAGC |
| 184 | 6534 | 6553 | TGAGGTATCCCCGGCGGGCA |
| 185 | 6535 | 6554 | GTGAGGTATCCCCGGCGGGC |
| 186 | 6536 | 6555 | GGTGAGGTATCCCCGGCGGG |
| 11 | 6537 | 6556 | TGGTGAGGTATCCCCGGCGG |
| 187 | 6538 | 6557 | TTGGTGAGGTATCCCCGGCG |
| 188 | 6539 | 6558 | CTTGGTGAGGTATCCCCGGC |
| 189 | 6540 | 6559 | TCTTGGTGAGGTATCCCCGG |
| 190 | 6541 | 6560 | ATCTTGGTGAGGTATCCCCG |
| 191 | 6542 | 6561 | GATCTTGGTGAGGTATCCCC |
| 12 | 6543 | 6562 | GGATCTTGGTGAGGTATCCC |
| 192 | 6544 | 6563 | AGGATCTTGGTGAGGTATCC |
| 193 | 6546 | 6565 | GCAGGATCTTGGTGAGGTAT |
| 194 | 6548 | 6567 | ATGCAGGATCTTGGTGAGGT |
| 195 | 6550 | 6569 | ACATGCAGGATCTTGGTGAG |
| 13 | 6552 | 6571 | AGACATGCAGGATCTTGGTG |
| 196 | 6554 | 6573 | GAAGACATGCAGGATCTTGG |
| 14 | 6557 | 6576 | ATGGAAGACATGCAGGATCT |
| 197 | 6565 | 6584 | AGAAGGCCATGGAAGACATG |
| 198 | 6575 | 6594 | GAAGCCAGGAAGAAGGCCAT |
| 15 | 6583 | 6602 | TTCACCAGGAAGCCAGGAAG |

TABLE 7-continued

Antisense sequences targeted to NT_032977.8 (SEQ ID NO: 2)

| SEQ ID NO | 5' Start Site to SEQ ID NO: 2 | 3' Start Site to SEQ ID NO: 2 | Sequence (5' to 3') |
|---|---|---|---|
| 199 | 6585 | 6604 | TCTTCACCAGGAAGCCAGGA |
| 16 | 6588 | 6607 | TCATCTTCACCAGGAAGCCA |
| 200 | 6590 | 6609 | ACTCATCTTCACCAGGAAGC |
| 201 | 6592 | 6611 | CCACTCATCTTCACCAGGAA |
| 202 | 6594 | 6613 | CGCCACTCATCTTCACCAGG |
| 203 | 6596 | 6615 | GTCGCCACTCATCTTCACCA |
| 204 | 6598 | 6617 | AGGTCGCCACTCATCTTCAC |
| 205 | 6600 | 6619 | GCAGGTCGCCACTCATCTTC |
| 206 | 6602 | 6621 | CAGCAGGTCGCCACTCATCT |
| 207 | 6604 | 6623 | TCCAGCAGGTCGCCACTCAT |
| 108 | 6652 | 6671 | CCCAGCCCTATCAGGAAGTG |
| 144 | 7099 | 7118 | TGACATCCAGGAGGGAGGAG |
| 91 | 7556 | 7575 | AGACTGATGGAAGGCATTGA |
| 131 | 7565 | 7584 | GTGTTGAGCAGACTGATGGA |
| 145 | 8836 | 8855 | TGACATCTTGTCTGGGAGCC |
| 90 | 8948 | 8967 | AGACTAGGAGCCTGAGTTTT |
| 125 | 9099 | 9118 | GGCCTGCAGAAGCCAGAGAG |
| 17 | 9130 | 9149 | CCTCGATGTAGTCGACATGG |
| 209 | 9149 | 9168 | GCAAAGACAGAGGAGTCCTC |
| 210 | 9207 | 9226 | TTCATCCGCCCGGTACCGTG |
| 211 | 9209 | 9228 | TATTCATCCGCCCGGTACCG |
| 18 | 9210 | 9229 | GTATTCATCCGCCCGGTACC |
| 212 | 9212 | 9231 | TGGTATTCATCCGCCCGGTA |
| 213 | 9214 | 9233 | GCTGGTATTCATCCGCCCGG |
| 214 | 9216 | 9235 | GGGCTGGTATTCATCCGCCC |
| 148 | 10252 | 10271 | TGGCAGCAACTCAGACATAT |
| 127 | 10633 | 10652 | GGTGGTAATTTGTCACAGCA |
| 84 | 11308 | 11327 | AAGGTCACACAGTTAAGAGT |
| 79 | 11472 | 11491 | AAATGCAGGGCTAAAATCAC |
| 88 | 12715 | 12734 | ACTGGATACATTGGCAGACA |
| 111 | 12928 | 12947 | CTAGAGGAACCACTAGATAT |
| 85 | 13681 | 13700 | ACAAATTCCCAGACTCAGCA |
| 100 | 13746 | 13765 | ATCTCAGGACAGGTGAGCAA |
| 116 | 13760 | 13779 | GAGTAGAGATTCTCATCTCA |
| 129 | 13816 | 13835 | GTGCCATCTGAACAGCACCT |
| 117 | 13828 | 13847 | GAGTCTTCTGAAGTGCCATC |
| 81 | 13903 | 13922 | AAGCAGGGCCTCAGGTGGAA |
| 110 | 13926 | 13945 | CCTGGAACCCCTGCAGCCAG |
| 152 | 13977 | 13996 | TTCAGGCAGGTTGCTGCTAG |
| 83 | 13986 | 14005 | AAGGAAGACTTCAGGCAGGT |
| 140 | 13998 | 14017 | TCAGCCAGGCCAAAGGAAGA |
| 137 | 14112 | 14131 | TAGGGAGAGCTCACAGATGC |
| 136 | 14122 | 14141 | TAGGAGAAAGTAGGGAGAGC |
| 132 | 14179 | 14198 | TAAAAGCTGCAAGAGACTCA |
| 139 | 14267 | 14286 | TCAGAGAAAACAGTCACCGA |
| 92 | 14397 | 14416 | AGAGACAGGAAGCTGCAGCT |
| 142 | 14404 | 14423 | TCATTTTAGAGACAGGAAGC |
| 113 | 14441 | 14460 | GAATAACAGTGATGTCTGGC |
| 138 | 14494 | 14513 | TCACAGCTCACCGAGTCTGC |
| 98 | 14524 | 14543 | AGTGTAAAATAAAGCCCCTA |
| 96 | 14601 | 14620 | AGGACCCAAGTCATCCTGCT |
| 124 | 14631 | 14650 | GGCCATCAGCTGGCAATGCT |
| 82 | 14670 | 14689 | AAGGAAAGGGAGGCCTAGAG |
| 133 | 14675 | 14694 | TAGACAAGGAAAGGGAGGCC |
| 103 | 14681 | 14700 | ATTTCATAGACAAGGAAAGG |
| 155 | 14801 | 14820 | CTTATAGTTAACACACAGAA |
| 156 | 14809 | 14828 | AAGTCAACCTTATAGTTAAC |
| 215 | 14877 | 14896 | ATACACCTCCACCAGGCTGC |
| 216 | 14888 | 14907 | GTGTCTAGGAGATACACCTC |
| 19 | 14891 | 14910 | CTGGTGTCTAGGAGATACAC |
| 217 | 14893 | 14912 | TGCTGGTGTCTAGGAGATAC |
| 20 | 14896 | 14915 | GTATGCTGGTGTCTAGGAGA |
| 21 | 14916 | 14935 | GATTTCCCGGTGGTCACTCT |
| 218 | 14918 | 14937 | TCGATTTCCCGGTGGTCACT |
| 219 | 14919 | 14938 | CTCGATTTCCCGGTGGTCAC |
| 220 | 14920 | 14939 | CCTCGATTTCCCGGTGGTCA |
| 221 | 14921 | 14940 | CCCTCGATTTCCCGGTGGTC |
| 22 | 14922 | 14941 | GCCCTCGATTTCCCGGTGGT |
| 222 | 14923 | 14942 | TGCCCTCGATTTCCCGGTGG |
| 223 | 14924 | 14943 | CTGCCCTCGATTTCCCGGTG |
| 224 | 14925 | 14944 | CCTGCCCTCGATTTCCCGGT |

TABLE 7-continued

Antisense sequences targeted to
NT_032977.8 (SEQ ID NO: 2)

| SEQ ID NO | 5' Start Site to SEQ ID NO: 2 | 3' Start Site to SEQ ID NO: 2 | Sequence (5' to 3') |
|---|---|---|---|
| 225 | 14926 | 14945 | CCCTGCCCTCGATTTCCCGG |
| 226 | 14930 | 14949 | ATGACCCTGCCCTCGATTTC |
| 227 | 14932 | 14951 | CCATGACCCTGCCCTCGATT |
| 228 | 14934 | 14953 | GACCATGACCCTGCCCTCGA |
| 23 | 14936 | 14955 | GTGACCATGACCCTGCCCTC |
| 229 | 14938 | 14957 | CGGTGACCATGACCCTGCCC |
| 230 | 14940 | 14959 | GTCGGTGACCATGACCCTGC |
| 231 | 14942 | 14961 | AAGTCGGTGACCATGACCCT |
| 232 | 14944 | 14963 | CGAAGTCGGTGACCATGACC |
| 24 | 14946 | 14965 | CTCGAAGTCGGTGACCATGA |
| 233 | 14954 | 14973 | GGCACATTCTCGAAGTCGGT |
| 25 | 14979 | 14998 | GTGGAAGCGGGTCCCGTCCT |
| 235 | 15254 | 15273 | GGTGGGTGCCATGACTGTCA |
| 236 | 15257 | 15276 | CCAGGTGGGTGCCATGACTG |
| 237 | 15261 | 15280 | CCTGCCAGGTGGGTGCCATG |
| 26 | 15264 | 15283 | ACCCCTGCCAGGTGGGTGCC |
| 238 | 15266 | 15285 | CCACCCCTGCCAGGTGGGTG |
| 27 | 15269 | 15288 | TGACCACCCCTGCCAGGTGG |
| 239 | 15271 | 15290 | GCTGACCACCCCTGCCAGGT |
| 240 | 15279 | 15298 | TCCCGGCCGCTGACCACCCC |
| 241 | 15283 | 15302 | GGCATCCCGGCCGCTGACCA |
| 242 | 15286 | 15305 | GCCGGCATCCCGGCCGCTGA |
| 243 | 15291 | 15310 | GCCACGCCGGCATCCCGGCC |
| 244 | 15292 | 15311 | GGCCACGCCGGCATCCCGGC |
| 245 | 15293 | 15312 | TGGCCACGCCGGCATCCCGG |
| 246 | 15294 | 15313 | TTGGCCACGCCGGCATCCCG |
| 247 | 15295 | 15314 | CTTGGCCACGCCGGCATCCC |
| 248 | 15296 | 15315 | CCTTGGCCACGCCGGCATCC |
| 249 | 15297 | 15316 | CCCTTGGCCACGCCGGCATC |
| 28 | 15298 | 15317 | ACCCTTGGCCACGCCGGCAT |
| 447 | 15298 | 15317 | ACCCTTGGTCACGCCGGCAT |
| 250 | 15299 | 15318 | CACCCTTGGCCACGCCGGCA |
| 251 | 15300 | 15319 | GCACCCTTGGCCACGCCGG |
| 252 | 15301 | 15320 | GGCACCCTTGGCCACGCCGG |
| 253 | 15302 | 15321 | TGGCACCCTTGGCCACGCCG |
| 254 | 15303 | 15322 | CTGGCACCCTTGGCCACGCC |
| 255 | 15304 | 15323 | GCTGGCACCCTTGGCCACGC |
| 256 | 15309 | 15328 | CGCATGCTGGCACCCTTGGC |
| 257 | 15330 | 15349 | CAGTTGAGCACGCGCAGGCT |
| 258 | 15332 | 15351 | GGCAGTTGAGCACGCGCAGG |
| 29 | 15334 | 15353 | TTGGCAGTTGAGCACGCGCA |
| 259 | 15336 | 15355 | CCTTGGCAGTTGAGCACGCG |
| 30 | 15339 | 15358 | TTCCCTTGGCAGTTGAGCAC |
| 260 | 15341 | 15360 | CCTTCCCTTGGCAGTTGAGC |
| 261 | 15345 | 15364 | GTGCCCTTCCCTTGGCAGTT |
| 262 | 15347 | 15366 | CCGTGCCCTTCCCTTGGCAG |
| 263 | 15358 | 15377 | GGTGCCGCTAACCGTGCCCT |
| 86 | 15471 | 15490 | ACAGCATTCTTGGTTAGGAG |
| 97 | 16134 | 16153 | AGTCAAGCTGCTGCCCAGAG |
| 120 | 16668 | 16687 | GCTAGTTATTAAGCACCTGC |
| 150 | 17267 | 17286 | TGTGAGCTCTGGCCCAGTGG |
| 115 | 18377 | 18396 | GAGTAAGGCAGGTTACTCTC |
| 134 | 18408 | 18427 | TAGATGTGACTAACATTTAA |
| 157 | 18561 | 18580 | AGGAACAAAGCCAAGGTCAC |
| 266 | 18591 | 18610 | TGGCTTTTCCGAATAAACTC |
| 32 | 18593 | 18612 | GCTGGCTTTTCCGAATAAAC |
| 267 | 18595 | 18614 | CAGCTGGCTTTTCCGAATAA |
| 268 | 18597 | 18616 | ACCAGCTGGCTTTTCCGAAT |
| 269 | 18599 | 18618 | GGACCAGCTGGCTTTTCCGA |
| 270 | 18603 | 18622 | GGCTGGACCAGCTGGCTTTT |
| 271 | 18614 | 18633 | GTGGCCCCACAGGCTGGACC |
| 272 | 18627 | 18646 | AGCAGCACCACCAGTGGCCC |
| 273 | 18649 | 18668 | GCTGTACCCACCCGCCAGGG |
| 274 | 18695 | 18714 | CGACCCAGCCCTCGCCAGG |
| 33 | 18705 | 18724 | GTGACCAGCACGACCCCAGC |
| 275 | 18707 | 18726 | CGGTGACCAGCACGACCCCA |
| 276 | 18709 | 18728 | AGCGGTGACCAGCACGACCC |
| 277 | 18711 | 18730 | GCAGCGGTGACCAGCACGAC |
| 278 | 18713 | 18732 | CGGCAGCGGTGACCAGCACG |
| 279 | 18714 | 18733 | CCGGCAGCGGTGACCAGCAC |
| 280 | 18717 | 18736 | TTGCCGGCAGCGGTGACCAG |

TABLE 7-continued

Antisense sequences targeted to
NT_032977.8 (SEQ ID NO: 2)

| SEQ ID NO | 5' Start Site to SEQ ID NO: 2 | 3' Start Site to SEQ ID NO: 2 | Sequence (5' to 3') |
|---|---|---|---|
| 281 | 18719 | 18738 | AGTTGCCGGCAGCGGTGACC |
| 282 | 18721 | 18740 | GAAGTTGCCGGCAGCGGTGA |
| 283 | 18723 | 18742 | CGGAAGTTGCCGGCAGCGGT |
| 284 | 18725 | 18744 | CCCGGAAGTTGCCGGCAGCG |
| 285 | 18727 | 18746 | GTCCCGGAAGTTGCCGGCAG |
| 105 | 19203 | 19222 | CACATTAGCCTTGCTCAAGT |
| 151 | 19913 | 19932 | TGTGATGACCTGGAAAGGTG |
| 288 | 19931 | 19950 | GGCATTGGTGGCCCCAACTG |
| 149 | 19933 | 19952 | TGGGCATTGGTGGCCCCAAC |
| 289 | 19941 | 19960 | GCTGGTCTTGGGCATTGGTG |
| 290 | 19954 | 19973 | CCCAGGGTCACCGGCTGGTC |
| 291 | 19956 | 19975 | TCCCCAGGGTCACCGGCTGG |
| 292 | 19958 | 19977 | AGTCCCCAGGGTCACCGGCT |
| 293 | 19960 | 19979 | AAAGTCCCCAGGGTCACCGG |
| 34 | 19962 | 19981 | CCAAAGTCCCCAGGGTCACC |
| 294 | 19964 | 19983 | CCCCAAAGTCCCCAGGGTCA |
| 128 | 19966 | 19985 | GTCCCCAAAGTCCCCAGGGT |
| 295 | 19969 | 19988 | TTGGTCCCCAAAGTCCCCAG |
| 35 | 19971 | 19990 | AGTTGGTCCCCAAAGTCCCC |
| 296 | 19973 | 19992 | AAAGTTGGTCCCCAAAGTCC |
| 36 | 19976 | 19995 | GCCAAAGTTGGTCCCCAAAG |
| 297 | 19978 | 19997 | CGGCCAAAGTTGGTCCCCAA |
| 298 | 19980 | 19999 | AGCGGCCAAAGTTGGTCCCC |
| 299 | 19982 | 20001 | ACAGCGGCCAAAGTTGGTCC |
| 300 | 19984 | 20003 | ACACAGCGGCCAAAGTTGGT |
| 301 | 19986 | 20005 | CCACACAGCGGCCAAAGTTG |
| 37 | 19988 | 20007 | GTCCACACAGCGGCCAAAGT |
| 302 | 19990 | 20009 | AGGTCCACACAGCGGCCAAA |
| 303 | 19992 | 20011 | AGAGGTCCACACAGCGGCCA |
| 304 | 19994 | 20013 | AAAGAGGTCCACACAGCGGC |
| 38 | 19997 | 20016 | GGCAAAGAGGTCCACACAGC |
| 305 | 20016 | 20035 | CAATGATGTCCTCCCCTGGG |
| 306 | 20023 | 20042 | GAGGCACCAATGATGTCCTC |
| 39 | 20025 | 20044 | TGGAGGCACCAATGATGTCC |
| 307 | 20027 | 20046 | GCTGGAGGCACCAATGATGT |
| 308 | 20029 | 20048 | TCGCTGGAGGCACCAATGAT |
| 309 | 20031 | 20050 | AGTCGCTGGAGGCACCAATG |
| 310 | 20033 | 20052 | GCAGTCGCTGGAGGCACCAA |
| 40 | 20036 | 20055 | GCTGCAGTCGCTGGAGGCAC |
| 311 | 20038 | 20057 | GTGCTGCAGTCGCTGGAGGC |
| 312 | 20040 | 20059 | AGGTGCTGCAGTCGCTGGAG |
| 313 | 20042 | 20061 | GCAGGTGCTGCAGTCGCTGG |
| 314 | 20043 | 20062 | AGCAGGTGCTGCAGTCGCTG |
| 315 | 20045 | 20064 | AAAGCAGGTGCTGCAGTCGC |
| 41 | 20047 | 20066 | ACAAAGCAGGTGCTGCAGTC |
| 316 | 20049 | 20068 | ACACAAAGCAGGTGCTGCAG |
| 317 | 20051 | 20070 | TGACACAAAGCAGGTGCTGC |
| 318 | 20061 | 20080 | TCCCACTCTGTGACACAAAG |
| 158 | 20100 | 20119 | GTGGTGACTTACCAGCCACG |
| 109 | 20188 | 20207 | CCCCTGCACAGAGCCTGGCA |
| 141 | 20624 | 20643 | TCATGGCTGCAATGCCTGGT |
| 320 | 20629 | 20648 | CAGCATCATGGCTGCAATGC |
| 321 | 20631 | 20650 | GACAGCATCATGGCTGCAAT |
| 322 | 20633 | 20652 | CAGACAGCATCATGGCTGCA |
| 43 | 20635 | 20654 | GGCAGACAGCATCATGGCTG |
| 323 | 20637 | 20656 | TCGGCAGACAGCATCATGGC |
| 324 | 20639 | 20658 | GCTCGGCAGACAGCATCATG |
| 325 | 20641 | 20660 | CGGCTCGGCAGACAGCATCA |
| 326 | 20643 | 20662 | TCCGGCTCGGCAGACAGCAT |
| 327 | 20657 | 20676 | CGGCCAGGGTGAGCTCCGGC |
| 328 | 20670 | 20689 | CTCTGCCTCAACTCGGCCAG |
| 329 | 20672 | 20691 | GTCTCTGCCTCAACTCGGCC |
| 330 | 20674 | 20693 | CAGTCTCTGCCTCAACTCGG |
| 331 | 20676 | 20695 | ATCAGTCTCTGCCTCAACTC |
| 332 | 20678 | 20697 | GGATCAGTCTCTGCCTCAAC |
| 333 | 20680 | 20699 | GTGGATCAGTCTCTGCCTCA |
| 334 | 20682 | 20701 | AAGTGGATCAGTCTCTGCCT |
| 44 | 20683 | 20702 | GAAGTGGATCAGTCTCTGCC |
| 335 | 20685 | 20704 | GAGAAGTGGATCAGTCTCTG |
| 336 | 20687 | 20706 | CAGAGAAGTGGATCAGTCTC |
| 337 | 20689 | 20708 | GGCAGAGAAGTGGATCAGTC |

TABLE 7-continued

Antisense sequences targeted to NT_032977.8 (SEQ ID NO: 2)

| SEQ ID NO | 5' Start Site to SEQ ID NO: 2 | 3' Start Site to SEQ ID NO: 2 | Sequence (5' to 3') |
|---|---|---|---|
| 45 | 20691 | 20710 | TTGGCAGAGAAGTGGATCAG |
| 338 | 20693 | 20712 | CTTTGGCAGAGAAGTGGATC |
| 46 | 20696 | 20715 | CATCTTTGGCAGAGAAGTGG |
| 339 | 20698 | 20717 | GACATCTTTGGCAGAGAAGT |
| 340 | 20700 | 20719 | ATGACATCTTTGGCAGAGAA |
| 47 | 20702 | 20721 | TGATGACATCTTTGGCAGAG |
| 341 | 20704 | 20723 | ATTGATGACATCTTTGGCAG |
| 342 | 20706 | 20725 | TCATTGATGACATCTTTGGC |
| 48 | 20709 | 20728 | GCCTCATTGATGACATCTTT |
| 343 | 20711 | 20730 | AGGCCTCATTGATGACATCT |
| 344 | 20713 | 20732 | CCAGGCCTCATTGATGACAT |
| 345 | 20715 | 20734 | AACCAGGCCTCATTGATGAC |
| 346 | 20717 | 20736 | GGAACCAGGCCTCATTGATG |
| 347 | 20718 | 20737 | GGGAACCAGGCCTCATTGAT |
| 348 | 20719 | 20738 | AGGGAACCAGGCCTCATTGA |
| 349 | 20720 | 20739 | CAGGGAACCAGGCCTCATTG |
| 49 | 20721 | 20740 | TCAGGGAACCAGGCCTCATT |
| 350 | 20722 | 20741 | CTCAGGGAACCAGGCCTCAT |
| 351 | 20723 | 20742 | CCTCAGGGAACCAGGCCTCA |
| 352 | 20724 | 20743 | TCCTCAGGGAACCAGGCCTC |
| 353 | 20725 | 20744 | GTCCTCAGGGAACCAGGCCT |
| 50 | 20726 | 20745 | GGTCCTCAGGGAACCAGGCC |
| 354 | 20727 | 20746 | TGGTCCTCAGGGAACCAGGC |
| 355 | 20728 | 20747 | CTGGTCCTCAGGGAACCAGG |
| 356 | 20729 | 20748 | GCTGGTCCTCAGGGAACCAG |
| 357 | 20730 | 20749 | CGCTGGTCCTCAGGGAACCA |
| 87 | 20733 | 20752 | ACCCGCTGGTCCTCAGGGAA |
| 358 | 20735 | 20754 | GTACCCGCTGGTCCTCAGGG |
| 359 | 20737 | 20756 | CAGTACCCGCTGGTCCTCAG |
| 51 | 20740 | 20759 | GGTCAGTACCCGCTGGTCCT |
| 119 | 20762 | 20781 | GCAGGGCGGCCACCAGGTTG |
| 360 | 20785 | 20804 | ACCTGCCCCATGGGTGCTGG |
| 93 | 20995 | 21014 | AGAGAGGAGGGCTTAAAGAA |
| 95 | 21082 | 21101 | AGCTGCCAACCTGCAAAAAG |
| 361 | 21088 | 21107 | CAAAACAGCTGCCAACCTGC |
| 53 | 21091 | 21110 | CTGCAAAACAGCTGCCAACC |
| 362 | 21093 | 21112 | TCCTGCAAAACAGCTGCCAA |
| 363 | 21095 | 21114 | AGTCCTGCAAAACAGCTGCC |
| 364 | 21106 | 21125 | GCTGACCATACAGTCCTGCA |
| 365 | 21118 | 21137 | GGCCCCGAGTGTGCTGACCA |
| 54 | 21121 | 21140 | GTAGGCCCCGAGTGTGCTGA |
| 366 | 21123 | 21142 | GTGTAGGCCCCGAGTGTGCT |
| 367 | 21125 | 21144 | CCGTGTAGGCCCCGAGTGTG |
| 368 | 21127 | 21146 | ATCCGTGTAGGCCCCGAGTG |
| 369 | 21129 | 21148 | CCATCCGTGTAGGCCCCGAG |
| 370 | 21131 | 21150 | GGCCATCCGTGTAGGCCCCG |
| 371 | 21133 | 21152 | GTGGCCATCCGTGTAGGCCC |
| 372 | 21181 | 21200 | CTGGAGCAGCTCAGCAGCTC |
| 460 | 21181 | 21194 | CAGCTCAGCAGCTC |
| 373 | 21183 | 21202 | AACTGGAGCAGCTCAGCAGC |
| 55 | 21186 | 21205 | AGAAACTGGAGCAGCTCAGC |
| 374 | 21188 | 21207 | GGAGAAACTGGAGCAGCTCA |
| 375 | 21190 | 21209 | CTGGAGAAACTGGAGCAGCT |
| 56 | 21192 | 21211 | TCCTGGAGAAACTGGAGCAG |
| 143 | 21481 | 21500 | TGAAAATCCATCCAGCACTG |
| 89 | 21589 | 21608 | AGAACCATGGAGCACCTGAG |
| 448 | 21692 | 21711 | CTGCCCTTCCACCAAAATGC |
| 449 | 21693 | 21712 | ACTGCCCTTCCACCAAAATG |
| 450 | 21694 | 21713 | CACTGCCCTTCCACCAAAAT |
| 451 | 21695 | 21714 | GCACTGCCCTTCCACCAAAA |
| 123 | 21696 | 21715 | GGCACTGCCCTTCCACCAAA |
| 452 | 21697 | 21716 | GGGCACTGCCCTTCCACCAA |
| 453 | 21698 | 21717 | TGGGCACTGCCCTTCCACCA |
| 454 | 21699 | 21718 | CTGGGCACTGCCCTTCCACC |
| 455 | 21700 | 21719 | GCTGGGCACTGCCCTTCCAC |
| 57 | 22096 | 22115 | CGTTGTGGGCCCGGCAGACC |
| 376 | 22133 | 22152 | CACCTGGCAATGGCGTAGAC |
| 377 | 22134 | 22153 | GCACCTGGCAATGGCGTAGA |
| 378 | 22135 | 22154 | AGCACCTGGCAATGGCGTAG |
| 379 | 22136 | 22155 | CAGCACCTGGCAATGGCGTA |
| 380 | 22137 | 22156 | GCAGCACCTGGCAATGGCGT |

TABLE 7-continued

Antisense sequences targeted to
NT_032977.8 (SEQ ID NO: 2)

| SEQ ID NO | 5' Start Site to SEQ ID NO: 2 | 3' Start Site to SEQ ID NO: 2 | Sequence (5' to 3') |
|---|---|---|---|
| 381 | 22138 | 22157 | GGCAGCACCTGGCAATGGCG |
| 382 | 22139 | 22158 | AGGCAGCACCTGGCAATGGC |
| 383 | 22140 | 22159 | CAGGCAGCACCTGGCAATGG |
| 384 | 22141 | 22160 | GCAGGCAGCACCTGGCAATG |
| 58 | 22142 | 22161 | AGCAGGCAGCACCTGGCAAT |
| 385 | 22143 | 22162 | TAGCAGGCAGCACCTGGCAA |
| 386 | 22144 | 22163 | GTAGCAGGCAGCACCTGGCA |
| 387 | 22189 | 22208 | TGGCCTCAGCTGGTGGAGCT |
| 388 | 22199 | 22218 | GTCCCCATGCTGGCCTCAGC |
| 389 | 22200 | 22219 | GGTCCCCATGCTGGCCTCAG |
| 390 | 22201 | 22220 | GGGTCCCCATGCTGGCCTCA |
| 391 | 22202 | 22221 | CGGGTCCCCATGCTGGCCTC |
| 392 | 22203 | 22222 | ACGGGTCCCCATGCTGGCCT |
| 59 | 22204 | 22223 | CACGGGTCCCCATGCTGGCC |
| 393 | 22205 | 22224 | ACACGGGTCCCCATGCTGGC |
| 394 | 22206 | 22225 | GACACGGGTCCCCATGCTGG |
| 395 | 22207 | 22226 | GGACACGGGTCCCCATGCTG |
| 396 | 22208 | 22227 | TGGACACGGGTCCCCATGCT |
| 397 | 22209 | 22228 | GTGGACACGGGTCCCCATGC |
| 398 | 22210 | 22229 | AGTGGACACGGGTCCCCATG |
| 399 | 22211 | 22230 | CAGTGGACACGGGTCCCCAT |
| 400 | 22212 | 22231 | GCAGTGGACACGGGTCCCCA |
| 401 | 22213 | 22232 | GGCAGTGGACACGGGTCCCC |
| 402 | 22214 | 22233 | TGGCAGTGGACACGGGTCCC |
| 403 | 22215 | 22234 | GTGGCAGTGGACACGGGTCC |
| 404 | 22216 | 22235 | GGTGGCAGTGGACACGGGTC |
| 405 | 22217 | 22236 | TGGTGGCAGTGGACACGGGT |
| 406 | 22220 | 22239 | TGTTGGTGGCAGTGGACACG |
| 126 | 22292 | 22311 | GGTGCATAAGGAGAAAGAGA |
| 408 | 23985 | 24004 | GTGCCAAGGTCCTCCACCTC |
| 409 | 24005 | 24024 | TCAGCACAGGCGGCTTGTGG |
| 410 | 24035 | 24054 | CCACGCACTGGTTGGGCTGA |
| 60 | 24095 | 24114 | CTTTGCATTCCAGACCTGGG |
| 411 | 24096 | 24115 | ACTTTGCATTCCAGACCTGG |
| 412 | 24097 | 24116 | GACTTTGCATTCCAGACCTG |
| 413 | 24098 | 24117 | TGACTTTGCATTCCAGACCT |
| 414 | 24099 | 24118 | TTGACTTTGCATTCCAGACC |
| 61 | 24100 | 24119 | CTTGACTTTGCATTCCAGAC |
| 415 | 24102 | 24121 | TCCTTGACTTTGCATTCCAG |
| 416 | 24115 | 24134 | CGGGATTCCATGCTCCTTGA |
| 147 | 24858 | 24877 | TGAGTTCATTTAAGAGTGGA |
| 118 | 24907 | 24926 | GCACCATCCAGACCAGAATC |
| 114 | 25413 | 25432 | GAGAGGTTCAGATCCAGGCC |
| 418 | 25994 | 26013 | GGAGGGCACTGCAGCCAGTC |
| 419 | 26112 | 26131 | CAGATGGCAACGGCTGTCAC |
| 420 | 26113 | 26132 | GCAGATGGCAACGGCTGTCA |
| 421 | 26114 | 26133 | AGCAGATGGCAACGGCTGTC |
| 422 | 26115 | 26134 | CAGCAGATGGCAACGGCTGT |
| 423 | 26116 | 26135 | GCAGCAGATGGCAACGGCTG |
| 62 | 26117 | 26136 | GGCAGCAGATGGCAACGGCT |
| 424 | 26118 | 26137 | CGGCAGCAGATGGCAACGGC |
| 425 | 26119 | 26138 | CCGGCAGCAGATGGCAACGG |
| 426 | 26120 | 26139 | TCCGGCAGCAGATGGCAACG |
| 427 | 26121 | 26140 | CTCCGGCAGCAGATGGCAAC |
| 428 | 26122 | 26141 | GCTCCGGCAGCAGATGGCAA |
| 429 | 26132 | 26151 | CCAGGTGCCGGCTCCGGCAG |
| 430 | 26142 | 26161 | GAGGCCTGCGCCAGGTGCCG |
| 154 | 26217 | 26236 | TTTTAAAGCTCAGCCCCAGC |
| 63 | 26222 | 26241 | AACCATTTTAAAGCTCAGCC |
| 64 | 26311 | 26330 | TCAAGGGCCAGGCCAGCAGC |
| 65 | 26316 | 26335 | CCCACTCAAGGGCCAGGCCA |
| 122 | 26389 | 26408 | GGAGGGAGCTTCCTGGCACC |
| 66 | 26404 | 26423 | ATGCCCCACAGTGAGGGAGG |
| 67 | 26413 | 26432 | AATGGTGAAATGCCCCACAG |
| 153 | 26456 | 26475 | TTGGGAGCAGCTGGCAGCAC |
| 68 | 26557 | 26576 | CATGGGAAGAATCCTGCCTC |
| 431 | 26635 | 26654 | ATGAGGGCCATCAGCACCTT |
| 432 | 26636 | 26655 | GATGAGGGCCATCAGCACCT |
| 433 | 26637 | 26656 | AGATGAGGGCCATCAGCACC |
| 434 | 26638 | 26657 | GAGATGAGGGCCATCAGCAC |
| 69 | 26639 | 26658 | GGAGATGAGGGCCATCAGCA |

TABLE 7-continued

Antisense sequences targeted to NT_032977.8 (SEQ ID NO: 2)

| SEQ ID NO | 5' Start Site to SEQ ID NO: 2 | 3' Start Site to SEQ ID NO: 2 | Sequence (5' to 3') |
|---|---|---|---|
| 435 | 26640 | 26659 | TGGAGATGAGGGCCATCAGC |
| 436 | 26641 | 26660 | CTGGAGATGAGGGCCATCAG |
| 437 | 26642 | 26661 | GCTGGAGATGAGGGCCATCA |
| 438 | 26643 | 26662 | AGCTGGAGATGAGGGCCATC |
| 461 | 26684 | 26697 | TTAATCAGGGAGCC |
| 70 | 26707 | 26726 | TAGATGCCATCCAGAAAGCT |
| 439 | 26709 | 26728 | GCTAGATGCCATCCAGAAAG |
| 440 | 26710 | 26729 | GGCTAGATGCCATCCAGAAA |
| 441 | 26711 | 26730 | TGGCTAGATGCCATCCAGAA |
| 442 | 26712 | 26731 | CTGGCTAGATGCCATCCAGA |
| 71 | 26713 | 26732 | TCTGGCTAGATGCCATCCAG |
| 443 | 26714 | 26733 | CTCTGGCTAGATGCCATCCA |
| 444 | 26715 | 26734 | CCTCTGGCTAGATGCCATCC |
| 445 | 26716 | 26735 | GCCTCTGGCTAGATGCCATC |
| 446 | 26717 | 26736 | AGCCTCTGGCTAGATGCCAT |
| 72 | 26790 | 26809 | GGCATAGAGCAGAGTAAAGG |
| 73 | 26795 | 26814 | AGCCTGGCATAGAGCAGAGT |
| 135 | 26801 | 26820 | TAGCACAGCCTGGCATAGAG |
| 112 | 27034 | 27053 | GAAGAGGCTTGGCTTCAGAG |
| 74 | 27040 | 27059 | AAGTAAGAAGAGGCTTGGCT |
| 75 | 27244 | 27263 | GCTCAAGGAGGGACAGTTGT |
| 76 | 27279 | 27298 | AAAGATAAATGTCTGCTTGC |
| 77 | 27284 | 27303 | ACCCAAAAGATAAATGTCTG |
| 78 | 27350 | 27369 | TCTTCAAGTTACAAAAGCAA |
| 99 | 27357 | 27376 | ATAAATATCTTCAAGTTACA |

In certain embodiments, gapmer antisense compounds are targeted to a PCSK9 nucleic acid. In certain such embodiments, gapmer antisense compounds are targeted to SEQ ID NO: 2. In certain such embodiments, the nucleotide sequences illustrated in Table 7 have a 5-10-5 gapmer motif. Table 8 illustrates gapmer antisense compounds targeted to SEQ ID NO: 2, having a 5-10-5 motif, where the gap segment comprises 2'-deoxynucleotides and each wing segment comprises nucleotides comprising a 2'-O-methoxyethyl sugar modification. Internucleoside linkages are phosphorthioate, and cytidines are 5-methylcytidines.

TABLE 8

Gapmer antisense compounds having a 5-10-5 motif targeted to SEQ ID NO: 2

| Isis No | Motif | SEQ ID NO | 5' Target Site on SEQ ID NO: 2 | 3' Target Site on SEQ ID NO: 2 | Mismatches | Sequence (5'-3') |
|---|---|---|---|---|---|---|
| 395149 | 5-10-5 | 4 | 2274 | 2293 | 0 | GCGCGGAATCCTGGCTGGGA |
| 395150 | 5-10-5 | 5 | 2381 | 2400 | 0 | GAGGAGACCTAGAGGCCGTG |
| 395151 | 5-10-5 | 6 | 2439 | 2458 | 0 | AGGACCGCCTGGAGCTGACG |
| 395152 | 5-10-5 | 7 | 2549 | 2568 | 0 | ACGCAAGGCTAGCACCAGCT |
| 399793 | 5-10-5 | 8 | 2556 | 2575 | 0 | CCTCGGAACGCAAGGCTAGC |
| 395153 | 5-10-5 | 9 | 2619 | 2638 | 0 | CCTTGGCGCAGCGGTGGAAG |
| 399837 | 5-10-5 | 107 | 3056 | 3075 | 0 | CCCACTATAATGGCAAGCCC |
| 399838 | 5-10-5 | 80 | 4306 | 4325 | 0 | AACCCAGTTCTAATGCACCT |
| 399839 | 5-10-5 | 106 | 5140 | 5159 | 0 | CCAGTCAGAGTAGAACAGAG |
| 395221 | 5-10-5 | 102 | 5590 | 5609 | 0 | ATGTGCAGAGATCAATCACA |
| 399840 | 5-10-5 | 121 | 5599 | 5618 | 0 | GGAGCCTACATGTGCAGAGA |
| 399841 | 5-10-5 | 94 | 5667 | 5686 | 0 | AGCATGGCACCAGCATCTGC |
| 395154 | 5-10-5 | 10 | 6498 | 6517 | 0 | GGCGGGCAGTGCGCTCTGAC |
| 395155 | 5-10-5 | 11 | 6537 | 6556 | 0 | TGGTGAGGTATCCCCGGCGG |

TABLE 8-continued

Gapmer antisense compounds having a 5-10-5 motif targeted to SEQ ID NO: 2

| Isis No | Motif | SEQ ID NO | 5' Target Site on SEQ ID NO:2 | 3' Target Site on SEQ ID NO: 2 | Mismatches | Sequence (5'-3') |
| --- | --- | --- | --- | --- | --- | --- |
| 399794 | 5-10-5 | 12 | 6543 | 6562 | 0 | GGATCTTGGTGAGGTATCCC |
| 399795 | 5-10-5 | 13 | 6552 | 6571 | 0 | AGACATGCAGGATCTTGGTG |
| 395156 | 5-10-5 | 14 | 6557 | 6576 | 0 | ATGGAAGACATGCAGGATCT |
| 395157 | 5-10-5 | 15 | 6583 | 6602 | 0 | TTCACCAGGAAGCCAGGAAG |
| 399796 | 5-10-5 | 16 | 6588 | 6607 | 0 | TCATCTTCACCAGGAAGCCA |
| 399842 | 5-10-5 | 108 | 6652 | 6671 | 0 | CCCAGCCCTATCAGGAAGTG |
| 399843 | 5-10-5 | 144 | 7099 | 7118 | 0 | TGACATCCAGGAGGGAGGAG |
| 399844 | 5-10-5 | 91 | 7556 | 7575 | 0 | AGACTGATGGAAGGCATTGA |
| 399845 | 5-10-5 | 131 | 7565 | 7584 | 0 | GTGTTGAGCAGACTGATGGA |
| 399846 | 5-10-5 | 145 | 8836 | 8855 | 0 | TGACATCTTGTCTGGGAGCC |
| 399847 | 5-10-5 | 90 | 8948 | 8967 | 0 | AGACTAGGAGCCTGAGTTTT |
| 399848 | 5-10-5 | 125 | 9099 | 9118 | 0 | GGCCTGCAGAAGCCAGAGAG |
| 395158 | 5-10-5 | 17 | 9130 | 9149 | 0 | CCTCGATGTAGTCGACATGG |
| 395159 | 5-10-5 | 18 | 9210 | 9229 | 0 | GTATTCATCCGCCCGGTACC |
| 399849 | 5-10-5 | 148 | 10252 | 10271 | 0 | TGGCAGCAACTCAGACATAT |
| 395222 | 5-10-5 | 127 | 10633 | 10652 | 0 | GGTGGTAATTTGTCACAGCA |
| 395223 | 5-10-5 | 84 | 11308 | 11327 | 0 | AAGGTCACACAGTTAAGAGT |
| 399850 | 5-10-5 | 79 | 11472 | 11491 | 0 | AAATGCAGGGCTAAAATCAC |
| 399851 | 5-10-5 | 88 | 12715 | 12734 | 0 | ACTGGATACATTGGCAGACA |
| 399852 | 5-10-5 | 111 | 12928 | 12947 | 0 | CTAGAGGAACCACTAGATAT |
| 395201 | 5-10-5 | 85 | 13681 | 13700 | 0 | ACAAATTCCCAGACTCAGCA |
| 399827 | 5-10-5 | 100 | 13746 | 13765 | 0 | ATCTCAGGACAGGTGAGCAA |
| 399828 | 5-10-5 | 116 | 13760 | 13779 | 0 | GAGTAGAGATTCTCATCTCA |
| 395202 | 5-10-5 | 129 | 13816 | 13835 | 0 | GTGCCATCTGAACAGCACCT |
| 399829 | 5-10-5 | 117 | 13828 | 13847 | 0 | GAGTCTTCTGAAGTGCCATC |
| 399830 | 5-10-5 | 81 | 13903 | 13922 | 0 | AAGCAGGGCCTCAGGTGGAA |
| 395203 | 5-10-5 | 110 | 13926 | 13945 | 0 | CCTGGAACCCTGCAGCCAG |
| 395204 | 5-10-5 | 152 | 13977 | 13996 | 0 | TTCAGGCAGGTTGCTGCTAG |
| 399831 | 5-10-5 | 83 | 13986 | 14005 | 0 | AAGGAAGACTTCAGGCAGGT |
| 395205 | 5-10-5 | 140 | 13998 | 14017 | 0 | TCAGCCAGGCCAAAGGAAGA |
| 399832 | 5-10-5 | 137 | 14112 | 14131 | 0 | TAGGGAGAGCTCACAGATGC |
| 395206 | 5-10-5 | 136 | 14122 | 14141 | 0 | TAGGAGAAAGTAGGGAGAGC |
| 395207 | 5-10-5 | 132 | 14179 | 14198 | 0 | TAAAAGCTGCAAGAGACTCA |
| 395208 | 5-10-5 | 139 | 14267 | 14286 | 0 | TCAGAGAAAACAGTCACCGA |
| 399833 | 5-10-5 | 92 | 14397 | 14416 | 0 | AGAGACAGGAAGCTGCAGCT |
| 395209 | 5-10-5 | 142 | 14404 | 14423 | 0 | TCATTTTAGAGACAGGAAGC |

TABLE 8-continued

Gapmer antisense compounds having a 5-10-5 motif targeted to SEQ ID NO: 2

| Isis No | Motif | SEQ ID NO | 5' Target Site on SEQ ID NO:2 | 3' Target Site on SEQ ID NO: 2 | Mismatches | Sequence (5'-3') |
|---|---|---|---|---|---|---|
| 395210 | 5-10-5 | 113 | 14441 | 14460 | 0 | GAATAACAGTGATGTCTGGC |
| 395211 | 5-10-5 | 138 | 14494 | 14513 | 0 | TCACAGCTCACCGAGTCTGC |
| 395212 | 5-10-5 | 98 | 14524 | 14543 | 0 | AGTGTAAAATAAAGCCCCTA |
| 395213 | 5-10-5 | 96 | 14601 | 14620 | 0 | AGGACCCAAGTCATCCTGCT |
| 395214 | 5-10-5 | 124 | 14631 | 14650 | 0 | GGCCATCAGCTGGCAATGCT |
| 399834 | 5-10-5 | 82 | 14670 | 14689 | 0 | AAGGAAAGGGAGGCCTAGAG |
| 395215 | 5-10-5 | 133 | 14675 | 14694 | 0 | TAGACAAGGAAAGGGAGGCC |
| 395216 | 5-10-5 | 103 | 14681 | 14700 | 0 | ATTTCATAGACAAGGAAAGG |
| 395217 | 5-10-5 | 155 | 14801 | 14820 | 0 | CTTATAGTTAACACACAGAA |
| 399835 | 5-10-5 | 156 | 14809 | 14828 | 0 | AAGTCAACCTTATAGTTAAC |
| 395160 | 5-10-5 | 19 | 14891 | 14910 | 0 | CTGGTGTCTAGGAGATACAC |
| 399797 | 5-10-5 | 20 | 14896 | 14915 | 0 | GTATGCTGGTGTCTAGGAGA |
| 395161 | 5-10-5 | 21 | 14916 | 14935 | 0 | GATTTCCCGGTGGTCACTCT |
| 399798 | 5-10-5 | 22 | 14922 | 14941 | 0 | GCCCTCGATTTCCCGGTGGT |
| 399799 | 5-10-5 | 23 | 14936 | 14955 | 0 | GTGACCATGACCCTGCCCTC |
| 395162 | 5-10-5 | 24 | 14946 | 14965 | 0 | CTCGAAGTCGGTGACCATGA |
| 395163 | 5-10-5 | 25 | 14979 | 14998 | 0 | GTGGAAGCGGGTCCCGTCCT |
| 395164 | 5-10-5 | 26 | 15264 | 15283 | 0 | ACCCCTGCCAGGTGGGTGCC |
| 399800 | 5-10-5 | 27 | 15269 | 15288 | 0 | TGACCACCCCTGCCAGGTGG |
| 395165 | 5-10-5 | 28 | 15298 | 15317 | 0 | ACCCTTGGCCACGCCGGCAT |
| 395166 | 5-10-5 | 29 | 15334 | 15353 | 0 | TTGGCAGTTGAGCACGCGCA |
| 399801 | 5-10-5 | 30 | 15339 | 15358 | 0 | TTCCCTTGGCAGTTGAGCAC |
| 399853 | 5-10-5 | 86 | 15471 | 15490 | 0 | ACAGCATTCTTGGTTAGGAG |
| 399854 | 5-10-5 | 97 | 16134 | 16153 | 0 | AGTCAAGCTGCTGCCCAGAG |
| 399855 | 5-10-5 | 120 | 16668 | 16687 | 0 | GCTAGTTATTAAGCACCTGC |
| 399856 | 5-10-5 | 150 | 17267 | 17286 | 0 | TGTGAGCTCTGGCCCAGTGG |
| 399857 | 5-10-5 | 115 | 18377 | 18396 | 0 | GAGTAAGGCAGGTTACTCTC |
| 399858 | 5-10-5 | 134 | 18408 | 18427 | 0 | TAGATGTGACTAACATTTAA |
| 395224 | 5-10-5 | 157 | 18561 | 18580 | 0 | AGGAACAAAGCCAAGGTCAC |
| 395168 | 5-10-5 | 32 | 18593 | 18612 | 0 | GCTGGCTTTTCCGAATAAAC |
| 395169 | 5-10-5 | 33 | 18705 | 18724 | 0 | GTGACCAGCACGACCCCAGC |
| 399859 | 5-10-5 | 105 | 19203 | 19222 | 0 | CACATTAGCCTTGCTCAAGT |
| 399860 | 5-10-5 | 151 | 19913 | 19932 | 0 | TGTGATGACCTGGAAAGGTG |
| 395170 | 5-10-5 | 149 | 19933 | 19952 | 0 | TGGGCATTGGTGGCCCCAAC |
| 395171 | 5-10-5 | 34 | 19962 | 19981 | 0 | CCAAAGTCCCCAGGGTCACC |
| 395172 | 5-10-5 | 128 | 19966 | 19985 | 0 | GTCCCCAAAGTCCCCAGGGT |
| 399802 | 5-10-5 | 35 | 19971 | 19990 | 0 | AGTTGGTCCCCAAAGTCCCC |

TABLE 8-continued

Gapmer antisense compounds having a 5-10-5 motif targeted to SEQ ID NO: 2

| Isis No | Motif | SEQ ID NO | 5' Target Site on SEQ ID NO:2 | 3' Target Site on SEQ ID NO: 2 | Mismatches | Sequence (5'-3') |
|---|---|---|---|---|---|---|
| 395173 | 5-10-5 | 36 | 19976 | 19995 | 0 | GCCAAAGTTGGTCCCCAAAG |
| 399803 | 5-10-5 | 37 | 19988 | 20007 | 0 | GTCCACACAGCGGCCAAAGT |
| 395174 | 5-10-5 | 38 | 19997 | 20016 | 0 | GGCAAAGAGGTCCACACAGC |
| 395175 | 5-10-5 | 39 | 20025 | 20044 | 0 | TGGAGGCACCAATGATGTCC |
| 399804 | 5-10-5 | 40 | 20036 | 20055 | 0 | GCTGCAGTCGCTGGAGGCAC |
| 399805 | 5-10-5 | 41 | 20047 | 20066 | 0 | ACAAAGCAGGTGCTGCAGTC |
| 399861 | 5-10-5 | 158 | 20100 | 20119 | 0 | GTGGTGACTTACCAGCCACG |
| 399862 | 5-10-5 | 109 | 20188 | 20207 | 0 | CCCCTGCACAGAGCCTGGCA |
| 399863 | 5-10-5 | 141 | 20624 | 20643 | 0 | TCATGGCTGCAATGCCTGGT |
| 399807 | 5-10-5 | 43 | 20635 | 20654 | 0 | GGCAGACAGCATCATGGCTG |
| 399808 | 5-10-5 | 44 | 20683 | 20702 | 0 | GAAGTGGATCAGTCTCTGCC |
| 395177 | 5-10-5 | 45 | 20691 | 20710 | 0 | TTGGCAGAGAAGTGGATCAG |
| 399809 | 5-10-5 | 46 | 20696 | 20715 | 0 | CATCTTTGGCAGAGAAGTGG |
| 399810 | 5-10-5 | 47 | 20702 | 20721 | 0 | TGATGACATCTTTGGCAGAG |
| 399811 | 5-10-5 | 48 | 20709 | 20728 | 0 | GCCTCATTGATGACATCTTT |
| 399812 | 5-10-5 | 49 | 20721 | 20740 | 0 | TCAGGGAACCAGGCCTCATT |
| 395178 | 5-10-5 | 50 | 20726 | 20745 | 0 | GGTCCTCAGGGAACCAGGCC |
| 395179 | 5-10-5 | 87 | 20733 | 20752 | 0 | ACCCGCTGGTCCTCAGGGAA |
| 399813 | 5-10-5 | 51 | 20740 | 20759 | 0 | GGTCAGTACCCGCTGGTCCT |
| 395180 | 5-10-5 | 119 | 20762 | 20781 | 0 | GCAGGGCGGCCACCAGGTTG |
| 399864 | 5-10-5 | 93 | 20995 | 21014 | 0 | AGAGAGGAGGGCTTAAAGAA |
| 399865 | 5-10-5 | 95 | 21082 | 21101 | 0 | AGCTGCCAACCTGCAAAAAG |
| 399814 | 5-10-5 | 53 | 21091 | 21110 | 0 | CTGCAAAACAGCTGCCAACC |
| 395182 | 5-10-5 | 54 | 21121 | 21140 | 0 | GTAGGCCCCGAGTGTGCTGA |
| 399815 | 5-10-5 | 55 | 21186 | 21205 | 0 | AGAAACTGGAGCAGCTCAGC |
| 399816 | 5-10-5 | 56 | 21192 | 21211 | 0 | TCCTGGAGAAACTGGAGCAG |
| 399866 | 5-10-5 | 143 | 21481 | 21500 | 0 | TGAAAATCCATCCAGCACTG |
| 399867 | 5-10-5 | 89 | 21589 | 21608 | 0 | AGAACCATGGAGCACCTGAG |
| 399868 | 5-10-5 | 123 | 21696 | 21715 | 0 | GGCACTGCCCTTCCACCAAA |
| 395183 | 5-10-5 | 57 | 22096 | 22115 | 0 | CGTTGTGGGCCCGGCAGACC |
| 395184 | 5-10-5 | 58 | 22142 | 22161 | 0 | AGCAGGCAGCACCTGGCAAT |
| 395185 | 5-10-5 | 59 | 22204 | 22223 | 0 | CACGGGTCCCCATGCTGGCC |
| 395225 | 5-10-5 | 126 | 22292 | 22311 | 0 | GGTGCATAAGGAGAAAGAGA |
| 395186 | 5-10-5 | 60 | 24095 | 24114 | 0 | CTTTGCATTCCAGACCTGGG |
| 399817 | 5-10-5 | 61 | 24100 | 24119 | 0 | CTTGACTTTGCATTCCAGAC |
| 395226 | 5-10-5 | 147 | 24858 | 24877 | 0 | TGAGTTCATTTAAGAGTGGA |

TABLE 8-continued

Gapmer antisense compounds having a 5-10-5 motif targeted to SEQ ID NO: 2

| Isis No | Motif | SEQ ID NO | 5' Target Site on SEQ ID NO:2 | 3' Target Site on SEQ ID NO: 2 | Mismatches | Sequence (5'-3') |
|---|---|---|---|---|---|---|
| 399869 | 5-10-5 | 118 | 24907 | 24926 | 0 | GCACCATCCAGACCAGAATC |
| 399870 | 5-10-5 | 114 | 25413 | 25432 | 0 | GAGAGGTTCAGATCCAGGCC |
| 395187 | 5-10-5 | 62 | 26117 | 26136 | 0 | GGCAGCAGATGGCAACGGCT |
| 395188 | 5-10-5 | 154 | 26217 | 26236 | 0 | TTTTAAAGCTCAGCCCCAGC |
| 399818 | 5-10-5 | 63 | 26222 | 26241 | 0 | AACCATTTTAAAGCTCAGCC |
| 395189 | 5-10-5 | 64 | 26311 | 26330 | 0 | TCAAGGGCCAGGCCAGCAGC |
| 399819 | 5-10-5 | 65 | 26316 | 26335 | 0 | CCCACTCAAGGGCCAGGCCA |
| 399820 | 5-10-5 | 122 | 26389 | 26408 | 0 | GGAGGGAGCTTCCTGGCACC |
| 395190 | 5-10-5 | 66 | 26404 | 26423 | 0 | ATGCCCCACAGTGAGGGAGG |
| 395191 | 5-10-5 | 67 | 26413 | 26432 | 0 | AATGGTGAAATGCCCCACAG |
| 395192 | 5-10-5 | 153 | 26456 | 26475 | 0 | TTGGGAGCAGCTGGCAGCAC |
| 395193 | 5-10-5 | 68 | 26557 | 26576 | 0 | CATGGGAAGAATCCTGCCTC |
| 395194 | 5-10-5 | 69 | 26639 | 26658 | 0 | GGAGATGAGGGCCATCAGCA |
| 395195 | 5-10-5 | 70 | 26707 | 26726 | 0 | TAGATGCCATCCAGAAAGCT |
| 399821 | 5-10-5 | 71 | 26713 | 26732 | 0 | TCTGGCTAGATGCCATCCAG |
| 395196 | 5-10-5 | 72 | 26790 | 26809 | 0 | GGCATAGAGCAGAGTAAAGG |
| 399822 | 5-10-5 | 73 | 26795 | 26814 | 0 | AGCCTGGCATAGAGCAGAGT |
| 399823 | 5-10-5 | 135 | 26801 | 26820 | 0 | TAGCACAGCCTGGCATAGAG |
| 395197 | 5-10-5 | 112 | 27034 | 27053 | 0 | GAAGAGGCTTGGCTTCAGAG |
| 399824 | 5-10-5 | 74 | 27040 | 27059 | 0 | AAGTAAGAAGAGGCTTGGCT |
| 395198 | 5-10-5 | 75 | 27244 | 27263 | 0 | GCTCAAGGAGGGACAGTTGT |
| 395199 | 5-10-5 | 76 | 27279 | 27298 | 0 | AAAGATAAATGTCTGCTTGC |
| 399825 | 5-10-5 | 77 | 27284 | 27303 | 0 | ACCCAAAAGATAAATGTCTG |
| 395200 | 5-10-5 | 78 | 27350 | 27369 | 0 | TCTTCAAGTTACAAAAGCAA |
| 399826 | 5-10-5 | 99 | 27357 | 27376 | 0 | ATAAATATCTTCAAGTTACA |
| 405861 | 5-10-5 | 162 | 2545 | 2564 | 0 | AAGGCTAGCACCAGCTCCTC |
| 405862 | 5-10-5 | 163 | 2546 | 2565 | 0 | CAAGGCTAGCACCAGCTCCT |
| 405863 | 5-10-5 | 164 | 2547 | 2566 | 0 | GCAAGGCTAGCACCAGCTCC |
| 405864 | 5-10-5 | 165 | 2548 | 2567 | 0 | CGCAAGGCTAGCACCAGCTC |
| 405865 | 5-10-5 | 166 | 2550 | 2569 | 0 | AACGCAAGGCTAGCACCAGC |
| 405866 | 5-10-5 | 167 | 2551 | 2570 | 0 | GAACGCAAGGCTAGCACCAG |
| 405867 | 5-10-5 | 168 | 2552 | 2571 | 0 | GGAACGCAAGGCTAGCACCA |
| 405868 | 5-10-5 | 169 | 2553 | 2572 | 0 | CGGAACGCAAGGCTAGCACC |
| 405869 | 5-10-5 | 218 | 14918 | 14937 | 0 | TCGATTTCCCGGTGGTCACT |
| 405870 | 5-10-5 | 219 | 14919 | 14938 | 0 | CTCGATTTCCCGGTGGTCAC |
| 405871 | 5-10-5 | 220 | 14920 | 14939 | 0 | CCTCGATTTCCCGGTGGTCA |
| 405872 | 5-10-5 | 221 | 14921 | 14940 | 0 | CCCTCGATTTCCCGGTGGTC |

TABLE 8-continued

Gapmer antisense compounds having a 5-10-5 motif targeted to SEQ ID NO: 2

| Isis No | Motif | SEQ ID NO | 5' Target Site on SEQ ID NO:2 | 3' Target Site on SEQ ID NO: 2 | Mismatches | Sequence (5'-3') |
|---|---|---|---|---|---|---|
| 405873 | 5-10-5 | 222 | 14923 | 14942 | 0 | TGCCCTCGATTTCCCGGTGG |
| 405874 | 5-10-5 | 223 | 14924 | 14943 | 0 | CTGCCCTCGATTTCCCGGTG |
| 405875 | 5-10-5 | 224 | 14925 | 14944 | 0 | CCTGCCCTCGATTTCCCGGT |
| 405876 | 5-10-5 | 225 | 14926 | 14945 | 0 | CCCTGCCCTCGATTTCCCGG |
| 405877 | 5-10-5 | 246 | 15294 | 15313 | 0 | TTGGCCACGCCGGCATCCCG |
| 405878 | 5-10-5 | 247 | 15295 | 15314 | 0 | CTTGGCCACGCCGGCATCCC |
| 405879 | 5-10-5 | 248 | 15296 | 15315 | 0 | CCTTGGCCACGCCGGCATCC |
| 405880 | 5-10-5 | 249 | 15297 | 15316 | 0 | CCCTTGGCCACGCCGGCATC |
| 405881 | 5-10-5 | 250 | 15299 | 15318 | 0 | CACCCTTGGCCACGCCGGCA |
| 405882 | 5-10-5 | 251 | 15300 | 15319 | 0 | GCACCCTTGGCCACGCCGGC |
| 405883 | 5-10-5 | 252 | 15301 | 15320 | 0 | GGCACCCTTGGCCACGCCGG |
| 405884 | 5-10-5 | 253 | 15302 | 15321 | 0 | TGGCACCCTTGGCCACGCCG |
| 405885 | 5-10-5 | 346 | 20717 | 20736 | 0 | GGAACCAGGCCTCATTGATG |
| 405886 | 5-10-5 | 347 | 20718 | 20737 | 0 | GGGAACCAGGCCTCATTGAT |
| 405887 | 5-10-5 | 348 | 20719 | 20738 | 0 | AGGGAACCAGGCCTCATTGA |
| 405888 | 5-10-5 | 349 | 20720 | 20739 | 0 | CAGGGAACCAGGCCTCATTG |
| 405889 | 5-10-5 | 350 | 20722 | 20741 | 0 | CTCAGGGAACCAGGCCTCAT |
| 405890 | 5-10-5 | 351 | 20723 | 20742 | 0 | CCTCAGGGAACCAGGCCTCA |
| 405891 | 5-10-5 | 352 | 20724 | 20743 | 0 | TCCTCAGGGAACCAGGCCTC |
| 405892 | 5-10-5 | 353 | 20725 | 20744 | 0 | GTCCTCAGGGAACCAGGCCT |
| 405893 | 5-10-5 | 431 | 26635 | 26654 | 0 | ATGAGGGCCATCAGCACCTT |
| 405894 | 5-10-5 | 432 | 26636 | 26655 | 0 | GATGAGGGCCATCAGCACCT |
| 405895 | 5-10-5 | 433 | 26637 | 26656 | 0 | AGATGAGGGCCATCAGCACC |
| 405896 | 5-10-5 | 434 | 26638 | 26657 | 0 | GAGATGAGGGCCATCAGCAC |
| 405897 | 5-10-5 | 435 | 26640 | 26659 | 0 | TGGAGATGAGGGCCATCAGC |
| 405898 | 5-10-5 | 436 | 26641 | 26660 | 0 | CTGGAGATGAGGGCCATCAG |
| 405899 | 5-10-5 | 437 | 26642 | 26661 | 0 | GCTGGAGATGAGGGCCATCA |
| 405900 | 5-10-5 | 438 | 26643 | 26662 | 0 | AGCTGGAGATGAGGGCCATC |
| 405901 | 5-10-5 | 439 | 26709 | 26728 | 0 | GCTAGATGCCATCCAGAAAG |
| 405902 | 5-10-5 | 440 | 26710 | 26729 | 0 | GGCTAGATGCCATCCAGAAA |
| 405903 | 5-10-5 | 441 | 26711 | 26730 | 0 | TGGCTAGATGCCATCCAGAA |
| 405904 | 5-10-5 | 442 | 26712 | 26731 | 0 | CTGGCTAGATGCCATCCAGA |
| 405905 | 5-10-5 | 443 | 26714 | 26733 | 0 | CTCTGGCTAGATGCCATCCA |
| 405906 | 5-10-5 | 444 | 26715 | 26734 | 0 | CCTCTGGCTAGATGCCATCC |
| 405907 | 5-10-5 | 445 | 26716 | 26735 | 0 | GCCTCTGGCTAGATGCCATC |
| 405908 | 5-10-5 | 446 | 26717 | 26736 | 0 | AGCCTCTGGCTAGATGCCAT |

TABLE 8-continued

Gapmer antisense compounds having a 5-10-5 motif targeted to SEQ ID NO: 2

| Isis No | Motif | SEQ ID NO | 5' Target Site on SEQ ID NO:2 | 3' Target Site on SEQ ID NO: 2 | Mismatches | Sequence (5'-3') |
|---|---|---|---|---|---|---|
| 405909 | 5-10-5 | 267 | 18595 | 18614 | 0 | CAGCTGGCTTTTCCGAATAA |
| 405910 | 5-10-5 | 268 | 18597 | 18616 | 0 | ACCAGCTGGCTTTTCCGAAT |
| 405911 | 5-10-5 | 269 | 18599 | 18618 | 0 | GGACCAGCTGGCTTTTCCGA |
| 405912 | 5-10-5 | 270 | 18603 | 18622 | 0 | GGCTGGACCAGCTGGCTTTT |
| 405913 | 5-10-5 | 275 | 18707 | 18726 | 0 | CGGTGACCAGCACGACCCCA |
| 405914 | 5-10-5 | 276 | 18709 | 18728 | 0 | AGCGGTGACCAGCACGACCC |
| 405915 | 5-10-5 | 277 | 18711 | 18730 | 0 | GCAGCGGTGACCAGCACGAC |
| 405916 | 5-10-5 | 278 | 18713 | 18732 | 0 | CGGCAGCGGTGACCAGCACG |
| 405917 | 5-10-5 | 280 | 18717 | 18736 | 0 | TTGCCGGCAGCGGTGACCAG |
| 405918 | 5-10-5 | 281 | 18719 | 18738 | 0 | AGTTGCCGGCAGCGGTGACC |
| 405919 | 5-10-5 | 282 | 18721 | 18740 | 0 | GAAGTTGCCGGCAGCGGTGA |
| 405920 | 5-10-5 | 283 | 18723 | 18742 | 0 | CGGAAGTTGCCGGCAGCGGT |
| 405921 | 5-10-5 | 284 | 18725 | 18744 | 0 | CCCGGAAGTTGCCGGCAGCG |
| 405922 | 5-10-5 | 285 | 18727 | 18746 | 0 | GTCCCGGAAGTTGCCGGCAG |
| 405923 | 5-10-5 | 288 | 19931 | 19950 | 0 | GGCATTGGTGGCCCCAACTG |
| 405924 | 5-10-5 | 290 | 19954 | 19973 | 0 | CCCAGGGTCACCGGCTGGTC |
| 405925 | 5-10-5 | 292 | 19958 | 19977 | 0 | AGTCCCCAGGGTCACCGGCT |
| 405926 | 5-10-5 | 293 | 19960 | 19979 | 0 | AAAGTCCCCAGGGTCACCGG |
| 405927 | 5-10-5 | 294 | 19964 | 19983 | 0 | CCCCAAAGTCCCCAGGGTCA |
| 405928 | 5-10-5 | 295 | 19969 | 19988 | 0 | TTGGTCCCCAAAGTCCCCAG |
| 405929 | 5-10-5 | 296 | 19973 | 19992 | 0 | AAAGTTGGTCCCCAAAGTCC |
| 405930 | 5-10-5 | 297 | 19978 | 19997 | 0 | CGGCCAAAGTTGGTCCCCAA |
| 405931 | 5-10-5 | 298 | 19980 | 19999 | 0 | AGCGGCCAAAGTTGGTCCCC |
| 405932 | 5-10-5 | 299 | 19982 | 20001 | 0 | ACAGCGGCCAAAGTTGGTCC |
| 405933 | 5-10-5 | 300 | 19984 | 20003 | 0 | ACACAGCGGCCAAAGTTGGT |
| 405934 | 5-10-5 | 301 | 19986 | 20005 | 0 | CCACACAGCGGCCAAAGTTG |
| 405935 | 5-10-5 | 302 | 19990 | 20009 | 0 | AGGTCCACACAGCGGCCAAA |
| 405936 | 5-10-5 | 304 | 19994 | 20013 | 0 | AAAGAGGTCCACACAGCGGC |
| 405937 | 5-10-5 | 306 | 20023 | 20042 | 0 | GAGGCACCAATGATGTCCTC |
| 405938 | 5-10-5 | 307 | 20027 | 20046 | 0 | GCTGGAGGCACCAATGATGT |
| 405939 | 5-10-5 | 308 | 20029 | 20048 | 0 | TCGCTGGAGGCACCAATGAT |
| 405940 | 5-10-5 | 309 | 20031 | 20050 | 0 | AGTCGCTGGAGGCACCAATG |
| 405941 | 5-10-5 | 310 | 20033 | 20052 | 0 | GCAGTCGCTGGAGGCACCAA |
| 405942 | 5-10-5 | 311 | 20038 | 20057 | 0 | GTGCTGCAGTCGCTGGAGGC |
| 405943 | 5-10-5 | 312 | 20040 | 20059 | 0 | AGGTGCTGCAGTCGCTGGAG |
| 405944 | 5-10-5 | 314 | 20043 | 20062 | 0 | AGCAGGTGCTGCAGTCGCTG |
| 405945 | 5-10-5 | 315 | 20045 | 20064 | 0 | AAAGCAGGTGCTGCAGTCGC |

TABLE 8-continued

Gapmer antisense compounds having a 5-10-5 motif targeted to SEQ ID NO: 2

| Isis No | Motif | SEQ ID NO | 5' Target Site on SEQ ID NO:2 | 3' Target Site on SEQ ID NO: 2 | Mismatches | Sequence (5'-3') |
|---|---|---|---|---|---|---|
| 405946 | 5-10-5 | 316 | 20049 | 20068 | 0 | ACACAAAGCAGGTGCTGCAG |
| 405947 | 5-10-5 | 317 | 20051 | 20070 | 0 | TGACACAAAGCAGGTGCTGC |
| 405949 | 5-10-5 | 320 | 20629 | 20648 | 0 | CAGCATCATGGCTGCAATGC |
| 405950 | 5-10-5 | 321 | 20631 | 20650 | 0 | GACAGCATCATGGCTGCAAT |
| 405951 | 5-10-5 | 322 | 20633 | 20652 | 0 | CAGACAGCATCATGGCTGCA |
| 405952 | 5-10-5 | 323 | 20637 | 20656 | 0 | TCGGCAGACAGCATCATGGC |
| 405953 | 5-10-5 | 325 | 20641 | 20660 | 0 | CGGCTCGGCAGACAGCATCA |
| 405954 | 5-10-5 | 326 | 20643 | 20662 | 0 | TCCGGCTCGGCAGACAGCAT |
| 405955 | 5-10-5 | 328 | 20670 | 20689 | 0 | CTCTGCCTCAACTCGGCCAG |
| 405956 | 5-10-5 | 329 | 20672 | 20691 | 0 | GTCTCTGCCTCAACTCGGCC |
| 405957 | 5-10-5 | 330 | 20674 | 20693 | 0 | CAGTCTCTGCCTCAACTCGG |
| 405958 | 5-10-5 | 331 | 20676 | 20695 | 0 | ATCAGTCTCTGCCTCAACTC |
| 405959 | 5-10-5 | 332 | 20678 | 20697 | 0 | GGATCAGTCTCTGCCTCAAC |
| 405960 | 5-10-5 | 333 | 20680 | 20699 | 0 | GTGGATCAGTCTCTGCCTCA |
| 405961 | 5-10-5 | 334 | 20682 | 20701 | 0 | AAGTGGATCAGTCTCTGCCT |
| 405962 | 5-10-5 | 335 | 20685 | 20704 | 0 | GAGAAGTGGATCAGTCTCTG |
| 405963 | 5-10-5 | 337 | 20689 | 20708 | 0 | GGCAGAGAAGTGGATCAGTC |
| 405964 | 5-10-5 | 338 | 20693 | 20712 | 0 | CTTTGGCAGAGAAGTGGATC |
| 405965 | 5-10-5 | 339 | 20698 | 20717 | 0 | GACATCTTTGGCAGAGAAGT |
| 405966 | 5-10-5 | 340 | 20700 | 20719 | 0 | ATGACATCTTTGGCAGAGAA |
| 405967 | 5-10-5 | 341 | 20704 | 20723 | 0 | ATTGATGACATCTTTGGCAG |
| 405968 | 5-10-5 | 342 | 20706 | 20725 | 0 | TCATTGATGACATCTTTGGC |
| 405969 | 5-10-5 | 343 | 20711 | 20730 | 0 | AGGCCTCATTGATGACATCT |
| 405970 | 5-10-5 | 344 | 20713 | 20732 | 0 | CCAGGCCTCATTGATGACAT |
| 405971 | 5-10-5 | 355 | 20728 | 20747 | 0 | CTGGTCCTCAGGGAACCAGG |
| 405972 | 5-10-5 | 357 | 20730 | 20749 | 0 | CGCTGGTCCTCAGGGAACCA |
| 405973 | 5-10-5 | 358 | 20735 | 20754 | 0 | GTACCCGCTGGTCCTCAGGG |
| 405974 | 5-10-5 | 359 | 20737 | 20756 | 0 | CAGTACCCGCTGGTCCTCAG |
| 405975 | 5-10-5 | 361 | 21088 | 21107 | 0 | CAAAACAGCTGCCAACCTGC |
| 405976 | 5-10-5 | 362 | 21093 | 21112 | 0 | TCCTGCAAAACAGCTGCCAA |
| 405977 | 5-10-5 | 363 | 21095 | 21114 | 0 | AGTCCTGCAAAACAGCTGCC |
| 405978 | 5-10-5 | 365 | 21118 | 21137 | 0 | GGCCCCGAGTGTGCTGACCA |
| 405979 | 5-10-5 | 366 | 21123 | 21142 | 0 | GTGTAGGCCCCGAGTGTGCT |
| 405980 | 5-10-5 | 367 | 21125 | 21144 | 0 | CCGTGTAGGCCCCGAGTGTG |
| 405981 | 5-10-5 | 368 | 21127 | 21146 | 0 | ATCCGTGTAGGCCCCGAGTG |
| 405982 | 5-10-5 | 370 | 21131 | 21150 | 0 | GGCCATCCGTGTAGGCCCCG |

TABLE 8-continued

Gapmer antisense compounds having a 5-10-5 motif targeted to SEQ ID NO: 2

| Isis No | Motif | SEQ ID NO | 5' Target Site on SEQ ID NO:2 | 3' Target Site on SEQ ID NO: 2 | Mismatches | Sequence (5'-3') |
|---|---|---|---|---|---|---|
| 405983 | 5-10-5 | 371 | 21133 | 21152 | 0 | GTGGCCATCCGTGTAGGCCC |
| 405984 | 5-10-5 | 372 | 21181 | 21200 | 0 | CTGGAGCAGCTCAGCAGCTC |
| 405985 | 5-10-5 | 373 | 21183 | 21202 | 0 | AACTGGAGCAGCTCAGCAGC |
| 405986 | 5-10-5 | 374 | 21188 | 21207 | 0 | GGAGAAACTGGAGCAGCTCA |
| 405987 | 5-10-5 | 375 | 21190 | 21209 | 0 | CTGGAGAAACTGGAGCAGCT |
| 405988 | 5-10-5 | 381 | 22138 | 22157 | 0 | GGCAGCACCTGGCAATGGCG |
| 405989 | 5-10-5 | 383 | 22140 | 22159 | 0 | CAGGCAGCACCTGGCAATGG |
| 405990 | 5-10-5 | 386 | 22144 | 22163 | 0 | GTAGCAGGCAGCACCTGGCA |
| 405991 | 5-10-5 | 394 | 22206 | 22225 | 0 | GACACGGGTCCCCATGCTGG |
| 405992 | 5-10-5 | 396 | 22208 | 22227 | 0 | TGGACACGGGTCCCCATGCT |
| 405993 | 5-10-5 | 398 | 22210 | 22229 | 0 | AGTGGACACGGGTCCCCATG |
| 405994 | 5-10-5 | 400 | 22212 | 22231 | 0 | GCAGTGGACACGGGTCCCCA |
| 405995 | 5-10-5 | 402 | 22214 | 22233 | 0 | TGGCAGTGGACACGGGTCCC |
| 405996 | 5-10-5 | 412 | 24097 | 24116 | 0 | GACTTTGCATTCCAGACCTG |
| 405997 | 5-10-5 | 415 | 24102 | 24121 | 0 | TCCTTGACTTTGCATTCCAG |
| 405998 | 5-10-5 | 426 | 26120 | 26139 | 0 | TCCGGCAGCAGATGGCAACG |
| 405999 | 5-10-5 | 160 | 2437 | 2456 | 0 | GACCGCCTGGAGCTGACGGT |
| 406003 | 5-10-5 | 178 | 6492 | 6511 | 0 | CAGTGCGCTCTGACTGCGAG |
| 406004 | 5-10-5 | 179 | 6494 | 6513 | 0 | GGCAGTGCGCTCTGACTGCG |
| 406005 | 5-10-5 | 180 | 6496 | 6515 | 0 | CGGGCAGTGCGCTCTGACTG |
| 406006 | 5-10-5 | 181 | 6499 | 6518 | 0 | CGGCGGGCAGTGCGCTCTGA |
| 406007 | 5-10-5 | 183 | 6532 | 6551 | 0 | AGGTATCCCCGGCGGGCAGC |
| 406008 | 5-10-5 | 188 | 6539 | 6558 | 0 | CTTGGTGAGGTATCCCCGGC |
| 406009 | 5-10-5 | 190 | 6541 | 6560 | 0 | ATCTTGGTGAGGTATCCCCG |
| 406010 | 5-10-5 | 193 | 6546 | 6565 | 0 | GCAGGATCTTGGTGAGGTAT |
| 406011 | 5-10-5 | 194 | 6548 | 6567 | 0 | ATGCAGGATCTTGGTGAGGT |
| 406012 | 5-10-5 | 195 | 6550 | 6569 | 0 | ACATGCAGGATCTTGGTGAG |
| 406013 | 5-10-5 | 196 | 6554 | 6573 | 0 | GAAGACATGCAGGATCTTGG |
| 406014 | 5-10-5 | 199 | 6585 | 6604 | 0 | TCTTCACCAGGAAGCCAGGA |
| 406015 | 5-10-5 | 200 | 6590 | 6609 | 0 | ACTCATCTTCACCAGGAAGC |
| 406016 | 5-10-5 | 201 | 6592 | 6611 | 0 | CCACTCATCTTCACCAGGAA |
| 406017 | 5-10-5 | 203 | 6596 | 6615 | 0 | GTCGCCACTCATCTTCACCA |
| 406018 | 5-10-5 | 204 | 6598 | 6617 | 0 | AGGTCGCCACTCATCTTCAC |
| 406019 | 5-10-5 | 205 | 6600 | 6619 | 0 | GCAGGTCGCCACTCATCTTC |
| 406020 | 5-10-5 | 206 | 6602 | 6621 | 0 | CAGCAGGTCGCCACTCATCT |
| 406021 | 5-10-5 | 210 | 9207 | 9226 | 0 | TTCATCCGCCCGGTACCGTG |
| 406022 | 5-10-5 | 211 | 9209 | 9228 | 0 | TATTCATCCGCCCGGTACCG |

TABLE 8-continued

Gapmer antisense compounds having a 5-10-5 motif targeted to SEQ ID NO: 2

| Isis No | Motif | SEQ ID NO | 5' Target Site on SEQ ID NO:2 | 3' Target Site on SEQ ID NO: 2 | Mismatches | Sequence (5'-3') |
|---|---|---|---|---|---|---|
| 406023 | 5-10-5 | 212 | 9212 | 9231 | 0 | TGGTATTCATCCGCCCGGTA |
| 406024 | 5-10-5 | 213 | 9214 | 9233 | 0 | GCTGGTATTCATCCGCCCGG |
| 406025 | 5-10-5 | 216 | 14888 | 14907 | 0 | GTGTCTAGGAGATACACCTC |
| 406026 | 5-10-5 | 217 | 14893 | 14912 | 0 | TGCTGGTGTCTAGGAGATAC |
| 406027 | 5-10-5 | 226 | 14930 | 14949 | 0 | ATGACCCTGCCCTCGATTTC |
| 406028 | 5-10-5 | 227 | 14932 | 14951 | 0 | CCATGACCCTGCCCTCGATT |
| 406029 | 5-10-5 | 228 | 14934 | 14953 | 0 | GACCATGACCCTGCCCTCGA |
| 406030 | 5-10-5 | 229 | 14938 | 14957 | 0 | CGGTGACCATGACCCTGCCC |
| 406031 | 5-10-5 | 230 | 14940 | 14959 | 0 | GTCGGTGACCATGACCCTGC |
| 406032 | 5-10-5 | 232 | 14944 | 14963 | 0 | CGAAGTCGGTGACCATGACC |
| 406033 | 5-10-5 | 237 | 15261 | 15280 | 0 | CCTGCCAGGTGGGTGCCATG |
| 406034 | 5-10-5 | 238 | 15266 | 15285 | 0 | CCACCCCTGCCAGGTGGGTG |
| 406035 | 5-10-5 | 239 | 15271 | 15290 | 0 | GCTGACCACCCCTGCCAGGT |
| 406036 | 5-10-5 | 241 | 15283 | 15302 | 0 | GGCATCCCGGCCGCTGACCA |
| 406037 | 5-10-5 | 242 | 15286 | 15305 | 0 | GCCGGCATCCCGGCCGCTGA |
| 406038 | 5-10-5 | 245 | 15293 | 15312 | 0 | TGGCCACGCCGGCATCCCGG |
| 406039 | 5-10-5 | 257 | 15330 | 15349 | 0 | CAGTTGAGCACGCGCAGGCT |
| 406040 | 5-10-5 | 258 | 15332 | 15351 | 0 | GGCAGTTGAGCACGCGCAGG |
| 406041 | 5-10-5 | 259 | 15336 | 15355 | 0 | CCTTGGCAGTTGAGCACGCG |
| 406042 | 5-10-5 | 260 | 15341 | 15360 | 0 | CCTTCCCTTGGCAGTTGAGC |
| 406043 | 5-10-5 | 261 | 15345 | 15364 | 0 | GTGCCCTTCCCTTGGCAGTT |
| 406044 | 5-10-5 | 262 | 15347 | 15366 | 0 | CCGTGCCCTTCCCTTGGCAG |
| 406045 | 5-10-5 | 266 | 18591 | 18610 | 0 | TGGCTTTTCCGAATAAACTC |
| 406478 | 5-10-5 | 448 | 21692 | 21711 | 0 | CTGCCCTTCCACCAAAATGC |
| 406479 | 5-10-5 | 449 | 21693 | 21712 | 0 | ACTGCCCTTCCACCAAAATG |
| 406480 | 5-10-5 | 450 | 21694 | 21713 | 0 | CACTGCCCTTCCACCAAAAT |
| 406481 | 5-10-5 | 451 | 21695 | 21714 | 0 | GCACTGCCCTTCCACCAAAA |
| 406482 | 5-10-5 | 452 | 21697 | 21716 | 0 | GGGCACTGCCCTTCCACCAA |
| 406483 | 5-10-5 | 453 | 21698 | 21717 | 0 | TGGGCACTGCCCTTCCACCA |
| 406484 | 5-10-5 | 454 | 21699 | 21718 | 0 | CTGGGCACTGCCCTTCCACC |
| 406485 | 5-10-5 | 455 | 21700 | 21719 | 0 | GCTGGGCACTGCCCTTCCAC |
| 408653 | 5-10-5 | 354 | 20727 | 20746 | 0 | TGGTCCTCAGGGAACCAGGC |
| 409126 | 5-10-5 | 447 | 15298 | 15317 | 1 | ACCCTTGGTCACGCCGGCAT |
| 410529 | 5-10-5 | 184 | 6534 | 6553 | 0 | TGAGGTATCCCCGGCGGGCA |
| 410530 | 5-10-5 | 185 | 6535 | 6554 | 0 | GTGAGGTATCCCCGGCGGGC |
| 410531 | 5-10-5 | 186 | 6536 | 6555 | 0 | GGTGAGGTATCCCCGGCGGG |

TABLE 8-continued

Gapmer antisense compounds having a 5-10-5 motif targeted to SEQ ID NO: 2

| Isis No | Motif | SEQ ID NO | 5' Target Site on SEQ ID NO:2 | 3' Target Site on SEQ ID NO: 2 | Mismatches | Sequence (5'-3') |
|---|---|---|---|---|---|---|
| 410532 | 5-10-5 | 187 | 6538 | 6557 | 0 | TTGGTGAGGTATCCCCGGCG |
| 410533 | 5-10-5 | 189 | 6540 | 6559 | 0 | TCTTGGTGAGGTATCCCCGG |
| 410534 | 5-10-5 | 191 | 6542 | 6561 | 0 | GATCTTGGTGAGGTATCCCC |
| 410535 | 5-10-5 | 192 | 6544 | 6563 | 0 | AGGATCTTGGTGAGGTATCC |
| 410536 | 5-10-5 | 243 | 15291 | 15310 | 0 | GCCACGCCGGCATCCCGGCC |
| 410537 | 5-10-5 | 244 | 15292 | 15311 | 0 | GGCCACGCCGGCATCCCGGC |
| 410538 | 5-10-5 | 254 | 15303 | 15322 | 0 | CTGGCACCCTTGGCCACGCC |
| 410539 | 5-10-5 | 255 | 15304 | 15323 | 0 | GCTGGCACCCTTGGCCACGC |
| 410540 | 5-10-5 | 356 | 20729 | 20748 | 0 | GCTGGTCCTCAGGGAACCAG |
| 410541 | 5-10-5 | 376 | 22133 | 22152 | 0 | CACCTGGCAATGGCGTAGAC |
| 410542 | 5-10-5 | 377 | 22134 | 22153 | 0 | GCACCTGGCAATGGCGTAGA |
| 410543 | 5-10-5 | 378 | 22135 | 22154 | 0 | AGCACCTGGCAATGGCGTAG |
| 410544 | 5-10-5 | 379 | 22136 | 22155 | 0 | CAGCACCTGGCAATGGCGTA |
| 410545 | 5-10-5 | 380 | 22137 | 22156 | 0 | GCAGCACCTGGCAATGGCGT |
| 410546 | 5-10-5 | 382 | 22139 | 22158 | 0 | AGGCAGCACCTGGCAATGGC |
| 410547 | 5-10-5 | 384 | 22141 | 22160 | 0 | GCAGGCAGCACCTGGCAATG |
| 410548 | 5-10-5 | 385 | 22143 | 22162 | 0 | TAGCAGGCAGCACCTGGCAA |
| 410549 | 5-10-5 | 388 | 22199 | 22218 | 0 | GTCCCCATGCTGGCCTCAGC |
| 410550 | 5-10-5 | 389 | 22200 | 22219 | 0 | GGTCCCCATGCTGGCCTCAG |
| 410551 | 5-10-5 | 390 | 22201 | 22220 | 0 | GGGTCCCCATGCTGGCCTCA |
| 410552 | 5-10-5 | 391 | 22202 | 22221 | 0 | CGGGTCCCCATGCTGGCCTC |
| 410553 | 5-10-5 | 392 | 22203 | 22222 | 0 | ACGGGTCCCCATGCTGGCCT |
| 410554 | 5-10-5 | 393 | 22205 | 22224 | 0 | ACACGGGTCCCCATGCTGGC |
| 410555 | 5-10-5 | 395 | 22207 | 22226 | 0 | GGACACGGGTCCCCATGCTG |
| 410556 | 5-10-5 | 397 | 22209 | 22228 | 0 | GTGGACACGGGTCCCCATGC |
| 410557 | 5-10-5 | 399 | 22211 | 22230 | 0 | CAGTGGACACGGGTCCCCAT |
| 410558 | 5-10-5 | 401 | 22213 | 22232 | 0 | GGCAGTGGACACGGGTCCCC |
| 410559 | 5-10-5 | 403 | 22215 | 22234 | 0 | GTGGCAGTGGACACGGGTCC |
| 410560 | 5-10-5 | 404 | 22216 | 22235 | 0 | GGTGGCAGTGGACACGGGTC |
| 410561 | 5-10-5 | 405 | 22217 | 22236 | 0 | TGGTGGCAGTGGACACGGGT |
| 410562 | 5-10-5 | 411 | 24096 | 24115 | 0 | ACTTTGCATTCCAGACCTGG |
| 410563 | 5-10-5 | 413 | 24098 | 24117 | 0 | TGACTTTGCATTCCAGACCT |
| 410564 | 5-10-5 | 414 | 24099 | 24118 | 0 | TTGACTTTGCATTCCAGACC |
| 410565 | 5-10-5 | 419 | 26112 | 26131 | 0 | CAGATGGCAACGGCTGTCAC |
| 410566 | 5-10-5 | 420 | 26113 | 26132 | 0 | GCAGATGGCAACGGCTGTCA |
| 410567 | 5-10-5 | 421 | 26114 | 26133 | 0 | AGCAGATGGCAACGGCTGTC |
| 410568 | 5-10-5 | 422 | 26115 | 26134 | 0 | CAGCAGATGGCAACGGCTGT |

TABLE 8-continued

Gapmer antisense compounds having a 5-10-5 motif targeted to SEQ ID NO: 2

| Isis No | Motif | SEQ ID NO | 5' Target Site on SEQ ID NO:2 | 3' Target Site on SEQ ID NO: 2 | Mismatches | Sequence (5'-3') |
|---|---|---|---|---|---|---|
| 410569 | 5-10-5 | 423 | 26116 | 26135 | 0 | GCAGCAGATGGCAACGGCTG |
| 410570 | 5-10-5 | 424 | 26118 | 26137 | 0 | CGGCAGCAGATGGCAACGGC |
| 410571 | 5-10-5 | 425 | 26119 | 26138 | 0 | CCGGCAGCAGATGGCAACGG |
| 410572 | 5-10-5 | 427 | 26121 | 26140 | 0 | CTCCGGCAGCAGATGGCAAC |
| 410573 | 5-10-5 | 428 | 26122 | 26141 | 0 | GCTCCGGCAGCAGATGGCAA |
| 410730 | 5-10-5 | 202 | 6594 | 6613 | 0 | CGCCACTCATCTTCACCAGG |
| 410731 | 5-10-5 | 207 | 6604 | 6623 | 0 | TCCAGCAGGTCGCCACTCAT |
| 410732 | 5-10-5 | 214 | 9216 | 9235 | 0 | GGGCTGGTATTCATCCGCCC |
| 410733 | 5-10-5 | 231 | 14942 | 14961 | 0 | AAGTCGGTGACCATGACCCT |
| 410734 | 5-10-5 | 279 | 18714 | 18733 | 0 | CCGGCAGCGGTGACCAGCAC |
| 410735 | 5-10-5 | 291 | 19956 | 19975 | 0 | TCCCCAGGGTCACCGGCTGG |
| 410736 | 5-10-5 | 303 | 19992 | 20011 | 0 | AGAGGTCCACACAGCGGCCA |
| 410737 | 5-10-5 | 313 | 20042 | 20061 | 0 | GCAGGTGCTGCAGTCGCTGG |
| 410738 | 5-10-5 | 324 | 20639 | 20658 | 0 | GCTCGGCAGACAGCATCATG |
| 410739 | 5-10-5 | 336 | 20687 | 20706 | 0 | CAGAGAAGTGGATCAGTCTC |
| 410740 | 5-10-5 | 345 | 20715 | 20734 | 0 | AACCAGGCCTCATTGATGAC |
| 410741 | 5-10-5 | 369 | 21129 | 21148 | 0 | CCATCCGTGTAGGCCCCGAG |
| 410742 | 5-10-5 | 159 | 2433 | 2452 | 0 | GCCTGGAGCTGACGGTGCCC |
| 410743 | 5-10-5 | 170 | 2560 | 2579 | 0 | TCCTCCTCGGAACGCAAGGC |
| 410744 | 5-10-5 | 171 | 2585 | 2604 | 0 | GTGCTCGGGTGCTTCGGCCA |
| 410745 | 5-10-5 | 172 | 2605 | 2624 | 0 | TGGAAGGTGGCTGTGGTTCC |
| 410746 | 5-10-5 | 176 | 6444 | 6463 | 0 | CGTAGGTGCCAGGCAACCTC |
| 410747 | 5-10-5 | 177 | 6482 | 6501 | 0 | TGACTGCGAGAGGTGGGTCT |
| 410748 | 5-10-5 | 182 | 6528 | 6547 | 0 | ATCCCCGGCGGGCAGCCTGG |
| 410749 | 5-10-5 | 197 | 6565 | 6584 | 0 | AGAAGGCCATGGAAGACATG |
| 410750 | 5-10-5 | 198 | 6575 | 6594 | 0 | GAAGCCAGGAAGAAGGCCAT |
| 410752 | 5-10-5 | 209 | 9149 | 9168 | 0 | GCAAAGACAGAGGAGTCCTC |
| 410753 | 5-10-5 | 215 | 14877 | 14896 | 0 | ATACACCTCCACCAGGCTGC |
| 410754 | 5-10-5 | 233 | 14954 | 14973 | 0 | GGCACATTCTCGAAGTCGGT |
| 410756 | 5-10-5 | 235 | 15254 | 15273 | 0 | GGTGGGTGCCATGACTGTCA |
| 410757 | 5-10-5 | 240 | 15279 | 15298 | 0 | TCCCGGCCGCTGACCACCCC |
| 410758 | 5-10-5 | 256 | 15309 | 15328 | 0 | CGCATGCTGGCACCCTTGGC |
| 410759 | 5-10-5 | 263 | 15358 | 15377 | 0 | GGTGCCGCTAACCGTGCCCT |
| 410761 | 5-10-5 | 271 | 18614 | 18633 | 0 | GTGGCCCCACAGGCTGGACC |
| 410762 | 5-10-5 | 272 | 18627 | 18646 | 0 | AGCAGCACCACCAGTGGCCC |
| 410763 | 5-10-5 | 273 | 18649 | 18668 | 0 | GCTGTACCCACCCGCCAGGG |

TABLE 8-continued

Gapmer antisense compounds having a 5-10-5 motif targeted to SEQ ID NO: 2

| Isis No | Motif | SEQ ID NO | 5' Target Site on SEQ ID NO:2 | 3' Target Site on SEQ ID NO: 2 | Mismatches | Sequence (5'-3') |
|---|---|---|---|---|---|---|
| 410764 | 5-10-5 | 274 | 18695 | 18714 | 0 | CGACCCCAGCCCTCGCCAGG |
| 410767 | 5-10-5 | 289 | 19941 | 19960 | 0 | GCTGGTCTTGGGCATTGGTG |
| 410768 | 5-10-5 | 305 | 20016 | 20035 | 0 | CAATGATGTCCTCCCCTGGG |
| 410769 | 5-10-5 | 318 | 20061 | 20080 | 0 | TCCCACTCTGTGACACAAAG |
| 410770 | 5-10-5 | 327 | 20657 | 20676 | 0 | CGGCCAGGGTGAGCTCCGGC |
| 410771 | 5-10-5 | 360 | 20785 | 20804 | 0 | ACCTGCCCCATGGGTGCTGG |
| 410772 | 5-10-5 | 364 | 21106 | 21125 | 0 | GCTGACCATACAGTCCTGCA |
| 410773 | 5-10-5 | 387 | 22189 | 22208 | 0 | TGGCCTCAGCTGGTGGAGCT |
| 410774 | 5-10-5 | 406 | 22220 | 22239 | 0 | TGTTGGTGGCAGTGGACACG |
| 410776 | 5-10-5 | 408 | 23985 | 24004 | 0 | GTGCCAAGGTCCTCCACCTC |
| 410777 | 5-10-5 | 409 | 24005 | 24024 | 0 | TCAGCACAGGCGGCTTGTGG |
| 410778 | 5-10-5 | 410 | 24035 | 24054 | 0 | CCACGCACTGGTTGGGCTGA |
| 410779 | 5-10-5 | 416 | 24115 | 24134 | 0 | CGGGATTCCATGCTCCTTGA |
| 410781 | 5-10-5 | 418 | 25994 | 26013 | 0 | GGAGGGCACTGCAGCCAGTC |
| 410782 | 5-10-5 | 429 | 26132 | 26151 | 0 | CCAGGTGCCGGCTCCGGCAG |
| 410783 | 5-10-5 | 430 | 26142 | 26161 | 0 | GAGGCCTGCGCCAGGTGCCG |

In certain embodiments, gap-widened antisense compounds are targeted to a PCSK9 nucleic acid. In certain such embodiments, gap-widened antisense compounds are targeted to SEQ ID NO: 2. In certain such embodiments, the nucleotide sequences illustrated in Table 7 have a 3-14-3 gap-widened motif. Table 9 illustrates gap-widened antisense compounds targeted to SEQ ID NO: 2, having a 3-14-3 motif, where the gap segment comprises 2'-deoxynucleotides and each wing segment comprises nucleotides comprising a 2'-O-methoxyethyl sugar modification. Internucleoside linkages are phosphorthioate, and cytidines are 5-methylcytidines.

TABLE 9

Gapmer antisense compounds having a 3-14-3 motif targeted to SEQ ID NO: 2

| Isis No | Motif | SEQ ID NO | 5' Target Site on SEQ ID NO: 2 | 3' Target Site on SEQ ID NO: 2 | Mismatches | Sequence (5'-3') |
|---|---|---|---|---|---|---|
| 399871 | 3-14-3 | 4 | 2274 | 2293 | 0 | GCGCGGAATCCTGGCTGGGA |
| 399872 | 3-14-3 | 5 | 2381 | 2400 | 0 | GAGGAGACCTAGAGGCCGTG |
| 399873 | 3-14-3 | 6 | 2439 | 2458 | 0 | AGGACCGCCTGGAGCTGACG |
| 399874 | 3-14-3 | 7 | 2549 | 2568 | 0 | ACGCAAGGCTAGCACCAGCT |
| 399875 | 3-14-3 | 9 | 2619 | 2638 | 0 | CCTTGGCGCAGCGGTGGAAG |
| 399876 | 3-14-3 | 10 | 6498 | 6517 | 0 | GGCGGGCAGTGCGCTCTGAC |
| 399877 | 3-14-3 | 11 | 6537 | 6556 | 0 | TGGTGAGGTATCCCCGGCGG |
| 399878 | 3-14-3 | 14 | 6557 | 6576 | 0 | ATGGAAGACATGCAGGATCT |
| 399879 | 3-14-3 | 15 | 6583 | 6602 | 0 | TTCACCAGGAAGCCAGGAAG |
| 399880 | 3-14-3 | 17 | 9130 | 9149 | 0 | CCTCGATGTAGTCGACATGG |
| 399881 | 3-14-3 | 18 | 9210 | 9229 | 0 | GTATTCATCCGCCCGGTACC |

TABLE 9-continued

Gapmer antisense compounds having a 3-14-3 motif targeted to SEQ ID NO: 2

| Isis No | Motif | SEQ ID NO | 5' Target Site on SEQ ID NO: 2 | 3' Target Site on SEQ ID NO: 2 | Mismatches | Sequence (5'-3') |
|---|---|---|---|---|---|---|
| 399882 | 3-14-3 | 19 | 14891 | 14910 | 0 | CTGGTGTCTAGGAGATACAC |
| 399883 | 3-14-3 | 21 | 14916 | 14935 | 0 | GATTTCCCGGTGGTCACTCT |
| 399884 | 3-14-3 | 24 | 14946 | 14965 | 0 | CTCGAAGTCGGTGACCATGA |
| 399885 | 3-14-3 | 25 | 14979 | 14998 | 0 | GTGGAAGCGGGTCCCGTCCT |
| 399886 | 3-14-3 | 26 | 15264 | 15283 | 0 | ACCCCTGCCAGGTGGGTGCC |
| 399887 | 3-14-3 | 28 | 15298 | 15317 | 0 | ACCCTTGGCCACGCCGGCAT |
| 399888 | 3-14-3 | 29 | 15334 | 15353 | 0 | TTGGCAGTTGAGCACGCGCA |
| 399890 | 3-14-3 | 32 | 18593 | 18612 | 0 | GCTGGCTTTTCCGAATAAAC |
| 399891 | 3-14-3 | 33 | 18705 | 18724 | 0 | GTGACCAGCACGACCCCAGC |
| 399892 | 3-14-3 | 149 | 19933 | 19952 | 0 | TGGGCATTGGTGGCCCCAAC |
| 399893 | 3-14-3 | 34 | 19962 | 19981 | 0 | CCAAAGTCCCCAGGGTCACC |
| 399894 | 3-14-3 | 128 | 19966 | 19985 | 0 | GTCCCCAAAGTCCCCAGGGT |
| 399895 | 3-14-3 | 36 | 19976 | 19995 | 0 | GCCAAAGTTGGTCCCCAAAG |
| 399896 | 3-14-3 | 38 | 19997 | 20016 | 0 | GGCAAAGAGGTCCACACAGC |
| 399897 | 3-14-3 | 39 | 20025 | 20044 | 0 | TGGAGGCACCAATGATGTCC |
| 399899 | 3-14-3 | 45 | 20691 | 20710 | 0 | TTGGCAGAGAAGTGGATCAG |
| 399900 | 3-14-3 | 50 | 20726 | 20745 | 0 | GGTCCTCAGGGAACCAGGCC |
| 399901 | 3-14-3 | 87 | 20733 | 20752 | 0 | ACCCGCTGGTCCTCAGGGAA |
| 399902 | 3-14-3 | 119 | 20762 | 20781 | 0 | GCAGGGCGGCCACCAGGTTG |
| 399904 | 3-14-3 | 54 | 21121 | 21140 | 0 | GTAGGCCCCGAGTGTGCTGA |
| 399905 | 3-14-3 | 57 | 22096 | 22115 | 0 | CGTTGTGGGCCCGGCAGACC |
| 399906 | 3-14-3 | 58 | 22142 | 22161 | 0 | AGCAGGCAGCACCTGGCAAT |
| 399907 | 3-14-3 | 59 | 22204 | 22223 | 0 | CACGGGTCCCCATGCTGGCC |
| 399908 | 3-14-3 | 60 | 24095 | 24114 | 0 | CTTTGCATTCCAGACCTGGG |
| 399909 | 3-14-3 | 62 | 26117 | 26136 | 0 | GGCAGCAGATGGCAACGGCT |
| 399910 | 3-14-3 | 154 | 26217 | 26236 | 0 | TTTTAAAGCTCAGCCCCAGC |
| 399911 | 3-14-3 | 64 | 26311 | 26330 | 0 | TCAAGGGCCAGGCCAGCAGC |
| 399912 | 3-14-3 | 66 | 26404 | 26423 | 0 | ATGCCCCACAGTGAGGGAGG |
| 399913 | 3-14-3 | 67 | 26413 | 26432 | 0 | AATGGTGAAATGCCCCACAG |
| 399914 | 3-14-3 | 153 | 26456 | 26475 | 0 | TTGGGAGCAGCTGGCAGCAC |
| 399915 | 3-14-3 | 68 | 26557 | 26576 | 0 | CATGGGAAGAATCCTGCCTC |
| 399916 | 3-14-3 | 69 | 26639 | 26658 | 0 | GGAGATGAGGGCCATCAGCA |
| 399917 | 3-14-3 | 70 | 26707 | 26726 | 0 | TAGATGCCATCCAGAAAGCT |
| 399918 | 3-14-3 | 72 | 26790 | 26809 | 0 | GGCATAGAGCAGAGTAAAGG |
| 399919 | 3-14-3 | 112 | 27034 | 27053 | 0 | GAAGAGGCTTGGCTTCAGAG |
| 399920 | 3-14-3 | 75 | 27244 | 27263 | 0 | GCTCAAGGAGGGACAGTTGT |

TABLE 9-continued

Gapmer antisense compounds having a 3-14-3 motif targeted to SEQ ID NO: 2

| Isis No | Motif | SEQ ID NO | 5' Target Site on SEQ ID NO: 2 | 3' Target Site on SEQ ID NO: 2 | Mismatches | Sequence (5'-3') |
|---|---|---|---|---|---|---|
| 399921 | 3-14-3 | 76 | 27279 | 27298 | 0 | AAAGATAAATGTCTGCTTGC |
| 399922 | 3-14-3 | 78 | 27350 | 27369 | 0 | TCTTCAAGTTACAAAAGCAA |
| 399923 | 3-14-3 | 85 | 13681 | 13700 | 0 | ACAAATTCCCAGACTCAGCA |
| 399924 | 3-14-3 | 129 | 13816 | 13835 | 0 | GTGCCATCTGAACAGCACCT |
| 399925 | 3-14-3 | 110 | 13926 | 13945 | 0 | CCTGGAACCCTGCAGCCAG |
| 399926 | 3-14-3 | 152 | 13977 | 13996 | 0 | TTCAGGCAGGTTGCTGCTAG |
| 399927 | 3-14-3 | 140 | 13998 | 14017 | 0 | TCAGCCAGGCCAAAGGAAGA |
| 399928 | 3-14-3 | 136 | 14122 | 14141 | 0 | TAGGAGAAAGTAGGGAGAGC |
| 399929 | 3-14-3 | 132 | 14179 | 14198 | 0 | TAAAAGCTGCAAGAGACTCA |
| 399930 | 3-14-3 | 139 | 14267 | 14286 | 0 | TCAGAGAAAACAGTCACCGA |
| 399931 | 3-14-3 | 142 | 14404 | 14423 | 0 | TCATTTTAGAGACAGGAAGC |
| 399932 | 3-14-3 | 113 | 14441 | 14460 | 0 | GAATAACAGTGATGTCTGGC |
| 399933 | 3-14-3 | 138 | 14494 | 14513 | 0 | TCACAGCTCACCGAGTCTGC |
| 399934 | 3-14-3 | 98 | 14524 | 14543 | 0 | AGTGTAAAATAAAGCCCCTA |
| 399935 | 3-14-3 | 96 | 14601 | 14620 | 0 | AGGACCCAAGTCATCCTGCT |
| 399936 | 3-14-3 | 124 | 14631 | 14650 | 0 | GGCCATCAGCTGGCAATGCT |
| 399937 | 3-14-3 | 133 | 14675 | 14694 | 0 | TAGACAAGGAAAGGGAGGCC |
| 399938 | 3-14-3 | 103 | 14681 | 14700 | 0 | ATTTCATAGACAAGGAAAGG |
| 399939 | 3-14-3 | 155 | 14801 | 14820 | 0 | CTTATAGTTAACACACAGAA |
| 399943 | 3-14-3 | 102 | 5590 | 5609 | 0 | ATGTGCAGAGATCAATCACA |
| 399944 | 3-14-3 | 127 | 10633 | 10652 | 0 | GGTGGTAATTTGTCACAGCA |
| 399945 | 3-14-3 | 84 | 11308 | 11327 | 0 | AAGGTCACACAGTTAAGAGT |
| 399946 | 3-14-3 | 157 | 18561 | 18580 | 0 | AGGAACAAAGCCAAGGTCAC |
| 399947 | 3-14-3 | 126 | 22292 | 22311 | 0 | GGTGCATAAGGAGAAAGAGA |
| 399948 | 3-14-3 | 147 | 24858 | 24877 | 0 | TGAGTTCATTTAAGAGTGGA |
| 399949 | 3-14-3 | 8 | 2556 | 2575 | 0 | CCTCGGAACGCAAGGCTAGC |
| 399950 | 3-14-3 | 12 | 6543 | 6562 | 0 | GGATCTTGGTGAGGTATCCC |
| 399951 | 3-14-3 | 13 | 6552 | 6571 | 0 | AGACATGCAGGATCTTGGTG |
| 399952 | 3-14-3 | 16 | 6588 | 6607 | 0 | TCATCTTCACCAGGAAGCCA |
| 399953 | 3-14-3 | 20 | 14896 | 14915 | 0 | GTATGCTGGTGTCTAGGAGA |
| 399954 | 3-14-3 | 22 | 14922 | 14941 | 0 | GCCCTCGATTTCCCGGTGGT |
| 399955 | 3-14-3 | 23 | 14936 | 14955 | 0 | GTGACCATGACCCTGCCCTC |
| 399956 | 3-14-3 | 27 | 15269 | 15288 | 0 | TGACCACCCTGCCAGGTGG |
| 399957 | 3-14-3 | 30 | 15339 | 15358 | 0 | TTCCCTTGGCAGTTGAGCAC |
| 399958 | 3-14-3 | 35 | 19971 | 19990 | 0 | AGTTGGTCCCCAAAGTCCCC |
| 399959 | 3-14-3 | 37 | 19988 | 20007 | 0 | GTCCACACAGCGGCCAAAGT |
| 399960 | 3-14-3 | 40 | 20036 | 20055 | 0 | GCTGCAGTCGCTGGAGGCAC |

TABLE 9-continued

Gapmer antisense compounds having a 3-14-3 motif targeted to SEQ ID NO: 2

| Isis No | Motif | SEQ ID NO | 5' Target Site on SEQ ID NO: 2 | 3' Target Site on SEQ ID NO: 2 | Mismatches | Sequence (5'-3') |
|---|---|---|---|---|---|---|
| 399961 | 3-14-3 | 41 | 20047 | 20066 | 0 | ACAAAGCAGGTGCTGCAGTC |
| 399963 | 3-14-3 | 43 | 20635 | 20654 | 0 | GGCAGACAGCATCATGGCTG |
| 399964 | 3-14-3 | 44 | 20683 | 20702 | 0 | GAAGTGGATCAGTCTCTGCC |
| 399965 | 3-14-3 | 46 | 20696 | 20715 | 0 | CATCTTTGGCAGAGAAGTGG |
| 399966 | 3-14-3 | 47 | 20702 | 20721 | 0 | TGATGACATCTTTGGCAGAG |
| 399967 | 3-14-3 | 48 | 20709 | 20728 | 0 | GCCTCATTGATGACATCTTT |
| 399968 | 3-14-3 | 49 | 20721 | 20740 | 0 | TCAGGGAACCAGGCCTCATT |
| 399969 | 3-14-3 | 51 | 20740 | 20759 | 0 | GGTCAGTACCCGCTGGTCCT |
| 399970 | 3-14-3 | 53 | 21091 | 21110 | 0 | CTGCAAAACAGCTGCCAACC |
| 399971 | 3-14-3 | 55 | 21186 | 21205 | 0 | AGAAACTGGAGCAGCTCAGC |
| 399972 | 3-14-3 | 56 | 21192 | 21211 | 0 | TCCTGGAGAAACTGGAGCAG |
| 399973 | 3-14-3 | 61 | 24100 | 24119 | 0 | CTTGACTTTGCATTCCAGAC |
| 399974 | 3-14-3 | 63 | 26222 | 26241 | 0 | AACCATTTTAAAGCTCAGCC |
| 399975 | 3-14-3 | 65 | 26316 | 26335 | 0 | CCCACTCAAGGGCCAGGCCA |
| 399976 | 3-14-3 | 122 | 26389 | 26408 | 0 | GGAGGGAGCTTCCTGGCACC |
| 399977 | 3-14-3 | 71 | 26713 | 26732 | 0 | TCTGGCTAGATGCCATCCAG |
| 399978 | 3-14-3 | 73 | 26795 | 26814 | 0 | AGCCTGGCATAGAGCAGAGT |
| 399979 | 3-14-3 | 135 | 26801 | 26820 | 0 | TAGCACAGCCTGGCATAGAG |
| 399980 | 3-14-3 | 74 | 27040 | 27059 | 0 | AAGTAAGAAGAGGCTTGGCT |
| 399981 | 3-14-3 | 77 | 27284 | 27303 | 0 | ACCCAAAAGATAAATGTCTG |
| 399982 | 3-14-3 | 99 | 27357 | 27376 | 0 | ATAAATATCTTCAAGTTACA |
| 399983 | 3-14-3 | 100 | 13746 | 13765 | 0 | ATCTCAGGACAGGTGAGCAA |
| 399984 | 3-14-3 | 116 | 13760 | 13779 | 0 | GAGTAGAGATTCTCATCTCA |
| 399985 | 3-14-3 | 117 | 13828 | 13847 | 0 | GAGTCTTCTGAAGTGCCATC |
| 399986 | 3-14-3 | 81 | 13903 | 13922 | 0 | AAGCAGGGCCTCAGGTGGAA |
| 399987 | 3-14-3 | 83 | 13986 | 14005 | 0 | AAGGAAGACTTCAGGCAGGT |
| 399988 | 3-14-3 | 137 | 14112 | 14131 | 0 | TAGGGAGAGCTCACAGATGC |
| 399989 | 3-14-3 | 92 | 14397 | 14416 | 0 | AGAGACAGGAAGCTGCAGCT |
| 399990 | 3-14-3 | 82 | 14670 | 14689 | 0 | AAGGAAAGGGAGGCCTAGAG |
| 399991 | 3-14-3 | 156 | 14809 | 14828 | 0 | AAGTCAACCTTATAGTTAAC |
| 399993 | 3-14-3 | 107 | 3056 | 3075 | 0 | CCCACTATAATGGCAAGCCC |
| 399994 | 3-14-3 | 80 | 4306 | 4325 | 0 | AACCCAGTTCTAATGCACCT |
| 399995 | 3-14-3 | 106 | 5140 | 5159 | 0 | CCAGTCAGAGTAGAACAGAG |
| 399996 | 3-14-3 | 121 | 5599 | 5618 | 0 | GGAGCCTACATGTGCAGAGA |
| 399997 | 3-14-3 | 94 | 5667 | 5686 | 0 | AGCATGGCACCAGCATCTGC |
| 399998 | 3-14-3 | 108 | 6652 | 6671 | 0 | CCCAGCCCTATCAGGAAGTG |

TABLE 9-continued

Gapmer antisense compounds having a 3-14-3 motif targeted to SEQ ID NO: 2

| Isis No | Motif | SEQ ID NO | 5' Target Site on SEQ ID NO: 2 | 3' Target Site on SEQ ID NO: 2 | Mismatches | Sequence (5'-3') |
|---|---|---|---|---|---|---|
| 399999 | 3-14-3 | 144 | 7099 | 7118 | 0 | TGACATCCAGGAGGGAGGAG |
| 400000 | 3-14-3 | 91 | 7556 | 7575 | 0 | AGACTGATGGAAGGCATTGA |
| 400001 | 3-14-3 | 131 | 7565 | 7584 | 0 | GTGTTGAGCAGACTGATGGA |
| 400002 | 3-14-3 | 145 | 8836 | 8855 | 0 | TGACATCTTGTCTGGGAGCC |
| 400003 | 3-14-3 | 90 | 8948 | 8967 | 0 | AGACTAGGAGCCTGAGTTTT |
| 400004 | 3-14-3 | 125 | 9099 | 9118 | 0 | GGCCTGCAGAAGCCAGAGAG |
| 400005 | 3-14-3 | 148 | 10252 | 10271 | 0 | TGGCAGCAACTCAGACATAT |
| 400006 | 3-14-3 | 79 | 11472 | 11491 | 0 | AAATGCAGGGCTAAAATCAC |
| 400007 | 3-14-3 | 88 | 12715 | 12734 | 0 | ACTGGATACATTGGCAGACA |
| 400008 | 3-14-3 | 111 | 12928 | 12947 | 0 | CTAGAGGAACCACTAGATAT |
| 400009 | 3-14-3 | 86 | 15471 | 15490 | 0 | ACAGCATTCTTGGTTAGGAG |
| 400010 | 3-14-3 | 97 | 16134 | 16153 | 0 | AGTCAAGCTGCTGCCCAGAG |
| 400011 | 3-14-3 | 120 | 16668 | 16687 | 0 | GCTAGTTATTAAGCACCTGC |
| 400012 | 3-14-3 | 150 | 17267 | 17286 | 0 | TGTGAGCTCTGGCCCAGTGG |
| 400013 | 3-14-3 | 115 | 18377 | 18396 | 0 | GAGTAAGGCAGGTTACTCTC |
| 400014 | 3-14-3 | 134 | 18408 | 18427 | 0 | TAGATGTGACTAACATTTAA |
| 400015 | 3-14-3 | 105 | 19203 | 19222 | 0 | CACATTAGCCTTGCTCAAGT |
| 400016 | 3-14-3 | 151 | 19913 | 19932 | 0 | TGTGATGACCTGGAAAGGTG |
| 400017 | 3-14-3 | 158 | 20100 | 20119 | 0 | GTGGTGACTTACCAGCCACG |
| 400018 | 3-14-3 | 109 | 20188 | 20207 | 0 | CCCCTGCACAGAGCCTGGCA |
| 400019 | 3-14-3 | 141 | 20624 | 20643 | 0 | TCATGGCTGCAATGCCTGGT |
| 400020 | 3-14-3 | 93 | 20995 | 21014 | 0 | AGAGAGGAGGGCTTAAAGAA |
| 400021 | 3-14-3 | 95 | 21082 | 21101 | 0 | AGCTGCCAACCTGCAAAAAG |
| 400022 | 3-14-3 | 143 | 21481 | 21500 | 0 | TGAAAATCCATCCAGCACTG |
| 400023 | 3-14-3 | 89 | 21589 | 21608 | 0 | AGAACCATGGAGCACCTGAG |
| 400024 | 3-14-3 | 123 | 21696 | 21715 | 0 | GGCACTGCCCTTCCACCAAA |
| 400025 | 3-14-3 | 118 | 24907 | 24926 | 0 | GCACCATCCAGACCAGAATC |
| 400026 | 3-14-3 | 114 | 25413 | 25432 | 0 | GAGAGGTTCAGATCCAGGCC |
| 405604 | 3-14-3 | 236 | 15257 | 15276 | 0 | CCAGGTGGGTGCCATGACTG |
| 405641 | 3-14-3 | 373 | 21183 | 21202 | 0 | AACTGGAGCAGCTCAGCAGC |
| 410574 | 3-14-3 | 184 | 6534 | 6553 | 0 | TGAGGTATCCCCGGCGGGCA |
| 410575 | 3-14-3 | 185 | 6535 | 6554 | 0 | GTGAGGTATCCCCGGCGGGC |
| 410576 | 3-14-3 | 186 | 6536 | 6555 | 0 | GGTGAGGTATCCCCGGCGGG |
| 410577 | 3-14-3 | 187 | 6538 | 6557 | 0 | TTGGTGAGGTATCCCCGGCG |
| 410578 | 3-14-3 | 188 | 6539 | 6558 | 0 | CTTGGTGAGGTATCCCCGGC |
| 410579 | 3-14-3 | 189 | 6540 | 6559 | 0 | TCTTGGTGAGGTATCCCCGG |
| 410580 | 3-14-3 | 190 | 6541 | 6560 | 0 | ATCTTGGTGAGGTATCCCCG |

TABLE 9-continued

Gapmer antisense compounds having a 3-14-3 motif targeted to SEQ ID NO: 2

| Isis No | Motif | SEQ ID NO | 5' Target Site on SEQ ID NO: 2 | 3' Target Site on SEQ ID NO: 2 | Mismatches | Sequence (5'-3') |
|---|---|---|---|---|---|---|
| 410581 | 3-14-3 | 191 | 6542 | 6561 | 0 | GATCTTGGTGAGGTATCCCC |
| 410582 | 3-14-3 | 192 | 6544 | 6563 | 0 | AGGATCTTGGTGAGGTATCC |
| 410583 | 3-14-3 | 243 | 15291 | 15310 | 0 | GCCACGCCGGCATCCCGGCC |
| 410584 | 3-14-3 | 244 | 15292 | 15311 | 0 | GGCCACGCCGGCATCCCGGC |
| 410585 | 3-14-3 | 245 | 15293 | 15312 | 0 | TGGCCACGCCGGCATCCCGG |
| 410586 | 3-14-3 | 246 | 15294 | 15313 | 0 | TTGGCCACGCCGGCATCCCG |
| 410587 | 3-14-3 | 247 | 15295 | 15314 | 0 | CTTGGCCACGCCGGCATCCC |
| 410588 | 3-14-3 | 248 | 15296 | 15315 | 0 | CCTTGGCCACGCCGGCATCC |
| 410589 | 3-14-3 | 249 | 15297 | 15316 | 0 | CCCTTGGCCACGCCGGCATC |
| 410590 | 3-14-3 | 250 | 15299 | 15318 | 0 | CACCCTTGGCCACGCCGGCA |
| 410591 | 3-14-3 | 251 | 15300 | 15319 | 0 | GCACCCTTGGCCACGCCGGC |
| 410592 | 3-14-3 | 252 | 15301 | 15320 | 0 | GGCACCCTTGGCCACGCCGG |
| 410593 | 3-14-3 | 253 | 15302 | 15321 | 0 | TGGCACCCTTGGCCACGCCG |
| 410594 | 3-14-3 | 254 | 15303 | 15322 | 0 | CTGGCACCCTTGGCCACGCC |
| 410595 | 3-14-3 | 255 | 15304 | 15323 | 0 | GCTGGCACCCTTGGCCACGC |
| 410596 | 3-14-3 | 348 | 20719 | 20738 | 0 | AGGGAACCAGGCCTCATTGA |
| 410597 | 3-14-3 | 349 | 20720 | 20739 | 0 | CAGGGAACCAGGCCTCATTG |
| 410598 | 3-14-3 | 350 | 20722 | 20741 | 0 | CTCAGGGAACCAGGCCTCAT |
| 410599 | 3-14-3 | 351 | 20723 | 20742 | 0 | CCTCAGGGAACCAGGCCTCA |
| 410600 | 3-14-3 | 352 | 20724 | 20743 | 0 | TCCTCAGGGAACCAGGCCTC |
| 410601 | 3-14-3 | 353 | 20725 | 20744 | 0 | GTCCTCAGGGAACCAGGCCT |
| 410602 | 3-14-3 | 354 | 20727 | 20746 | 0 | TGGTCCTCAGGGAACCAGGC |
| 410603 | 3-14-3 | 355 | 20728 | 20747 | 0 | CTGGTCCTCAGGGAACCAGG |
| 410604 | 3-14-3 | 356 | 20729 | 20748 | 0 | GCTGGTCCTCAGGGAACCAG |
| 410605 | 3-14-3 | 376 | 22133 | 22152 | 0 | CACCTGGCAATGGCGTAGAC |
| 410606 | 3-14-3 | 377 | 22134 | 22153 | 0 | GCACCTGGCAATGGCGTAGA |
| 410607 | 3-14-3 | 378 | 22135 | 22154 | 0 | AGCACCTGGCAATGGCGTAG |
| 410608 | 3-14-3 | 379 | 22136 | 22155 | 0 | CAGCACCTGGCAATGGCGTA |
| 410609 | 3-14-3 | 380 | 22137 | 22156 | 0 | GCAGCACCTGGCAATGGCGT |
| 410610 | 3-14-3 | 381 | 22138 | 22157 | 0 | GGCAGCACCTGGCAATGGCG |
| 410611 | 3-14-3 | 382 | 22139 | 22158 | 0 | AGGCAGCACCTGGCAATGGC |
| 410612 | 3-14-3 | 383 | 22140 | 22159 | 0 | CAGGCAGCACCTGGCAATGG |
| 410613 | 3-14-3 | 384 | 22141 | 22160 | 0 | GCAGGCAGCACCTGGCAATG |
| 410614 | 3-14-3 | 385 | 22143 | 22162 | 0 | TAGCAGGCAGCACCTGGCAA |
| 410615 | 3-14-3 | 388 | 22199 | 22218 | 0 | GTCCCCATGCTGGCCTCAGC |
| 410616 | 3-14-3 | 389 | 22200 | 22219 | 0 | GGTCCCCATGCTGGCCTCAG |

TABLE 9-continued

Gapmer antisense compounds having a 3-14-3 motif targeted to SEQ ID NO: 2

| Isis No | Motif | SEQ ID NO | 5' Target Site on SEQ ID NO: 2 | 3' Target Site on SEQ ID NO: 2 | Mismatches | Sequence (5'-3') |
|---|---|---|---|---|---|---|
| 410617 | 3-14-3 | 390 | 22201 | 22220 | 0 | GGGTCCCCATGCTGGCCTCA |
| 410618 | 3-14-3 | 391 | 22202 | 22221 | 0 | CGGGTCCCCATGCTGGCCTC |
| 410619 | 3-14-3 | 392 | 22203 | 22222 | 0 | ACGGGTCCCCATGCTGGCCT |
| 410620 | 3-14-3 | 393 | 22205 | 22224 | 0 | ACACGGGTCCCCATGCTGGC |
| 410621 | 3-14-3 | 394 | 22206 | 22225 | 0 | GACACGGGTCCCCATGCTGG |
| 410622 | 3-14-3 | 395 | 22207 | 22226 | 0 | GGACACGGGTCCCCATGCTG |
| 410623 | 3-14-3 | 396 | 22208 | 22227 | 0 | TGGACACGGGTCCCCATGCT |
| 410624 | 3-14-3 | 397 | 22209 | 22228 | 0 | GTGGACACGGGTCCCCATGC |
| 410625 | 3-14-3 | 398 | 22210 | 22229 | 0 | AGTGGACACGGGTCCCCATG |
| 410626 | 3-14-3 | 399 | 22211 | 22230 | 0 | CAGTGGACACGGGTCCCCAT |
| 410627 | 3-14-3 | 400 | 22212 | 22231 | 0 | GCAGTGGACACGGGTCCCCA |
| 410628 | 3-14-3 | 401 | 22213 | 22232 | 0 | GGCAGTGGACACGGGTCCCC |
| 410629 | 3-14-3 | 402 | 22214 | 22233 | 0 | TGGCAGTGGACACGGGTCCC |
| 410630 | 3-14-3 | 403 | 22215 | 22234 | 0 | GTGGCAGTGGACACGGGTCC |
| 410631 | 3-14-3 | 404 | 22216 | 22235 | 0 | GGTGGCAGTGGACACGGGTC |
| 410632 | 3-14-3 | 405 | 22217 | 22236 | 0 | TGGTGGCAGTGGACACGGGT |
| 410633 | 3-14-3 | 411 | 24096 | 24115 | 0 | ACTTTGCATTCCAGACCTGG |
| 410634 | 3-14-3 | 412 | 24097 | 24116 | 0 | GACTTTGCATTCCAGACCTG |
| 410635 | 3-14-3 | 413 | 24098 | 24117 | 0 | TGACTTTGCATTCCAGACCT |
| 410636 | 3-14-3 | 414 | 24099 | 24118 | 0 | TTGACTTTGCATTCCAGACC |
| 410637 | 3-14-3 | 419 | 26112 | 26131 | 0 | CAGATGGCAACGGCTGTCAC |
| 410638 | 3-14-3 | 420 | 26113 | 26132 | 0 | GCAGATGGCAACGGCTGTCA |
| 410639 | 3-14-3 | 421 | 26114 | 26133 | 0 | AGCAGATGGCAACGGCTGTC |
| 410640 | 3-14-3 | 422 | 26115 | 26134 | 0 | CAGCAGATGGCAACGGCTGT |
| 410641 | 3-14-3 | 423 | 26116 | 26135 | 0 | GCAGCAGATGGCAACGGCTG |
| 410642 | 3-14-3 | 424 | 26118 | 26137 | 0 | CGGCAGCAGATGGCAACGGC |
| 410643 | 3-14-3 | 425 | 26119 | 26138 | 0 | CCGGCAGCAGATGGCAACGG |
| 410644 | 3-14-3 | 426 | 26120 | 26139 | 0 | TCCGGCAGCAGATGGCAACG |
| 410645 | 3-14-3 | 427 | 26121 | 26140 | 0 | CTCCGGCAGCAGATGGCAAC |
| 410646 | 3-14-3 | 428 | 26122 | 26141 | 0 | GCTCCGGCAGCAGATGGCAA |

In certain embodiments, gap-widened antisense compounds are targeted to a PCSK9 nucleic acid. In certain such embodiments, gap-widened antisense compounds are targeted to SEQ ID NO: 2. In certain such embodiments, the internucleotide sequences illustrated in Table 7 have a 2-13-5 gap-widened motif. Table 10 illustrates gap-widened antisense compounds targeted to SEQ ID NO: 2, having a 2-13-5 motif, where the gap segment comprises 2'-deoxynucleotides and each wing segment comprises nucleotides comprising a 2'-O-methoxyethyl sugar modification. Internucleoside linkages are phosphorthioate, and cytidines are 5-methylcytidines.

TABLE 10

Gapmer antisense compounds having a 2-13-5 motif targeted to SEQ ID NO: 2

| Isis No | Motif | SEQ ID NO | 5' Target Site on SEQ ID NO: 2 | 3' Target Site on SEQ ID NO: 2 | Mismatches | Sequence (5'-3') |
|---|---|---|---|---|---|---|
| 410647 | 2-13-5 | 184 | 6534 | 6553 | 0 | TGAGGTATCCCCGGCGGCA |
| 410648 | 2-13-5 | 185 | 6535 | 6554 | 0 | GTGAGGTATCCCCGGCGGC |
| 410649 | 2-13-5 | 186 | 6536 | 6555 | 0 | GGTGAGGTATCCCCGGCGGG |
| 410650 | 2-13-5 | 11 | 6537 | 6556 | 0 | TGGTGAGGTATCCCCGGCGG |
| 410651 | 2-13-5 | 187 | 6538 | 6557 | 0 | TTGGTGAGGTATCCCCGGCG |
| 410652 | 2-13-5 | 188 | 6539 | 6558 | 0 | CTTGGTGAGGTATCCCCGGC |
| 410653 | 2-13-5 | 189 | 6540 | 6559 | 0 | TCTTGGTGAGGTATCCCCGG |
| 410654 | 2-13-5 | 190 | 6541 | 6560 | 0 | ATCTTGGTGAGGTATCCCCG |
| 410655 | 2-13-5 | 191 | 6542 | 6561 | 0 | GATCTTGGTGAGGTATCCCC |
| 410656 | 2-13-5 | 12 | 6543 | 6562 | 0 | GGATCTTGGTGAGGTATCCC |
| 410657 | 2-13-5 | 192 | 6544 | 6563 | 0 | AGGATCTTGGTGAGGTATCC |
| 410658 | 2-13-5 | 243 | 15291 | 15310 | 0 | GCCACGCCGGCATCCCGGCC |
| 410659 | 2-13-5 | 244 | 15292 | 15311 | 0 | GGCCACGCCGGCATCCCGGC |
| 410660 | 2-13-5 | 245 | 15293 | 15312 | 0 | TGGCCACGCCGGCATCCCGG |
| 410661 | 2-13-5 | 246 | 15294 | 15313 | 0 | TTGGCCACGCCGGCATCCCG |
| 410662 | 2-13-5 | 247 | 15295 | 15314 | 0 | CTTGGCCACGCCGGCATCCC |
| 410663 | 2-13-5 | 248 | 15296 | 15315 | 0 | CCTTGGCCACGCCGGCATCC |
| 410664 | 2-13-5 | 249 | 15297 | 15316 | 0 | CCCTTGGCCACGCCGGCATC |
| 410665 | 2-13-5 | 28 | 15298 | 15317 | 0 | ACCCTTGGCCACGCCGGCAT |
| 410666 | 2-13-5 | 250 | 15299 | 15318 | 0 | CACCCTTGGCCACGCCGGCA |
| 410667 | 2-13-5 | 251 | 15300 | 15319 | 0 | GCACCCTTGGCCACGCCGGC |
| 410668 | 2-13-5 | 252 | 15301 | 15320 | 0 | GGCACCCTTGGCCACGCCGG |
| 410669 | 2-13-5 | 253 | 15302 | 15321 | 0 | TGGCACCCTTGGCCACGCCG |
| 410670 | 2-13-5 | 254 | 15303 | 15322 | 0 | CTGGCACCCTTGGCCACGCC |
| 410671 | 2-13-5 | 255 | 15304 | 15323 | 0 | GCTGGCACCCTTGGCCACGC |
| 410672 | 2-13-5 | 348 | 20719 | 20738 | 0 | AGGGAACCAGGCCTCATTGA |
| 410673 | 2-13-5 | 349 | 20720 | 20739 | 0 | CAGGGAACCAGGCCTCATTG |
| 410674 | 2-13-5 | 49 | 20721 | 20740 | 0 | TCAGGGAACCAGGCCTCATT |
| 410675 | 2-13-5 | 350 | 20722 | 20741 | 0 | CTCAGGGAACCAGGCCTCAT |
| 410676 | 2-13-5 | 351 | 20723 | 20742 | 0 | CCTCAGGGAACCAGGCCTCA |
| 410677 | 2-13-5 | 352 | 20724 | 20743 | 0 | TCCTCAGGGAACCAGGCCTC |
| 410678 | 2-13-5 | 353 | 20725 | 20744 | 0 | GTCCTCAGGGAACCAGGCCT |
| 410679 | 2-13-5 | 50 | 20726 | 20745 | 0 | GGTCCTCAGGGAACCAGGCC |
| 410680 | 2-13-5 | 354 | 20727 | 20746 | 0 | TGGTCCTCAGGGAACCAGGC |
| 410681 | 2-13-5 | 355 | 20728 | 20747 | 0 | CTGGTCCTCAGGGAACCAGG |
| 410682 | 2-13-5 | 356 | 20729 | 20748 | 0 | GCTGGTCCTCAGGGAACCAG |
| 410683 | 2-13-5 | 376 | 22133 | 22152 | 0 | CACCTGGCAATGGCGTAGAC |
| 410684 | 2-13-5 | 377 | 22134 | 22153 | 0 | GCACCTGGCAATGGCGTAGA |
| 410685 | 2-13-5 | 378 | 22135 | 22154 | 0 | AGCACCTGGCAATGGCGTAG |
| 410686 | 2-13-5 | 379 | 22136 | 22155 | 0 | CAGCACCTGGCAATGGCGTA |
| 410687 | 2-13-5 | 380 | 22137 | 22156 | 0 | GCAGCACCTGGCAATGGCGT |
| 410688 | 2-13-5 | 381 | 22138 | 22157 | 0 | GGCAGCACCTGGCAATGGCG |
| 410689 | 2-13-5 | 382 | 22139 | 22158 | 0 | AGGCAGCACCTGGCAATGGC |
| 410690 | 2-13-5 | 383 | 22140 | 22159 | 0 | CAGGCAGCACCTGGCAATGG |

TABLE 10-continued

Gapmer antisense compounds having a 2-13-5 motif targeted to SEQ ID NO: 2

| Isis No | Motif | SEQ ID NO | 5' Target Site on SEQ ID NO: 2 | 3' Target Site on SEQ ID NO: 2 | Mismatches | Sequence (5'-3') |
|---|---|---|---|---|---|---|
| 410691 | 2-13-5 | 384 | 2214 | 2160 | 0 | GCAGGCAGCACCTGGCAATG |
| 410692 | 2-13-5 | 58 | 2214 | 2161 | 0 | AGCAGGCAGCACCTGGCAAT |
| 410693 | 2-13-5 | 385 | 2214 | 2162 | 0 | TAGCAGGCAGCACCTGGCAA |
| 410694 | 2-13-5 | 388 | 2219 | 2218 | 0 | GTCCCCATGCTGGCCTCAGC |
| 410695 | 2-13-5 | 389 | 2220 | 2219 | 0 | GGTCCCCATGCTGGCCTCAG |
| 410696 | 2-13-5 | 390 | 2220 | 2220 | 0 | GGGTCCCCATGCTGGCCTCA |
| 410697 | 2-13-5 | 391 | 2220 | 2221 | 0 | CGGGTCCCCATGCTGGCCTC |
| 410698 | 2-13-5 | 392 | 2220 | 2222 | 0 | ACGGGTCCCCATGCTGGCCT |
| 410699 | 2-13-5 | 59 | 2220 | 2223 | 0 | CACGGGTCCCCATGCTGGCC |
| 410700 | 2-13-5 | 393 | 2220 | 2224 | 0 | ACACGGGTCCCCATGCTGGC |
| 410701 | 2-13-5 | 394 | 2220 | 2225 | 0 | GACACGGGTCCCCATGCTGG |
| 410702 | 2-13-5 | 395 | 2220 | 2226 | 0 | GGACACGGGTCCCCATGCTG |
| 410703 | 2-13-5 | 396 | 2220 | 2227 | 0 | TGGACACGGGTCCCCATGCT |
| 410704 | 2-13-5 | 397 | 2220 | 2228 | 0 | GTGGACACGGGTCCCCATGC |
| 410705 | 2-13-5 | 398 | 2221 | 2229 | 0 | AGTGGACACGGGTCCCCATG |
| 410706 | 2-13-5 | 399 | 2221 | 2230 | 0 | CAGTGGACACGGGTCCCCAT |
| 410707 | 2-13-5 | 400 | 2221 | 2231 | 0 | GCAGTGGACACGGGTCCCCA |
| 410708 | 2-13-5 | 401 | 2221 | 2232 | 0 | GGCAGTGGACACGGGTCCCC |
| 410709 | 2-13-5 | 402 | 2221 | 2233 | 0 | TGGCAGTGGACACGGGTCCC |
| 410710 | 2-13-5 | 403 | 2221 | 2234 | 0 | GTGGCAGTGGACACGGGTCC |
| 410711 | 2-13-5 | 404 | 2221 | 2235 | 0 | GGTGGCAGTGGACACGGGTC |
| 410712 | 2-13-5 | 405 | 2221 | 2236 | 0 | TGGTGGCAGTGGACACGGGT |
| 410713 | 2-13-5 | 60 | 2409 | 2411 | 0 | CTTTGCATTCCAGACCTGGG |
| 410714 | 2-13-5 | 411 | 2409 | 2411 | 0 | ACTTTGCATTCCAGACCTGG |
| 410715 | 2-13-5 | 412 | 2409 | 2411 | 0 | GACTTTGCATTCCAGACCTG |
| 410716 | 2-13-5 | 413 | 2409 | 2411 | 0 | TGACTTTGCATTCCAGACCT |
| 410717 | 2-13-5 | 414 | 2409 | 2411 | 0 | TTGACTTTGCATTCCAGACC |
| 410718 | 2-13-5 | 61 | 2410 | 2411 | 0 | CTTGACTTTGCATTCCAGAC |
| 410719 | 2-13-5 | 419 | 2611 | 2613 | 0 | CAGATGGCAACGGCTGTCAC |
| 410720 | 2-13-5 | 420 | 2611 | 2613 | 0 | GCAGATGGCAACGGCTGTCA |
| 410721 | 2-13-5 | 421 | 2611 | 2613 | 0 | AGCAGATGGCAACGGCTGTC |
| 410722 | 2-13-5 | 422 | 2611 | 2613 | 0 | CAGCAGATGGCAACGGCTGT |
| 410723 | 2-13-5 | 423 | 2611 | 2613 | 0 | GCAGCAGATGGCAACGGCTG |
| 410724 | 2-13-5 | 62 | 2611 | 2613 | 0 | GGCAGCAGATGGCAACGGCT |
| 410725 | 2-13-5 | 424 | 2611 | 2613 | 0 | CGGCAGCAGATGGCAACGGC |
| 410726 | 2-13-5 | 425 | 2611 | 2613 | 0 | CCGGCAGCAGATGGCAACGG |
| 410727 | 2-13-5 | 426 | 2612 | 2613 | 0 | TCCGGCAGCAGATGGCAACG |
| 410728 | 2-13-5 | 427 | 2612 | 2614 | 0 | CTCCGGCAGCAGATGGCAAC |
| 410729 | 2-13-5 | 428 | 2612 | 2614 | 0 | GCTCCGGCAGCAGATGGCAA |

In certain embodiments, gap-widened antisense compounds are targeted to a PCSK9 nucleic acid. In certain such embodiments, gap-widened antisense compounds are targeted to SEQ ID NO: 2. In certain such embodiments, the nucleotide sequences illustrated in Table 7 have a 3-13-4 gap-widened motif. Table 11 illustrates gap-widened antisense compounds targeted to SEQ ID NO: 2, having a 3-13-4 motif, where the gap segment comprises 2'-deoxynucleotides and each wing segment comprises nucleotides comprising a 2'-O-methoxyethyl sugar modification. Internucleoside linkages are phosphorthioate, and cytidines are 5-methylcytidines.

TABLE 11

Gapmer antisense compounds having a 3-13-4 motif targeted to SEQ ID NO: 2

| Isis No | Motif | SEQ ID NO | 5' Target Site on SEQ ID NO: 2 | 3' Target Site on SEQ ID NO: 2 | Mismatches | Sequence (5'-3') |
|---|---|---|---|---|---|---|
| 405526 | 3-13-4 | 236 | 15257 | 15276 | 0 | CCAGGTGGGTGCCATGACTG |
| 405557 | 3-13-4 | 50 | 20726 | 20745 | 0 | GGTCCTCAGGGAACCAGGCC |
| 405564 | 3-13-4 | 373 | 21183 | 21202 | 0 | AACTGGAGCAGCTCAGCAGC |

The following embodiments set forth target regions of PCSK9 nucleic acids. Also illustrated are examples of antisense compounds targeted to the target regions. It is understood that the sequence set forth in each SEQ ID NO is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

In certain embodiments, antisense compounds target a range of a PCSK9 nucleic acid. In certain embodiment, such compounds contain at least an 8 nucleotide core sequence in common. In certain embodiments, such compounds sharing at least an 8 nucleotide core sequence targets the following nucleotide regions of SEQ ID NO: 2: 2274-2400, 2274-2575, 2433-2570, 2433-2579, 2549-2575, 2552-2579, 2585-2638, 2605-2638, 3056-3075, 4150-5159, 4306-4325, 5590-5618, 5667-5686, 6444-6463, 6482-6518, 6492-6518, 6528-6555, 6528-6623, 6534-6561, 6535-6562, 6536-6563, 6537-6563, 6538-6565, 6539-6565, 6540-6567, 6541-6567, 6542-6569, 6546-6573, 6557-6584, 6575-6602, 6585-6611, 6594-6621, 6596-6623, 6652-6671, 7099-7118, 7556-7584, 8836-8855, 8948-8967, 9099-9118, 9099-9168, 9130-9168, 9207-9233, 9207-9235, 9209-9235, 10252-10271, 10633-10652, 11308-11491, 12715-12734, 12928-12947, 13681-13700, 13746-13779, 13816-13847, 13903-13945, 13977-14141, 14179-14198, 14267-14286, 14397-14423, 14441-14460, 14494-14513, 14494-14543, 14524-14543, 14601-14650, 14670-14700, 14675-14700, 14801-14828, 14877-14912, 14877-14915, 14877-14973, 14916-14943, 14916-14973, 14925-14951, 14934-14963, 14946-14973, 14979-14998, 15254-15280, 15254-15328, 15264-15290, 15279-15305, 15291-15318, 15292-15319, 15293-15320, 15294-15321, 15294-15321, 15295-15322, 15296-15315, 15296-15323, 15297-15323, 15298-15323, 15299-15323, 15300-15323, 15301-15328, 15330-15355, 15330-15490, 15339-15366, 15358-15490, 16134-16153, 16668-16687, 17267-17286, 18377-18427, 18561-18580, 18591-18618, 18591-18646, 18591-18668, 18695-18746, 18705-18730, 18709-18736, 18719-18746, 19203-20080, 19931-19952, 19954-19981, 19964-19990, 19973-19999, 19982-20009, 19992-20016, 20016-20042, 20025-20052, 20036-20062, 20045-20070, 20100-20119, 20188-20207, 20624-20650, 20624-20759, 20629-20804, 20633-20660, 20635-20781, 20643-20662, 20657-20676, 20670-20697, 20680-20706, 20683-20781, 20689-20715, 20698-20725, 20709-20736, 20717-20744, 20718-20745, 20719-20746, 20720-20747, 20721-20748, 20722-20749, 20727-20752, 20735-20759, 20762-21014, 20785-21014, 21082-21107, 21082-21152, 21091-21114, 21118-21144, 21127-21152, 21181-21209, 21181-21211, 21183-21211, 21481-21500, 21589-21608, 21692-21719, 22000-22227, 22096-22115, 22096-22223, 22096-22311, 22133-22160, 22133-22163, 22134-22161, 22135-22162, 22136-22163, 22137-22163, 22138-22163, 22189-22239, 22199-22226, 22199-22227, 22200-22227, 22201-22228, 22202-22229, 22203-22230, 22204-22231, 22205-22232, 22206-22233, 22207-22234, 22208-22235, 22209-22236, 22210-22236, 22210-22239, 22211-22236, 22212-22239, 22292-22311, 23985-24054, 24035-24134, 24095-24121, 24858-24877, 24907-24926, 25413-25432, 25994-26013, 26112-26139, 26112-26161, 26112-27303, 26113-26140, 26114-26141, 26115-26141, 26116-26141, 26117-26141, 26117-26475, 26118-26141, 26120-26141, 26132-26151, 26142-26161, 26217-26241, 26311-26335, 26389-26432, 26456-26576, 26635-26662, 26707-26734, 26707-26736, 26790-26820, 27034-27263, 27279-27303, or 27350-27376.

In certain embodiments, a target region is nucleotides 2274-2400 of SEQ ID NO: 2. In certain embodiments, an antisense compound is targeted to nucleotides 2274-2400 of SEQ ID NO: 2. In certain embodiments, an antisense compound targeted to a PCSK9 nucleic acid comprises a nucleotide sequence selected from SEQ ID NOs: 4 or 5. In certain such embodiments, an antisense compound targeted to nucleotides 2274-2400 of SEQ ID NO: 2 is selected from ISIS NOs: 395149, 399871, 395150 or 399872.

In certain embodiments, a target region is nucleotides 2274-2575 of SEQ ID NO: 2. In certain embodiments, an antisense compound is targeted to nucleotides 2274-2575 of SEQ ID NO: 2. In certain embodiments, an antisense compound targeted to a PCSK9 nucleic acid comprises a nucleotide sequence selected from SEQ ID NOs: 4, 5, 6, 7, 8, 159, 160, 162, 163, 164, 165, 166, 167, 168 or 169. In certain such embodiments, an antisense compound targeted to nucleotides 2274-2575 of SEQ ID NO: 2 is selected from ISIS NOs: 395149, 399871, 395150, 399872, 410742, 405999, 395151, 399873, 405861, 405862, 405863, 405864, 395152, 399874, 405865, 405866, 405867, 405868, 399793, or 399949.

In certain embodiments, a target region is nucleotides 2433-2570 of SEQ ID NO: 2. In certain embodiments, an antisense compound is targeted to nucleotides 2433-2570 of SEQ ID NO: 2. In certain embodiments, an antisense compound targeted to a PCSK9 nucleic acid comprises a nucleotide sequence selected from SEQ ID NOs: 6, 7, 159, 160, 162, 163, 164, 165, 166, or 167. In certain such embodiments, an antisense compound targeted to nucleotides 2433-2570 of SEQ ID NO: 2 is selected from ISIS NOs: 395151, 395152, 399873, 399874, 405861, 405862, 405863, 405864, 405865, 405866, 405999, or 410742.

In certain embodiments, a target region is nucleotides 2433-2579 of SEQ ID NO: 2. In certain embodiments, an antisense compound is targeted to nucleotides 2433-2579 of SEQ ID NO: 2. In certain embodiments, an antisense compound targeted to a PCSK9 nucleic acid comprises a nucleotide sequence selected from SEQ ID NOs: 6, 7, 8, 159, 160, 162, 163, 164, 165, 166, 167, 168, 169, or 170. In certain such embodiments, an antisense compound targeted to nucleotides 2433-2579 of SEQ ID NO: 2 is selected from ISIS NOs: 395151, 395152, 399793, 399873, 399874, 399949, 405861, 405862, 405863, 405864, 405865, 405866, 405867, 405868, 405999, 410742, or 410743.

In certain embodiments, a target region is nucleotides 2549-2575 of SEQ ID NO: 2. In certain embodiments, an antisense compound is targeted to nucleotides 2549-2575 of SEQ ID NO: 2. In certain embodiments, an antisense compound targeted to a PCSK9 nucleic acid comprises a nucleotide sequence selected from SEQ ID NOs: 7, 8, 166, 167, 168 or 169. In certain such embodiments, an antisense compound targeted to nucleotides 2549-2575 of SEQ ID NO: 2 is selected from ISIS NOs: 395152, 399793, 399874, 399949, 405865, 405866, 405867, or 405868.

In certain embodiments, a target region is nucleotides 2552-2579 of SEQ ID NO: 2. In certain embodiments, an antisense compound is targeted to nucleotides 2552-2579 of SEQ ID NO: 2. In certain embodiments, an antisense compound targeted to a PCSK9 nucleic acid comprises a nucleotide sequence selected from SEQ ID NOs: 8, 168, 169 or 170. In certain such embodiments, an antisense compound targeted to nucleotides 2552-2579 of SEQ ID NO: 2 is selected from ISIS NOs: 399793, 399949, 405867, 405868, or 410743.

In certain embodiments, a target region is nucleotides 2585-2638 of SEQ ID NO: 2. In certain embodiments, an antisense compound is targeted to nucleotides 2585-2638 of SEQ ID NO: 2. In certain embodiments, an antisense compound targeted to a PCSK9 nucleic acid comprises a nucleotide sequence selected from SEQ ID NOs: 9, 171 or 172. In certain such embodiments, an antisense compound targeted to nucleotides 2585-2638 of SEQ ID NO: 2 is selected from ISIS NOs: 395153, 399875, 410744, or 410745.

In certain embodiments, a target region is nucleotides 2605-2638 of SEQ ID NO: 2. In certain embodiments, an antisense compound is targeted to nucleotides 2605-2638 of SEQ ID NO: 2. In certain embodiments, an antisense compound targeted to a PCSK9 nucleic acid comprises a nucleotide sequence selected from SEQ ID NOs: 8, 168 or 169. In certain such embodiments, an antisense compound targeted to nucleotides 2605-2638 of SEQ ID NO: 2 is selected from ISIS NOs: 410745, 395153, or 399875.

In certain embodiments, a target region is nucleotides 3056-3075 of SEQ ID NO: 2. In certain embodiments, an antisense compound is targeted to nucleotides 3056-3075 of SEQ ID NO: 2. In certain embodiments, an antisense compound targeted to a PCSK9 nucleic acid comprises a nucleotide sequence selected from SEQ ID NOs: 107. In certain such embodiments, an antisense compound targeted to nucleotides 3056-3075 of SEQ ID NO: 2 is selected from ISIS NOs: 399837 or 399993.

In certain embodiments, a target region is nucleotides 4150-5159 of SEQ ID NO: 2. In certain embodiments, an antisense compound is targeted to nucleotides 4150-5159 of SEQ ID NO: 2. In certain embodiments, an antisense compound targeted to a PCSK9 nucleic acid comprises a nucleotide sequence selected from SEQ ID NOs: 106. In certain such embodiments, an antisense compound targeted to nucleotides 4150-5159 of SEQ ID NO: 2 is selected from ISIS NOs: 399839 or 399995.

In certain embodiments, a target region is nucleotides 4306-4325 of SEQ ID NO: 2. In certain embodiments, an antisense compound is targeted to nucleotides 4306-4325 of SEQ ID NO: 2. In certain embodiments, an antisense compound targeted to a PCSK9 nucleic acid comprises a nucleotide sequence selected from SEQ ID NOs: 80. In certain such embodiments, an antisense compound targeted to nucleotides 4306-4325 of SEQ ID NO: 2 is selected from ISIS NOs: 399838 or 399994.

In certain embodiments, a target region is nucleotides 5590-5618 of SEQ ID NO: 2. In certain embodiments, an antisense compound is targeted to nucleotides 5590-5618 of SEQ ID NO: 2. In certain embodiments, an antisense compound targeted to a PCSK9 nucleic acid comprises a nucleotide sequence selected from SEQ ID NOs: 102 or 121. In certain such embodiments, an antisense compound targeted to nucleotides 5590-5618 of SEQ ID NO: 2 is selected from ISIS NOs: 395221, 399840, 399943, or 399996.

In certain embodiments, a target region is nucleotides 5667-5686 of SEQ ID NO: 2. In certain embodiments, an antisense compound is targeted to nucleotides 5667-5686 of SEQ ID NO: 2. In certain embodiments, an antisense compound targeted to a PCSK9 nucleic acid comprises a nucleotide sequence selected from SEQ ID NOs: 94. In certain such embodiments, an antisense compound targeted to nucleotides 5667-5686 of SEQ ID NO: 2 is selected from ISIS NOs: 399841 or 399997.

In certain embodiments, a target region is nucleotides 6444-6463 of SEQ ID NO: 2. In certain embodiments, an antisense compound is targeted to nucleotides 6444-6463 of SEQ ID NO: 2. In certain embodiments, an antisense compound targeted to a PCSK9 nucleic acid comprises a nucleotide sequence selected from SEQ ID NOs: 176. In certain such embodiments, an antisense compound targeted to nucleotides 6444-6463 of SEQ ID NO: 2 is selected from ISIS NOs: 410746.

In certain embodiments, a target region is nucleotides 6482-6518 of SEQ ID NO: 2. In certain embodiments, an antisense compound is targeted to nucleotides 6482-6518 of SEQ ID NO: 2. In certain embodiments, an antisense compound targeted to a PCSK9 nucleic acid comprises a nucleotide sequence selected from SEQ ID NOs: 10, 177, 178, 179, 180 or 181. In certain such embodiments, an antisense compound targeted to nucleotides 6482-6518 of SEQ ID NO: 2 is selected from ISIS NOs: 395154, 399876, 406003, 406004, 406005, 406006 or 410747.

In certain embodiments, a target region is nucleotides 6492-6518 of SEQ ID NO: 2. In certain embodiments, an antisense compound is targeted to nucleotides 6492-6518 of SEQ ID NO: 2. In certain embodiments, an antisense compound targeted to a PCSK9 nucleic acid comprises a nucleotide sequence selected from SEQ ID NOs: 10, 178, 179, 180 or 181. In certain such embodiments, an antisense compound targeted to nucleotides 6492-6518 of SEQ ID NO: 2 is selected from ISIS NOs: 395154, 399876, 406003, 406004, 406005 or 406006.

In certain embodiments, a target region is nucleotides 6528-6555 of SEQ ID NO: 2. In certain embodiments, an antisense compound is targeted to nucleotides 6528-6555 of SEQ ID NO: 2. In certain embodiments, an antisense compound targeted to a PCSK9 nucleic acid comprises a nucleotide sequence selected from SEQ ID NOs: 182, 183, 184, 185 or 186. In certain such embodiments, an antisense compound targeted to nucleotides 6528-6555 of SEQ ID NO: 2 is selected from ISIS NOs: 406007, 410529, 410530, 410531, 410574, 410575, 410576, 410647, 410648, 410649 or 410748.

In certain embodiments, a target region is nucleotides 6528-6623 of SEQ ID NO: 2. In certain embodiments, an antisense compound is targeted to nucleotides 6528-6623 of SEQ ID NO: 2. In certain embodiments, an antisense compound targeted to a PCSK9 nucleic acid comprises a nucleotide sequence selected from SEQ ID NOs: 11, 12, 13, 13, 14, 15, 16, 182, 183, 184, 185, 186, 187, 188, 189, 190, 191, 192, 192, 193, 194, 195, 196, 197, 198, 199, 200, 201, 202, 203, 204, 205, 206, or 207. In certain such embodiments, an antisense compound targeted to nucleotides 6528-6623 of SEQ ID NO: 2 is selected from ISIS NOs: 395155, 395156, 395157, 399794, 399795, 399796, 399877, 399878, 399879, 399950, 399951, 399952, 406007, 406008, 406009, 406010, 406011, 406012, 406013, 406014, 406015, 406016, 406017, 406018, 406019, 406020, 410529, 410530, 410531, 410532, 410533, 410534, 410535, 410574, 410575, 410576, 410577, 410578, 410579, 410580, 410581, 410582, 410647, 410648, 410649, 410650, 410651, 410652, 410653, 410654, 410655, 410656, 410657, 410730, 410731, 410748, 410749, or 410750.

In certain embodiments, a target region is nucleotides 6534-6561 of SEQ ID NO: 2. In certain embodiments, an antisense compound is targeted to nucleotides 6534-6561 of SEQ ID NO: 2. In certain embodiments, an antisense compound targeted to a PCSK9 nucleic acid comprises a nucleotide sequence selected from SEQ ID NOs: 11, 184, 185, 186, 187, 188, 189, 190 or 191. In certain such embodiments, an antisense compound targeted to nucleotides 6534-6561 of SEQ ID NO: 2 is selected from ISIS NOs: 395155, 399877, 406008, 406009, 410529, 410530, 410531, 410532, 410533, 410534, 410574, 410575, 410576, 410577, 410578, 410579, 410580, 410581, 410647, 410648, 410649, 410650, 410651, 410652, 410653, 410654, or 410655.

In certain embodiments, a target region is nucleotides 6535-6562 of SEQ ID NO: 2. In certain embodiments, an antisense compound is targeted to nucleotides 6535-6562 of SEQ ID NO: 2. In certain embodiments, an antisense compound targeted to a PCSK9 nucleic acid comprises a nucleotide sequence selected from SEQ ID NOs: 11, 12, 185, 186, 187, 188, 189, 190 or 191. In certain such embodiments, an antisense compound targeted to nucleotides 6535-6562 of SEQ ID NO: 2 is selected from ISIS NOs: 395155, 399794, 399877, 399950, 406008, 406009, 410530, 410531, 410532, 410533, 410534, 410575, 410576, 410577, 410578, 410579, 410580, 410581, 410648, 410649, 410650, 410651, 410652, 410653, 410654, 410655 or 410656.

In certain embodiments, a target region is nucleotides 6536-6563 of SEQ ID NO: 2. In certain embodiments, an antisense compound is targeted to nucleotides 6536-6563 of SEQ ID NO: 2. In certain embodiments, an antisense compound targeted to a PCSK9 nucleic acid comprises a nucleotide sequence selected from SEQ ID NOs: 11, 12, 186, 187, 188, 189, 190, 191 or 192. In certain such embodiments, an antisense compound targeted to nucleotides 6536-6563 of SEQ ID NO: 2 is selected from ISIS NOs: 395155, 399794, 399877, 399950, 406008, 406009, 410531, 410532, 410533, 410534, 410535, 410576, 410577, 410578, 410579, 410580, 410581, 410582, 410649, 410650, 410651, 410652, 410653, 410654, 410655, 410656 or 410657.

In certain embodiments, a target region is nucleotides 6537-6563 of SEQ ID NO: 2. In certain embodiments, an antisense compound is targeted to nucleotides 6537-6563 of SEQ ID NO: 2. In certain embodiments, an antisense compound targeted to a PCSK9 nucleic acid comprises a nucleotide sequence selected from SEQ ID NOs: 11, 12, 187, 188, 189, 190, 191 or 192. In certain such embodiments, an antisense compound targeted to nucleotides 6537-6563 of SEQ ID NO: 2 is selected from ISIS NOs: 395155, 399794, 399877, 399950, 406008, 406009, 410532, 410533, 410534, 410535, 410577, 410578, 410579, 410580, 410581, 410582, 410650, 410651, 410652, 410653, 410654, 410655, 410656 or 410657.

In certain embodiments, a target region is nucleotides 6538-6565 of SEQ ID NO: 2. In certain embodiments, an antisense compound is targeted to nucleotides 6538-6565 of SEQ ID NO: 2. In certain embodiments, an antisense compound targeted to a PCSK9 nucleic acid comprises a nucleotide sequence selected from SEQ ID NOs: 12, 187, 188, 189, 190, 191, 192 or 193. In certain such embodiments, an antisense compound targeted to nucleotides 6538-6565 of SEQ ID NO: 2 is selected from ISIS NOs: 399794, 399950, 406008, 406009, 406010, 410532, 410533, 410534, 410535, 410577, 410578, 410579, 410580, 410581, 410582, 410651, 410652, 410653, 410654, 410655, 410656 or 410657.

In certain embodiments, a target region is nucleotides 6539-6565 of SEQ ID NO: 2. In certain embodiments, an antisense compound is targeted to nucleotides 6539-6565 of SEQ ID NO: 2. In certain embodiments, an antisense compound targeted to a PCSK9 nucleic acid comprises a nucleotide sequence selected from SEQ ID NOs: 12, 188, 189, 190, 191, 192 or 193. In certain such embodiments, an antisense compound targeted to nucleotides 6539-6565 of SEQ ID NO: 2 is selected from ISIS NOs: 399794, 399950, 406008, 406009, 406010, 410533, 410534, 410535, 410578, 410579, 410580, 410581, 410582, 410652, 410653, 410654, 410655, 410656 or 410657.

In certain embodiments, a target region is nucleotides 6540-6567 of SEQ ID NO: 2. In certain embodiments, an antisense compound is targeted to nucleotides 6540-6567 of SEQ ID NO: 2. In certain embodiments, an antisense compound targeted to a PCSK9 nucleic acid comprises a nucleotide sequence selected from SEQ ID NOs: 12, 189, 190, 191, 192, 193 or 194. In certain such embodiments, an antisense compound targeted to nucleotides 6540-6567 of SEQ ID NO: 2 is selected from ISIS NOs: 399794, 399950, 406009, 406010, 406011, 410533, 410534, 410535, 410579, 410580, 410581, 410582, 410653, 410654, 410655, 410656 or 410657.

In certain embodiments, a target region is nucleotides 6541-6567 of SEQ ID NO: 2. In certain embodiments, an antisense compound is targeted to nucleotides 6541-6567 of SEQ ID NO: 2. In certain embodiments, an antisense compound targeted to a PCSK9 nucleic acid comprises a nucleotide sequence selected from SEQ ID NOs: 12, 190, 191, 192, 193 or 194. In certain such embodiments, an antisense compound targeted to nucleotides 6541-6567 of SEQ ID NO: 2 is selected from ISIS NOs: 399794, 399950, 406009, 406010, 406011, 410534, 410535, 410580, 410581, 410582, 410654, 410655, 410656 or 410657.

In certain embodiments, a target region is nucleotides 6542-6569 of SEQ ID NO: 2. In certain embodiments, an antisense compound is targeted to nucleotides 6542-6569 of SEQ ID NO: 2. In certain embodiments, an antisense compound targeted to a PCSK9 nucleic acid comprises a nucleotide sequence selected from SEQ ID NOs: 12, 191, 192, 193, 194 or 195. In certain such embodiments, an antisense compound targeted to nucleotides 6542-6569 of SEQ ID NO: 2 is selected from ISIS NOs: 399794, 399950, 406010, 406011, 406012, 410534, 410535, 410581, 410582, 410655, 410656 or 410657.

In certain embodiments, a target region is nucleotides 6546-6573 of SEQ ID NO: 2. In certain embodiments, an antisense compound is targeted to nucleotides 6546-6573 of SEQ ID NO: 2. In certain embodiments, an antisense compound targeted to a PCSK9 nucleic acid comprises a nucleotide sequence selected from SEQ ID NOs: 13, 193, 194, 195 or 196. In certain such embodiments, an antisense compound targeted to nucleotides 6546-6573 of SEQ ID NO: 2 is selected from ISIS NOs: 399795, 399951, 406010, 406011, 406012 or 406013.

In certain embodiments, a target region is nucleotides 6557-6584 of SEQ ID NO: 2. In certain embodiments, an antisense compound is targeted to nucleotides 6557-6584 of SEQ ID NO: 2. In certain embodiments, an antisense compound targeted to a PCSK9 nucleic acid comprises a nucleotide sequence selected from SEQ ID NOs: 14, 197 or 198. In certain such embodiments, an antisense compound targeted to nucleotides 6557-6584 of SEQ ID NO: 2 is selected from ISIS NOs: 395156, 399878, 410749 or 410750.

In certain embodiments, a target region is nucleotides 6575-6602 of SEQ ID NO: 2. In certain embodiments, an antisense compound is targeted to nucleotides 6575-6602 of SEQ ID NO: 2. In certain embodiments, an antisense compound targeted to a PCSK9 nucleic acid comprises a nucleotide sequence selected from SEQ ID NOs: 15 or 198. In certain such embodiments, an antisense compound targeted to nucleotides 6575-6602 of SEQ ID NO: 2 is selected from ISIS NOs: 395157, 399879 or 410750.

In certain embodiments, a target region is nucleotides 6585-6611 of SEQ ID NO: 2. In certain embodiments, an antisense compound is targeted to nucleotides 6585-6611 of SEQ ID NO: 2. In certain embodiments, an antisense compound targeted to a PCSK9 nucleic acid comprises a nucleotide sequence selected from SEQ ID NOs: 16, 199, 200 or 201. In certain such embodiments, an antisense compound targeted to nucleotides 6585-6611 of SEQ ID NO: 2 is selected from ISIS NOs: 399796, 399952, 406014, 406015 or 406016.

In certain embodiments, a target region is nucleotides 6594-6621 of SEQ ID NO: 2. In certain embodiments, an antisense compound is targeted to nucleotides 6594-6621 of SEQ ID NO: 2. In certain embodiments, an antisense compound targeted to a PCSK9 nucleic acid comprises a nucleotide sequence selected from SEQ ID NOs: 202, 203, 204, 205 or 206. In certain such embodiments, an antisense compound targeted to nucleotides 6594-6621 of SEQ ID NO: 2 is selected from ISIS NOs: 406017, 406018, 406019, 406020 or 410730.

In certain embodiments, a target region is nucleotides 6596-6623 of SEQ ID NO: 2. In certain embodiments, an antisense compound is targeted to nucleotides 6596-6623 of SEQ ID NO: 2. In certain embodiments, an antisense compound targeted to a PCSK9 nucleic acid comprises a nucleotide sequence selected from SEQ ID NOs: 203, 204, 205, 206 or 207. In certain such embodiments, an antisense compound targeted to nucleotides 6596-6623 of SEQ ID NO: 2 is selected from ISIS NOs: 406017, 406018, 406019, 406020 or 410731.

In certain embodiments, a target region is nucleotides 6652-6671 of SEQ ID NO: 2. In certain embodiments, an antisense compound is targeted to nucleotides 6652-6671 of SEQ ID NO: 2. In certain embodiments, an antisense compound targeted to a PCSK9 nucleic acid comprises a nucleotide sequence selected from SEQ ID NOs: 108. In certain such embodiments, an antisense compound targeted to nucleotides 6652-6671 of SEQ ID NO: 2 is selected from ISIS NOs: 399842 or 399998.

In certain embodiments, a target region is nucleotides 7099-7118 of SEQ ID NO: 2. In certain embodiments, an antisense compound is targeted to nucleotides 7099-7118 of SEQ ID NO: 2. In certain embodiments, an antisense compound targeted to a PCSK9 nucleic acid comprises a nucleotide sequence selected from SEQ ID NOs: 114. In certain such embodiments, an antisense compound targeted to nucleotides 7099-7118 of SEQ ID NO: 2 is selected from ISIS NOs: 399843 or 399999.

In certain embodiments, a target region is nucleotides 7556-7584 of SEQ ID NO: 2. In certain embodiments, an antisense compound is targeted to nucleotides 7556-7584 of SEQ ID NO: 2. In certain embodiments, an antisense compound targeted to a PCSK9 nucleic acid comprises a nucleotide sequence selected from SEQ ID NOs: 91 or 131. In certain such embodiments, an antisense compound targeted to nucleotides 7556-7584 of SEQ ID NO: 2 is selected from ISIS NOs: 399844, 399845, 400000 or 400001.

In certain embodiments, a target region is nucleotides 8836-8855 of SEQ ID NO: 2. In certain embodiments, an antisense compound is targeted to nucleotides 8836-8855 of SEQ ID NO: 2. In certain embodiments, an antisense compound targeted to a PCSK9 nucleic acid comprises a nucleotide sequence selected from SEQ ID NOs: 145. In certain such embodiments, an antisense compound targeted to nucleotides 8836-8855 of SEQ ID NO: 2 is selected from ISIS NOs: 399846 or 400002.

In certain embodiments, a target region is nucleotides 8948-8967 of SEQ ID NO: 2. In certain embodiments, an antisense compound is targeted to nucleotides 8948-8967 of SEQ ID NO: 2. In certain embodiments, an antisense compound targeted to a PCSK9 nucleic acid comprises a nucleotide sequence selected from SEQ ID NOs: 90. In certain such embodiments, an antisense compound targeted to nucleotides 8948-8967 of SEQ ID NO: 2 is selected from ISIS NOs: 399847 or 400003.

In certain embodiments, a target region is nucleotides 9099-9118 of SEQ ID NO: 2. In certain embodiments, an antisense compound is targeted to nucleotides 9099-9118 of SEQ ID NO: 2. In certain embodiments, an antisense compound targeted to a PCSK9 nucleic acid comprises a nucleotide sequence selected from SEQ ID NOs: 125. In certain such embodiments, an antisense compound targeted to nucleotides 9099-9118 of SEQ ID NO: 2 is selected from ISIS NOs: 399848 or 400004.

In certain embodiments, a target region is nucleotides 9099-9168 of SEQ ID NO: 2. In certain embodiments, an antisense compound is targeted to nucleotides 9099-9168 of SEQ ID NO: 2. In certain embodiments, an antisense compound targeted to a PCSK9 nucleic acid comprises a nucleotide sequence selected from SEQ ID NOs: 17, 125 or 209. In certain such embodiments, an antisense compound targeted to nucleotides 9099-9168 of SEQ ID NO: 2 is selected from ISIS NOs: 395158, 399848, 399880, 400004 or 410752.

In certain embodiments, a target region is nucleotides 9130-9168 of SEQ ID NO: 2. In certain embodiments, an antisense compound is targeted to nucleotides 9130-9168 of SEQ ID NO: 2. In certain embodiments, an antisense compound targeted to a PCSK9 nucleic acid comprises a nucleotide sequence selected from SEQ ID NOs: 17. In certain such embodiments, an antisense compound targeted to nucleotides 9130-9168 of SEQ ID NO: 2 is selected from ISIS NOs: 395158 or 399880.

In certain embodiments, a target region is nucleotides 9207-9233 of SEQ ID NO: 2. In certain embodiments, an antisense compound is targeted to nucleotides 9207-9233 of SEQ ID NO: 2. In certain embodiments, an antisense compound targeted to a PCSK9 nucleic acid comprises a nucleotide sequence selected from SEQ ID NOs: 18, 210, 211, 212 or 213. In certain such embodiments, an antisense compound targeted to nucleotides 9207-9233 of SEQ ID NO: 2 is selected from ISIS NOs: 395159, 399881, 406021, 406022, 406023 or 406024.

In certain embodiments, a target region is nucleotides 9207-9235 of SEQ ID NO: 2. In certain embodiments, an antisense compound is targeted to nucleotides 9207-9235 of SEQ ID NO: 2. In certain embodiments, an antisense compound targeted to a PCSK9 nucleic acid comprises a nucleotide sequence selected from SEQ ID NOs: 18, 210, 211, 212, 213 or 214. In certain such embodiments, an antisense compound targeted to nucleotides 9207-9235 of SEQ ID NO: 2 is selected from ISIS NOs: 395159, 399881, 406021, 406022, 406023, 406024 or 410732.

In certain embodiments, a target region is nucleotides 9209-9235 of SEQ ID NO: 2. In certain embodiments, an antisense compound is targeted to nucleotides 9209-9235 of SEQ ID NO: 2. In certain embodiments, an antisense compound targeted to a PCSK9 nucleic acid comprises a nucleotide sequence selected from SEQ ID NOs: 18, 211, 212, 213 or 214. In certain such embodiments, an antisense compound targeted to nucleotides 9209-9235 of SEQ ID NO: 2 is selected from ISIS NOs: 395159, 399881, 406022, 406023, 406024 or 410732.

In certain embodiments, a target region is nucleotides 10252-10271 of SEQ ID NO: 2. In certain embodiments, an antisense compound is targeted to nucleotides 10252-10271 of SEQ ID NO: 2. In certain embodiments, an antisense compound targeted to a PCSK9 nucleic acid comprises a nucleotide sequence selected from SEQ ID NOs: 148. In certain such embodiments, an antisense compound targeted to nucleotides 10252-10271 of SEQ ID NO: 2 is selected from ISIS NOs: 399849 or 400005.

In certain embodiments, a target region is nucleotides 10633-10652 of SEQ ID NO: 2. In certain embodiments, an antisense compound is targeted to nucleotides 10633-10652 of SEQ ID NO: 2. In certain embodiments, an antisense compound targeted to a PCSK9 nucleic acid comprises a nucleotide sequence selected from SEQ ID NOs: 127. In certain such embodiments, an antisense compound targeted to nucleotides 10633-10652 of SEQ ID NO: 2 is selected from ISIS NOs: 395222 or 399944.

In certain embodiments, a target region is nucleotides 11308-11491 of SEQ ID NO: 2. In certain embodiments, an antisense compound is targeted to nucleotides 11308-11491 of SEQ ID NO: 2. In certain embodiments, an antisense compound targeted to a PCSK9 nucleic acid comprises a nucleotide sequence selected from SEQ ID NOs: 79 or 84. In certain such embodiments, an antisense compound targeted to nucleotides 11308-11491 of SEQ ID NO: 2 is selected from ISIS NOs: 395223, 399850, 399945 or 400006.

In certain embodiments, a target region is nucleotides 12715-12734 of SEQ ID NO: 2. In certain embodiments, an antisense compound is targeted to nucleotides 12715-12734 of SEQ ID NO: 2. In certain embodiments, an antisense compound targeted to a PCSK9 nucleic acid comprises a nucleotide sequence selected from SEQ ID NOs: 88. In certain such embodiments, an antisense compound targeted to nucleotides 12715-12734 of SEQ ID NO: 2 is selected from ISIS NOs: 399851 or 400007.

In certain embodiments, a target region is nucleotides 12928-12947 of SEQ ID NO: 2. In certain embodiments, an antisense compound is targeted to nucleotides 12928-12947 of SEQ ID NO: 2. In certain embodiments, an antisense compound targeted to a PCSK9 nucleic acid comprises a nucleotide sequence selected from SEQ ID NOs: 111. In certain such embodiments, an antisense compound targeted to nucleotides 12928-12947 of SEQ ID NO: 2 is selected from ISIS NOs: 399852 or 400008.

In certain embodiments, a target region is nucleotides 13681-13700 of SEQ ID NO: 2. In certain embodiments, an antisense compound is targeted to nucleotides 13681-13700 of SEQ ID NO: 2. In certain embodiments, an antisense compound targeted to a PCSK9 nucleic acid comprises a nucleotide sequence selected from SEQ ID NOs: 85. In certain such embodiments, an antisense compound targeted to nucleotides 13681-13700 of SEQ ID NO: 2 is selected from ISIS NOs: 395201 or 399923.

In certain embodiments, a target region is nucleotides 13746-13779 of SEQ ID NO: 2. In certain embodiments, an antisense compound is targeted to nucleotides 13746-13779 of SEQ ID NO: 2. In certain embodiments, an antisense compound targeted to a PCSK9 nucleic acid comprises a nucleotide sequence selected from SEQ ID NOs: 100 or 116. In certain such embodiments, an antisense compound targeted to nucleotides 13746-13779 of SEQ ID NO: 2 is selected from ISIS NOs: 399827, 399828, 399983 or 399984.

In certain embodiments, a target region is nucleotides 13816-13847 of SEQ ID NO: 2. In certain embodiments, an antisense compound is targeted to nucleotides 13816-13847 of SEQ ID NO: 2. In certain embodiments, an antisense compound targeted to a PCSK9 nucleic acid comprises a nucleotide sequence selected from SEQ ID NOs: 117 or 129. In certain such embodiments, an antisense compound targeted to nucleotides 13816-13847 of SEQ ID NO: 2 is selected from ISIS NOs: 395202, 399829, 399924 or 399985.

In certain embodiments, a target region is nucleotides 13903-13945 of SEQ ID NO: 2. In certain embodiments, an antisense compound is targeted to nucleotides 13903-13945 of SEQ ID NO: 2. In certain embodiments, an antisense compound targeted to a PCSK9 nucleic acid comprises a nucleotide sequence selected from SEQ ID NOs: 81 or 110. In certain such embodiments, an antisense compound targeted to nucleotides 13903-13945 of SEQ ID NO: 2 is selected from ISIS NOs: 395203, 399830, 399925 or 399986.

In certain embodiments, a target region is nucleotides 13977-14141 of SEQ ID NO: 2. In certain embodiments, an antisense compound is targeted to nucleotides 13977-14141 of SEQ ID NO: 2. In certain embodiments, an antisense compound targeted to a PCSK9 nucleic acid comprises a nucleotide sequence selected from SEQ ID NOs: 83, 136, 137, 140 or 152. In certain such embodiments, an antisense compound targeted to nucleotides 13977-14141 of SEQ ID NO: 2 is selected from ISIS NOs: 395204, 395205, 395206, 399831, 399832, 399926, 399927, 399928, 399987 or 399988.

In certain embodiments, a target region is nucleotides 14179-14198 of SEQ ID NO: 2. In certain embodiments, an antisense compound is targeted to nucleotides 14179-14198 of SEQ ID NO: 2. In certain embodiments, an antisense compound targeted to a PCSK9 nucleic acid comprises a nucleotide sequence selected from SEQ ID NOs: 132. In certain such embodiments, an antisense compound targeted to nucleotides 14179-14198 of SEQ ID NO: 2 is selected from ISIS NOs: 395207 or 399929.

In certain embodiments, a target region is nucleotides 14267-14286 of SEQ ID NO: 2. In certain embodiments, an antisense compound is targeted to nucleotides 14267-14286 of SEQ ID NO: 2. In certain embodiments, an antisense compound targeted to a PCSK9 nucleic acid comprises a nucleotide sequence selected from SEQ ID NOs: 139. In certain such embodiments, an antisense compound targeted to nucleotides 14267-14286 of SEQ ID NO: 2 is selected from ISIS NOs: 395208 or 399930.

In certain embodiments, a target region is nucleotides 14397-14423 of SEQ ID NO: 2. In certain embodiments, an antisense compound is targeted to nucleotides 14397-14423 of SEQ ID NO: 2. In certain embodiments, an antisense compound targeted to a PCSK9 nucleic acid comprises a nucleotide sequence selected from SEQ ID NOs: 92 or 142. In certain such embodiments, an antisense compound targeted to nucleotides 14397-14423 of SEQ ID NO: 2 is selected from ISIS NOs: 395209, 399833, 399931 or 399989.

In certain embodiments, a target region is nucleotides 14441-14460 of SEQ ID NO: 2. In certain embodiments, an antisense compound is targeted to nucleotides 14441-14460 of SEQ ID NO: 2. In certain embodiments, an antisense compound targeted to a PCSK9 nucleic acid comprises a nucleotide sequence selected from SEQ ID NOs: 113. In certain such embodiments, an antisense compound targeted to nucleotides 14441-14460 of SEQ ID NO: 2 is selected from ISIS NOs: 395210 or 399932.

In certain embodiments, a target region is nucleotides 14494-14513 of SEQ ID NO: 2. In certain embodiments, an antisense compound is targeted to nucleotides 14494-14513 of SEQ ID NO: 2. In certain embodiments, an antisense compound targeted to a PCSK9 nucleic acid comprises a nucleotide sequence selected from SEQ ID NOs: 138. In certain such embodiments, an antisense compound targeted to nucleotides 14494-14513 of SEQ ID NO: 2 is selected from ISIS NOs: 395211 or 399933.

In certain embodiments, a target region is nucleotides 14494-14543 of SEQ ID NO: 2. In certain embodiments, an antisense compound is targeted to nucleotides 14494-14543 of SEQ ID NO: 2. In certain embodiments, an antisense compound targeted to a PCSK9 nucleic acid comprises a nucleotide sequence selected from SEQ ID NOs: 98 or 138. In certain such embodiments, an antisense compound targeted to nucleotides 14494-14543 of SEQ ID NO: 2 is selected from ISIS NOs: 395211, 395212, 399933 or 399934.

In certain embodiments, a target region is nucleotides 14524-14543 of SEQ ID NO: 2. In certain embodiments, an antisense compound is targeted to nucleotides 14524-14543 of SEQ ID NO: 2. In certain embodiments, an antisense compound targeted to a PCSK9 nucleic acid comprises a nucleotide sequence selected from SEQ ID NOs: 98. In certain such embodiments, an antisense compound targeted to nucleotides 14524-14543 of SEQ ID NO: 2 is selected from ISIS NOs: 395212 or 399934.

In certain embodiments, a target region is nucleotides 14601-14650 of SEQ ID NO: 2. In certain embodiments, an antisense compound is targeted to nucleotides 14601-14650 of SEQ ID NO: 2. In certain embodiments, an antisense compound targeted to a PCSK9 nucleic acid comprises a nucleotide sequence selected from SEQ ID NOs: 96 or 124. In certain such embodiments, an antisense compound targeted to nucleotides 14601-14650 of SEQ ID NO: 2 is selected from ISIS NOs: 395213, 395214, 399935 or 399936.

In certain embodiments, a target region is nucleotides 14670-14700 of SEQ ID NO: 2. In certain embodiments, an antisense compound is targeted to nucleotides 14670-14700 of SEQ ID NO: 2. In certain embodiments, an antisense compound targeted to a PCSK9 nucleic acid comprises a nucleotide sequence selected from SEQ ID NOs: 82, 103 or 133. In certain embodiments, an antisense compound targeted to nucleotides 14670-14700 of SEQ ID NO: 2 is selected from ISIS NOs: 395215, 395216, 399834, 399937, 399938 or 399990.

In certain embodiments, a target region is nucleotides 14675-14700 of SEQ ID NO: 2. In certain embodiments, an antisense compound is targeted to nucleotides 14675-14700 of SEQ ID NO: 2. In certain embodiments, an antisense compound targeted to a PCSK9 nucleic acid comprises a nucleotide sequence selected from SEQ ID NOs: 103 or 133. In certain such embodiments, an antisense compound targeted to nucleotides 14675-14700 of SEQ ID NO: 2 is selected from ISIS NOs: 395215, 395216, 399937 or 399938.

In certain embodiments, a target region is nucleotides 14801-14828 of SEQ ID NO: 2. In certain embodiments, an antisense compound is targeted to nucleotides 14801-14828 of SEQ ID NO: 2. In certain embodiments, an antisense compound targeted to a PCSK9 nucleic acid comprises a nucleotide sequence selected from SEQ ID NOs: 155 or 156. In certain such embodiments, an antisense compound targeted to nucleotides 14801-14828 of SEQ ID NO: 2 is selected from ISIS NOs: 395217, 399835, 399939 or 399991.

In certain embodiments, a target region is nucleotides 14877-14912 of SEQ ID NO: 2. In certain embodiments, an antisense compound is targeted to nucleotides 14877-14912 of SEQ ID NO: 2. In certain embodiments, an antisense compound targeted to a PCSK9 nucleic acid comprises a nucleotide sequence selected from SEQ ID NOs: 19, 215, 216 or 217. In certain such embodiments, an antisense compound targeted to nucleotides 14877-14912 of SEQ ID NO: 2 is selected from ISIS NOs: 395160, 399882, 406025, 406026 or 410753.

In certain embodiments, a target region is nucleotides 14877-14915 of SEQ ID NO: 2. In certain embodiments, an antisense compound is targeted to nucleotides 14877-14915 of SEQ ID NO: 2. In certain embodiments, an antisense compound targeted to a PCSK9 nucleic acid comprises a nucleotide sequence selected from SEQ ID NOs: 19, 20, 215, 216 or 217. In certain such embodiments, an antisense compound targeted to nucleotides 14877-14915 of SEQ ID NO: 2 is selected from ISIS NOs: 395160, 399797, 399882, 399953, 406025, 406026 or 410753.

In certain embodiments, a target region is nucleotides 14877-14973 of SEQ ID NO: 2. In certain embodiments, an antisense compound is targeted to nucleotides 14877-14973 of SEQ ID NO: 2. In certain embodiments, an antisense compound targeted to a PCSK9 nucleic acid comprises a nucleotide sequence selected from SEQ ID NOs: 19, 20, 21, 22, 23, 24, 215, 216, 217, 218, 219, 220, 221, 222, 223, 224, 225, 226, 227, 228, 229, 230, 231, 232, or 233. In certain such embodiments, an antisense compound targeted to nucleotides 14877-14973 of SEQ ID NO: 2 is selected from ISIS NOs: 395160, 395161, 395162, 399797, 399798, 399799, 399882, 399883, 399884, 399953, 399954, 399955, 405869, 405870, 405871, 405872, 405873, 405874, 405875, 405876, 406025, 406026, 406027, 406028, 406029, 406030, 406031, 406032, 410733, 410753, or 410754.

In certain embodiments, a target region is nucleotides 14916-14943 of SEQ ID NO: 2. In certain embodiments, an antisense compound is targeted to nucleotides 14916-14943 of SEQ ID NO: 2. In certain embodiments, an antisense compound targeted to a PCSK9 nucleic acid comprises a nucleotide sequence selected from SEQ ID NOs: 21, 22, 218, 219, 220, 221, 222 or 223. In certain such embodiments, an antisense compound targeted to nucleotides 14916-14943 of SEQ ID NO: 2 is selected from ISIS NOs: 395161, 399798, 399883, 399954, 405869, 405870, 405871, 405872, 405873 or 405874.

In certain embodiments, a target region is nucleotides 14916-14973 of SEQ ID NO: 2. In certain embodiments, an antisense compound is targeted to nucleotides 14916-14973 of SEQ ID NO: 2. In certain embodiments, an antisense compound targeted to a PCSK9 nucleic acid comprises a nucleotide sequence selected from SEQ ID NOs: 21, 22, 23, 24, 218, 219, 220, 221, 222, 223, 224, 225, 226, 227, 228, 229, 230, 231, 232, or 223. In certain such embodiments, an antisense compound targeted to nucleotides 14916-14973 of SEQ ID NO: 2 is selected from ISIS NOs: 395161, 395162, 399798, 399799, 399883, 399884, 399954, 399955, 405869, 405870, 405871, 405872, 405873, 405874, 405875, 405876, 406027, 406028, 406029, 406030, 406031, 406032, 410733, or 410754.

In certain embodiments, a target region is nucleotides 14925-14951 of SEQ ID NO: 2. In certain embodiments, an antisense compound is targeted to nucleotides 14925-14951 of SEQ ID NO: 2. In certain embodiments, an antisense compound targeted to a PCSK9 nucleic acid comprises a nucleotide sequence selected from SEQ ID NOs: 224, 225, 226 or 227. In certain such embodiments, an antisense compound targeted to nucleotides 14925-14951 of SEQ ID NO: 2 is selected from ISIS NOs: 405875, 405876, 406027 or 406028.

In certain embodiments, a target region is nucleotides 14934-14963 of SEQ ID NO: 2. In certain embodiments, an antisense compound is targeted to nucleotides 14934-14963 of SEQ ID NO: 2. In certain embodiments, an antisense compound targeted to a PCSK9 nucleic acid comprises a nucleotide sequence selected from SEQ ID NOs: 23, 228, 229, 230, 231 or 232. In certain such embodiments, an antisense compound targeted to nucleotides 14934-14963 of SEQ ID NO: 2 is selected from ISIS NOs: 399799, 399955, 406029, 406030, 406031, 406032 or 410733.

In certain embodiments, a target region is nucleotides 14946-14973 of SEQ ID NO: 2. In certain embodiments, an antisense compound is targeted to nucleotides 14946-14973 of SEQ ID NO: 2. In certain embodiments, an antisense compound targeted to a PCSK9 nucleic acid comprises a nucleotide sequence selected from SEQ ID NOs: 24 or 233. In certain such embodiments, an antisense compound targeted to nucleotides 14946-14973 of SEQ ID NO: 2 is selected from ISIS NOs: 395162, 399884 or 410754.

In certain embodiments, a target region is nucleotides 14979-14998 of SEQ ID NO: 2. In certain embodiments, an antisense compound is targeted to nucleotides 14979-14998 of SEQ ID NO: 2. In certain embodiments, an antisense compound targeted to a PCSK9 nucleic acid comprises a nucleotide sequence selected from SEQ ID NOs: 25. In certain such embodiments, an antisense compound targeted to nucleotides 14979-14998 of SEQ ID NO: 2 is selected from ISIS NOs: 395163 or 399885.

In certain embodiments, a target region is nucleotides 15254-15280 of SEQ ID NO: 2. In certain embodiments, an antisense compound is targeted to nucleotides 15254-15280 of SEQ ID NO: 2. In certain embodiments, an antisense compound targeted to a PCSK9 nucleic acid comprises a nucleotide sequence selected from SEQ ID NOs: 235, 236 or 237. In certain such embodiments, an antisense compound targeted to nucleotides 15254-15280 of SEQ ID NO: 2 is selected from ISIS NOs: 405526, 405604, 406033 or 410756.

In certain embodiments, a target region is nucleotides 15254-15328 of SEQ ID NO: 2. In certain embodiments, an antisense compound is targeted to nucleotides 15254-15328 of SEQ ID NO: 2. In certain embodiments, an antisense compound targeted to a PCSK9 nucleic acid comprises a nucleotide sequence selected from SEQ ID NOs: 26, 27, 28, 235, 236, 237, 238, 239, 240, 241, 242, 243, 243, 243, 244, 245, 246, 247, 248, 249, 250, 251, 252, 253, 254, 255, 256, or 447. In certain such embodiments, an antisense compound targeted to nucleotides 15254-15328 of SEQ ID NO: 2 is selected from ISIS NOs: 395164, 395165, 399800, 399886, 399887, 399956, 405526, 405604, 405877, 405878, 405879, 405880, 405881, 405882, 405883, 405884, 406033, 406034, 406035, 406036, 406037, 406038, 409126, 410536, 410537, 410538, 410539, 410583, 410584, 410585, 410586, 410587, 410588, 410589, 410590, 410591, 410592, 410593, 410594, 410595, 410658, 410659, 410660, 410661, 410662, 410663, 410664, 410665, 410666, 410667, 410668, 410669, 410670, 410671, 410756, 410757, or 410758.

In certain embodiments, a target region is nucleotides 15264-15290 of SEQ ID NO: 2. In certain embodiments, an antisense compound is targeted to nucleotides 15264-15290 of SEQ ID NO: 2. In certain embodiments, an antisense compound targeted to a PCSK9 nucleic acid comprises a nucleotide sequence selected from SEQ ID NOs: 26, 27, 238 or 239. In certain such embodiments, an antisense compound targeted to nucleotides 15264-15290 of SEQ ID NO: 2 is selected from ISIS NOs: 395164, 399800, 399886, 399956, 406034, or 406035.

In certain embodiments, a target region is nucleotides 15279-15305 of SEQ ID NO: 2. In certain embodiments, an antisense compound is targeted to nucleotides 15279-15305 of SEQ ID NO: 2. In certain embodiments, an antisense compound targeted to a PCSK9 nucleic acid comprises a nucleotide sequence selected from SEQ ID NOs: 240, 241 or 242. In certain such embodiments, an antisense compound targeted to nucleotides 15279-15305 of SEQ ID NO: 2 is selected from ISIS NOs: 406036, 406037, or 410757.

In certain embodiments, a target region is nucleotides 15291-15318 of SEQ ID NO: 2. In certain embodiments, an antisense compound is targeted to nucleotides 15291-15318 of SEQ ID NO: 2. In certain embodiments, an antisense compound targeted to a PCSK9 nucleic acid comprises a nucleotide sequence selected from SEQ ID NOs: 28, 243, 244, 245, 246, 247, 248, 249, 250, or 447. In certain such embodiments, an antisense compound targeted to nucleotides 15291-15318 of SEQ ID NO: 2 is selected from ISIS NOs: 395165, 399887, 405877, 405878, 405879, 405880, 405881, 406038, 409126, 410536, 410537, 410583, 410584, 410585, 410586, 410587, 410588, 410589, 410590, 410658, 410659, 410660, 410661, 410662, 410663, 410664, 410665, or 410666.

In certain embodiments, a target region is nucleotides 15292-15319 of SEQ ID NO: 2. In certain embodiments, an antisense compound is targeted to nucleotides 15292-15319 of SEQ ID NO: 2. In certain embodiments, an antisense compound targeted to a PCSK9 nucleic acid comprises a nucleotide sequence selected from SEQ ID NOs: 28, 244, 245, 246, 247, 248, 249, 250 or 447. In certain such embodiments, an antisense compound targeted to nucleotides 15292-15319 of SEQ ID NO: 2 is selected from ISIS NOs: 395165, 399887, 405877, 405878, 405879, 405880, 405881, 406038, 409126, 410537, 410584, 410585, 410586, 410587, 410588, 410589, 410590, 410659, 410660, 410661, 410662, 410663, 410664, 410665, or 410666.

In certain embodiments, a target region is nucleotides 15293-15320 of SEQ ID NO: 2. In certain embodiments, an antisense compound is targeted to nucleotides 15293-15320 of SEQ ID NO: 2. In certain embodiments, an antisense compound targeted to a PCSK9 nucleic acid comprises a nucleotide sequence selected from SEQ ID NOs: 28, 245, 246, 247, 248, 249, 250, 251, 252 or 447. In certain such embodiments, an antisense compound targeted to nucleotides 15293-15320 of SEQ ID NO: 2 is selected from ISIS NOs: 395165, 399887, 405877, 405878, 405879, 405880, 405881, 405882, 405883, 406038, 409126, 410585, 410586, 410587, 410588, 410589, 410590, 410591, 410592, 410660, 410661, 410662, 410663, 410664, 410665, 410666, 410667, or 410668.

In certain embodiments, a target region is nucleotides 15294-15321 of SEQ ID NO: 2. In certain embodiments, an antisense compound is targeted to nucleotides 15294-15321 of SEQ ID NO: 2. In certain embodiments, an antisense compound targeted to a PCSK9 nucleic acid comprises a nucleotide sequence selected from SEQ ID NOs: 28, 246, 247, 248, 249, 250, 251, 252, 253 or 447. In certain such embodiments, an antisense compound targeted to nucleotides 15294-15321 of SEQ ID NO: 2 is selected from ISIS NOs: 395165, 399887, 405877, 405878, 405879, 405880, 405881, 405882, 405883, 405884, 409126, 410586, 410587, 410588, 410589, 410590, 410591, 410592, 410593, 410661, 410662, 410663, 410664, 410665, 410666, 410667, 410668 or 410669.

In certain embodiments, a target region is nucleotides 15294-15321 of SEQ ID NO: 2. In certain embodiments, an antisense compound is targeted to nucleotides 15294-15321 of SEQ ID NO: 2. In certain embodiments, an antisense compound targeted to a PCSK9 nucleic acid comprises a nucleotide sequence selected from SEQ ID NOs: 28, 246, 247, 248, 249, 250, 251, 252, 253 or 447. In certain such embodiments, an antisense compound targeted to nucleotides 15294-15321 of SEQ ID NO: 2 is selected from ISIS NOs: 395165, 399887, 405877, 405878, 405879, 405880, 405881, 405882, 405883, 405884, 409126, 410586, 410587, 410588, 410589, 410590, 410591, 410592, 410593, 410661, 410662, 410663, 410664, 410665, 410666, 410667, 410668 or 410669.

In certain embodiments, a target region is nucleotides 15295-15322 of SEQ ID NO: 2. In certain embodiments, an antisense compound is targeted to nucleotides 15295-15322 of SEQ ID NO: 2. In certain embodiments, an antisense compound targeted to a PCSK9 nucleic acid comprises a nucleotide sequence selected from SEQ ID NOs: 28, 247, 248, 249, 250, 250, 251, 252, 253, 254 or 447. In certain such embodiments, an antisense compound targeted to nucleotides 15295-15322 of SEQ ID NO: 2 is selected from ISIS NOs: 395165, 399887, 405878, 405879, 405880, 405881, 405882, 405883, 405884, 409126, 410538, 410587, 410588, 410589, 410590, 410591, 410592, 410593, 410594, 410662, 410663, 410664, 410665, 410666, 410667, 410668, 410669 or 410670.

In certain embodiments, a target region is nucleotides 15296-15315 of SEQ ID NO: 2. In certain embodiments, an antisense compound is targeted to nucleotides 15296-15315 of SEQ ID NO: 2. In one such embodiment, an antisense compound targeted to nucleotides 15296-15315 of SEQ ID NO: 2 is ISIS NO: 405879.

In certain embodiments, a target region is nucleotides 15296-15323 of SEQ ID NO: 2. In certain embodiments, an antisense compound is targeted to nucleotides 15296-15323 of SEQ ID NO: 2. In certain embodiments, an antisense compound targeted to a PCSK9 nucleic acid comprises a nucleotide sequence selected from SEQ ID NOs: 28, 248, 249, 250, 251, 252, 253, 254, 255 or 447. In certain such embodiments, an antisense compound targeted to nucleotides 15296-15323 of SEQ ID NO: 2 is selected from ISIS NOs: 395165, 399887, 405879, 405880, 405881, 405882, 405883, 405884, 409126, 410538, 410539, 410588, 410589, 410590, 410591, 410592, 410593, 410594, 410595, 410663, 410664, 410665, 410666, 410667, 410668, 410669, 410670 or 410671.

In certain embodiments, a target region is nucleotides 15297-15323 of SEQ ID NO: 2. In certain embodiments, an antisense compound is targeted to nucleotides 15297-15323 of SEQ ID NO: 2. In certain embodiments, an antisense compound targeted to a PCSK9 nucleic acid comprises a nucleotide sequence selected from SEQ ID NOs: 28, 249, 250, 251, 252, 253, 254, 255 or 447. In certain such embodiments, an antisense compound targeted to nucleotides 15297-15323 of SEQ ID NO: 2 is selected from ISIS NOs: 395165, 399887, 405880, 405881, 405882, 405883, 405884, 409126, 410538, 410539, 410589, 410590, 410591, 410592, 410593, 410594, 410595, 410664, 410665, 410666, 410667, 410668, 410669, 410670 or 410671.

In certain embodiments, a target region is nucleotides 15298-15323 of SEQ ID NO: 2. In certain embodiments, an antisense compound is targeted to nucleotides 15298-15323 of SEQ ID NO: 2. In certain embodiments, an antisense compound targeted to a PCSK9 nucleic acid comprises a nucleotide sequence selected from SEQ ID NOs: 28, 250, 251, 252, 253, 254, 255 or 447. In certain such embodiments, an antisense compound targeted to nucleotides 15298-15323 of SEQ ID NO: 2 is selected from ISIS NOs: 395165, 399887, 405881, 405882, 405883, 405884, 409126, 410538, 410539, 410590, 410591, 410592, 410593, 410594, 410595, 410665, 410666, 410667, 410668, 410669, 410670 or 410671.

In certain embodiments, a target region is nucleotides 15299-15323 of SEQ ID NO: 2. In certain embodiments, an antisense compound is targeted to nucleotides 15299-15323 of SEQ ID NO: 2. In certain embodiments, an antisense compound targeted to a PCSK9 nucleic acid comprises a nucleotide sequence selected from SEQ ID NOs: 250, 251, 252, 253, 254 or 255. In certain such embodiments, an antisense compound targeted to nucleotides 15299-15323 of SEQ ID NO: 2 is selected from ISIS NOs: 405881, 405882, 405883, 405884, 410538, 410539, 410590, 410591, 410592, 410593, 410594, 410595, 410666, 410667, 410668, 410669, 410670 or 410671.

In certain embodiments, a target region is nucleotides 15300-15323 of SEQ ID NO: 2. In certain embodiments, an antisense compound is targeted to nucleotides 15300-15323 of SEQ ID NO: 2. In certain embodiments, an antisense compound targeted to a PCSK9 nucleic acid comprises a nucleotide sequence selected from SEQ ID NOs: 251, 252, 253, 254 or 255. In certain such embodiments, an antisense compound targeted to nucleotides 15300-15323 of SEQ ID NO: 2 is selected from ISIS NOs: 405882, 405883, 405884, 410538, 410539, 410591, 410592, 410593, 410594, 410595, 410667, 410668, 410669, 410670 or 410671.

In certain embodiments, a target region is nucleotides 15301-15328 of SEQ ID NO: 2. In certain embodiments, an antisense compound is targeted to nucleotides 15301-15328 of SEQ ID NO: 2. In certain embodiments, an antisense compound targeted to a PCSK9 nucleic acid comprises a nucleotide sequence selected from SEQ ID NOs: 252, 253, 254, 255 or 256. In certain such embodiments, an antisense compound targeted to nucleotides 15301-15328 of SEQ ID NO: 2 is selected from ISIS NOs: 405883, 405884, 410538, 410539, 410592, 410593, 410594, 410595, 410668, 410669, 410670, 410671 or 410758.

In certain embodiments, a target region is nucleotides 15330-15355 of SEQ ID NO: 2. In certain embodiments, an antisense compound is targeted to nucleotides 15330-15355 of SEQ ID NO: 2. In certain embodiments, an antisense compound targeted to a PCSK9 nucleic acid comprises a nucleotide sequence selected from SEQ ID NOs: 29, 257, 258 or 259. In certain such embodiments, an antisense compound targeted to nucleotides 15330-15355 of SEQ ID NO: 2 is selected from ISIS NOs: 395166, 399888, 406039, 406040 or 406041.

In certain embodiments, a target region is nucleotides 15330-15490 of SEQ ID NO: 2. In certain embodiments, an antisense compound is targeted to nucleotides 15330-15490 of SEQ ID NO: 2. In certain embodiments, an antisense compound targeted to a PCSK9 nucleic acid comprises a nucleotide sequence selected from SEQ ID NOs: 29, 30, 86, 257, 258, 259, 260, 261, 262 or 263. In certain such embodiments, an antisense compound targeted to nucleotides 15330-15490 of SEQ ID NO: 2 is selected from ISIS NOs: 395166, 399801, 399853, 399888, 399957, 400009, 406039, 406040, 406041, 406042, 406043, 406044 or 410759.

In certain embodiments, a target region is nucleotides 15339-15366 of SEQ ID NO: 2. In certain embodiments, an antisense compound is targeted to nucleotides 15339-15366 of SEQ ID NO: 2. In certain embodiments, an antisense compound targeted to a PCSK9 nucleic acid comprises a nucleotide sequence selected from SEQ ID NOs: 30, 260, 261 or 262. In certain such embodiments, an antisense compound targeted to nucleotides 15339-15366 of SEQ ID NO: 2 is selected from ISIS NOs: 399801, 399957, 406042, 406043 or 406044.

In certain embodiments, a target region is nucleotides 15358-15490 of SEQ ID NO: 2. In certain embodiments, an antisense compound is targeted to nucleotides 15358-15490 of SEQ ID NO: 2. In certain embodiments, an antisense compound targeted to a PCSK9 nucleic acid comprises a nucleotide sequence selected from SEQ ID NOs: 86 or 263. In certain such embodiments, an antisense compound targeted to nucleotides 15358-15490 of SEQ ID NO: 2 is selected from ISIS NOs: 399853, 400009 or 410759.

In certain embodiments, a target region is nucleotides 16134-16153 of SEQ ID NO: 2. In certain embodiments, an antisense compound is targeted to nucleotides 16134-16153 of SEQ ID NO: 2. In certain embodiments, an antisense compound targeted to a PCSK9 nucleic acid comprises a nucleotide sequence selected from SEQ ID NOs: 97. In certain such embodiments, an antisense compound targeted to nucleotides 16134-16153 of SEQ ID NO: 2 is selected from ISIS NOs: 399854 or 400010.

In certain embodiments, a target region is nucleotides 16668-16687 of SEQ ID NO: 2. In certain embodiments, an antisense compound is targeted to nucleotides 16668-16687 of SEQ ID NO: 2. In certain embodiments, an antisense compound targeted to a PCSK9 nucleic acid comprises a nucleotide sequence selected from SEQ ID NOs: 120. In certain such embodiments, an antisense compound targeted to nucleotides 16668-16687 of SEQ ID NO: 2 is selected from ISIS NOs: 399855 or 400011.

In certain embodiments, a target region is nucleotides 17267-17286 of SEQ ID NO: 2. In certain embodiments, an antisense compound is targeted to nucleotides 17267-17286 of SEQ ID NO: 2. In certain embodiments, an antisense compound targeted to a PCSK9 nucleic acid comprises a nucleotide sequence selected from SEQ ID NOs: 150. In certain such embodiments, an antisense compound targeted to nucleotides 17267-17286 of SEQ ID NO: 2 is selected from ISIS NOs: 399856 or 400012.

In certain embodiments, a target region is nucleotides 18377-18427 of SEQ ID NO: 2. In certain embodiments, an antisense compound is targeted to nucleotides 18377-18427 of SEQ ID NO: 2. In certain embodiments, an antisense compound targeted to a PCSK9 nucleic acid comprises a nucleotide sequence selected from SEQ ID NOs: 115 or 134. In certain such embodiments, an antisense compound targeted to nucleotides 18377-18427 of SEQ ID NO: 2 is selected from ISIS NOs: 399857, 399858, 400013 or 400014.

In certain embodiments, a target region is nucleotides 18561-18580 of SEQ ID NO: 2. In certain embodiments, an antisense compound is targeted to nucleotides 18561-18580 of SEQ ID NO: 2. In certain embodiments, an antisense compound targeted to a PCSK9 nucleic acid comprises a nucleotide sequence selected from SEQ ID NOs: 157. In certain such embodiments, an antisense compound targeted to nucleotides 18561-18580 of SEQ ID NO: 2 is selected from ISIS NOs: 395224 or 399946.

In certain embodiments, a target region is nucleotides 18591-18618 of SEQ ID NO: 2. In certain embodiments, an antisense compound is targeted to nucleotides 18591-18618 of SEQ ID NO: 2. In certain embodiments, an antisense compound targeted to a PCSK9 nucleic acid comprises a nucleotide sequence selected from SEQ ID NOs: 32, 266, 267, 268 or 269. In certain such embodiments, an antisense compound targeted to nucleotides 18591-18618 of SEQ ID NO: 2 is selected from ISIS NOs: 395168, 399890, 405909, 405910, 405911 or 406045.

In certain embodiments, a target region is nucleotides 18591-18646 of SEQ ID NO: 2. In certain embodiments, an antisense compound is targeted to nucleotides 18591-18646 of SEQ ID NO: 2. In certain embodiments, an antisense compound targeted to a PCSK9 nucleic acid comprises a nucleotide sequence selected from SEQ ID NOs: 32, 32, 266, 267, 268, 269, 270, 271 or 272. In certain such embodiments, an antisense compound targeted to nucleotides 18591-18646 of SEQ ID NO: 2 is selected from ISIS NOs: 395168, 399890, 405909, 405910, 405911, 405912, 406045, 410761 or 410762.

In certain embodiments, a target region is nucleotides 18591-18668 of SEQ ID NO: 2. In certain embodiments, an antisense compound is targeted to nucleotides 18591-18668 of SEQ ID NO: 2. In certain embodiments, an antisense compound targeted to a PCSK9 nucleic acid comprises a nucleotide sequence selected from SEQ ID NOs: 32, 266, 267, 268, 269, 270, 271, 272 or 273. In certain such embodiments, an antisense compound targeted to nucleotides 18591-18668 of SEQ ID NO: 2 is selected from ISIS NOs: 395168, 399890, 405909, 405910, 405911, 405912, 406045, 410761, 410762 or 410763.

In certain embodiments, a target region is nucleotides 18695-18746 of SEQ ID NO: 2. In certain embodiments, an antisense compound is targeted to nucleotides 18695-18746 of SEQ ID NO: 2. In certain embodiments, an antisense compound targeted to a PCSK9 nucleic acid comprises a nucleotide sequence selected from SEQ ID NOs: 33, 274, 275, 276, 277, 278, 279, 280, 281, 282, 283, 284 or 285. In certain such embodiments, an antisense compound targeted to nucleotides 18695-18746 of SEQ ID NO: 2 is selected from ISIS NOs: 395169, 399891, 405913, 405914, 405915, 405916, 405917, 405918, 405919, 405920, 405921, 405922, 410734 or 410764.

In certain embodiments, a target region is nucleotides 18705-18730 of SEQ ID NO: 2. In certain embodiments, an antisense compound is targeted to nucleotides 18705-18730 of SEQ ID NO: 2. In certain embodiments, an antisense compound targeted to a PCSK9 nucleic acid comprises a nucleotide sequence selected from SEQ ID NOs: 33, 275, 276 or 277. In certain such embodiments, an antisense compound targeted to nucleotides 18705-18730 of SEQ ID NO: 2 is selected from ISIS NOs: 395169, 399891, 405913, 405914 or 405915.

In certain embodiments, a target region is nucleotides 18709-18736 of SEQ ID NO: 2. In certain embodiments, an antisense compound is targeted to nucleotides 18709-18736 of SEQ ID NO: 2. In certain embodiments, an antisense compound targeted to a PCSK9 nucleic acid comprises a nucleotide sequence selected from SEQ ID NOs: 276, 277, 278, 279 or 280. In certain such embodiments, an antisense compound targeted to nucleotides 18709-18736 of SEQ ID NO: 2 is selected from ISIS NOs: 405914, 405915, 405916, 405917 or 410734.

In certain embodiments, a target region is nucleotides 18719-18746 of SEQ ID NO: 2. In certain embodiments, an antisense compound is targeted to nucleotides 18719-18746 of SEQ ID NO: 2. In certain embodiments, an antisense compound targeted to a PCSK9 nucleic acid comprises a nucleotide sequence selected from SEQ ID NOs: 281, 282, 283, 284 or 285. In certain such embodiments, an antisense compound targeted to nucleotides 18719-18746 of SEQ ID NO: 2 is selected from ISIS NOs: 405918, 405919, 405920, 405921 or 405922.

In certain embodiments, a target region is nucleotides 19203-20080 of SEQ ID NO: 2. In certain embodiments, an antisense compound is targeted to nucleotides 19203-20080 of SEQ ID NO: 2. In certain embodiments, an antisense compound targeted to a PCSK9 nucleic acid comprises a nucleotide sequence selected from SEQ ID NOs: 34, 35, 36, 37, 38, 39, 40, 41, 105, 128, 149, 151, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317 or 318. In certain such embodiments, an antisense compound targeted to nucleotides 19203-20080 of SEQ ID NO: 2 is selected from ISIS NOs: 395170, 395171, 395172, 395173, 395174, 395175, 399802, 399803, 399804, 399805, 399859, 399860, 399892, 399893, 399894, 399895, 399896, 399897, 399958, 399959, 399960, 399961, 400015, 400016, 405923, 405924, 405925, 405926, 405927, 405928, 405929, 405930, 405931, 405932, 405933, 405934, 405935, 405936, 405937, 405938, 405939, 405940, 405941, 405942, 405943, 405944, 405945, 405946, 405947, 410735, 410736, 410737, 410767, 410768 or 410769.

In certain embodiments, a target region is nucleotides 19931-19952 of SEQ ID NO: 2. In certain embodiments, an antisense compound is targeted to nucleotides 19931-19952 of SEQ ID NO: 2. In certain embodiments, an antisense compound targeted to a PCSK9 nucleic acid comprises a nucleotide sequence selected from SEQ ID NOs: 149 or 188. In certain such embodiments, an antisense compound targeted to nucleotides 19931-19952 of SEQ ID NO: 2 is selected from ISIS NOs: 395170, 399892 or 405923.

In certain embodiments, a target region is nucleotides 19954-19981 of SEQ ID NO: 2. In certain embodiments, an antisense compound is targeted to nucleotides 19954-19981 of SEQ ID NO: 2. In certain embodiments, an antisense compound targeted to a PCSK9 nucleic acid comprises a nucleotide sequence selected from SEQ ID NOs: 34, 290, 291, 292 or 293. In certain such embodiments, an antisense compound targeted to nucleotides 19954-19981 of SEQ ID NO: 2 is selected from ISIS NOs: 395171, 399893, 405924, 405925, 405926 or 410735.

In certain embodiments, a target region is nucleotides 19964-19990 of SEQ ID NO: 2. In certain embodiments, an antisense compound is targeted to nucleotides 19964-19990 of SEQ ID NO: 2. In certain embodiments, an antisense compound targeted to a PCSK9 nucleic acid comprises a nucleotide sequence selected from SEQ ID NOs: 35, 128, 128, 294 or 295. In certain such embodiments, an antisense compound targeted to nucleotides 19964-19990 of SEQ ID NO: 2 is selected from ISIS NOs: 395172, 399802, 399894, 399958, 405927 or 405928.

In certain embodiments, a target region is nucleotides 19973-19999 of SEQ ID NO: 2. In certain embodiments, an antisense compound is targeted to nucleotides 19973-19999 of SEQ ID NO: 2. In certain embodiments, an antisense compound targeted to a PCSK9 nucleic acid comprises a nucleotide sequence selected from SEQ ID NOs: 36, 296, 297 or 298. In certain such embodiments, an antisense compound targeted to nucleotides 19973-19999 of SEQ ID NO: 2 is selected from ISIS NOs: 395173, 399895, 405929, 405930 or 405931.

In certain embodiments, a target region is nucleotides 19982-20009 of SEQ ID NO: 2. In certain embodiments, an antisense compound is targeted to nucleotides 19982-20009 of SEQ ID NO: 2. In certain embodiments, an antisense compound targeted to a PCSK9 nucleic acid comprises a nucleotide sequence selected from SEQ ID NOs: 37, 299, 300, 301 or 302. In certain such embodiments, an antisense compound targeted to nucleotides 19982-20009 of SEQ ID NO: 2 is selected from ISIS NOs: 399803, 399959, 405932, 405933, 405934 or 405935.

In certain embodiments, a target region is nucleotides 19992-20016 of SEQ ID NO: 2. In certain embodiments, an antisense compound is targeted to nucleotides 19992-20016 of SEQ ID NO: 2. In certain embodiments, an antisense compound targeted to a PCSK9 nucleic acid comprises a nucleotide sequence selected from SEQ ID NOs: 38, 303 or 304. In certain such embodiments, an antisense compound targeted to nucleotides 19992-20016 of SEQ ID NO: 2 is selected from ISIS NOs: 395174, 399896, 405936 or 410736.

In certain embodiments, a target region is nucleotides 20016-20042 of SEQ ID NO: 2. In certain embodiments, an antisense compound is targeted to nucleotides 20016-20042 of SEQ ID NO: 2. In certain embodiments, an antisense compound targeted to a PCSK9 nucleic acid comprises a nucleotide sequence selected from SEQ ID NOs: 305 or 306. In certain such embodiments, an antisense compound targeted to nucleotides 20016-20042 of SEQ ID NO: 2 is selected from ISIS NOs: 405937 or 410768.

In certain embodiments, a target region is nucleotides 20025-20052 of SEQ ID NO: 2. In certain embodiments, an antisense compound is targeted to nucleotides 20025-20052 of SEQ ID NO: 2. In certain embodiments, an antisense compound targeted to a PCSK9 nucleic acid comprises a nucleotide sequence selected from SEQ ID NOs: 39, 307, 308, 309 or 310. In certain such embodiments, an antisense compound targeted to nucleotides 20025-20052 of SEQ ID NO: 2 is selected from ISIS NOs: 395175, 399897, 405938, 405939, 405940 or 405941.

In certain embodiments, a target region is nucleotides 20036-20062 of SEQ ID NO: 2. In certain embodiments, an antisense compound is targeted to nucleotides 20036-20062 of SEQ ID NO: 2. In certain embodiments, an antisense compound targeted to a PCSK9 nucleic acid comprises a nucleotide sequence selected from SEQ ID NOs: 40, 311, 312, 313 or 314. In certain such embodiments, an antisense compound targeted to nucleotides 20036-20062 of SEQ ID NO: 2 is selected from ISIS NOs: 399804, 399960, 405942, 405943, 405944 or 410737.

In certain embodiments, a target region is nucleotides 20045-20070 of SEQ ID NO: 2. In certain embodiments, an antisense compound is targeted to nucleotides 20045-20070 of SEQ ID NO: 2. In certain embodiments, an antisense compound targeted to a PCSK9 nucleic acid comprises a nucleotide sequence selected from SEQ ID NOs: 41, 315, 316 or 317. In certain such embodiments, an antisense compound targeted to nucleotides 20045-20070 of SEQ ID NO: 2 is selected from ISIS NOs: 399805, 399961, 405945, 405946 or 405947.

In certain embodiments, a target region is nucleotides 20100-20119 of SEQ ID NO: 2. In certain embodiments, an antisense compound is targeted to nucleotides 20100-20119 of SEQ ID NO: 2. In certain embodiments, an antisense compound targeted to a PCSK9 nucleic acid comprises a nucleotide sequence selected from SEQ ID NOs: 158. In certain such embodiments, an antisense compound targeted to nucleotides 20100-20119 of SEQ ID NO: 2 is selected from ISIS NOs: 399861 or 400017.

In certain embodiments, a target region is nucleotides 20188-20207 of SEQ ID NO: 2. In certain embodiments, an antisense compound is targeted to nucleotides 20188-20207 of SEQ ID NO: 2. In certain embodiments, an antisense compound targeted to a PCSK9 nucleic acid comprises a nucleotide sequence selected from SEQ ID NOs: 109. In certain such embodiments, an antisense compound targeted to nucleotides 20188-20207 of SEQ ID NO: 2 is selected from ISIS NOs: 399862 or 400018.

In certain embodiments, a target region is nucleotides 20624-20650 of SEQ ID NO: 2. In certain embodiments, an antisense compound is targeted to nucleotides 20624-20650 of SEQ ID NO: 2. In certain embodiments, an antisense compound targeted to a PCSK9 nucleic acid comprises a nucleotide sequence selected from SEQ ID NOs: 141, 320 or 321. In certain such embodiments, an antisense compound targeted to nucleotides 20624-20650 of SEQ ID NO: 2 is selected from ISIS NOs: 399863, 400019, 405949 or 405950.

In certain embodiments, a target region is nucleotides 20624-20759 of SEQ ID NO: 2. In certain embodiments, an antisense compound is targeted to nucleotides 20624-20759 of SEQ ID NO: 2. In certain embodiments, an antisense compound targeted to a PCSK9 nucleic acid comprises a nucleotide sequence selected from SEQ ID NOs: 43, 44, 45, 46, 47, 48, 49, 50, 51, 87, 141, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358 or 359. In certain such embodiments, an antisense compound targeted to nucleotides 20624-20759 of SEQ ID NO: 2 is selected from ISIS NOs: 395177, 395178, 395179, 399807, 399808, 399809, 399810, 399811, 399812, 399813, 399863, 399899, 399900, 399901, 399963, 399964, 399965, 399966, 399967, 399968, 399969, 400019, 405557, 405885, 405886, 405887, 405888, 405889, 405890, 405891, 405892, 405949, 405950, 405951, 405952, 405953, 405954, 405955, 405956, 405957, 405958, 405959, 405960, 405961, 405962, 405963, 405964, 405965, 405966, 405967, 405968, 405969, 405970, 405971, 405972, 405973, 405974, 408653, 410540, 410596, 410597, 410598, 410599, 410600, 410601, 410602, 410603, 410604, 410672, 410673, 410674, 410675, 410676, 410677, 410678, 410679, 410680, 410681, 410682, 410738, 410739, 410740 or 410770.

In certain embodiments, a target region is nucleotides 20629-20804 of SEQ ID NO: 2. In certain embodiments, an antisense compound is targeted to nucleotides 20629-20804 of SEQ ID NO: 2. In certain embodiments, an antisense compound targeted to a PCSK9 nucleic acid comprises a nucleotide sequence selected from SEQ ID NOs: 43, 44, 45, 46, 47, 48, 49, 50, 51, 87, 119, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 356, 357, 358, 359 or 360. In certain such embodiments, an antisense compound targeted to nucleotides 20629-20804 of SEQ ID NO: 2 is selected from ISIS NOs: 395177, 395178, 395179, 395180, 399807, 399808, 399809, 399810, 399811, 399812, 399813, 399899, 399900, 399901, 399902, 399963, 399964, 399965, 399966, 399967, 399968, 399969, 405557, 405885, 405886, 405887, 405888, 405889, 405890, 405891, 405892, 405949, 405950, 405951, 405952, 405953, 405954, 405955, 405956, 405957, 405958, 405959, 405960, 405961, 405962, 405963, 405964, 405965, 405966, 405967, 405968, 405969, 405970, 405971, 405972, 405973, 405974, 408653, 410540, 410596, 410597, 410598, 410599, 410600, 410601, 410602, 410603, 410604, 410672, 410673, 410674, 410675, 410676, 410677, 410678, 410679, 410680, 410681, 410682, 410738, 410739, 410740, 410770 or 410771.

In certain embodiments, a target region is nucleotides 20633-20660 of SEQ ID NO: 2. In certain embodiments, an antisense compound is targeted to nucleotides 20633-20660 of SEQ ID NO: 2. In certain embodiments, an antisense compound targeted to a PCSK9 nucleic acid comprises a nucleotide sequence selected from SEQ ID NOs: 43, 322, 323, 324 or 325. In certain such embodiments, an antisense compound targeted to nucleotides 20633-20660 of SEQ ID NO: 2 is selected from ISIS NOs: 399807, 399963, 405951, 405952, 405953 or 410738.

In certain embodiments, a target region is nucleotides 20635-20781 of SEQ ID NO: 2. In certain embodiments, an antisense compound is targeted to nucleotides 20635-20781 of SEQ ID NO: 2. In certain embodiments, an antisense compound targeted to a PCSK9 nucleic acid comprises a nucleotide sequence selected from SEQ ID NOs: 43, 44, 45, 46, 47, 48, 49, 50, 51, 87, 119, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358 or 359. In certain such embodiments, an antisense compound targeted to nucleotides 20635-20781 of SEQ ID NO: 2 is selected from ISIS NOs: 395177, 395178, 395179, 395180, 399807, 399808, 399809, 399810, 399811, 399812, 399813, 399899, 399900, 399901, 399902, 399963, 399964, 399965, 399966, 399967, 399968, 399969, 405557, 405885, 405886, 405887, 405888, 405889, 405890, 405891, 405892, 405952, 405953, 405954, 405955, 405956, 405957, 405958, 405959, 405960, 405961, 405962, 405963, 405964, 405965, 405966, 405967, 405968, 405969, 405970, 405971, 405972, 405973, 405974, 408653, 410540, 410596, 410597, 410598, 410599, 410600, 410601, 410602, 410603, 410604, 410672, 410673, 410674, 410675, 410676, 410677, 410678, 410679, 410680, 410681, 410682, 410738, 410739, 410740 or 410770.

In certain embodiments, a target region is nucleotides 20643-20662 of SEQ ID NO: 2. In certain embodiments, an antisense compound is targeted to nucleotides 20643-20662 of SEQ ID NO: 2. In certain embodiments, an antisense compound targeted to a PCSK9 nucleic acid comprises a nucleotide sequence selected from SEQ ID NOs: 326. In certain such embodiments, an antisense compound targeted to nucleotides 20643-20662 of SEQ ID NO: 2 is selected from ISIS NOs: 405954.

In certain embodiments, a target region is nucleotides 20657-20676 of SEQ ID NO: 2. In certain embodiments, an antisense compound is targeted to nucleotides 20657-20676 of SEQ ID NO: 2. In certain embodiments, an antisense compound targeted to a PCSK9 nucleic acid comprises a nucleotide sequence selected from SEQ ID NOs: 327. In certain such embodiments, an antisense compound targeted to nucleotides 20657-20676 of SEQ ID NO: 2 is selected from ISIS NOs: 410770.

In certain embodiments, a target region is nucleotides 20670-20697 of SEQ ID NO: 2. In certain embodiments, an antisense compound is targeted to nucleotides 20670-20697 of SEQ ID NO: 2. In certain embodiments, an antisense compound targeted to a PCSK9 nucleic acid comprises a nucleotide sequence selected from SEQ ID NOs: 328, 329, 330, 331 or 332. In certain such embodiments, an antisense compound targeted to nucleotides 20670-20697 of SEQ ID NO: 2 is selected from ISIS NOs: 405955, 405956, 405957, 405958 or 405959.

In certain embodiments, a target region is nucleotides 20680-20706 of SEQ ID NO: 2. In certain embodiments, an antisense compound is targeted to nucleotides 20680-20706 of SEQ ID NO: 2. In certain embodiments, an antisense compound targeted to a PCSK9 nucleic acid comprises a nucleotide sequence selected from SEQ ID NOs: 44, 333, 334, 335 or 336. In certain such embodiments, an antisense compound targeted to nucleotides 20680-20706 of SEQ ID NO: 2 is selected from ISIS NOs: 399808, 399964, 405960, 405961, 405962 or 410739.

In certain embodiments, a target region is nucleotides 20683-20781 of SEQ ID NO: 2. In certain embodiments, an antisense compound is targeted to nucleotides 20683-20781 of SEQ ID NO: 2. In certain embodiments, an antisense compound targeted to a PCSK9 nucleic acid comprises a nucleotide sequence selected from SEQ ID NOs: 44, 45, 46, 47, 48, 49, 50, 51, 87, 119, 335, 336, 337, 338, 339, 340, 341, 342, 343, 344, 345, 346, 347, 348, 349, 350, 351, 352, 353, 354, 355, 356, 357, 358 or 359. In certain such embodiments, an antisense compound targeted to nucleotides 20683-20781 of SEQ ID NO: 2 is selected from ISIS NOs: 395177, 395178, 395179, 395180, 399808, 399809, 399810, 399811, 399812, 399813, 399899, 399900, 399901, 399902, 399964, 399965, 399966, 399967, 399968, 399969, 405557, 405885, 405886, 405887, 405888, 405889, 405890, 405891, 405892, 405962, 405963, 405964, 405965, 405966, 405967, 405968, 405969, 405970, 405971, 405972, 405973, 405974, 408653, 410540, 410596, 410597, 410598, 410599, 410600, 410601, 410602, 410603, 410604, 410672, 410673, 410674, 410675, 410676, 410677, 410678, 410679, 410680, 410681, 410682, 410739 or 410740.

In certain embodiments, a target region is nucleotides 20689-20715 of SEQ ID NO: 2. In certain embodiments, an antisense compound is targeted to nucleotides 20689-20715 of SEQ ID NO: 2. In certain embodiments, an antisense compound targeted to a PCSK9 nucleic acid comprises a nucleotide sequence selected from SEQ ID NOs: 45, 46, 337 or 338. In certain such embodiments, an antisense compound targeted to nucleotides 20689-20715 of SEQ ID NO: 2 is selected from ISIS NOs: 395177, 399809, 399899, 399965, 405963 or 405964.

In certain embodiments, a target region is nucleotides 20698-20725 of SEQ ID NO: 2. In certain embodiments, an antisense compound is targeted to nucleotides 20698-20725 of SEQ ID NO: 2. In certain embodiments, an antisense compound targeted to a PCSK9 nucleic acid comprises a nucleotide sequence selected from SEQ ID NOs: 47, 47, 339, 340, 341 or 342. In certain such embodiments, an antisense compound targeted to nucleotides 20698-20725 of SEQ ID NO: 2 is selected from ISIS NOs: 399810, 399966, 405965, 405966, 405967 or 405968.

In certain embodiments, a target region is nucleotides 20709-20736 of SEQ ID NO: 2. In certain embodiments, an antisense compound is targeted to nucleotides 20709-20736 of SEQ ID NO: 2. In certain embodiments, an antisense compound targeted to a PCSK9 nucleic acid comprises a nucleotide sequence selected from SEQ ID NOs: 48, 48, 343, 344, 345 or 346. In certain such embodiments, an antisense compound targeted to nucleotides 20709-20736 of SEQ ID NO: 2 is selected from ISIS NOs: 399811, 399967, 405885, 405969, 405970 or 410740.

In certain embodiments, a target region is nucleotides 20717-20744 of SEQ ID NO: 2. In certain embodiments, an antisense compound is targeted to nucleotides 20717-20744 of SEQ ID NO: 2. In certain embodiments, an antisense compound targeted to a PCSK9 nucleic acid comprises a nucleotide sequence selected from SEQ ID NOs: 49, 346, 347, 348, 349, 350, 351, 352 or 353. In certain such embodiments, an antisense compound targeted to nucleotides 20717-20744 of SEQ ID NO: 2 is selected from ISIS NOs: 399812, 399968, 405885, 405886, 405887, 405888, 405889, 405890, 405891, 405892, 410596, 410597, 410598, 410599, 410600, 410601, 410672, 410673, 410674, 410675, 410676, 410677 or 410678.

In certain embodiments, a target region is nucleotides 20718-20745 of SEQ ID NO: 2. In certain embodiments, an antisense compound is targeted to nucleotides 20718-20745 of SEQ ID NO: 2. In certain embodiments, an antisense compound targeted to a PCSK9 nucleic acid comprises a nucleotide sequence selected from SEQ ID NOs: 49, 50, 347, 348, 349, 350, 351, 352 or 353. In certain such embodiments, an antisense compound targeted to nucleotides 20718-20745 of SEQ ID NO: 2 is selected from ISIS NOs: 395178, 399812, 399900, 399968, 405557, 405886, 405887, 405888, 405889, 405890, 405891, 405892, 410596, 410597, 410598, 410599, 410600, 410601, 410672, 410673, 410674, 410675, 410676, 410677, 410678 or 410679.

In certain embodiments, a target region is nucleotides 20719-20746 of SEQ ID NO: 2. In certain embodiments, an antisense compound is targeted to nucleotides 20719-20746 of SEQ ID NO: 2. In certain embodiments, an antisense compound targeted to a PCSK9 nucleic acid comprises a nucleotide sequence selected from SEQ ID NOs: 49, 50, 348, 349, 350, 351, 352, 353 or 354. In certain such embodiments, an antisense compound targeted to nucleotides 20719-20746 of SEQ ID NO: 2 is selected from ISIS NOs: 395178, 399812, 399900, 399968, 405557, 405887, 405888, 405889, 405890, 405891, 405892, 408653, 410596, 410597, 410598, 410599, 410600, 410601, 410602, 410672, 410673, 410674, 410675, 410676, 410677, 410678, 410679 or 410680.

In certain embodiments, a target region is nucleotides 20720-20747 of SEQ ID NO: 2. In certain embodiments, an antisense compound is targeted to nucleotides 20720-20747 of SEQ ID NO: 2. In certain embodiments, an antisense compound targeted to a PCSK9 nucleic acid comprises a nucleotide sequence selected from SEQ ID NOs: 49, 50, 349, 350, 351, 352, 353, 354 or 355. In certain such embodiments, an antisense compound targeted to nucleotides 20720-20747 of SEQ ID NO: 2 is selected from ISIS NOs: 395178, 399812, 399900, 399968, 405557, 405888, 405889, 405890, 405891, 405892, 405971, 408653, 410597, 410598, 410599, 410600, 410601, 410602, 410603, 410673, 410674, 410675, 410676, 410677, 410678, 410679, 410680 or 410681.

In certain embodiments, a target region is nucleotides 20721-20748 of SEQ ID NO: 2. In certain embodiments, an antisense compound is targeted to nucleotides 20721-20748 of SEQ ID NO: 2. In certain embodiments, an antisense compound targeted to a PCSK9 nucleic acid comprises a nucleotide sequence selected from SEQ ID NOs: 49, 50, 350, 351, 352, 353, 354, 355 or 356. In certain such embodiments, an antisense compound targeted to nucleotides 20721-20748 of SEQ ID NO: 2 is selected from ISIS NOs: 395178, 399812, 399900, 399968, 405557, 405889, 405890, 405891, 405892, 405971, 408653, 410540, 410598, 410599, 410600, 410601, 410602, 410603, 410604, 410674, 410675, 410676, 410677, 410678, 410679, 410680, 410681 or 410682.

In certain embodiments, a target region is nucleotides 20722-20749 of SEQ ID NO: 2. In certain embodiments, an antisense compound is targeted to nucleotides 20722-20749 of SEQ ID NO: 2. In certain embodiments, an antisense compound targeted to a PCSK9 nucleic acid comprises a nucleotide sequence selected from SEQ ID NOs: 50, 350, 351, 352, 353, 354, 355, 356 or 357. In certain such embodiments, an antisense compound targeted to nucleotides 20722-20749 of SEQ ID NO: 2 is selected from ISIS NOs: 395178, 399900, 405557, 405889, 405890, 405891, 405892, 405971, 405972, 408653, 410540, 410598, 410599, 410600, 410601, 410602, 410603, 410604, 410675, 410676, 410677, 410678, 410679, 410680, 410681 or 410682.

In certain embodiments, a target region is nucleotides 20727-20752 of SEQ ID NO: 2. In certain embodiments, an antisense compound is targeted to nucleotides 20727-20752 of SEQ ID NO: 2. In certain embodiments, an antisense compound targeted to a PCSK9 nucleic acid comprises a nucleotide sequence selected from SEQ ID NOs: 87, 354, 355, 356 or 357. In certain such embodiments, an antisense compound targeted to nucleotides 20727-20752 of SEQ ID NO: 2 is selected from ISIS NOs: 395179, 399901, 405971, 405972, 408653, 410540, 410602, 410603, 410604, 410680, 410681 or 410682.

In certain embodiments, a target region is nucleotides 20735-20759 of SEQ ID NO: 2. In certain embodiments, an antisense compound is targeted to nucleotides 20735-20759 of SEQ ID NO: 2. In certain embodiments, an antisense compound targeted to a PCSK9 nucleic acid comprises a nucleotide sequence selected from SEQ ID NOs: 51, 358 or 359. In certain such embodiments, an antisense compound targeted to nucleotides 20735-20759 of SEQ ID NO: 2 is selected from ISIS NOs: 399813, 399969, 405973 or 405974.

In certain embodiments, a target region is nucleotides 20762-21014 of SEQ ID NO: 2. In certain embodiments, an antisense compound is targeted to nucleotides 20762-21014 of SEQ ID NO: 2. In certain embodiments, an antisense compound targeted to a PCSK9 nucleic acid comprises a nucleotide sequence selected from SEQ ID NOs: 93, 119 or 360. In certain such embodiments, an antisense compound targeted to nucleotides 20762-21014 of SEQ ID NO: 2 is selected from ISIS NOs: 395180, 399864, 399902, 400020 or 410771.

In certain embodiments, a target region is nucleotides 20785-21014 of SEQ ID NO: 2. In certain embodiments, an antisense compound is targeted to nucleotides 20785-21014 of SEQ ID NO: 2. In certain embodiments, an antisense compound targeted to a PCSK9 nucleic acid comprises a nucleotide sequence selected from SEQ ID NOs: 93 or 360. In certain such embodiments, an antisense compound targeted to nucleotides 20785-21014 of SEQ ID NO: 2 is selected from ISIS NOs: 399864, 400020 or 410771.

In certain embodiments, a target region is nucleotides 21082-21107 of SEQ ID NO: 2. In certain embodiments, an antisense compound is targeted to nucleotides 21082-21107 of SEQ ID NO: 2. In certain embodiments, an antisense compound targeted to a PCSK9 nucleic acid comprises a nucleotide sequence selected from SEQ ID NOs: 95 or 361. In certain such embodiments, an antisense compound targeted to nucleotides 21082-21107 of SEQ ID NO: 2 is selected from ISIS NOs: 399865, 400021 or 405975.

In certain embodiments, a target region is nucleotides 21082-21152 of SEQ ID NO: 2. In certain embodiments, an antisense compound is targeted to nucleotides 21082-21152 of SEQ ID NO: 2. In certain embodiments, an antisense compound targeted to a PCSK9 nucleic acid comprises a nucleotide sequence selected from SEQ ID NOs: 53, 54, 95, 361, 362, 363, 364, 365, 366, 367, 368, 369, 370 or 371. In certain such embodiments, an antisense compound targeted to nucleotides 21082-21152 of SEQ ID NO: 2 is selected from ISIS NOs: 395182, 399814, 399865, 399904, 399970, 400021, 405975, 405976, 405977, 405978, 405979, 405980, 405981, 405982, 405983, 410741 or 410772.

In certain embodiments, a target region is nucleotides 21091-21114 of SEQ ID NO: 2. In certain embodiments, an antisense compound is targeted to nucleotides 21091-21114 of SEQ ID NO: 2. In certain embodiments, an antisense compound targeted to a PCSK9 nucleic acid comprises a nucleotide sequence selected from SEQ ID NOs: 53, 362 or 363. In certain such embodiments, an antisense compound targeted to nucleotides 21091-21114 of SEQ ID NO: 2 is selected from ISIS NOs: 399814, 399970, 405976 or 405977.

In certain embodiments, a target region is nucleotides 21118-21144 of SEQ ID NO: 2. In certain embodiments, an antisense compound is targeted to nucleotides 21118-21144 of SEQ ID NO: 2. In certain embodiments, an antisense compound targeted to a PCSK9 nucleic acid comprises a nucleotide sequence selected from SEQ ID NOs: 54, 365, 366 or 367. In certain such embodiments, an antisense compound targeted to nucleotides 21118-21144 of SEQ ID NO: 2 is selected from ISIS NOs: 395182, 399904, 405978, 405979 or 405980.

In certain embodiments, a target region is nucleotides 21127-21152 of SEQ ID NO: 2. In certain embodiments, an antisense compound is targeted to nucleotides 21127-21152 of SEQ ID NO: 2. In certain embodiments, an antisense compound targeted to a PCSK9 nucleic acid comprises a nucleotide sequence selected from SEQ ID NOs: 368, 369, 370 or 371. In certain such embodiments, an antisense compound targeted to nucleotides 21127-21152 of SEQ ID NO: 2 is selected from ISIS NOs: 405981, 405982, 405983 or 410741.

In certain embodiments, a target region is nucleotides 21181-21209 of SEQ ID NO: 2. In certain embodiments, an antisense compound is targeted to nucleotides 21181-21209 of SEQ ID NO: 2. In certain embodiments, an antisense compound targeted to a PCSK9 nucleic acid comprises a nucleotide sequence selected from SEQ ID NOs: 55, 372, 373, 374 or 375. In certain such embodiments, an antisense compound targeted to nucleotides 21181-21209 of SEQ ID NO: 2 is selected from ISIS NOs: 399815, 399971, 405564, 405641, 405984, 405985, 405986 or 405987.

In certain embodiments, a target region is nucleotides 21181-21211 of SEQ ID NO: 2. In certain embodiments, an antisense compound is targeted to nucleotides 21181-21211 of SEQ ID NO: 2. In certain embodiments, an antisense compound targeted to a PCSK9 nucleic acid comprises a nucleotide sequence selected from SEQ ID NOs: 55, 56, 372, 373, 374 or 375. In certain such embodiments, an antisense compound targeted to nucleotides 21181-21211 of SEQ ID NO: 2 is selected from ISIS NOs: 399815, 399816, 399971, 399972, 405564, 405641, 405984, 405985, 405986 or 405987.

In certain embodiments, a target region is nucleotides 21183-21211 of SEQ ID NO: 2. In certain embodiments, an antisense compound is targeted to nucleotides 21183-21211 of SEQ ID NO: 2. In certain embodiments, an antisense compound targeted to a PCSK9 nucleic acid comprises a nucleotide sequence selected from SEQ ID NOs: 55, 56, 373, 374 or 375. In certain such embodiments, an antisense compound targeted to nucleotides 21183-21211 of SEQ ID NO: 2 is selected from ISIS NOs: 399815, 399816, 399971, 399972, 405564, 405641, 405985, 405986 or 405987.

In certain embodiments, a target region is nucleotides 21481-21500 of SEQ ID NO: 2. In certain embodiments, an antisense compound is targeted to nucleotides 21481-21500 of SEQ ID NO: 2. In certain embodiments, an antisense compound targeted to a PCSK9 nucleic acid comprises a nucleotide sequence selected from SEQ ID NOs: 143. In certain such embodiments, an antisense compound targeted to nucleotides 21481-21500 of SEQ ID NO: 2 is selected from ISIS NOs: 399866 or 400022.

In certain embodiments, a target region is nucleotides 21589-21608 of SEQ ID NO: 2. In certain embodiments, an antisense compound is targeted to nucleotides 21589-21608 of SEQ ID NO: 2. In certain embodiments, an antisense compound targeted to a PCSK9 nucleic acid comprises a nucleotide sequence selected from SEQ ID NOs: 89. In certain such embodiments, an antisense compound targeted to nucleotides 21589-21608 of SEQ ID NO: 2 is selected from ISIS NOs: 399867 or 400023.

In certain embodiments, a target region is nucleotides 21692-21719 of SEQ ID NO: 2. In certain embodiments, an antisense compound is targeted to nucleotides 21692-21719 of SEQ ID NO: 2. In certain embodiments, an antisense compound targeted to a PCSK9 nucleic acid comprises a nucleotide sequence selected from SEQ ID NOs: 123, 448, 449, 450, 451, 452, 453, 454 or 455. In certain such embodiments, an antisense compound targeted to nucleotides 21692-21719 of SEQ ID NO: 2 is selected from ISIS NOs: 399868, 400024, 406478, 406479, 406480, 406481, 406482, 406483, 406484 or 406485.

In certain embodiments, a target region is nucleotides 22000-22227 of SEQ ID NO: 2. In certain embodiments, an antisense compound is targeted to nucleotides 22000-22227 of SEQ ID NO: 2. In certain embodiments, an antisense compound targeted to a PCSK9 nucleic acid comprises a nucleotide sequence selected from SEQ ID NOs: 59, 389, 390, 391, 392, 393, 394, 395 or 396. In certain such embodiments, an antisense compound targeted to nucleotides 22000-22227 of SEQ ID NO: 2 is selected from ISIS NOs: 395185, 399907, 405991, 405992, 410550, 410551, 410552, 410553, 410554, 410555, 410616, 410617, 410618, 410619, 410620, 410621, 410622, 410623, 410695, 410696, 410697, 410698, 410699, 410700, 410701, 410702 or 410703.

In certain embodiments, a target region is nucleotides 22096-22115 of SEQ ID NO: 2. In certain embodiments, an antisense compound is targeted to nucleotides 22096-22115 of SEQ ID NO: 2. In certain embodiments, an antisense compound targeted to a PCSK9 nucleic acid comprises a nucleotide sequence selected from SEQ ID NOs: 57. In certain such embodiments, an antisense compound targeted to nucleotides 22096-22115 of SEQ ID NO: 2 is selected from ISIS NOs: 395183 or 399905.

In certain embodiments, a target region is nucleotides 22096-22223 of SEQ ID NO: 2. In certain embodiments, an antisense compound is targeted to nucleotides 22096-22223 of SEQ ID NO: 2. In certain embodiments, an antisense compound targeted to a PCSK9 nucleic acid comprises a nucleotide sequence selected from SEQ ID NOs: 57, 58, 59, 376, 377, 378, 379, 380, 381, 382, 383, 384, 385, 386, 387, 388, 389, 390, 391 or 392. In certain such embodiments, an antisense compound targeted to nucleotides 22096-22223 of SEQ ID NO: 2 is selected from ISIS NOs: 395183, 395184, 395185, 399905, 399906, 399907, 405988, 405989, 405990, 410541, 410542, 410543, 410544, 410545, 410546, 410547, 410548, 410549, 410550, 410551, 410552, 410553, 410605, 410606, 410607, 410608, 410609, 410610, 410611, 410612, 410613, 410614, 410615, 410616, 410617, 410618, 410619, 410683, 410684, 410685, 410686, 410687, 410688, 410689, 410690, 410691, 410692, 410693, 410694, 410695, 410696, 410697, 410698, 410699 or 410773.

In certain embodiments, a target region is nucleotides 22096-22311 of SEQ ID NO: 2. In certain embodiments, an antisense compound is targeted to nucleotides 22096-22311 of SEQ ID NO: 2. In certain embodiments, an antisense compound targeted to a PCSK9 nucleic acid comprises a nucleotide sequence selected from SEQ ID NOs: 57, 58, 59, 126, 126, 376, 377, 378, 379, 380, 381, 382, 383, 384, 385, 386, 387, 388, 389, 390, 391, 392, 393, 394, 395, 396, 397, 398, 399, 400, 401, 401, 401, 402, 402, 402, 403, 403, 403, 404, 404, 404, 405, 405, 405 or 406. In certain such embodiments, an antisense compound targeted to nucleotides 22096-22311 of SEQ ID NO: 2 is selected from ISIS NOs: 395183, 395184, 395185, 395225, 399905, 399906, 399907, 399947, 405988, 405989, 405990, 405991, 405992, 405993, 405994, 405995, 410541, 410542, 410543, 410544, 410545, 410546, 410547, 410548, 410549, 410550, 410551, 410552, 410553, 410554, 410555, 410556, 410557, 410558, 410559, 410560, 410561, 410605, 410606, 410607, 410608, 410609, 410610, 410611, 410612, 410613, 410614, 410615, 410616, 410617, 410618, 410619, 410620, 410621, 410622, 410623, 410624, 410625, 410626, 410627, 410628, 410629, 410630, 410631, 410632, 410683, 410684, 410685, 410686, 410687, 410688, 410689, 410690, 410691, 410692, 410693, 410694, 410695, 410696, 410697, 410698, 410699, 410700, 410701, 410702, 410703, 410704, 410705, 410706, 410707, 410708, 410709, 410710, 410711, 410712, 410773 or 410774.

In certain embodiments, a target region is nucleotides 22133-22160 of SEQ ID NO: 2. In certain embodiments, an antisense compound is targeted to nucleotides 22133-22160 of SEQ ID NO: 2. In certain embodiments, an antisense compound targeted to a PCSK9 nucleic acid comprises a nucleotide sequence selected from SEQ ID NOs: 376, 377, 378, 379, 380, 381, 382, 383 or 384. In certain such embodiments, an antisense compound targeted to nucleotides 22133-22160 of SEQ ID NO: 2 is selected from ISIS NOs: 405988, 405989, 410541, 410542, 410543, 410544, 410545, 410546, 410547, 410605, 410606, 410607, 410608, 410609, 410610, 410611, 410612, 410613, 410683, 410684, 410685, 410686, 410687, 410688, 410689, 410690 or 410691.

In certain embodiments, a target region is nucleotides 22133-22163 of SEQ ID NO: 2. In certain embodiments, an antisense compound is targeted to nucleotides 22133-22163 of SEQ ID NO: 2. In certain embodiments, an antisense compound targeted to a PCSK9 nucleic acid comprises a nucleotide sequence selected from SEQ ID NOs: 58, 376, 377, 378, 379, 380, 381, 382, 383, 384, 385 or 386. In certain such embodiments, an antisense compound targeted to nucleotides 22133-22163 of SEQ ID NO: 2 is selected from ISIS NOs: 395184, 399906, 405988, 405989, 405990, 410541, 410542, 410543, 410544, 410545, 410546, 410547, 410548, 410605, 410606, 410607, 410608, 410609, 410610, 410611, 410612, 410613, 410614, 410683, 410684, 410685, 410686, 410687, 410688, 410689, 410690, 410691, 410692 or 410693.

In certain embodiments, a target region is nucleotides 22134-22161 of SEQ ID NO: 2. In certain embodiments, an antisense compound is targeted to nucleotides 22134-22161 of SEQ ID NO: 2. In certain embodiments, an antisense compound targeted to a PCSK9 nucleic acid comprises a nucleotide sequence selected from SEQ ID NOs: 58, 377, 378, 379, 380, 381, 382, 383 or 384. In certain such embodiments, an antisense compound targeted to nucleotides 22134-22161 of SEQ ID NO: 2 is selected from ISIS NOs: 395184, 399906, 405988, 405989, 410542, 410543, 410544, 410545, 410546, 410547, 410606, 410607, 410608, 410609, 410610, 410611, 410612, 410613, 410684, 410685, 410686, 410687, 410688, 410689, 410690, 410691 or 410692.

In certain embodiments, a target region is nucleotides 22135-22162 of SEQ ID NO: 2. In certain embodiments, an antisense compound is targeted to nucleotides 22135-22162 of SEQ ID NO: 2. In certain embodiments, an antisense compound targeted to a PCSK9 nucleic acid comprises a nucleotide sequence selected from SEQ ID NOs: 58, 378, 379, 380, 381, 382, 383, 384 or 385. In certain such embodiments, an antisense compound targeted to nucleotides 22135-22162 of SEQ ID NO: 2 is selected from ISIS NOs: 395184, 399906, 405988, 405989, 410543, 410544, 410545, 410546, 410547, 410548, 410607, 410608, 410609, 410610, 410611, 410612, 410613, 410614, 410685, 410686, 410687, 410688, 410689, 410690, 410691, 410692 or 410693.

In certain embodiments, a target region is nucleotides 22136-22163 of SEQ ID NO: 2. In certain embodiments, an antisense compound is targeted to nucleotides 22136-22163 of SEQ ID NO: 2. In certain embodiments, an antisense compound targeted to a PCSK9 nucleic acid comprises a nucleotide sequence selected from SEQ ID NOs: 58, 379, 380, 381, 382, 383, 384, 385 or 386. In certain such embodiments, an antisense compound targeted to nucleotides 22136-22163 of SEQ ID NO: 2 is selected from ISIS NOs: 395184, 399906, 405988, 405989, 405990, 410544, 410545, 410546, 410547, 410548, 410608, 410609, 410610, 410611, 410612, 410613, 410614, 410686, 410687, 410688, 410689, 410690, 410691, 410692 or 410693.

In certain embodiments, a target region is nucleotides 22137-22163 of SEQ ID NO: 2. In certain embodiments, an antisense compound is targeted to nucleotides 22137-22163 of SEQ ID NO: 2. In certain embodiments, an antisense compound targeted to a PCSK9 nucleic acid comprises a nucleotide sequence selected from SEQ ID NOs: 58, 380, 381, 382, 383, 384, 385 or 386. In certain such embodiments, an antisense compound targeted to nucleotides 22137-22163 of SEQ ID NO: 2 is selected from ISIS NOs: 395184, 399906, 405988, 405989, 405990, 410545, 410546, 410547, 410548, 410609, 410610, 410611, 410612, 410613, 410614, 410687, 410688, 410689, 410690, 410691, 410692 or 410693.

In certain embodiments, a target region is nucleotides 22138-22163 of SEQ ID NO: 2. In certain embodiments, an antisense compound is targeted to nucleotides 22138-22163 of SEQ ID NO: 2. In certain embodiments, an antisense compound targeted to a PCSK9 nucleic acid comprises a nucleotide sequence selected from SEQ ID NOs: 58, 381, 382, 383, 384, 385 or 386. In certain such embodiments, an antisense compound targeted to nucleotides 22138-22163 of SEQ ID NO: 2 is selected from ISIS NOs: 395184, 399906, 405988, 405989, 405990, 410546, 410547, 410548, 410610, 410611, 410612, 410613, 410614, 410688, 410689, 410690, 410691, 410692 or 410693.

In certain embodiments, a target region is nucleotides 22189-22239 of SEQ ID NO: 2. In certain embodiments, an antisense compound is targeted to nucleotides 22189-22239 of SEQ ID NO: 2. In certain embodiments, an antisense compound targeted to a PCSK9 nucleic acid comprises a nucleotide sequence selected from SEQ ID NOs: 59, 387, 388, 389, 390, 391, 392, 393, 394, 395, 396, 397, 398, 399, 400, 401, 402, 403, 404, 405 or 406. In certain such embodiments, an antisense compound targeted to nucleotides 22189-22239 of SEQ ID NO: 2 is selected from ISIS NOs: 395185, 399907, 405991, 405992, 405993, 405994, 405995, 410549, 410550, 410551, 410552, 410553, 410554, 410555, 410556, 410557, 410558, 410559, 410560, 410561, 410615, 410616, 410617, 410618, 410619, 410620, 410621, 410622, 410623, 410624, 410625, 410626, 410627, 410628, 410629, 410630, 410631, 410632, 410694, 410695, 410696, 410697, 410698, 410699, 410700, 410701, 410702, 410703, 410704, 410705, 410706, 410707, 410708, 410709, 410710, 410711, 410712, 410773 or 410774.

In certain embodiments, a target region is nucleotides 22199-22226 of SEQ ID NO: 2. In certain embodiments, an antisense compound is targeted to nucleotides 22199-22226 of SEQ ID NO: 2. In certain embodiments, an antisense compound targeted to a PCSK9 nucleic acid comprises a nucleotide sequence selected from SEQ ID NOs: 59, 388, 389, 390, 391, 392, 393, 394 or 395. In certain such embodiments, an antisense compound targeted to nucleotides 22199-22226 of SEQ ID NO: 2 is selected from ISIS NOs: 395185, 399907, 405991, 410549, 410550, 410551, 410552, 410553, 410554, 410555, 410615, 410616, 410617, 410618, 410619, 410620, 410621, 410622, 410694, 410695, 410696, 410697, 410698, 410699, 410700, 410701 or 410702.

In certain embodiments, a target region is nucleotides 22199-22227 of SEQ ID NO: 2. In certain embodiments, an antisense compound is targeted to nucleotides 22199-22227 of SEQ ID NO: 2. In certain embodiments, an antisense compound targeted to a PCSK9 nucleic acid comprises a nucleotide sequence selected from SEQ ID NOs: 59, 388, 389, 390, 391, 392, 393, 394, 395 or 396. In certain such embodiments, an antisense compound targeted to nucleotides 22199-22227 of SEQ ID NO: 2 is selected from ISIS NOs: 395185, 399907, 405991, 405992, 410549, 410550, 410551, 410552, 410553, 410554, 410555, 410615, 410616, 410617, 410618, 410619, 410620, 410621, 410622, 410623, 410694, 410695, 410696, 410697, 410698, 410699, 410700, 410701, 410702 or 410703.

In certain embodiments, a target region is nucleotides 22200-22227 of SEQ ID NO: 2. In certain embodiments, an antisense compound is targeted to nucleotides 22200-22227 of SEQ ID NO: 2. In certain embodiments, an antisense compound targeted to a PCSK9 nucleic acid comprises a nucleotide sequence selected from SEQ ID NOs: 59, 389, 390, 391, 392, 393, 394, 395 or 396. In certain such embodiments, an antisense compound targeted to nucleotides 22200-22227 of SEQ ID NO: 2 is selected from ISIS NOs: 395185, 399907, 405991, 405992, 410550, 410551, 410552, 410553, 410554, 410555, 410616, 410617, 410618, 410619, 410620, 410621, 410622, 410623, 410695, 410696, 410697, 410698, 410699, 410700, 410701, 410702 or 410703.

In certain embodiments, a target region is nucleotides 22201-22228 of SEQ ID NO: 2. In certain embodiments, an antisense compound is targeted to nucleotides 22201-22228 of SEQ ID NO: 2. In certain embodiments, an antisense compound targeted to a PCSK9 nucleic acid comprises a nucleotide sequence selected from SEQ ID NOs: 59, 390, 391, 392, 393, 394, 395, 396 or 397. In certain such embodiments, an antisense compound targeted to nucleotides 22201-22228 of SEQ ID NO: 2 is selected from ISIS NOs: 395185, 399907, 405991, 405992, 410551, 410552, 410553, 410554, 410555, 410556, 410617, 410618, 410619, 410620, 410621, 410622, 410623, 410624, 410696, 410697, 410698, 410699, 410700, 410701, 410702, 410703 or 410704.

In certain embodiments, a target region is nucleotides 22202-22229 of SEQ ID NO: 2. In certain embodiments, an antisense compound is targeted to nucleotides 22202-22229 of SEQ ID NO: 2. In certain embodiments, an antisense compound targeted to a PCSK9 nucleic acid comprises a nucleotide sequence selected from SEQ ID NOs: 59, 391, 392, 393, 394, 395, 396, 397 or 398. In certain such embodiments, an antisense compound targeted to nucleotides 22202-22229 of SEQ ID NO: 2 is selected from ISIS NOs: 395185, 399907, 405991, 405992, 405993, 410552, 410553, 410554, 410555, 410556, 410618, 410619, 410620, 410621, 410622, 410623, 410624, 410625, 410697, 410698, 410699, 410700, 410701, 410702, 410703, 410704 or 410705.

In certain embodiments, a target region is nucleotides 22203-22230 of SEQ ID NO: 2. In certain embodiments, an antisense compound is targeted to nucleotides 22203-22230 of SEQ ID NO: 2. In certain embodiments, an antisense compound targeted to a PCSK9 nucleic acid comprises a nucleotide sequence selected from SEQ ID NOs: 59, 392, 393, 394, 395, 396, 397, 398 or 399. In certain such embodiments, an antisense compound targeted to nucleotides 22203-22230 of SEQ ID NO: 2 is selected from ISIS NOs: 395185, 399907, 405991, 405992, 405993, 410553, 410554, 410555, 410556, 410557, 410619, 410620, 410621, 410622, 410623, 410624, 410625, 410626, 410698, 410699, 410700, 410701, 410702, 410703, 410704, 410705 or 410706.

In certain embodiments, a target region is nucleotides 22204-22231 of SEQ ID NO: 2. In certain embodiments, an antisense compound is targeted to nucleotides 22204-22231 of SEQ ID NO: 2. In certain embodiments, an antisense compound targeted to a PCSK9 nucleic acid comprises a nucleotide sequence selected from SEQ ID NOs: 59, 393, 394, 395, 396, 397, 398, 399 or 400. In certain such embodiments, an antisense compound targeted to nucleotides 22204-22231 of SEQ ID NO: 2 is selected from ISIS NOs: 395185, 399907, 405991, 405992, 405993, 405994, 410554, 410555, 410556, 410557, 410620, 410621, 410622, 410623, 410624, 410625, 410626, 410627, 410699, 410700, 410701, 410702, 410703, 410704, 410705, 410706 or 410707.

In certain embodiments, a target region is nucleotides 22205-22232 of SEQ ID NO: 2. In certain embodiments, an antisense compound is targeted to nucleotides 22205-22232 of SEQ ID NO: 2. In certain embodiments, an antisense compound targeted to a PCSK9 nucleic acid comprises a nucleotide sequence selected from SEQ ID NOs: 393, 394, 395, 396, 397, 398, 399, 400 or 401. In certain such embodiments, an antisense compound targeted to nucleotides 22205-22232 of SEQ ID NO: 2 is selected from ISIS NOs: 405991, 405992, 405993, 405994, 410554, 410555, 410556, 410557, 410558, 410620, 410621, 410622, 410623, 410624, 410625, 410626, 410627, 410628, 410700, 410701, 410702, 410703, 410704, 410705, 410706, 410707 or 410708.

In certain embodiments, a target region is nucleotides 22206-22233 of SEQ ID NO: 2. In certain embodiments, an antisense compound is targeted to nucleotides 22206-22233 of SEQ ID NO: 2. In certain embodiments, an antisense compound targeted to a PCSK9 nucleic acid comprises a nucleotide sequence selected from SEQ ID NOs: 394, 395, 396, 397, 398, 399, 400, 401 or 402. In certain such embodiments, an antisense compound targeted to nucleotides 22206-22233 of SEQ ID NO: 2 is selected from ISIS NOs: 405991, 405992, 405993, 405994, 405995, 410555, 410556, 410557, 410558, 410621, 410622, 410623, 410624, 410625, 410626, 410627, 410628, 410629, 410701, 410702, 410703, 410704, 410705, 410706, 410707, 410708 or 410709.

In certain embodiments, a target region is nucleotides 22207-22234 of SEQ ID NO: 2. In certain embodiments, an antisense compound is targeted to nucleotides 22207-22234 of SEQ ID NO: 2. In certain embodiments, an antisense compound targeted to a PCSK9 nucleic acid comprises a nucleotide sequence selected from SEQ ID NOs: 395, 396, 397, 398, 399, 400, 401, 402 or 403. In certain such embodiments, an antisense compound targeted to nucleotides 22207-22234 of SEQ ID NO: 2 is selected from ISIS NOs: 405992, 405993, 405994, 405995, 410555, 410556, 410557, 410558, 410559, 410622, 410623, 410624, 410625, 410626, 410627, 410628, 410629, 410630, 410702, 410703, 410704, 410705, 410706, 410707, 410708, 410709 or 410710.

In certain embodiments, a target region is nucleotides 22208-22235 of SEQ ID NO: 2. In certain embodiments, an antisense compound is targeted to nucleotides 22208-22235 of SEQ ID NO: 2. In certain embodiments, an antisense compound targeted to a PCSK9 nucleic acid comprises a nucleotide sequence selected from SEQ ID NOs: 396, 397, 398, 399, 400, 401, 402, 403 or 404. In certain such embodiments, an antisense compound targeted to nucleotides 22208-22235 of SEQ ID NO: 2 is selected from ISIS NOs: 405992, 405993, 405994, 405995, 410556, 410557, 410558, 410559, 410560, 410623, 410624, 410625, 410626, 410627, 410628, 410629, 410630, 410631, 410703, 410704, 410705, 410706, 410707, 410708, 410709, 410710 or 410711.

In certain embodiments, a target region is nucleotides 22209-22236 of SEQ ID NO: 2. In certain embodiments, an antisense compound is targeted to nucleotides 22209-22236 of SEQ ID NO: 2. In certain embodiments, an antisense compound targeted to a PCSK9 nucleic acid comprises a nucleotide sequence selected from SEQ ID NOs: 397, 398, 399, 400, 401, 402, 403, 404 or 405. In certain such embodiments, an antisense compound targeted to nucleotides 22209-22236 of SEQ ID NO: 2 is selected from ISIS NOs: 405993, 405994, 405995, 410556, 410557, 410558, 410559, 410560, 410561, 410624, 410625, 410626, 410627, 410628, 410629, 410630, 410631, 410632, 410704, 410705, 410706, 410707, 410708, 410709, 410710, 410711 or 410712.

In certain embodiments, a target region is nucleotides 22210-22236 of SEQ ID NO: 2. In certain embodiments, an antisense compound is targeted to nucleotides 22210-22236 of SEQ ID NO: 2. In certain embodiments, an antisense compound targeted to a PCSK9 nucleic acid comprises a nucleotide sequence selected from SEQ ID NOs: 398, 399, 400, 401, 402, 403, 404 or 405. In certain such embodiments, an antisense compound targeted to nucleotides 22210-22236 of SEQ ID NO: 2 is selected from ISIS NOs: 405993, 405994, 405995, 410557, 410558, 410559, 410560, 410561, 410625, 410626, 410627, 410628, 410629, 410630, 410631, 410632, 410705, 410706, 410707, 410708, 410709, 410710, 410711 or 410712.

In certain embodiments, a target region is nucleotides 22210-22239 of SEQ ID NO: 2. In certain embodiments, an antisense compound is targeted to nucleotides 22210-22239 of SEQ ID NO: 2. In certain embodiments, an antisense compound targeted to a PCSK9 nucleic acid comprises a nucleotide sequence selected from SEQ ID NOs: 398, 399, 400, 401, 402, 403, 404, 405 or 405. In certain such embodiments, an antisense compound targeted to nucleotides 22210-22239 of SEQ ID NO: 2 is selected from ISIS NOs: 405993, 405994, 405995, 410557, 410558, 410559, 410560, 410561, 410625, 410626, 410627, 410628, 410629, 410630, 410631, 410632, 410705, 410706, 410707, 410708, 410709, 410710, 410711, 410712 or 410774.

In certain embodiments, a target region is nucleotides 22211-22236 of SEQ ID NO: 2. In certain embodiments, an antisense compound is targeted to nucleotides 22211-22236 of SEQ ID NO: 2. In certain embodiments, an antisense compound targeted to a PCSK9 nucleic acid comprises a nucleotide sequence selected from SEQ ID NOs: 399, 400, 401, 402, 403, 404 or 405. In certain such embodiments, an antisense compound targeted to nucleotides 22211-22236 of SEQ ID NO: 2 is selected from ISIS NOs: 405994, 405995, 410557, 410558, 410559, 410560, 410561, 410626, 410627, 410628, 410629, 410630, 410631, 410632, 410706, 410707, 410708, 410709, 410710, 410711 or 410712.

In certain embodiments, a target region is nucleotides 22212-22239 of SEQ ID NO: 2. In certain embodiments, an antisense compound is targeted to nucleotides 22212-22239 of SEQ ID NO: 2. In certain embodiments, an antisense compound targeted to a PCSK9 nucleic acid comprises a nucleotide sequence selected from SEQ ID NOs: 400, 401, 402, 403, 404, 405 or 406. In certain such embodiments, an antisense compound targeted to nucleotides 22212-22239 of SEQ ID NO: 2 is selected from ISIS NOs: 405994, 405995, 410558, 410559, 410560, 410561, 410627, 410628, 410629, 410630, 410631, 410632, 410707, 410708, 410709, 410710, 410711, 410712 or 410774.

In certain embodiments, a target region is nucleotides 22292-22311 of SEQ ID NO: 2. In certain embodiments, an antisense compound is targeted to nucleotides 22292-22311 of SEQ ID NO: 2. In certain embodiments, an antisense compound targeted to a PCSK9 nucleic acid comprises a nucleotide sequence selected from SEQ ID NOs: 126. In certain such embodiments, an antisense compound targeted to nucleotides 22292-22311 of SEQ ID NO: 2 is selected from ISIS NOs: 395225 or 399947.

In certain embodiments, a target region is nucleotides 23985-24054 of SEQ ID NO: 2. In certain embodiments, an antisense compound is targeted to nucleotides 23985-24054 of SEQ ID NO: 2. In certain embodiments, an antisense compound targeted to a PCSK9 nucleic acid comprises a nucleotide sequence selected from SEQ ID NOs: 408, 409 or 410. In certain such embodiments, an antisense compound targeted to nucleotides 23985-24054 of SEQ ID NO: 2 is selected from ISIS NOs: 410776, 410777 or 410778.

In certain embodiments, a target region is nucleotides 24035-24134 of SEQ ID NO: 2. In certain embodiments, an antisense compound is targeted to nucleotides 24035-24134 of SEQ ID NO: 2. In certain embodiments, an antisense compound targeted to a PCSK9 nucleic acid comprises a nucleotide sequence selected from SEQ ID NOs: 60, 61, 410, 411, 412, 413, 414, 415 or 416. In certain such embodiments, an antisense compound targeted to nucleotides 24035-24134 of SEQ ID NO: 2 is selected from ISIS NOs: 395186, 399817, 399908, 399973, 405996, 405997, 410562, 410563, 410564, 410633, 410634, 410635, 410636, 410713, 410714, 410715, 410716, 410717, 410718, 410778 or 410779.

In certain embodiments, a target region is nucleotides 24095-24121 of SEQ ID NO: 2. In certain embodiments, an antisense compound is targeted to nucleotides 24095-24121 of SEQ ID NO: 2. In certain embodiments, an antisense compound targeted to a PCSK9 nucleic acid comprises a nucleotide sequence selected from SEQ ID NOs: 60, 61, 411, 412, 413, 414 or 415. In certain such embodiments, an antisense compound targeted to nucleotides 24095-24121 of SEQ ID NO: 2 is selected from ISIS NOs: 395186, 399817, 399908, 399973, 405996, 405997, 410562, 410563, 410564, 410633, 410634, 410635, 410636, 410713, 410714, 410715, 410716, 410717 or 410718.

In certain embodiments, a target region is nucleotides 24858-24877 of SEQ ID NO: 2. In certain embodiments, an antisense compound is targeted to nucleotides 24858-24877 of SEQ ID NO: 2. In certain embodiments, an antisense compound targeted to a PCSK9 nucleic acid comprises a nucleotide sequence selected from SEQ ID NOs: 147. In certain such embodiments, an antisense compound targeted to nucleotides 24858-24877 of SEQ ID NO: 2 is selected from ISIS NOs: 395226 or 399948.

In certain embodiments, a target region is nucleotides 24907-24926 of SEQ ID NO: 2. In certain embodiments, an antisense compound is targeted to nucleotides 24907-24926 of SEQ ID NO: 2. In certain embodiments, an antisense compound targeted to a PCSK9 nucleic acid comprises a nucleotide sequence selected from SEQ ID NOs: 118. In certain such embodiments, an antisense compound targeted to nucleotides 24907-24926 of SEQ ID NO: 2 is selected from ISIS NOs: 399869 or 400025.

In certain embodiments, a target region is nucleotides 25413-25432 of SEQ ID NO: 2. In certain embodiments, an antisense compound is targeted to nucleotides 25413-25432 of SEQ ID NO: 2. In certain embodiments, an antisense compound targeted to a PCSK9 nucleic acid comprises a nucleotide sequence selected from SEQ ID NOs: 114. In certain such embodiments, an antisense compound targeted to nucleotides 25413-25432 of SEQ ID NO: 2 is selected from ISIS NOs: 399870 or 400026.

In certain embodiments, a target region is nucleotides 25994-26013 of SEQ ID NO: 2. In certain embodiments, an antisense compound is targeted to nucleotides 25994-26013 of SEQ ID NO: 2. In certain embodiments, an antisense compound targeted to a PCSK9 nucleic acid comprises a nucleotide sequence selected from SEQ ID NOs: 418. In certain such embodiments, an antisense compound targeted to nucleotides 25994-26013 of SEQ ID NO: 2 is selected from ISIS NOs: 410781.

In certain embodiments, a target region is nucleotides 26112-26139 of SEQ ID NO: 2. In certain embodiments, an antisense compound is targeted to nucleotides 26112-26139 of SEQ ID NO: 2. In certain embodiments, an antisense compound targeted to a PCSK9 nucleic acid comprises a nucleotide sequence selected from SEQ ID NOs: 62, 419, 420, 421, 422, 423, 424, 425 or 426. In certain such embodiments, an antisense compound targeted to nucleotides 26112-26139 of SEQ ID NO: 2 is selected from ISIS NOs: 395187, 399909, 405998, 410565, 410566, 410567, 410568, 410569, 410570, 410571, 410637, 410638, 410639, 410640, 410641, 410642, 410643, 410644, 410719, 410720, 410721, 410722, 410723, 410724, 410725, 410726 or 410727.

In certain embodiments, a target region is nucleotides 26112-26161 of SEQ ID NO: 2. In certain embodiments, an antisense compound is targeted to nucleotides 26112-26161 of SEQ ID NO: 2. In certain embodiments, an antisense compound targeted to a PCSK9 nucleic acid comprises a nucleotide sequence selected from SEQ ID NOs: 62, 419, 420, 421, 422, 423, 424, 425, 426, 427, 428, 429 or 430. In certain such embodiments, an antisense compound targeted to nucleotides 26112-26161 of SEQ ID NO: 2 is selected from ISIS NOs: 395187, 399909, 405998, 410565, 410566, 410567, 410568, 410569, 410570, 410571, 410572, 410573, 410637, 410638, 410639, 410640, 410641, 410642, 410643, 410644, 410645, 410646, 410719, 410720, 410721, 410722, 410723, 410724, 410725, 410726, 410727, 410728, 410729, 410782 or 410783.

In certain embodiments, a target region is nucleotides 26112-27303 of SEQ ID NO: 2. In certain embodiments, an antisense compound is targeted to nucleotides 26112-27303 of SEQ ID NO: 2. In certain embodiments, an antisense compound targeted to a PCSK9 nucleic acid comprises a nucleotide sequence selected from SEQ ID NOs: 62, 63, 64, 65, 66, 67, 68, 69, 70, 71, 72, 73, 74, 75, 76, 77, 112, 122, 135, 153, 154, 419, 420, 421, 422, 423, 424, 425, 426, 427, 428, 429, 430, 431, 432, 433, 434, 435, 436, 437, 438, 439, 440, 441, 442, 443, 444, 445 or 446. In certain such embodiments, an antisense compound targeted to nucleotides 26112-27303 of SEQ ID NO: 2 is selected from ISIS NOs: 395187, 395188, 395189, 395190, 395191, 395192, 395193, 395194, 395195, 395196, 395197, 395198, 395199, 399818, 399819, 399820, 399821, 399822, 399823, 399824, 399825, 399909, 399910, 399911, 399912, 399913, 399914, 399915, 399916, 399917, 399918, 399919, 399920, 399921, 399974, 399975, 399976, 399977, 399978, 399979, 399980, 399981, 405893, 405894, 405895, 405896, 405897, 405898, 405899, 405900, 405901, 405902, 405903, 405904, 405905, 405906, 405907, 405908, 405998, 410565, 410566, 410567, 410568, 410569, 410570, 410571, 410572, 410573, 410637, 410638, 410639, 410640, 410641, 410642, 410643, 410644, 410645, 410646, 410719, 410720, 410721, 410722, 410723, 410724, 410725, 410726, 410727, 410728, 410729, 410782 or 410783.

In certain embodiments, a target region is nucleotides 26113-26140 of SEQ ID NO: 2. In certain embodiments, an antisense compound is targeted to nucleotides 26113-26140 of SEQ ID NO: 2. In certain embodiments, an antisense compound targeted to a PCSK9 nucleic acid comprises a nucleotide sequence selected from SEQ ID NOs: 62, 420, 421, 422, 423, 424, 425, 426 or 427. In certain such embodiments, an antisense compound targeted to nucleotides 26113-26140 of SEQ ID NO: 2 is selected from ISIS NOs: 395187, 399909, 405998, 410566, 410567, 410568, 410569, 410570, 410571, 410572, 410638, 410639, 410640, 410641, 410642, 410643, 410644, 410645, 410720, 410721, 410722, 410723, 410724, 410725, 410726, 410727 or 410728.

In certain embodiments, a target region is nucleotides 26114-26141 of SEQ ID NO: 2. In certain embodiments, an antisense compound is targeted to nucleotides 26114-26141 of SEQ ID NO: 2. In certain embodiments, an antisense compound targeted to a PCSK9 nucleic acid comprises a nucleotide sequence selected from SEQ ID NOs: 62, 421, 422, 423, 424, 425, 426, 427 or 248. In certain such embodiments, an antisense compound targeted to nucleotides 26114-26141 of SEQ ID NO: 2 is selected from ISIS NOs: 395187, 399909, 405998, 410567, 410568, 410569, 410570, 410571, 410572, 410573, 410639, 410640, 410641, 410642, 410643, 410644, 410645, 410646, 410721, 410722, 410723, 410724, 410725, 410726, 410727, 410728 or 410729.

In certain embodiments, a target region is nucleotides 26115-26141 of SEQ ID NO: 2. In certain embodiments, an antisense compound is targeted to nucleotides 26115-26141 of SEQ ID NO: 2. In certain embodiments, an antisense compound targeted to a PCSK9 nucleic acid comprises a nucleotide sequence selected from SEQ ID NOs: 62, 422, 423, 424, 425, 426, 427 or 248. In certain such embodiments, an antisense compound targeted to nucleotides 26115-26141 of SEQ ID NO: 2 is selected from ISIS NOs: 395187, 399909, 405998, 410568, 410569, 410570, 410571, 410572, 410573, 410640, 410641, 410642, 410643, 410644, 410645, 410646, 410722, 410723, 410724, 410725, 410726, 410727, 410728 or 410729.

In certain embodiments, a target region is nucleotides 26116-26141 of SEQ ID NO: 2. In certain embodiments, an antisense compound is targeted to nucleotides 26116-26141 of SEQ ID NO: 2. In certain embodiments, an antisense compound targeted to a PCSK9 nucleic acid comprises a nucleotide sequence selected from SEQ ID NOs: 62, 423, 424, 425, 426, 427 or 428. In certain such embodiments, an antisense compound targeted to nucleotides 26116-26141 of SEQ ID NO: 2 is selected from ISIS NOs: 395187, 399909, 405998, 410569, 410570, 410571, 410572, 410573, 410641, 410642, 410643, 410644, 410645, 410646, 410723, 410724, 410725, 410726, 410727 or 410728.

In certain embodiments, a target region is nucleotides 26117-26141 of SEQ ID NO: 2. In certain embodiments, an antisense compound is targeted to nucleotides 26117-26141 of SEQ ID NO: 2. In certain embodiments, an antisense compound targeted to a PCSK9 nucleic acid comprises a nucleotide sequence selected from SEQ ID NOs: 62, 424, 425, 426, 427 or 428. In certain such embodiments, an antisense compound targeted to nucleotides 26117-26141 of SEQ ID NO: 2 is selected from ISIS NOs: 395187, 399909, 405998, 410570, 410571, 410572, 410573, 410642, 410643, 410644, 410645, 410646, 410724, 410725, 410726, 410727, 410728 or 410729.

In certain embodiments, a target region is nucleotides 26117-26475 of SEQ ID NO: 2. In certain embodiments, an antisense compound is targeted to nucleotides 26117-26475 of SEQ ID NO: 2. In certain embodiments, an antisense compound targeted to a PCSK9 nucleic acid comprises a nucleotide sequence selected from SEQ ID NOs: 62, 63, 64, 65, 66, 67, 122, 153, 154, 424, 425, 426, 427, 428, 429 or 430. In certain such embodiments, an antisense compound targeted to nucleotides 26117-26475 of SEQ ID NO: 2 is selected from ISIS NOs: 395187, 395188, 395189, 395190, 395191, 395192, 399818, 399819, 399820, 399909, 399910, 399911, 399912, 399913, 399914, 399974, 399975, 399976, 405998, 410570, 410571, 410572, 410573, 410642, 410643, 410644, 410645, 410646, 410724, 410725, 410726, 410727, 410728, 410729, 410782 or 410783.

In certain embodiments, a target region is nucleotides 26118-26141 of SEQ ID NO: 2. In certain embodiments, an antisense compound is targeted to nucleotides 26118-26141 of SEQ ID NO: 2. In certain embodiments, an antisense compound targeted to a PCSK9 nucleic acid comprises a nucleotide sequence selected from SEQ ID NOs: 424, 425, 426, 427 or 428. In certain such embodiments, an antisense compound targeted to nucleotides 26118-26141 of SEQ ID NO: 2 is selected from ISIS NOs: 405998, 410570, 410571, 410572, 410573, 410642, 410643, 410644, 410645, 410646, 410725, 410726, 410727, 410728 or 410729.

In certain embodiments, a target region is nucleotides 26120-26141 of SEQ ID NO: 2. In certain embodiments, an antisense compound is targeted to nucleotides 26120-26141 of SEQ ID NO: 2. In certain embodiments, an antisense compound targeted to a PCSK9 nucleic acid comprises a nucleotide sequence selected from SEQ ID NOs: 426, 427 or 428. In certain such embodiments, an antisense compound targeted to nucleotides 26120-26141 of SEQ ID NO: 2 is selected from ISIS NOs: 405998, 410572, 410573, 410644, 410645, 410646, 410727, 410728 or 410729.

In certain embodiments, a target region is nucleotides 26132-26151 of SEQ ID NO: 2. In certain embodiments, an antisense compound is targeted to nucleotides 26132-26151 of SEQ ID NO: 2. In certain embodiments, an antisense compound targeted to a PCSK9 nucleic acid comprises a nucleotide sequence selected from SEQ ID NOs: 429. In certain such embodiments, an antisense compound targeted to nucleotides 26132-26151 of SEQ ID NO: 2 is selected from ISIS NOs: 410782.

In certain embodiments, a target region is nucleotides 26142-26161 of SEQ ID NO: 2. In certain embodiments, an antisense compound is targeted to nucleotides 26142-26161 of SEQ ID NO: 2. In certain embodiments, an antisense compound targeted to a PCSK9 nucleic acid comprises a nucleotide sequence selected from SEQ ID NOs: 430. In certain such embodiments, an antisense compound targeted to nucleotides 26142-26161 of SEQ ID NO: 2 is selected from ISIS NOs: 410783.

In certain embodiments, a target region is nucleotides 26217-26241 of SEQ ID NO: 2. In certain embodiments, an antisense compound is targeted to nucleotides 26217-26241 of SEQ ID NO: 2. In certain embodiments, an antisense compound targeted to a PCSK9 nucleic acid comprises a nucleotide sequence selected from SEQ ID NOs: 63 or 154. In certain such embodiments, an antisense compound targeted to nucleotides 26217-26241 of SEQ ID NO: 2 is selected from ISIS NOs: 395188, 399818 or 399910.

In certain embodiments, a target region is nucleotides 26311-26335 of SEQ ID NO: 2. In certain embodiments, an antisense compound is targeted to nucleotides 26311-26335 of SEQ ID NO: 2. In certain embodiments, an antisense compound targeted to a PCSK9 nucleic acid comprises a nucleotide sequence selected from SEQ ID NOs: 64 or 65. In certain such embodiments, an antisense compound targeted to nucleotides 26311-26335 of SEQ ID NO: 2 is selected from ISIS NOs: 395189, 399819, 399911 or 399975.

In certain embodiments, a target region is nucleotides 26389-26432 of SEQ ID NO: 2. In certain embodiments, an antisense compound is targeted to nucleotides 26389-26432 of SEQ ID NO: 2. In certain embodiments, an antisense compound targeted to a PCSK9 nucleic acid comprises a nucleotide sequence selected from SEQ ID NOs: 66, 67 or 122. In certain such embodiments, an antisense compound targeted to nucleotides 26389-26432 of SEQ ID NO: 2 is selected from ISIS NOs: 395190, 395191, 399820, 399912, 399913 or 399976.

In certain embodiments, a target region is nucleotides 26456-26576 of SEQ ID NO: 2. In certain embodiments, an antisense compound is targeted to nucleotides 26456-26576 of SEQ ID NO: 2. In certain embodiments, an antisense compound targeted to a PCSK9 nucleic acid comprises a nucleotide sequence selected from SEQ ID NOs: 68 or 153. In certain such embodiments, an antisense compound targeted to nucleotides 26456-26576 of SEQ ID NO: 2 is selected from ISIS NOs: 395192, 395193, 399914 or 399915.

In certain embodiments, a target region is nucleotides 26635-26662 of SEQ ID NO: 2. In certain embodiments, an antisense compound is targeted to nucleotides 26635-26662 of SEQ ID NO: 2. In certain embodiments, an antisense compound targeted to a PCSK9 nucleic acid comprises a nucleotide sequence selected from SEQ ID NOs: 69, 431, 432, 433, 434, 435, 436, 437 or 438. In certain such embodiments, an antisense compound targeted to nucleotides 26635-26662 of SEQ ID NO: 2 is selected from ISIS NOs: 395194, 399916, 405893, 405894, 405895, 405896, 405897, 405898, 405899 or 405900.

In certain embodiments, a target region is nucleotides 26707-26734 of SEQ ID NO: 2. In certain embodiments, an antisense compound is targeted to nucleotides 26707-26734 of SEQ ID NO: 2. In certain embodiments, an antisense compound targeted to a PCSK9 nucleic acid comprises a nucleotide sequence selected from SEQ ID NOs: 70, 71, 439, 440, 441, 442, 443 or 444. In certain such embodiments, an antisense compound targeted to nucleotides 26707-26734 of SEQ ID NO: 2 is selected from ISIS NOs: 395195, 399821, 399917, 399977, 405901, 405902, 405903, 405904, 405905 or 405906.

In certain embodiments, a target region is nucleotides 26707-26736 of SEQ ID NO: 2. In certain embodiments, an antisense compound is targeted to nucleotides 26707-26736 of SEQ ID NO: 2. In certain embodiments, an antisense compound targeted to a PCSK9 nucleic acid comprises a nucleotide sequence selected from SEQ ID NOs: 70, 71, 439, 440, 441, 442, 443, 444, 445 or 446. In certain such embodiments, an antisense compound targeted to nucleotides 26707-26736 of SEQ ID NO: 2 is selected from ISIS NOs: 395195, 399821, 399917, 399977, 405901, 405902, 405903, 405904, 405905, 405906, 405907 or 405908.

In certain embodiments, a target region is nucleotides 26790-26820 of SEQ ID NO: 2. In certain embodiments, an antisense compound is targeted to nucleotides 26790-26820 of SEQ ID NO: 2. In certain embodiments, an antisense compound targeted to a PCSK9 nucleic acid comprises a nucleotide sequence selected from SEQ ID NOs: 72, 73 or 135. In certain such embodiments, an antisense compound targeted to nucleotides 26790-26820 of SEQ ID NO: 2 is selected from ISIS NOs: 395196, 399822, 399823, 399918, 399978 or 399979.

In certain embodiments, a target region is nucleotides 27034-27263 of SEQ ID NO: 2. In certain embodiments, an antisense compound is targeted to nucleotides 27034-27263 of SEQ ID NO: 2. In certain embodiments, an antisense compound targeted to a PCSK9 nucleic acid comprises a nucleotide sequence selected from SEQ ID NOs: 74, 75 or 112. In certain such embodiments, an antisense compound targeted to nucleotides 27034-27263 of SEQ ID NO: 2 is selected from ISIS NOs: 395197, 395198, 399824, 399919, 399920 or 399980.

In certain embodiments, a target region is nucleotides 27279-27303 of SEQ ID NO: 2. In certain embodiments, an antisense compound is targeted to nucleotides 27279-27303 of SEQ ID NO: 2. In certain embodiments, an antisense compound targeted to a PCSK9 nucleic acid comprises a nucleotide sequence selected from SEQ ID NOs: 76 or 77. In certain such embodiments, an antisense compound targeted to nucleotides 27279-27303 of SEQ ID NO: 2 is selected from ISIS NOs: 395199, 399825, 399921 or 399981.

In certain embodiments, a target region is nucleotides 27350-27376 of SEQ ID NO: 2. In certain embodiments, an antisense compound is targeted to nucleotides 27350-27376 of SEQ ID NO: 2. In certain embodiments, an antisense compound targeted to a PCSK9 nucleic acid comprises a nucleotide sequence selected from SEQ ID NOs: 78 or 99. In certain such embodiments, an antisense compound targeted to nucleotides 27350-27376 of SEQ ID NO: 2 is selected from ISIS NOs: 395200, 399826, 399922 or 399982.

In certain embodiments, antisense compounds target a PCSK9 nucleic acid having the sequence of GENBANK® Accession No. AK124635.1, first deposited with GENBANK® on Sep. 8, 2003, and incorporated herein as SEQ ID NO: 3. In certain such embodiments, an antisense oligonucleotide is targeted to SEQ ID NO: 3. In certain such embodiments, an antisense oligonucleotide that is targeted to SEQ ID NO: 3 is at least 90% complementary to SEQ ID NO: 1. In certain such embodiments, an antisense oligonucleotide that is targeted to SEQ ID NO: 3 is at least 95% complementary to SEQ ID NO: 3. In certain such embodiments, an antisense oligonucleotide that is targeted to SEQ ID NO: 3 is 100% complementary to SEQ ID NO: 3. In certain such embodiments, an antisense oligonucleotide comprises a nucleotide sequence selected from a nucleotide sequence set forth in Table 12.

TABLE 12

Nucleotide sequences targeted to AK124635.1 (SEQ ID NO: 3)

| SEQ ID NO | 5' Target Site on SEQ ID NO: 3 | 3' Target Site on SEQ ID NO: 3 | Sequences (5'-3') |
|---|---|---|---|
| 85 | 155 | 174 | ACAAATTCCCAGACTCAGCA |
| 100 | 220 | 239 | ATCTCAGGACAGGTGAGCAA |
| 116 | 234 | 253 | GAGTAGAGATTCTCATCTCA |
| 129 | 290 | 309 | GTGCCATCTGAACAGCACCT |
| 117 | 302 | 321 | GAGTCTTCTGAAGTGCCATC |
| 81 | 377 | 396 | AAGCAGGGCCTCAGGTGGAA |
| 110 | 400 | 419 | CCTGGAACCCTGCAGCCAG |
| 152 | 451 | 470 | TTCAGGCAGGTTGCTGCTAG |
| 83 | 460 | 479 | AAGGAAGACTTCAGGCAGGT |
| 140 | 472 | 491 | TCAGCCAGGCCAAAGGAAGA |
| 137 | 586 | 605 | TAGGGAGAGCTCACAGATGC |
| 136 | 596 | 615 | TAGGAGAAAGTAGGGAGAGC |
| 132 | 653 | 672 | TAAAAGCTGCAAGAGACTCA |
| 139 | 741 | 760 | TCAGAGAAAACAGTCACCGA |
| 92 | 871 | 890 | AGAGACAGGAAGCTGCAGCT |
| 142 | 878 | 897 | TCATTTTAGAGACAGGAAGC |
| 113 | 915 | 934 | GAATAACAGTGATGTCTGGC |
| 138 | 968 | 987 | TCACAGCTCACCGAGTCTGC |
| 98 | 998 | 1017 | AGTGTAAAATAAAGCCCCTA |

TABLE 12-continued

Nucleotide sequences targeted to AK124635.1 (SEQ ID NO: 3)

| SEQ ID NO | 5' Target Site on SEQ ID NO: 3 | 3' Target Site on SEQ ID NO: 3 | Sequences (5'-3') |
|---|---|---|---|
| 96 | 1075 | 1094 | AGGACCCAAGTCATCCTGCT |
| 124 | 1105 | 1124 | GGCCATCAGCTGGCAATGCT |
| 82 | 1144 | 1163 | AAGGAAAGGGAGGCCTAGAG |
| 133 | 1149 | 1168 | TAGACAAGGAAAGGGAGGCC |
| 103 | 1155 | 1174 | ATTTCATAGACAAGGAAAGG |
| 155 | 1275 | 1294 | CTTATAGTTAACACACAGAA |
| 156 | 1283 | 1302 | AAGTCAACCTTATAGTTAAC |
| 146 | 1315 | 1334 | TGACATTTGTGGGAGAGGAG |
| 161 | 1322 | 1341 | TCCAAGGTGACATTTGTGGG |
| 215 | 1351 | 1370 | ATACACCTCCACCAGGCTGC |
| 216 | 1362 | 1381 | GTGTCTAGGAGATACACCTC |
| 19 | 1365 | 1384 | CTGGTGTCTAGGAGATACAC |
| 217 | 1367 | 1386 | TGCTGGTGTCTAGGAGATAC |
| 20 | 1370 | 1389 | GTATGCTGGTGTCTAGGAGA |
| 21 | 1390 | 1409 | GATTTCCCGGTGGTCACTCT |
| 218 | 1392 | 1411 | TCGATTTCCCGGTGGTCACT |
| 219 | 1393 | 1412 | CTCGATTTCCCGGTGGTCAC |
| 220 | 1394 | 1413 | CCTCGATTTCCCGGTGGTCA |
| 221 | 1395 | 1414 | CCCTCGATTTCCCGGTGGTC |
| 22 | 1396 | 1415 | GCCCTCGATTTCCCGGTGGT |
| 222 | 1397 | 1416 | TGCCCTCGATTTCCCGGTGG |
| 223 | 1398 | 1417 | CTGCCCTCGATTTCCCGGTG |
| 224 | 1399 | 1418 | CCTGCCCTCGATTTCCCGGT |
| 225 | 1400 | 1419 | CCCTGCCCTCGATTTCCCGG |
| 226 | 1404 | 1423 | ATGACCCTGCCCTCGATTTC |
| 227 | 1406 | 1425 | CCATGACCCTGCCCTCGATT |
| 228 | 1408 | 1427 | GACCATGACCCTGCCCTCGA |
| 23 | 1410 | 1429 | GTGACCATGACCCTGCCCTC |
| 229 | 1412 | 1431 | CGGTGACCATGACCCTGCCC |
| 230 | 1414 | 1433 | GTCGGTGACCATGACCCTGC |
| 231 | 1416 | 1435 | AAGTCGGTGACCATGACCCT |
| 232 | 1418 | 1437 | CGAAGTCGGTGACCATGACC |
| 24 | 1420 | 1439 | CTCGAAGTCGGTGACCATGA |
| 233 | 1428 | 1447 | GGCACATTCTCGAAGTCGGT |
| 25 | 1453 | 1472 | GTGGAAGCGGGTCCCGTCCT |
| 234 | 1463 | 1482 | TGGCCTGTCTGTGGAAGCGG |

TABLE 12-continued

Nucleotide sequences targeted to AK124635.1
(SEQ ID NO: 3)

| SEQ ID NO | 5' Target Site on SEQ ID NO: 3 | 3' Target Site on SEQ ID NO: 3 | Sequences (5'-3') |
|---|---|---|---|
| 235 | 1490 | 1509 | GGTGGGTGCCATGACTGTCA |
| 236 | 1493 | 1512 | CCAGGTGGGTGCCATGACTG |
| 237 | 1497 | 1516 | CCTGCCAGGTGGGTGCCATG |
| 26 | 1500 | 1519 | ACCCCTGCCAGGTGGGTGCC |
| 238 | 1502 | 1521 | CCACCCCTGCCAGGTGGGTG |
| 27 | 1505 | 1524 | TGACCACCCCTGCCAGGTGG |
| 239 | 1507 | 1526 | GCTGACCACCCCTGCCAGGT |
| 240 | 1515 | 1534 | TCCCGGCCGCTGACCACCCC |
| 241 | 1519 | 1538 | GGCATCCCGGCCGCTGACCA |
| 242 | 1522 | 1541 | GCCGGCATCCCGGCCGCTGA |
| 243 | 1527 | 1546 | GCCACGCCGGCATCCCGGCC |
| 244 | 1528 | 1547 | GGCCACGCCGGCATCCCGGC |
| 245 | 1529 | 1548 | TGGCCACGCCGGCATCCCGG |
| 246 | 1530 | 1549 | TTGGCCACGCCGGCATCCCG |
| 247 | 1531 | 1550 | CTTGGCCACGCCGGCATCCC |
| 248 | 1532 | 1551 | CCTTGGCCACGCCGGCATCC |
| 249 | 1533 | 1552 | CCCTTGGCCACGCCGGCATC |
| 28 | 1534 | 1553 | ACCCTTGGCCACGCCGGCAT |
| 447 | 1534 | 1553 | ACCCTTGGTCACGCCGGCAT |
| 250 | 1535 | 1554 | CACCCTTGGCCACGCCGGCA |
| 251 | 1536 | 1555 | GCACCCTTGGCCACGCCGGC |
| 252 | 1537 | 1556 | GGCACCCTTGGCCACGCCGG |
| 253 | 1538 | 1557 | TGGCACCCTTGGCCACGCCG |
| 254 | 1539 | 1558 | CTGGCACCCTTGGCCACGCC |
| 255 | 1540 | 1559 | GCTGGCACCCTTGGCCACGC |
| 256 | 1545 | 1564 | CGCATGCTGGCACCCTTGGC |
| 257 | 1566 | 1585 | CAGTTGAGCACGCGCAGGCT |
| 258 | 1568 | 1587 | GGCAGTTGAGCACGCGCAGG |
| 29 | 1570 | 1589 | TTGGCAGTTGAGCACGCGCA |
| 259 | 1572 | 1591 | CCTTGGCAGTTGAGCACGCG |
| 30 | 1575 | 1594 | TTCCCTTGGCAGTTGAGCAC |
| 260 | 1577 | 1596 | CCTTCCCTTGGCAGTTGAGC |
| 261 | 1581 | 1600 | GTGCCCTTCCCTTGGCAGTT |
| 262 | 1583 | 1602 | CCGTGCCCTTCCCTTGGCAG |
| 263 | 1594 | 1613 | GGTGCCGCTAACCGTGCCCT |
| 264 | 1606 | 1625 | CAGGCCTATGAGGGTGCCGC |
| 31 | 1607 | 1626 | CCAGGCCTATGAGGGTGCCG |
| 458 | 1609 | 1622 | GCCTATGAGGGTGC |
| 459 | 1614 | 1627 | TCCAGGCCTATGAG |
| 265 | 1618 | 1637 | CCGAATAAACTCCAGGCCTA |
| 266 | 1626 | 1645 | TGGCTTTTCCGAATAAACTC |
| 32 | 1628 | 1647 | GCTGGCTTTTCCGAATAAAC |
| 267 | 1630 | 1649 | CAGCTGGCTTTTCCGAATAA |
| 268 | 1632 | 1651 | ACCAGCTGGCTTTTCCGAAT |
| 269 | 1634 | 1653 | GGACCAGCTGGCTTTTCCGA |
| 270 | 1638 | 1657 | GGCTGGACCAGCTGGCTTTT |
| 271 | 1649 | 1668 | GTGGCCCCACAGGCTGGACC |
| 272 | 1662 | 1681 | AGCAGCACCACCAGTGGCCC |
| 273 | 1684 | 1703 | GCTGTACCCACCCGCCAGGG |
| 274 | 1730 | 1749 | CGACCCCAGCCCTCGCCAGG |
| 33 | 1740 | 1759 | GTGACCAGCACGACCCCAGC |
| 275 | 1742 | 1761 | CGGTGACCAGCACGACCCCA |
| 276 | 1744 | 1763 | AGCGGTGACCAGCACGACCC |
| 277 | 1746 | 1765 | GCAGCGGTGACCAGCACGAC |
| 278 | 1748 | 1767 | CGGCAGCGGTGACCAGCACG |
| 279 | 1749 | 1768 | CCGGCAGCGGTGACCAGCAC |
| 280 | 1752 | 1771 | TTGCCGGCAGCGGTGACCAG |
| 281 | 1754 | 1773 | AGTTGCCGGCAGCGGTGACC |
| 282 | 1756 | 1775 | GAAGTTGCCGGCAGCGGTGA |
| 283 | 1758 | 1777 | CGGAAGTTGCCGGCAGCGGT |
| 284 | 1760 | 1779 | CCCGGAAGTTGCCGGCAGCG |
| 285 | 1762 | 1781 | GTCCGGAAGTTGCCGGCAG |
| 306 | 1820 | 1839 | GAGGCACCAATGATGTCCTC |
| 39 | 1822 | 1841 | TGGAGGCACCAATGATGTCC |
| 307 | 1824 | 1843 | GCTGGAGGCACCAATGATGT |
| 308 | 1826 | 1845 | TCGCTGGAGGCACCAATGAT |
| 309 | 1828 | 1847 | AGTCGCTGGAGGCACCAATG |
| 310 | 1830 | 1849 | GCAGTCGCTGGAGGCACCAA |
| 40 | 1833 | 1852 | GCTGCAGTCGCTGGAGGCAC |
| 311 | 1835 | 1854 | GTGCTGCAGTCGCTGGAGGC |
| 312 | 1837 | 1856 | AGGTGCTGCAGTCGCTGGAG |
| 313 | 1839 | 1858 | GCAGGTGCTGCAGTCGCTGG |

TABLE 12-continued

Nucleotide sequences targeted to AK124635.1 (SEQ ID NO: 3)

| SEQ ID NO | 5' Target Site on SEQ ID NO: 3 | 3' Target Site on SEQ ID NO: 3 | Sequences (5'-3') |
|---|---|---|---|
| 314 | 1840 | 1859 | AGCAGGTGCTGCAGTCGCTG |
| 315 | 1842 | 1861 | AAAGCAGGTGCTGCAGTCGC |
| 41 | 1844 | 1863 | ACAAAGCAGGTGCTGCAGTC |
| 316 | 1846 | 1865 | ACACAAAGCAGGTGCTGCAG |
| 317 | 1848 | 1867 | TGACACAAAGCAGGTGCTGC |
| 318 | 1858 | 1877 | TCCCACTCTGTGACACAAAG |
| 101 | 1898 | 1917 | ATGGCTGCAATGCCAGCCAC |
| 319 | 1900 | 1919 | TCATGGCTGCAATGCCAGCC |
| 42 | 1903 | 1922 | GCATCATGGCTGCAATGCCA |
| 320 | 1905 | 1924 | CAGCATCATGGCTGCAATGC |
| 321 | 1907 | 1926 | GACAGCATCATGGCTGCAAT |
| 322 | 1909 | 1928 | CAGACAGCATCATGGCTGCA |
| 43 | 1911 | 1930 | GGCAGACAGCATCATGGCTG |
| 323 | 1913 | 1932 | TCGGCAGACAGCATCATGGC |
| 324 | 1915 | 1934 | GCTCGGCAGACAGCATCATG |
| 325 | 1917 | 1936 | CGGCTCGGCAGACAGCATCA |
| 326 | 1919 | 1938 | TCCGGCTCGGCAGACAGCAT |
| 327 | 1933 | 1952 | CGGCCAGGGTGAGCTCCGGC |
| 328 | 1946 | 1965 | CTCTGCCTCAACTCGGCCAG |
| 329 | 1948 | 1967 | GTCTCTGCCTCAACTCGGCC |
| 330 | 1950 | 1969 | CAGTCTCTGCCTCAACTCGG |
| 331 | 1952 | 1971 | ATCAGTCTCTGCCTCAACTC |
| 332 | 1954 | 1973 | GGATCAGTCTCTGCCTCAAC |
| 333 | 1956 | 1975 | GTGGATCAGTCTCTGCCTCA |
| 334 | 1958 | 1977 | AAGTGGATCAGTCTCTGCCT |
| 44 | 1959 | 1978 | GAAGTGGATCAGTCTCTGCC |
| 335 | 1961 | 1980 | GAGAAGTGGATCAGTCTCTG |
| 336 | 1963 | 1982 | CAGAGAAGTGGATCAGTCTC |
| 337 | 1965 | 1984 | GGCAGAGAAGTGGATCAGTC |
| 45 | 1967 | 1986 | TTGGCAGAGAAGTGGATCAG |
| 338 | 1969 | 1988 | CTTTGGCAGAGAAGTGGATC |
| 46 | 1972 | 1991 | CATCTTTGGCAGAGAAGTGG |
| 339 | 1974 | 1993 | GACATCTTTGGCAGAGAAGT |
| 340 | 1976 | 1995 | ATGACATCTTTGGCAGAGAA |
| 47 | 1978 | 1997 | TGATGACATCTTTGGCAGAG |
| 341 | 1980 | 1999 | ATTGATGACATCTTTGGCAG |
| 342 | 1982 | 2001 | TCATTGATGACATCTTTGGC |
| 48 | 1985 | 2004 | GCCTCATTGATGACATCTTT |
| 343 | 1987 | 2006 | AGGCCTCATTGATGACATCT |
| 344 | 1989 | 2008 | CCAGGCCTCATTGATGACAT |
| 345 | 1991 | 2010 | AACCAGGCCTCATTGATGAC |
| 346 | 1993 | 2012 | GGAACCAGGCCTCATTGATG |
| 347 | 1994 | 2013 | GGGAACCAGGCCTCATTGAT |
| 348 | 1995 | 2014 | AGGGAACCAGGCCTCATTGA |
| 349 | 1996 | 2015 | CAGGGAACCAGGCCTCATTG |
| 49 | 1997 | 2016 | TCAGGGAACCAGGCCTCATT |
| 350 | 1998 | 2017 | CTCAGGGAACCAGGCCTCAT |
| 351 | 1999 | 2018 | CCTCAGGGAACCAGGCCTCA |
| 352 | 2000 | 2019 | TCCTCAGGGAACCAGGCCTC |
| 353 | 2001 | 2020 | GTCCTCAGGGAACCAGGCCT |
| 50 | 2002 | 2021 | GGTCCTCAGGGAACCAGGCC |
| 354 | 2003 | 2022 | TGGTCCTCAGGGAACCAGGC |
| 355 | 2004 | 2023 | CTGGTCCTCAGGGAACCAGG |
| 356 | 2005 | 2024 | GCTGGTCCTCAGGGAACCAG |
| 357 | 2006 | 2025 | CGCTGGTCCTCAGGGAACCA |
| 87 | 2009 | 2028 | ACCCGCTGGTCCTCAGGGAA |
| 358 | 2011 | 2030 | GTACCCGCTGGTCCTCAGGG |
| 359 | 2013 | 2032 | CAGTACCCGCTGGTCCTCAG |
| 51 | 2016 | 2035 | GGTCAGTACCCGCTGGTCCT |
| 119 | 2038 | 2057 | GCAGGGCGGCCACCAGGTTG |
| 360 | 2061 | 2080 | ACCTGCCCCATGGGTGCTGG |
| 52 | 2073 | 2092 | AAACAGCTGCCAACCTGCCC |
| 361 | 2075 | 2094 | CAAAACAGCTGCCAACCTGC |
| 53 | 2078 | 2097 | CTGCAAAACAGCTGCCAACC |
| 362 | 2080 | 2099 | TCCTGCAAAACAGCTGCCAA |
| 363 | 2082 | 2101 | AGTCCTGCAAAACAGCTGCC |
| 104 | 2085 | 2104 | CACAGTCCTGCAAAACAGCT |
| 130 | 2095 | 2114 | GTGCTGACCACACAGTCCTG |
| 365 | 2105 | 2124 | GGCCCGAGTGTGCTGACCA |
| 54 | 2108 | 2127 | GTAGGCCCCGAGTGTGCTGA |
| 366 | 2110 | 2129 | GTGTAGGCCCCGAGTGTGCT |
| 367 | 2112 | 2131 | CCGTGTAGGCCCCGAGTGTG |

TABLE 12-continued

Nucleotide sequences targeted to AK124635.1 (SEQ ID NO: 3)

| SEQ ID NO | 5' Target Site on SEQ ID NO: 3 | 3' Target Site on SEQ ID NO: 3 | Sequences (5'-3') |
|---|---|---|---|
| 368 | 2114 | 2133 | ATCCGTGTAGGCCCCGAGTG |
| 369 | 2116 | 2135 | CCATCCGTGTAGGCCCCGAG |
| 370 | 2118 | 2137 | GGCCATCCGTGTAGGCCCG |
| 371 | 2120 | 2139 | GTGGCCATCCGTGTAGGCCC |
| 372 | 2168 | 2187 | CTGGAGCAGCTCAGCAGCTC |
| 460 | 2168 | 2181 | CAGCTCAGCAGCTC |
| 373 | 2170 | 2189 | AACTGGAGCAGCTCAGCAGC |
| 55 | 2173 | 2192 | AGAAACTGGAGCAGCTCAGC |
| 374 | 2175 | 2194 | GGAGAAACTGGAGCAGCTCA |
| 375 | 2177 | 2196 | CTGGAGAAACTGGAGCAGCT |
| 56 | 2179 | 2198 | TCCTGGAGAAACTGGAGCAG |
| 408 | 2245 | 2264 | GTGCCAAGGTCCTCCACCTC |
| 409 | 2265 | 2284 | TCAGCACAGGCGGTTGTGG |
| 410 | 2295 | 2314 | CCACGCACTGGTTGGGCTGA |
| 60 | 2355 | 2374 | CTTTGCATTCCAGACCTGGG |
| 411 | 2356 | 2375 | ACTTTGCATTCCAGACCTGG |
| 412 | 2357 | 2376 | GACTTTGCATTCCAGACCTG |
| 413 | 2358 | 2377 | TGACTTTGCATTCCAGACCT |
| 414 | 2359 | 2378 | TTGACTTTGCATTCCAGACC |
| 61 | 2360 | 2379 | CTTGACTTTGCATTCCAGAC |
| 415 | 2362 | 2381 | TCCTTGACTTTGCATTCCAG |
| 416 | 2375 | 2394 | CGGGATTCCATGCTCCTTGA |
| 417 | 2405 | 2424 | GCAGGCCACGGTCACCTGCT |
| 418 | 2442 | 2461 | GGAGGGCACTGCAGCCAGTC |
| 419 | 2560 | 2579 | CAGATGGCAACGGCTGTCAC |
| 420 | 2561 | 2580 | GCAGATGGCAACGGCTGTCA |
| 421 | 2562 | 2581 | AGCAGATGGCAACGGCTGTC |
| 422 | 2563 | 2582 | CAGCAGATGGCAACGGCTGT |
| 423 | 2564 | 2583 | GCAGCAGATGGCAACGGCTG |
| 62 | 2565 | 2584 | GGCAGCAGATGGCAACGGCT |
| 424 | 2566 | 2585 | CGGCAGCAGATGGCAACGGC |
| 425 | 2567 | 2586 | CCGGCAGCAGATGGCAACGG |
| 426 | 2568 | 2587 | TCCGGCAGCAGATGGCAACG |
| 427 | 2569 | 2588 | CTCCGGCAGCAGATGGCAAC |
| 428 | 2570 | 2589 | GCTCCGGCAGCAGATGGCAA |
| 429 | 2580 | 2599 | CCAGGTGCCGGCTCCGGCAG |
| 430 | 2590 | 2609 | GAGGCCTGCGCCAGGTGCCG |
| 154 | 2665 | 2684 | TTTTAAAGCTCAGCCCCAGC |
| 63 | 2670 | 2689 | AACCATTTTAAAGCTCAGCC |
| 64 | 2759 | 2778 | TCAAGGGCCAGGCCAGCAGC |
| 65 | 2764 | 2783 | CCCACTCAAGGGCCAGGCCA |
| 122 | 2837 | 2856 | GGAGGGAGCTTCCTGGCACC |
| 66 | 2852 | 2871 | ATGCCCCACAGTGAGGGAGG |
| 67 | 2861 | 2880 | AATGGTGAAATGCCCCACAG |
| 153 | 2904 | 2923 | TTGGGAGCAGCTGGCAGCAC |
| 68 | 3005 | 3024 | CATGGGAAGAATCCTGCCTC |
| 431 | 3083 | 3102 | ATGAGGGCCATCAGCACCTT |
| 432 | 3084 | 3103 | GATGAGGGCCATCAGCACCT |
| 433 | 3085 | 3104 | AGATGAGGGCCATCAGCACC |
| 434 | 3086 | 3105 | GAGATGAGGGCCATCAGCAC |
| 69 | 3087 | 3106 | GGAGATGAGGGCCATCAGCA |
| 435 | 3088 | 3107 | TGGAGATGAGGGCCATCAGC |
| 436 | 3089 | 3108 | CTGGAGATGAGGGCCATCAG |
| 437 | 3090 | 3109 | GCTGGAGATGAGGGCCATCA |
| 438 | 3091 | 3110 | AGCTGGAGATGAGGGCCATC |
| 461 | 3132 | 3145 | TTAATCAGGGAGCC |
| 70 | 3155 | 3174 | TAGATGCCATCCAGAAAGCT |
| 439 | 3157 | 3176 | GCTAGATGCCATCCAGAAAG |
| 440 | 3158 | 3177 | GGCTAGATGCCATCCAGAAA |
| 441 | 3159 | 3178 | TGGCTAGATGCCATCCAGAA |
| 442 | 3160 | 3179 | CTGGCTAGATGCCATCCAGA |
| 71 | 3161 | 3180 | TCTGGCTAGATGCCATCCAG |
| 443 | 3162 | 3181 | CTCTGGCTAGATGCCATCCA |
| 444 | 3163 | 3182 | CCTCTGGCTAGATGCCATCC |
| 445 | 3164 | 3183 | GCCTCTGGCTAGATGCCATC |
| 446 | 3165 | 3184 | AGCCTCTGGCTAGATGCCAT |

TABLE 12-continued

Nucleotide sequences targeted to AK124635.1 (SEQ ID NO: 3)

| SEQ ID NO | 5' Target Site on SEQ ID NO: 3 | 3' Target Site on SEQ ID NO: 3 | Sequences (5'-3') |
|---|---|---|---|
| 72 | 3238 | 3257 | GGCATAGAGCAGAGTAAAGG |
| 73 | 3243 | 3262 | AGCCTGGCATAGAGCAGAGT |
| 135 | 3249 | 3268 | TAGCACAGCCTGGCATAGAG |
| 112 | 3482 | 3501 | GAAGAGGCTTGGCTTCAGAG |
| 74 | 3488 | 3507 | AAGTAAGAAGAGGCTTGGCT |
| 75 | 3692 | 3711 | GCTCAAGGAGGGACAGTTGT |
| 76 | 3727 | 3746 | AAAGATAAATGTCTGCTTGC |
| 77 | 3732 | 3751 | ACCCAAAAGATAAATGTCTG |
| 78 | 3798 | 3817 | TCTTCAAGTTACAAAAGCAA |
| 99 | 3805 | 3824 | ATAAATATCTTCAAGTTACA |

In certain embodiments, gapmer antisense compounds are targeted to a PCSK9 nucleic acid. In certain such embodiments, gapmer antisense compounds are targeted to SEQ ID NO: 3. In certain such embodiments, the nucleotide sequences illustrated in Table 12 have a 5-10-5 gapmer motif. Table 13 illustrates gapmer antisense compounds targeted to SEQ ID NO: 3, having a 5-10-5 motif, where the gap segment comprises 2'-deoxynucleotides and each wing segment comprises nucleotides comprising a 2'-O-methoxyethyl sugar modification. Internucleoside linkages are phosphorthioate, and cytidines are 5-methylcytidines.

TABLE 13

Gapmer antisense compounds having a 5-10-5 motif targeted to SEQ ID NO: 3

| Isis No | Motif | SEQ ID NO | 5' Target Site on SEQ ID NO: 3 | 3' Target Site on SEQ ID NO: 3 | Mismatches | Sequence (5'-3') |
|---|---|---|---|---|---|---|
| 395201 | 5-10-5 | 85 | 155 | 174 | 0 | ACAAATTCCCAGACTCAGCA |
| 399827 | 5-10-5 | 100 | 220 | 239 | 0 | ATCTCAGGACAGGTGAGCAA |
| 399828 | 5-10-5 | 116 | 234 | 253 | 0 | GAGTAGAGATTCTCATCTCA |
| 395202 | 5-10-5 | 129 | 290 | 309 | 0 | GTGCCATCTGAACAGCACCT |
| 399829 | 5-10-5 | 117 | 302 | 321 | 0 | GAGTCTTCTGAAGTGCCATC |
| 399830 | 5-10-5 | 81 | 377 | 396 | 0 | AAGCAGGGCCTCAGGTGGAA |
| 395203 | 5-10-5 | 110 | 400 | 419 | 0 | CCTGGAACCCCTGCAGCCAG |
| 395204 | 5-10-5 | 152 | 451 | 470 | 0 | TTCAGGCAGGTTGCTGCTAG |
| 399831 | 5-10-5 | 83 | 460 | 479 | 0 | AAGGAAGACTTCAGGCAGGT |
| 395205 | 5-10-5 | 140 | 472 | 491 | 0 | TCAGCCAGGCCAAAGGAAGA |
| 399832 | 5-10-5 | 137 | 586 | 605 | 0 | TAGGGAGAGCTCACAGATGC |
| 395206 | 5-10-5 | 136 | 596 | 615 | 0 | TAGGAGAAAGTAGGGAGAGC |
| 395207 | 5-10-5 | 132 | 653 | 672 | 0 | TAAAAGCTGCAAGAGACTCA |
| 395208 | 5-10-5 | 139 | 741 | 760 | 0 | TCAGAGAAAACAGTCACCGA |
| 399833 | 5-10-5 | 92 | 871 | 890 | 0 | AGAGACAGGAAGCTGCAGCT |
| 395209 | 5-10-5 | 142 | 878 | 897 | 0 | TCATTTTAGAGACAGGAAGC |
| 395210 | 5-10-5 | 113 | 915 | 934 | 0 | GAATAACAGTGATGTCTGGC |
| 395211 | 5-10-5 | 138 | 968 | 987 | 0 | TCACAGCTCACCGAGTCTGC |
| 395212 | 5-10-5 | 98 | 998 | 1017 | 0 | AGTGTAAAATAAAGCCCCTA |
| 395213 | 5-10-5 | 96 | 1075 | 1094 | 0 | AGGACCCAAGTCATCCTGCT |
| 395214 | 5-10-5 | 124 | 1105 | 1124 | 0 | GGCCATCAGCTGGCAATGCT |
| 399834 | 5-10-5 | 82 | 1144 | 1163 | 0 | AAGGAAGGGAGGCCTAGAG |

TABLE 13-continued

Gapmer antisense compounds having a 5-10-5 motif targeted to SEQ ID NO: 3

| Isis No | Motif | SEQ ID NO | 5' Target Site on SEQ ID NO: 3 | 3' Target Site on SEQ ID NO: 3 | Mismatches | Sequence (5'-3') |
|---|---|---|---|---|---|---|
| 395215 | 5-10-5 | 133 | 1149 | 1168 | 0 | TAGACAAGGAAAGGGAGGCC |
| 395216 | 5-10-5 | 103 | 1155 | 1174 | 0 | ATTTCATAGACAAGGAAAGG |
| 395217 | 5-10-5 | 155 | 1275 | 1294 | 0 | CTTATAGTTAACACACAGAA |
| 399835 | 5-10-5 | 156 | 1283 | 1302 | 0 | AAGTCAACCTTATAGTTAAC |
| 395218 | 5-10-5 | 146 | 1315 | 1334 | 0 | TGACATTTGTGGGAGAGGAG |
| 395219 | 5-10-5 | 161 | 1322 | 1341 | 0 | TCCAAGGTGACATTTGTGGG |
| 395160 | 5-10-5 | 19 | 1365 | 1384 | 0 | CTGGTGTCTAGGAGATACAC |
| 399797 | 5-10-5 | 20 | 1370 | 1389 | 0 | GTATGCTGGTGTCTAGGAGA |
| 395161 | 5-10-5 | 21 | 1390 | 1409 | 0 | GATTTCCCGGTGGTCACTCT |
| 399798 | 5-10-5 | 22 | 1396 | 1415 | 0 | GCCCTCGATTTCCCGGTGGT |
| 399799 | 5-10-5 | 23 | 1410 | 1429 | 0 | GTGACCATGACCCTGCCCTC |
| 395162 | 5-10-5 | 24 | 1420 | 1439 | 0 | CTCGAAGTCGGTGACCATGA |
| 395163 | 5-10-5 | 25 | 1453 | 1472 | 0 | GTGGAAGCGGGTCCCGTCCT |
| 395164 | 5-10-5 | 26 | 1500 | 1519 | 0 | ACCCCTGCCAGGTGGGTGCC |
| 399800 | 5-10-5 | 27 | 1505 | 1524 | 0 | TGACCACCCTGCCAGGTGG |
| 395165 | 5-10-5 | 28 | 1534 | 1553 | 0 | ACCCTTGGCCACGCCGGCAT |
| 395166 | 5-10-5 | 29 | 1570 | 1589 | 0 | TTGGCAGTTGAGCACGCGCA |
| 399801 | 5-10-5 | 30 | 1575 | 1594 | 0 | TTCCCTTGGCAGTTGAGCAC |
| 395167 | 5-10-5 | 31 | 1607 | 1626 | 0 | CCAGGCCTATGAGGGTGCCG |
| 395168 | 5-10-5 | 32 | 1628 | 1647 | 0 | GCTGGCTTTTCCGAATAAAC |
| 395169 | 5-10-5 | 33 | 1740 | 1759 | 0 | GTGACCAGCACGACCCCAGC |
| 395175 | 5-10-5 | 39 | 1822 | 1841 | 0 | TGGAGGCACCAATGATGTCC |
| 399804 | 5-10-5 | 40 | 1833 | 1852 | 0 | GCTGCAGTCGCTGGAGGCAC |
| 399805 | 5-10-5 | 41 | 1844 | 1863 | 0 | ACAAAGCAGGTGCTGCAGTC |
| 395176 | 5-10-5 | 101 | 1898 | 1917 | 0 | ATGGCTGCAATGCCAGCCAC |
| 399806 | 5-10-5 | 42 | 1903 | 1922 | 0 | GCATCATGGCTGCAATGCCA |
| 399807 | 5-10-5 | 43 | 1911 | 1930 | 0 | GGCAGACAGCATCATGGCTG |
| 399808 | 5-10-5 | 44 | 1959 | 1978 | 0 | GAAGTGGATCAGTCTCTGCC |
| 395177 | 5-10-5 | 45 | 1967 | 1986 | 0 | TTGGCAGAGAAGTGGATCAG |
| 399809 | 5-10-5 | 46 | 1972 | 1991 | 0 | CATCTTTGGCAGAGAAGTGG |
| 399810 | 5-10-5 | 47 | 1978 | 1997 | 0 | TGATGACATCTTTGGCAGAG |
| 399811 | 5-10-5 | 48 | 1985 | 2004 | 0 | GCCTCATTGATGACATCTTT |
| 399812 | 5-10-5 | 49 | 1997 | 2016 | 0 | TCAGGGAACCAGGCCTCATT |
| 395178 | 5-10-5 | 50 | 2002 | 2021 | 0 | GGTCCTCAGGGAACCAGGCC |
| 395179 | 5-10-5 | 87 | 2009 | 2028 | 0 | ACCCGCTGGTCCTCAGGGAA |
| 399813 | 5-10-5 | 51 | 2016 | 2035 | 0 | GGTCAGTACCCGCTGGTCCT |

TABLE 13-continued

Gapmer antisense compounds having a 5-10-5 motif targeted to SEQ ID NO: 3

| Isis No | Motif | SEQ ID NO | 5' Target Site on SEQ ID NO: 3 | 3' Target Site on SEQ ID NO: 3 | Mismatches | Sequence (5'-3') |
|---|---|---|---|---|---|---|
| 395180 | 5-10-5 | 119 | 2038 | 2057 | 0 | GCAGGGCGGCCACCAGGTTG |
| 395181 | 5-10-5 | 52 | 2073 | 2092 | 0 | AAACAGCTGCCAACCTGCCC |
| 399814 | 5-10-5 | 53 | 2078 | 2097 | 0 | CTGCAAAACAGCTGCCAACC |
| 395220 | 5-10-5 | 104 | 2085 | 2104 | 0 | CACAGTCCTGCAAAACAGCT |
| 399836 | 5-10-5 | 130 | 2095 | 2114 | 0 | GTGCTGACCACACAGTCCTG |
| 395182 | 5-10-5 | 54 | 2108 | 2127 | 0 | GTAGGCCCCGAGTGTGCTGA |
| 399815 | 5-10-5 | 55 | 2173 | 2192 | 0 | AGAAACTGGAGCAGCTCAGC |
| 399816 | 5-10-5 | 56 | 2179 | 2198 | 0 | TCCTGGAGAAACTGGAGCAG |
| 395186 | 5-10-5 | 60 | 2355 | 2374 | 0 | CTTTGCATTCCAGACCTGGG |
| 399817 | 5-10-5 | 61 | 2360 | 2379 | 0 | CTTGACTTTGCATTCCAGAC |
| 395187 | 5-10-5 | 62 | 2565 | 2584 | 0 | GGCAGCAGATGGCAACGGCT |
| 395188 | 5-10-5 | 154 | 2665 | 2684 | 0 | TTTTAAAGCTCAGCCCCAGC |
| 399818 | 5-10-5 | 63 | 2670 | 2689 | 0 | AACCATTTTAAAGCTCAGCC |
| 395189 | 5-10-5 | 64 | 2759 | 2778 | 0 | TCAAGGGCCAGGCCAGCAGC |
| 399819 | 5-10-5 | 65 | 2764 | 2783 | 0 | CCCACTCAAGGGCCAGGCCA |
| 399820 | 5-10-5 | 122 | 2837 | 2856 | 0 | GGAGGGAGCTTCCTGGCACC |
| 395190 | 5-10-5 | 66 | 2852 | 2871 | 0 | ATGCCCCACAGTGAGGGAGG |
| 395191 | 5-10-5 | 67 | 2861 | 2880 | 0 | AATGGTGAAATGCCCCACAG |
| 395192 | 5-10-5 | 153 | 2904 | 2923 | 0 | TTGGGAGCAGCTGGCAGCAC |
| 395193 | 5-10-5 | 68 | 3005 | 3024 | 0 | CATGGGAAGAATCCTGCCTC |
| 395194 | 5-10-5 | 69 | 3087 | 3106 | 0 | GGAGATGAGGGCCATCAGCA |
| 395195 | 5-10-5 | 70 | 3155 | 3174 | 0 | TAGATGCCATCCAGAAAGCT |
| 399821 | 5-10-5 | 71 | 3161 | 3180 | 0 | TCTGGCTAGATGCCATCCAG |
| 395196 | 5-10-5 | 72 | 3238 | 3257 | 0 | GGCATAGAGCAGAGTAAAGG |
| 399822 | 5-10-5 | 73 | 3243 | 3262 | 0 | AGCCTGGCATAGAGCAGAGT |
| 399823 | 5-10-5 | 135 | 3249 | 3268 | 0 | TAGCACAGCCTGGCATAGAG |
| 395197 | 5-10-5 | 112 | 3482 | 3501 | 0 | GAAGAGGCTTGGCTTCAGAG |
| 399824 | 5-10-5 | 74 | 3488 | 3507 | 0 | AAGTAAGAAGAGGCTTGGCT |
| 395198 | 5-10-5 | 75 | 3692 | 3711 | 0 | GCTCAAGGAGGGACAGTTGT |
| 395199 | 5-10-5 | 76 | 3727 | 3746 | 0 | AAAGATAAATGTCTGCTTGC |
| 399825 | 5-10-5 | 77 | 3732 | 3751 | 0 | ACCCAAAAGATAAATGTCTG |
| 395200 | 5-10-5 | 78 | 3798 | 3817 | 0 | TCTTCAAGTTACAAAAGCAA |
| 399826 | 5-10-5 | 99 | 3805 | 3824 | 0 | ATAAATATCTTCAAGTTACA |
| 405869 | 5-10-5 | 218 | 1392 | 1411 | 0 | TCGATTTCCCGGTGGTCACT |
| 405870 | 5-10-5 | 219 | 1393 | 1412 | 0 | CTCGATTTCCCGGTGGTCAC |
| 405871 | 5-10-5 | 220 | 1394 | 1413 | 0 | CCTCGATTTCCCGGTGGTCA |
| 405872 | 5-10-5 | 221 | 1395 | 1414 | 0 | CCCTCGATTTCCCGGTGGTC |

TABLE 13-continued

Gapmer antisense compounds having a 5-10-5 motif targeted to SEQ ID NO: 3

| Isis No | Motif | SEQ ID NO | 5' Target Site on SEQ ID NO: 3 | 3' Target Site on SEQ ID NO: 3 | Mismatches | Sequence (5'-3') |
|---|---|---|---|---|---|---|
| 405873 | 5-10-5 | 222 | 1397 | 1416 | 0 | TGCCCTCGATTTCCCGGTGG |
| 405874 | 5-10-5 | 223 | 1398 | 1417 | 0 | CTGCCCTCGATTTCCCGGTG |
| 405875 | 5-10-5 | 224 | 1399 | 1418 | 0 | CCTGCCCTCGATTTCCCGGT |
| 405876 | 5-10-5 | 225 | 1400 | 1419 | 0 | CCCTGCCCTCGATTTCCCGG |
| 405877 | 5-10-5 | 246 | 1530 | 1549 | 0 | TTGGCCACGCCGGCATCCCG |
| 405878 | 5-10-5 | 247 | 1531 | 1550 | 0 | CTTGGCCACGCCGGCATCCC |
| 405879 | 5-10-5 | 248 | 1532 | 1551 | 0 | CCTTGGCCACGCCGGCATCC |
| 405880 | 5-10-5 | 249 | 1533 | 1552 | 0 | CCCTTGGCCACGCCGGCATC |
| 405881 | 5-10-5 | 250 | 1535 | 1554 | 0 | CACCCTTGGCCACGCCGGCA |
| 405882 | 5-10-5 | 251 | 1536 | 1555 | 0 | GCACCCTTGGCCACGCCGGC |
| 405883 | 5-10-5 | 252 | 1537 | 1556 | 0 | GGCACCCTTGGCCACGCCGG |
| 405884 | 5-10-5 | 253 | 1538 | 1557 | 0 | TGGCACCCTTGGCCACGCCG |
| 405885 | 5-10-5 | 346 | 1993 | 2012 | 0 | GGAACCAGGCCTCATTGATG |
| 405886 | 5-10-5 | 347 | 1994 | 2013 | 0 | GGGAACCAGGCCTCATTGAT |
| 405887 | 5-10-5 | 348 | 1995 | 2014 | 0 | AGGGAACCAGGCCTCATTGA |
| 405888 | 5-10-5 | 349 | 1996 | 2015 | 0 | CAGGGAACCAGGCCTCATTG |
| 405889 | 5-10-5 | 350 | 1998 | 2017 | 0 | CTCAGGGAACCAGGCCTCAT |
| 405890 | 5-10-5 | 351 | 1999 | 2018 | 0 | CCTCAGGGAACCAGGCCTCA |
| 405891 | 5-10-5 | 352 | 2000 | 2019 | 0 | TCCTCAGGGAACCAGGCCTC |
| 405892 | 5-10-5 | 353 | 2001 | 2020 | 0 | GTCCTCAGGGAACCAGGCCT |
| 405893 | 5-10-5 | 431 | 3083 | 3102 | 0 | ATGAGGGCCATCAGCACCTT |
| 405894 | 5-10-5 | 432 | 3084 | 3103 | 0 | GATGAGGGCCATCAGCACCT |
| 405895 | 5-10-5 | 433 | 3085 | 3104 | 0 | AGATGAGGGCCATCAGCACC |
| 405896 | 5-10-5 | 434 | 3086 | 3105 | 0 | GAGATGAGGGCCATCAGCAC |
| 405897 | 5-10-5 | 435 | 3088 | 3107 | 0 | TGGAGATGAGGGCCATCAGC |
| 405898 | 5-10-5 | 436 | 3089 | 3108 | 0 | CTGGAGATGAGGGCCATCAG |
| 405899 | 5-10-5 | 437 | 3090 | 3109 | 0 | GCTGGAGATGAGGGCCATCA |
| 405900 | 5-10-5 | 438 | 3091 | 3110 | 0 | AGCTGGAGATGAGGGCCATC |
| 405901 | 5-10-5 | 439 | 3157 | 3176 | 0 | GCTAGATGCCATCCAGAAAG |
| 405902 | 5-10-5 | 440 | 3158 | 3177 | 0 | GGCTAGATGCCATCCAGAAA |
| 405903 | 5-10-5 | 441 | 3159 | 3178 | 0 | TGGCTAGATGCCATCCAGAA |
| 405904 | 5-10-5 | 442 | 3160 | 3179 | 0 | CTGGCTAGATGCCATCCAGA |
| 405905 | 5-10-5 | 443 | 3162 | 3181 | 0 | CTCTGGCTAGATGCCATCCA |
| 405906 | 5-10-5 | 444 | 3163 | 3182 | 0 | CCTCTGGCTAGATGCCATCC |
| 405907 | 5-10-5 | 445 | 3164 | 3183 | 0 | GCCTCTGGCTAGATGCCATC |
| 405908 | 5-10-5 | 446 | 3165 | 3184 | 0 | AGCCTCTGGCTAGATGCCAT |

TABLE 13-continued

Gapmer antisense compounds having a 5-10-5 motif targeted to SEQ ID NO: 3

| Isis No | Motif | SEQ ID NO | 5' Target Site on SEQ ID NO: 3 | 3' Target Site on SEQ ID NO: 3 | Mismatches | Sequence (5'-3') |
|---|---|---|---|---|---|---|
| 405909 | 5-10-5 | 267 | 1630 | 1649 | 0 | CAGCTGGCTTTTCCGAATAA |
| 405910 | 5-10-5 | 268 | 1632 | 1651 | 0 | ACCAGCTGGCTTTTCCGAAT |
| 405911 | 5-10-5 | 269 | 1634 | 1653 | 0 | GGACCAGCTGGCTTTTCCGA |
| 405912 | 5-10-5 | 270 | 1638 | 1657 | 0 | GGCTGGACCAGCTGGCTTTT |
| 405913 | 5-10-5 | 275 | 1742 | 1761 | 0 | CGGTGACCAGCACGACCCCA |
| 405914 | 5-10-5 | 276 | 1744 | 1763 | 0 | AGCGGTGACCAGCACGACCC |
| 405915 | 5-10-5 | 277 | 1746 | 1765 | 0 | GCAGCGGTGACCAGCACGAC |
| 405916 | 5-10-5 | 278 | 1748 | 1767 | 0 | CGGCAGCGGTGACCAGCACG |
| 405917 | 5-10-5 | 280 | 1752 | 1771 | 0 | TTGCCGGCAGCGGTGACCAG |
| 405918 | 5-10-5 | 281 | 1754 | 1773 | 0 | AGTTGCCGGCAGCGGTGACC |
| 405919 | 5-10-5 | 282 | 1756 | 1775 | 0 | GAAGTTGCCGGCAGCGGTGA |
| 405920 | 5-10-5 | 283 | 1758 | 1777 | 0 | CGGAAGTTGCCGGCAGCGGT |
| 405921 | 5-10-5 | 284 | 1760 | 1779 | 0 | CCCGGAAGTTGCCGGCAGCG |
| 405922 | 5-10-5 | 285 | 1762 | 1781 | 0 | GTCCCGGAAGTTGCCGGCAG |
| 405937 | 5-10-5 | 306 | 1820 | 1839 | 0 | GAGGCACCAATGATGTCCTC |
| 405938 | 5-10-5 | 307 | 1824 | 1843 | 0 | GCTGGAGGCACCAATGATGT |
| 405939 | 5-10-5 | 308 | 1826 | 1845 | 0 | TCGCTGGAGGCACCAATGAT |
| 405940 | 5-10-5 | 309 | 1828 | 1847 | 0 | AGTCGCTGGAGGCACCAATG |
| 405941 | 5-10-5 | 310 | 1830 | 1849 | 0 | GCAGTCGCTGGAGGCACCAA |
| 405942 | 5-10-5 | 311 | 1835 | 1854 | 0 | GTGCTGCAGTCGCTGGAGGC |
| 405943 | 5-10-5 | 312 | 1837 | 1856 | 0 | AGGTGCTGCAGTCGCTGGAG |
| 405944 | 5-10-5 | 314 | 1840 | 1859 | 0 | AGCAGGTGCTGCAGTCGCTG |
| 405945 | 5-10-5 | 315 | 1842 | 1861 | 0 | AAAGCAGGTGCTGCAGTCGC |
| 405946 | 5-10-5 | 316 | 1846 | 1865 | 0 | ACACAAAGCAGGTGCTGCAG |
| 405947 | 5-10-5 | 317 | 1848 | 1867 | 0 | TGACACAAAGCAGGTGCTGC |
| 405948 | 5-10-5 | 319 | 1900 | 1919 | 0 | TCATGGCTGCAATGCCAGCC |
| 405949 | 5-10-5 | 320 | 1905 | 1924 | 0 | CAGCATCATGGCTGCAATGC |
| 405950 | 5-10-5 | 321 | 1907 | 1926 | 0 | GACAGCATCATGGCTGCAAT |
| 405951 | 5-10-5 | 322 | 1909 | 1928 | 0 | CAGACAGCATCATGGCTGCA |
| 405952 | 5-10-5 | 323 | 1913 | 1932 | 0 | TCGGCAGACAGCATCATGGC |
| 405953 | 5-10-5 | 325 | 1917 | 1936 | 0 | CGGCTCGGCAGACAGCATCA |
| 405954 | 5-10-5 | 326 | 1919 | 1938 | 0 | TCCGGCTCGGCAGACAGCAT |
| 405955 | 5-10-5 | 328 | 1946 | 1965 | 0 | CTCTGCCTCAACTCGGCAG |
| 405956 | 5-10-5 | 329 | 1948 | 1967 | 0 | GTCTCTGCCTCAACTCGGCC |
| 405957 | 5-10-5 | 330 | 1950 | 1969 | 0 | CAGTCTCTGCCTCAACTCGG |
| 405958 | 5-10-5 | 331 | 1952 | 1971 | 0 | ATCAGTCTCTGCCTCAACTC |
| 405959 | 5-10-5 | 332 | 1954 | 1973 | 0 | GGATCAGTCTCTGCCTCAAC |

TABLE 13-continued

Gapmer antisense compounds having a 5-10-5 motif targeted to SEQ ID NO: 3

| Isis No | Motif | SEQ ID NO | 5' Target Site on SEQ ID NO: 3 | 3' Target Site on SEQ ID NO: 3 | Mismatches | Sequence (5'-3') |
|---|---|---|---|---|---|---|
| 405960 | 5-10-5 | 333 | 1956 | 1975 | 0 | GTGGATCAGTCTCTGCCTCA |
| 405961 | 5-10-5 | 334 | 1958 | 1977 | 0 | AAGTGGATCAGTCTCTGCCT |
| 405962 | 5-10-5 | 335 | 1961 | 1980 | 0 | GAGAAGTGGATCAGTCTCTG |
| 405963 | 5-10-5 | 337 | 1965 | 1984 | 0 | GGCAGAGAAGTGGATCAGTC |
| 405964 | 5-10-5 | 338 | 1969 | 1988 | 0 | CTTTGGCAGAGAAGTGGATC |
| 405965 | 5-10-5 | 339 | 1974 | 1993 | 0 | GACATCTTTGGCAGAGAAGT |
| 405966 | 5-10-5 | 340 | 1976 | 1995 | 0 | ATGACATCTTTGGCAGAGAA |
| 405967 | 5-10-5 | 341 | 1980 | 1999 | 0 | ATTGATGACATCTTTGGCAG |
| 405968 | 5-10-5 | 342 | 1982 | 2001 | 0 | TCATTGATGACATCTTTGGC |
| 405969 | 5-10-5 | 343 | 1987 | 2006 | 0 | AGGCCTCATTGATGACATCT |
| 405970 | 5-10-5 | 344 | 1989 | 2008 | 0 | CCAGGCCTCATTGATGACAT |
| 405971 | 5-10-5 | 355 | 2004 | 2023 | 0 | CTGGTCCTCAGGGAACCAGG |
| 405972 | 5-10-5 | 357 | 2006 | 2025 | 0 | CGCTGGTCCTCAGGGAACCA |
| 405973 | 5-10-5 | 358 | 2011 | 2030 | 0 | GTACCCGCTGGTCCTCAGGG |
| 405974 | 5-10-5 | 359 | 2013 | 2032 | 0 | CAGTACCCGCTGGTCCTCAG |
| 405975 | 5-10-5 | 361 | 2075 | 2094 | 0 | CAAAACAGCTGCCAACCTGC |
| 405976 | 5-10-5 | 362 | 2080 | 2099 | 0 | TCCTGCAAAACAGCTGCCAA |
| 405977 | 5-10-5 | 363 | 2082 | 2101 | 0 | AGTCCTGCAAAACAGCTGCC |
| 405978 | 5-10-5 | 365 | 2105 | 2124 | 0 | GGCCCCGAGTGTGCTGACCA |
| 405979 | 5-10-5 | 366 | 2110 | 2129 | 0 | GTGTAGGCCCCGAGTGTGCT |
| 405980 | 5-10-5 | 367 | 2112 | 2131 | 0 | CCGTGTAGGCCCCGAGTGTG |
| 405981 | 5-10-5 | 368 | 2114 | 2133 | 0 | ATCCGTGTAGGCCCCGAGTG |
| 405982 | 5-10-5 | 370 | 2118 | 2137 | 0 | GGCCATCCGTGTAGGCCCCG |
| 405983 | 5-10-5 | 371 | 2120 | 2139 | 0 | GTGGCCATCCGTGTAGGCCC |
| 405984 | 5-10-5 | 372 | 2168 | 2187 | 0 | CTGGAGCAGCTCAGCAGCTC |
| 405985 | 5-10-5 | 373 | 2170 | 2189 | 0 | AACTGGAGCAGCTCAGCAGC |
| 405986 | 5-10-5 | 374 | 2175 | 2194 | 0 | GGAGAAACTGGAGCAGCTCA |
| 405987 | 5-10-5 | 375 | 2177 | 2196 | 0 | CTGGAGAAACTGGAGCAGCT |
| 405996 | 5-10-5 | 412 | 2357 | 2376 | 0 | GACTTTGCATTCCAGACCTG |
| 405997 | 5-10-5 | 415 | 2362 | 2381 | 0 | TCCTTGACTTTGCATTCCAG |
| 405998 | 5-10-5 | 426 | 2568 | 2587 | 0 | TCCGGCAGCAGATGGCAACG |
| 406025 | 5-10-5 | 216 | 1362 | 1381 | 0 | GTGTCTAGGAGATACACCTC |
| 406026 | 5-10-5 | 217 | 1367 | 1386 | 0 | TGCTGGTGTCTAGGAGATAC |
| 406027 | 5-10-5 | 226 | 1404 | 1423 | 0 | ATGACCCTGCCCTCGATTTC |
| 406028 | 5-10-5 | 227 | 1406 | 1425 | 0 | CCATGACCCTGCCCTCGATT |
| 406029 | 5-10-5 | 228 | 1408 | 1427 | 0 | GACCATGACCCTGCCCTCGA |

TABLE 13-continued

Gapmer antisense compounds having a 5-10-5 motif targeted to SEQ ID NO: 3

| Isis No | Motif | SEQ ID NO | 5' Target Site on SEQ ID NO: 3 | 3' Target Site on SEQ ID NO: 3 | Mismatches | Sequence (5'-3') |
|---|---|---|---|---|---|---|
| 406030 | 5-10-5 | 229 | 1412 | 1431 | 0 | CGGTGACCATGACCCTGCCC |
| 406031 | 5-10-5 | 230 | 1414 | 1433 | 0 | GTCGGTGACCATGACCCTGC |
| 406032 | 5-10-5 | 232 | 1418 | 1437 | 0 | CGAAGTCGGTGACCATGACC |
| 406033 | 5-10-5 | 237 | 1497 | 1516 | 0 | CCTGCCAGGTGGGTGCCATG |
| 406034 | 5-10-5 | 238 | 1502 | 1521 | 0 | CCACCCCTGCCAGGTGGGTG |
| 406035 | 5-10-5 | 239 | 1507 | 1526 | 0 | GCTGACCACCCCTGCCAGGT |
| 406036 | 5-10-5 | 241 | 1519 | 1538 | 0 | GGCATCCCGGCCGCTGACCA |
| 406037 | 5-10-5 | 242 | 1522 | 1541 | 0 | GCCGGCATCCCGGCCGCTGA |
| 406038 | 5-10-5 | 245 | 1529 | 1548 | 0 | TGGCCACGCCGGCATCCCGG |
| 406039 | 5-10-5 | 257 | 1566 | 1585 | 0 | CAGTTGAGCACGCGCAGGCT |
| 406040 | 5-10-5 | 258 | 1568 | 1587 | 0 | GGCAGTTGAGCACGCGCAGG |
| 406041 | 5-10-5 | 259 | 1572 | 1591 | 0 | CCTTGGCAGTTGAGCACGCG |
| 406042 | 5-10-5 | 260 | 1577 | 1596 | 0 | CCTTCCCTTGGCAGTTGAGC |
| 406043 | 5-10-5 | 261 | 1581 | 1600 | 0 | GTGCCCTTCCCTTGGCAGTT |
| 406044 | 5-10-5 | 262 | 1583 | 1602 | 0 | CCGTGCCCTTCCCTTGGCAG |
| 406045 | 5-10-5 | 266 | 1626 | 1645 | 0 | TGGCTTTTCCGAATAAACTC |
| 408642 | 5-10-5 | 264 | 1606 | 1625 | 0 | CAGGCCTATGAGGGTGCCGC |
| 408653 | 5-10-5 | 354 | 2003 | 2022 | 0 | TGGTCCTCAGGGAACCAGGC |
| 409126 | 5-10-5 | 447 | 1534 | 1553 | 1 | ACCCTTGGTCACGCCGGCAT |
| 410536 | 5-10-5 | 243 | 1527 | 1546 | 0 | GCCACGCCGGCATCCCGGCC |
| 410537 | 5-10-5 | 244 | 1528 | 1547 | 0 | GGCCACGCCGGCATCCCGGC |
| 410538 | 5-10-5 | 254 | 1539 | 1558 | 0 | CTGGCACCCTTGGCCACGCC |
| 410539 | 5-10-5 | 255 | 1540 | 1559 | 0 | GCTGGCACCCTTGGCCACGC |
| 410540 | 5-10-5 | 356 | 2005 | 2024 | 0 | GCTGGTCCTCAGGGAACCAG |
| 410562 | 5-10-5 | 411 | 2356 | 2375 | 0 | ACTTTGCATTCCAGACCTGG |
| 410563 | 5-10-5 | 413 | 2358 | 2377 | 0 | TGACTTTGCATTCCAGACCT |
| 410564 | 5-10-5 | 414 | 2359 | 2378 | 0 | TTGACTTTGCATTCCAGACC |
| 410565 | 5-10-5 | 419 | 2560 | 2579 | 0 | CAGATGGCAACGGCTGTCAC |
| 410566 | 5-10-5 | 420 | 2561 | 2580 | 0 | GCAGATGGCAACGGCTGTCA |
| 410567 | 5-10-5 | 421 | 2562 | 2581 | 0 | AGCAGATGGCAACGGCTGTC |
| 410568 | 5-10-5 | 422 | 2563 | 2582 | 0 | CAGCAGATGGCAACGGCTGT |
| 410569 | 5-10-5 | 423 | 2564 | 2583 | 0 | GCAGCAGATGGCAACGGCTG |
| 410570 | 5-10-5 | 424 | 2566 | 2585 | 0 | CGGCAGCAGATGGCAACGGC |
| 410571 | 5-10-5 | 425 | 2567 | 2586 | 0 | CCGGCAGCAGATGGCAACGG |
| 410572 | 5-10-5 | 427 | 2569 | 2588 | 0 | CTCCGGCAGCAGATGGCAAC |
| 410573 | 5-10-5 | 428 | 2570 | 2589 | 0 | GCTCCGGCAGCAGATGGCAA |
| 410733 | 5-10-5 | 231 | 1416 | 1435 | 0 | AAGTCGGTGACCATGACCCT |

TABLE 13-continued

Gapmer antisense compounds having a 5-10-5 motif targeted to SEQ ID NO: 3

| Isis No | Motif | SEQ ID NO | 5' Target Site on SEQ ID NO: 3 | 3' Target Site on SEQ ID NO: 3 | Mismatches | Sequence (5'-3') |
|---|---|---|---|---|---|---|
| 410734 | 5-10-5 | 279 | 1749 | 1768 | 0 | CCGGCAGCGGTGACCAGCAC |
| 410737 | 5-10-5 | 313 | 1839 | 1858 | 0 | GCAGGTGCTGCAGTCGCTGG |
| 410738 | 5-10-5 | 324 | 1915 | 1934 | 0 | GCTCGGCAGACAGCATCATG |
| 410739 | 5-10-5 | 336 | 1963 | 1982 | 0 | CAGAGAAGTGGATCAGTCTC |
| 410740 | 5-10-5 | 345 | 1991 | 2010 | 0 | AACCAGGCCTCATTGATGAC |
| 410741 | 5-10-5 | 369 | 2116 | 2135 | 0 | CCATCCGTGTAGGCCCCGAG |
| 410753 | 5-10-5 | 215 | 1351 | 1370 | 0 | ATACACCTCCACCAGGCTGC |
| 410754 | 5-10-5 | 233 | 1428 | 1447 | 0 | GGCACATTCTCGAAGTCGGT |
| 410755 | 5-10-5 | 234 | 1463 | 1482 | 0 | TGGCCTGTCTGTGGAAGCGG |
| 410756 | 5-10-5 | 235 | 1490 | 1509 | 0 | GGTGGGTGCCATGACTGTCA |
| 410757 | 5-10-5 | 240 | 1515 | 1534 | 0 | TCCCGGCCGCTGACCACCCC |
| 410758 | 5-10-5 | 256 | 1545 | 1564 | 0 | CGCATGCTGGCACCCTTGGC |
| 410759 | 5-10-5 | 263 | 1594 | 1613 | 0 | GGTGCCGCTAACCGTGCCCT |
| 410760 | 5-10-5 | 265 | 1618 | 1637 | 0 | CCGAATAAACTCCAGGCCTA |
| 410761 | 5-10-5 | 271 | 1649 | 1668 | 0 | GTGGCCCCACAGGCTGGACC |
| 410762 | 5-10-5 | 272 | 1662 | 1681 | 0 | AGCAGCACCACCAGTGGCCC |
| 410763 | 5-10-5 | 273 | 1684 | 1703 | 0 | GCTGTACCCACCCGCCAGGG |
| 410764 | 5-10-5 | 274 | 1730 | 1749 | 0 | CGACCCCAGCCCTCGCCAGG |
| 410769 | 5-10-5 | 318 | 1858 | 1877 | 0 | TCCCACTCTGTGACACAAAG |
| 410770 | 5-10-5 | 327 | 1933 | 1952 | 0 | CGGCCAGGGTGAGCTCCGGC |
| 410771 | 5-10-5 | 360 | 2061 | 2080 | 0 | ACCTGCCCCATGGGTGCTGG |
| 410776 | 5-10-5 | 408 | 2245 | 2264 | 0 | GTGCCAAGGTCCTCCACCTC |
| 410777 | 5-10-5 | 409 | 2265 | 2284 | 0 | TCAGCACAGGCGGCTTGTGG |
| 410778 | 5-10-5 | 410 | 2295 | 2314 | 0 | CCACGCACTGGTTGGGCTGA |
| 410779 | 5-10-5 | 416 | 2375 | 2394 | 0 | CGGGATTCCATGCTCCTTGA |
| 410780 | 5-10-5 | 417 | 2405 | 2424 | 0 | GCAGGCCACGGTCACCTGCT |
| 410781 | 5-10-5 | 418 | 2442 | 2461 | 0 | GGAGGGCACTGCAGCCAGTC |
| 410782 | 5-10-5 | 429 | 2580 | 2599 | 0 | CCAGGTGCCGGCTCCGGCAG |
| 410783 | 5-10-5 | 430 | 2590 | 2609 | 0 | GAGGCCTGCGCCAGGTGCCG |

In certain embodiments, gap-widened antisense compounds are targeted to a PCSK9 nucleic acid. In certain such embodiments, gap-widened antisense compounds are targeted to SEQ ID NO: 3. In certain such embodiments, the internucleotide sequences illustrated in Table 12 have a 3-14-3 gap-widened motif. Table 14 illustrates gap-widened antisense compounds targeted to SEQ ID NO: 3, having a 3-14-3 motif, where the gap segment comprises 2'-deoxynucleotides and each wing segment comprises nucleotides comprising a 2'-O-methoxyethyl sugar modification. Internucleoside linkages are phosphorthioate, and cytidines are 5-methylcytidines.

TABLE 14

Gapmer antisense compounds having a 3-14-3 motif targeted to SEQ ID NO: 3

| Isis No | Motif | SEQ ID NO | 5' Target Site on SEQ ID NO: 3 | 3' Target Site on SEQ ID NO: 3 | Mismatches | Sequence (5'-3') |
|---|---|---|---|---|---|---|
| 399923 | 3-14-3 | 85 | 155 | 174 | 0 | ACAAATTCCCAGACTCAGCA |
| 399983 | 3-14-3 | 100 | 220 | 239 | 0 | ATCTCAGGACAGGTGAGCAA |
| 399984 | 3-14-3 | 116 | 234 | 253 | 0 | GAGTAGAGATTCTCATCTCA |
| 399924 | 3-14-3 | 129 | 290 | 309 | 0 | GTGCCATCTGAACAGCACCT |
| 399985 | 3-14-3 | 117 | 302 | 321 | 0 | GAGTCTTCTGAAGTGCCATC |
| 399986 | 3-14-3 | 81 | 377 | 396 | 0 | AAGCAGGGCCTCAGGTGGAA |
| 399925 | 3-14-3 | 110 | 400 | 419 | 0 | CCTGGAACCCCTGCAGCCAG |
| 399926 | 3-14-3 | 152 | 451 | 470 | 0 | TTCAGGCAGGTTGCTGCTAG |
| 399987 | 3-14-3 | 83 | 460 | 479 | 0 | AAGGAAGACTTCAGGCAGGT |
| 399927 | 3-14-3 | 140 | 472 | 491 | 0 | TCAGCCAGGCCAAAGGAAGA |
| 399988 | 3-14-3 | 137 | 586 | 605 | 0 | TAGGGAGAGCTCACAGATGC |
| 399928 | 3-14-3 | 136 | 596 | 615 | 0 | TAGGAGAAAGTAGGGAGAGC |
| 399929 | 3-14-3 | 132 | 653 | 672 | 0 | TAAAAGCTGCAAGAGACTCA |
| 399930 | 3-14-3 | 139 | 741 | 760 | 0 | TCAGAGAAAACAGTCACCGA |
| 399989 | 3-14-3 | 92 | 871 | 890 | 0 | AGAGACAGGAAGCTGCAGCT |
| 399931 | 3-14-3 | 142 | 878 | 897 | 0 | TCATTTTAGAGACAGGAAGC |
| 399932 | 3-14-3 | 113 | 915 | 934 | 0 | GAATAACAGTGATGTCTGGC |
| 399933 | 3-14-3 | 138 | 968 | 987 | 0 | TCACAGCTCACCGAGTCTGC |
| 399934 | 3-14-3 | 98 | 998 | 1017 | 0 | AGTGTAAAATAAAGCCCCTA |
| 399935 | 3-14-3 | 96 | 1075 | 1094 | 0 | AGGACCCAAGTCATCCTGCT |
| 399936 | 3-14-3 | 124 | 1105 | 1124 | 0 | GGCCATCAGCTGGCAATGCT |
| 399990 | 3-14-3 | 82 | 1144 | 1163 | 0 | AAGGAAAGGGAGGCCTAGAG |
| 399937 | 3-14-3 | 133 | 1149 | 1168 | 0 | TAGACAAGGAAAGGGAGGCC |
| 399938 | 3-14-3 | 103 | 1155 | 1174 | 0 | ATTTCATAGACAAGGAAAGG |
| 399939 | 3-14-3 | 155 | 1275 | 1294 | 0 | CTTATAGTTAACACACAGAA |
| 399991 | 3-14-3 | 156 | 1283 | 1302 | 0 | AAGTCAACCTTATAGTTAAC |
| 399940 | 3-14-3 | 146 | 1315 | 1334 | 0 | TGACATTTGTGGGAGAGGAG |
| 399941 | 3-14-3 | 161 | 1322 | 1341 | 0 | TCCAAGGTGACATTTGTGGG |
| 399882 | 3-14-3 | 19 | 1365 | 1384 | 0 | CTGGTGTCTAGGAGATACAC |
| 399953 | 3-14-3 | 20 | 1370 | 1389 | 0 | GTATGCTGGTGTCTAGGAGA |
| 399883 | 3-14-3 | 21 | 1390 | 1409 | 0 | GATTTCCCGGTGGTCACTCT |
| 399954 | 3-14-3 | 22 | 1396 | 1415 | 0 | GCCCTCGATTTCCCGGTGGT |
| 399955 | 3-14-3 | 23 | 1410 | 1429 | 0 | GTGACCATGACCCTGCCCTC |
| 399884 | 3-14-3 | 24 | 1420 | 1439 | 0 | CTCGAAGTCGGTGACCATGA |
| 399885 | 3-14-3 | 25 | 1453 | 1472 | 0 | GTGGAAGCGGGTCCCGTCCT |
| 399886 | 3-14-3 | 26 | 1500 | 1519 | 0 | ACCCCTGCCAGGTGGGTGCC |
| 399956 | 3-14-3 | 27 | 1505 | 1524 | 0 | TGACCACCCCTGCCAGGTGG |

TABLE 14-continued

Gapmer antisense compounds having a 3-14-3 motif targeted to SEQ ID NO: 3

| Isis No | Motif | SEQ ID NO | 5' Target Site on SEQ ID NO: 3 | 3' Target Site on SEQ ID NO: 3 | Mismatches | Sequence (5'-3') |
|---|---|---|---|---|---|---|
| 399887 | 3-14-3 | 28 | 1534 | 1553 | 0 | ACCCTTGGCCACGCCGGCAT |
| 399888 | 3-14-3 | 29 | 1570 | 1589 | 0 | TTGGCAGTTGAGCACGCGCA |
| 399957 | 3-14-3 | 30 | 1575 | 1594 | 0 | TTCCCTTGGCAGTTGAGCAC |
| 399889 | 3-14-3 | 31 | 1607 | 1626 | 0 | CCAGGCCTATGAGGGTGCCG |
| 399890 | 3-14-3 | 32 | 1628 | 1647 | 0 | GCTGGCTTTTCCGAATAAAC |
| 399891 | 3-14-3 | 33 | 1740 | 1759 | 0 | GTGACCAGCACGACCCCAGC |
| 399897 | 3-14-3 | 39 | 1822 | 1841 | 0 | TGGAGGCACCAATGATGTCC |
| 399960 | 3-14-3 | 40 | 1833 | 1852 | 0 | GCTGCAGTCGCTGGAGGCAC |
| 399961 | 3-14-3 | 41 | 1844 | 1863 | 0 | ACAAAGCAGGTGCTGCAGTC |
| 399898 | 3-14-3 | 101 | 1898 | 1917 | 0 | ATGGCTGCAATGCCAGCCAC |
| 399962 | 3-14-3 | 42 | 1903 | 1922 | 0 | GCATCATGGCTGCAATGCCA |
| 399963 | 3-14-3 | 43 | 1911 | 1930 | 0 | GGCAGACAGCATCATGGCTG |
| 399964 | 3-14-3 | 44 | 1959 | 1978 | 0 | GAAGTGGATCAGTCTCTGCC |
| 399899 | 3-14-3 | 45 | 1967 | 1986 | 0 | TTGGCAGAGAAGTGGATCAG |
| 399965 | 3-14-3 | 46 | 1972 | 1991 | 0 | CATCTTTGGCAGAGAAGTGG |
| 399966 | 3-14-3 | 47 | 1978 | 1997 | 0 | TGATGACATCTTTGGCAGAG |
| 399967 | 3-14-3 | 48 | 1985 | 2004 | 0 | GCCTCATTGATGACATCTTT |
| 399968 | 3-14-3 | 49 | 1997 | 2016 | 0 | TCAGGGAACCAGGCCTCATT |
| 399900 | 3-14-3 | 50 | 2002 | 2021 | 0 | GGTCCTCAGGGAACCAGGCC |
| 399901 | 3-14-3 | 87 | 2009 | 2028 | 0 | ACCCGCTGGTCCTCAGGGAA |
| 399969 | 3-14-3 | 51 | 2016 | 2035 | 0 | GGTCAGTACCCGCTGGTCCT |
| 399902 | 3-14-3 | 119 | 2038 | 2057 | 0 | GCAGGGCGGCCACCAGGTTG |
| 399903 | 3-14-3 | 52 | 2073 | 2092 | 0 | AAACAGCTGCCAACCTGCCC |
| 399970 | 3-14-3 | 53 | 2078 | 2097 | 0 | CTGCAAAACAGCTGCCAACC |
| 399942 | 3-14-3 | 104 | 2085 | 2104 | 0 | CACAGTCCTGCAAAACAGCT |
| 399992 | 3-14-3 | 130 | 2095 | 2114 | 0 | GTGCTGACCACACAGTCCTG |
| 399904 | 3-14-3 | 54 | 2108 | 2127 | 0 | GTAGGCCCCGAGTGTGCTGA |
| 399971 | 3-14-3 | 55 | 2173 | 2192 | 0 | AGAAACTGGAGCAGCTCAGC |
| 399972 | 3-14-3 | 56 | 2179 | 2198 | 0 | TCCTGGAGAAACTGGAGCAG |
| 399908 | 3-14-3 | 60 | 2355 | 2374 | 0 | CTTTGCATTCCAGACCTGGG |
| 399973 | 3-14-3 | 61 | 2360 | 2379 | 0 | CTTGACTTTGCATTCCAGAC |
| 399909 | 3-14-3 | 62 | 2565 | 2584 | 0 | GGCAGCAGATGGCAACGGCT |
| 399910 | 3-14-3 | 154 | 2665 | 2684 | 0 | TTTTAAAGCTCAGCCCCAGC |
| 399974 | 3-14-3 | 63 | 2670 | 2689 | 0 | AACCATTTTAAAGCTCAGCC |
| 399911 | 3-14-3 | 64 | 2759 | 2778 | 0 | TCAAGGGCCAGGCCAGCAGC |
| 399975 | 3-14-3 | 65 | 2764 | 2783 | 0 | CCCACTCAAGGGCCAGGCCA |

TABLE 14-continued

Gapmer antisense compounds having a 3-14-3 motif targeted to SEQ ID NO: 3

| Isis No | Motif | SEQ ID NO | 5' Target Site on SEQ ID NO: 3 | 3' Target Site on SEQ ID NO: 3 | Mismatches | Sequence (5'-3') |
|---|---|---|---|---|---|---|
| 399976 | 3-14-3 | 122 | 2837 | 2856 | 0 | GGAGGGAGCTTCCTGGCACC |
| 399912 | 3-14-3 | 66 | 2852 | 2871 | 0 | ATGCCCCACAGTGAGGGAGG |
| 399913 | 3-14-3 | 67 | 2861 | 2880 | 0 | AATGGTGAAATGCCCCACAG |
| 399914 | 3-14-3 | 153 | 2904 | 2923 | 0 | TTGGGAGCAGCTGGCAGCAC |
| 399915 | 3-14-3 | 68 | 3005 | 3024 | 0 | CATGGGAAGAATCCTGCCTC |
| 399916 | 3-14-3 | 69 | 3087 | 3106 | 0 | GGAGATGAGGGCCATCAGCA |
| 399917 | 3-14-3 | 70 | 3155 | 3174 | 0 | TAGATGCCATCCAGAAAGCT |
| 399977 | 3-14-3 | 71 | 3161 | 3180 | 0 | TCTGGCTAGATGCCATCCAG |
| 399918 | 3-14-3 | 72 | 3238 | 3257 | 0 | GGCATAGAGCAGAGTAAAGG |
| 399978 | 3-14-3 | 73 | 3243 | 3262 | 0 | AGCCTGGCATAGAGCAGAGT |
| 399979 | 3-14-3 | 135 | 3249 | 3268 | 0 | TAGCACAGCCTGGCATAGAG |
| 399919 | 3-14-3 | 112 | 3482 | 3501 | 0 | GAAGAGGCTTGGCTTCAGAG |
| 399980 | 3-14-3 | 74 | 3488 | 3507 | 0 | AAGTAAGAAGAGGCTTGGCT |
| 399920 | 3-14-3 | 75 | 3692 | 3711 | 0 | GCTCAAGGAGGGACAGTTGT |
| 399921 | 3-14-3 | 76 | 3727 | 3746 | 0 | AAAGATAAATGTCTGCTTGC |
| 399981 | 3-14-3 | 77 | 3732 | 3751 | 0 | ACCCAAAAGATAAATGTCTG |
| 399922 | 3-14-3 | 78 | 3798 | 3817 | 0 | TCTTCAAGTTACAAAAGCAA |
| 399982 | 3-14-3 | 99 | 3805 | 3824 | 0 | ATAAATATCTTCAAGTTACA |
| 405604 | 3-14-3 | 236 | 1493 | 1512 | 0 | CCAGGTGGGTGCCATGACTG |
| 405641 | 3-14-3 | 373 | 2170 | 2189 | 0 | AACTGGAGCAGCTCAGCAGC |
| 410583 | 3-14-3 | 243 | 1527 | 1546 | 0 | GCCACGCCGGCATCCCGGCC |
| 410584 | 3-14-3 | 244 | 1528 | 1547 | 0 | GGCCACGCCGGCATCCCGGC |
| 410585 | 3-14-3 | 245 | 1529 | 1548 | 0 | TGGCCACGCCGGCATCCCGG |
| 410586 | 3-14-3 | 246 | 1530 | 1549 | 0 | TTGGCCACGCCGGCATCCCG |
| 410587 | 3-14-3 | 247 | 1531 | 1550 | 0 | CTTGGCCACGCCGGCATCCC |
| 410588 | 3-14-3 | 248 | 1532 | 1551 | 0 | CCTTGGCCACGCCGGCATCC |
| 410589 | 3-14-3 | 249 | 1533 | 1552 | 0 | CCCTTGGCCACGCCGGCATC |
| 410590 | 3-14-3 | 250 | 1535 | 1554 | 0 | CACCCTTGGCCACGCCGGCA |
| 410591 | 3-14-3 | 251 | 1536 | 1555 | 0 | GCACCCTTGGCCACGCCGGC |
| 410592 | 3-14-3 | 252 | 1537 | 1556 | 0 | GGCACCCTTGGCCACGCCGG |
| 410593 | 3-14-3 | 253 | 1538 | 1557 | 0 | TGGCACCCTTGGCCACGCCG |
| 410594 | 3-14-3 | 254 | 1539 | 1558 | 0 | CTGGCACCCTTGGCCACGCC |
| 410595 | 3-14-3 | 255 | 1540 | 1559 | 0 | GCTGGCACCCTTGGCCACGC |
| 410596 | 3-14-3 | 348 | 1995 | 2014 | 0 | AGGGAACCAGGCCTCATTGA |
| 410597 | 3-14-3 | 349 | 1996 | 2015 | 0 | CAGGGAACCAGGCCTCATTG |
| 410598 | 3-14-3 | 350 | 1998 | 2017 | 0 | CTCAGGGAACCAGGCCTCAT |
| 410599 | 3-14-3 | 351 | 1999 | 2018 | 0 | CCTCAGGGAACCAGGCCTCA |

TABLE 14-continued

Gapmer antisense compounds having a 3-14-3 motif targeted to SEQ ID NO: 3

| Isis No | Motif | SEQ ID NO | 5' Target Site on SEQ ID NO: 3 | 3' Target Site on SEQ ID NO: 3 | Mismatches | Sequence (5'-3') |
|---|---|---|---|---|---|---|
| 410600 | 3-14-3 | 352 | 2000 | 2019 | 0 | TCCTCAGGGAACCAGGCCTC |
| 410601 | 3-14-3 | 353 | 2001 | 2020 | 0 | GTCCTCAGGGAACCAGGCCT |
| 410602 | 3-14-3 | 354 | 2003 | 2022 | 0 | TGGTCCTCAGGGAACCAGGC |
| 410603 | 3-14-3 | 355 | 2004 | 2023 | 0 | CTGGTCCTCAGGGAACCAGG |
| 410604 | 3-14-3 | 356 | 2005 | 2024 | 0 | GCTGGTCCTCAGGGAACCAG |
| 410633 | 3-14-3 | 411 | 2356 | 2375 | 0 | ACTTTGCATTCCAGACCTGG |
| 410634 | 3-14-3 | 412 | 2357 | 2376 | 0 | GACTTTGCATTCCAGACCTG |
| 410635 | 3-14-3 | 413 | 2358 | 2377 | 0 | TGACTTTGCATTCCAGACCT |
| 410636 | 3-14-3 | 414 | 2359 | 2378 | 0 | TTGACTTTGCATTCCAGACC |
| 410637 | 3-14-3 | 419 | 2560 | 2579 | 0 | CAGATGGCAACGGCTGTCAC |
| 410638 | 3-14-3 | 420 | 2561 | 2580 | 0 | GCAGATGGCAACGGCTGTCA |
| 410639 | 3-14-3 | 421 | 2562 | 2581 | 0 | AGCAGATGGCAACGGCTGTC |
| 410640 | 3-14-3 | 422 | 2563 | 2582 | 0 | CAGCAGATGGCAACGGCTGT |
| 410641 | 3-14-3 | 423 | 2564 | 2583 | 0 | GCAGCAGATGGCAACGGCTG |
| 410642 | 3-14-3 | 424 | 2566 | 2585 | 0 | CGGCAGCAGATGGCAACGGC |
| 410643 | 3-14-3 | 425 | 2567 | 2586 | 0 | CCGGCAGCAGATGGCAACGG |
| 410644 | 3-14-3 | 426 | 2568 | 2587 | 0 | TCCGGCAGCAGATGGCAACG |
| 410645 | 3-14-3 | 427 | 2569 | 2588 | 0 | CTCCGGCAGCAGATGGCAAC |
| 410646 | 3-14-3 | 428 | 2570 | 2589 | 0 | GCTCCGGCAGCAGATGGCAA |

In certain embodiments, gap-widened antisense compounds are targeted to a PCSK9 nucleic acid. In certain such embodiments, gap-widened antisense compounds are targeted to SEQ ID NO: 3. In certain such embodiments, the nucleotide sequences illustrated in Table 12 have a 2-13-5 gap-widened motif. Table 15 illustrates gap-widened antisense compounds targeted to SEQ ID NO: 3, having a 2-13-5 motif, where the gap segment comprises 2'-deoxynucleotides and each wing segment comprises nucleotides comprising a 2'-O-methoxyethyl sugar modification. Internucleoside linkages are phosphorthioate, and cytidines are 5-methylcytidines.

TABLE 15

Gapmer antisense compounds having a 2-13-5 motif targeted to SEQ ID NO: 3

| ISIS No | Motiff | SEQ ID NO | 5' Target Site to SEQ ID NO: 3 | 3' Target Site to SEQ ID NO: 3 | Mismatches | Sequences (5'-3') |
|---|---|---|---|---|---|---|
| 410658 | 2-13-5 | 243 | 1527 | 1546 | 0 | GCCACGCCGGCATCCCGGCC |
| 410659 | 2-13-5 | 244 | 1528 | 1547 | 0 | GGCCACGCCGGCATCCCGGC |
| 410660 | 2-13-5 | 245 | 1529 | 1548 | 0 | TGGCCACGCCGGCATCCCGG |
| 410661 | 2-13-5 | 246 | 1530 | 1549 | 0 | TTGGCCACGCCGGCATCCCG |
| 410662 | 2-13-5 | 247 | 1531 | 1550 | 0 | CTTGGCCACGCCGGCATCCC |
| 410663 | 2-13-5 | 248 | 1532 | 1551 | 0 | CCTTGGCCACGCCGGCATCC |

TABLE 15-continued

Gapmer antisense compounds having a 2-13-5 motif targeted to SEQ ID NO: 3

| ISIS No | Motif | SEQ ID NO | 5' Target Site to SEQ ID NO: 3 | 3' Target Site to SEQ ID NO: 3 | Mismatches | Sequences (5'-3') |
|---|---|---|---|---|---|---|
| 410664 | 2-13-5 | 249 | 1533 | 1552 | 0 | CCCTTGGCCACGCCGGCATC |
| 410665 | 2-13-5 | 28 | 1534 | 1553 | 0 | ACCCTTGGCCACGCCGGCAT |
| 410666 | 2-13-5 | 250 | 1535 | 1554 | 0 | CACCCTTGGCCACGCCGGCA |
| 410667 | 2-13-5 | 251 | 1536 | 1555 | 0 | GCACCCTTGGCCACGCCGGC |
| 410668 | 2-13-5 | 252 | 1537 | 1556 | 0 | GGCACCCTTGGCCACGCCGG |
| 410669 | 2-13-5 | 253 | 1538 | 1557 | 0 | TGGCACCCTTGGCCACGCCG |
| 410670 | 2-13-5 | 254 | 1539 | 1558 | 0 | CTGGCACCCTTGGCCACGCC |
| 410671 | 2-13-5 | 255 | 1540 | 1559 | 0 | GCTGGCACCCTTGGCCACGC |
| 410672 | 2-13-5 | 348 | 1995 | 2014 | 0 | AGGGAACCAGGCCTCATTGA |
| 410673 | 2-13-5 | 349 | 1996 | 2015 | 0 | CAGGGAACCAGGCCTCATTG |
| 410674 | 2-13-5 | 49 | 1997 | 2016 | 0 | TCAGGGAACCAGGCCTCATT |
| 410675 | 2-13-5 | 350 | 1998 | 2017 | 0 | CTCAGGGAACCAGGCCTCAT |
| 410676 | 2-13-5 | 351 | 1999 | 2018 | 0 | CCTCAGGGAACCAGGCCTCA |
| 410677 | 2-13-5 | 352 | 2000 | 2019 | 0 | TCCTCAGGGAACCAGGCCTC |
| 410678 | 2-13-5 | 353 | 2001 | 2020 | 0 | GTCCTCAGGGAACCAGGCCT |
| 410679 | 2-13-5 | 50 | 2002 | 2021 | 0 | GGTCCTCAGGGAACCAGGCC |
| 410680 | 2-13-5 | 354 | 2003 | 2022 | 0 | TGGTCCTCAGGGAACCAGGC |
| 410681 | 2-13-5 | 355 | 2004 | 2023 | 0 | CTGGTCCTCAGGGAACCAGG |
| 410682 | 2-13-5 | 356 | 2005 | 2024 | 0 | GCTGGTCCTCAGGGAACCAG |
| 410713 | 2-13-5 | 60 | 2355 | 2374 | 0 | CTTTGCATTCCAGACCTGGG |
| 410714 | 2-13-5 | 411 | 2356 | 2375 | 0 | ACTTTGCATTCCAGACCTGG |
| 410715 | 2-13-5 | 412 | 2357 | 2376 | 0 | GACTTTGCATTCCAGACCTG |
| 410716 | 2-13-5 | 413 | 2358 | 2377 | 0 | TGACTTTGCATTCCAGACCT |
| 410717 | 2-13-5 | 414 | 2359 | 2378 | 0 | TTGACTTTGCATTCCAGACC |
| 410718 | 2-13-5 | 61 | 2360 | 2379 | 0 | CTTGACTTTGCATTCCAGAC |
| 410719 | 2-13-5 | 419 | 2560 | 2579 | 0 | CAGATGGCAACGGCTGTCAC |
| 410720 | 2-13-5 | 420 | 2561 | 2580 | 0 | GCAGATGGCAACGGCTGTCA |
| 410721 | 2-13-5 | 421 | 2562 | 2581 | 0 | AGCAGATGGCAACGGCTGTC |
| 410722 | 2-13-5 | 422 | 2563 | 2582 | 0 | CAGCAGATGGCAACGGCTGT |
| 410723 | 2-13-5 | 423 | 2564 | 2583 | 0 | GCAGCAGATGGCAACGGCTG |
| 410724 | 2-13-5 | 62 | 2565 | 2584 | 0 | GGCAGCAGATGGCAACGGCT |
| 410725 | 2-13-5 | 424 | 2566 | 2585 | 0 | CGGCAGCAGATGGCAACGGC |
| 410726 | 2-13-5 | 425 | 2567 | 2586 | 0 | CCGGCAGCAGATGGCAACGG |
| 410727 | 2-13-5 | 426 | 2568 | 2587 | 0 | TCCGGCAGCAGATGGCAACG |
| 410728 | 2-13-5 | 427 | 2569 | 2588 | 0 | CTCCGGCAGCAGATGGCAAC |
| 410729 | 2-13-5 | 428 | 2570 | 2589 | 0 | GCTCCGGCAGCAGATGGCAA |

The following embodiments set forth target regions of PCSK9 nucleic acids. Also illustrated are examples of antisense compounds targeted to the target regions. It is understood that the sequence set forth in each SEQ ID NO is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

In certain embodiments, antisense compounds target a range of a PCSK9 nucleic acid. In certain embodiment, such compounds contain at least an 8 nucleotide core sequence in common. In certain embodiments, such compounds sharing at least an 8 nucleotide core sequence targets the following nucleotide regions of SEQ ID NO: 3: 220-253, 290-321, 377-419, 451-615, 653-672, 741-760, 871-897, 915-934, 968-1017, 1075-1124, 1075-1174, 1144-1174, 1275-1302, 1315-1341, 1351-1389, 1351-1447, 1365-1439, 1390-1417, 1390-1429, 1390-1439, 1399-1425, 1408-1435, 1420-1447, 1453-1482, 1490-1516, 1490-1564, 1500-1526, 1515-1541, 1527-1553, 1527-1554, 1528-1554, 1529-1555, 1529-1556, 1530-1556, 1530-1557, 1531-1557, 1532-1551, 1532-1558, 1533-1559, 1534-1559, 1535-1559, 1536-1559, 1537-1564, 1566-1602, 1566-1681, 1606-1626, 1618-1645, 1626-1653, 1684-1703, 1730-1781, 1740-1767, 1749-1775, 1758-1781, 1820-1847, 1820-1877, 1822-2198, 1830-1856, 1839-1865, 1840-1867, 1898-1924, 1898-2035, 1903-2127, 1907-1934, 1911-1938, 1946-1971, 1954-1980, 1959-2035, 1959-2057, 1963-1988, 1967-2035, 1972-1999, 1982-2008, 1991-2018, 1993-2019, 1995-2022, 1996-2023, 1997-2024, 1998-2025, 1999-2025, 2000-2025, 2009-2035, 2038-2139, 2061-2139, 2073-2099, 2078-2104, 2105-2131, 2112-2139, 2168-2198, 2170-2177, 2245-2284, 2295-2394, 2355-2381, 2355-2394, 2405-2461, 2560-2587, 2560-2609, 2561-2588, 2562-2589, 2563-2589, 2564-2589, 2565-2589, 2566-2589, 2567-2589, 2568-2589, 2665-2689, 2759-2783, 2837-2880, 2904-2923, 3005-3024, 3005-3174, 3083-3110, 3155-3184, 3238-3268, 3482-3711, or 3727-3751, or 3798-3824.

In certain embodiments, a target region is nucleotides 290-321 of SEQ ID NO: 3. In certain embodiments, an antisense compound is targeted to nucleotides 290-321 of SEQ ID NO: 3. In certain embodiments, an antisense compound targeted to a PCSK9 nucleic acid comprises a nucleotide sequence selected from SEQ ID NOs: 117 or 129. In certain such embodiments, an antisense compound targeted to nucleotides 290-321 of SEQ ID NO: 3 is selected from ISIS NOs: 395202, 399924, 399829 or 399985.

In certain embodiments, a target region is nucleotides 220-253 of SEQ ID NO: 3. In certain embodiments, an antisense compound is targeted to nucleotides 220-253 of SEQ ID NO: 3. In certain embodiments, an antisense compound targeted to a PCSK9 nucleic acid comprises a nucleotide sequence selected from SEQ ID NOs: 100 or 116. In certain such embodiments, an antisense compound targeted to nucleotides 220-253 of SEQ ID NO: 3 is selected from ISIS NOs: 399827, 399983, 399828 or 399984.

In certain embodiments, a target region is nucleotides 377-419 of SEQ ID NO: 3. In certain embodiments, an antisense compound is targeted to nucleotides 377-419 of SEQ ID NO: 3. In certain embodiments, an antisense compound targeted to a PCSK9 nucleic acid comprises a nucleotide sequence selected from SEQ ID NOs: 81 or 110. In certain such embodiments, an antisense compound targeted to nucleotides 377-419 of SEQ ID NO: 3 is selected from ISIS NOs: 399830, 399986, 395203 or 399925.

In certain embodiments, a target region is nucleotides 451-615 of SEQ ID NO: 3. In certain embodiments, an antisense compound is targeted to nucleotides 451-615 of SEQ ID NO: 3. In certain embodiments, an antisense compound targeted to a PCSK9 nucleic acid comprises a nucleotide sequence selected from SEQ ID NOs: 152, 140, 137 or 136. In certain such embodiments, an antisense compound targeted to nucleotides 451-615 of SEQ ID NO: 3 is selected from ISIS NOs: 395204, 399926, 399831, 399987, 395205, 399927, 399832, 399988, 395206 or 399928.

In certain embodiments, a target region is nucleotides 653-672 of SEQ ID NO: 3. In certain embodiments, an antisense compound is targeted to nucleotides 653-672 of SEQ ID NO: 3. In certain embodiments, an antisense compound targeted to a PCSK9 nucleic acid comprises a nucleotide sequence selected from SEQ ID NOs: 132. In certain such embodiments, an antisense compound targeted to nucleotides 653-672 of SEQ ID NO: 3 is selected from ISIS NOs: 395207 or 399929.

In certain embodiments, a target region is nucleotides 741-760 of SEQ ID NO: 3. In certain embodiments, an antisense compound is targeted to nucleotides 741-760 of SEQ ID NO: 3. In certain embodiments, an antisense compound targeted to a PCSK9 nucleic acid comprises a nucleotide sequence selected from SEQ ID NOs: 139. In certain such embodiments, an antisense compound targeted to nucleotides 741-760 of SEQ ID NO: 3 is selected from ISIS NOs: 395208 or 399930.

In certain embodiments, a target region is nucleotides 871-897 of SEQ ID NO: 3. In certain embodiments, an antisense compound is targeted to nucleotides 871-897 of SEQ ID NO: 3. In certain embodiments, an antisense compound targeted to a PCSK9 nucleic acid comprises a nucleotide sequence selected from SEQ ID NOs: 92 or 142. In certain such embodiments, an antisense compound targeted to nucleotides 871-897 of SEQ ID NO: 3 is selected from ISIS NOs: 399833, 399989, 395209 or 399931.

In certain embodiments, a target region is nucleotides 915-934 of SEQ ID NO: 3. In certain embodiments, an antisense compound is targeted to nucleotides 915-934 of SEQ ID NO: 3. In certain embodiments, an antisense compound targeted to a PCSK9 nucleic acid comprises a nucleotide sequence selected from SEQ ID NOs: 113. In certain such embodiments, an antisense compound targeted to nucleotides 915-934 of SEQ ID NO: 3 is selected from ISIS NOs: 395210 or 399932.

In certain embodiments, a target region is nucleotides 968-1017 of SEQ ID NO: 3. In certain embodiments, an antisense compound is targeted to nucleotides 968-1017 of SEQ ID NO: 3. In certain embodiments, an antisense compound targeted to a PCSK9 nucleic acid comprises a nucleotide sequence selected from SEQ ID NOs: 98 or 138. In certain such embodiments, an antisense compound targeted to nucleotides 968-1017 of SEQ ID NO: 3 is selected from ISIS NOs: 395211, 399933, 395212, or 399934.

In certain embodiments, a target region is nucleotides 1075-1124 of SEQ ID NO: 3. In certain embodiments, an antisense compound is targeted to nucleotides 1075-1124 of SEQ ID NO: 3. In certain embodiments, an antisense compound targeted to a PCSK9 nucleic acid comprises a nucleotide sequence selected from SEQ ID NOs: 96 or 124. In certain such embodiments, an antisense compound targeted to nucleotides 1075-1124 of SEQ ID NO: 3 is selected from ISIS NOs: 395213, 399935, 395214, or 399936.

In certain embodiments, a target region is nucleotides 1075-1174 of SEQ ID NO: 3. In certain embodiments, an antisense compound is targeted to nucleotides 1075-1174 of SEQ ID NO: 3. In certain embodiments, an antisense compound targeted to a PCSK9 nucleic acid comprises a nucleotide sequence selected from SEQ ID NOs: 82, 96, 103, 124, or 133. In certain such embodiments, an antisense compound targeted to nucleotides 1075-1174 of SEQ ID NO: 3 is selected from ISIS NOs: 395213, 399935, 395214, 399936, 399834, 399990, 395215, 399937, 395216, or 399938.

In certain embodiments, a target region is nucleotides 1144-1174 of SEQ ID NO: 3. In certain embodiments, an antisense compound is targeted to nucleotides 1144-1174 of SEQ ID NO: 3. In certain embodiments, an antisense compound targeted to a PCSK9 nucleic acid comprises a nucleotide sequence selected from SEQ ID NOs: 82, 133 or 103. In certain such embodiments, an antisense compound targeted to nucleotides 1144-1174 of SEQ ID NO: 3 is selected from ISIS NOs: 399834, 399990, 395215, 399937, 395216 or 399938.

In certain embodiments, a target region is nucleotides 1275-1302 of SEQ ID NO: 3. In certain embodiments, an antisense compound is targeted to nucleotides 1275-1302 of SEQ ID NO: 3. In certain embodiments, an antisense compound targeted to a PCSK9 nucleic acid comprises a nucleotide sequence selected from SEQ ID NOs: 155 or 156. In certain such embodiments, an antisense compound targeted to nucleotides 1275-1302 of SEQ ID NO: 3 is selected from ISIS NOs: 395217, 399939, 399835 or 399991.

In certain embodiments, a target region is nucleotides 1315-1341 of SEQ ID NO: 3. In certain embodiments, an antisense compound is targeted to nucleotides 1315-1341 of SEQ ID NO: 3. In certain embodiments, an antisense compound targeted to a PCSK9 nucleic acid comprises a nucleotide sequence selected from SEQ ID NOs: 146 or 161. In certain such embodiments, an antisense compound targeted to nucleotides 1315-1341 of SEQ ID NO: 3 is selected from ISIS NOs: 395218, 399940, 395219 or 399941.

In certain embodiments, a target region is nucleotides 1351-1389 of SEQ ID NO: 3. In certain embodiments, an antisense compound is targeted to nucleotides 1351-1389 of SEQ ID NO: 3. In certain embodiments, an antisense compound targeted to a PCSK9 nucleic acid comprises a nucleotide sequence selected from SEQ ID NOs: 215, 216, 19, 217 or 20. In certain such embodiments, an antisense compound targeted to nucleotides 1351-1389 of SEQ ID NO: 3 is selected from ISIS NOs: 410753, 406025, 395160, 399882, 406026, 399797 or 399953.

In certain embodiments, a target region is nucleotides 1351-1447 of SEQ ID NO: 3. In certain embodiments, an antisense compound is targeted to nucleotides 1351-1447 of SEQ ID NO: 3. In certain embodiments, an antisense compound targeted to a PCSK9 nucleic acid comprises a nucleotide sequence selected from SEQ ID NOs: 215, 216, 19, 217, 20, 21, 218, 219, 220, 221, 22, 222, 223, 224, 225, 226, 227, 228, 23, 229, 230, 231, 232, 24, or 233. In certain such embodiments, an antisense compound targeted to nucleotides 1351-1447 of SEQ ID NO: 3 is selected from ISIS NOs: 410753, 406025, 395160, 399882, 406026, 399797, 399953, 395161, 399883, 405869, 405870, 405871, 405872, 399798, 399954, 405873, 405874, 405875, 405876, 406027, 406028, 406029, 399799, 399955, 406030, 406031, 410733, 406032, 395162, 399884 or 410754.

In certain embodiments, a target region is nucleotides 1365-1439 of SEQ ID NO: 3. In certain embodiments, an antisense compound is targeted to nucleotides 1365-1439 of SEQ ID NO: 3. In certain embodiments, an antisense compound targeted to a PCSK9 nucleic acid comprises a nucleotide sequence selected from SEQ ID NOs: 19, 20, 21, 22, 23, 24, 217, 218, 219, 220, 221, 222, 223, 224, 225, 226, 227, 228, 229, 230, 231, or 232. In certain such embodiments, an antisense compound targeted to nucleotides 1365-1439 of SEQ ID NO: 3 is selected from ISIS NOs: 395160, 399882, 406026, 399797, 399953, 395161, 399883, 405869, 405870, 405871, 405872, 399798, 399954, 405873, 405874, 405875, 405876, 406027, 406028, 406029, 399799, 399955, 406030, 406031, 410733, 406032, 395162, or 399884.

In certain embodiments, a target region is nucleotides 1390-1417 of SEQ ID NO: 3. In certain embodiments, an antisense compound is targeted to nucleotides 1390-1417 of SEQ ID NO: 3. In certain embodiments, an antisense compound targeted to a PCSK9 nucleic acid comprises a nucleotide sequence selected from SEQ ID NOs: 21, 218, 219, 220, 221, 22, 222 or 223. In certain such embodiments, an antisense compound targeted to nucleotides 1390-1417 of SEQ ID NO: 3 is selected from ISIS NOs: 395161, 399883, 405869, 405870, 405871, 405872, 399798, 399954, 405873 or 405874.

In certain embodiments, a target region is nucleotides 1390-1429 of SEQ ID NO: 3. In certain embodiments, an antisense compound is targeted to nucleotides 1390-1429 of SEQ ID NO: 3. In certain embodiments, an antisense compound targeted to a PCSK9 nucleic acid comprises a nucleotide sequence selected from SEQ ID NOs: 21, 22, 23, 217, 218, 219, 220, 221, 222, 223, 224, 225, 226, 227, or 228. In certain such embodiments, an antisense compound targeted to nucleotides 1390-1429 of SEQ ID NO: 3 is selected from ISIS NOs: 395160, 399882, 406026, 399797, 399953, 395161, 399883, 405869, 405870, 405871, 405872, 399798, 399954, 405873, 405874, 405875, 405876, 406027, 406028, 406029, 399799, or 399955.

In certain embodiments, a target region is nucleotides 1390-1439 of SEQ ID NO: 3. In certain embodiments, an antisense compound is targeted to nucleotides 1390-1439 of SEQ ID NO: 3. In certain embodiments, an antisense compound targeted to a PCSK9 nucleic acid comprises a nucleotide sequence selected from SEQ ID NOs: 21, 22, 23, 24, 217, 218, 219, 220, 221, 222, 223, 224, 225, 226, 227, 228, 229, 230, 231, or 232. In certain such embodiments, an antisense compound targeted to nucleotides 1390-1439 of SEQ ID NO: 3 is selected from ISIS NOs: 395160, 399882, 406026, 399797, 399953, 395161, 399883, 405869, 405870, 405871, 405872, 399798, 399954, 405873, 405874, 405875, 405876, 406027, 406028, 406029, 399799, 399955, 406030, 406031, 410733, 406032, 395162, or 399884.

In certain embodiments, a target region is nucleotides 1399-1425 of SEQ ID NO: 3. In certain embodiments, an antisense compound is targeted to nucleotides 1399-1425 of SEQ ID NO: 3. In certain embodiments, an antisense compound targeted to a PCSK9 nucleic acid comprises a nucleotide sequence selected from SEQ ID NOs: 224, 225, 226 or 227. In certain such embodiments, an antisense compound targeted to nucleotides 1399-1425 of SEQ ID NO: 3 is selected from ISIS NOs: 405875, 405876, 406027 or 406028.

In certain embodiments, a target region is nucleotides 1408-1435 of SEQ ID NO: 3. In certain embodiments, an antisense compound is targeted to nucleotides 1408-1435 of SEQ ID NO: 3. In certain embodiments, an antisense compound targeted to a PCSK9 nucleic acid comprises a nucleotide sequence selected from SEQ ID NOs: 228, 23, 229, 230 or 231. In certain such embodiments, an antisense compound targeted to nucleotides 1408-1435 of SEQ ID NO: 3 is selected from ISIS NOs: 406029, 399799, 399955, 406030, 406031 or 410733.

In certain embodiments, a target region is nucleotides 1420-1447 of SEQ ID NO: 3. In certain embodiments, an antisense compound is targeted to nucleotides 1420-1447 of SEQ ID NO: 3. In certain embodiments, an antisense compound targeted to a PCSK9 nucleic acid comprises a nucleotide sequence selected from SEQ ID NOs: 24 or 233. In certain such embodiments, an antisense compound targeted to nucleotides 1420-1447 of SEQ ID NO: 3 is selected from ISIS NOs: 395162, 399884 or 410754.

In certain embodiments, a target region is nucleotides 1453-1482 of SEQ ID NO: 3. In certain embodiments, an antisense compound is targeted to nucleotides 1453-1482 of SEQ ID NO: 3. In certain embodiments, an antisense compound targeted to a PCSK9 nucleic acid comprises a nucleotide sequence selected from SEQ ID NOs: 25 or 234. In certain such embodiments, an antisense compound targeted to nucleotides 1453-1482 of SEQ ID NO: 3 is selected from ISIS NOs: 395163, 399885 or 410755.

In certain embodiments, a target region is nucleotides 1490-1516 of SEQ ID NO: 3. In certain embodiments, an antisense compound is targeted to nucleotides 1490-1516 of SEQ ID NO: 3. In certain embodiments, an antisense compound targeted to a PCSK9 nucleic acid comprises a nucleotide sequence selected from SEQ ID NOs: 235, 236, or 237. In certain such embodiments, an antisense compound targeted to nucleotides 1490-1516 of SEQ ID NO: 3 is selected from ISIS NOs: 410756, 405604, or 406033.

In certain embodiments, a target region is nucleotides 1490-1564 of SEQ ID NO: 3. In certain embodiments, an antisense compound is targeted to nucleotides 1490-1564 of SEQ ID NO: 3. In certain embodiments, an antisense compound targeted to a PCSK9 nucleic acid comprises a nucleotide sequence selected from SEQ ID NOs: 235, 236, 237, 26, 238, 27, 239, 240, 241, 242, 243, 244, 245, 246, 247, 248, 249, 447, 28, 250, 251, 252, 253, 254, 255, or 256. In certain such embodiments, an antisense compound targeted to nucleotides 1490-1564 of SEQ ID NO: 3 is selected from ISIS NOs: 410756, 405604, 406033, 395164, 399886, 406034, 399800, 399956, 406035, 410757, 406036, 406037, 410536, 410583, 410658, 410537, 410584, 410659, 406038, 410585, 410660, 405877, 410586, 410661, 405878, 410587, 410662, 405879, 410588, 410663, 405880, 410589, or 410758.

In certain embodiments, a target region is nucleotides 1500-1526 of SEQ ID NO: 3. In certain embodiments, an antisense compound is targeted to nucleotides 1500-1526 of SEQ ID NO: 3. In certain embodiments, an antisense compound targeted to a PCSK9 nucleic acid comprises a nucleotide sequence selected from SEQ ID NOs: 26, 238, 27, or 239. In certain such embodiments, an antisense compound targeted to nucleotides 1500-1526 of SEQ ID NO: 3 is selected from ISIS NOs: 395164, 399886, 406034, 399800, 399956, or 406035.

In certain embodiments, a target region is nucleotides 1515-1541 of SEQ ID NO: 3. In certain embodiments, an antisense compound is targeted to nucleotides 1515-1541 of SEQ ID NO: 3. In certain embodiments, an antisense compound targeted to a PCSK9 nucleic acid comprises a nucleotide sequence selected from SEQ ID NOs: 240, 241, or 242. In certain such embodiments, an antisense compound targeted to nucleotides 1515-1541 of SEQ ID NO: 3 is selected from ISIS NOs: 399886, 406034, 399800, 399956, or 406035.

In certain embodiments, a target region is nucleotides 1527-1553 of SEQ ID NO: 3. In certain embodiments, an antisense compound is targeted to nucleotides 1527-1553 of SEQ ID NO: 3. In certain embodiments, an antisense compound targeted to a PCSK9 nucleic acid comprises a nucleotide sequence selected from SEQ ID NOs: 243, 244, 245, 246, 247, 248, 447, 28 or 249. In certain such embodiments, an antisense compound targeted to nucleotides 1527-1553 of SEQ ID NO: 3 is selected from ISIS NOs: 410536, 410583, 410658, 410537, 410584, 410659, 406038, 410585, 410660, 405877, 410586, 410661, 405878, 410587, 410662, 405879, 410588, 410663, 405880, 410589, 410664, 395165, 399887, or 410665.

In certain embodiments, a target region is nucleotides 1527-1554 of SEQ ID NO: 3. In certain embodiments, an antisense compound is targeted to nucleotides 1527-1554 of SEQ ID NO: 3. In certain embodiments, an antisense compound targeted to a PCSK9 nucleic acid comprises a nucleotide sequence selected from SEQ ID NOs: 243, 244, 245, 246, 247, 248, 249, 447, 28, or 250. In certain such embodiments, an antisense compound targeted to nucleotides 1527-1554 of SEQ ID NO: 3 is selected from ISIS NOs: 410536, 410583, 410658, 410537, 410584, 410659, 406038, 410585, 410660, 405877, 410586, 410661, 405878, 410587, 410662, 405879, 410588, 410663, 405880, 410589, 410664, 395165, 399887, 405881, 410590, 410666, or 410665.

In certain embodiments, a target region is nucleotides 1528-1554 of SEQ ID NO: 3. In certain embodiments, an antisense compound is targeted to nucleotides 1528-1554 of SEQ ID NO: 3. In certain embodiments, an antisense compound targeted to a PCSK9 nucleic acid comprises a nucleotide sequence selected from SEQ ID NOs: 244, 245, 246, 247, 248, 249, 447, 28, or 250. In certain such embodiments, an antisense compound targeted to nucleotides 1528-1554 of SEQ ID NO: 3 is selected from ISIS NOs: 410537, 410584, 410659, 406038, 410585, 410660, 405877, 410586, 410661, 405878, 410587, 410662, 405879, 410588, 410663, 405880, 410589, 410664, 395165, 399887, 409126, 410665, or 405881.

In certain embodiments, a target region is nucleotides 1529-1555 of SEQ ID NO: 3. In certain embodiments, an antisense compound is targeted to nucleotides 1529-1555 of SEQ ID NO: 3. In certain embodiments, an antisense compound targeted to a PCSK9 nucleic acid comprises a nucleotide sequence selected from SEQ ID NOs: 245, 246, 247, 248, 249, 447, 28, 250 or 251. In certain such embodiments, an antisense compound targeted to nucleotides 1529-1555 of SEQ ID NO: 3 is selected from ISIS NOs: 406038, 395165, 399887, 405877, 405878, 405879, 405880, 405881, 405882, 409126, 410585, 410586, 410587, 410588, 410589, 410590, 410591, 410660, 410661, 410662, 410663, 410664, 410665, 410666, 410667, or 410667.

In certain embodiments, a target region is nucleotides 1529-1556 of SEQ ID NO: 3. In certain embodiments, an antisense compound is targeted to nucleotides 1529-1556 of SEQ ID NO: 3. In certain embodiments, an antisense compound targeted to a PCSK9 nucleic acid comprises a nucleotide sequence selected from SEQ ID NOs: 245, 246, 247, 248, 249, 447, 28, 250, 251, or 252. In certain such embodiments, an antisense compound targeted to nucleotides 1529-1556 of SEQ ID NO: 3 is selected from ISIS NOs: 406038, 395165, 399887, 405877, 405878, 405879, 405880, 405881, 405882, 405883, 409126, 410585, 410586, 410587, 410588, 410589, 410590, 410591, 410592, 410660, 410661, 410662, 410663, 410664, 410665, 410666, 410667, or 410668.

In certain embodiments, a target region is nucleotides 1530-1556 of SEQ ID NO: 3. In certain embodiments, an antisense compound is targeted to nucleotides 1530-1556 of SEQ ID NO: 3. In certain embodiments, an antisense compound targeted to a PCSK9 nucleic acid comprises a nucleotide sequence selected from SEQ ID NOs: 246, 247, 248, 249, 447, 28, 250, 251, or 252. In certain such embodiments, an antisense compound targeted to nucleotides 1530-1556 of SEQ ID NO: 3 is selected from ISIS NOs: 406038, 395165, 399887, 405877, 405878, 405879, 405880, 405881, 405882, 405883, 409126, 410585, 410586, 410587, 410588, 410589, 410590, 410591, 410592, 410660, 410661, 410662, 410663, 410664, 410665, 410666, 410667, 405884, 410593, 410669 or 410668.

In certain embodiments, a target region is nucleotides 1530-1557 of SEQ ID NO: 3. In certain embodiments, an antisense compound is targeted to nucleotides 1530-1557 of SEQ ID NO: 3. In certain embodiments, an antisense compound targeted to a PCSK9 nucleic acid comprises a nucleotide sequence selected from SEQ ID NOs: 28, 246, 247, 248, 249, 250, 251, 252, 253, or 447. In certain such embodiments, an antisense compound targeted to nucleotides 1530-1557 of SEQ ID NO: 3 is selected from ISIS NOs: 395165, 399887, 405877, 405878, 405879, 405880, 405881, 405882, 405883, 405884, 409126, 410586, 410587, 410588, 410589, 410590, 410591, 410592, 410593, 410661, 410662, 410663, 410664, 410665, 410666, 410667, 410668, or 410669.

In certain embodiments, a target region is nucleotides 1531-1557 of SEQ ID NO: 3. In certain embodiments, an antisense compound is targeted to nucleotides 1531-1557 of SEQ ID NO: 3. In certain embodiments, an antisense compound targeted to a PCSK9 nucleic acid comprises a nucleotide sequence selected from SEQ ID NOs: 28, 247, 248, 249, 250, 251, 252, 253, or 447. In certain such embodiments, an antisense compound targeted to nucleotides 1531-1557 of SEQ ID NO: 3 is selected from ISIS NOs: 395165, 399887, 405878, 405879, 405880, 405881, 405882, 405883, 405884, 409126, 410587, 410588, 410589, 410590, 410591, 410592, 410593, 410662, 410663, 410664, 410665, 410666, 410667, 410668, or 410669.

In certain embodiments, a target region is nucleotides 1532-1551 of SEQ ID NO: 3. In certain embodiments, an antisense compound is targeted to nucleotides 1532-1551 of SEQ ID NO: 3. In one such embodiment, an antisense compound targeted to nucleotides 1532-1551 of SEQ ID NO: 3 is ISIS NO: 405879.

In certain embodiments, a target region is nucleotides 1532-1558 of SEQ ID NO: 3. In certain embodiments, an antisense compound is targeted to nucleotides 1532-1558 of SEQ ID NO: 3. In certain embodiments, an antisense compound targeted to a PCSK9 nucleic acid comprises a nucleotide sequence selected from SEQ ID NOs: 28, 248, 249, 250, 251, 252, 253, 254 or 447. In certain such embodiments, an antisense compound targeted to nucleotides 1532-1558 of SEQ ID NO: 3 is selected from ISIS NOs: 405879, 410588, 410663, 405880, 410589, 410664, 395165, 399887, 410665, 405881, 410590, 410666, 405882, 410591, 410667, 405883, 410592, 410668, 405884, 410593, 410669, 410538, 410594, or 410670.

In certain embodiments, a target region is nucleotides 1533-1559 of SEQ ID NO: 3. In certain embodiments, an antisense compound is targeted to nucleotides 1533-1559 of SEQ ID NO: 3. In certain embodiments, an antisense compound targeted to a PCSK9 nucleic acid comprises a nucleotide sequence selected from SEQ ID NOs: 28, 249, 250, 251, 252, 253, 254, 255 or 447. In certain such embodiments, an antisense compound targeted to nucleotides 1533-1559 of SEQ ID NO: 3 is selected from ISIS NOs: 405880, 410589, 410664, 395165, 399887, 410665, 405881, 410590, 410666, 405882, 410591, 410667, 405883, 410592, 410668, 405884, 410593, 410669, 410538, 410594, 410670, 410539, 410595, or 410671.

In certain embodiments, a target region is nucleotides 1534-1559 of SEQ ID NO: 3. In certain embodiments, an antisense compound is targeted to nucleotides 1534-1559 of SEQ ID NO: 3. In certain embodiments, an antisense compound targeted to a PCSK9 nucleic acid comprises a nucleotide sequence selected from SEQ ID NOs: 28, 250, 251, 252, 253, 254, 255 or 447. In certain such embodiments, an antisense compound targeted to nucleotides 1534-1559 of SEQ ID NO: 3 is selected from ISIS NOs: 395165, 399887, 410665, 405881, 410590, 410666, 405882, 410591, 410667, 405883, 410592, 410668, 405884, 410593, 410669, 410538, 410594, 410670, or 410671.

In certain embodiments, a target region is nucleotides 1535-1559 of SEQ ID NO: 3. In certain embodiments, an antisense compound is targeted to nucleotides 1535-1559 of SEQ ID NO: 3. In certain embodiments, an antisense compound targeted to a PCSK9 nucleic acid comprises a nucleotide sequence selected from SEQ ID NOs: 250, 251, 252, 253, 254, 255 or 447. In certain such embodiments, an antisense compound targeted to nucleotides 1535-1559 of SEQ ID NO: 3 is selected from ISIS NOs: 405881, 410590, 410666, 405882, 410591, 410667, 405883, 410592, 410668, 405884, 410593, 410669, 410538, 410594 or 410671.

In certain embodiments, a target region is nucleotides 1536-1559 of SEQ ID NO: 3. In certain embodiments, an antisense compound is targeted to nucleotides 1536-1559 of SEQ ID NO: 3. In certain embodiments, an antisense compound targeted to a PCSK9 nucleic acid comprises a nucleotide sequence selected from SEQ ID NOs: 251, 252, 253, 254, or 255. In certain such embodiments, an antisense compound targeted to nucleotides 1536-1559 of SEQ ID NO: 3 is selected from ISIS NOs: 405882, 410591, 410667, 405883, 410592, 410668, 405884, 410593, 410669, 410538, 410594, 410670, 410539, 410595, or 410671.

In certain embodiments, a target region is nucleotides 1537-1564 of SEQ ID NO: 3. In certain embodiments, an antisense compound is targeted to nucleotides 1537-1564 of SEQ ID NO: 3. In certain embodiments, an antisense compound targeted to a PCSK9 nucleic acid comprises a nucleotide sequence selected from SEQ ID NOs: 251, 252, 253, 254, 255, or 256. In certain such embodiments, an antisense compound targeted to nucleotides 1537-1564 of SEQ ID NO: 3 is selected from ISIS NOs: 405882, 410591, 410667, 405883, 410592, 410668, 405884, 410593, 410669, 410538, 410594, 410670, 410539, 410595, 410671, or 410758.

In certain embodiments, a target region is nucleotides 1566-1602 of SEQ ID NO: 3. In certain embodiments, an antisense compound is targeted to nucleotides 1566-1602 of SEQ ID NO: 3. In certain embodiments, an antisense compound targeted to a PCSK9 nucleic acid comprises a nucleotide sequence selected from SEQ ID NOs: 29, 30, 31, 32, 257, 258, 259, 260, 261, or 262. In certain such embodiments, an antisense compound targeted to nucleotides 1566-1602 of SEQ ID NO: 3 is selected from ISIS NOs: 395166, 395167, 395168, 399801, 399888, 399889, 399890, 399957, 405909, 405910, 405911, 405912, 406039, 406040, 406041, 406042, 406043, or 406044.

In certain embodiments, a target region is nucleotides 1566-1681 of SEQ ID NO: 3. In certain embodiments, an antisense compound is targeted to nucleotides 1566-1681 of SEQ ID NO: 3. In certain embodiments, an antisense compound targeted to a PCSK9 nucleic acid comprises a nucleotide sequence selected from SEQ ID NOs: 29, 30, 31, 32, 257, 258, 259, 260, 261, 262, 263, 264, 265, 266, 267, 268, 269, 270, 271, or 272. In certain such embodiments, an antisense compound targeted to nucleotides 1566-1681 of SEQ ID NO: 3 is selected from ISIS NOs: 395166, 395167, 395168, 399801, 399888, 399889, 399890, 399957, 405909, 405910, 405911, 405912, 406039, 406040, 406041, 406042, 406043, 406044, 406045, 408642, 410759, 410760, 410761, or 410762.

In certain embodiments, a target region is nucleotides 1606-1626 of SEQ ID NO: 3. In certain embodiments, an antisense compound is targeted to nucleotides 1606-1626 of SEQ ID NO: 3. In certain embodiments, an antisense compound targeted to a PCSK9 nucleic acid comprises a nucleotide sequence selected from SEQ ID NOs: 264 or 31. In certain such embodiments, an antisense compound targeted to nucleotides 1606-1626 of SEQ ID NO: 3 is selected from ISIS NOs: 408642, 395167, or 399889.

In certain embodiments, a target region is nucleotides 1618-1645 of SEQ ID NO: 3. In certain embodiments, an antisense compound is targeted to nucleotides 1618-1645 of SEQ ID NO: 3. In certain embodiments, an antisense compound targeted to a PCSK9 nucleic acid comprises a nucleotide sequence selected from SEQ ID NOs: 265 or 266. In certain such embodiments, an antisense compound targeted to nucleotides 1618-1645 of SEQ ID NO: 3 is selected from ISIS NOs: 410760 or 406045.

In certain embodiments, a target region is nucleotides 1626-1653 of SEQ ID NO: 3. In certain embodiments, an antisense compound is targeted to nucleotides 1626-1653 of SEQ ID NO: 3. In certain embodiments, an antisense compound targeted to a PCSK9 nucleic acid comprises a nucleotide sequence selected from SEQ ID NOs: 32, 266, 267, 268, or 269. In certain such embodiments, an antisense compound targeted to nucleotides 1626-1653 of SEQ ID NO: 3 is selected from ISIS NOs: 395168, 399890, 405909, 405910, 405911, or 406045.

In certain embodiments, a target region is nucleotides 1684-1703 of SEQ ID NO: 3. In certain embodiments, an antisense compound is targeted to nucleotides 1684-1703 of SEQ ID NO: 3. In certain embodiments, an antisense compound targeted to a PCSK9 nucleic acid comprises a nucleotide sequence selected from SEQ ID NOs: 273. In certain such embodiments, an antisense compound targeted to nucleotides 1684-1703 of SEQ ID NO: 3 is selected from ISIS NOs: 410763.

In certain embodiments, a target region is nucleotides 1730-1781 of SEQ ID NO: 3. In certain embodiments, an antisense compound is targeted to nucleotides 1730-1781 of SEQ ID NO: 3. In certain embodiments, an antisense compound targeted to a PCSK9 nucleic acid comprises a nucleotide sequence selected from SEQ ID NOs: 33, 33, 274, 275, 276, 277, 278, 279, 280, 281, 282, 283, 284, or 285. In certain such embodiments, an antisense compound targeted to nucleotides 1730-1781 of SEQ ID NO: 3 is selected from ISIS NOs: 395169, 399891, 405913, 405914, 405915, 405916, 405917, 405918, 405919, 405920, 405921, 405922, 410734, or 410764.

In certain embodiments, a target region is nucleotides 1740-1767 of SEQ ID NO: 3. In certain embodiments, an antisense compound is targeted to nucleotides 1740-1767 of SEQ ID NO: 3. In certain embodiments, an antisense compound targeted to a PCSK9 nucleic acid comprises a nucleotide sequence selected from SEQ ID NOs: 33, 275, 276, 277, or 278. In certain such embodiments, an antisense compound targeted to nucleotides 1740-1767 of SEQ ID NO: 3 is selected from ISIS NOs: 395169, 399891, 405913, 405914, 405915, or 405916.

In certain embodiments, a target region is nucleotides 1749-1775 of SEQ ID NO: 3. In certain embodiments, an antisense compound is targeted to nucleotides 1749-1775 of SEQ ID NO: 3. In certain embodiments, an antisense compound targeted to a PCSK9 nucleic acid comprises a nucleotide sequence selected from SEQ ID NOs: 279, 280, 281 or 282. In certain such embodiments, an antisense compound targeted to nucleotides 1749-1775 of SEQ ID NO: 3 is selected from ISIS NOs: 410734, 405917, 405918 or 405919.

In certain embodiments, a target region is nucleotides 1758-1781 of SEQ ID NO: 3. In certain embodiments, an antisense compound is targeted to nucleotides 1758-1781 of SEQ ID NO: 3. In certain embodiments, an antisense compound targeted to a PCSK9 nucleic acid comprises a nucleotide sequence selected from SEQ ID NOs: 283, 284, or 285. In certain such embodiments, an antisense compound targeted to nucleotides 1758-1781 of SEQ ID NO: 3 is selected from ISIS NOs: 405920, 405921, or 405922.

In certain embodiments, a target region is nucleotides 1820-1847 of SEQ ID NO: 3. In certain embodiments, an antisense compound is targeted to nucleotides 1820-1847 of SEQ ID NO: 3. In certain embodiments, an antisense compound targeted to a PCSK9 nucleic acid comprises a nucleotide sequence selected from SEQ ID NOs: 39, 306, 307, 308, or 309. In certain such embodiments, an antisense compound targeted to nucleotides 1820-1847 of SEQ ID NO: 3 is selected from ISIS NOs: 395175, 399897, 405937, 405938, 405939, or 405940.

In certain embodiments, a target region is nucleotides 1820-1877 of SEQ ID NO: 3. In certain embodiments, an antisense compound is targeted to nucleotides 1820-1877 of SEQ ID NO: 3. In certain embodiments, an antisense compound targeted to a PCSK9 nucleic acid comprises a nucleotide sequence selected from SEQ ID NOs: 39, 40, 41, 306, 307, 308, 309, 310, 311, 312, 313, 314, 315, 316, 317, or 318. In certain such embodiments, an antisense compound targeted to nucleotides 1820-1877 of SEQ ID NO: 3 is selected from ISIS NOs: 395175, 399804, 399805, 399897, 399960, 399961, 405937, 405938, 405939, 405940, 405941, 405942, 405943, 405944, 405945, 405946, 405947, 410737, or 410769.

In certain embodiments, a target region is nucleotides 1822-2198 of SEQ ID NO: 3. In certain embodiments, an antisense compound is targeted to nucleotides 1822-2198 of SEQ ID NO: 3. In certain embodiments, an antisense compound targeted to a PCSK9 nucleic acid comprises a nucleotide sequence selected from SEQ ID NOs: 39, 307, 308, 309, 310, 40, 311, 312, 313, 314, 315, 41, 41, 316, 317, 318, 101, 319, 42, 320, 321, 322, 43, 323, 324, 325, 326, 327, 328, 329, 330, 331, 332, 333, 334, 44, 335, 336, 337, 45, 338, 46, 339, 340, 47, 341, 342, 48, 343, 344, 345, 346, 347, 3, or 366. In certain such embodiments, an antisense compound targeted to nucleotides 1822-2198 of SEQ ID NO: 3 is selected from ISIS NOs: 395175, 399897, 405938, 405939, 405940, 405941, 399804, 399960, 405942, 405943, 410737, 405944, 405945, 399805, 399961, 405946, 405947, 410769, 395176, 399898, 405948, 399806, 399962, 405949, 405950, 405951, 399807, 399963, 405952, 410738, 405953, 405954, or 405979.

In certain embodiments, a target region is nucleotides 1830-1856 of SEQ ID NO: 3. In certain embodiments, an antisense compound is targeted to nucleotides 1830-1856 of SEQ ID NO: 3. In certain embodiments, an antisense compound targeted to a PCSK9 nucleic acid comprises a nucleotide sequence selected from SEQ ID NOs: 40, 310, 311, or 312. In certain such embodiments, an antisense compound targeted to nucleotides 1830-1856 of SEQ ID NO: 3 is selected from ISIS NOs: 399804, 399960, 405941, 405942, or 405943.

In certain embodiments, a target region is nucleotides 1839-1865 of SEQ ID NO: 3. In certain embodiments, an antisense compound is targeted to nucleotides 1839-1865 of SEQ ID NO: 3. In certain embodiments, an antisense compound targeted to a PCSK9 nucleic acid comprises a nucleotide sequence selected from SEQ ID NOs: 41, 313, 314, 315, or 316. In certain such embodiments, an antisense compound targeted to nucleotides 1839-1865 of SEQ ID NO: 3 is selected from ISIS NOs: 399805, 399961, 405944, 405945, 405946, or 410737.

In certain embodiments, a target region is nucleotides 1840-1867 of SEQ ID NO: 3. In certain embodiments, an antisense compound is targeted to nucleotides 1840-1867 of SEQ ID NO: 3. In certain embodiments, an antisense compound targeted to a PCSK9 nucleic acid comprises a nucleotide sequence selected from SEQ ID NOs: 314, 315, 316, or 317. In certain such embodiments, an antisense compound targeted to nucleotides 1840-1867 of SEQ ID NO: 3 is selected from ISIS NOs: 399961, 405944, 405945, 405946, 410737, or 405947.

In certain embodiments, a target region is nucleotides 1898-1924 of SEQ ID NO: 3. In certain embodiments, an antisense compound is targeted to nucleotides 1898-1924 of SEQ ID NO: 3. In certain embodiments, an antisense compound targeted to a PCSK9 nucleic acid comprises a nucleotide sequence selected from SEQ ID NOs: 42, 101, 319, or 320. In certain such embodiments, an antisense compound targeted to nucleotides 1898-1924 of SEQ ID NO: 3 is selected from ISIS NOs: 395176, 399898, 405948, 399806, 399962, 405949, or 405949.

In certain embodiments, a target region is nucleotides 1898-2035 of SEQ ID NO: 3. In certain embodiments, an antisense compound is targeted to nucleotides 1898-2035 of SEQ ID NO: 3. In certain embodiments, an antisense compound targeted to a PCSK9 nucleic acid comprises a nucleotide sequence selected from SEQ ID NOs: 42, 43, 44, 45, 46, 47, 48, 49, 50, 51, 87, 101, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, or 359. In certain such embodiments, an antisense compound targeted to nucleotides 1898-2035 of SEQ ID NO: 3 is selected from ISIS NOs: 395176, 395177, 395178, 395179, 399806, 399807, 399808, 399809, 399810, 399811, 399812, 399813, 399898, 399899, 399900, 399901, 399962, 399963, 399964, 399965, 399966, 399967, 399968, 399969, 405885, 405886, 405887, 405888, 405889, 405890, 405891, 405892, 405948, 405949, 405950, 405951, 405952, 405953, 405954, 405955, 405956, 405957, 405958, 405959, 405960, 405961, 405962, 405963, 405964, 405965, 405966, 405967, 405968, 405969, 405970, 405971, 405972, 405973, 405974, 408653, 410540, 410596, 410597, 410598, 410599, 410600, 410601, 410602, 410603, 410604, 410672, 410673, 410674, 410675, 410676, 410677, 410678, 410679, 410680, 410681, 410682, 410738, 410739, 410740, or 410770.

In certain embodiments, a target region is nucleotides 1903-2127 of SEQ ID NO: 3. In certain embodiments, an antisense compound is targeted to nucleotides 1903-2127 of SEQ ID NO: 3. In certain embodiments, an antisense compound targeted to a PCSK9 nucleic acid comprises a nucleotide sequence selected from SEQ ID NOs: 42, 320, 321, 322, 43, 323, 324, 325, 326, 327, 328, 329, 330, 331, 332, 333, 334, 44, 335, 336, 337, 45, 338, 46, 339, 340, 47, 341, 342, 48, 343, 344, 345, 346, 347, 348, 349, 49, 350, 351, 352, 353, 50, 354, 355, 356, 357, 87, 358, 359, 51, 119, 360, or 54. In certain such embodiments, an antisense compound targeted to nucleotides 1903-2127 of SEQ ID NO: 3 is selected from ISIS NOs: 399806, 399962, 405949, 405950, 405951, 399807, 399963, 405952, 410738, 405953, 405954, 410770, 405955, 405956, 405957, 405958, 405959, 405960, 405961, 399808, 399964, 405962, 410739, 405963, 395177, 399899, 405964, 399809, 399965, 405965, 405966, 399810, or 399967.

In certain embodiments, a target region is nucleotides 1907-1934 of SEQ ID NO: 3. In certain embodiments, an antisense compound is targeted to nucleotides 1907-1934 of SEQ ID NO: 3. In certain embodiments, an antisense compound targeted to a PCSK9 nucleic acid comprises a nucleotide sequence selected from SEQ ID NOs: 43, 321, 322, 323, or 324. In certain such embodiments, an antisense compound targeted to nucleotides 1907-1934 of SEQ ID NO: 3 is selected from ISIS NOs: 405950, 405951, 399807, 399963, 405952, or 410738.

In certain embodiments, a target region is nucleotides 1911-1938 of SEQ ID NO: 3. In certain embodiments, an antisense compound is targeted to nucleotides 1911-1938 of SEQ ID NO: 3. In certain embodiments, an antisense compound targeted to a PCSK9 nucleic acid comprises a nucleotide sequence selected from SEQ ID NOs: 43, 323, 324, 325, or 326. In certain such embodiments, an antisense compound targeted to nucleotides 1911-1938 of SEQ ID NO: 3 is selected from ISIS NOs: 399807, 399963, 405952, 410738, 405953, or 405954.

In certain embodiments, a target region is nucleotides 1946-1971 of SEQ ID NO: 3. In certain embodiments, an antisense compound is targeted to nucleotides 1946-1971 of SEQ ID NO: 3. In certain embodiments, an antisense compound targeted to a PCSK9 nucleic acid comprises a nucleotide sequence selected from SEQ ID NOs: 328, 329, 330, or 331. In certain such embodiments, an antisense compound targeted to nucleotides 1946-1971 of SEQ ID NO: 3 is selected from ISIS NOs: 405955, 405956, 405957, or 405958.

In certain embodiments, a target region is nucleotides 1954-1980 of SEQ ID NO: 3. In certain embodiments, an antisense compound is targeted to nucleotides 1954-1980 of SEQ ID NO: 3. In certain embodiments, an antisense compound targeted to a PCSK9 nucleic acid comprises a nucleotide sequence selected from SEQ ID NOs: 44, 332, 333, 334, or 335. In certain such embodiments, an antisense compound targeted to nucleotides 1954-1980 of SEQ ID NO: 3 is selected from ISIS NOs: 405959, 405960, 405961, 399808, 399964, or 405962.

In certain embodiments, a target region is nucleotides 1959-2035 of SEQ ID NO: 3. In certain embodiments, an antisense compound is targeted to nucleotides 1959-2035 of SEQ ID NO: 3. In certain embodiments, an antisense compound targeted to a PCSK9 nucleic acid comprises a nucleotide sequence selected from SEQ ID NOs: 44, 335, 336, 337, 45, 338, 46, 339, 340, 47, 341, 342, 48, 343, 344, 345, 346, 347, 348, 349, 49, 350, 351, 352, 353, 50, 354, 355, 356, 357, 87, 358, 359, or 51. In certain such embodiments, an antisense compound targeted to nucleotides 1959-2035 of SEQ ID NO: 3 is selected from ISIS NOs: 399808, 399964, 405962, 410739, 405963, 395177, 399899, 405964, 399809, 399965, 405965, 405966, 399810, 399966, 405967, 405968, 399811, 399967, 405969, 405970, 410740, 405885, 405886, 405887, 410596, 410672, 405888, 410597, 410673, 399812, 399968, 410674, or 399969.

In certain embodiments, a target region is nucleotides 1959-2057 of SEQ ID NO: 3. In certain embodiments, an antisense compound is targeted to nucleotides 1959-2057 of SEQ ID NO: 3. In certain embodiments, an antisense compound targeted to a PCSK9 nucleic acid comprises a nucleotide sequence selected from SEQ ID NOs: 44, 335, 336, 337, 45, 338, 46, 339, 340, 47, 341, 342, 48, 343, 344, 345, 346, 347, 348, 349, 49, 350, 351, 352, 353, 50, 354, 355, 356, 357, 87, 358, 359, 51, or 119. In certain such embodiments, an antisense compound targeted to nucleotides 1959-2057 of SEQ ID NO: 3 is selected from ISIS NOs: 399808, 399964, 405962, 410739, 405963, 395177, 399899, 405964, 399809, 399965, 405965, 405966, 399810, 399966, 405967, 405968, 399811, 399967, 405969, 405970, 410740, 405885, 405886, 405887, 410596, 410672, 405888, 410597, 410673, 399812, 399968, 410674, or 399902.

In certain embodiments, a target region is nucleotides 1963-1988 of SEQ ID NO: 3. In certain embodiments, an antisense compound is targeted to nucleotides 1963-1988 of SEQ ID NO: 3. In certain embodiments, an antisense compound targeted to a PCSK9 nucleic acid comprises a nucleotide sequence selected from SEQ ID NOs: 45, 336, 337 or 338. In certain such embodiments, an antisense compound targeted to nucleotides 1963-1988 of SEQ ID NO: 3 is selected from ISIS NOs: 410739, 405963, 395177, 399899, or 405964.

In certain embodiments, a target region is nucleotides 1967-2035 of SEQ ID NO: 3. In certain embodiments, an antisense compound is targeted to nucleotides 1967-2035 of SEQ ID NO: 3. In certain embodiments, an antisense compound targeted to a PCSK9 nucleic acid comprises a nucleotide sequence selected from SEQ ID NOs: 45, 338, 46, 339, 340, 47, 341, 342, 48, 343, 344, 345, 346, 347, 348, 349, 49, 350, 351, 352, 353, 50, 354, 355, 356, 357, 87, 358, 359 or 51. In certain such embodiments, an antisense compound targeted to nucleotides 1967-2035 of SEQ ID NO: 3 is selected from ISIS NOs: 395177, 399899, 405964, 399809, 399965, 405965, 405966, 399810, 399966, 405967, 405968, 399811, 399967, 405969, 405970, 410740, 405885, 405886, 405887, 410596, 410672, 405888, 410597, 410673, 399812, 399968, 410674, 405889, 410598, 410675, 405890, 410599, or 399969.

In certain embodiments, a target region is nucleotides 1972-1999 of SEQ ID NO: 3. In certain embodiments, an antisense compound is targeted to nucleotides 1972-1999 of SEQ ID NO: 3. In certain embodiments, an antisense compound targeted to a PCSK9 nucleic acid comprises a nucleotide sequence selected from SEQ ID NOs: 46, 47, 339, 340, or 341. In certain such embodiments, an antisense compound targeted to nucleotides 1972-1999 of SEQ ID NO: 3 is selected from ISIS NOs: 399809, 399965, 405965, 405966, 399810, 399966, or 405967.

In certain embodiments, a target region is nucleotides 1982-2008 of SEQ ID NO: 3. In certain embodiments, an antisense compound is targeted to nucleotides 1982-2008 of SEQ ID NO: 3. In certain embodiments, an antisense compound targeted to a PCSK9 nucleic acid comprises a nucleotide sequence selected from SEQ ID NOs: 48, 342, 343, or 344. In certain such embodiments, an antisense compound targeted to nucleotides 1982-2008 of SEQ ID NO: 3 is selected from ISIS NOs: 405968, 399811, 399967, 405969, or 405970.

In certain embodiments, a target region is nucleotides 1991-2018 of SEQ ID NO: 3. In certain embodiments, an antisense compound is targeted to nucleotides 1991-2018 of SEQ ID NO: 3. In certain embodiments, an antisense compound targeted to a PCSK9 nucleic acid comprises a nucleotide sequence selected from SEQ ID NOs: 49, 345, 346, 347, 348, 349, 350, or 351. In certain such embodiments, an antisense compound targeted to nucleotides 1991-2018 of SEQ ID NO: 3 is selected from ISIS NOs: 399812, 399968, 405885, 405886, 405887, 405888, 405889, 405890, 410596, 410597, 410598, 410599, 410672, 410673, 410674, 410675, 410676, or 410740.

In certain embodiments, a target region is nucleotides 1993-2019 of SEQ ID NO: 3. In certain embodiments, an antisense compound is targeted to nucleotides 1993-2019 of SEQ ID NO: 3. In certain embodiments, an antisense compound targeted to a PCSK9 nucleic acid comprises a nucleotide sequence selected from SEQ ID NOs: 49, 346, 347, 348, 349, 350, or 354. In certain such embodiments, an antisense compound targeted to nucleotides 1993-2019 of SEQ ID NO: 3 is selected from ISIS NOs: 405885, 405887, 410596, 410672, 405888, 410597, 410673, 399812, 399968, 410674, 405889, 410598, 410675, 405890, 410599, 410676, 405891, 410600, or 410677.

In certain embodiments, a target region is nucleotides 1995-2022 of SEQ ID NO: 3. In certain embodiments, an antisense compound is targeted to nucleotides 1995-2022 of SEQ ID NO: 3. In certain embodiments, an antisense compound targeted to a PCSK9 nucleic acid comprises a nucleotide sequence selected from SEQ ID NOs: 348, 349, 350, 351, 352, 353, 50, or 351 In certain such embodiments, an antisense compound targeted to nucleotides 1995-2022 of SEQ ID NO: 3 is selected from ISIS NOs: 405887, 410596, 410672, 405888, 410597, 410673, 399812, 399968, 410674, 405889, 410598, 410675, 405890, 410599, 410676, 405891, 410600, 405892, 410601, 410678, 395178, 399900, 410679, 408653, 410602, or 410680.

In certain embodiments, a target region is nucleotides 1996-2023 of SEQ ID NO: 3. In certain embodiments, an antisense compound is targeted to nucleotides 1996-2023 of SEQ ID NO: 3. In certain embodiments, an antisense compound targeted to a PCSK9 nucleic acid comprises a nucleotide sequence selected from SEQ ID NOs: 49, 50, 349, 350, 351, 352, 353, 354, or 355. In certain such embodiments, an antisense compound targeted to nucleotides 1996-2023 of SEQ ID NO: 3 is selected from ISIS NOs: 395178, 399812, 399900, 399968, 405888, 405889, 405890, 405891, 405892, 405971, 408653, 410597, 410598, 410599, 410600, 410601, 410602, 410603, 410673, 410674, 410675, 410676, 410677, 410678, 410679, 410680, or 410681.

In certain embodiments, a target region is nucleotides 1997-2024 of SEQ ID NO: 3. In certain embodiments, an antisense compound is targeted to nucleotides 1997-2024 of SEQ ID NO: 3. In certain embodiments, an antisense compound targeted to a PCSK9 nucleic acid comprises a nucleotide sequence selected from SEQ ID NOs: 49, 50, 350, 351, 352, 353, 354, 355, or 356. In certain such embodiments, an antisense compound targeted to nucleotides 1997-2024 of SEQ ID NO: 3 is selected from ISIS NOs: 399812, 399968, 410674, 405889, 410598, 410675, 405890, 410599, 410676, 405891, 410600, 410677, 405892, 410601, 410678, 395178, 399900, 410679, 408653, 410602, 410680, 405971, 410603, 410681, 410540, 410604, or 410682.

In certain embodiments, a target region is nucleotides 1998-2025 of SEQ ID NO: 3. In certain embodiments, an antisense compound is targeted to nucleotides 1998-2025 of SEQ ID NO: 3. In certain embodiments, an antisense compound targeted to a PCSK9 nucleic acid comprises a nucleotide sequence selected from SEQ ID NOs: 50, 350, 351, 352, 353, 354, 355, 356 or 357. In certain such embodiments, an antisense compound targeted to nucleotides 1998-2025 of SEQ ID NO: 3 is selected from ISIS NOs: 405889, 410598, 410675, 405890, 410599, 410676, 405891, 410600, 410677, 405892, 410601, 410678, 395178, 399900, 410679, 408653, 410602, 410680, 405971, 410603, 410681, 410540, 410604, 410682, or 405972.

In certain embodiments, a target region is nucleotides 1999-2025 of SEQ ID NO: 3. In certain embodiments, an antisense compound is targeted to nucleotides 1999-2025 of SEQ ID NO: 3. In certain embodiments, an antisense compound targeted to a PCSK9 nucleic acid comprises a nucleotide sequence selected from SEQ ID NOs: 50, 351, 352, 353, 354, 355, 356, or 357. In certain such embodiments, an antisense compound targeted to nucleotides 1999-2025 of SEQ ID NO: 3 is selected from ISIS NOs: 405889, 410598, 410675, 405890, 410599, 410676, 405891, 410600, 410677, 405892, 410601, 410678, 395178, 399900, 410679, 408653, 410602, 410680, 405971, 410603, 410681, 410540, 410604, 410682, or 405972.

In certain embodiments, a target region is nucleotides 2000-2025 of SEQ ID NO: 3. In certain embodiments, an antisense compound is targeted to nucleotides 2000-2025 of SEQ ID NO: 3. In certain embodiments, an antisense compound targeted to a PCSK9 nucleic acid comprises a nucleotide sequence selected from SEQ ID NOs: 351, 352, 353, 354, 355, 356, or 357. In certain such embodiments, an antisense compound targeted to nucleotides 2000-2025 of SEQ ID NO: 3 is selected from ISIS NOs: 405890, 410599, 410676, 405891, 410600, 410677, 405892, 410601, 410678, 395178, 399900, 410679, 408653, 410602, 410680, 405971, 410603, 410681, 410540, 410604, 410682, or 405972.

In certain embodiments, a target region is nucleotides 2009-2035 of SEQ ID NO: 3. In certain embodiments, an antisense compound is targeted to nucleotides 2009-2035 of SEQ ID NO: 3. In certain embodiments, an antisense compound targeted to a PCSK9 nucleic acid comprises a nucleotide sequence selected from SEQ ID NOs: 51, 87, 358, or 359. In certain such embodiments, an antisense compound targeted to nucleotides 2009-2035 of SEQ ID NO: 3 is selected from ISIS NOs: 395179, 399813, 399901, 399969, 405973, or 405974.

In certain embodiments, a target region is nucleotides 2038-2139 of SEQ ID NO: 3. In certain embodiments, an antisense compound is targeted to nucleotides 2038-2139 of SEQ ID NO: 3. In certain embodiments, an antisense compound targeted to a PCSK9 nucleic acid comprises a nucleotide sequence selected from SEQ ID NOs: 52, 53, 54, 104, 119, 130, 360, 361, 362, 363, 365, 366, 367, 368, 369, 370, or 371. In certain such embodiments, an antisense compound targeted to nucleotides 2038-2139 of SEQ ID NO: 3 is selected from ISIS NOs: 395180, 395181, 395182, 395220, 399814, 399836, 399902, 399903, 399904, 399942, 399970, 399992, 405975, 405976, 405977, 405978, 405979, 405980, 405981, 405982, 405983, 410741, or 410771.

In certain embodiments, a target region is nucleotides 2061-2139 of SEQ ID NO: 3. In certain embodiments, an antisense compound is targeted to nucleotides 2061-2139 of SEQ ID NO: 3. In certain embodiments, an antisense compound targeted to a PCSK9 nucleic acid comprises a nucleotide sequence selected from SEQ ID NOs: 52, 53, 54, 104, 130, 360, 361, 362, 363, 365, 366, 367, 368, 369, 370, or 371. In certain such embodiments, an antisense compound targeted to nucleotides 2061-2139 of SEQ ID NO: 3 is selected from ISIS NOs: 395181, 395182, 395220, 399814, 399836, 399903, 399904, 399942, 399970, 399992, 405975, 405976, 405977, 405978, 405979, 405980, 405981, 405982, 405983, 410741, or 410771.

In certain embodiments, a target region is nucleotides 2073-2099 of SEQ ID NO: 3. In certain embodiments, an antisense compound is targeted to nucleotides 2073-2099 of SEQ ID NO: 3. In certain embodiments, an antisense compound targeted to a PCSK9 nucleic acid comprises a nucleotide sequence selected from SEQ ID NOs: 52, 53, 361, or 362. In certain such embodiments, an antisense compound targeted to nucleotides 2073-2099 of SEQ ID NO: 3 is selected from ISIS NOs: 395181, 399814, 399903, 399970, 405975, or 405976.

In certain embodiments, a target region is nucleotides 2078-2104 of SEQ ID NO: 3. In certain embodiments, an antisense compound is targeted to nucleotides 2078-2104 of SEQ ID NO: 3. In certain embodiments, an antisense compound targeted to a PCSK9 nucleic acid comprises a nucleotide sequence selected from SEQ ID NOs: 53, 104, 362, or 363. In certain such embodiments, an antisense compound targeted to nucleotides 2078-2104 of SEQ ID NO: 3 is selected from ISIS NOs: 395220, 399814, 399942, 399970, 405976, or 405977.

In certain embodiments, a target region is nucleotides 2105-2131 of SEQ ID NO: 3. In certain embodiments, an antisense compound is targeted to nucleotides 2105-2131 of SEQ ID NO: 3. In certain embodiments, an antisense compound targeted to a PCSK9 nucleic acid comprises a nucleotide sequence selected from SEQ ID NOs: 54, 365, 366, or 367. In certain such embodiments, an antisense compound targeted to nucleotides 2105-2131 of SEQ ID NO: 3 is selected from ISIS NOs: 395182, 399904, 405978, 405979, or 405980.

In certain embodiments, a target region is nucleotides 2112-2139 of SEQ ID NO: 3. In certain embodiments, an antisense compound is targeted to nucleotides 2112-2139 of SEQ ID NO: 3. In certain embodiments, an antisense compound targeted to a PCSK9 nucleic acid comprises a nucleotide sequence selected from SEQ ID NOs: 367, 368, 369, 370, or 371. In certain such embodiments, an antisense compound targeted to nucleotides 2112-2139 of SEQ ID NO: 3 is selected from ISIS NOs: 405980, 405981, 410741, 405982, or 405983.

In certain embodiments, a target region is nucleotides 2168-2198 of SEQ ID NO: 3. In certain embodiments, an antisense compound is targeted to nucleotides 2168-2198 of SEQ ID NO: 3. In certain embodiments, an antisense compound targeted to a PCSK9 nucleic acid comprises a nucleotide sequence selected from SEQ ID NOs: 55, 56, 372, 373, 374, or 375. In certain such embodiments, an antisense compound targeted to nucleotides 2168-2198 of SEQ ID NO: 3 is selected from ISIS NOs: 399815, 399816, 399971, 399972, 405641, 405984, 405985, 405986, or 405987.

In certain embodiments, a target region is nucleotides 2170-2177 of SEQ ID NO: 3. In certain embodiments, an antisense compound is targeted to nucleotides 2170-2177 of SEQ ID NO: 3. In certain embodiments, an antisense compound targeted to a PCSK9 nucleic acid comprises a nucleotide sequence selected from SEQ ID NOs: 55, 373, 374, or 375. In certain such embodiments, an antisense compound targeted to nucleotides 2170-2177 of SEQ ID NO: 3 is selected from ISIS NOs: 399815, 399971, 405641, 405985, 405986, or 405987.

In certain embodiments, a target region is nucleotides 2245-2284 of SEQ ID NO: 3. In certain embodiments, an antisense compound is targeted to nucleotides 2245-2284 of SEQ ID NO: 3. In certain embodiments, an antisense compound targeted to a PCSK9 nucleic acid comprises a nucleotide sequence selected from SEQ ID NOs: 408 or 409. In certain such embodiments, an antisense compound targeted to nucleotides 2245-2284 of SEQ ID NO: 3 is selected from ISIS NOs: 410776 or 410777.

In certain embodiments, a target region is nucleotides 2295-2394 of SEQ ID NO: 3. In certain embodiments, an antisense compound is targeted to nucleotides 2295-2394 of SEQ ID NO: 3. In certain embodiments, an antisense compound targeted to a PCSK9 nucleic acid comprises a nucleotide sequence selected from SEQ ID NOs: 60, 61, 410, 411, 412, 413, 414, 415, or 416. In certain such embodiments, an antisense compound targeted to nucleotides 2295-2394 of SEQ ID NO: 3 is selected from ISIS NOs: 395186, 399817, 399908, 399973, 405996, 405997, 410562, 410563, 410564, 410633, 410634, 410635, 410636, 410713, 410714, 410715, 410716, 410717, 410718, 410778, or 410779.

In certain embodiments, a target region is nucleotides 2355-2381 of SEQ ID NO: 3. In certain embodiments, an antisense compound is targeted to nucleotides 2355-2381 of SEQ ID NO: 3. In certain embodiments, an antisense compound targeted to a PCSK9 nucleic acid comprises a nucleotide sequence selected from SEQ ID NOs: 60, 61, 411, 412, 413, 414, or 415. In certain such embodiments, an antisense compound targeted to nucleotides 2355-2381 of SEQ ID NO: 3 is selected from ISIS NOs: 395186, 399817, 399908, 399973, 405996, 405997, 410562, 410563, 410564, 410633, 410634, 410635, 410636, 410713, 410714, 410715, 410716, 410717, or 410718.

In certain embodiments, a target region is nucleotides 2355-2394 of SEQ ID NO: 3. In certain embodiments, an antisense compound is targeted to nucleotides 2355-2394 of SEQ ID NO: 3. In certain embodiments, an antisense compound targeted to a PCSK9 nucleic acid comprises a nucleotide sequence selected from SEQ ID NOs: 60, 61, 411, 412, 413, 414, 415, or 416. In certain such embodiments, an antisense compound targeted to nucleotides 2355-2394 of SEQ ID NO: 3 is selected from ISIS NOs: 395186, 399817, 399908, 399973, 405996, 405997, 410562, 410563, 410564, 410633, 410634, 410635, 410636, 410713, 410714, 410715, 410716, 410717, or 410779.

In certain embodiments, a target region is nucleotides 2405-2461 of SEQ ID NO: 3. In certain embodiments, an antisense compound is targeted to nucleotides 2405-2461 of SEQ ID NO: 3. In certain embodiments, an antisense compound targeted to a PCSK9 nucleic acid comprises a nucleotide sequence selected from SEQ ID NOs: 417 or 418. In certain such embodiments, an antisense compound targeted to nucleotides 2405-2461 of SEQ ID NO: 3 is selected from ISIS NOs: 410780 or 410781.

In certain embodiments, a target region is nucleotides 2560-2587 of SEQ ID NO: 3. In certain embodiments, an antisense compound is targeted to nucleotides 2560-2587 of SEQ ID NO: 3. In certain embodiments, an antisense compound targeted to a PCSK9 nucleic acid comprises a nucleotide sequence selected from SEQ ID NOs: 62, 419, 420, 421, 422, 423, 424, 425, or 426. In certain such embodiments, an antisense compound targeted to nucleotides 2560-2587 of SEQ ID NO: 3 is selected from ISIS NOs: 395187, 399909, 405998, 410565, 410566, 410567, 410568, 410569, 410570, 410571, 410637, 410638, 410639, 410640, 410641, 410642, 410643, 410644, 410719, 410720, 410721, 410722, 410723, 410724, 410725, 410726, or 410727.

In certain embodiments, a target region is nucleotides 2560-2609 of SEQ ID NO: 3. In certain embodiments, an antisense compound is targeted to nucleotides 2560-2609 of SEQ ID NO: 3. In certain embodiments, an antisense compound targeted to a PCSK9 nucleic acid comprises a nucleotide sequence selected from SEQ ID NOs: 62, 419, 420, 421, 422, 423, 424, 425, 426, 427, 428, 429, or 430. In certain such embodiments, an antisense compound targeted to nucleotides 2560-2609 of SEQ ID NO: 3 is selected from ISIS NOs: 395187, 399909, 405998, 410565, 410566, 410567, 410568, 410569, 410570, 410571, 410572, 410573, 410637, 410638, 410639, 410640, 410641, 410642, 410643, 410644, 410645, 410646, 410719, 410720, 410721, 410722, 410723, 410724, 410725, 410726, 410727, 410728, or 410783.

In certain embodiments, a target region is nucleotides 2561-2588 of SEQ ID NO: 3. In certain embodiments, an antisense compound is targeted to nucleotides 2561-2588 of SEQ ID NO: 3. In certain embodiments, an antisense compound targeted to a PCSK9 nucleic acid comprises a nucleotide sequence selected from SEQ ID NOs: 420, 421, 422, 423, 424, 425, 426, 427, or 62. In certain such embodiments, an antisense compound targeted to nucleotides 2561-2588 of SEQ ID NO: 3 is selected from ISIS NOs: 410566, 410638, 410720, 410567, 410639, 410721, 410568, 410640, 410722, 410569, 410641, 410723, 395187, 399909, 410724, 410570, 410642, 410725, 410571, 410643, 410726, 405988, 405998, 410644, 410727, 410572, 410645, or 410728.

In certain embodiments, a target region is nucleotides 2562-2589 of SEQ ID NO: 3. In certain embodiments, an antisense compound is targeted to nucleotides 2562-2589 of SEQ ID NO: 3. In certain embodiments, an antisense compound targeted to a PCSK9 nucleic acid comprises a nucleotide sequence selected from SEQ ID NOs: 62, 421, 422, 423, 424, 425, 426, 427, or 428. In certain such embodiments, an antisense compound targeted to nucleotides 2562-2589 of SEQ ID NO: 3 is selected from ISIS NOs: 395187, 399909, 405998, 410567, 410568, 410569, 410570, 410571, 410572, 410573, 410639, 410640, 410641, 410642, 410643, 410644, 410645, 410646, 410721, 410722, 410723, 410724, 410725, 410726, 410727, 410728, or 410729.

In certain embodiments, a target region is nucleotides 2563-2589 of SEQ ID NO: 3. In certain embodiments, an antisense compound is targeted to nucleotides 2563-2589 of SEQ ID NO: 3. In certain embodiments, an antisense compound targeted to a PCSK9 nucleic acid comprises a nucleotide sequence selected from SEQ ID NOs: 422, 423, 424, 425, 426, 427, 428 or 62. In certain such embodiments, an antisense compound targeted to nucleotides 2563-2589 of SEQ ID NO: 3 is selected from ISIS NOs: 410568, 410640, 410722, 410569, 410641, 410723, 395187, 399909, 410724, 410570, 410642, 410725, 410571, 410643, 410726, 405988, 405998, 410644, 410727, 410572, 410645, 410728, 410573, 410646, or 410729.

In certain embodiments, a target region is nucleotides 2564-2589 of SEQ ID NO: 3. In certain embodiments, an antisense compound is targeted to nucleotides 2564-2589 of SEQ ID NO: 3. In certain embodiments, an antisense compound targeted to a PCSK9 nucleic acid comprises a nucleotide sequence selected from SEQ ID NOs: 423, 424, 425, 426, 427, 428 or 62. In certain such embodiments, an antisense compound targeted to nucleotides 2564-2589 of SEQ ID NO: 3 is selected from ISIS NOs: 410569, 410641, 410723, 395187, 399909, 410724, 410570, 410642, 410725, 410571, 410643, 410726, 405988, 405998, 410644, 410727, 410572, 410645, 410728, 410573, 410646, or 410729.

In certain embodiments, a target region is nucleotides 2565-2589 of SEQ ID NO: 3. In certain embodiments, an antisense compound is targeted to nucleotides 2565-2589 of SEQ ID NO: 3. In certain embodiments, an antisense compound targeted to a PCSK9 nucleic acid comprises a nucleotide sequence selected from SEQ ID NOs: 424, 425, 426, 427, 428 or 62. In certain such embodiments, an antisense compound targeted to nucleotides 2565-2589 of SEQ ID NO: 3 is selected from ISIS NOs: 395187, 399909, 410724, 410570, 410642, 410725, 410571, 410643, 410726, 405988, 405998, 410644, 410727, 410572, 410645, 410728, 410573, 410646, or 410729.

In certain embodiments, a target region is nucleotides 2566-2589 of SEQ ID NO: 3. In certain embodiments, an antisense compound is targeted to nucleotides 2566-2589 of SEQ ID NO: 3. In certain embodiments, an antisense compound targeted to a PCSK9 nucleic acid comprises a nucleotide sequence selected from SEQ ID NOs: 424, 425, 426, 427, or 428. In certain such embodiments, an antisense compound targeted to nucleotides 2566-2589 of SEQ ID NO: 3 is selected from ISIS NOs: 410570, 410642, 410725, 410571, 410643, 410726, 405988, 405998, 410644, 410727, 410572, 410645, 410728, 410573, 410646, or 410729.

In certain embodiments, a target region is nucleotides 2567-2589 of SEQ ID NO: 3. In certain embodiments, an antisense compound is targeted to nucleotides 2567-2589 of SEQ ID NO: 3. In certain embodiments, an antisense compound targeted to a PCSK9 nucleic acid comprises a nucleotide sequence selected from SEQ ID NOs: 425, 426, 427, or 428. In certain such embodiments, an antisense compound targeted to nucleotides 2567-2589 of SEQ ID NO: 3 is selected from ISIS NOs: 410571, 410643, 410726, 405988, 405998, 410644, 410727, 410572, 410645, 410728, 410573, 410646, or 410729.

In certain embodiments, a target region is nucleotides 2568-2589 of SEQ ID NO: 3. In certain embodiments, an antisense compound is targeted to nucleotides 2568-2589 of SEQ ID NO: 3. In certain embodiments, an antisense compound targeted to a PCSK9 nucleic acid comprises a nucleotide sequence selected from SEQ ID NOs: 426, 427 or 428. In certain such embodiments, an antisense compound targeted to nucleotides 2568-2589 of SEQ ID NO: 3 is selected from ISIS NOs: 405988, 405998, 410644, 410727, 410572, 410645, 410728, 410573, 410646, or 410729.

In certain embodiments, a target region is nucleotides 2665-2689 of SEQ ID NO: 3. In certain embodiments, an antisense compound is targeted to nucleotides 2665-2689 of SEQ ID NO: 3. In certain embodiments, an antisense compound targeted to a PCSK9 nucleic acid comprises a nucleotide sequence selected from SEQ ID NOs: 63 or 154. In certain such embodiments, an antisense compound targeted to nucleotides 2665-2689 of SEQ ID NO: 3 is selected from ISIS NOs: 395188, 399910, 399818, or 399974.

In certain embodiments, a target region is nucleotides 2759-2783 of SEQ ID NO: 3. In certain embodiments, an antisense compound is targeted to nucleotides 2759-2783 SEQ ID NO: 3. In certain embodiments, an antisense compound targeted to a PCSK9 nucleic acid comprises a nucleotide sequence selected from SEQ ID NOs: 64 or 65. In certain such embodiments, an antisense compound targeted to nucleotides 2759-2783 of SEQ ID NO: 3 is selected from ISIS NOs: 395189, 399911, 399819, or 399975.

In certain embodiments, a target region is nucleotides 2837-2880 of SEQ ID NO: 3. In certain embodiments, an antisense compound is targeted to nucleotides 2837-2880 of SEQ ID NO: 3. In certain embodiments, an antisense compound targeted to a PCSK9 nucleic acid comprises a nucleotide sequence selected from SEQ ID NOs: 66, 67, or 122. In certain such embodiments, an antisense compound targeted to nucleotides 2837-2880 of SEQ ID NO: 3 is selected from ISIS NOs: 399820, 399976, 395190, 399912, 395191, or 399913.

In certain embodiments, a target region is nucleotides 2904-2923 of SEQ ID NO: 3. In certain embodiments, an antisense compound is targeted to nucleotides 2904-2923 SEQ ID NO: 3. In certain embodiments, an antisense compound targeted to a PCSK9 nucleic acid comprises a nucleotide sequence selected from SEQ ID NOs: 153. In certain such embodiments, an antisense compound targeted to nucleotides 2904-2923 of SEQ ID NO: 3 is selected from ISIS NOs: 395192 or 399914.

In certain embodiments, a target region is nucleotides 3005-3024 of SEQ ID NO: 3. In certain embodiments, an antisense compound is targeted to nucleotides 3005-3024 of SEQ ID NO: 3. In certain embodiments, an antisense compound targeted to a PCSK9 nucleic acid comprises a nucleotide sequence selected from SEQ ID NOs: 68. In certain such embodiments, an antisense compound targeted to nucleotides 3005-3024 of SEQ ID NO: 3 is selected from ISIS NOs: 395193 or 399915.

In certain embodiments, a target region is nucleotides 3005-3174 of SEQ ID NO: 3. In certain embodiments, an antisense compound is targeted to nucleotides 3005-3174 of SEQ ID NO: 3. In certain embodiments, an antisense compound targeted to a PCSK9 nucleic acid comprises a nucleotide sequence selected from SEQ ID NOs: 68, 431, 432, 433, 434, 69, 435, 436, 437, 438 or 70. In certain such embodiments, an antisense compound targeted to nucleotides 3005-3174 of SEQ ID NO: 3 is selected from ISIS NOs: 395193, 399915, 405893, 405894, 405895, 405896, 395194, 399916, 405897, 405898, 405899, 405900, 395195, or 399917.

In certain embodiments, a target region is nucleotides 3083-3110 of SEQ ID NO: 3. In certain embodiments, an antisense compound is targeted to nucleotides 3083-3110 of SEQ ID NO: 3. In certain embodiments, an antisense compound targeted to a PCSK9 nucleic acid comprises a nucleotide sequence selected from SEQ ID NOs: 69, 69, 431, 432, 433, 434, 435, 436, 437, or 438. In certain such embodiments, an antisense compound targeted to nucleotides 3083-3110 of SEQ ID NO: 3 is selected from ISIS NOs: 395194, 399916, 405893, 405894, 405895, 405896, 405897, 405898, 405899, or 405900.

In certain embodiments, a target region is nucleotides 3155-3184 of SEQ ID NO: 3. In certain embodiments, an antisense compound is targeted to nucleotides 3155-3184 of SEQ ID NO: 3. In certain embodiments, an antisense compound targeted to a PCSK9 nucleic acid comprises a nucleotide sequence selected from SEQ ID NOs: 70, 71, 439, 440, 441, 442, 443, 444, 445, or 446. In certain such embodiments, an antisense compound targeted to nucleotides 3155-3184 of SEQ ID NO: 3 is selected from ISIS NOs: 395195, 399821, 399917, 399977, 405901, 405902, 405903, 405904, 405905, 405906, 405907, or 405908.

In certain embodiments, a target region is nucleotides 3238-3268 of SEQ ID NO: 3. In certain embodiments, an antisense compound is targeted to nucleotides 3238-3268 of SEQ ID NO: 3. In certain embodiments, an antisense compound targeted to a PCSK9 nucleic acid comprises a nucleotide sequence selected from SEQ ID NOs: 72, 73, or 135. In certain such embodiments, an antisense compound targeted to nucleotides 3238-3268 of SEQ ID NO: 3 is selected from ISIS NOs: 395196, 399822, 399823, 399918, 399978, or 399979.

In certain embodiments, a target region is nucleotides 3482-3711 of SEQ ID NO: 3. In certain embodiments, an antisense compound is targeted to nucleotides 3482-3711 of SEQ ID NO: 3. In certain embodiments, an antisense compound targeted to a PCSK9 nucleic acid comprises a nucleotide sequence selected from SEQ ID NOs: 74, 75, or 112. In certain such embodiments, an antisense compound targeted to nucleotides 3482-3711 of SEQ ID NO: 3 is selected from ISIS NOs: 395197, 395198, 399824, 399919, 399920, or 399980.

In certain embodiments, a target region is nucleotides 3727-3751 of SEQ ID NO: 3. In certain embodiments, an antisense compound is targeted to nucleotides 3727-3751 of SEQ ID NO: 3. In certain embodiments, an antisense compound targeted to a PCSK9 nucleic acid comprises a nucleotide sequence selected from SEQ ID NOs: 76 or 77. In certain such embodiments, an antisense compound targeted to nucleotides 3727-3751 of SEQ ID NO: 3 is selected from ISIS NOs: 395199, 399921, 399825, or 399981.

In certain embodiments, a target region is nucleotides 3798-3824 of SEQ ID NO: 3. In certain embodiments, an antisense compound is targeted to nucleotides 3798-3824 of SEQ ID NO: 3. In certain embodiments, an antisense compound targeted to a PCSK9 nucleic acid comprises a nucleotide sequence selected from SEQ ID NOs: 78 or 99. In certain such embodiments, an antisense compound targeted to nucleotides 3798-3824 of SEQ ID NO: 3 is selected from ISIS NOs: 395200, 399922, 399826, or 399982.

In certain embodiments, short gapmer antisense compounds are targeted to a PCSK9 nucleic acid. In certain such embodiments, gapmer antisense compounds are targeted to SEQ ID NO: 1, SEQ ID NO: 2 and/or SEQ ID NO: 3. In certain such embodiments, the nucleotide sequences illustrated in Table 15.1 have a 2-10-2 gapmer motif. Table 15.1 illustrates gapmer antisense compounds targeted to SEQ ID NO: 1, SEQ ID NO: 2 and/or SEQ ID NO: 3, having a 2-10-2 motif, where the gap segment comprises 2'-deoxynucleotides and each wing segment comprises nucleotides comprising a 2'-O-methoxyethyl sugar modification. Internucleoside linkages are phosphorthioate, and cytidines are 5-methylcytidines.

TABLE 15.1

Gapmer antisense compounds having a 2-10-2 motif targeted to SEQ ID NO: 1, SEQ ID NO: 2 and/or SEQ ID NO: 3

| Target SEQ ID NO | ISIS NO | Motif | OligoSeq | 5' Target Site on SEQ ID NO: 1 | 3' Target Site on SEQ ID NO: 1 | SEQ ID NO |
|---|---|---|---|---|---|---|
| 1 | 406539 | 2-10-2 | GCCTATGAGGGTGC | 1079 | 1092 | 458 |
| 1 | 406540 | 2-10-2 | TCCAGGCCTATGAG | 1084 | 1097 | 459 |
| 1 | 406551 | 2-10-2 | CAGCTCAGCAGCTC | 1735 | 1748 | 460 |
| 1 | 406595 | 2-10-2 | TTAATCAGGGAGCC | 2877 | 2890 | 461 |
| 2 | 406551 | 2-10-2 | CAGCTCAGCAGCTC | 21181 | 21194 | 460 |
| 2 | 406595 | 2-10-2 | TTAATCAGGGAGCC | 26684 | 26697 | 461 |
| 3 | 406539 | 2-10-2 | GCCTATGAGGGTGC | 1609 | 1622 | 458 |
| 3 | 406540 | 2-10-2 | TCCAGGCCTATGAG | 1614 | 1627 | 459 |
| 3 | 406551 | 2-10-2 | CAGCTCAGCAGCTC | 2168 | 2181 | 460 |
| 3 | 406595 | 2-10-2 | TTAATCAGGGAGCC | 3132 | 3145 | 461 |

In a certain embodiment, a short antisense compound has increased potency compared to a 20 nucleotide compound. In a certain embodiment such short antisense compound and 20 nucleotide compound target the same region. In a certain embodiment, a short antisense compound has increased potency compared to a 20 nucleotide compound containing the sequence of the short antisense compound.

In certain embodiments, the desired effect is a reduction in mRNA target nucleic acid levels. In other embodiments, the desired effect is reduction of levels of protein encoded by the target nucleic acid or a phenotypic change associated with the target nucleic acid.

In one embodiment, a target region is a structurally defined region of the nucleic acid. For example, a target region may encompass a 3' UTR, a 5' UTR, an exon, an intron, a coding region, a translation initiation region, translation termination region, or other defined nucleic acid region. In other embodiments, a target region may encompass the sequence from a 5' target site of one target segment within the target region to a 3' target site of another target segment within the target region.

Targeting includes determination of at least one target segment to which an antisense compound hybridizes, such that a desired effect occurs. A target region may contain one or more target segments. Multiple target segments within a target region may be overlapping. Alternatively, they may be non-overlapping. In one embodiment, target segments within a target region are separated by no more than about 10 nucleotides on the target nucleic acid. In another embodiment, target segments within a target region are separated by no more than about 5 nucleotides on the target nucleic acid. In additional embodiments, target segments are contiguous.

Suitable target segments may be found within a 5' UTR, a coding region, a 3' UTR, an intron, or an exon. Target segments containing a start codon or a stop codon are also suitable target segments.

The determination of suitable target segments may include a comparison of the sequence of a target nucleic acid to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences).

There may be variation in activity (e.g., as defined by percent reduction of target nucleic acid levels) of the antisense compounds within an active target region. In one embodiment, reductions in PCSK9 mRNA levels are indicative of inhibition of PCSK9 expression. Reductions in levels of a PCSK9 protein are also indicative of inhibition of target mRNA expression. Further, phenotypic changes are indicative of inhibition of PCSK9 expression. For example, a decrease in LDL-C levels is indicative of inhibition of PCSK9 expression.

Hybridization

For example, hybridization may occur between an antisense compound disclosed herein and a PCSK9 nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In one embodiment, the antisense compounds provided herein are specifically hybridizable with a PCSK9 nucleic acid.

The PCSK9 sequences targeted by some of the preferred antisense compounds disclosed in Table 1 are shown in FIG. 1. The antisense compounds are labeled with the corresponding Isis number. The bar in FIG. 1 labeled "NM_174936.2" displays the relative position of the target sequences within GENBANK® Accession No. NM_174936.2, first deposited with GENBANK® on Jun. 1, 2003 (SEQ ID NO: 1). The bar below that shows the corresponding structural elements of the PCSK9 mRNA, where "CDS" is the protein-encoding region of the mRNA and "UTRs" are the 5' and 3' untranslated regions. As shown in FIG. 1, the sequences targeted by the present antisense compounds are found in the protein-encoding region of the PCSK9 mRNA.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as a PCSK9 nucleic acid).

Non-complementary nucleobases between an antisense compound and a PCSK9 nucleic acid may be tolerated provided that the antisense compound remains able to specifically hybridize to a target nucleic acid. Moreover, an antisense compound may hybridize over one or more segments of a PCSK9 nucleic acid such that intervening or adjacent segments are not involved in the hybridization event (e.g., a loop structure, mismatch or hairpin structure).

In some embodiments, the antisense compounds provided herein are at least 70%, at least 75%, at least 80%, at least 85%, at least 90%, at least 95%, at least 96%, at least 97%, at least 98% or at least 99% complementary to a PCSK9 nucleic acid. Percent complementarity of an antisense compound with a target nucleic acid can be determined using routine methods.

In other embodiments, the antisense compounds provided herein are fully complementary (i.e, 100% complementary) to a target nucleic acid. For example, antisense compound may be fully complementary to a PCSK9 nucleic acid. As used herein, "fully complementary" means each nucleobase of an antisense compound is capable of precise base pairing with the corresponding nucleobases of a target nucleic acid.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e., linked) or non-contiguous. In one embodiment, a non-complementary nucleobase is located in the wing segment of a gapmer antisense oligonucleotide.

In one embodiment, antisense compounds up to 20 nucleobases in length comprise no more than 4, no more than 3, no more than 2 or no more than 1 non-complementary nucleobase(s) relative to a target nucleic acid, such as a PCSK9 nucleic acid.

In another embodiment, antisense compounds up to 30 nucleobases in length comprise no more than 6, no more than 5, no more than 4, no more than 3, no more than 2 or no more than 1 non-complementary nucleobase(s) relative to a target nucleic acid, such as a PCSK9 nucleic acid.

The antisense compounds provided herein also include those which are complementary to a portion of a target nucleic acid. As used herein, "portion" refers to a defined number of contiguous (i.e., linked) nucleobases within a region or segment of a target nucleic acid. A "portion" can also refer to a defined number of contiguous nucleobases of an antisense compound. In one embodiment, the antisense compounds are complementary to at least an 8 nucleobase portion of a target segment. In another embodiment, the antisense compounds are complementary to at least a 12 nucleobase portion of a target segment. In yet another embodiment, the antisense compounds are complementary to at least a 15 nucleobase portion of a target segment.

Identity

The antisense compounds provided herein may also have a defined percent identity to a particular nucleotide sequence, SEQ ID NO, or compound represented by a specific Isis number. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In one embodiment, the antisense compounds are at least 70%, at least 75%, at least 80%, at least 85%, at least 90%, at least 95% or 100% identical to one or more of the antisense compounds disclosed herein.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e., non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In one embodiment, antisense compounds targeted to a PCSK9 nucleic acid comprise one or more modified internucleoside linkages. In some embodiments, the modified internucleoside linkages are phosphorothioate linkages. In other embodiments, each internucleoside linkage of an antisense compound is a phosphorothioate internucleoside linkage.

Modified Sugar Moieties

Antisense compounds targeted to a PCSK9 nucleic acid may contain one or more nucleotides having modified sugar moieties. Sugar modifications may impart nuclease stability, binding affinity or some other beneficial biological property to the antisense compounds. The furanosyl sugar ring of a nucleoside can be modified in a number of ways including, but not limited to: addition of a substituent group, particularly at the 2' position; bridging of two non-geminal ring atoms to form a bicyclic nucleic acid (BNA); and substitution of an atom or group such as —S—, —N(R)— or —C($R_1$)($R_2$) (R=H, C1-C12 alkyl or a protecting group) for the ring oxygen at the 4'-position and combinations of these such as for example a 2'-F-5'-methyl substituted nucleoside (see WO 2008/101157, published Aug. 21, 2008, for other disclosed 5',2'-bis substituted nucleosides) or replacement of the ribosyl ring oxygen atom with S with further substitution at the 2'-position (see U.S. Published Application No. 2005/0130923, published on Jun. 16, 2005) or alternatively 5'-substitution of a BNA (see WO 2007/134181, published Nov. 22, 2007, wherein LNA is substituted with for example a 5'-methyl or a 5'-vinyl group).

Modified sugars include, but are not limited to: substituted sugars, especially 2'-substituted sugars having a 2'-F, 2'-OCH$_3$ (2'-OMe) or a 2'-O(CH$_2$)$_2$—OCH$_3$ (2'-O-methoxyethyl or 2'-MOE) substituent group; and bicyclic modified sugars (BNAs), having a 4'-(CH$_2$)$_n$—O-2' bridge, where n=1 or n=2, including α-L-methyleneoxy (4'-CH2-O-2' or 4'-α-L-(CH2)-O-2' (α-L-LNA)) BNA, β-D-methyleneoxy (4'-CH2-O-2' or 4'-β-D-(CH2)-O-2' (β-D-LNA)) BNA and ethyleneoxy (4'-(CH2)$_2$-O-2' (ENA)) BNA. BNAs also include 4'-(CH2)-S-2' and 4'-C(CH3)2-O-2' (see International Application No. PCT/US2008/068922); 4'-CH(CH3)-O-2' and 4'-CH(CH2OCH3)-O-2' (see U.S. Pat. No. 7,399,845, issued Jul. 15, 2008); 4'-CH2-N(OCH3)-2' (see International Application No. PCT/US2008/064591); 4'-CH2-O—N(CH3)-2' (see U.S. Published Application No. 2004/0171570, published Sep. 2, 2004); 4'-CH2-N(R)—O-2' (see U.S. Pat. No. 7,427,672, issued Sep. 23, 2008); 4'-CH2-C(CH3)-2' and 4'-CH2-C(=CH2)-2' (see International Application No. PCT/US2008/066154); and wherein R is, independently, H, C1-C12 alkyl, or a protecting group. Bicyclic modified sugars also include (6'S)-6'methyl BNA, aminooxy (4'-CH2-O—N(R)-2') BNA, oxyamino (4'-CH2-N(R)—O-2') BNA wherein R is, independently, H, a protecting group or C1-C12 alkyl. Examples of nucleosides having modified sugar moieties also include without limitation nucleosides comprising 5'-vinyl, 5'-methyl (R or S) and 4'-S.

The substituent at the 2' position can also be selected from allyl, amino, azido, thio, O-allyl, O—C1-C10 alkyl, OCF$_3$, O(CH$_2$)$_2$SCH$_3$, O(CH$_2$)$_2$—O—N(Rm)(Rn), and O—CH$_2$—C(=O)—N(Rm)(Rn), where each Rm and Rn is, independently, H or substituted or unsubstituted C1-C10 alkyl.

In certain embodiments, such BNA modified nucleotides are high-affinity nucleotides and their incorporation into antisense compounds allows for increased potency and improved therapeutic index. Methods for the preparations of modified sugars are well known to those skilled in the art.

In certain embodiments, nucleosides are modified by substitution of the ribosyl ring with a sugar surrogate. Such modification includes without limitation, replacement of the ribosyl ring with a surrogate ring system (sometimes referred to as DNA analogs) such as a morpholino ring, a cyclohexenyl ring, a cyclohexyl ring or a tetrahydropyranyl ring such as one having one of the formula:

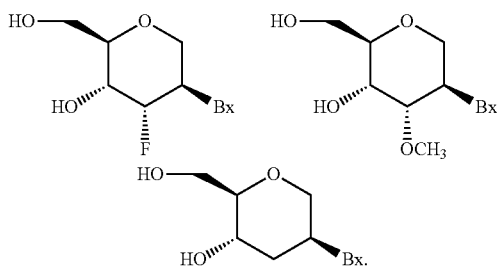

Many other bicyclo and tricyclo sugar surrogate ring systems are also know in the art that can be used to modify nucleosides for incorporation into antisense compounds. Such ring systems can undergo various additional substitutions to enhance activity.

Methods for the preparations of modified sugars are well known to those skilled in the art.

In nucleotides having modified sugar moieties (including substitution of a sugar surrogate), the nucleobase moieties (natural, modified or a combination thereof) are maintained for hybridization with an appropriate nucleic acid target.

In one embodiment, antisense compounds targeted to a PCSK9 nucleic acid comprise one or more nucleotides having modified sugar moieties. In a suitable embodiment, the modified sugar moiety is 2'-MOE. In other embodiments, the 2'-MOE modified nucleotides are arranged in a gapmer motif.

Modified Nucleobases

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications may impart nuclease stability, binding affinity or some other beneficial biological property to antisense compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an antisense compound for a target nucleic acid. For example, 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278).

Additional unmodified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties may also include those in which the purine or pyrimidine base is replaced with other heterocycles, for example 7-deaza-adenine, 7-deazaguanosine, 2-aminopyridine and 2-pyridone. Nucleobases that are particularly useful for increasing the binding affinity of antisense compounds include 5-substituted pyrimidines, 6-azapyrimidines and N-2, N-6 and 0-6 substituted purines, including 2 aminopropyladenine, 5-propynyluracil and 5-propynylcytosine.

In one embodiment, antisense compounds targeted to a PCSK9 nucleic acid comprise one or more modified nucleobases. In an additional embodiment, gap-widened antisense oligonucleotides targeted to a PCSK9 nucleic acid comprise one or more modified nucleobases. In some embodiments, the modified nucleobase is 5-methylcytosine. In further embodiments, each cytosine is a 5-methylcytosine.

Compositions and Methods for Formulating Pharmaceutical Compositions

Antisense oligonucleotides may be admixed with pharmaceutically acceptable active and/or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

Antisense compound targeted to a PCSK9 nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to a PCSK9 nucleic acid and a pharmaceutically acceptable diluent. In one embodiment, the pharmaceutically acceptable diluent is PBS. In other embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

In certain embodiments, pharmaceutical compositions of the present invention comprise one or more oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition of the present invention is prepared using known techniques, including, but not limited to mixing, dissolving, granulating, dragee-making, levigating, emulsifying, encapsulating, entrapping or tabletting processes.

In certain embodiments, a pharmaceutical composition of the present invention is a liquid (e.g., a suspension, elixir and/or solution). In certain of such embodiments, a liquid pharmaceutical composition is prepared using ingredients known in the art, including, but not limited to, water, glycols, oils, alcohols, flavoring agents, preservatives, and coloring agents.

In certain embodiments, a pharmaceutical composition of the present invention is a solid (e.g., a powder, tablet, and/or capsule). In certain of such embodiments, a solid pharmaceutical composition comprising one or more oligonucleotides is prepared using ingredients known in the art, including, but not limited to, starches, sugars, diluents, granulating agents, lubricants, binders, and disintegrating agents.

In certain embodiments, a pharmaceutical composition of the present invention is formulated as a depot preparation. Certain such depot preparations are typically longer acting than non-depot preparations. In certain embodiments, such preparations are administered by implantation (for example subcutaneously or intramuscularly) or by intramuscular injection. In certain embodiments, depot preparations are prepared using suitable polymeric or hydrophobic materials (for example an emulsion in an acceptable oil) or ion exchange resins, or as sparingly soluble derivatives, for example, as a sparingly soluble salt.

In certain embodiments, a pharmaceutical composition of the present invention comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition of the present invention comprises one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, a pharmaceutical composition of the present invention comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™, and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition of the present invention comprises a sustained-release system. A non-limiting example of such a sustained-release system is a semi-permeable matrix of solid hydrophobic polymers. In certain embodiments, sustained-release systems may, depending on their chemical nature, release pharmaceutical agents over a period of hours, days, weeks or months.

In certain embodiments, a pharmaceutical composition of the present invention is prepared for oral administration. In certain of such embodiments, a pharmaceutical composition is formulated by combining one or more oligonucleotides with one or more pharmaceutically acceptable carriers. Certain of such carriers enable pharmaceutical compositions to be formulated as tablets, pills, dragees, capsules, liquids, gels, syrups, slurries, suspensions and the like, for oral ingestion by a subject. In certain embodiments, pharmaceutical compositions for oral use are obtained by mixing oligonucleotide and one or more solid excipient. Suitable excipients include, but are not limited to, fillers, such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In certain embodiments, such a mixture is optionally ground and auxiliaries are optionally added. In certain embodiments, pharmaceutical compositions are formed to obtain tablets or dragee cores. In certain embodiments, disintegrating agents (e.g., cross-linked polyvinyl pyrrolidone, agar, or alginic acid or a salt thereof, such as sodium alginate) are added.

In certain embodiments, dragee cores are provided with coatings. In certain such embodiments, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to tablets or dragee coatings.

In certain embodiments, pharmaceutical compositions for oral administration are push-fit capsules made of gelatin. Certain of such push-fit capsules comprise one or more pharmaceutical agents of the present invention in admixture with one or more filler such as lactose, binders such as starches, and/or lubricants such as talc or magnesium stearate and, optionally, stabilizers. In certain embodiments, pharmaceutical compositions for oral administration are soft, sealed capsules made of gelatin and a plasticizer, such as glycerol or sorbitol. In certain soft capsules, one or more pharmaceutical agents of the present invention are be dissolved or suspended in suitable liquids, such as fatty oils, liquid paraffin, or liquid polyethylene glycols. In addition, stabilizers may be added.

In certain embodiments, pharmaceutical compositions are prepared for buccal administration. Certain of such pharmaceutical compositions are tablets or lozenges formulated in conventional manner.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a pharmaceutical composition is prepared for administration by inhalation. Certain of such pharmaceutical compositions for inhalation are prepared in the form of an aerosol spray in a pressurized pack or a nebulizer. Certain of such pharmaceutical compositions comprise a propellant, e.g., dichlorodifluoromethane, trichlorofluoromethane, dichlorotetrafluoroethane, carbon dioxide or other suitable gas. In certain embodiments using a pressurized aerosol, the dosage unit may be determined with a valve that delivers a metered amount. In certain embodiments, capsules and cartridges for use in an inhaler or insufflator may be formulated. Certain of such formulations comprise a powder mixture of a pharmaceutical agent of the invention and a suitable powder base such as lactose or starch.

In certain embodiments, a pharmaceutical composition is prepared for rectal administration, such as a suppositories or retention enema. Certain of such pharmaceutical compositions comprise known ingredients, such as cocoa butter and/or other glycerides.

In certain embodiments, a pharmaceutical composition is prepared for topical administration. Certain of such pharmaceutical compositions comprise bland moisturizing bases, such as ointments or creams. Exemplary suitable ointment bases include, but are not limited to, petrolatum, petrolatum plus volatile silicones, lanolin and water in oil emulsions such as Eucerin™, available from Beiersdorf (Cincinnati, Ohio). Exemplary suitable cream bases include, but are not limited to, Nivea™ Cream, available from Beiersdorf (Cincinnati, Ohio), cold cream (USP), Purpose Cream™, available from Johnson & Johnson (New Brunswick, N.J.), hydrophilic ointment (USP) and Lubriderm™, available from Pfizer (Morris Plains, N.J.).

In certain embodiments, a pharmaceutical composition of the present invention comprises an oligonucleotide in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, one or more oligonucleotides of the present invention is formulated as a prodrug. In certain embodiments, upon in vivo administration, a prodrug is chemically converted to the biologically, pharmaceutically or therapeutically more active form of the oligonucleotide. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, a prodrug is produced by modifying a pharmaceutically active compound such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392).

In certain embodiments, a pharmaceutical composition comprising one or more pharmaceutical agents of the present invention is useful for treating a conditions or disorders in a mammalian, and particularly in a human, subject. Suitable administration routes include, but are not limited to, oral, rectal, transmucosal, intestinal, enteral, topical, suppository, through inhalation, intrathecal, intraventricular, intraperitoneal, intranasal, intraocular and parenteral (e.g., intravenous, intramuscular, intramedullary, and subcutaneous). In certain embodiments, pharmaceutical intrathecals are administered to achieve local rather than systemic exposures. For example, pharmaceutical compositions may be injected directly in the area of desired effect (e.g., in the renal or cardiac area).

In certain embodiments, a pharmaceutical composition of the present invention is administered in the form of a dosage unit (e.g., tablet, capsule, bolus, etc.). In certain embodiments, such pharmaceutical compositions comprise an oligonucleotide in a dose selected from 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 270 mg, 280 mg, 285 mg, 290 mg, 295 mg, 300 mg, 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 670 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, and 800 mg. In certain such embodiments, a pharmaceutical composition of the present invention comprises a dose of oligonucleotide selected from 25 mg, 50 mg, 75 mg, 100 mg, 150 mg, 200 mg, 250 mg, 300 mg, 350 mg, 400 mg, 500 mg, 600 mg, 700 mg, and 800 mg. In certain embodiments, a pharmaceutical composition is comprises a dose of oligonucleotide selected from 50 mg, 100 mg, 150 mg, 200 mg, 250 mg, 300 mg, and 400 mg. In certain embodiments the dose is administered at intervals ranging from more than once per day, once per day, once per week, twice per week, three times per week, four times per week, five times per week, 6 times per week, once per month to once per three months, for as long as needed to sustain the desired effect.

In a further aspect, a pharmaceutical agent is sterile lyophilized oligonucleotide that is reconstituted with a suitable diluent, e.g., sterile water for injection. The reconstituted product is administered as a subcutaneous injection or as an intravenous infusion after dilution into saline. The lyophilized drug product consists of the oligonucleotide which has been prepared in water for injection, adjusted to pH 7.0-9.0 with acid or base during preparation, and then lyophilized. The lyophilized oligonucleotide may be 25-800 mg of the oligonucleotide. It is understood that this encompasses 25, 50, 75, 100, 125, 150, 175, 200, 225, 250, 275, 300, 325, 350, 375, 425, 450, 475, 500, 525, 550, 575, 600, 625, 650, 675, 700, 725, 750, 775, and 800 mg of lyophilized oligonucleotide. The lyophilized drug product may be packaged in a 2 mL Type I, clear glass vial (ammonium sulfate-treated), stoppered with a bromobutyl rubber closure and sealed with an aluminum FLIP-OFF® overseal. In one embodiment, the lyophilized pharmaceutical agent comprises ISIS 405879.

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the oligonucleotide(s) of the formulation.

Conjugated Antisense Compounds

Antisense compounds may be covalently linked to one or more moieties or conjugates which enhance the activity, visualization of cellular distribution, or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Cell Culture and Antisense Compounds Treatment

The effects of antisense compounds on the level, activity or expression of PCSK9 nucleic acids can be tested in vitro in a variety of cell types. Cell types used for such analyses are available from commercial vendors (e.g., American Type Culture Collection, Manassas, Va.; Zen-Bio, Inc., Research Triangle Park, N.C.; Clonetics Corporation, Walkersville, Md.) and cells are cultured according to the vendor's instructions using commercially available reagents (e.g., Invitrogen Life Technologies, Carlsbad, Calif.). Illustrative cell types include, but are not limited to, HepG2 cells, Hep3B cells, and primary hepatocytes.

In Vitro Testing of Antisense Oligonucleotides

Described herein are methods for treatment of cells with antisense oligonucleotides, which can be modified appropriately for treatment with other antisense compounds.

In general, cells are treated with antisense oligonucleotides when they cells reach approximately 60-80% confluency in culture.

One reagent commonly used to introduce antisense oligonucleotides into cultured cells includes the cationic lipid transfection reagent LIPOFECTIN® (Invitrogen, Carlsbad, Calif.). Antisense oligonucleotides are mixed with LIPOFECTIN® in OPTI-MEM® 1 (Invitrogen, Carlsbad, Calif.) to achieve the desired final concentration of antisense oligonucleotide and a LIPOFECTIN® concentration that typically ranges 2 to 12 ug/mL per 100 nM antisense oligonucleotide.

Another reagent used to introduce antisense oligonucleotides into cultured cells includes LIPOFECTAMINE® (Invitrogen, Carlsbad, Calif.). Antisense oligonucleotide is mixed with LIPOFECTAMINE® in OPTI-MEM® 1 reduced serum medium (Invitrogen, Carlsbad, Calif.) to achieve the desired concentration of antisense oligonucleotide and a LIPOFECTAMINE® concentration that typically ranges 2 to 12 ug/mL per 100 nM antisense oligonucleotide.

Cells are treated with antisense oligonucleotides by routine methods. Cells are typically harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM.

RNA Isolation

RNA analysis can be performed on total cellular RNA or poly(A)+ mRNA. Methods of RNA isolation are well known in the art. RNA is prepared using methods well known in the art, for example, using the TRIZOL® Reagent (Invitrogen, Carlsbad, Calif.) according to the manufacturer's recommended protocols.

Analysis of Inhibition of Target Levels or Expression

Inhibition of levels or expression of a PCSK9 nucleic acid can be assayed in a variety of ways known in the art. For example, target nucleic acid levels can be quantitated by, e.g., Northern blot analysis, competitive polymerase chain reaction (PCR), or quantitative real-time PCR. RNA analysis can be performed on total cellular RNA or poly(A)+ mRNA. Methods of RNA isolation are well known in the art. Northern blot analysis is also routine in the art. Quantitative real-time PCR can be conveniently accomplished using the commercially available ABI PRISM® 7600, 7700, or 7900 Sequence Detection System, available from PE-Applied Biosystems, Foster City, Calif. and used according to manufacturer's instructions.

Quantitative Real-Time PCR Analysis of Target RNA Levels

Quantitation of target RNA levels may be accomplished by quantitative real-time PCR using the ABI PRISM® 7600, 7700, or 7900 Sequence Detection System (PE-Applied Biosystems, Foster City, Calif.) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents are obtained from Invitrogen (Carlsbad, Calif.). RT, real-time-PCR reactions are carried out by methods well known to those skilled in the art.

Gene (or RNA) target quantities obtained by real time PCR are normalized using either the expression level of a gene whose expression is constant, such as GAPDH, or by quantifying total RNA using RIBOGREEN® (Invitrogen, Inc. Carlsbad, Calif.). GAPDH expression is quantified by real time PCR, by being run simultaneously with the target, multiplexing, or separately. Total RNA is quantified using RIBOGREEN® RNA quantification reagent (Invitrogen, Inc. Carlsbad, Calif.). Methods of RNA quantification by RIBOGREEN® are taught in Jones, L. J., et al, (Analytical Biochemistry, 1998, 265, 368-374). A CYTOFLUOR® 4000 instrument (PE Applied Biosystems) is used to measure RIBOGREEN® fluorescence.

Probes and primers are designed to hybridize to a PCSK9 nucleic acid. Methods for designing real-time PCR probes and primers are well known in the art, and may include the use of software such as PRIMER EXPRESS® Software (Applied Biosystems, Foster City, Calif.).

Analysis of Protein Levels

Antisense inhibition of PCSK9 nucleic acids can be assessed by measuring PCSK9 protein levels. Protein levels of PCSK9 can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Antibodies useful for the detection of human and rat PCSK9 are commercially available.

Serum Lipid Analysis

Plasma concentrations of total cholesterol, LDL-C, HDL-C, free cholesterol, triglycerides, glucose, ketones, transaminases, and phospholipids can be measured using an automated clinical chemistry analyzer (Hitachi Olympus AU400e, Melville, N.Y.). Serum lipoprotein and cholesterol profiling can be performed as described by Crooke et al., Lipid Res. (2005) 46: 872-884, using a Beckman System Gold 126 HPLC system, a 507e refrigerated autosampler, a 126 photodiode array detector (Beckman Instruments, Fullerton, Calif.), and a Superose 6 HR 10/30 column (Pfizer, Chicago, Ill.). HDL, LDL and VLDL fractions are measured at a wavelength of 505 nm and validated with a cholesterol calibration kit. (Sigma).

Liver Triglyceride Analysis

Liver triglyceride content can be measured according to routine experimental procedures, for example, per procedures described by Desai et al., Diabetes (2001) 50: 2287-2295. Liver triglyceride content may be measured after antisense inhibition of PCSK9 for 6 weeks.

In Vivo Testing of Antisense Compounds

Antisense compounds, for example, antisense oligonucleotides, are tested in animals to assess their ability to inhibit expression of PCSK9 and produce phenotypic changes, such as decreases in LDL-C. Testing may be performed in normal animals, or in experimental disease models. For administration to animals, antisense oligonucleotides are formulated in a pharmaceutically acceptable diluent, such as phosphate-buffered saline. Administration includes parenteral routes of administration, such as intraperitoneal, intravenous, and subcutaneous. Calculation of antisense oligonucleotide dosage and dosing frequency is within the abilities of those skilled in the art, and depends upon factors such as route of administration and animal body weight. Following a period of treatment with antisense oligonucleotides, RNA is isolated from various tissues and changes in PCSK9 nucleic acid expression are measured. Changes in PCSK9 protein levels may also be measured.

Nonlimiting Disclosure and Incorporation by Reference

The following examples serve only to illustrate the methods, antisense oligonucleotides, and compositions provided and are not intended to limit the same. Each of the references, GENBANK® accession numbers, and the like recited in the present application is incorporated herein by reference in its entirety.

EXAMPLES

Example 1: Antisense Inhibition of Human PCSK9: A549 Cells

Antisense oligonucleotides targeted to a PCSK9 nucleic acid were tested for their effects on PCSK9 mRNA in vitro. Cultured A549 cells at a density of 4000 cells per well in a 96-well plate were treated with 60 nM of antisense oligonucleotide. After a treatment period of approximately 24 hours, RNA was isolated from the cells and PCSK9 mRNA levels were measured by quantitative real-time PCR, as described herein. PCSK9 mRNA levels were adjusted according to total RNA content as measured by RIBOGREEN®. Results are presented as percent inhibition of PCSK9, relative to untreated control cells. Antisense oligonucleotides that exhibited at least 30% inhibition of PCSK9 expression are shown in Table 16.

The motif column indicates the wing-gap-wing motif of each antisense oligonucleotide. Antisense oligonucleotides were designed as 5-10-5 gapmers, or alternatively as 3-14-3 gapmers, where the gap segment comprises 2'-deoxynucleotides and each wing segment comprises 2'-MOE nucleotides. As illustrated in Table 16, a single nucleobase sequence may be represented by a 5-10-5 motif as well as a 3-14-3 motif "5' target site" indicates the 5'-most nucleotide which the antisense oligonucleotide is targeted on the indicated GENBANK Accession No.

TABLE 16

Antisense inhibition of PCSK9 in human cells (Cell type A549)

| IsisNo | SEQ ID NO | 5' Target Site | Target Nucleic Acid | Sequence | Motif | % Inhibition |
|---|---|---|---|---|---|---|
| 395150 | 5 | 242 | NM_174936.2 | GAGGAGACCTAGAGGCCGTG | 5-10-5 | 57 |
| 395151 | 6 | 300 | NM_174936.2 | AGGACCGCCTGGAGCTGACG | 5-10-5 | 77 |
| 395152 | 7 | 410 | NM_174936.2 | ACGCAAGGCTAGCACCAGCT | 5-10-5 | 81 |
| 395153 | 9 | 480 | NM_174936.2 | CCTTGGCGCAGCGGTGGAAG | 5-10-5 | 51 |
| 395154 | 10 | 561 | NM_174936.2 | GGCGGGCAGTGCGCTCTGAC | 5-10-5 | 40 |
| 395155 | 11 | 600 | NM_174936.2 | TGGTGAGGTATCCCCGGCGG | 5-10-5 | 79 |
| 395156 | 14 | 620 | NM_174936.2 | ATGGAAGACATGCAGGATCT | 5-10-5 | 75 |
| 395157 | 15 | 646 | NM_174936.2 | TTCACCAGGAAGCCAGGAAG | 5-10-5 | 72 |
| 395158 | 17 | 705 | NM_174936.2 | CCTCGATGTAGTCGACATGG | 5-10-5 | 61 |
| 395159 | 18 | 785 | NM_174936.2 | GTATTCATCCGCCCGGTACC | 5-10-5 | 35 |
| 395160 | 19 | 835 | NM_174936.2 | CTGGTGTCTAGGAGATACAC | 5-10-5 | 47 |
| 395161 | 21 | 860 | NM_174936.2 | GATTTCCCGGTGGTCACTCT | 5-10-5 | 70 |
| 395162 | 24 | 890 | NM_174936.2 | CTCGAAGTCGGTGACCATGA | 5-10-5 | 52 |
| 395163 | 25 | 923 | NM_174936.2 | GTGGAAGCGGGTCCCGTCCT | 5-10-5 | 73 |

TABLE 16-continued

Antisense inhibition of PCSK9 in human cells (Cell type A549)

| IsisNo | SEQ ID NO | 5' Target Site | Target Nucleic Acid | Sequence | Motif | % Inhibition |
|---|---|---|---|---|---|---|
| 395164 | 26 | 970 | NM_174936.2 | ACCCCTGCCAGGTGGGTGCC | 5-10-5 | 69 |
| 395165 | 28 | 1004 | NM_174936.2 | ACCCTTGGCCACGCCGGCAT | 5-10-5 | 81 |
| 395166 | 29 | 1040 | NM_174936.2 | TTGGCAGTTGAGCACGCGCA | 5-10-5 | 65 |
| 395167 | 31 | 1077 | NM_174936.2 | CCAGGCCTATGAGGGTGCCG | 5-10-5 | 34 |
| 395168 | 32 | 1098 | NM_174936.2 | GCTGGCTTTTCCGAATAAAC | 5-10-5 | 69 |
| 395169 | 33 | 1210 | NM_174936.2 | GTGACCAGCACGACCCCAGC | 5-10-5 | 61 |
| 395171 | 34 | 1326 | NM_174936.2 | CCAAAGTCCCCAGGGTCACC | 5-10-5 | 38 |
| 395173 | 36 | 1340 | NM_174936.2 | GCCAAAGTTGGTCCCCAAAG | 5-10-5 | 64 |
| 395174 | 38 | 1361 | NM_174936.2 | GGCAAAGAGGTCCACACAGC | 5-10-5 | 72 |
| 395175 | 39 | 1389 | NM_174936.2 | TGGAGGCACCAATGATGTCC | 5-10-5 | 41 |
| 395177 | 45 | 1534 | NM_174936.2 | TTGGCAGAGAAGTGGATCAG | 5-10-5 | 41 |
| 395178 | 50 | 1569 | NM_174936.2 | GGTCCTCAGGGAACCAGGCC | 5-10-5 | 67 |
| 395181 | 52 | 1640 | NM_174936.2 | AAACAGCTGCCAACCTGCCC | 5-10-5 | 37 |
| 395182 | 54 | 1675 | NM_174936.2 | GTAGGCCCCGAGTGTGCTGA | 5-10-5 | 51 |
| 395183 | 57 | 1812 | NM_174936.2 | CGTTGTGGGCCCGGCAGACC | 5-10-5 | 74 |
| 395184 | 58 | 1858 | NM_174936.2 | AGCAGGCAGCACCTGGCAAT | 5-10-5 | 61 |
| 395185 | 59 | 1920 | NM_174936.2 | CACGGGTCCCCATGCTGGCC | 5-10-5 | 73 |
| 395186 | 60 | 2100 | NM_174936.2 | CTTTGCATTCCAGACCTGGG | 5-10-5 | 83 |
| 395187 | 62 | 2310 | NM_174936.2 | GGCAGCAGATGGCAACGGCT | 5-10-5 | 80 |
| 395189 | 64 | 2504 | NM_174936.2 | TCAAGGGCCAGGCCAGCAGC | 5-10-5 | 65 |
| 395190 | 66 | 2597 | NM_174936.2 | ATGCCCCACAGTGAGGGAGG | 5-10-5 | 60 |
| 395191 | 67 | 2606 | NM_174936.2 | AATGGTGAAATGCCCCACAG | 5-10-5 | 76 |
| 395193 | 68 | 2750 | NM_174936.2 | CATGGGAAGAATCCTGCCTC | 5-10-5 | 48 |
| 395194 | 69 | 2832 | NM_174936.2 | GGAGATGAGGGCCATCAGCA | 5-10-5 | 64 |
| 395195 | 70 | 2900 | NM_174936.2 | TAGATGCCATCCAGAAAGCT | 5-10-5 | 44 |
| 395196 | 72 | 2983 | NM_174936.2 | GGCATAGAGCAGAGTAAAGG | 5-10-5 | 39 |
| 395198 | 75 | 3437 | NM_174936.2 | GCTCAAGGAGGGACAGTTGT | 5-10-5 | 73 |
| 395199 | 76 | 3472 | NM_174936.2 | AAAGATAAATGTCTGCTTGC | 5-10-5 | 83 |
| 395200 | 78 | 3543 | NM_174936.2 | TCTTCAAGTTACAAAAGCAA | 5-10-5 | 40 |
| 395202 | 129 | 13816 | NT_032977.8 | GTGCCATCTGAACAGCACCT | 5-10-5 | 36 |
| 395203 | 110 | 13926 | NT_032977.8 | CCTGGAACCCTGCAGCCAG | 5-10-5 | 64 |
| 395204 | 152 | 13977 | NT_032977.8 | TTCAGGCAGGTTGCTGCTAG | 5-10-5 | 55 |
| 395206 | 136 | 14122 | NT_032977.8 | TAGGAGAAAGTAGGGAGAGC | 5-10-5 | 45 |
| 395207 | 132 | 14179 | NT_032977.8 | TAAAAGCTGCAAGAGACTCA | 5-10-5 | 49 |
| 395208 | 139 | 14267 | NT_032977.8 | TCAGAGAAAACAGTCACCGA | 5-10-5 | 56 |
| 395209 | 142 | 14404 | NT_032977.8 | TCATTTTAGAGACAGGAAGC | 5-10-5 | 73 |
| 395210 | 113 | 14441 | NT_032977.8 | GAATAACAGTGATGTCTGGC | 5-10-5 | 82 |

TABLE 16-continued

Antisense inhibition of PCSK9 in human cells (Cell type A549)

| IsisNo | SEQ ID NO | 5' Target Site | Target Nucleic Acid | Sequence | Motif | % Inhibition |
|---|---|---|---|---|---|---|
| 395211 | 138 | 14494 | NT_032977.8 | TCACAGCTCACCGAGTCTGC | 5-10-5 | 60 |
| 395212 | 98 | 14524 | NT_032977.8 | AGTGTAAAATAAAGCCCCTA | 5-10-5 | 50 |
| 395213 | 96 | 14601 | NT_032977.8 | AGGACCCAAGTCATCCTGCT | 5-10-5 | 57 |
| 395214 | 124 | 14631 | NT_032977.8 | GGCCATCAGCTGGCAATGCT | 5-10-5 | 50 |
| 395215 | 133 | 14675 | NT_032977.8 | TAGACAAGGAAAGGGAGGCC | 5-10-5 | 60 |
| 395216 | 103 | 14681 | NT_032977.8 | ATTTCATAGACAAGGAAAGG | 5-10-5 | 51 |
| 395218 | 146 | 1315 | AK124635.1 | TGACATTTGTGGGAGAGGAG | 5-10-5 | 35 |
| 395220 | 104 | 2085 | AK124635.1 | CACAGTCCTGCAAAACAGCT | 5-10-5 | 54 |
| 395221 | 102 | 5590 | NT_032977.8 | ATGTGCAGAGATCAATCACA | 5-10-5 | 69 |
| 395222 | 127 | 10633 | NT_032977.8 | GGTGGTAATTTGTCACAGCA | 5-10-5 | 64 |
| 395223 | 84 | 11308 | NT_032977.8 | AAGGTCACACAGTTAAGAGT | 5-10-5 | 55 |
| 395226 | 147 | 24858 | NT_032977.8 | TGAGTTCATTTAAGAGTGGA | 5-10-5 | 42 |
| 399793 | 8 | 417 | NM_174936.2 | CCTCGGAACGCAAGGCTAGC | 5-10-5 | 71 |
| 399794 | 12 | 606 | NM_174936.2 | GGATCTTGGTGAGGTATCCC | 5-10-5 | 42 |
| 399795 | 13 | 615 | NM_174936.2 | AGACATGCAGGATCTTGGTG | 5-10-5 | 54 |
| 399796 | 16 | 651 | NM_174936.2 | TCATCTTCACCAGGAAGCCA | 5-10-5 | 50 |
| 399797 | 20 | 840 | NM_174936.2 | GTATGCTGGTGTCTAGGAGA | 5-10-5 | 38 |
| 399798 | 22 | 866 | NM_174936.2 | GCCCTCGATTTCCCGGTGGT | 5-10-5 | 54 |
| 399799 | 23 | 880 | NM_174936.2 | GTGACCATGACCCTGCCCTC | 5-10-5 | 75 |
| 399800 | 27 | 975 | NM_174936.2 | TGACCACCCCTGCCAGGTGG | 5-10-5 | 67 |
| 399801 | 30 | 1045 | NM_174936.2 | TTCCCTTGGCAGTTGAGCAC | 5-10-5 | 79 |
| 399802 | 35 | 1335 | NM_174936.2 | AGTTGGTCCCCAAAGTCCCC | 5-10-5 | 71 |
| 399803 | 37 | 1352 | NM_174936.2 | GTCCACACAGCGGCCAAAGT | 5-10-5 | 63 |
| 399804 | 40 | 1400 | NM_174936.2 | GCTGCAGTCGCTGGAGGCAC | 5-10-5 | 46 |
| 399805 | 41 | 1411 | NM_174936.2 | ACAAAGCAGGTGCTGCAGTC | 5-10-5 | 46 |
| 399806 | 42 | 1470 | NM_174936.2 | GCATCATGGCTGCAATGCCA | 5-10-5 | 85 |
| 399807 | 43 | 1478 | NM_174936.2 | GGCAGACAGCATCATGGCTG | 5-10-5 | 71 |
| 399808 | 44 | 1526 | NM_174936.2 | GAAGTGGATCAGTCTCTGCC | 5-10-5 | 38 |
| 399809 | 46 | 1539 | NM_174936.2 | CATCTTTGGCAGAGAAGTGG | 5-10-5 | 53 |
| 399810 | 47 | 1545 | NM_174936.2 | TGATGACATCTTTGGCAGAG | 5-10-5 | 63 |
| 399811 | 48 | 1552 | NM_174936.2 | GCCTCATTGATGACATCTTT | 5-10-5 | 61 |
| 399812 | 49 | 1564 | NM_174936.2 | TCAGGGAACCAGGCCTCATT | 5-10-5 | 46 |
| 399813 | 51 | 1583 | NM_174936.2 | GGTCAGTACCCGCTGGTCCT | 5-10-5 | 72 |
| 399814 | 53 | 1645 | NM_174936.2 | CTGCAAAACAGCTGCCAACC | 5-10-5 | 88 |
| 399815 | 55 | 1740 | NM_174936.2 | AGAAACTGGAGCAGCTCAGC | 5-10-5 | 38 |
| 399816 | 56 | 1746 | NM_174936.2 | TCCTGGAGAAACTGGAGCAG | 5-10-5 | 51 |
| 399817 | 61 | 2105 | NM_174936.2 | CTTGACTTTGCATTCCAGAC | 5-10-5 | 84 |

TABLE 16-continued

Antisense inhibition of PCSK9 in human cells (Cell type A549)

| IsisNo | SEQ ID NO | 5' Target Site | Target Nucleic Acid | Sequence | Motif | % Inhibition |
|---|---|---|---|---|---|---|
| 399818 | 63 | 2415 | NM_174936.2 | AACCATTTTAAAGCTCAGCC | 5-10-5 | 68 |
| 399819 | 65 | 2509 | NM_174936.2 | CCCACTCAAGGGCCAGGCCA | 5-10-5 | 87 |
| 399821 | 71 | 2906 | NM_174936.2 | TCTGGCTAGATGCCATCCAG | 5-10-5 | 83 |
| 399822 | 73 | 2988 | NM_174936.2 | AGCCTGGCATAGAGCAGAGT | 5-10-5 | 70 |
| 399824 | 74 | 3233 | NM_174936.2 | AAGTAAGAAGAGGCTTGGCT | 5-10-5 | 43 |
| 399825 | 77 | 3477 | NM_174936.2 | ACCCAAAAGATAAATGTCTG | 5-10-5 | 61 |
| 399827 | 100 | 13746 | NT_032977.8 | ATCTCAGGACAGGTGAGCAA | 5-10-5 | 81 |
| 399828 | 116 | 13760 | NT_032977.8 | GAGTAGAGATTCTCATCTCA | 5-10-5 | 73 |
| 399829 | 117 | 13828 | NT_032977.8 | GAGTCTTCTGAAGTGCCATC | 5-10-5 | 65 |
| 399831 | 83 | 13986 | NT_032977.8 | AAGGAAGACTTCAGGCAGGT | 5-10-5 | 52 |
| 399833 | 92 | 14397 | NT_032977.8 | AGAGACAGGAAGCTGCAGCT | 5-10-5 | 54 |
| 399834 | 82 | 14670 | NT_032977.8 | AAGGAAAGGGAGGCCTAGAG | 5-10-5 | 44 |
| 399836 | 130 | 2095 | AK124635.1 | GTGCTGACCACACAGTCCTG | 5-10-5 | 96 |
| 399837 | 107 | 3056 | NT_032977.8 | CCCACTATAATGGCAAGCCC | 5-10-5 | 83 |
| 399838 | 80 | 4306 | NT_032977.8 | AACCCAGTTCTAATGCACCT | 5-10-5 | 81 |
| 399839 | 106 | 5140 | NT_032977.8 | CCAGTCAGAGTAGAACAGAG | 5-10-5 | 68 |
| 399840 | 121 | 5599 | NT_032977.8 | GGAGCCTACATGTGCAGAGA | 5-10-5 | 46 |
| 399841 | 94 | 5667 | NT_032977.8 | AGCATGGCACCAGCATCTGC | 5-10-5 | 59 |
| 399842 | 108 | 6652 | NT_032977.8 | CCCAGCCCTATCAGGAAGTG | 5-10-5 | 67 |
| 399843 | 144 | 7099 | NT_032977.8 | TGACATCCAGGAGGGAGGAG | 5-10-5 | 33 |
| 399844 | 91 | 7556 | NT_032977.8 | AGACTGATGGAAGGCATTGA | 5-10-5 | 56 |
| 399845 | 131 | 7565 | NT_032977.8 | GTGTTGAGCAGACTGATGGA | 5-10-5 | 48 |
| 399846 | 145 | 8836 | NT_032977.8 | TGACATCTTGTCTGGGAGCC | 5-10-5 | 58 |
| 399847 | 90 | 8948 | NT_032977.8 | AGACTAGGAGCCTGAGTTTT | 5-10-5 | 38 |
| 399849 | 148 | 10252 | NT_032977.8 | TGGCAGCAACTCAGACATAT | 5-10-5 | 74 |
| 399851 | 88 | 12715 | NT_032977.8 | ACTGGATACATTGGCAGACA | 5-10-5 | 62 |
| 399852 | 111 | 12928 | NT_032977.8 | CTAGAGGAACCACTAGATAT | 5-10-5 | 66 |
| 399854 | 97 | 16134 | NT_032977.8 | AGTCAAGCTGCTGCCCAGAG | 5-10-5 | 82 |
| 399855 | 120 | 16668 | NT_032977.8 | GCTAGTTATTAAGCACCTGC | 5-10-5 | 71 |
| 399856 | 150 | 17267 | NT_032977.8 | TGTGAGCTCTGGCCCAGTGG | 5-10-5 | 64 |
| 399857 | 115 | 18377 | NT_032977.8 | GAGTAAGGCAGGTTACTCTC | 5-10-5 | 79 |
| 399858 | 134 | 18408 | NT_032977.8 | TAGATGTGACTAACATTTAA | 5-10-5 | 57 |
| 399859 | 105 | 19203 | NT_032977.8 | CACATTAGCCTTGCTCAAGT | 5-10-5 | 75 |
| 399860 | 151 | 19913 | NT_032977.8 | TGTGATGACCTGGAAAGGTG | 5-10-5 | 36 |
| 399862 | 109 | 20188 | NT_032977.8 | CCCCTGCACAGAGCCTGGCA | 5-10-5 | 59 |
| 399863 | 141 | 20624 | NT_032977.8 | TCATGGCTGCAATGCCTGGT | 5-10-5 | 46 |
| 399864 | 93 | 20995 | NT_032977.8 | AGAGAGGAGGGCTTAAAGAA | 5-10-5 | 30 |

TABLE 16-continued

Antisense inhibition of PCSK9 in human cells (Cell type A549)

| IsisNo | SEQ ID NO | 5' Target Site | Target Nucleic Acid | Sequence | Motif | % Inhibition |
|---|---|---|---|---|---|---|
| 399865 | 95 | 21082 | NT_032977.8 | AGCTGCCAACCTGCAAAAAG | 5-10-5 | 75 |
| 399866 | 143 | 21481 | NT_032977.8 | TGAAAATCCATCCAGCACTG | 5-10-5 | 74 |
| 399867 | 89 | 21589 | NT_032977.8 | AGAACCATGGAGCACCTGAG | 5-10-5 | 84 |
| 399868 | 123 | 21696 | NT_032977.8 | GGCACTGCCCTTCCACCAAA | 5-10-5 | 53 |
| 399869 | 118 | 24907 | NT_032977.8 | GCACCATCCAGACCAGAATC | 5-10-5 | 49 |
| 399870 | 114 | 25413 | NT_032977.8 | GAGAGGTTCAGATCCAGGCC | 5-10-5 | 66 |
| 399871 | 4 | 135 | NM_174936.2 | GCGCGGAATCCTGGCTGGGA | 3-14-3 | 40 |
| 399872 | 5 | 242 | NM_174936.2 | GAGGAGACCTAGAGGCCGTG | 3-14-3 | 64 |
| 399873 | 6 | 300 | NM_174936.2 | AGGACCGCCTGGAGCTGACG | 3-14-3 | 65 |
| 399874 | 7 | 410 | NM_174936.2 | ACGCAAGGCTAGCACCAGCT | 3-14-3 | 80 |
| 399875 | 9 | 480 | NM_174936.2 | CCTTGGCGCAGCGGTGGAAG | 3-14-3 | 67 |
| 399876 | 10 | 561 | NM_174936.2 | GGCGGGCAGTGCGCTCTGAC | 3-14-3 | 62 |
| 399877 | 11 | 600 | NM_174936.2 | TGGTGAGGTATCCCCGGCGG | 3-14-3 | 73 |
| 399878 | 14 | 620 | NM_174936.2 | ATGGAAGACATGCAGGATCT | 3-14-3 | 54 |
| 399879 | 15 | 646 | NM_174936.2 | TTCACCAGGAAGCCAGGAAG | 3-14-3 | 75 |
| 399880 | 17 | 705 | NM_174936.2 | CCTCGATGTAGTCGACATGG | 3-14-3 | 80 |
| 399881 | 18 | 785 | NM_174936.2 | GTATTCATCCGCCCGGTACC | 3-14-3 | 63 |
| 399882 | 19 | 835 | NM_174936.2 | CTGGTGTCTAGGAGATACAC | 3-14-3 | 66 |
| 399883 | 21 | 860 | NM_174936.2 | GATTTCCCGGTGGTCACTCT | 3-14-3 | 59 |
| 399884 | 24 | 890 | NM_174936.2 | CTCGAAGTCGGTGACCATGA | 3-14-3 | 71 |
| 399885 | 25 | 923 | NM_174936.2 | GTGGAAGCGGGTCCCGTCCT | 3-14-3 | 73 |
| 399886 | 26 | 970 | NM_174936.2 | ACCCCTGCCAGGTGGGTGCC | 3-14-3 | 76 |
| 399887 | 28 | 1004 | NM_174936.2 | ACCCTTGGCCACGCCGGCAT | 3-14-3 | 54 |
| 399888 | 29 | 1040 | NM_174936.2 | TTGGCAGTTGAGCACGCGCA | 3-14-3 | 75 |
| 399889 | 31 | 1077 | NM_174936.2 | CCAGGCCTATGAGGGTGCCG | 3-14-3 | 84 |
| 399890 | 32 | 1098 | NM_174936.2 | GCTGGCTTTTCCGAATAAAC | 3-14-3 | 73 |
| 399891 | 33 | 1210 | NM_174936.2 | GTGACCAGCACGACCCCAGC | 3-14-3 | 99 |
| 399892 | 149 | 1297 | NM_174936.2 | TGGGCATTGGTGGCCCCAAC | 3-14-3 | 61 |
| 399893 | 34 | 1326 | NM_174936.2 | CCAAAGTCCCCAGGGTCACC | 3-14-3 | 54 |
| 399894 | 128 | 1330 | NM_174936.2 | GTCCCCAAAGTCCCCAGGGT | 3-14-3 | 80 |
| 399895 | 36 | 1340 | NM_174936.2 | GCCAAAGTTGGTCCCCAAAG | 3-14-3 | 82 |
| 399896 | 38 | 1361 | NM_174936.2 | GGCAAAGAGGTCCACACAGC | 3-14-3 | 83 |
| 399897 | 39 | 1389 | NM_174936.2 | TGGAGGCACCAATGATGTCC | 3-14-3 | 70 |
| 399898 | 101 | 1465 | NM_174936.2 | ATGGCTGCAATGCCAGCCAC | 3-14-3 | 37 |
| 399899 | 45 | 1534 | NM_174936.2 | TTGGCAGAGAAGTGGATCAG | 3-14-3 | 64 |
| 399900 | 50 | 1569 | NM_174936.2 | GGTCCTCAGGGAACCAGGCC | 3-14-3 | 82 |
| 399901 | 87 | 1576 | NM_174936.2 | ACCCGCTGGTCCTCAGGGAA | 3-14-3 | 76 |

TABLE 16-continued

Antisense inhibition of PCSK9 in human cells (Cell type A549)

| IsisNo | SEQ ID NO | 5' Target Site | Target Nucleic Acid | Sequence | Motif | % Inhibition |
|---|---|---|---|---|---|---|
| 399902 | 119 | 1605 | NM_174936.2 | GCAGGGCGGCCACCAGGTTG | 3-14-3 | 39 |
| 399903 | 52 | 1640 | NM_174936.2 | AAACAGCTGCCAACCTGCCC | 3-14-3 | 73 |
| 399904 | 54 | 1675 | NM_174936.2 | GTAGGCCCCGAGTGTGCTGA | 3-14-3 | 81 |
| 399905 | 57 | 1812 | NM_174936.2 | CGTTGTGGGCCCGGCAGACC | 3-14-3 | 80 |
| 399906 | 58 | 1858 | NM_174936.2 | AGCAGGCAGCACCTGGCAAT | 3-14-3 | 92 |
| 399907 | 59 | 1920 | NM_174936.2 | CACGGGTCCCCATGCTGGCC | 3-14-3 | 95 |
| 399908 | 60 | 2100 | NM_174936.2 | CTTTGCATTCCAGACCTGGG | 3-14-3 | 84 |
| 399909 | 62 | 2310 | NM_174936.2 | GGCAGCAGATGGCAACGGCT | 3-14-3 | 73 |
| 399910 | 154 | 2410 | NM_174936.2 | TTTTAAAGCTCAGCCCCAGC | 3-14-3 | 57 |
| 399911 | 64 | 2504 | NM_174936.2 | TCAAGGGCCAGGCCAGCAGC | 3-14-3 | 82 |
| 399912 | 66 | 2597 | NM_174936.2 | ATGCCCCACAGTGAGGGAGG | 3-14-3 | 68 |
| 399913 | 67 | 2606 | NM_174936.2 | AATGGTGAAATGCCCCACAG | 3-14-3 | 92 |
| 399914 | 153 | 2649 | NM_174936.2 | TTGGGAGCAGCTGGCAGCAC | 3-14-3 | 59 |
| 399915 | 68 | 2750 | NM_174936.2 | CATGGGAAGAATCCTGCCTC | 3-14-3 | 78 |
| 399916 | 69 | 2832 | NM_174936.2 | GGAGATGAGGGCCATCAGCA | 3-14-3 | 71 |
| 399917 | 70 | 2900 | NM_174936.2 | TAGATGCCATCCAGAAAGCT | 3-14-3 | 81 |
| 399918 | 72 | 2983 | NM_174936.2 | GGCATAGAGCAGAGTAAAGG | 3-14-3 | 82 |
| 399919 | 112 | 3227 | NM_174936.2 | GAAGAGGCTTGGCTTCAGAG | 3-14-3 | 57 |
| 399920 | 75 | 3437 | NM_174936.2 | GCTCAAGGAGGGACAGTTGT | 3-14-3 | 84 |
| 399921 | 76 | 3472 | NM_174936.2 | AAAGATAAATGTCTGCTTGC | 3-14-3 | 78 |
| 399922 | 78 | 3543 | NM_174936.2 | TCTTCAAGTTACAAAAGCAA | 3-14-3 | 61 |
| 399923 | 85 | 13681 | NT_032977.8 | ACAAATTCCCAGACTCAGCA | 3-14-3 | 82 |
| 399924 | 129 | 13816 | NT_032977.8 | GTGCCATCTGAACAGCACCT | 3-14-3 | 84 |
| 399925 | 110 | 13926 | NT_032977.8 | CCTGGAACCCTGCAGCCAG | 3-14-3 | 73 |
| 399926 | 152 | 13977 | NT_032977.8 | TTCAGGCAGGTTGCTGCTAG | 3-14-3 | 47 |
| 399927 | 140 | 13998 | NT_032977.8 | TCAGCCAGGCCAAAGGAAGA | 3-14-3 | 78 |
| 399928 | 136 | 14122 | NT_032977.8 | TAGGAGAAAGTAGGGAGAGC | 3-14-3 | 47 |
| 399929 | 132 | 14179 | NT_032977.8 | TAAAAGCTGCAAGAGACTCA | 3-14-3 | 69 |
| 399930 | 139 | 14267 | NT_032977.8 | TCAGAGAAAACAGTCACCGA | 3-14-3 | 82 |
| 399931 | 142 | 14404 | NT_032977.8 | TCATTTTAGAGACAGGAAGC | 3-14-3 | 79 |
| 399932 | 113 | 14441 | NT_032977.8 | GAATAACAGTGATGTCTGGC | 3-14-3 | 83 |
| 399933 | 138 | 14494 | NT_032977.8 | TCACAGCTCACCGAGTCTGC | 3-14-3 | 78 |
| 399934 | 98 | 14524 | NT_032977.8 | AGTGTAAAATAAAGCCCCTA | 3-14-3 | 79 |
| 399935 | 96 | 14601 | NT_032977.8 | AGGACCCAAGTCATCCTGCT | 3-14-3 | 89 |
| 399936 | 124 | 14631 | NT_032977.8 | GGCCATCAGCTGGCAATGCT | 3-14-3 | 70 |
| 399937 | 133 | 14675 | NT_032977.8 | TAGACAAGGAAAGGGAGGCC | 3-14-3 | 78 |
| 399938 | 103 | 14681 | NT_032977.8 | ATTTCATAGACAAGGAAAGG | 3-14-3 | 67 |

TABLE 16-continued

Antisense inhibition of PCSK9 in human cells (Cell type A549)

| IsisNo | SEQ ID NO | 5' Target Site | Target Nucleic Acid | Sequence | Motif | % Inhibition |
|---|---|---|---|---|---|---|
| 399940 | 146 | 1315 | AK124635.1 | TGACATTTGTGGGAGAGGAG | 3-14-3 | 35 |
| 399942 | 104 | 2085 | AK124635.1 | CACAGTCCTGCAAAACAGCT | 3-14-3 | 75 |
| 399943 | 102 | 5590 | NT_032977.8 | ATGTGCAGAGATCAATCACA | 3-14-3 | 64 |
| 399944 | 127 | 10633 | NT_032977.8 | GGTGGTAATTTGTCACAGCA | 3-14-3 | 73 |
| 399945 | 84 | 11308 | NT_032977.8 | AAGGTCACACAGTTAAGAGT | 3-14-3 | 89 |
| 399947 | 126 | 22292 | NT_032977.8 | GGTGCATAAGGAGAAAGAGA | 3-14-3 | 70 |
| 399948 | 147 | 24858 | NT_032977.8 | TGAGTTCATTTAAGAGTGGA | 3-14-3 | 46 |
| 399949 | 8 | 417 | NM_174936.2 | CCTCGGAACGCAAGGCTAGC | 3-14-3 | 74 |
| 399950 | 12 | 606 | NM_174936.2 | GGATCTTGGTGAGGTATCCC | 3-14-3 | 68 |
| 399951 | 13 | 615 | NM_174936.2 | AGACATGCAGGATCTTGGTG | 3-14-3 | 67 |
| 399952 | 16 | 651 | NM_174936.2 | TCATCTTCACCAGGAAGCCA | 3-14-3 | 74 |
| 399953 | 20 | 840 | NM_174936.2 | GTATGCTGGTGTCTAGGAGA | 3-14-3 | 59 |
| 399954 | 22 | 866 | NM_174936.2 | GCCCTCGATTTCCCGGTGGT | 3-14-3 | 83 |
| 399955 | 23 | 880 | NM_174936.2 | GTGACCATGACCCTGCCCTC | 3-14-3 | 62 |
| 399956 | 27 | 975 | NM_174936.2 | TGACCACCCCTGCCAGGTGG | 3-14-3 | 78 |
| 399957 | 30 | 1045 | NM_174936.2 | TTCCCTTGGCAGTTGAGCAC | 3-14-3 | 82 |
| 399958 | 35 | 1335 | NM_174936.2 | AGTTGGTCCCCAAAGTCCCC | 3-14-3 | 78 |
| 399959 | 37 | 1352 | NM_174936.2 | GTCCACACAGCGGCCAAAGT | 3-14-3 | 89 |
| 399960 | 40 | 1400 | NM_174936.2 | GCTGCAGTCGCTGGAGGCAC | 3-14-3 | 64 |
| 399961 | 41 | 1411 | NM_174936.2 | ACAAAGCAGGTGCTGCAGTC | 3-14-3 | 63 |
| 399962 | 42 | 1470 | NM_174936.2 | GCATCATGGCTGCAATGCCA | 3-14-3 | 68 |
| 399963 | 43 | 1478 | NM_174936.2 | GGCAGACAGCATCATGGCTG | 3-14-3 | 70 |
| 399964 | 44 | 1526 | NM_174936.2 | GAAGTGGATCAGTCTCTGCC | 3-14-3 | 70 |
| 399965 | 46 | 1539 | NM_174936.2 | CATCTTTGGCAGAGAAGTGG | 3-14-3 | 49 |
| 399966 | 47 | 1545 | NM_174936.2 | TGATGACATCTTTGGCAGAG | 3-14-3 | 78 |
| 399967 | 48 | 1552 | NM_174936.2 | GCCTCATTGATGACATCTTT | 3-14-3 | 82 |
| 399968 | 49 | 1564 | NM_174936.2 | TCAGGGAACCAGGCCTCATT | 3-14-3 | 71 |
| 399969 | 51 | 1583 | NM_174936.2 | GGTCAGTACCCGCTGGTCCT | 3-14-3 | 82 |
| 399970 | 53 | 1645 | NM_174936.2 | CTGCAAAACAGCTGCCAACC | 3-14-3 | 74 |
| 399971 | 55 | 1740 | NM_174936.2 | AGAAACTGGAGCAGCTCAGC | 3-14-3 | 48 |
| 399972 | 56 | 1746 | NM_174936.2 | TCCTGGAGAAACTGGAGCAG | 3-14-3 | 63 |
| 399973 | 61 | 2105 | NM_174936.2 | CTTGACTTTGCATTCCAGAC | 3-14-3 | 74 |
| 399974 | 63 | 2415 | NM_174936.2 | AACCATTTTAAAGCTCAGCC | 3-14-3 | 71 |
| 399975 | 65 | 2509 | NM_174936.2 | CCCACTCAAGGGCCAGGCCA | 3-14-3 | 91 |
| 399976 | 122 | 2582 | NM_174936.2 | GGAGGGAGCTTCCTGGCACC | 3-14-3 | 67 |
| 399977 | 71 | 2906 | NM_174936.2 | TCTGGCTAGATGCCATCCAG | 3-14-3 | 89 |
| 399978 | 73 | 2988 | NM_174936.2 | AGCCTGGCATAGAGCAGAGT | 3-14-3 | 80 |

TABLE 16-continued

Antisense inhibition of PCSK9 in human cells (Cell type A549)

| IsisNo | SEQ ID NO | 5' Target Site | Target Nucleic Acid | Sequence | Motif | % Inhibition |
|---|---|---|---|---|---|---|
| 399979 | 135 | 2994 | NM_174936.2 | TAGCACAGCCTGGCATAGAG | 3-14-3 | 83 |
| 399980 | 74 | 3233 | NM_174936.2 | AAGTAAGAAGAGGCTTGGCT | 3-14-3 | 50 |
| 399981 | 77 | 3477 | NM_174936.2 | ACCCAAAAGATAAATGTCTG | 3-14-3 | 55 |
| 399982 | 99 | 3550 | NM_174936.2 | ATAAATATCTTCAAGTTACA | 3-14-3 | 36 |
| 399983 | 100 | 13746 | NT_032977.8 | ATCTCAGGACAGGTGAGCAA | 3-14-3 | 96 |
| 399984 | 116 | 13760 | NT_032977.8 | GAGTAGAGATTCTCATCTCA | 3-14-3 | 71 |
| 399985 | 117 | 13828 | NT_032977.8 | GAGTCTTCTGAAGTGCCATC | 3-14-3 | 76 |
| 399986 | 81 | 13903 | NT_032977.8 | AAGCAGGGCCTCAGGTGGAA | 3-14-3 | 68 |
| 399987 | 83 | 13986 | NT_032977.8 | AAGGAAGACTTCAGGCAGGT | 3-14-3 | 59 |
| 399988 | 137 | 14112 | NT_032977.8 | TAGGGAGAGCTCACAGATGC | 3-14-3 | 31 |
| 399989 | 92 | 14397 | NT_032977.8 | AGAGACAGGAAGCTGCAGCT | 3-14-3 | 65 |
| 399990 | 82 | 14670 | NT_032977.8 | AAGGAAAGGGAGGCCTAGAG | 3-14-3 | 59 |
| 399992 | 130 | 2095 | AK124635.1 | GTGCTGACCACACAGTCCTG | 3-14-3 | 94 |
| 399993 | 107 | 3056 | NT_032977.8 | CCCACTATAATGGCAAGCCC | 3-14-3 | 76 |
| 399994 | 80 | 4306 | NT_032977.8 | AACCCAGTTCTAATGCACCT | 3-14-3 | 82 |
| 399995 | 106 | 5140 | NT_032977.8 | CCAGTCAGAGTAGAACAGAG | 3-14-3 | 74 |
| 399996 | 121 | 5599 | NT_032977.8 | GGAGCCTACATGTGCAGAGA | 3-14-3 | 65 |
| 399997 | 94 | 5667 | NT_032977.8 | AGCATGGCACCAGCATCTGC | 3-14-3 | 77 |
| 399998 | 108 | 6652 | NT_032977.8 | CCCAGCCCTATCAGGAAGTG | 3-14-3 | 78 |
| 399999 | 144 | 7099 | NT_032977.8 | TGACATCCAGGAGGGAGGAG | 3-14-3 | 43 |
| 400000 | 91 | 7556 | NT_032977.8 | AGACTGATGGAAGGCATTGA | 3-14-3 | 84 |
| 400001 | 131 | 7565 | NT_032977.8 | GTGTTGAGCAGACTGATGGA | 3-14-3 | 73 |
| 400002 | 145 | 8836 | NT_032977.8 | TGACATCTTGTCTGGGAGCC | 3-14-3 | 82 |
| 400003 | 90 | 8948 | NT_032977.8 | AGACTAGGAGCCTGAGTTTT | 3-14-3 | 48 |
| 400004 | 125 | 9099 | NT_032977.8 | GGCCTGCAGAAGCCAGAGAG | 3-14-3 | 45 |
| 400005 | 148 | 10252 | NT_032977.8 | TGGCAGCAACTCAGACATAT | 3-14-3 | 73 |
| 400006 | 79 | 11472 | NT_032977.8 | AAATGCAGGGCTAAAATCAC | 3-14-3 | 78 |
| 400007 | 88 | 12715 | NT_032977.8 | ACTGGATACATTGGCAGACA | 3-14-3 | 77 |
| 400008 | 111 | 12928 | NT_032977.8 | CTAGAGGAACCACTAGATAT | 3-14-3 | 78 |
| 400009 | 86 | 15471 | NT_032977.8 | ACAGCATTCTTGGTTAGGAG | 3-14-3 | 73 |
| 400010 | 97 | 16134 | NT_032977.8 | AGTCAAGCTGCTGCCCAGAG | 3-14-3 | 74 |
| 400011 | 120 | 16668 | NT_032977.8 | GCTAGTTATTAAGCACCTGC | 3-14-3 | 75 |
| 400012 | 150 | 17267 | NT_032977.8 | TGTGAGCTCTGGCCCAGTGG | 3-14-3 | 64 |
| 400013 | 115 | 18377 | NT_032977.8 | GAGTAAGGCAGGTTACTCTC | 3-14-3 | 88 |
| 400014 | 134 | 18408 | NT_032977.8 | TAGATGTGACTAACATTTAA | 3-14-3 | 58 |
| 400015 | 105 | 19203 | NT_032977.8 | CACATTAGCCTTGCTCAAGT | 3-14-3 | 89 |
| 400018 | 109 | 20188 | NT_032977.8 | CCCCTGCACAGAGCCTGGCA | 3-14-3 | 62 |

TABLE 16-continued

Antisense inhibition of PCSK9 in human cells (Cell type A549)

| IsisNo | SEQ ID NO | 5' Target Site | Target Nucleic Acid | Sequence | Motif | % Inhibition |
|---|---|---|---|---|---|---|
| 400019 | 141 | 20624 | NT_032977.8 | TCATGGCTGCAATGCCTGGT | 3-14-3 | 47 |
| 400020 | 93 | 20995 | NT_032977.8 | AGAGAGGAGGGCTTAAAGAA | 3-14-3 | 66 |
| 400021 | 95 | 21082 | NT_032977.8 | AGCTGCCAACCTGCAAAAAG | 3-14-3 | 61 |
| 400022 | 143 | 21481 | NT_032977.8 | TGAAAATCCATCCAGCACTG | 3-14-3 | 90 |
| 400023 | 89 | 21589 | NT_032977.8 | AGAACCATGGAGCACCTGAG | 3-14-3 | 83 |
| 400024 | 123 | 21696 | NT_032977.8 | GGCACTGCCCTTCCACCAAA | 3-14-3 | 79 |
| 400025 | 118 | 24907 | NT_032977.8 | GCACCATCCAGACCAGAATC | 3-14-3 | 78 |
| 400026 | 114 | 25413 | NT_032977.8 | GAGAGGTTCAGATCCAGGCC | 3-14-3 | 81 |

Antisense oligonucleotides with the following ISIS Nos exhibited at least 80% inhibition of PCSK9 mRNA levels: 399806, 399814, 399817, 399819, 399821, 399827, 399836, 399837, 399854, 399867, 399889, 399891, 399906, 399907, 399908, 399913, 399920, 399924, 399935, 399945, 399959, 399975, 399977, 399983, 399992, 400000, 400013, 400015, 400022, and 400023. The target segments to which these antisense oligonucleotides are targeted are active target segments. The target regions to which these antisense oligonucleotides are targeted are active target regions.

ISIS Nos 399814, 399819, 399836, 399891, 399906, 399907, 399913, 399935, 399945, 399959, 399975, 399977, 399983, 399992, 400013, 400015, and 400022 each exhibited at least 85% inhibition of PCSK9 mRNA levels.

ISIS Nos 399836, 399891, 399906, 399907, 399913, 399975, 399983, 399992, and 400022 each exhibited at least 90% inhibition of PCSK9 mRNA levels.

Example 2: Antisense Inhibition of Human PCSK9 in HepG2 Cells

Antisense oligonucleotides were tested for their ability to inhibit the expression of PCSK9 mRNA in cultured HepG2 cells. HepG2 cells at a density of 10000 cells per well in a 96-well plate were treated with 1500 nM of antisense oligonucleotide. After a treatment period of approximately 24 hours, RNA was isolated from the cells and PCSK9 mRNA levels were measured by quantitative real-time PCR, as described herein. PCSK9 mRNA levels were adjusted according to total RNA content as measured by RIBOGREEN®. Results are presented as percent inhibition of PCSK9, relative to untreated control cells.

Isis Nos. 399819, 395149, 395150, 395151, 395152, 395153, 395154, 395155, 395156, 395157, 395158, 395161, 395162, 395163, 395164, 395165, 395166, 395167, 395168, 395172, 395173, 395174, 395178, 395179, 395182, 395183, 395185, 395186, 395187, 395189, 395190, 395191, 395193, 395194, 395195, 395198, 395199, 395203, 395207, 395210, 395211, 395213, 395214, 395221, 395222, 399793, 399794, 399795, 399798, 399801, 399803, 399804, 399806, 399807, 399812, 399813, 399814, 399816, 399817, 399820, 399821, 399822, 399823, 399827, 399828, 399829, 399833, 399834, 399836, 399837, 399841, 399844, 399846, 399848, 399849, 399851, 399852, 399854, 399855, 399856, 399857, 399862, 399865, 399867, 399868, 399872, 399873, 399874, 399875, 399876, 399877, 399879, 399880, 399883, 399884, 399885, 399886, 399887, 399888, 399889, 399890, 399891, 399892, 399894, 399895, 399896, 399900, 399901, 399902, 399904, 399905, 399906, 399907, 399908, 399909, 399911, 399912, 399913, 399915, 399916, 399918, 399920, 399921, 399924, 399925, 399929, 399931, 399935, 399936, 399937, 399943, 399944, 399945, 399949, 399950, 399954, 399957, 399959, 399960, 399962, 399963, 399966, 399967, 399968, 399969, 399970, 399972, 399973, 399975, 399976, 399977, 399978, 399979, 399983, 399984, 399985, 399986, 399989, 399990, 399992, 399996, 399997, 399998, 400000, 400001, 400002, 400004, 400005, 400007, 400008, 400009, 400010, 400012, 400013, 400015, 400018, 400021, 400023, 400024, 400025, and 400026 each inhibited PCSK9 by at least 70% in this experiment. The target segments to which these antisense oligonucleotides are targeted are active target segments. The target regions to which these antisense oligonucleotides are targeted are active target regions.

Isis Nos 399819, 395150, 395152, 395153, 395154, 395155, 395156, 395158, 395163, 395164, 395165, 395166, 395167, 395168, 395173, 395178, 395183, 395185, 395186, 395187, 395189, 395190, 395193, 395194, 395199, 395203, 395210, 395213, 395214, 399793, 399798, 399801, 399804, 399806, 399813, 399816, 399820, 399821, 399822, 399836, 399849, 399856, 399857, 399862, 399868, 399875, 399877, 399880, 399885, 399886, 399887, 399888, 399889, 399890, 399894, 399896, 399900, 399901, 399904, 399905, 399906, 399907, 399911, 399912, 399916, 399920, 399925, 399935, 399936, 399937, 399945, 399954, 399957, 399959, 399960, 399962, 399968, 399969, 399973, 399976, 399977, 399978, 399989, 399992, 400002, 400004, 400007, 400012, 400013, 400023, and 400024 each inhibited PCSK9 by at least 80% in this experiment.

Isis Nos 399819, 395152, 395153, 395155, 395156, 395158, 395163, 395164, 395165, 395166, 395168, 395178, 395183, 395185, 395187, 395189, 395190, 395194, 395199, 395203, 395214, 399793, 399804, 399813, 399821, 399822, 399836, 399856, 399868, 399877, 399887, 399888, 399890, 399900, 399904, 399905, 399907, 399911, 399912, 399916, 399925, 399936, 399954, 399960, 399962, 399969, 399976, 399977, 399978, 399989, 399992, 400012, 400013, 400023, and 400024 each inhibited PCSK9 by at least 85% in this experiment.

Isis Nos 399819, 395165, 395183, 395185, 399868, 399900, 399907, 399911, 399912, 399916, 399936, 399969, and 400024 each inhibited PCSK9 by at least 90% in this experiment.

Example 3: Antisense Inhibition of Human PCSK9 (Hep3B Cells)

Antisense oligonucleotides targeted to a PCSK9 nucleic acid were tested for their effects on PCSK9 mRNA in vitro. Cultured Hep3B cells at a density of 4000 cells per well in a 96-well plate were treated with 75 nM of antisense oligonucleotide. After a treatment period of approximately 24 hours, RNA was isolated from the cells and PCSK9 mRNA levels were measured by quantitative real-time PCR, as described herein. PCSK9 mRNA levels were adjusted according to total RNA content as measured by RIBOGREEN®. Results are presented as percent inhibition of PCSK9, relative to untreated control cells. Antisense oligonucleotides that exhibited at least 30% inhibition of PCSK9 expression are shown in Tables 17, 18, and 19.

The motif column indicates the wing-gap-wing motif of each antisense oligonucleotide. Antisense oligonucleotides were designed as 5-10-5 gapmers, or alternatively as 3-14-3 gapmers, or alternatively as 2-13-5 gapmers where the gap segment comprises 2'-deoxynucleotides and each wing segment comprises 2'-MOE nucleotides. As illustrated in Table 17, 18 and 19, a single nucleobase sequence may be represented by a 5-10-5 motif as well as a 3-14-3 motif as well as a 2-13-5 motif. "5' target site" indicates the 5'-most nucleotide which the antisense oligonucleotide is targeted on the indicated GENBANK Accession No.

TABLE 17

Antisense inhibition of PCSK9 in human cells (Hep3B) targeting SEQ ID NO: 1

| Isis No. | 5' Target Site to SEQ ID NO: 1 | 3' Target Site to SEQ ID NO: 1 | Sequence 5'-3' | Motif | % inhibition | SEQ ID NO |
|---|---|---|---|---|---|---|
| 410742 | 294 | 313 | GCCTGGAGCTGACGGTGCCC | 5-10-5 | 75.1 | 159 |
| 405999 | 298 | 317 | GACCGCCTGGAGCTGACGGT | 5-10-5 | 70.3 | 160 |
| 395151 | 300 | 319 | AGGACCGCCTGGAGCTGACG | 5-10-5 | 57.3 | 6 |
| 405861 | 406 | 425 | AAGGCTAGCACCAGCTCCTC | 5-10-5 | 90.5 | 162 |
| 405862 | 407 | 426 | CAAGGCTAGCACCAGCTCCT | 5-10-5 | 92.3 | 163 |
| 405863 | 408 | 427 | GCAAGGCTAGCACCAGCTCC | 5-10-5 | 82.6 | 164 |
| 405864 | 409 | 428 | CGCAAGGCTAGCACCAGCTC | 5-10-5 | 91.8 | 165 |
| 395152 | 410 | 429 | ACGCAAGGCTAGCACCAGCT | 5-10-5 | 93.3 | 7 |
| 405865 | 411 | 430 | AACGCAAGGCTAGCACCAGC | 5-10-5 | 84.6 | 166 |
| 405866 | 412 | 431 | GAACGCAAGGCTAGCACCAG | 5-10-5 | 81.8 | 167 |
| 405867 | 413 | 432 | GGAACGCAAGGCTAGCACCA | 5-10-5 | 74.0 | 168 |
| 405868 | 414 | 433 | CGGAACGCAAGGCTAGCACC | 5-10-5 | 76.8 | 169 |
| 399793 | 417 | 436 | CCTCGGAACGCAAGGCTAGC | 5-10-5 | 77.9 | 8 |
| 410743 | 421 | 440 | TCCTCCTCGGAACGCAAGGC | 5-10-5 | 76.7 | 170 |
| 410744 | 446 | 465 | GTGCTCGGGTGCTTCGGCCA | 5-10-5 | 76.9 | 171 |
| 410745 | 466 | 485 | TGGAAGGTGGCTGTGGTTCC | 5-10-5 | 41.7 | 172 |
| 395153 | 480 | 499 | CCTTGGCGCAGCGGTGGAAG | 5-10-5 | 81.1 | 9 |
| 406000 | 482 | 501 | ATCCTTGGCGCAGCGGTGGA | 5-10-5 | 79.1 | 173 |
| 406001 | 484 | 503 | GGATCCTTGGCGCAGCGGTG | 5-10-5 | 63.1 | 174 |
| 406002 | 488 | 507 | CCACGGATCCTTGGCGCAGC | 5-10-5 | 80.8 | 175 |
| 410746 | 507 | 526 | CGTAGGTGCCAGGCAACCTC | 5-10-5 | 44.8 | 176 |
| 410747 | 545 | 564 | TGACTGCGAGAGGTGGGTCT | 5-10-5 | NA | 177 |
| 406003 | 555 | 574 | CAGTGCGCTCTGACTGCGAG | 5-10-5 | 84.2 | 178 |
| 406004 | 557 | 576 | GGCAGTGCGCTCTGACTGCG | 5-10-5 | 56.4 | 179 |
| 406005 | 559 | 578 | CGGGCAGTGCGCTCTGACTG | 5-10-5 | 83.4 | 180 |
| 406006 | 562 | 581 | CGGCGGGCAGTGCGCTCTGA | 5-10-5 | 71.0 | 181 |

TABLE 17-continued

Antisense inhibition of PCSK9 in human cells (Hep3B) targeting SEQ ID NO: 1

| Isis No. | 5' Target Site to SEQ ID NO: 1 | 3' Target Site to SEQ ID NO: 1 | Sequence 5'-3' | Motif | % inhibition | SEQ ID NO |
|---|---|---|---|---|---|---|
| 410748 | 591 | 610 | ATCCCCGGCGGGCAGCCTGG | 5-10-5 | 56.0 | 182 |
| 406007 | 595 | 614 | AGGTATCCCCGGCGGGCAGC | 5-10-5 | 76.3 | 183 |
| 410574 | 597 | 616 | TGAGGTATCCCCGGCGGGCA | 3-14-3 | 69.1 | 184 |
| 410529 | 597 | 616 | TGAGGTATCCCCGGCGGGCA | 5-10-5 | 77.4 | 184 |
| 410647 | 597 | 616 | TGAGGTATCCCCGGCGGGCA | 2-13-5 | 90.7 | 184 |
| 410575 | 598 | 617 | GTGAGGTATCCCCGGCGGGC | 3-14-3 | 71.5 | 185 |
| 410648 | 598 | 617 | GTGAGGTATCCCCGGCGGGC | 2-13-5 | 82.8 | 185 |
| 410530 | 598 | 617 | GTGAGGTATCCCCGGCGGGC | 5-10-5 | 83.2 | 185 |
| 410649 | 599 | 618 | GGTGAGGTATCCCCGGCGGG | 2-13-5 | 53.5 | 186 |
| 410576 | 599 | 618 | GGTGAGGTATCCCCGGCGGG | 3-14-3 | 56.2 | 186 |
| 410531 | 599 | 618 | GGTGAGGTATCCCCGGCGGG | 5-10-5 | 63.6 | 186 |
| 410650 | 600 | 619 | TGGTGAGGTATCCCCGGCGG | 2-13-5 | 86.1 | 11 |
| 399877 | 600 | 619 | TGGTGAGGTATCCCCGGCGG | 3-14-3 | 92.6 | 11 |
| 395155 | 600 | 619 | TGGTGAGGTATCCCCGGCGG | 5-10-5 | 92.7 | 11 |
| 410577 | 601 | 620 | TTGGTGAGGTATCCCCGGCG | 3-14-3 | 62.4 | 187 |
| 410532 | 601 | 620 | TTGGTGAGGTATCCCCGGCG | 5-10-5 | 63.5 | 187 |
| 410651 | 601 | 620 | TTGGTGAGGTATCCCCGGCG | 2-13-5 | 75.5 | 187 |
| 410652 | 602 | 621 | CTTGGTGAGGTATCCCCGGC | 2-13-5 | 81.2 | 188 |
| 410578 | 602 | 621 | CTTGGTGAGGTATCCCCGGC | 3-14-3 | 83.3 | 188 |
| 406008 | 602 | 621 | CTTGGTGAGGTATCCCCGGC | 5-10-5 | 95.2 | 188 |
| 410653 | 603 | 622 | TCTTGGTGAGGTATCCCCGG | 2-13-5 | 68.9 | 189 |
| 410579 | 603 | 622 | TCTTGGTGAGGTATCCCCGG | 3-14-3 | 74.0 | 189 |
| 410533 | 603 | 622 | TCTTGGTGAGGTATCCCCGG | 5-10-5 | 79.0 | 189 |
| 410580 | 604 | 623 | ATCTTGGTGAGGTATCCCCG | 3-14-3 | 62.3 | 190 |
| 410654 | 604 | 623 | ATCTTGGTGAGGTATCCCCG | 2-13-5 | 65.2 | 190 |
| 406009 | 604 | 623 | ATCTTGGTGAGGTATCCCCG | 5-10-5 | 90.7 | 190 |
| 410534 | 605 | 624 | GATCTTGGTGAGGTATCCCC | 5-10-5 | 59.8 | 191 |
| 410581 | 605 | 624 | GATCTTGGTGAGGTATCCCC | 3-14-3 | 72.9 | 191 |
| 410655 | 605 | 624 | GATCTTGGTGAGGTATCCCC | 2-13-5 | 77.4 | 191 |
| 399794 | 606 | 625 | GGATCTTGGTGAGGTATCCC | 5-10-5 | 56.5 | 12 |
| 410656 | 606 | 625 | GGATCTTGGTGAGGTATCCC | 2-13-5 | 68.0 | 12 |
| 399950 | 606 | 625 | GGATCTTGGTGAGGTATCCC | 3-14-3 | 74.4 | 12 |
| 410535 | 607 | 626 | AGGATCTTGGTGAGGTATCC | 5-10-5 | 65.7 | 192 |
| 410582 | 607 | 626 | AGGATCTTGGTGAGGTATCC | 3-14-3 | 69.5 | 192 |
| 410657 | 607 | 626 | AGGATCTTGGTGAGGTATCC | 2-13-5 | 73.1 | 192 |
| 406010 | 609 | 628 | GCAGGATCTTGGTGAGGTAT | 5-10-5 | 56.9 | 193 |
| 406011 | 611 | 630 | ATGCAGGATCTTGGTGAGGT | 5-10-5 | 70.7 | 194 |

TABLE 17-continued

Antisense inhibition of PCSK9 in human cells (Hep3B) targeting SEQ ID NO: 1

| Isis No. | 5' Target Site to SEQ ID NO: 1 | 3' Target Site to SEQ ID NO: 1 | Sequence 5'-3' | Motif | % inhibition | SEQ ID NO |
|---|---|---|---|---|---|---|
| 406012 | 613 | 632 | ACATGCAGGATCTTGGTGAG | 5-10-5 | 69.1 | 195 |
| 406013 | 617 | 636 | GAAGACATGCAGGATCTTGG | 5-10-5 | 77.4 | 196 |
| 395156 | 620 | 639 | ATGGAAGACATGCAGGATCT | 5-10-5 | 76.7 | 14 |
| 410749 | 628 | 647 | AGAAGGCCATGGAAGACATG | 5-10-5 | 59.4 | 197 |
| 410750 | 638 | 657 | GAAGCCAGGAAGAAGGCCAT | 5-10-5 | 57.5 | 198 |
| 399879 | 646 | 665 | TTCACCAGGAAGCCAGGAAG | 3-14-3 | 91.9 | 15 |
| 406014 | 648 | 667 | TCTTCACCAGGAAGCCAGGA | 5-10-5 | 94.0 | 199 |
| 406015 | 653 | 672 | ACTCATCTTCACCAGGAAGC | 5-10-5 | 78.8 | 200 |
| 406016 | 655 | 674 | CCACTCATCTTCACCAGGAA | 5-10-5 | 87.2 | 201 |
| 410730 | 657 | 676 | CGCCACTCATCTTCACCAGG | 5-10-5 | 85.4 | 202 |
| 406017 | 659 | 678 | GTCGCCACTCATCTTCACCA | 5-10-5 | 76.3 | 203 |
| 406018 | 661 | 680 | AGGTCGCCACTCATCTTCAC | 5-10-5 | 63.2 | 204 |
| 406019 | 663 | 682 | GCAGGTCGCCACTCATCTTC | 5-10-5 | 68.1 | 205 |
| 406020 | 665 | 684 | CAGCAGGTCGCCACTCATCT | 5-10-5 | 83.7 | 206 |
| 410731 | 667 | 686 | TCCAGCAGGTCGCCACTCAT | 5-10-5 | 72.9 | 207 |
| 410751 | 685 | 704 | GGCAACTTCAAGGCCAGCTC | 5-10-5 | 84.6 | 208 |
| 395158 | 705 | 724 | CCTCGATGTAGTCGACATGG | 5-10-5 | 93.9 | 17 |
| 410752 | 724 | 743 | GCAAAGACAGAGGAGTCCTC | 5-10-5 | 76.3 | 209 |
| 406021 | 782 | 801 | TTCATCCGCCCGGTACCGTG | 5-10-5 | 79.6 | 210 |
| 406022 | 784 | 803 | TATTCATCCGCCCGGTACCG | 5-10-5 | 78.7 | 211 |
| 406023 | 787 | 806 | TGGTATTCATCCGCCCGGTA | 5-10-5 | 92.5 | 212 |
| 406024 | 789 | 808 | GCTGGTATTCATCCGCCCGG | 5-10-5 | 69.7 | 213 |
| 410732 | 791 | 810 | GGGCTGGTATTCATCCGCCC | 5-10-5 | 30.4 | 214 |
| 410753 | 821 | 840 | ATACACCTCCACCAGGCTGC | 5-10-5 | 72.8 | 215 |
| 406025 | 832 | 851 | GTGTCTAGGAGATACACCTC | 5-10-5 | 74.2 | 216 |
| 406026 | 837 | 856 | TGCTGGTGTCTAGGAGATAC | 5-10-5 | 80.5 | 217 |
| 405869 | 862 | 881 | TCGATTTCCCGGTGGTCACT | 5-10-5 | 87.6 | 218 |
| 405870 | 863 | 882 | CTCGATTTCCCGGTGGTCAC | 5-10-5 | 83.3 | 219 |
| 405871 | 864 | 883 | CCTCGATTTCCCGGTGGTCA | 5-10-5 | 87.0 | 220 |
| 405872 | 865 | 884 | CCCTCGATTTCCCGGTGGTC | 5-10-5 | 88.2 | 221 |
| 399798 | 866 | 885 | GCCCTCGATTTCCCGGTGGT | 5-10-5 | 84.3 | 22 |
| 399954 | 866 | 885 | GCCCTCGATTTCCCGGTGGT | 3-14-3 | 90.3 | 22 |
| 405873 | 867 | 886 | TGCCCTCGATTTCCCGGTGG | 5-10-5 | 90.0 | 222 |
| 405874 | 868 | 887 | CTGCCCTCGATTTCCCGGTG | 5-10-5 | 91.4 | 223 |
| 405875 | 869 | 888 | CCTGCCCTCGATTTCCCGGT | 5-10-5 | 93.5 | 224 |
| 405876 | 870 | 889 | CCCTGCCCTCGATTTCCCGG | 5-10-5 | 90.1 | 225 |

TABLE 17-continued

Antisense inhibition of PCSK in human cells (Hep3B) targeting SEQ ID NO: 1

| Isis No. | 5' Target Site to SEQ ID NO: 1 | 3' Target Site to SEQ ID NO: 1 | Sequence 5'-3' | Motif | % inhibition | SEQ ID NO |
|---|---|---|---|---|---|---|
| 406027 | 874 | 893 | ATGACCCTGCCCTCGATTTC | 5-10-5 | 73.9 | 226 |
| 406028 | 876 | 895 | CCATGACCCTGCCCTCGATT | 5-10-5 | 92.3 | 227 |
| 406029 | 878 | 897 | GACCATGACCCTGCCCTCGA | 5-10-5 | 91.4 | 228 |
| 406030 | 882 | 901 | CGGTGACCATGACCCTGCCC | 5-10-5 | 95.6 | 229 |
| 406031 | 884 | 903 | GTCGGTGACCATGACCCTGC | 5-10-5 | 89.6 | 230 |
| 410733 | 886 | 905 | AAGTCGGTGACCATGACCCT | 5-10-5 | 65.7 | 231 |
| 406032 | 888 | 907 | CGAAGTCGGTGACCATGACC | 5-10-5 | 88.5 | 232 |
| 410754 | 898 | 917 | GGCACATTCTCGAAGTCGGT | 5-10-5 | 80.1 | 233 |
| 395163 | 923 | 942 | GTGGAAGCGGGTCCCGTCCT | 5-10-5 | 83.9 | 25 |
| 410755 | 933 | 952 | TGGCCTGTCTGTGGAAGCGG | 5-10-5 | NA | 234 |
| 410756 | 960 | 979 | GGTGGGTGCCATGACTGTCA | 5-10-5 | 67.1 | 235 |
| 406033 | 967 | 986 | CCTGCCAGGTGGGTGCCATG | 5-10-5 | 91.2 | 237 |
| 406034 | 972 | 991 | CCACCCCTGCCAGGTGGGTG | 5-10-5 | 59.3 | 238 |
| 406035 | 977 | 996 | GCTGACCACCCCTGCCAGGT | 5-10-5 | 91.7 | 239 |
| 410757 | 985 | 1004 | TCCCGGCCGCTGACCACCCC | 5-10-5 | 88.9 | 240 |
| 406036 | 989 | 1008 | GGCATCCCGGCCGCTGACCA | 5-10-5 | 84.0 | 241 |
| 406037 | 992 | 1011 | GCCGGCATCCCGGCCGCTGA | 5-10-5 | 55.9 | 242 |
| 410536 | 997 | 1016 | GCCACGCCGGCATCCCGGCC | 5-10-5 | 63.7 | 243 |
| 410658 | 997 | 1016 | GCCACGCCGGCATCCCGGCC | 2-13-5 | 82.0 | 243 |
| 410583 | 997 | 1016 | GCCACGCCGGCATCCCGGCC | 3-14-3 | 87.3 | 243 |
| 410537 | 998 | 1017 | GGCCACGCCGGCATCCCGGC | 5-10-5 | 58.5 | 244 |
| 410659 | 998 | 1017 | GGCCACGCCGGCATCCCGGC | 2-13-5 | 73.7 | 244 |
| 410584 | 998 | 1017 | GGCCACGCCGGCATCCCGGC | 3-14-3 | 79.5 | 244 |
| 410660 | 999 | 1018 | TGGCCACGCCGGCATCCCGG | 2-13-5 | 63.0 | 245 |
| 410585 | 999 | 1018 | TGGCCACGCCGGCATCCCGG | 3-14-3 | 73.2 | 245 |
| 406038 | 999 | 1018 | TGGCCACGCCGGCATCCCGG | 5-10-5 | 86.3 | 245 |
| 410661 | 1000 | 1019 | TTGGCCACGCCGGCATCCCG | 2-13-5 | 53.3 | 246 |
| 410586 | 1000 | 1019 | TTGGCCACGCCGGCATCCCG | 3-14-3 | 60.3 | 246 |
| 405877 | 1000 | 1019 | TTGGCCACGCCGGCATCCCG | 5-10-5 | 83.2 | 246 |
| 410587 | 1001 | 1020 | CTTGGCCACGCCGGCATCCC | 3-14-3 | 63.2 | 247 |
| 410662 | 1001 | 1020 | CTTGGCCACGCCGGCATCCC | 2-13-5 | 67.3 | 247 |
| 405878 | 1001 | 1020 | CTTGGCCACGCCGGCATCCC | 5-10-5 | 91.4 | 247 |
| 410588 | 1002 | 1021 | CCTTGGCCACGCCGGCATCC | 3-14-3 | 65.3 | 248 |
| 410663 | 1002 | 1021 | CCTTGGCCACGCCGGCATCC | 2-13-5 | 67.9 | 248 |
| 405879 | 1002 | 1021 | CCTTGGCCACGCCGGCATCC | 5-10-5 | 94.1 | 248 |
| 410589 | 1003 | 1022 | CCCTTGGCCACGCCGGCATC | 3-14-3 | 80.1 | 249 |
| 410664 | 1003 | 1022 | CCCTTGGCCACGCCGGCATC | 2-13-5 | 81.9 | 249 |

TABLE 17-continued

Antisense inhibition of PCSK9 in human cells (Hep3B) targeting SEQ ID NO: 1

| Isis No. | 5' Target Site to SEQ ID NO: 1 | 3' Target Site to SEQ ID NO: 1 | Sequence 5'-3' | Motif | % inhibition | SEQ ID NO |
|---|---|---|---|---|---|---|
| 405880 | 1003 | 1022 | CCCTTGGCCACGCCGGCATC | 5-10-5 | 93.5 | 249 |
| 410665 | 1004 | 1023 | ACCCTTGGCCACGCCGGCAT | 2-13-5 | 78.7 | 28 |
| 399887 | 1004 | 1023 | ACCCTTGGCCACGCCGGCAT | 3-14-3 | 91.9 | 28 |
| 395165 | 1004 | 1023 | ACCCTTGGCCACGCCGGCAT | 5-10-5 | 96.7 | 28 |
| 410590 | 1005 | 1024 | CACCCTTGGCCACGCCGGCA | 3-14-3 | 82.2 | 250 |
| 410666 | 1005 | 1024 | CACCCTTGGCCACGCCGGCA | 2-13-5 | 82.7 | 250 |
| 405881 | 1005 | 1024 | CACCCTTGGCCACGCCGGCA | 5-10-5 | 98.3 | 250 |
| 410667 | 1006 | 1025 | GCACCCTTGGCCACGCCGGC | 2-13-5 | 84.7 | 251 |
| 410591 | 1006 | 1025 | GCACCCTTGGCCACGCCGGC | 3-14-3 | 86.3 | 251 |
| 405882 | 1006 | 1025 | GCACCCTTGGCCACGCCGGC | 5-10-5 | 91.6 | 251 |
| 410668 | 1007 | 1026 | GGCACCCTTGGCCACGCCGG | 2-13-5 | 91.4 | 252 |
| 405883 | 1007 | 1026 | GGCACCCTTGGCCACGCCGG | 5-10-5 | 92.5 | 252 |
| 410592 | 1007 | 1026 | GGCACCCTTGGCCACGCCGG | 3-14-3 | 93.4 | 252 |
| 410669 | 1008 | 1027 | TGGCACCCTTGGCCACGCCG | 2-13-5 | 69.0 | 253 |
| 410593 | 1008 | 1027 | TGGCACCCTTGGCCACGCCG | 3-14-3 | 88.8 | 253 |
| 405884 | 1008 | 1027 | TGGCACCCTTGGCCACGCCG | 5-10-5 | 90.8 | 253 |
| 410670 | 1009 | 1028 | CTGGCACCCTTGGCCACGCC | 2-13-5 | 74.9 | 254 |
| 410594 | 1009 | 1028 | CTGGCACCCTTGGCCACGCC | 3-14-3 | 75.2 | 254 |
| 410538 | 1009 | 1028 | CTGGCACCCTTGGCCACGCC | 5-10-5 | 78.2 | 254 |
| 410539 | 1010 | 1029 | GCTGGCACCCTTGGCCACGC | 5-10-5 | 61.9 | 255 |
| 410595 | 1010 | 1029 | GCTGGCACCCTTGGCCACGC | 3-14-3 | 83.1 | 255 |
| 410671 | 1010 | 1029 | GCTGGCACCCTTGGCCACGC | 2-13-5 | 83.3 | 255 |
| 410758 | 1015 | 1034 | CGCATGCTGGCACCCTTGGC | 5-10-5 | 73.6 | 256 |
| 406039 | 1036 | 1055 | CAGTTGAGCACGCGCAGGCT | 5-10-5 | 91.2 | 257 |
| 406040 | 1038 | 1057 | GGCAGTTGAGCACGCGCAGG | 5-10-5 | 96.5 | 258 |
| 399888 | 1040 | 1059 | TTGGCAGTTGAGCACGCGCA | 3-14-3 | 90.9 | 29 |
| 395166 | 1040 | 1059 | TTGGCAGTTGAGCACGCGCA | 5-10-5 | 96.2 | 29 |
| 406041 | 1042 | 1061 | CCTTGGCAGTTGAGCACGCG | 5-10-5 | 96.6 | 259 |
| 399801 | 1045 | 1064 | TTCCCTTGGCAGTTGAGCAC | 5-10-5 | 95.6 | 30 |
| 406042 | 1047 | 1066 | CCTTCCCTTGGCAGTTGAGC | 5-10-5 | 92.0 | 260 |
| 406043 | 1051 | 1070 | GTGCCCTTCCCTTGGCAGTT | 5-10-5 | 91.9 | 261 |
| 406044 | 1053 | 1072 | CCGTGCCCTTCCCTTGGCAG | 5-10-5 | 95.4 | 262 |
| 410759 | 1064 | 1083 | GGTGCCGCTAACCGTGCCCT | 5-10-5 | 83.7 | 263 |
| 410760 | 1088 | 1107 | CCGAATAAACTCCAGGCCTA | 5-10-5 | 96.7 | 265 |
| 406045 | 1096 | 1115 | TGGCTTTTCCGAATAAACTC | 5-10-5 | 88.4 | 266 |
| 395168 | 1098 | 1117 | GCTGGCTTTTCCGAATAAAC | 5-10-5 | 91.9 | 32 |

TABLE 17-continued

Antisense inhibition of PCSK in human cells (Hep3B) targeting SEQ ID NO: 1

| Isis No. | 5' Target Site to SEQ ID NO: 1 | 3' Target Site to SEQ ID NO: 1 | Sequence 5'-3' | Motif | % inhibition | SEQ ID NO |
|---|---|---|---|---|---|---|
| 405909 | 1100 | 1119 | CAGCTGGCTTTTCCGAATAA | 5-10-5 | 80.3 | 267 |
| 405910 | 1102 | 1121 | ACCAGCTGGCTTTTCCGAAT | 5-10-5 | 90.9 | 268 |
| 405911 | 1104 | 1123 | GGACCAGCTGGCTTTTCCGA | 5-10-5 | 88.0 | 269 |
| 405912 | 1108 | 1127 | GGCTGGACCAGCTGGCTTTT | 5-10-5 | 78.2 | 270 |
| 410761 | 1119 | 1138 | GTGGCCCCACAGGCTGGACC | 5-10-5 | 53.7 | 271 |
| 410762 | 1132 | 1151 | AGCAGCACCACCAGTGGCCC | 5-10-5 | 57.6 | 272 |
| 410763 | 1154 | 1173 | GCTGTACCCACCCGCCAGGG | 5-10-5 | 68.8 | 273 |
| 410764 | 1200 | 1219 | CGACCCCAGCCCTCGCCAGG | 5-10-5 | 66.3 | 274 |
| 399891 | 1210 | 1229 | GTGACCAGCACGACCCCAGC | 3-14-3 | 91.1 | 33 |
| 405913 | 1212 | 1231 | CGGTGACCAGCACGACCCCA | 5-10-5 | 93.8 | 275 |
| 405914 | 1214 | 1233 | AGCGGTGACCAGCACGACCC | 5-10-5 | 90.4 | 276 |
| 405915 | 1216 | 1235 | GCAGCGGTGACCAGCACGAC | 5-10-5 | 86.8 | 277 |
| 405916 | 1218 | 1237 | CGGCAGCGGTGACCAGCACG | 5-10-5 | 91.3 | 278 |
| 410734 | 1219 | 1238 | CCGGCAGCGGTGACCAGCAC | 5-10-5 | 65.8 | 279 |
| 405917 | 1222 | 1241 | TTGCCGGCAGCGGTGACCAG | 5-10-5 | 62.0 | 280 |
| 405918 | 1224 | 1243 | AGTTGCCGGCAGCGGTGACC | 5-10-5 | 33.5 | 281 |
| 405919 | 1226 | 1245 | GAAGTTGCCGGCAGCGGTGA | 5-10-5 | 68.2 | 282 |
| 405920 | 1228 | 1247 | CGGAAGTTGCCGGCAGCGGT | 5-10-5 | 86.2 | 283 |
| 405921 | 1230 | 1249 | CCCGGAAGTTGCCGGCAGCG | 5-10-5 | 85.5 | 284 |
| 405922 | 1232 | 1251 | GTCCCGGAAGTTGCCGGCAG | 5-10-5 | 86.0 | 285 |
| 410765 | 1273 | 1292 | ATGACCTCGGGAGCTGAGGC | 5-10-5 | 50.4 | 286 |
| 410766 | 1283 | 1302 | CCCAACTGTGATGACCTCGG | 5-10-5 | 70.6 | 287 |
| 405923 | 1295 | 1314 | GGCATTGGTGGCCCCAACTG | 5-10-5 | 94.3 | 288 |
| 410767 | 1305 | 1324 | GCTGGTCTTGGGCATTGGTG | 5-10-5 | 65.1 | 289 |
| 405924 | 1318 | 1337 | CCCAGGGTCACCGGCTGGTC | 5-10-5 | 93.1 | 290 |
| 410735 | 1320 | 1339 | TCCCCAGGGTCACCGGCTGG | 5-10-5 | 78.1 | 291 |
| 405925 | 1322 | 1341 | AGTCCCCAGGGTCACCGGCT | 5-10-5 | 93.5 | 292 |
| 405926 | 1324 | 1343 | AAAGTCCCCAGGGTCACCGG | 5-10-5 | 94.6 | 293 |
| 405927 | 1328 | 1347 | CCCCAAAGTCCCCAGGGTCA | 5-10-5 | 94.5 | 294 |
| 405928 | 1333 | 1352 | TTGGTCCCCAAAGTCCCCAG | 5-10-5 | 90.0 | 295 |
| 405929 | 1337 | 1356 | AAAGTTGGTCCCCAAAGTCC | 5-10-5 | 85.5 | 296 |
| 399895 | 1340 | 1359 | GCCAAAGTTGGTCCCCAAAG | 3-14-3 | 84.6 | 36 |
| 395173 | 1340 | 1359 | GCCAAAGTTGGTCCCCAAAG | 5-10-5 | 94.8 | 36 |
| 405930 | 1342 | 1361 | CGGCCAAAGTTGGTCCCCAA | 5-10-5 | 92.9 | 297 |
| 405931 | 1344 | 1363 | AGCGGCCAAAGTTGGTCCCC | 5-10-5 | 88.8 | 298 |
| 405932 | 1346 | 1365 | ACAGCGGCCAAAGTTGGTCC | 5-10-5 | 90.6 | 299 |
| 405933 | 1348 | 1367 | ACACAGCGGCCAAAGTTGGT | 5-10-5 | NA | 300 |

TABLE 17-continued

Antisense inhibition of PCSK9 in human cells (Hep3B) targeting SEQ ID NO: 1

| Isis No. | 5' Target Site to SEQ ID NO: 1 | 3' Target Site to SEQ ID NO: 1 | Sequence 5'-3' | Motif | % inhibition | SEQ ID NO |
|---|---|---|---|---|---|---|
| 405934 | 1350 | 1369 | CCACACAGCGGCCAAAGTTG | 5-10-5 | 92.7 | 301 |
| 405935 | 1354 | 1373 | AGGTCCACACAGCGGCCAAA | 5-10-5 | 86.0 | 302 |
| 410736 | 1356 | 1375 | AGAGGTCCACACAGCGGCCA | 5-10-5 | 73.8 | 303 |
| 405936 | 1358 | 1377 | AAAGAGGTCCACACAGCGGC | 5-10-5 | 93.9 | 304 |
| 410768 | 1380 | 1399 | CAATGATGTCCTCCCCTGGG | 5-10-5 | 79.7 | 305 |
| 405937 | 1387 | 1406 | GAGGCACCAATGATGTCCTC | 5-10-5 | 77.7 | 306 |
| 405938 | 1391 | 1410 | GCTGGAGGCACCAATGATGT | 5-10-5 | 75.5 | 307 |
| 405939 | 1393 | 1412 | TCGCTGGAGGCACCAATGAT | 5-10-5 | 70.6 | 308 |
| 405940 | 1395 | 1414 | AGTCGCTGGAGGCACCAATG | 5-10-5 | 84.4 | 309 |
| 405941 | 1397 | 1416 | GCAGTCGCTGGAGGCACCAA | 5-10-5 | 90.1 | 310 |
| 399804 | 1400 | 1419 | GCTGCAGTCGCTGGAGGCAC | 5-10-5 | 80.8 | 40 |
| 399960 | 1400 | 1419 | GCTGCAGTCGCTGGAGGCAC | 3-14-3 | 82.4 | 40 |
| 405942 | 1402 | 1421 | GTGCTGCAGTCGCTGGAGGC | 5-10-5 | 69.8 | 311 |
| 405943 | 1404 | 1423 | AGGTGCTGCAGTCGCTGGAG | 5-10-5 | 83.6 | 312 |
| 410737 | 1406 | 1425 | GCAGGTGCTGCAGTCGCTGG | 5-10-5 | 49.8 | 313 |
| 405944 | 1407 | 1426 | AGCAGGTGCTGCAGTCGCTG | 5-10-5 | 80.7 | 314 |
| 405945 | 1409 | 1428 | AAAGCAGGTGCTGCAGTCGC | 5-10-5 | 41.1 | 315 |
| 405946 | 1413 | 1432 | ACACAAAGCAGGTGCTGCAG | 5-10-5 | 70.4 | 316 |
| 405947 | 1415 | 1434 | TGACACAAAGCAGGTGCTGC | 5-10-5 | 72.5 | 317 |
| 410769 | 1425 | 1444 | TCCCACTCTGTGACACAAAG | 5-10-5 | 84.9 | 318 |
| 405948 | 1467 | 1486 | TCATGGCTGCAATGCCAGCC | 5-10-5 | 45.9 | 319 |
| 399806 | 1470 | 1489 | GCATCATGGCTGCAATGCCA | 5-10-5 | 82.8 | 42 |
| 399962 | 1470 | 1489 | GCATCATGGCTGCAATGCCA | 3-14-3 | 86.1 | 42 |
| 405949 | 1472 | 1491 | CAGCATCATGGCTGCAATGC | 5-10-5 | 84.9 | 320 |
| 405950 | 1474 | 1493 | GACAGCATCATGGCTGCAAT | 5-10-5 | 76.9 | 321 |
| 405951 | 1476 | 1495 | CAGACAGCATCATGGCTGCA | 5-10-5 | 75.4 | 322 |
| 405952 | 1480 | 1499 | TCGGCAGACAGCATCATGGC | 5-10-5 | 85.1 | 323 |
| 410738 | 1482 | 1501 | GCTCGGCAGACAGCATCATG | 5-10-5 | 68.4 | 324 |
| 405953 | 1484 | 1503 | CGGCTCGGCAGACAGCATCA | 5-10-5 | 93.6 | 325 |
| 405954 | 1486 | 1505 | TCCGGCTCGGCAGACAGCAT | 5-10-5 | 87.5 | 326 |
| 410770 | 1500 | 1519 | CGGCCAGGGTGAGCTCCGGC | 5-10-5 | 68.5 | 327 |
| 405955 | 1513 | 1532 | CTCTGCCTCAACTCGGCCAG | 5-10-5 | 94.2 | 328 |
| 405956 | 1515 | 1534 | GTCTCTGCCTCAACTCGGCC | 5-10-5 | 94.3 | 329 |
| 405958 | 1519 | 1538 | ATCAGTCTCTGCCTCAACTC | 5-10-5 | 80.3 | 331 |
| 405959 | 1521 | 1540 | GGATCAGTCTCTGCCTCAAC | 5-10-5 | 95.4 | 332 |
| 405960 | 1523 | 1542 | GTGGATCAGTCTCTGCCTCA | 5-10-5 | 90.1 | 333 |

TABLE 17-continued

Antisense inhibition of PCSK in human cells (Hep3B) targeting SEQ ID NO: 1

| Isis No. | 5' Target Site to SEQ ID NO: 1 | 3' Target Site to SEQ ID NO: 1 | Sequence 5'-3' | Motif | % inhibition | SEQ ID NO |
|---|---|---|---|---|---|---|
| 405961 | 1525 | 1544 | AAGTGGATCAGTCTCTGCCT | 5-10-5 | 88.8 | 334 |
| 405962 | 1528 | 1547 | GAGAAGTGGATCAGTCTCTG | 5-10-5 | 56.1 | 335 |
| 410739 | 1530 | 1549 | CAGAGAAGTGGATCAGTCTC | 5-10-5 | NA | 336 |
| 405963 | 1532 | 1551 | GGCAGAGAAGTGGATCAGTC | 5-10-5 | 59.7 | 337 |
| 405964 | 1536 | 1555 | CTTTGGCAGAGAAGTGGATC | 5-10-5 | 45.3 | 338 |
| 405965 | 1541 | 1560 | GACATCTTTGGCAGAGAAGT | 5-10-5 | 55.9 | 339 |
| 405966 | 1543 | 1562 | ATGACATCTTTGGCAGAGAA | 5-10-5 | 51.3 | 340 |
| 405967 | 1547 | 1566 | ATTGATGACATCTTTGGCAG | 5-10-5 | 64.4 | 341 |
| 405968 | 1549 | 1568 | TCATTGATGACATCTTTGGC | 5-10-5 | 74.6 | 342 |
| 399967 | 1552 | 1571 | GCCTCATTGATGACATCTTT | 3-14-3 | 80.1 | 48 |
| 405969 | 1554 | 1573 | AGGCCTCATTGATGACATCT | 5-10-5 | 63.0 | 343 |
| 405970 | 1556 | 1575 | CCAGGCCTCATTGATGACAT | 5-10-5 | 66.8 | 344 |
| 410740 | 1558 | 1577 | AACCAGGCCTCATTGATGAC | 5-10-5 | 46.8 | 345 |
| 405885 | 1560 | 1579 | GGAACCAGGCCTCATTGATG | 5-10-5 | 73.4 | 346 |
| 410596 | 1562 | 1581 | AGGGAACCAGGCCTCATTGA | 3-14-3 | NA | 348 |
| 410672 | 1562 | 1581 | AGGGAACCAGGCCTCATTGA | 2-13-5 | NA | 348 |
| 405887 | 1562 | 1581 | AGGGAACCAGGCCTCATTGA | 5-10-5 | NA | 348 |
| 410597 | 1563 | 1582 | CAGGGAACCAGGCCTCATTG | 3-14-3 | NA | 349 |
| 405888 | 1563 | 1582 | CAGGGAACCAGGCCTCATTG | 5-10-5 | NA | 349 |
| 410673 | 1563 | 1582 | CAGGGAACCAGGCCTCATTG | 2-13-5 | NA | 349 |
| 410674 | 1564 | 1583 | TCAGGGAACCAGGCCTCATT | 2-13-5 | 60.7 | 49 |
| 399812 | 1564 | 1583 | TCAGGGAACCAGGCCTCATT | 5-10-5 | 68.7 | 49 |
| 399968 | 1564 | 1583 | TCAGGGAACCAGGCCTCATT | 3-14-3 | 84.5 | 49 |
| 410598 | 1565 | 1584 | CTCAGGGAACCAGGCCTCAT | 3-14-3 | 74.5 | 350 |
| 410675 | 1565 | 1584 | CTCAGGGAACCAGGCCTCAT | 2-13-5 | 76.9 | 350 |
| 405889 | 1565 | 1584 | CTCAGGGAACCAGGCCTCAT | 5-10-5 | 80.2 | 350 |
| 410599 | 1566 | 1585 | CCTCAGGGAACCAGGCCTCA | 3-14-3 | 70.6 | 351 |
| 410676 | 1566 | 1585 | CCTCAGGGAACCAGGCCTCA | 2-13-5 | 77.8 | 351 |
| 405890 | 1566 | 1585 | CCTCAGGGAACCAGGCCTCA | 5-10-5 | 87.7 | 351 |
| 410600 | 1567 | 1586 | TCCTCAGGGAACCAGGCCTC | 3-14-3 | 76.5 | 352 |
| 410677 | 1567 | 1586 | TCCTCAGGGAACCAGGCCTC | 2-13-5 | 88.4 | 352 |
| 405891 | 1567 | 1586 | TCCTCAGGGAACCAGGCCTC | 5-10-5 | 96.1 | 352 |
| 405892 | 1568 | 1587 | GTCCTCAGGGAACCAGGCCT | 5-10-5 | 71.4 | 353 |
| 410601 | 1568 | 1587 | GTCCTCAGGGAACCAGGCCT | 3-14-3 | 72.7 | 353 |
| 410678 | 1568 | 1587 | GTCCTCAGGGAACCAGGCCT | 2-13-5 | 75.0 | 353 |
| 395178 | 1569 | 1588 | GGTCCTCAGGGAACCAGGCC | 5-10-5 | 76.7 | 50 |
| 410679 | 1569 | 1588 | GGTCCTCAGGGAACCAGGCC | 2-13-5 | 77.6 | 50 |

TABLE 17-continued

Antisense inhibition of PCSK9 in human cells (Hep3B) targeting SEQ ID NO: 1

| Isis No. | 5' Target Site to SEQ ID NO: 1 | 3' Target Site to SEQ ID NO: 1 | Sequence 5'-3' | Motif | % inhibition | SEQ ID NO |
|---|---|---|---|---|---|---|
| 399900 | 1569 | 1588 | GGTCCTCAGGGAACCAGGCC | 3-14-3 | 92.0 | 50 |
| 408653 | 1570 | 1589 | TGGTCCTCAGGGAACCAGGC | 5-10-5 | 42.5 | 354 |
| 410602 | 1570 | 1589 | TGGTCCTCAGGGAACCAGGC | 3-14-3 | 66.5 | 354 |
| 410680 | 1570 | 1589 | TGGTCCTCAGGGAACCAGGC | 2-13-5 | 71.6 | 354 |
| 410603 | 1571 | 1590 | CTGGTCCTCAGGGAACCAGG | 3-14-3 | 40.8 | 355 |
| 410681 | 1571 | 1590 | CTGGTCCTCAGGGAACCAGG | 2-13-5 | 44.4 | 355 |
| 405971 | 1571 | 1590 | CTGGTCCTCAGGGAACCAGG | 5-10-5 | 65.5 | 355 |
| 410540 | 1572 | 1591 | GCTGGTCCTCAGGGAACCAG | 5-10-5 | 50.9 | 356 |
| 410682 | 1572 | 1591 | GCTGGTCCTCAGGGAACCAG | 2-13-5 | 54.1 | 356 |
| 410604 | 1572 | 1591 | GCTGGTCCTCAGGGAACCAG | 3-14-3 | 62.5 | 356 |
| 405972 | 1573 | 1592 | CGCTGGTCCTCAGGGAACCA | 5-10-5 | 77.6 | 357 |
| 405973 | 1578 | 1597 | GTACCCGCTGGTCCTCAGGG | 5-10-5 | 83.8 | 358 |
| 405974 | 1580 | 1599 | CAGTACCCGCTGGTCCTCAG | 5-10-5 | 89.0 | 359 |
| 399813 | 1583 | 1602 | GGTCAGTACCCGCTGGTCCT | 5-10-5 | 72.4 | 51 |
| 399969 | 1583 | 1602 | GGTCAGTACCCGCTGGTCCT | 3-14-3 | 93.4 | 51 |
| 410771 | 1628 | 1647 | ACCTGCCCCATGGGTGCTGG | 5-10-5 | NA | 360 |
| 395181 | 1640 | 1659 | AAACAGCTGCCAACCTGCCC | 5-10-5 | 87.5 | 52 |
| 405975 | 1642 | 1661 | CAAAACAGCTGCCAACCTGC | 5-10-5 | 77.4 | 361 |
| 405976 | 1647 | 1666 | TCCTGCAAAACAGCTGCCAA | 5-10-5 | 81.2 | 362 |
| 405977 | 1649 | 1668 | AGTCCTGCAAAACAGCTGCC | 5-10-5 | 89.5 | 363 |
| 410772 | 1660 | 1679 | GCTGACCATACAGTCCTGCA | 5-10-5 | 91.2 | 364 |
| 405978 | 1672 | 1691 | GGCCCCGAGTGTGCTGACCA | 5-10-5 | 95.3 | 365 |
| 399904 | 1675 | 1694 | GTAGGCCCCGAGTGTGCTGA | 3-14-3 | 92.6 | 54 |
| 405979 | 1677 | 1696 | GTGTAGGCCCCGAGTGTGCT | 5-10-5 | 85.5 | 366 |
| 405980 | 1679 | 1698 | CCGTGTAGGCCCCGAGTGTG | 5-10-5 | 86.5 | 367 |
| 405981 | 1681 | 1700 | ATCCGTGTAGGCCCCGAGTG | 5-10-5 | 77.8 | 368 |
| 410741 | 1683 | 1702 | CCATCCGTGTAGGCCCCGAG | 5-10-5 | 78.4 | 369 |
| 405982 | 1685 | 1704 | GGCCATCCGTGTAGGCCCCG | 5-10-5 | 86.7 | 370 |
| 405983 | 1687 | 1706 | GTGGCCATCCGTGTAGGCCC | 5-10-5 | 73.1 | 371 |
| 405984 | 1735 | 1754 | CTGGAGCAGCTCAGCAGCTC | 5-10-5 | 83.4 | 372 |
| 405985 | 1737 | 1756 | AACTGGAGCAGCTCAGCAGC | 5-10-5 | 50.7 | 373 |
| 405986 | 1742 | 1761 | GGAGAAACTGGAGCAGCTCA | 5-10-5 | 75.6 | 374 |
| 405987 | 1744 | 1763 | CTGGAGAAACTGGAGCAGCT | 5-10-5 | 88.0 | 375 |
| 399905 | 1812 | 1831 | CGTTGTGGGCCCGGCAGACC | 3-14-3 | 91.2 | 57 |
| 395183 | 1812 | 1831 | CGTTGTGGGCCCGGCAGACC | 5-10-5 | 93.1 | 57 |
| 410541 | 1849 | 1868 | CACCTGGCAATGGCGTAGAC | 5-10-5 | 46.1 | 376 |

TABLE 17-continued

Antisense inhibition of PCSK in human cells (Hep3B) targeting SEQ ID NO: 1

| Isis No. | 5' Target Site to SEQ ID NO: 1 | 3' Target Site to SEQ ID NO: 1 | Sequence 5'-3' | Motif | % inhibition | SEQ ID NO |
|---|---|---|---|---|---|---|
| 410605 | 1849 | 1868 | CACCTGGCAATGGCGTAGAC | 3-14-3 | 67.4 | 376 |
| 410683 | 1849 | 1868 | CACCTGGCAATGGCGTAGAC | 2-13-5 | 71.8 | 376 |
| 410606 | 1850 | 1869 | GCACCTGGCAATGGCGTAGA | 3-14-3 | 74.3 | 377 |
| 410542 | 1850 | 1869 | GCACCTGGCAATGGCGTAGA | 5-10-5 | 75.5 | 377 |
| 410684 | 1850 | 1869 | GCACCTGGCAATGGCGTAGA | 2-13-5 | 78.7 | 377 |
| 410543 | 1851 | 1870 | AGCACCTGGCAATGGCGTAG | 5-10-5 | 76.4 | 378 |
| 410685 | 1851 | 1870 | AGCACCTGGCAATGGCGTAG | 2-13-5 | 76.9 | 378 |
| 410607 | 1851 | 1870 | AGCACCTGGCAATGGCGTAG | 3-14-3 | 77.1 | 378 |
| 410544 | 1852 | 1871 | CAGCACCTGGCAATGGCGTA | 5-10-5 | 62.7 | 379 |
| 410608 | 1852 | 1871 | CAGCACCTGGCAATGGCGTA | 3-14-3 | 69.6 | 379 |
| 410686 | 1852 | 1871 | CAGCACCTGGCAATGGCGTA | 2-13-5 | 81.0 | 379 |
| 410545 | 1853 | 1872 | GCAGCACCTGGCAATGGCGT | 5-10-5 | 75.5 | 380 |
| 410687 | 1853 | 1872 | GCAGCACCTGGCAATGGCGT | 2-13-5 | 79.2 | 380 |
| 410609 | 1853 | 1872 | GCAGCACCTGGCAATGGCGT | 3-14-3 | 83.2 | 380 |
| 410610 | 1854 | 1873 | GGCAGCACCTGGCAATGGCG | 3-14-3 | 67.5 | 381 |
| 410688 | 1854 | 1873 | GGCAGCACCTGGCAATGGCG | 2-13-5 | 89.3 | 381 |
| 405988 | 1854 | 1873 | GGCAGCACCTGGCAATGGCG | 5-10-5 | 95.9 | 381 |
| 410546 | 1855 | 1874 | AGGCAGCACCTGGCAATGGC | 5-10-5 | 74.8 | 382 |
| 410689 | 1855 | 1874 | AGGCAGCACCTGGCAATGGC | 2-13-5 | 83.9 | 382 |
| 410611 | 1855 | 1874 | AGGCAGCACCTGGCAATGGC | 3-14-3 | 88.2 | 382 |
| 410612 | 1856 | 1875 | CAGGCAGCACCTGGCAATGG | 3-14-3 | 72.8 | 383 |
| 410690 | 1856 | 1875 | CAGGCAGCACCTGGCAATGG | 2-13-5 | 74.8 | 383 |
| 405989 | 1856 | 1875 | CAGGCAGCACCTGGCAATGG | 5-10-5 | 88.1 | 383 |
| 410547 | 1857 | 1876 | GCAGGCAGCACCTGGCAATG | 5-10-5 | 63.0 | 384 |
| 410691 | 1857 | 1876 | GCAGGCAGCACCTGGCAATG | 2-13-5 | 70.2 | 384 |
| 410613 | 1857 | 1876 | GCAGGCAGCACCTGGCAATG | 3-14-3 | 76.7 | 384 |
| 395184 | 1858 | 1877 | AGCAGGCAGCACCTGGCAAT | 5-10-5 | 68.5 | 58 |
| 410692 | 1858 | 1877 | AGCAGGCAGCACCTGGCAAT | 2-13-5 | 69.1 | 58 |
| 399906 | 1858 | 1877 | AGCAGGCAGCACCTGGCAAT | 3-14-3 | 94.2 | 58 |
| 410614 | 1859 | 1878 | TAGCAGGCAGCACCTGGCAA | 3-14-3 | 36.6 | 385 |
| 410548 | 1859 | 1878 | TAGCAGGCAGCACCTGGCAA | 5-10-5 | 75.0 | 385 |
| 410693 | 1859 | 1878 | TAGCAGGCAGCACCTGGCAA | 2-13-5 | 82.0 | 385 |
| 405990 | 1860 | 1879 | GTAGCAGGCAGCACCTGGCA | 5-10-5 | 96.8 | 386 |
| 410773 | 1905 | 1924 | TGGCCTCAGCTGGTGGAGCT | 5-10-5 | 61.3 | 387 |
| 410549 | 1915 | 1934 | GTCCCCATGCTGGCCTCAGC | 5-10-5 | 63.0 | 388 |
| 410615 | 1915 | 1934 | GTCCCCATGCTGGCCTCAGC | 3-14-3 | 72.5 | 388 |
| 410694 | 1915 | 1934 | GTCCCCATGCTGGCCTCAGC | 2-13-5 | 74.8 | 388 |

TABLE 17-continued

Antisense inhibition of PCSK9 in human cells (Hep3B) targeting SEQ ID NO: 1

| Isis No. | 5' Target Site to SEQ ID NO: 1 | 3' Target Site to SEQ ID NO: 1 | Sequence 5'-3' | Motif | % inhibition | SEQ ID NO |
|---|---|---|---|---|---|---|
| 410550 | 1916 | 1935 | GGTCCCCATGCTGGCCTCAG | 5-10-5 | 69.4 | 389 |
| 410616 | 1916 | 1935 | GGTCCCCATGCTGGCCTCAG | 3-14-3 | 80.7 | 389 |
| 410695 | 1916 | 1935 | GGTCCCCATGCTGGCCTCAG | 2-13-5 | 85.5 | 389 |
| 410551 | 1917 | 1936 | GGGTCCCCATGCTGGCCTCA | 5-10-5 | 68.7 | 390 |
| 410696 | 1917 | 1936 | GGGTCCCCATGCTGGCCTCA | 2-13-5 | 86.3 | 390 |
| 410617 | 1917 | 1936 | GGGTCCCCATGCTGGCCTCA | 3-14-3 | 86.5 | 390 |
| 410552 | 1918 | 1937 | CGGGTCCCCATGCTGGCCTC | 5-10-5 | 77.9 | 391 |
| 410618 | 1918 | 1937 | CGGGTCCCCATGCTGGCCTC | 3-14-3 | 86.7 | 391 |
| 410697 | 1918 | 1937 | CGGGTCCCCATGCTGGCCTC | 2-13-5 | 87.0 | 391 |
| 410553 | 1919 | 1938 | ACGGGTCCCCATGCTGGCCT | 5-10-5 | 72.8 | 392 |
| 410619 | 1919 | 1938 | ACGGGTCCCCATGCTGGCCT | 3-14-3 | 84.1 | 392 |
| 410698 | 1919 | 1938 | ACGGGTCCCCATGCTGGCCT | 2-13-5 | 87.0 | 392 |
| 410699 | 1920 | 1939 | CACGGGTCCCCATGCTGGCC | 2-13-5 | 79.5 | 59 |
| 395185 | 1920 | 1939 | CACGGGTCCCCATGCTGGCC | 5-10-5 | 92.7 | 59 |
| 399907 | 1920 | 1939 | CACGGGTCCCCATGCTGGCC | 3-14-3 | 93.7 | 59 |
| 410620 | 1921 | 1940 | ACACGGGTCCCCATGCTGGC | 3-14-3 | 74.4 | 393 |
| 410554 | 1921 | 1940 | ACACGGGTCCCCATGCTGGC | 5-10-5 | 79.7 | 393 |
| 410700 | 1921 | 1940 | ACACGGGTCCCCATGCTGGC | 2-13-5 | 84.4 | 393 |
| 410621 | 1922 | 1941 | GACACGGGTCCCCATGCTGG | 3-14-3 | 76.0 | 394 |
| 410701 | 1922 | 1941 | GACACGGGTCCCCATGCTGG | 2-13-5 | 83.4 | 394 |
| 405991 | 1922 | 1941 | GACACGGGTCCCCATGCTGG | 5-10-5 | 91.9 | 394 |
| 410555 | 1923 | 1942 | GGACACGGGTCCCCATGCTG | 5-10-5 | 77.0 | 395 |
| 410622 | 1923 | 1942 | GGACACGGGTCCCCATGCTG | 3-14-3 | 79.8 | 395 |
| 410702 | 1923 | 1942 | GGACACGGGTCCCCATGCTG | 2-13-5 | 85.0 | 395 |
| 410703 | 1924 | 1943 | TGGACACGGGTCCCCATGCT | 2-13-5 | 70.4 | 396 |
| 410623 | 1924 | 1943 | TGGACACGGGTCCCCATGCT | 3-14-3 | 78.9 | 396 |
| 405992 | 1924 | 1943 | TGGACACGGGTCCCCATGCT | 5-10-5 | 89.3 | 396 |
| 410704 | 1925 | 1944 | GTGGACACGGGTCCCCATGC | 2-13-5 | 78.6 | 397 |
| 410556 | 1925 | 1944 | GTGGACACGGGTCCCCATGC | 5-10-5 | 81.4 | 397 |
| 410624 | 1925 | 1944 | GTGGACACGGGTCCCCATGC | 3-14-3 | 82.8 | 397 |
| 410625 | 1926 | 1945 | AGTGGACACGGGTCCCCATG | 3-14-3 | 64.4 | 398 |
| 410705 | 1926 | 1945 | AGTGGACACGGGTCCCCATG | 2-13-5 | 74.7 | 398 |
| 405993 | 1926 | 1945 | AGTGGACACGGGTCCCCATG | 5-10-5 | 85.5 | 398 |
| 410706 | 1927 | 1946 | CAGTGGACACGGGTCCCCAT | 2-13-5 | 70.8 | 399 |
| 410557 | 1927 | 1946 | CAGTGGACACGGGTCCCCAT | 5-10-5 | 74.2 | 399 |
| 410626 | 1927 | 1946 | CAGTGGACACGGGTCCCCAT | 3-14-3 | 76.8 | 399 |

TABLE 17-continued

Antisense inhibition of PCSK in human cells (Hep3B) targeting SEQ ID NO: 1

| Isis No. | 5' Target Site to SEQ ID NO: 1 | 3' Target Site to SEQ ID NO: 1 | Sequence 5'-3' | Motif | % inhibition | SEQ ID NO |
|---|---|---|---|---|---|---|
| 410627 | 1928 | 1947 | GCAGTGGACACGGGTCCCCA | 3-14-3 | 71.4 | 400 |
| 410707 | 1928 | 1947 | GCAGTGGACACGGGTCCCCA | 2-13-5 | 72.8 | 400 |
| 405994 | 1928 | 1947 | GCAGTGGACACGGGTCCCCA | 5-10-5 | 95.2 | 400 |
| 410708 | 1929 | 1948 | GGCAGTGGACACGGGTCCCC | 2-13-5 | 79.0 | 401 |
| 410628 | 1929 | 1948 | GGCAGTGGACACGGGTCCCC | 3-14-3 | 88.1 | 401 |
| 410558 | 1929 | 1948 | GGCAGTGGACACGGGTCCCC | 5-10-5 | 88.9 | 401 |
| 410629 | 1930 | 1949 | TGGCAGTGGACACGGGTCCC | 3-14-3 | 66.5 | 402 |
| 410709 | 1930 | 1949 | TGGCAGTGGACACGGGTCCC | 2-13-5 | 66.9 | 402 |
| 405995 | 1930 | 1949 | TGGCAGTGGACACGGGTCCC | 5-10-5 | 92.4 | 402 |
| 410630 | 1931 | 1950 | GTGGCAGTGGACACGGGTCC | 3-14-3 | 54.1 | 403 |
| 410710 | 1931 | 1950 | GTGGCAGTGGACACGGGTCC | 2-13-5 | 61.4 | 403 |
| 410559 | 1931 | 1950 | GTGGCAGTGGACACGGGTCC | 5-10-5 | 77.5 | 403 |
| 410711 | 1932 | 1951 | GGTGGCAGTGGACACGGGTC | 2-13-5 | NA | 404 |
| 410631 | 1932 | 1951 | GGTGGCAGTGGACACGGGTC | 3-14-3 | NA | 404 |
| 410560 | 1932 | 1951 | GGTGGCAGTGGACACGGGTC | 5-10-5 | 42.5 | 404 |
| 410712 | 1933 | 1952 | TGGTGGCAGTGGACACGGGT | 2-13-5 | NA | 405 |
| 410632 | 1933 | 1952 | TGGTGGCAGTGGACACGGGT | 3-14-3 | NA | 405 |
| 410561 | 1933 | 1952 | TGGTGGCAGTGGACACGGGT | 5-10-5 | NA | 405 |
| 410774 | 1936 | 1955 | TGTTGGTGGCAGTGGACACG | 5-10-5 | 47.8 | 406 |
| 410775 | 1962 | 1981 | AGCTGCAGCCTGTGAGGACG | 5-10-5 | 36.3 | 407 |
| 410776 | 1990 | 2009 | GTGCCAAGGTCCTCCACCTC | 5-10-5 | 77.3 | 408 |
| 410777 | 2010 | 2029 | TCAGCACAGGCGGCTTGTGG | 5-10-5 | 40.0 | 409 |
| 410778 | 2040 | 2059 | CCACGCACTGGTTGGGCTGA | 5-10-5 | 52.7 | 410 |
| 399908 | 2100 | 2119 | CTTTGCATTCCAGACCTGGG | 3-14-3 | 74.9 | 60 |
| 410713 | 2100 | 2119 | CTTTGCATTCCAGACCTGGG | 2-13-5 | 84.9 | 60 |
| 395186 | 2100 | 2119 | CTTTGCATTCCAGACCTGGG | 5-10-5 | 93.7 | 60 |
| 410714 | 2101 | 2120 | ACTTTGCATTCCAGACCTGG | 2-13-5 | 82.4 | 411 |
| 410633 | 2101 | 2120 | ACTTTGCATTCCAGACCTGG | 3-14-3 | 83.8 | 411 |
| 410562 | 2101 | 2120 | ACTTTGCATTCCAGACCTGG | 5-10-5 | 87.3 | 411 |
| 410715 | 2102 | 2121 | GACTTTGCATTCCAGACCTG | 2-13-5 | 80.5 | 412 |
| 410634 | 2102 | 2121 | GACTTTGCATTCCAGACCTG | 3-14-3 | 81.8 | 412 |
| 405996 | 2102 | 2121 | GACTTTGCATTCCAGACCTG | 5-10-5 | 91.0 | 412 |
| 410563 | 2103 | 2122 | TGACTTTGCATTCCAGACCT | 5-10-5 | 75.4 | 413 |
| 410635 | 2103 | 2122 | TGACTTTGCATTCCAGACCT | 3-14-3 | 75.9 | 413 |
| 410716 | 2103 | 2122 | TGACTTTGCATTCCAGACCT | 2-13-5 | 88.3 | 413 |
| 410636 | 2104 | 2123 | TTGACTTTGCATTCCAGACC | 3-14-3 | 61.3 | 414 |
| 410564 | 2104 | 2123 | TTGACTTTGCATTCCAGACC | 5-10-5 | 71.3 | 414 |

TABLE 17-continued

Antisense inhibition of PCSK9 in human cells (Hep3B) targeting SEQ ID NO: 1

| Isis No. | 5' Target Site to SEQ ID NO: 1 | 3' Target Site to SEQ ID NO: 1 | Sequence 5'-3' | Motif | % inhibition | SEQ ID NO |
|---|---|---|---|---|---|---|
| 410717 | 2104 | 2123 | TTGACTTTGCATTCCAGACC | 2-13-5 | 76.7 | 414 |
| 410718 | 2105 | 2124 | CTTGACTTTGCATTCCAGAC | 2-13-5 | 55.8 | 61 |
| 399973 | 2105 | 2124 | CTTGACTTTGCATTCCAGAC | 3-14-3 | 82.1 | 61 |
| 399817 | 2105 | 2124 | CTTGACTTTGCATTCCAGAC | 5-10-5 | 93.6 | 61 |
| 405997 | 2107 | 2126 | TCCTTGACTTTGCATTCCAG | 5-10-5 | 95.6 | 415 |
| 410779 | 2120 | 2139 | CGGGATTCCATGCTCCTTGA | 5-10-5 | 79.7 | 416 |
| 410780 | 2150 | 2169 | GCAGGCCACGGTCACCTGCT | 5-10-5 | 60.9 | 417 |
| 410781 | 2187 | 2206 | GGAGGGCACTGCAGCCAGTC | 5-10-5 | 66.0 | 418 |
| 410719 | 2305 | 2324 | CAGATGGCAACGGCTGTCAC | 2-13-5 | 61.0 | 419 |
| 410637 | 2305 | 2324 | CAGATGGCAACGGCTGTCAC | 3-14-3 | 66.0 | 419 |
| 410565 | 2305 | 2324 | CAGATGGCAACGGCTGTCAC | 5-10-5 | 71.6 | 419 |
| 410638 | 2306 | 2325 | GCAGATGGCAACGGCTGTCA | 3-14-3 | 71.9 | 420 |
| 410720 | 2306 | 2325 | GCAGATGGCAACGGCTGTCA | 2-13-5 | 75.1 | 420 |
| 410566 | 2306 | 2325 | GCAGATGGCAACGGCTGTCA | 5-10-5 | 77.7 | 420 |
| 410639 | 2307 | 2326 | AGCAGATGGCAACGGCTGTC | 3-14-3 | 67.7 | 421 |
| 410721 | 2307 | 2326 | AGCAGATGGCAACGGCTGTC | 2-13-5 | 68.8 | 421 |
| 410567 | 2307 | 2326 | AGCAGATGGCAACGGCTGTC | 5-10-5 | 72.1 | 421 |
| 410568 | 2308 | 2327 | CAGCAGATGGCAACGGCTGT | 5-10-5 | 54.2 | 422 |
| 410640 | 2308 | 2327 | CAGCAGATGGCAACGGCTGT | 3-14-3 | 57.7 | 422 |
| 410722 | 2308 | 2327 | CAGCAGATGGCAACGGCTGT | 2-13-5 | 59.2 | 422 |
| 410569 | 2309 | 2328 | GCAGCAGATGGCAACGGCTG | 5-10-5 | 57.7 | 423 |
| 410641 | 2309 | 2328 | GCAGCAGATGGCAACGGCTG | 3-14-3 | 66.1 | 423 |
| 410723 | 2309 | 2328 | GCAGCAGATGGCAACGGCTG | 2-13-5 | 81.1 | 423 |
| 399909 | 2310 | 2329 | GGCAGCAGATGGCAACGGCT | 3-14-3 | 69.9 | 62 |
| 410724 | 2310 | 2329 | GGCAGCAGATGGCAACGGCT | 2-13-5 | 87.4 | 62 |
| 395187 | 2310 | 2329 | GGCAGCAGATGGCAACGGCT | 5-10-5 | 92.7 | 62 |
| 410642 | 2311 | 2330 | CGGCAGCAGATGGCAACGGC | 3-14-3 | 70.4 | 424 |
| 410725 | 2311 | 2330 | CGGCAGCAGATGGCAACGGC | 2-13-5 | 75.6 | 424 |
| 410570 | 2311 | 2330 | CGGCAGCAGATGGCAACGGC | 5-10-5 | 78.3 | 424 |
| 410571 | 2312 | 2331 | CCGGCAGCAGATGGCAACGG | 5-10-5 | 52.8 | 425 |
| 410643 | 2312 | 2331 | CCGGCAGCAGATGGCAACGG | 3-14-3 | 59.8 | 425 |
| 410726 | 2312 | 2331 | CCGGCAGCAGATGGCAACGG | 2-13-5 | 69.8 | 425 |
| 410644 | 2313 | 2332 | TCCGGCAGCAGATGGCAACG | 3-14-3 | 59.0 | 426 |
| 410727 | 2313 | 2332 | TCCGGCAGCAGATGGCAACG | 2-13-5 | 68.3 | 426 |
| 405998 | 2313 | 2332 | TCCGGCAGCAGATGGCAACG | 5-10-5 | 75.6 | 426 |
| 410572 | 2314 | 2333 | CTCCGGCAGCAGATGGCAAC | 5-10-5 | 40.9 | 427 |

TABLE 17-continued

Antisense inhibition of PCSK9 in human cells (Hep3B) targeting SEQ ID NO: 1

| Isis No. | 5' Target Site to SEQ ID NO: 1 | 3' Target Site to SEQ ID NO: 1 | Sequence 5'-3' | Motif | % inhibition | SEQ ID NO |
|---|---|---|---|---|---|---|
| 410728 | 2314 | 2333 | CTCCGGCAGCAGATGGCAAC | 2-13-5 | 56.4 | 427 |
| 410645 | 2314 | 2333 | CTCCGGCAGCAGATGGCAAC | 3-14-3 | 70.2 | 427 |
| 410729 | 2315 | 2334 | GCTCCGGCAGCAGATGGCAA | 2-13-5 | 67.7 | 428 |
| 410573 | 2315 | 2334 | GCTCCGGCAGCAGATGGCAA | 5-10-5 | 71.8 | 428 |
| 410646 | 2315 | 2334 | GCTCCGGCAGCAGATGGCAA | 3-14-3 | 72.8 | 428 |
| 410782 | 2325 | 2344 | CCAGGTGCCGGCTCCGGCAG | 5-10-5 | 43.2 | 429 |
| 410783 | 2335 | 2354 | GAGGCCTGCGCCAGGTGCCG | 5-10-5 | 63.7 | 430 |
| 399819 | 2509 | 2528 | CCCACTCAAGGGCCAGGCCA | 5-10-5 | 93.4 | 65 |
| 399912 | 2597 | 2616 | ATGCCCCACAGTGAGGGAGG | 3-14-3 | 84.3 | 66 |
| 405893 | 2828 | 2847 | ATGAGGGCCATCAGCACCTT | 5-10-5 | 93.9 | 431 |
| 405894 | 2829 | 2848 | GATGAGGGCCATCAGCACCT | 5-10-5 | 93.9 | 432 |
| 405895 | 2830 | 2849 | AGATGAGGGCCATCAGCACC | 5-10-5 | 91.8 | 433 |
| 405896 | 2831 | 2850 | GAGATGAGGGCCATCAGCAC | 5-10-5 | 88.5 | 434 |
| 395194 | 2832 | 2851 | GGAGATGAGGGCCATCAGCA | 5-10-5 | 90.0 | 69 |
| 399916 | 2832 | 2851 | GGAGATGAGGGCCATCAGCA | 3-14-3 | 94.5 | 69 |
| 405897 | 2833 | 2852 | TGGAGATGAGGGCCATCAGC | 5-10-5 | 85.1 | 435 |
| 405898 | 2834 | 2853 | CTGGAGATGAGGGCCATCAG | 5-10-5 | 86.9 | 436 |
| 405899 | 2835 | 2854 | GCTGGAGATGAGGGCCATCA | 5-10-5 | 91.5 | 437 |
| 405900 | 2836 | 2855 | AGCTGGAGATGAGGGCCATC | 5-10-5 | 83.7 | 438 |
| 405901 | 2902 | 2921 | GCTAGATGCCATCCAGAAAG | 5-10-5 | 88.4 | 439 |
| 405902 | 2903 | 2922 | GGCTAGATGCCATCCAGAAA | 5-10-5 | 89.3 | 440 |
| 405903 | 2904 | 2923 | TGGCTAGATGCCATCCAGAA | 5-10-5 | 92.6 | 441 |
| 405904 | 2905 | 2924 | CTGGCTAGATGCCATCCAGA | 5-10-5 | 90.4 | 442 |
| 399821 | 2906 | 2925 | TCTGGCTAGATGCCATCCAG | 5-10-5 | 91.7 | 71 |
| 405905 | 2907 | 2926 | CTCTGGCTAGATGCCATCCA | 5-10-5 | 90.7 | 443 |
| 405906 | 2908 | 2927 | CCTCTGGCTAGATGCCATCC | 5-10-5 | 93.3 | 444 |
| 405907 | 2909 | 2928 | GCCTCTGGCTAGATGCCATC | 5-10-5 | 90.2 | 445 |
| 405908 | 2910 | 2929 | AGCCTCTGGCTAGATGCCAT | 5-10-5 | 83.3 | 446 |
| 399978 | 2988 | 3007 | AGCCTGGCATAGAGCAGAGT | 3-14-3 | 96.4 | 73 |

Antisense oligonucleotides that exhibited less than 30% inhibition of PCSK9 mRNA levels were marked with "NA".

Antisense oligonucleotides with the following ISIS Nos exhibited at least 80% inhibition of PCSK9 mRNA levels: 395152, 395153, 395155, 395158, 395163, 395165, 395166, 395168, 395173, 395181, 395183, 395185, 395186, 395187, 395194, 399798, 399801, 399804, 399806, 399817, 399819, 399821, 399877, 399879, 399887, 399888, 399891, 399895, 399900, 399904, 399905, 399906, 399907, 399912, 399916, 399954, 399960, 399962, 399967, 399968, 399969, 399973, 399978, 405861, 405862, 405863, 405864, 405865, 405866, 405869, 405870, 405871, 405872, 405873, 405874, 405875, 405876, 405877, 405878, 405879, 405880, 405881, 405882, 405883, 405884, 405889, 405890, 405891, 405893, 405894, 405895, 405896, 405897, 405898, 405899, 405900, 405901, 405902, 405903, 405904, 405905, 405906, 405907, 405908, 405909, 405910, 405911, 405913, 405914, 405915, 405916, 405920, 405921, 405922, 405923, 405924, 405925, 405926, 405927, 405928, 405929, 405930, 405931, 405932, 405934, 405935, 405936, 405940, 405941, 405943, 405944, 405949, 405952, 405953, 405954, 405955, 405956, 405958, 405959, 405960, 405961, 405973, 405974, 405976, 405977, 405978, 405979, 405980, 405982, 405984, 405987, 405988, 405989, 405990, 405991, 405992, 405993, 405994, 405995, 405996, 405997, 406002, 406003, 406005, 406008, 406009, 406014, 406016, 406020, 406023, 406026, 406028, 406029, 406030, 406031, 406032, 406033, 406035, 406036, 406038, 406039, 406040, 406041, 406042, 406043, 406044, 406045, 410530, 410556, 410558, 410562, 410578, 410583, 410589, 410590, 410591, 410592, 410593, 410595, 410609, 410611, 410616, 410617, 410618, 410619, 410624, 410628, 410633, 410634, 410647, 410648, 410650, 410652, 410658, 410664, 410666, 410667, 410668, 410671, 410677, 410686, 410688, 410689, 410693, 410695, 410696, 410697, 410698, 410700, 410701, 410702, 410713, 410714, 410715, 410716, 410723, 410724, 410730, 410751, 410754, 410757, 410759, 410760, 410769, and 410772. The target segments to which these antisense oligonucleotides are targeted are active target segments. The target regions to which these antisense oligonucleotides are targeted are active target regions.

ISIS Nos 395152, 395155, 395158, 395165, 395166, 395168, 395173, 395181, 395183, 395185, 395186, 395187, 395194, 399801, 399817, 399819, 399821, 399877, 399879, 399887, 399888, 399891, 399900, 399904, 399905, 399906, 399907, 399916, 399954, 399962, 399969, 399978, 405861, 405862, 405864, 405869, 405871, 405872, 405873, 405874, 405875, 405876, 405878, 405879, 405880, 405881, 405882, 405883, 405884, 405890, 405891, 405893, 405894, 405895, 405896, 405897, 405898, 405899, 405901, 405902, 405903, 405904, 405905, 405906, 405907, 405910, 405911, 405913, 405914, 405915, 405916, 405920, 405921, 405922, 405923, 405924, 405925, 405926, 405927, 405928, 405929, 405930, 405931, 405932, 405934, 405935, 405936, 405941, 405952, 405953, 405954, 405955, 405956, 405959, 405960, 405961, 405974, 405977, 405978, 405979, 405980, 405982, 405987, 405988, 405989, 405990, 405991, 405992, 405993, 405994, 405995, 405996, 405997, 406008, 406009, 406014, 406016, 406023, 406028, 406029, 406030, 406031, 406032, 406033, 406035, 406038, 406039, 406040, 406041, 406042, 406043, 406044, 406045, 410558, 410562, 410583, 410591, 410592, 410593, 410611, 410617, 410618, 410628, 410647, 410650, 410668, 410677, 410688, 410695, 410696, 410697, 410698, 410702, 410716, 410724, 410730, 410757, 410760, and 410772 each exhibited at least 85% inhibition of PCSK9 mRNA levels.

ISIS Nos 395152, 395155, 395158, 395165, 395166, 395168, 395173, 395183, 395185, 395186, 395187, 395194, 399801, 399817, 399819, 399821, 399877, 399879, 399887, 399888, 399891, 399900, 399904, 399905, 399906, 399907, 399916, 399954, 399969, 399978, 405861, 405862, 405864, 405873, 405874, 405875, 405876, 405878, 405879, 405880, 405881, 405882, 405883, 405884, 405891, 405893, 405894, 405895, 405899, 405903, 405904, 405905, 405906, 405907, 405910, 405913, 405914, 405916, 405923, 405924, 405925, 405926, 405927, 405928, 405930, 405932, 405934, 405936, 405941, 405953, 405955, 405956, 405959, 405960, 405978, 405988, 405990, 405991, 405994, 405995, 405996, 405997, 406008, 406009, 406014, 406023, 406028, 406029, 406030, 406033, 406035, 406039, 406040, 406041, 406042, 406043, 406044, 410592, 410647, 410668, 410760, and 410772 each exhibited at least 90% inhibition of PCSK9 mRNA levels.

ISIS Nos 395165, 395166, 399801, 399978, 405881, 405891, 405959, 405978, 405988, 405990, 405994, 405997, 406008, 406030, 406040, 406041, 406044, and 410760 each exhibited at least 95% inhibition of PCSK9 mRNA levels.

TABLE 18

Antisense inhibition of PCSK9 in human cells (Hep3B) targeting SEQ ID NO: 2

| Isis No. | 5' Target Site to SEQ ID NO: 2 | 3' Target Site to SEQ ID NO: 2 | Sequence 5'-3' | Motif | % inhibition | SEQ ID NO: |
|---|---|---|---|---|---|---|
| 410742 | 2433 | 2452 | GCCTGGAGCTGACGGTGCCC | 5-10-5 | 75.1 | 159 |
| 405999 | 2437 | 2456 | GACCGCCTGGAGCTGACGGT | 5-10-5 | 70.3 | 160 |
| 395151 | 2439 | 2458 | AGGACCGCCTGGAGCTGACG | 5-10-5 | 57.3 | 6 |
| 405861 | 2545 | 2564 | AAGGCTAGCACCAGCTCCTC | 5-10-5 | 90.5 | 162 |
| 405862 | 2546 | 2565 | CAAGGCTAGCACCAGCTCCT | 5-10-5 | 92.3 | 163 |
| 405863 | 2547 | 2566 | GCAAGGCTAGCACCAGCTCC | 5-10-5 | 82.6 | 164 |
| 405864 | 2548 | 2567 | CGCAAGGCTAGCACCAGCTC | 5-10-5 | 91.8 | 165 |
| 395152 | 2549 | 2568 | ACGCAAGGCTAGCACCAGCT | 5-10-5 | 93.3 | 7 |
| 405865 | 2550 | 2569 | AACGCAAGGCTAGCACCAGC | 5-10-5 | 84.6 | 166 |
| 405866 | 2551 | 2570 | GAACGCAAGGCTAGCACCAG | 5-10-5 | 81.8 | 167 |
| 405867 | 2552 | 2571 | GGAACGCAAGGCTAGCACCA | 5-10-5 | 74.0 | 168 |
| 405868 | 2553 | 2572 | CGGAACGCAAGGCTAGCACC | 5-10-5 | 76.8 | 169 |
| 399793 | 2556 | 2575 | CCTCGGAACGCAAGGCTAGC | 5-10-5 | 77.9 | 8 |
| 410743 | 2560 | 2579 | TCCTCCTCGGAACGCAAGGC | 5-10-5 | 76.7 | 170 |
| 410744 | 2585 | 2604 | GTGCTCGGGTGCTTCGGCCA | 5-10-5 | 76.9 | 171 |
| 410745 | 2605 | 2624 | TGGAAGGTGGCTGTGGTTCC | 5-10-5 | 41.7 | 172 |
| 395153 | 2619 | 2638 | CCTTGGCGCAGCGGTGGAAG | 5-10-5 | 81.1 | 9 |

TABLE 18-continued

Antisense inhibition of PCSK9 in human cells (Hep3B) targeting SEQ ID NO: 2

| Isis No. | 5' Target Site to SEQ ID NO: 2 | 3' Target Site to SEQ ID NO: 2 | Sequence 5'-3' | Motif | % inhibition | SEQ ID NO: |
|---|---|---|---|---|---|---|
| 410746 | 6444 | 6463 | CGTAGGTGCCAGGCAACCTC | 5-10-5 | 44.8 | 176 |
| 410747 | 6482 | 6501 | TGACTGCGAGAGGTGGGTCT | 5-10-5 | NA | 177 |
| 406003 | 6492 | 6511 | CAGTGCGCTCTGACTGCGAG | 5-10-5 | 84.2 | 178 |
| 406004 | 6494 | 6513 | GGCAGTGCGCTCTGACTGCG | 5-10-5 | 56.4 | 179 |
| 406005 | 6496 | 6515 | CGGGCAGTGCGCTCTGACTG | 5-10-5 | 83.4 | 180 |
| 406006 | 6499 | 6518 | CGGCGGGCAGTGCGCTCTGA | 5-10-5 | 71.0 | 181 |
| 410748 | 6528 | 6547 | ATCCCCGGCGGGCAGCCTGG | 5-10-5 | 56.0 | 182 |
| 406007 | 6532 | 6551 | AGGTATCCCCGGCGGGCAGC | 5-10-5 | 76.3 | 183 |
| 410574 | 6534 | 6553 | TGAGGTATCCCCGGCGGGCA | 3-14-3 | 69.1 | 184 |
| 410529 | 6534 | 6553 | TGAGGTATCCCCGGCGGGCA | 5-10-5 | 77.4 | 184 |
| 410647 | 6534 | 6553 | TGAGGTATCCCCGGCGGGCA | 2-13-5 | 90.7 | 184 |
| 410575 | 6535 | 6554 | GTGAGGTATCCCCGGCGGGC | 3-14-3 | 71.5 | 185 |
| 410648 | 6535 | 6554 | GTGAGGTATCCCCGGCGGGC | 2-13-5 | 82.8 | 185 |
| 410530 | 6535 | 6554 | GTGAGGTATCCCCGGCGGGC | 5-10-5 | 83.2 | 185 |
| 410649 | 6536 | 6555 | GGTGAGGTATCCCCGGCGGG | 2-13-5 | 53.5 | 186 |
| 410576 | 6536 | 6555 | GGTGAGGTATCCCCGGCGGG | 3-14-3 | 56.2 | 186 |
| 410531 | 6536 | 6555 | GGTGAGGTATCCCCGGCGGG | 5-10-5 | 63.6 | 186 |
| 410650 | 6537 | 6556 | TGGTGAGGTATCCCCGGCGG | 2-13-5 | 86.1 | 11 |
| 399877 | 6537 | 6556 | TGGTGAGGTATCCCCGGCGG | 3-14-3 | 92.6 | 11 |
| 395155 | 6537 | 6556 | TGGTGAGGTATCCCCGGCGG | 5-10-5 | 92.7 | 11 |
| 410577 | 6538 | 6557 | TTGGTGAGGTATCCCCGGCG | 3-14-3 | 62.4 | 187 |
| 410532 | 6538 | 6557 | TTGGTGAGGTATCCCCGGCG | 5-10-5 | 63.5 | 187 |
| 410651 | 6538 | 6557 | TTGGTGAGGTATCCCCGGCG | 2-13-5 | 75.5 | 187 |
| 410652 | 6539 | 6558 | CTTGGTGAGGTATCCCCGGC | 2-13-5 | 81.2 | 188 |
| 410578 | 6539 | 6558 | CTTGGTGAGGTATCCCCGGC | 3-14-3 | 83.3 | 188 |
| 406008 | 6539 | 6558 | CTTGGTGAGGTATCCCCGGC | 5-10-5 | 95.2 | 188 |
| 410653 | 6540 | 6559 | TCTTGGTGAGGTATCCCCGG | 2-13-5 | 68.9 | 189 |
| 410579 | 6540 | 6559 | TCTTGGTGAGGTATCCCCGG | 3-14-3 | 74.0 | 189 |
| 410533 | 6540 | 6559 | TCTTGGTGAGGTATCCCCGG | 5-10-5 | 79.0 | 189 |
| 410580 | 6541 | 6560 | ATCTTGGTGAGGTATCCCCG | 3-14-3 | 62.3 | 190 |
| 410654 | 6541 | 6560 | ATCTTGGTGAGGTATCCCCG | 2-13-5 | 65.2 | 190 |
| 406009 | 6541 | 6560 | ATCTTGGTGAGGTATCCCCG | 5-10-5 | 90.7 | 190 |
| 410534 | 6542 | 6561 | GATCTTGGTGAGGTATCCCC | 5-10-5 | 59.8 | 191 |
| 410581 | 6542 | 6561 | GATCTTGGTGAGGTATCCCC | 3-14-3 | 72.9 | 191 |
| 410655 | 6542 | 6561 | GATCTTGGTGAGGTATCCCC | 2-13-5 | 77.4 | 191 |
| 399794 | 6543 | 6562 | GGATCTTGGTGAGGTATCCC | 5-10-5 | 56.5 | 12 |

TABLE 18-continued

Antisense inhibition of PCSK9 in human cells (Hep3B) targeting SEQ ID NO: 2

| Isis No. | 5' Target Site to SEQ ID NO: 2 | 3' Target Site to SEQ ID NO: 2 | Sequence 5'-3' | Motif | % inhibition | SEQ ID NO: |
|---|---|---|---|---|---|---|
| 410656 | 6543 | 6562 | GGATCTTGGTGAGGTATCCC | 2-13-5 | 68.0 | 12 |
| 399950 | 6543 | 6562 | GGATCTTGGTGAGGTATCCC | 3-14-3 | 74.4 | 12 |
| 410535 | 6544 | 6563 | AGGATCTTGGTGAGGTATCC | 5-10-5 | 65.7 | 192 |
| 410582 | 6544 | 6563 | AGGATCTTGGTGAGGTATCC | 3-14-3 | 69.5 | 192 |
| 410657 | 6544 | 6563 | AGGATCTTGGTGAGGTATCC | 2-13-5 | 73.1 | 192 |
| 406010 | 6546 | 6565 | GCAGGATCTTGGTGAGGTAT | 5-10-5 | 56.9 | 193 |
| 406011 | 6548 | 6567 | ATGCAGGATCTTGGTGAGGT | 5-10-5 | 70.7 | 194 |
| 406012 | 6550 | 6569 | ACATGCAGGATCTTGGTGAG | 5-10-5 | 69.1 | 195 |
| 406013 | 6554 | 6573 | GAAGACATGCAGGATCTTGG | 5-10-5 | 77.4 | 196 |
| 395156 | 6557 | 6576 | ATGGAAGACATGCAGGATCT | 5-10-5 | 76.7 | 14 |
| 410749 | 6565 | 6584 | AGAAGGCCATGGAAGACATG | 5-10-5 | 59.4 | 197 |
| 410750 | 6575 | 6594 | GAAGCCAGGAAGAAGGCCAT | 5-10-5 | 57.5 | 198 |
| 399879 | 6583 | 6602 | TTCACCAGGAAGCCAGGAAG | 3-14-3 | 91.9 | 15 |
| 406014 | 6585 | 6604 | TCTTCACCAGGAAGCCAGGA | 5-10-5 | 94.0 | 199 |
| 406015 | 6590 | 6609 | ACTCATCTTCACCAGGAAGC | 5-10-5 | 78.8 | 200 |
| 406016 | 6592 | 6611 | CCACTCATCTTCACCAGGAA | 5-10-5 | 87.2 | 201 |
| 410730 | 6594 | 6613 | CGCCACTCATCTTCACCAGG | 5-10-5 | 85.4 | 202 |
| 406017 | 6596 | 6615 | GTCGCCACTCATCTTCACCA | 5-10-5 | 76.3 | 203 |
| 406018 | 6598 | 6617 | AGGTCGCCACTCATCTTCAC | 5-10-5 | 63.2 | 204 |
| 406019 | 6600 | 6619 | GCAGGTCGCCACTCATCTTC | 5-10-5 | 68.1 | 205 |
| 406020 | 6602 | 6621 | CAGCAGGTCGCCACTCATCT | 5-10-5 | 83.7 | 206 |
| 410731 | 6604 | 6623 | TCCAGCAGGTCGCCACTCAT | 5-10-5 | 72.9 | 207 |
| 395158 | 9130 | 9149 | CCTCGATGTAGTCGACATGG | 5-10-5 | 93.9 | 17 |
| 410752 | 9149 | 9168 | GCAAAGACAGAGGAGTCCTC | 5-10-5 | 76.3 | 209 |
| 406021 | 9207 | 9226 | TTCATCCGCCCGGTACCGTG | 5-10-5 | 79.6 | 210 |
| 406022 | 9209 | 9228 | TATTCATCCGCCCGGTACCG | 5-10-5 | 78.7 | 211 |
| 406023 | 9212 | 9231 | TGGTATTCATCCGCCCGGTA | 5-10-5 | 92.5 | 212 |
| 406024 | 9214 | 9233 | GCTGGTATTCATCCGCCCGG | 5-10-5 | 69.7 | 213 |
| 410732 | 9216 | 9235 | GGGCTGGTATTCATCCGCCC | 5-10-5 | 30.4 | 214 |
| 399935 | 14601 | 14620 | AGGACCCAAGTCATCCTGCT | 3-14-3 | 81.1 | 96 |
| 399936 | 14631 | 14650 | GGCCATCAGCTGGCAATGCT | 3-14-3 | 89.0 | 124 |
| 410753 | 14877 | 14896 | ATACACCTCCACCAGGCTGC | 5-10-5 | 72.8 | 315 |
| 406025 | 14888 | 14907 | GTGTCTAGGAGATACACCTC | 5-10-5 | 74.2 | 216 |
| 406026 | 14893 | 14912 | TGCTGGTGTCTAGGAGATAC | 5-10-5 | 80.5 | 217 |
| 405869 | 14918 | 14937 | TCGATTTCCCGGTGGTCACT | 5-10-5 | 87.6 | 218 |
| 405870 | 14919 | 14938 | CTCGATTTCCCGGTGGTCAC | 5-10-5 | 83.3 | 219 |

TABLE 18-continued

Antisense inhibition of PCSK9 in human cells (Hep3B) targeting SEQ ID NO: 2

| Isis No. | 5' Target Site to SEQ ID NO: 2 | 3' Target Site to SEQ ID NO: 2 | Sequence 5'-3' | Motif | % inhibition | SEQ ID NO: |
|---|---|---|---|---|---|---|
| 405871 | 14920 | 14939 | CCTCGATTTCCCGGTGGTCA | 5-10-5 | 87.0 | 220 |
| 405872 | 14921 | 14940 | CCCTCGATTTCCCGGTGGTC | 5-10-5 | 88.2 | 221 |
| 399798 | 14922 | 14941 | GCCCTCGATTTCCCGGTGGT | 5-10-5 | 84.3 | 22 |
| 399954 | 14922 | 14941 | GCCCTCGATTTCCCGGTGGT | 3-14-3 | 90.3 | 22 |
| 405873 | 14923 | 14942 | TGCCCTCGATTTCCCGGTGG | 5-10-5 | 90.0 | 222 |
| 405874 | 14924 | 14943 | CTGCCCTCGATTTCCCGGTG | 5-10-5 | 91.4 | 223 |
| 405875 | 14925 | 14944 | CCTGCCCTCGATTTCCCGGT | 5-10-5 | 93.5 | 224 |
| 405876 | 14926 | 14945 | CCCTGCCCTCGATTTCCCGG | 5-10-5 | 90.1 | 225 |
| 406027 | 14930 | 14949 | ATGACCCTGCCCTCGATTTC | 5-10-5 | 73.9 | 226 |
| 406028 | 14932 | 14951 | CCATGACCCTGCCCTCGATT | 5-10-5 | 92.3 | 227 |
| 406029 | 14934 | 14953 | GACCATGACCCTGCCCTCGA | 5-10-5 | 91.4 | 228 |
| 406030 | 14938 | 14957 | CGGTGACCATGACCCTGCCC | 5-10-5 | 95.6 | 229 |
| 406031 | 14940 | 14959 | GTCGGTGACCATGACCCTGC | 5-10-5 | 89.6 | 230 |
| 410733 | 14942 | 14961 | AAGTCGGTGACCATGACCCT | 5-10-5 | 65.7 | 231 |
| 406032 | 14944 | 14963 | CGAAGTCGGTGACCATGACC | 5-10-5 | 88.5 | 232 |
| 410754 | 14954 | 14973 | GGCACATTCTCGAAGTCGGT | 5-10-5 | 80.1 | 233 |
| 395163 | 14979 | 14998 | GTGGAAGCGGGTCCCGTCCT | 5-10-5 | 83.9 | 25 |
| 410756 | 15254 | 15273 | GGTGGGTGCCATGACTGTCA | 5-10-5 | 67.1 | 235 |
| 406033 | 15261 | 15280 | CCTGCCAGGTGGGTGCCATG | 5-10-5 | 91.2 | 237 |
| 406034 | 15266 | 15285 | CCACCCCTGCCAGGTGGGTG | 5-10-5 | 59.3 | 238 |
| 406035 | 15271 | 15290 | GCTGACCACCCCTGCCAGGT | 5-10-5 | 91.7 | 239 |
| 410757 | 15279 | 15298 | TCCCGGCCGCTGACCACCCC | 5-10-5 | 88.9 | 240 |
| 406036 | 15283 | 15302 | GGCATCCCGGCCGCTGACCA | 5-10-5 | 84.0 | 241 |
| 406037 | 15286 | 15305 | GCCGGCATCCCGGCCGCTGA | 5-10-5 | 55.9 | 242 |
| 410536 | 15291 | 15310 | GCCACGCCGGCATCCCGGCC | 5-10-5 | 63.7 | 243 |
| 410658 | 15291 | 15310 | GCCACGCCGGCATCCCGGCC | 2-13-5 | 82.0 | 243 |
| 410583 | 15291 | 15310 | GCCACGCCGGCATCCCGGCC | 3-14-3 | 87.3 | 243 |
| 410537 | 15292 | 15311 | GGCCACGCCGGCATCCCGGC | 5-10-5 | 58.5 | 244 |
| 410659 | 15292 | 15311 | GGCCACGCCGGCATCCCGGC | 2-13-5 | 73.7 | 244 |
| 410584 | 15292 | 15311 | GGCCACGCCGGCATCCCGGC | 3-14-3 | 79.5 | 244 |
| 410660 | 15293 | 15312 | TGGCCACGCCGGCATCCCGG | 2-13-5 | 63.0 | 245 |
| 410585 | 15293 | 15312 | TGGCCACGCCGGCATCCCGG | 3-14-3 | 73.2 | 245 |
| 406038 | 15293 | 15312 | TGGCCACGCCGGCATCCCGG | 5-10-5 | 86.3 | 245 |
| 410661 | 15294 | 15313 | TTGGCCACGCCGGCATCCCG | 2-13-5 | 53.3 | 246 |
| 410586 | 15294 | 15313 | TTGGCCACGCCGGCATCCCG | 3-14-3 | 60.3 | 246 |
| 405877 | 15294 | 15313 | TTGGCCACGCCGGCATCCCG | 5-10-5 | 83.2 | 246 |

TABLE 18-continued

Antisense inhibition of PCSK9 in human cells (Hep3B) targeting SEQ ID NO: 2

| Isis No. | 5' Target Site to SEQ ID NO: 2 | 3' Target Site to SEQ ID NO: 2 | Sequence 5'-3' | Motif | % inhibition | SEQ ID NO: |
|---|---|---|---|---|---|---|
| 410587 | 15295 | 15314 | CTTGGCCACGCCGGCATCCC | 3-14-3 | 63.2 | 247 |
| 410662 | 15295 | 15314 | CTTGGCCACGCCGGCATCCC | 2-13-5 | 67.3 | 247 |
| 405878 | 15295 | 15314 | CTTGGCCACGCCGGCATCCC | 5-10-5 | 91.4 | 247 |
| 410588 | 15296 | 15315 | CCTTGGCCACGCCGGCATCC | 3-14-3 | 65.3 | 248 |
| 410663 | 15296 | 15315 | CCTTGGCCACGCCGGCATCC | 2-13-5 | 67.9 | 248 |
| 405879 | 15296 | 15315 | CCTTGGCCACGCCGGCATCC | 5-10-5 | 94.1 | 248 |
| 410589 | 15297 | 15316 | CCCTTGGCCACGCCGGCATC | 3-14-3 | 80.1 | 249 |
| 410664 | 15297 | 15316 | CCCTTGGCCACGCCGGCATC | 2-13-5 | 81.9 | 249 |
| 405880 | 15297 | 15316 | CCCTTGGCCACGCCGGCATC | 5-10-5 | 93.5 | 249 |
| 410665 | 15298 | 15317 | ACCCTTGGCCACGCCGGCAT | 2-13-5 | 78.7 | 28 |
| 399887 | 15298 | 15317 | ACCCTTGGCCACGCCGGCAT | 3-14-3 | 91.9 | 28 |
| 395165 | 15298 | 15317 | ACCCTTGGCCACGCCGGCAT | 5-10-5 | 96.7 | 28 |
| 410590 | 15299 | 15318 | CACCCTTGGCCACGCCGGCA | 3-14-3 | 82.2 | 250 |
| 410666 | 15299 | 15318 | CACCCTTGGCCACGCCGGCA | 2-13-5 | 82.7 | 250 |
| 405881 | 15299 | 15318 | CACCCTTGGCCACGCCGGCA | 5-10-5 | 98.3 | 250 |
| 410667 | 15300 | 15319 | GCACCCTTGGCCACGCCGGC | 2-13-5 | 84.7 | 251 |
| 410591 | 15300 | 15319 | GCACCCTTGGCCACGCCGGC | 3-14-3 | 86.3 | 251 |
| 405882 | 15300 | 15319 | GCACCCTTGGCCACGCCGGC | 5-10-5 | 91.6 | 251 |
| 410668 | 15301 | 15320 | GGCACCCTTGGCCACGCCGG | 2-13-5 | 91.4 | 252 |
| 405883 | 15301 | 15320 | GGCACCCTTGGCCACGCCGG | 5-10-5 | 92.5 | 252 |
| 410592 | 15301 | 15320 | GGCACCCTTGGCCACGCCGG | 3-14-3 | 93.4 | 252 |
| 410669 | 15302 | 15321 | TGGCACCCTTGGCCACGCCG | 2-13-5 | 69.0 | 253 |
| 410593 | 15302 | 15321 | TGGCACCCTTGGCCACGCCG | 3-14-3 | 88.8 | 253 |
| 405884 | 15302 | 15321 | TGGCACCCTTGGCCACGCCG | 5-10-5 | 90.8 | 253 |
| 410670 | 15303 | 15322 | CTGGCACCCTTGGCCACGCC | 2-13-5 | 74.9 | 254 |
| 410594 | 15303 | 15322 | CTGGCACCCTTGGCCACGCC | 3-14-3 | 75.2 | 254 |
| 410538 | 15303 | 15322 | CTGGCACCCTTGGCCACGCC | 5-10-5 | 78.2 | 254 |
| 410539 | 15304 | 15323 | GCTGGCACCCTTGGCCACGC | 5-10-5 | 61.9 | 255 |
| 410595 | 15304 | 15323 | GCTGGCACCCTTGGCCACGC | 3-14-3 | 83.1 | 255 |
| 410671 | 15304 | 15323 | GCTGGCACCCTTGGCCACGC | 2-13-5 | 83.3 | 255 |
| 410758 | 15309 | 15328 | CGCATGCTGGCACCCTTGGC | 5-10-5 | 73.6 | 256 |
| 406039 | 15330 | 15349 | CAGTTGAGCACGCGCAGGCT | 5-10-5 | 91.2 | 257 |
| 406040 | 15332 | 15351 | GGCAGTTGAGCACGCGCAGG | 5-10-5 | 96.5 | 258 |
| 399888 | 15334 | 15353 | TTGGCAGTTGAGCACGCGCA | 3-14-3 | 90.9 | 29 |
| 395166 | 15334 | 15353 | TTGGCAGTTGAGCACGCGCA | 5-10-5 | 96.2 | 29 |
| 406041 | 15336 | 15355 | CCTTGGCAGTTGAGCACGCG | 5-10-5 | 96.6 | 259 |

TABLE 18-continued

Antisense inhibition of PCSK9 in human cells (Hep3B) targeting SEQ ID NO: 2

| Isis No. | 5' Target Site to SEQ ID NO: 2 | 3' Target Site to SEQ ID NO: 2 | Sequence 5'-3' | Motif | % inhibition | SEQ ID NO: |
|---|---|---|---|---|---|---|
| 399801 | 15339 | 15358 | TTCCCTTGGCAGTTGAGCAC | 5-10-5 | 95.6 | 30 |
| 406042 | 15341 | 15360 | CCTTCCCTTGGCAGTTGAGC | 5-10-5 | 92.0 | 260 |
| 406043 | 15345 | 15364 | GTGCCCTTCCCTTGGCAGTT | 5-10-5 | 91.9 | 261 |
| 406044 | 15347 | 15366 | CCGTGCCCTTCCCTTGGCAG | 5-10-5 | 95.4 | 262 |
| 410759 | 15358 | 15377 | GGTGCCGCTAACCGTGCCCT | 5-10-5 | 83.7 | 263 |
| 406045 | 18591 | 18610 | TGGCTTTTCCGAATAAACTC | 5-10-5 | 88.4 | 266 |
| 395168 | 18593 | 18612 | GCTGGCTTTTCCGAATAAAC | 5-10-5 | 91.9 | 32 |
| 405909 | 18595 | 18614 | CAGCTGGCTTTTCCGAATAA | 5-10-5 | 80.3 | 267 |
| 405910 | 18597 | 18616 | ACCAGCTGGCTTTTCCGAAT | 5-10-5 | 90.9 | 268 |
| 405911 | 18599 | 18618 | GGACCAGCTGGCTTTTCCGA | 5-10-5 | 88.0 | 269 |
| 405912 | 18603 | 18622 | GGCTGGACCAGCTGGCTTTT | 5-10-5 | 78.2 | 270 |
| 410761 | 18614 | 18633 | GTGGCCCCACAGGCTGGACC | 5-10-5 | 53.7 | 271 |
| 410762 | 18627 | 18646 | AGCAGCACCACCAGTGGCCC | 5-10-5 | 57.6 | 272 |
| 410763 | 18649 | 18668 | GCTGTACCCACCCGCCAGGG | 5-10-5 | 68.8 | 273 |
| 410764 | 18695 | 18714 | CGACCCCAGCCCTCGCCAGG | 5-10-5 | 66.3 | 274 |
| 399891 | 18705 | 18724 | GTGACCAGCACGACCCCAGC | 3-14-3 | 91.1 | 33 |
| 405913 | 18707 | 18726 | CGGTGACCAGCACGACCCCA | 5-10-5 | 93.8 | 275 |
| 405914 | 18709 | 18728 | AGCGGTGACCAGCACGACCC | 5-10-5 | 90.4 | 276 |
| 405915 | 18711 | 18730 | GCAGCGGTGACCAGCACGAC | 5-10-5 | 86.8 | 277 |
| 405916 | 18713 | 18732 | CGGCAGCGGTGACCAGCACG | 5-10-5 | 91.3 | 278 |
| 410734 | 18714 | 18733 | CCGGCAGCGGTGACCAGCAC | 5-10-5 | 65.8 | 279 |
| 405917 | 18717 | 18736 | TTGCCGGCAGCGGTGACCAG | 5-10-5 | 62.0 | 280 |
| 405918 | 18719 | 18738 | AGTTGCCGGCAGCGGTGACC | 5-10-5 | 33.5 | 281 |
| 405919 | 18721 | 18740 | GAAGTTGCCGGCAGCGGTGA | 5-10-5 | 68.2 | 282 |
| 405920 | 18723 | 18742 | CGGAAGTTGCCGGCAGCGGT | 5-10-5 | 86.2 | 283 |
| 405921 | 18725 | 18744 | CCCGGAAGTTGCCGGCAGCG | 5-10-5 | 85.5 | 284 |
| 405922 | 18727 | 18746 | GTCCCGGAAGTTGCCGGCAG | 5-10-5 | 86.0 | 285 |
| 405923 | 19931 | 19950 | GGCATTGGTGGCCCCAACTG | 5-10-5 | 94.3 | 288 |
| 410767 | 19941 | 19960 | GCTGGTCTTGGGCATTGGTG | 5-10-5 | 65.1 | 289 |
| 405924 | 19954 | 19973 | CCCAGGGTCACCGGCTGGTC | 5-10-5 | 93.1 | 290 |
| 410735 | 19956 | 19975 | TCCCCAGGGTCACCGGCTGG | 5-10-5 | 78.1 | 291 |
| 405925 | 19958 | 19977 | AGTCCCCAGGGTCACCGGCT | 5-10-5 | 93.5 | 292 |
| 405926 | 19960 | 19979 | AAAGTCCCCAGGGTCACCGG | 5-10-5 | 94.6 | 293 |
| 405927 | 19964 | 19983 | CCCCAAAGTCCCCAGGGTCA | 5-10-5 | 94.5 | 294 |
| 405928 | 19969 | 19988 | TTGGTCCCCAAAGTCCCCAG | 5-10-5 | 90.0 | 295 |
| 405929 | 19973 | 19992 | AAAGTTGGTCCCCAAAGTCC | 5-10-5 | 85.5 | 296 |

TABLE 18-continued

Antisense inhibition of PCSK9 in human cells (Hep3B) targeting SEQ ID NO: 2

| Isis No. | 5' Target Site to SEQ ID NO: 2 | 3' Target Site to SEQ ID NO: 2 | Sequence 5'-3' | Motif | % inhibition | SEQ ID NO: |
|---|---|---|---|---|---|---|
| 399895 | 19976 | 19995 | GCCAAAGTTGGTCCCCAAAG | 3-14-3 | 84.6 | 36 |
| 395173 | 19976 | 19995 | GCCAAAGTTGGTCCCCAAAG | 5-10-5 | 94.8 | 36 |
| 405930 | 19978 | 19997 | CGGCCAAAGTTGGTCCCCAA | 5-10-5 | 92.9 | 297 |
| 405931 | 19980 | 19999 | AGCGGCCAAAGTTGGTCCCC | 5-10-5 | 88.8 | 298 |
| 405932 | 19982 | 20001 | ACAGCGGCCAAAGTTGGTCC | 5-10-5 | 90.6 | 299 |
| 405933 | 19984 | 20003 | ACACAGCGGCCAAAGTTGGT | 5-10-5 | NA | 300 |
| 405934 | 19986 | 20005 | CCACACAGCGGCCAAAGTTG | 5-10-5 | 92.7 | 301 |
| 405935 | 19990 | 20009 | AGGTCCACACAGCGGCCAAA | 5-10-5 | 86.0 | 302 |
| 410736 | 19992 | 20011 | AGAGGTCCACACAGCGGCCA | 5-10-5 | 73.8 | 303 |
| 405936 | 19994 | 20013 | AAAGAGGTCCACACAGCGGC | 5-10-5 | 93.9 | 304 |
| 410768 | 20016 | 20035 | CAATGATGTCCTCCCCTGGG | 5-10-5 | 79.7 | 305 |
| 405937 | 20023 | 20042 | GAGGCACCAATGATGTCCTC | 5-10-5 | 77.7 | 306 |
| 405938 | 20027 | 20046 | GCTGGAGGCACCAATGATGT | 5-10-5 | 75.5 | 307 |
| 405939 | 20029 | 20048 | TCGCTGGAGGCACCAATGAT | 5-10-5 | 70.6 | 308 |
| 405940 | 20031 | 20050 | AGTCGCTGGAGGCACCAATG | 5-10-5 | 84.4 | 309 |
| 405941 | 20033 | 20052 | GCAGTCGCTGGAGGCACCAA | 5-10-5 | 90.1 | 310 |
| 399804 | 20036 | 20055 | GCTGCAGTCGCTGGAGGCAC | 5-10-5 | 80.8 | 40 |
| 399960 | 20036 | 20055 | GCTGCAGTCGCTGGAGGCAC | 3-14-3 | 82.4 | 40 |
| 405942 | 20038 | 20057 | GTGCTGCAGTCGCTGGAGGC | 5-10-5 | 69.8 | 311 |
| 405943 | 20040 | 20059 | AGGTGCTGCAGTCGCTGGAG | 5-10-5 | 83.6 | 312 |
| 410737 | 20042 | 20061 | GCAGGTGCTGCAGTCGCTGG | 5-10-5 | 49.8 | 313 |
| 405944 | 20043 | 20062 | AGCAGGTGCTGCAGTCGCTG | 5-10-5 | 80.7 | 314 |
| 405945 | 20045 | 20064 | AAAGCAGGTGCTGCAGTCGC | 5-10-5 | 41.1 | 315 |
| 405946 | 20049 | 20068 | ACACAAAGCAGGTGCTGCAG | 5-10-5 | 70.4 | 316 |
| 405947 | 20051 | 20070 | TGACACAAAGCAGGTGCTGC | 5-10-5 | 72.5 | 317 |
| 410769 | 20061 | 20080 | TCCCACTCTGTGACACAAAG | 5-10-5 | 84.9 | 318 |
| 405949 | 20629 | 20648 | CAGCATCATGGCTGCAATGC | 5-10-5 | 84.9 | 320 |
| 405950 | 20631 | 20650 | GACAGCATCATGGCTGCAAT | 5-10-5 | 76.9 | 321 |
| 405951 | 20633 | 20652 | CAGACAGCATCATGGCTGCA | 5-10-5 | 75.4 | 322 |
| 405952 | 20637 | 20656 | TCGGCAGACAGCATCATGGC | 5-10-5 | 85.1 | 323 |
| 410738 | 20639 | 20658 | GCTCGGCAGACAGCATCATG | 5-10-5 | 68.4 | 324 |
| 405953 | 20641 | 20660 | CGGCTCGGCAGACAGCATCA | 5-10-5 | 93.6 | 325 |
| 405954 | 20643 | 20662 | TCCGGCTCGGCAGACAGCAT | 5-10-5 | 87.5 | 326 |
| 410770 | 20657 | 20676 | CGGCCAGGGTGAGCTCCGGC | 5-10-5 | 68.5 | 327 |
| 405955 | 20670 | 20689 | CTCTGCCTCAACTCGGCCAG | 5-10-5 | 94.2 | 328 |
| 405956 | 20672 | 20691 | GTCTCTGCCTCAACTCGGCC | 5-10-5 | 94.3 | 329 |

TABLE 18-continued

Antisense inhibition of PCSK9 in human cells (Hep3B) targeting SEQ ID NO: 2

| Isis No. | 5' Target Site to SEQ ID NO: 2 | 3' Target Site to SEQ ID NO: 2 | Sequence 5'-3' | Motif | % inhibition | SEQ ID NO: |
|---|---|---|---|---|---|---|
| 405958 | 20676 | 20695 | ATCAGTCTCTGCCTCAACT | 5-10-5 | 80.3 | 331 |
| 405959 | 20678 | 20697 | GGATCAGTCTCTGCCTCAAC | 5-10-5 | 95.4 | 332 |
| 405960 | 20680 | 20699 | GTGGATCAGTCTCTGCCTCA | 5-10-5 | 90.1 | 333 |
| 405961 | 20682 | 20701 | AAGTGGATCAGTCTCTGCCT | 5-10-5 | 88.8 | 334 |
| 405962 | 20685 | 20704 | GAGAAGTGGATCAGTCTCTG | 5-10-5 | 56.1 | 335 |
| 410739 | 20687 | 20706 | CAGAGAAGTGGATCAGTCTC | 5-10-5 | NA | 336 |
| 405963 | 20689 | 20708 | GGCAGAGAAGTGGATCAGTC | 5-10-5 | 59.7 | 337 |
| 405964 | 20693 | 20712 | CTTTGGCAGAGAAGTGGATC | 5-10-5 | 45.3 | 338 |
| 405965 | 20698 | 20717 | GACATCTTTGGCAGAGAAGT | 5-10-5 | 55.9 | 339 |
| 405966 | 20700 | 20719 | ATGACATCTTTGGCAGAGAA | 5-10-5 | 51.3 | 340 |
| 405967 | 20704 | 20723 | ATTGATGACATCTTTGGCAG | 5-10-5 | 64.4 | 341 |
| 405968 | 20706 | 20725 | TCATTGATGACATCTTTGGC | 5-10-5 | 74.6 | 342 |
| 399967 | 20709 | 20728 | GCCTCATTGATGACATCTTT | 3-14-3 | 80.1 | 48 |
| 405969 | 20711 | 20730 | AGGCCTCATTGATGACATCT | 5-10-5 | 63.0 | 343 |
| 405970 | 20713 | 20732 | CCAGGCCTCATTGATGACAT | 5-10-5 | 66.8 | 344 |
| 410740 | 20715 | 20734 | AACCAGGCCTCATTGATGAC | 5-10-5 | 46.8 | 345 |
| 405885 | 20717 | 20736 | GGAACCAGGCCTCATTGATG | 5-10-5 | 73.4 | 346 |
| 410596 | 20719 | 20738 | AGGGAACCAGGCCTCATTGA | 3-14-3 | NA | 348 |
| 410672 | 20719 | 20738 | AGGGAACCAGGCCTCATTGA | 2-13-5 | NA | 348 |
| 405887 | 20719 | 20738 | AGGGAACCAGGCCTCATTGA | 5-10-5 | NA | 348 |
| 410597 | 20720 | 20739 | CAGGGAACCAGGCCTCATTG | 3-14-3 | NA | 349 |
| 405888 | 20720 | 20739 | CAGGGAACCAGGCCTCATTG | 5-10-5 | NA | 349 |
| 410673 | 20720 | 20739 | CAGGGAACCAGGCCTCATTG | 2-13-5 | NA | 349 |
| 410674 | 20721 | 20740 | TCAGGGAACCAGGCCTCATT | 2-13-5 | 60.7 | 49 |
| 399812 | 20721 | 20740 | TCAGGGAACCAGGCCTCATT | 5-10-5 | 68.7 | 49 |
| 399968 | 20721 | 20740 | TCAGGGAACCAGGCCTCATT | 3-14-3 | 84.5 | 49 |
| 410598 | 20722 | 20741 | CTCAGGGAACCAGGCCTCAT | 3-14-3 | 74.5 | 350 |
| 410675 | 20722 | 20741 | CTCAGGGAACCAGGCCTCAT | 2-13-5 | 76.9 | 350 |
| 405889 | 20722 | 20741 | CTCAGGGAACCAGGCCTCAT | 5-10-5 | 80.2 | 350 |
| 410599 | 20723 | 20742 | CCTCAGGGAACCAGGCCTCA | 3-14-3 | 70.6 | 351 |
| 410676 | 20723 | 20742 | CCTCAGGGAACCAGGCCTCA | 2-13-5 | 77.8 | 351 |
| 405890 | 20723 | 20742 | CCTCAGGGAACCAGGCCTCA | 5-10-5 | 87.7 | 351 |
| 410600 | 20724 | 20743 | TCCTCAGGGAACCAGGCCTC | 3-14-3 | 76.5 | 352 |
| 410677 | 20724 | 20743 | TCCTCAGGGAACCAGGCCTC | 2-13-5 | 88.4 | 352 |
| 405891 | 20724 | 20743 | TCCTCAGGGAACCAGGCCTC | 5-10-5 | 96.1 | 352 |
| 405892 | 20725 | 20744 | GTCCTCAGGGAACCAGGCCT | 5-10-5 | 71.4 | 353 |

TABLE 18-continued

Antisense inhibition of PCSK9 in human cells (Hep3B) targeting SEQ ID NO: 2

| Isis No. | 5' Target Site to SEQ ID NO: 2 | 3' Target Site to SEQ ID NO: 2 | Sequence 5'-3' | Motif | % inhibition | SEQ ID NO: |
|---|---|---|---|---|---|---|
| 410601 | 20725 | 20744 | GTCCTCAGGGAACCAGGCCT | 3-14-3 | 72.7 | 353 |
| 410678 | 20725 | 20744 | GTCCTCAGGGAACCAGGCCT | 2-13-5 | 75.0 | 353 |
| 395178 | 20726 | 20745 | GGTCCTCAGGGAACCAGGCC | 5-10-5 | 76.7 | 50 |
| 410679 | 20726 | 20745 | GGTCCTCAGGGAACCAGGCC | 2-13-5 | 77.6 | 50 |
| 399900 | 20726 | 20745 | GGTCCTCAGGGAACCAGGCC | 3-14-3 | 92.0 | 50 |
| 408653 | 20727 | 20746 | TGGTCCTCAGGGAACCAGGC | 5-10-5 | 42.5 | 354 |
| 410602 | 20727 | 20746 | TGGTCCTCAGGGAACCAGGC | 3-14-3 | 66.5 | 354 |
| 410680 | 20727 | 20746 | TGGTCCTCAGGGAACCAGGC | 2-13-5 | 71.6 | 354 |
| 410603 | 20728 | 20747 | CTGGTCCTCAGGGAACCAGG | 3-14-3 | 40.8 | 355 |
| 410681 | 20728 | 20747 | CTGGTCCTCAGGGAACCAGG | 2-13-5 | 44.4 | 355 |
| 405971 | 20728 | 20747 | CTGGTCCTCAGGGAACCAGG | 5-10-5 | 65.5 | 355 |
| 410540 | 20729 | 20748 | GCTGGTCCTCAGGGAACCAG | 5-10-5 | 50.9 | 356 |
| 410682 | 20729 | 20748 | GCTGGTCCTCAGGGAACCAG | 2-13-5 | 54.1 | 356 |
| 410604 | 20729 | 20748 | GCTGGTCCTCAGGGAACCAG | 3-14-3 | 62.5 | 356 |
| 405972 | 20730 | 20749 | CGCTGGTCCTCAGGGAACCA | 5-10-5 | 77.6 | 357 |
| 405973 | 20735 | 20754 | GTACCCGCTGGTCCTCAGGG | 5-10-5 | 83.8 | 358 |
| 405974 | 20737 | 20756 | CAGTACCCGCTGGTCCTCAG | 5-10-5 | 89.0 | 359 |
| 399813 | 20740 | 20759 | GGTCAGTACCCGCTGGTCCT | 5-10-5 | 72.4 | 51 |
| 399969 | 20740 | 20759 | GGTCAGTACCCGCTGGTCCT | 3-14-3 | 93.4 | 51 |
| 410771 | 20785 | 20804 | ACCTGCCCCATGGGTGCTGG | 5-10-5 | NA | 360 |
| 405975 | 21088 | 21107 | CAAAACAGCTGCCAACCTGC | 5-10-5 | 77.4 | 361 |
| 405976 | 21093 | 21112 | TCCTGCAAAACAGCTGCCAA | 5-10-5 | 81.2 | 362 |
| 405977 | 21095 | 21114 | AGTCCTGCAAAACAGCTGCC | 5-10-5 | 89.5 | 363 |
| 410772 | 21106 | 21125 | GCTGACCATACAGTCCTGCA | 5-10-5 | 91.2 | 264 |
| 405978 | 21118 | 21137 | GGCCCCGAGTGTGCTGACCA | 5-10-5 | 95.3 | 365 |
| 399904 | 21121 | 21140 | GTAGGCCCCGAGTGTGCTGA | 3-14-3 | 92.6 | 54 |
| 405979 | 21123 | 21142 | GTGTAGGCCCCGAGTGTGCT | 5-10-5 | 85.5 | 366 |
| 405980 | 21125 | 21144 | CCGTGTAGGCCCCGAGTGTG | 5-10-5 | 86.5 | 367 |
| 405981 | 21127 | 21146 | ATCCGTGTAGGCCCCGAGTG | 5-10-5 | 77.8 | 368 |
| 410741 | 21129 | 21148 | CCATCCGTGTAGGCCCCGAG | 5-10-5 | 78.4 | 369 |
| 405982 | 21131 | 21150 | GGCCATCCGTGTAGGCCCCG | 5-10-5 | 86.7 | 370 |
| 405983 | 21133 | 21152 | GTGGCCATCCGTGTAGGCCC | 5-10-5 | 73.1 | 371 |
| 405984 | 21181 | 21200 | CTGGAGCAGCTCAGCAGCTC | 5-10-5 | 83.4 | 372 |
| 405985 | 21183 | 21202 | AACTGGAGCAGCTCAGCAGC | 5-10-5 | 50.7 | 373 |
| 405986 | 21188 | 21207 | GGAGAAACTGGAGCAGCTCA | 5-10-5 | 75.6 | 374 |
| 405987 | 21190 | 21209 | CTGGAGAAACTGGAGCAGCT | 5-10-5 | 88.0 | 375 |

TABLE 18-continued

Antisense inhibition of PCSK9 in human cells (Hep3B) targeting SEQ ID NO: 2

| Isis No. | 5' Target Site to SEQ ID NO: 2 | 3' Target Site to SEQ ID NO: 2 | Sequence 5'-3' | Motif | % inhibition | SEQ ID NO: |
|---|---|---|---|---|---|---|
| 399868 | 21696 | 21715 | GGCACTGCCCTTCCACCAAA | 5-10-5 | 85.8 | 123 |
| 399905 | 22096 | 22115 | CGTTGTGGGCCCGGCAGACC | 3-14-3 | 91.2 | 57 |
| 395183 | 22096 | 22115 | CGTTGTGGGCCCGGCAGACC | 5-10-5 | 93.1 | 57 |
| 410541 | 22133 | 22152 | CACCTGGCAATGGCGTAGAC | 5-10-5 | 46.1 | 376 |
| 410605 | 22133 | 22152 | CACCTGGCAATGGCGTAGAC | 3-14-3 | 67.4 | 376 |
| 410683 | 22133 | 22152 | CACCTGGCAATGGCGTAGAC | 2-13-5 | 71.8 | 376 |
| 410606 | 22134 | 22153 | GCACCTGGCAATGGCGTAGA | 3-14-3 | 74.3 | 377 |
| 410542 | 22134 | 22153 | GCACCTGGCAATGGCGTAGA | 5-10-5 | 75.5 | 377 |
| 410684 | 22134 | 22153 | GCACCTGGCAATGGCGTAGA | 2-13-5 | 78.7 | 377 |
| 410543 | 22135 | 22154 | AGCACCTGGCAATGGCGTAG | 5-10-5 | 76.4 | 378 |
| 410685 | 22135 | 22154 | AGCACCTGGCAATGGCGTAG | 2-13-5 | 76.9 | 378 |
| 410607 | 22135 | 22154 | AGCACCTGGCAATGGCGTAG | 3-14-3 | 77.1 | 378 |
| 410544 | 22136 | 22155 | CAGCACCTGGCAATGGCGTA | 5-10-5 | 62.7 | 379 |
| 410608 | 22136 | 22155 | CAGCACCTGGCAATGGCGTA | 3-14-3 | 69.6 | 379 |
| 410686 | 22136 | 22155 | CAGCACCTGGCAATGGCGTA | 2-13-5 | 81.0 | 379 |
| 410545 | 22137 | 22156 | GCAGCACCTGGCAATGGCGT | 5-10-5 | 75.5 | 380 |
| 410687 | 22137 | 22156 | GCAGCACCTGGCAATGGCGT | 2-13-5 | 79.2 | 380 |
| 410609 | 22137 | 22156 | GCAGCACCTGGCAATGGCGT | 3-14-3 | 83.2 | 380 |
| 410610 | 22138 | 22157 | GGCAGCACCTGGCAATGGCG | 3-14-3 | 67.5 | 381 |
| 410688 | 22138 | 22157 | GGCAGCACCTGGCAATGGCG | 2-13-5 | 89.3 | 381 |
| 405988 | 22138 | 22157 | GGCAGCACCTGGCAATGGCG | 5-10-5 | 95.9 | 381 |
| 410546 | 22139 | 22158 | AGGCAGCACCTGGCAATGGC | 5-10-5 | 74.8 | 382 |
| 410689 | 22139 | 22158 | AGGCAGCACCTGGCAATGGC | 2-13-5 | 83.9 | 382 |
| 410611 | 22139 | 22158 | AGGCAGCACCTGGCAATGGC | 3-14-3 | 88.2 | 382 |
| 410612 | 22140 | 22159 | CAGGCAGCACCTGGCAATGG | 3-14-3 | 72.8 | 383 |
| 410690 | 22140 | 22159 | CAGGCAGCACCTGGCAATGG | 2-13-5 | 74.8 | 383 |
| 405989 | 22140 | 22159 | CAGGCAGCACCTGGCAATGG | 5-10-5 | 88.1 | 383 |
| 410547 | 22141 | 22160 | GCAGGCAGCACCTGGCAATG | 5-10-5 | 63.0 | 384 |
| 410691 | 22141 | 22160 | GCAGGCAGCACCTGGCAATG | 2-13-5 | 70.2 | 384 |
| 410613 | 22141 | 22160 | GCAGGCAGCACCTGGCAATG | 3-14-3 | 76.7 | 384 |
| 395184 | 22142 | 22161 | AGCAGGCAGCACCTGGCAAT | 5-10-5 | 68.5 | 58 |
| 410692 | 22142 | 22161 | AGCAGGCAGCACCTGGCAAT | 2-13-5 | 69.1 | 58 |
| 399906 | 22142 | 22161 | AGCAGGCAGCACCTGGCAAT | 3-14-3 | 94.2 | 58 |
| 410614 | 22143 | 22162 | TAGCAGGCAGCACCTGGCAA | 3-14-3 | 36.6 | 385 |
| 410548 | 22143 | 22162 | TAGCAGGCAGCACCTGGCAA | 5-10-5 | 75.0 | 385 |
| 410693 | 22143 | 22162 | TAGCAGGCAGCACCTGGCAA | 2-13-5 | 82.0 | 385 |

TABLE 18-continued

Antisense inhibition of PCSK9 in human cells (Hep3B) targeting SEQ ID NO: 2

| Isis No. | 5' Target Site to SEQ ID NO: 2 | 3' Target Site to SEQ ID NO: 2 | Sequence 5'-3' | Motif | % inhibition | SEQ ID NO: |
|---|---|---|---|---|---|---|
| 405990 | 22144 | 22163 | GTAGCAGGCAGCACCTGGCA | 5-10-5 | 96.8 | 386 |
| 410773 | 22189 | 22208 | TGGCCTCAGCTGGTGGAGCT | 5-10-5 | 61.3 | 387 |
| 410549 | 22199 | 22218 | GTCCCCATGCTGGCCTCAGC | 5-10-5 | 63.0 | 388 |
| 410615 | 22199 | 22218 | GTCCCCATGCTGGCCTCAGC | 3-14-3 | 72.5 | 388 |
| 410694 | 22199 | 22218 | GTCCCCATGCTGGCCTCAGC | 2-13-5 | 74.8 | 388 |
| 410550 | 22200 | 22219 | GGTCCCCATGCTGGCCTCAG | 5-10-5 | 69.4 | 389 |
| 410616 | 22200 | 22219 | GGTCCCCATGCTGGCCTCAG | 3-14-3 | 80.7 | 389 |
| 410695 | 22200 | 22219 | GGTCCCCATGCTGGCCTCAG | 2-13-5 | 85.5 | 389 |
| 410551 | 22201 | 22220 | GGGTCCCCATGCTGGCCTCA | 5-10-5 | 68.7 | 390 |
| 410696 | 22201 | 22220 | GGGTCCCCATGCTGGCCTCA | 2-13-5 | 86.3 | 390 |
| 410617 | 22201 | 22220 | GGGTCCCCATGCTGGCCTCA | 3-14-3 | 86.5 | 390 |
| 410552 | 22202 | 22221 | CGGGTCCCCATGCTGGCCTC | 5-10-5 | 77.9 | 391 |
| 410618 | 22202 | 22221 | CGGGTCCCCATGCTGGCCTC | 3-14-3 | 86.7 | 391 |
| 410697 | 22202 | 22221 | CGGGTCCCCATGCTGGCCTC | 2-13-5 | 87.0 | 391 |
| 410553 | 22203 | 22222 | ACGGGTCCCCATGCTGGCCT | 5-10-5 | 72.8 | 392 |
| 410619 | 22203 | 22222 | ACGGGTCCCCATGCTGGCCT | 3-14-3 | 84.1 | 392 |
| 410698 | 22203 | 22222 | ACGGGTCCCCATGCTGGCCT | 2-13-5 | 87.0 | 392 |
| 410699 | 22204 | 22223 | CACGGGTCCCCATGCTGGCC | 2-13-5 | 79.5 | 59 |
| 395185 | 22204 | 22223 | CACGGGTCCCCATGCTGGCC | 5-10-5 | 92.7 | 59 |
| 399907 | 22204 | 22223 | CACGGGTCCCCATGCTGGCC | 3-14-3 | 93.7 | 59 |
| 410620 | 22205 | 22224 | ACACGGGTCCCCATGCTGGC | 3-14-3 | 74.4 | 393 |
| 410554 | 22205 | 22224 | ACACGGGTCCCCATGCTGGC | 5-10-5 | 79.7 | 393 |
| 410700 | 22205 | 22224 | ACACGGGTCCCCATGCTGGC | 2-13-5 | 84.4 | 393 |
| 410621 | 22206 | 22225 | GACACGGGTCCCCATGCTGG | 3-14-3 | 76.0 | 394 |
| 410701 | 22206 | 22225 | GACACGGGTCCCCATGCTGG | 2-13-5 | 83.4 | 394 |
| 405991 | 22206 | 22225 | GACACGGGTCCCCATGCTGG | 5-10-5 | 91.9 | 394 |
| 410555 | 22207 | 22226 | GGACACGGGTCCCCATGCTG | 5-10-5 | 77.0 | 395 |
| 410622 | 22207 | 22226 | GGACACGGGTCCCCATGCTG | 3-14-3 | 79.8 | 395 |
| 410702 | 22207 | 22226 | GGACACGGGTCCCCATGCTG | 2-13-5 | 85.0 | 395 |
| 410703 | 22208 | 22227 | TGGACACGGGTCCCCATGCT | 2-13-5 | 70.4 | 396 |
| 410623 | 22208 | 22227 | TGGACACGGGTCCCCATGCT | 3-14-3 | 78.9 | 396 |
| 405992 | 22208 | 22227 | TGGACACGGGTCCCCATGCT | 5-10-5 | 89.3 | 396 |
| 410704 | 22209 | 22228 | GTGGACACGGGTCCCCATGC | 2-13-5 | 78.6 | 397 |
| 410556 | 22209 | 22228 | GTGGACACGGGTCCCCATGC | 5-10-5 | 81.4 | 397 |
| 410624 | 22209 | 22228 | GTGGACACGGGTCCCCATGC | 3-14-3 | 82.8 | 397 |
| 410625 | 22210 | 22229 | AGTGGACACGGGTCCCCATG | 3-14-3 | 64.4 | 398 |

TABLE 18-continued

Antisense inhibition of PCSK9 in human cells (Hep3B) targeting SEQ ID NO: 2

| Isis No. | 5' Target Site to SEQ ID NO: 2 | 3' Target Site to SEQ ID NO: 2 | Sequence 5'-3' | Motif | % inhibition | SEQ ID NO: |
|---|---|---|---|---|---|---|
| 410705 | 22210 | 22229 | AGTGGACACGGGTCCCCATG | 2-13-5 | 74.7 | 398 |
| 405993 | 22210 | 22229 | AGTGGACACGGGTCCCCATG | 5-10-5 | 85.5 | 398 |
| 410706 | 22211 | 22230 | CAGTGGACACGGGTCCCCAT | 2-13-5 | 70.8 | 399 |
| 410557 | 22211 | 22230 | CAGTGGACACGGGTCCCCAT | 5-10-5 | 74.2 | 399 |
| 410626 | 22211 | 22230 | CAGTGGACACGGGTCCCCAT | 3-14-3 | 76.8 | 399 |
| 410627 | 22212 | 22231 | GCAGTGGACACGGGTCCCCA | 3-14-3 | 71.4 | 400 |
| 410707 | 22212 | 22231 | GCAGTGGACACGGGTCCCCA | 2-13-5 | 72.8 | 400 |
| 405994 | 22212 | 22231 | GCAGTGGACACGGGTCCCCA | 5-10-5 | 95.2 | 400 |
| 410708 | 22213 | 22232 | GGCAGTGGACACGGGTCCCC | 2-13-5 | 79.0 | 401 |
| 410628 | 22213 | 22232 | GGCAGTGGACACGGGTCCCC | 3-14-3 | 88.1 | 401 |
| 410558 | 22213 | 22232 | GGCAGTGGACACGGGTCCCC | 5-10-5 | 88.9 | 401 |
| 410629 | 22214 | 22233 | TGGCAGTGGACACGGGTCCC | 3-14-3 | 66.5 | 402 |
| 410709 | 22214 | 22233 | TGGCAGTGGACACGGGTCCC | 2-13-5 | 66.9 | 402 |
| 405995 | 22214 | 22233 | TGGCAGTGGACACGGGTCCC | 5-10-5 | 92.4 | 402 |
| 410630 | 22215 | 22234 | GTGGCAGTGGACACGGGTCC | 3-14-3 | 54.1 | 403 |
| 410710 | 22215 | 22234 | GTGGCAGTGGACACGGGTCC | 2-13-5 | 61.4 | 403 |
| 410559 | 22215 | 22234 | GTGGCAGTGGACACGGGTCC | 5-10-5 | 77.5 | 403 |
| 410711 | 22216 | 22235 | GGTGGCAGTGGACACGGGTC | 2-13-5 | NA | 404 |
| 410631 | 22216 | 22235 | GGTGGCAGTGGACACGGGTC | 3-14-3 | NA | 404 |
| 410560 | 22216 | 22235 | GGTGGCAGTGGACACGGGTC | 5-10-5 | 42.5 | 404 |
| 410712 | 22217 | 22236 | TGGTGGCAGTGGACACGGGT | 2-13-5 | NA | 405 |
| 410632 | 22217 | 22236 | TGGTGGCAGTGGACACGGGT | 3-14-3 | NA | 405 |
| 410561 | 22217 | 22236 | TGGTGGCAGTGGACACGGGT | 5-10-5 | NA | 405 |
| 410774 | 22220 | 22239 | TGTTGGTGGCAGTGGACACG | 5-10-5 | 47.8 | 406 |
| 410776 | 23985 | 24004 | GTGCCAAGGTCCTCCACCTC | 5-10-5 | 77.3 | 408 |
| 410777 | 24005 | 24024 | TCAGCACAGGCGGCTTGTGG | 5-10-5 | 40.0 | 409 |
| 410778 | 24035 | 24054 | CCACGCACTGGTTGGGCTGA | 5-10-5 | 52.7 | 410 |
| 399908 | 24095 | 24114 | CTTTGCATTCCAGACCTGGG | 3-14-3 | 74.9 | 60 |
| 410713 | 24095 | 24114 | CTTTGCATTCCAGACCTGGG | 2-13-5 | 84.9 | 60 |
| 395186 | 24095 | 24114 | CTTTGCATTCCAGACCTGGG | 5-10-5 | 93.7 | 60 |
| 410714 | 24096 | 24115 | ACTTTGCATTCCAGACCTGG | 2-13-5 | 82.4 | 411 |
| 410633 | 24096 | 24115 | ACTTTGCATTCCAGACCTGG | 3-14-3 | 83.8 | 411 |
| 410562 | 24096 | 24115 | ACTTTGCATTCCAGACCTGG | 5-10-5 | 87.3 | 411 |
| 410715 | 24097 | 24116 | GACTTTGCATTCCAGACCTG | 2-13-5 | 80.5 | 412 |
| 410634 | 24097 | 24116 | GACTTTGCATTCCAGACCTG | 3-14-3 | 81.8 | 412 |
| 405996 | 24097 | 24116 | GACTTTGCATTCCAGACCTG | 5-10-5 | 91.0 | 412 |

TABLE 18-continued

Antisense inhibition of PCSK9 in human cells (Hep3B) targeting SEQ ID NO: 2

| Isis No. | 5' Target Site to SEQ ID NO: 2 | 3' Target Site to SEQ ID NO: 2 | Sequence 5'-3' | Motif | % inhibition | SEQ ID NO: |
|---|---|---|---|---|---|---|
| 410563 | 24098 | 24117 | TGACTTTGCATTCCAGACCT | 5-10-5 | 75.4 | 413 |
| 410635 | 24098 | 24117 | TGACTTTGCATTCCAGACCT | 3-14-3 | 75.9 | 413 |
| 410716 | 24098 | 24117 | TGACTTTGCATTCCAGACCT | 2-13-5 | 88.3 | 413 |
| 410636 | 24099 | 24118 | TTGACTTTGCATTCCAGACC | 3-14-3 | 61.3 | 414 |
| 410564 | 24099 | 24118 | TTGACTTTGCATTCCAGACC | 5-10-5 | 71.3 | 414 |
| 410717 | 24099 | 24118 | TTGACTTTGCATTCCAGACC | 2-13-5 | 76.7 | 414 |
| 410718 | 24100 | 24119 | CTTGACTTTGCATTCCAGAC | 2-13-5 | 55.8 | 61 |
| 399973 | 24100 | 24119 | CTTGACTTTGCATTCCAGAC | 3-14-3 | 82.1 | 61 |
| 399817 | 24100 | 24119 | CTTGACTTTGCATTCCAGAC | 5-10-5 | 93.6 | 61 |
| 405997 | 24102 | 24121 | TCCTTGACTTTGCATTCCAG | 5-10-5 | 95.6 | 415 |
| 410779 | 24115 | 24134 | CGGGATTCCATGCTCCTTGA | 5-10-5 | 79.7 | 416 |
| 410781 | 25994 | 26013 | GGAGGGCACTGCAGCCAGTC | 5-10-5 | 66.0 | 418 |
| 410719 | 26112 | 26131 | CAGATGGCAACGGCTGTCAC | 2-13-5 | 61.0 | 419 |
| 410637 | 26112 | 26131 | CAGATGGCAACGGCTGTCAC | 3-14-3 | 66.0 | 419 |
| 410565 | 26112 | 26131 | CAGATGGCAACGGCTGTCAC | 5-10-5 | 71.6 | 419 |
| 410638 | 26113 | 26132 | GCAGATGGCAACGGCTGTCA | 3-14-3 | 71.9 | 420 |
| 410720 | 26113 | 26132 | GCAGATGGCAACGGCTGTCA | 2-13-5 | 75.1 | 420 |
| 410566 | 26113 | 26132 | GCAGATGGCAACGGCTGTCA | 5-10-5 | 77.7 | 420 |
| 410639 | 26114 | 26133 | AGCAGATGGCAACGGCTGTC | 3-14-3 | 67.7 | 421 |
| 410721 | 26114 | 26133 | AGCAGATGGCAACGGCTGTC | 2-13-5 | 68.8 | 421 |
| 410567 | 26114 | 26133 | AGCAGATGGCAACGGCTGTC | 5-10-5 | 72.1 | 421 |
| 410568 | 26115 | 26134 | CAGCAGATGGCAACGGCTGT | 5-10-5 | 54.2 | 422 |
| 410640 | 26115 | 26134 | CAGCAGATGGCAACGGCTGT | 3-14-3 | 57.7 | 422 |
| 410722 | 26115 | 26134 | CAGCAGATGGCAACGGCTGT | 2-13-5 | 59.2 | 422 |
| 410569 | 26116 | 26135 | GCAGCAGATGGCAACGGCTG | 5-10-5 | 57.7 | 423 |
| 410641 | 26116 | 26135 | GCAGCAGATGGCAACGGCTG | 3-14-3 | 66.1 | 423 |
| 410723 | 26116 | 26135 | GCAGCAGATGGCAACGGCTG | 2-13-5 | 81.1 | 423 |
| 399909 | 26117 | 26136 | GGCAGCAGATGGCAACGGCT | 3-14-3 | 69.9 | 62 |
| 410724 | 26117 | 26136 | GGCAGCAGATGGCAACGGCT | 2-13-5 | 87.4 | 62 |
| 395187 | 26117 | 26136 | GGCAGCAGATGGCAACGGCT | 5-10-5 | 92.7 | 62 |
| 410642 | 26118 | 26137 | CGGCAGCAGATGGCAACGGC | 3-14-3 | 70.4 | 424 |
| 410725 | 26118 | 26137 | CGGCAGCAGATGGCAACGGC | 2-13-5 | 75.6 | 424 |
| 410570 | 26118 | 26137 | CGGCAGCAGATGGCAACGGC | 5-10-5 | 78.3 | 424 |
| 410571 | 26119 | 26138 | CCGGCAGCAGATGGCAACGG | 5-10-5 | 52.8 | 425 |
| 410643 | 26119 | 26138 | CCGGCAGCAGATGGCAACGG | 3-14-3 | 59.8 | 425 |
| 410726 | 26119 | 26138 | CCGGCAGCAGATGGCAACGG | 2-13-5 | 69.8 | 425 |

TABLE 18-continued

Antisense inhibition of PCSK9 in human cells (Hep3B) targeting SEQ ID NO: 2

| Isis No. | 5' Target Site to SEQ ID NO: 2 | 3' Target Site to SEQ ID NO: 2 | Sequence 5'-3' | Motif | % inhibition | SEQ ID NO: |
|---|---|---|---|---|---|---|
| 410644 | 26120 | 26139 | TCCGGCAGCAGATGGCAACG | 3-14-3 | 59.0 | 426 |
| 410727 | 26120 | 26139 | TCCGGCAGCAGATGGCAACG | 2-13-5 | 68.3 | 426 |
| 405998 | 26120 | 26139 | TCCGGCAGCAGATGGCAACG | 5-10-5 | 75.6 | 426 |
| 410572 | 26121 | 26140 | CTCCGGCAGCAGATGGCAAC | 5-10-5 | 40.9 | 427 |
| 410728 | 26121 | 26140 | CTCCGGCAGCAGATGGCAAC | 2-13-5 | 56.4 | 427 |
| 410645 | 26121 | 26140 | CTCCGGCAGCAGATGGCAAC | 3-14-3 | 70.2 | 427 |
| 410729 | 26122 | 26141 | GCTCCGGCAGCAGATGGCAA | 2-13-5 | 67.7 | 428 |
| 410573 | 26122 | 26141 | GCTCCGGCAGCAGATGGCAA | 5-10-5 | 71.8 | 428 |
| 410646 | 26122 | 26141 | GCTCCGGCAGCAGATGGCAA | 3-14-3 | 72.8 | 428 |
| 410782 | 26132 | 26151 | CCAGGTGCCGGCTCCGGCAG | 5-10-5 | 43.2 | 429 |
| 410783 | 26142 | 26161 | GAGGCCTGCGCCAGGTGCCG | 5-10-5 | 63.7 | 430 |
| 399819 | 26316 | 26335 | CCCACTCAAGGGCCAGGCCA | 5-10-5 | 93.4 | 65 |
| 399912 | 26404 | 26423 | ATGCCCCACAGTGAGGGAGG | 3-14-3 | 84.3 | 66 |
| 405893 | 26635 | 26654 | ATGAGGGCCATCAGCACCTT | 5-10-5 | 93.9 | 431 |
| 405894 | 26636 | 26655 | GATGAGGGCCATCAGCACCT | 5-10-5 | 93.9 | 432 |
| 405895 | 26637 | 26656 | AGATGAGGGCCATCAGCACC | 5-10-5 | 91.8 | 433 |
| 405896 | 26638 | 26657 | GAGATGAGGGCCATCAGCAC | 5-10-5 | 88.5 | 434 |
| 395194 | 26639 | 26658 | GGAGATGAGGGCCATCAGCA | 5-10-5 | 90.0 | 69 |
| 399916 | 26639 | 26658 | GGAGATGAGGGCCATCAGCA | 3-14-3 | 94.5 | 69 |
| 405897 | 26640 | 26659 | TGGAGATGAGGGCCATCAGC | 5-10-5 | 85.1 | 435 |
| 405898 | 26641 | 26660 | CTGGAGATGAGGGCCATCAG | 5-10-5 | 86.9 | 436 |
| 405899 | 26642 | 26661 | GCTGGAGATGAGGGCCATCA | 5-10-5 | 91.5 | 437 |
| 405900 | 26643 | 26662 | AGCTGGAGATGAGGGCCATC | 5-10-5 | 83.7 | 438 |
| 405901 | 26709 | 26728 | GCTAGATGCCATCCAGAAAG | 5-10-5 | 88.4 | 439 |
| 405902 | 26710 | 26729 | GGCTAGATGCCATCCAGAAA | 5-10-5 | 89.3 | 440 |
| 405903 | 26711 | 26730 | TGGCTAGATGCCATCCAGAA | 5-10-5 | 92.6 | 441 |
| 405904 | 26712 | 26731 | CTGGCTAGATGCCATCCAGA | 5-10-5 | 90.4 | 442 |
| 399821 | 26713 | 26732 | TCTGGCTAGATGCCATCCAG | 5-10-5 | 91.7 | 71 |
| 405905 | 26714 | 26733 | CTCTGGCTAGATGCCATCCA | 5-10-5 | 90.7 | 443 |
| 405906 | 26715 | 26734 | CCTCTGGCTAGATGCCATCC | 5-10-5 | 93.3 | 444 |
| 405907 | 26716 | 26735 | GCCTCTGGCTAGATGCCATC | 5-10-5 | 90.2 | 445 |
| 405908 | 26717 | 26736 | AGCCTCTGGCTAGATGCCAT | 5-10-5 | 83.3 | 446 |
| 399978 | 26795 | 26814 | AGCCTGGCATAGAGCAGAGT | 3-14-3 | 96.4 | 73 |

Antisense oligonucleotides that exhibited less than 30% inhibition of PCSK9 mRNA levels were marked with "NA".

Antisense oligonucleotides with the following ISIS Nos exhibited at least 80% inhibition of PCSK9 mRNA levels: 395152, 395153, 395155, 395158, 395163, 395165, 395166, 395168, 395173, 395183, 395185, 395186, 395187, 395194, 399798, 399801, 399804, 399817, 399819, 399821, 399868, 399877, 399879, 399887, 399888, 399891, 399895, 399900, 399904, 399905, 399906, 399907, 399912, 399916, 399935, 399936, 399954, 399960, 399967, 399968, 399969, 399973, 399978, 405861, 405862, 405863, 405864, 405865, 405866, 405869, 405870, 405871, 405872, 405873, 405874, 405875, 405876, 405877, 405878, 405879, 405880, 405881, 405882, 405883, 405884, 405889, 405890, 405891, 405893, 405894, 405895, 405896, 405897, 405898, 405899, 405900, 405901, 405902, 405903, 405904, 405905, 405906, 405907, 405908, 405909, 405910, 405911, 405913, 405914, 405915, 405916, 405920, 405921, 405922, 405923, 405924, 405925, 405926, 405927, 405928, 405929, 405930, 405931, 405932, 405934, 405935, 405936, 405940, 405941, 405943, 405944, 405949, 405952, 405953, 405954, 405955, 405956, 405958, 405959, 405960, 405961, 405973, 405974, 405976, 405977, 405978, 405979, 405980, 405982, 405984, 405987, 405988, 405989, 405990, 405991, 405992, 405993, 405994, 405995, 405996, 405997, 406003, 406005, 406008, 406009, 406014, 406016, 406020, 406023, 406026, 406028, 406029, 406030, 406031, 406032, 406033, 406035, 406036, 406038, 406039, 406040, 406041, 406042, 406043, 406044, 406045, 410530, 410556, 410558, 410562, 410578, 410583, 410589, 410590, 410591, 410592, 410593, 410595, 410609, 410611, 410616, 410617, 410618, 410619, 410624, 410628, 410633, 410634, 410647, 410648, 410650, 410652, 410658, 410664, 410666, 410667, 410668, 410671, 410677, 410686, 410688, 410689, 410693, 410695, 410696, 410697, 410698, 410700, 410701, 410702, 410713, 410714, 410715, 410716, 410723, 410724, 410730, 410754, 410757, 410759, 410769, and 410772. The target segments to which these antisense oligonucleotides are targeted are active target segments. The target regions to which these antisense oligonucleotides are targeted are active target regions.

ISIS Nos 395152, 395155, 395158, 395165, 395166, 395168, 395173, 395183, 395185, 395186, 395187, 395194, 399801, 399817, 399819, 399821, 399868, 399877, 399879, 399887, 399888, 399891, 399900, 399904, 399905, 399906, 399907, 399916, 399936, 399954, 399969, 399978, 405861, 405862, 405864, 405869, 405871, 405872, 405873, 405874, 405875, 405876, 405878, 405879, 405880, 405881, 405882, 405883, 405884, 405890, 405891, 405893, 405894, 405895, 405896, 405897, 405898, 405899, 405901, 405902, 405903, 405904, 405905, 405906, 405907, 405910, 405911, 405913, 405914, 405915, 405916, 405920, 405921, 405922, 405923, 405924, 405925, 405926, 405927, 405928, 405929, 405930, 405931, 405932, 405934, 405935, 405936, 405941, 405952, 405953, 405954, 405955, 405956, 405959, 405960, 405961, 405974, 405977, 405978, 405979, 405980, 405982, 405987, 405988, 405989, 405990, 405991, 405992, 405993, 405994, 405995, 405996, 405997, 406008, 406009, 406014, 406016, 406023, 406028, 406029, 406030, 406031, 406032, 406033, 406035, 406038, 406039, 406040, 406041, 406042, 406043, 406044, 406045, 410558, 410562, 410583, 410591, 410592, 410593, 410611, 410617, 410618, 410628, 410647, 410650, 410668, 410677, 410688, 410695, 410696, 410697, 410698, 410702, 410716, 410724, 410730, 410757, and 410772 each exhibited at least 85% inhibition of PCSK9 mRNA levels.

ISIS Nos 395152, 395155, 395158, 395165, 395166, 395168, 395173, 395183, 395185, 395186, 395187, 399801, 399817, 399819, 399821, 399877, 399879, 399887, 399888, 399891, 399900, 399904, 399905, 399906, 399907, 399916, 399969, 399978, 405862, 405864, 405874, 405875, 405878, 405879, 405880, 405881, 405882, 405883, 405884, 405891, 405893, 405894, 405895, 405899, 405903, 405906, 405910, 405913, 405916, 405923, 405924, 405925, 405926, 405927, 405930, 405934, 405936, 405953, 405955, 405956, 405959, 405978, 405988, 405990, 405991, 405994, 405995, 405996, 405997, 406008, 406014, 406023, 406028, 406029, 406030, 406033, 406035, 406039, 406040, 406041, 406042, 406043, 406044, 410592, 410647, 410668, and 410772 each exhibited at least 90% inhibition of PCSK9 mRNA levels.

ISIS Nos 395165, 395166, 399801, 399978, 405881, 405891, 405959, 405978, 405988, 405990, 405994, 405997, 406008, 406030, 406040, 406041, and 406044 each exhibited at least 95% inhibition of PCSK9 mRNA levels.

TABLE 19

Antisense inhibition of PCSK9 in human cells (Hep3B) targeting SEQ ID NO: 3

| Isis No. | 5' Target Site to SEQ ID NO: 3 | 3' Target Site to SEQ ID NO: 3 | Sequence 5'-3' | Motif | % inhibition | SEQ ID NO: |
|---|---|---|---|---|---|---|
| 399935 | 1075 | 1094 | AGGACCCAAGTCATCCTGCT | 3-14-3 | 81.1 | 96 |
| 399936 | 1105 | 1124 | GGCCATCAGCTGGCAATGCT | 3-14-3 | 89.0 | 124 |
| 410753 | 1351 | 1370 | ATACACCTCCACCAGGCTGC | 5-10-5 | 72.8 | 215 |
| 406025 | 1362 | 1381 | GTGTCTAGGAGATACACCTC | 5-10-5 | 74.2 | 216 |
| 406026 | 1367 | 1386 | TGCTGGTGTCTAGGAGATAC | 5-10-5 | 80.5 | 217 |
| 405869 | 1392 | 1411 | TCGATTTCCCGGTGGTCACT | 5-10-5 | 87.6 | 218 |
| 405870 | 1393 | 1412 | CTCGATTTCCCGGTGGTCAC | 5-10-5 | 83.3 | 219 |
| 405871 | 1394 | 1413 | CCTCGATTTCCCGGTGGTCA | 5-10-5 | 87.0 | 220 |
| 405872 | 1395 | 1414 | CCCTCGATTTCCCGGTGGTC | 5-10-5 | 88.2 | 221 |
| 399798 | 1396 | 1415 | GCCCTCGATTTCCCGGTGGT | 5-10-5 | 84.3 | 22 |

TABLE 19-continued

Antisense inhibition of PCSK9 in human cells (Hep3B) targeting SEQ ID NO: 3

| Isis No. | 5' Target Site to SEQ ID NO: 3 | 3' Target Site to SEQ ID NO: 3 | Sequence 5'-3' | Motif | % inhibition | SEQ ID NO: |
|---|---|---|---|---|---|---|
| 399954 | 1396 | 1415 | GCCCTCGATTTCCCGGTGGT | 3-14-3 | 90.3 | 22 |
| 405873 | 1397 | 1416 | TGCCCTCGATTTCCCGGTGG | 5-10-5 | 90.0 | 222 |
| 405874 | 1398 | 1417 | CTGCCCTCGATTTCCCGGTG | 5-10-5 | 91.4 | 223 |
| 405875 | 1399 | 1418 | CCTGCCCTCGATTTCCCGGT | 5-10-5 | 93.5 | 224 |
| 405876 | 1400 | 1419 | CCCTGCCCTCGATTTCCCGG | 5-10-5 | 90.1 | 225 |
| 406027 | 1404 | 1423 | ATGACCCTGCCCTCGATTTC | 5-10-5 | 73.9 | 226 |
| 406028 | 1406 | 1425 | CCATGACCCTGCCCTCGATT | 5-10-5 | 92.3 | 227 |
| 406029 | 1408 | 1427 | GACCATGACCCTGCCCTCGA | 5-10-5 | 91.4 | 228 |
| 406030 | 1412 | 1431 | CGGTGACCATGACCCTGCCC | 5-10-5 | 95.6 | 229 |
| 406031 | 1414 | 1433 | GTCGGTGACCATGACCCTGC | 5-10-5 | 89.6 | 230 |
| 410733 | 1416 | 1435 | AAGTCGGTGACCATGACCCT | 5-10-5 | 65.7 | 231 |
| 406032 | 1418 | 1437 | CGAAGTCGGTGACCATGACC | 5-10-5 | 88.5 | 232 |
| 410754 | 1428 | 1447 | GGCACATTCTCGAAGTCGGT | 5-10-5 | 80.1 | 233 |
| 395163 | 1453 | 1472 | GTGGAAGCGGGTCCCGTCCT | 5-10-5 | 83.9 | 25 |
| 410755 | 1463 | 1482 | TGGCCTGTCTGTGGAAGCGG | 5-10-5 | NA | 234 |
| 410756 | 1490 | 1509 | GGTGGGTGCCATGACTGTCA | 5-10-5 | 67.1 | 235 |
| 406033 | 1497 | 1516 | CCTGCCAGGTGGGTGCCATG | 5-10-5 | 91.2 | 237 |
| 406034 | 1502 | 1521 | CCACCCCTGCCAGGTGGGTG | 5-10-5 | 59.3 | 238 |
| 406035 | 1507 | 1526 | GCTGACCACCCCTGCCAGGT | 5-10-5 | 91.7 | 239 |
| 410757 | 1515 | 1534 | TCCCGGCCGCTGACCACCCC | 5-10-5 | 88.9 | 240 |
| 406036 | 1519 | 1538 | GGCATCCCGGCCGCTGACCA | 5-10-5 | 84.0 | 241 |
| 406037 | 1522 | 1541 | GCCGGCATCCCGGCCGCTGA | 5-10-5 | 55.9 | 242 |
| 410536 | 1527 | 1546 | GCCACGCCGGCATCCCGGCC | 5-10-5 | 63.7 | 243 |
| 410658 | 1527 | 1546 | GCCACGCCGGCATCCCGGCC | 2-13-5 | 82.0 | 243 |
| 410583 | 1527 | 1546 | GCCACGCCGGCATCCCGGCC | 3-14-3 | 87.3 | 243 |
| 410537 | 1528 | 1547 | GGCCACGCCGGCATCCCGGC | 5-10-5 | 58.5 | 244 |
| 410659 | 1528 | 1547 | GGCCACGCCGGCATCCCGGC | 2-13-5 | 73.7 | 244 |
| 410584 | 1528 | 1547 | GGCCACGCCGGCATCCCGGC | 3-14-3 | 79.5 | 244 |
| 410660 | 1529 | 1548 | TGGCCACGCCGGCATCCCGG | 2-13-5 | 63.0 | 245 |
| 410585 | 1529 | 1548 | TGGCCACGCCGGCATCCCGG | 3-14-3 | 73.2 | 245 |
| 406038 | 1529 | 1548 | TGGCCACGCCGGCATCCCGG | 5-10-5 | 86.3 | 245 |
| 410661 | 1530 | 1549 | TTGGCCACGCCGGCATCCCG | 2-13-5 | 53.3 | 246 |
| 410586 | 1530 | 1549 | TTGGCCACGCCGGCATCCCG | 3-14-3 | 60.3 | 246 |
| 405877 | 1530 | 1549 | TTGGCCACGCCGGCATCCCG | 5-10-5 | 83.2 | 246 |
| 410587 | 1531 | 1550 | CTTGGCCACGCCGGCATCCC | 3-14-3 | 63.2 | 247 |
| 410662 | 1531 | 1550 | CTTGGCCACGCCGGCATCCC | 2-13-5 | 67.3 | 247 |

TABLE 19-continued

Antisense inhibition of PCSK9 in human cells (Hep3B) targeting SEQ ID NO: 3

| Isis No. | 5' Target Site to SEQ ID NO: 3 | 3' Target Site to SEQ ID NO: 3 | Sequence 5'-3' | Motif | % inhibition | SEQ ID NO: |
|---|---|---|---|---|---|---|
| 405878 | 1531 | 1550 | CTTGGCCACGCCGGCATCCC | 5-10-5 | 91.4 | 247 |
| 410588 | 1532 | 1551 | CCTTGGCCACGCCGGCATCC | 3-14-3 | 65.3 | 248 |
| 410663 | 1532 | 1551 | CCTTGGCCACGCCGGCATCC | 2-13-5 | 67.9 | 248 |
| 405879 | 1532 | 1551 | CCTTGGCCACGCCGGCATCC | 5-10-5 | 94.1 | 248 |
| 410589 | 1533 | 1552 | CCCTTGGCCACGCCGGCATC | 3-14-3 | 80.1 | 249 |
| 410664 | 1533 | 1552 | CCCTTGGCCACGCCGGCATC | 2-13-5 | 81.9 | 249 |
| 405880 | 1533 | 1552 | CCCTTGGCCACGCCGGCATC | 5-10-5 | 93.5 | 249 |
| 410665 | 1534 | 1553 | ACCCTTGGCCACGCCGGCAT | 2-13-5 | 78.7 | 28 |
| 399887 | 1534 | 1553 | ACCCTTGGCCACGCCGGCAT | 3-14-3 | 91.9 | 28 |
| 395165 | 1534 | 1553 | ACCCTTGGCCACGCCGGCAT | 5-10-5 | 96.7 | 28 |
| 410590 | 1535 | 1554 | CACCCTTGGCCACGCCGGCA | 3-14-3 | 82.2 | 250 |
| 410666 | 1535 | 1554 | CACCCTTGGCCACGCCGGCA | 2-13-5 | 82.7 | 250 |
| 405881 | 1535 | 1554 | CACCCTTGGCCACGCCGGCA | 5-10-5 | 98.3 | 250 |
| 410667 | 1536 | 1555 | GCACCCTTGGCCACGCCGGC | 2-13-5 | 84.7 | 251 |
| 410591 | 1536 | 1555 | GCACCCTTGGCCACGCCGGC | 3-14-3 | 86.3 | 251 |
| 405882 | 1536 | 1555 | GCACCCTTGGCCACGCCGGC | 5-10-5 | 91.6 | 251 |
| 410668 | 1537 | 1556 | GGCACCCTTGGCCACGCCGG | 2-13-5 | 91.4 | 252 |
| 405883 | 1537 | 1556 | GGCACCCTTGGCCACGCCGG | 5-10-5 | 92.5 | 252 |
| 410592 | 1537 | 1556 | GGCACCCTTGGCCACGCCGG | 3-14-3 | 93.4 | 252 |
| 410669 | 1538 | 1557 | TGGCACCCTTGGCCACGCCG | 2-13-5 | 69.0 | 253 |
| 410593 | 1538 | 1557 | TGGCACCCTTGGCCACGCCG | 3-14-3 | 88.8 | 253 |
| 405884 | 1538 | 1557 | TGGCACCCTTGGCCACGCCG | 5-10-5 | 90.8 | 253 |
| 410670 | 1539 | 1558 | CTGGCACCCTTGGCCACGCC | 2-13-5 | 74.9 | 254 |
| 410594 | 1539 | 1558 | CTGGCACCCTTGGCCACGCC | 3-14-3 | 75.2 | 254 |
| 410538 | 1539 | 1558 | CTGGCACCCTTGGCCACGCC | 5-10-5 | 78.2 | 254 |
| 410539 | 1540 | 1559 | GCTGGCACCCTTGGCCACGC | 5-10-5 | 61.9 | 255 |
| 410595 | 1540 | 1559 | GCTGGCACCCTTGGCCACGC | 3-14-3 | 83.1 | 255 |
| 410671 | 1540 | 1559 | GCTGGCACCCTTGGCCACGC | 2-13-5 | 83.3 | 255 |
| 410758 | 1545 | 1564 | CGCATGCTGGCACCCTTGGC | 5-10-5 | 73.6 | 256 |
| 406039 | 1566 | 1585 | CAGTTGAGCACGCGCAGGCT | 5-10-5 | 91.2 | 257 |
| 406040 | 1568 | 1587 | GGCAGTTGAGCACGCGCAGG | 5-10-5 | 96.5 | 258 |
| 399888 | 1570 | 1589 | TTGGCAGTTGAGCACGCGCA | 3-14-3 | 90.9 | 29 |
| 395166 | 1570 | 1589 | TTGGCAGTTGAGCACGCGCA | 5-10-5 | 96.2 | 29 |
| 406041 | 1572 | 1591 | CCTTGGCAGTTGAGCACGCG | 5-10-5 | 96.6 | 259 |
| 399801 | 1575 | 1594 | TTCCCTTGGCAGTTGAGCAC | 5-10-5 | 95.6 | 30 |
| 406042 | 1577 | 1596 | CCTTCCCTTGGCAGTTGAGC | 5-10-5 | 92.0 | 260 |

TABLE 19-continued

Antisense inhibition of PCSK9 in human cells (Hep3B) targeting SEQ ID NO: 3

| Isis No. | 5' Target Site to SEQ ID NO: 3 | 3' Target Site to SEQ ID NO: 3 | Sequence 5'-3' | Motif | % inhibition | SEQ ID NO: |
|---|---|---|---|---|---|---|
| 406043 | 1581 | 1600 | GTGCCCTTCCCTTGGCAGTT | 5-10-5 | 91.9 | 261 |
| 406044 | 1583 | 1602 | CCGTGCCCTTCCCTTGGCAG | 5-10-5 | 95.4 | 262 |
| 410759 | 1594 | 1613 | GGTGCCGCTAACCGTGCCCT | 5-10-5 | 83.7 | 263 |
| 410760 | 1618 | 1637 | CCGAATAAACTCCAGGCCTA | 5-10-5 | 96.7 | 265 |
| 406045 | 1626 | 1645 | TGGCTTTTCCGAATAAACTC | 5-10-5 | 88.4 | 266 |
| 395168 | 1628 | 1647 | GCTGGCTTTTCCGAATAAAC | 5-10-5 | 91.9 | 32 |
| 405909 | 1630 | 1649 | CAGCTGGCTTTTCCGAATAA | 5-10-5 | 80.3 | 267 |
| 405910 | 1632 | 1651 | ACCAGCTGGCTTTTCCGAAT | 5-10-5 | 90.9 | 268 |
| 405911 | 1634 | 1653 | GGACCAGCTGGCTTTTCCGA | 5-10-5 | 88.0 | 269 |
| 405912 | 1638 | 1657 | GGCTGGACCAGCTGGCTTTT | 5-10-5 | 78.2 | 270 |
| 410761 | 1649 | 1668 | GTGGCCCCACAGGCTGGACC | 5-10-5 | 53.7 | 271 |
| 410762 | 1662 | 1681 | AGCAGCACCACCAGTGGCCC | 5-10-5 | 57.6 | 272 |
| 410763 | 1684 | 1703 | GCTGTACCCACCCGCCAGGG | 5-10-5 | 68.8 | 273 |
| 410764 | 1730 | 1749 | CGACCCCAGCCCTCGCCAGG | 5-10-5 | 66.3 | 274 |
| 399891 | 1740 | 1759 | GTGACCAGCACGACCCCAGC | 3-14-3 | 91.1 | 33 |
| 405913 | 1742 | 1761 | CGGTGACCAGCACGACCCCA | 5-10-5 | 93.8 | 275 |
| 405914 | 1744 | 1763 | AGCGGTGACCAGCACGACCC | 5-10-5 | 90.4 | 276 |
| 405915 | 1746 | 1765 | GCAGCGGTGACCAGCACGAC | 5-10-5 | 86.8 | 277 |
| 405916 | 1748 | 1767 | CGGCAGCGGTGACCAGCACG | 5-10-5 | 91.3 | 278 |
| 410734 | 1749 | 1768 | CCGGCAGCGGTGACCAGCAC | 5-10-5 | 65.8 | 249 |
| 405917 | 1752 | 1771 | TTGCCGGCAGCGGTGACCAG | 5-10-5 | 62.0 | 280 |
| 405918 | 1754 | 1773 | AGTTGCCGGCAGCGGTGACC | 5-10-5 | 33.5 | 281 |
| 405919 | 1756 | 1775 | GAAGTTGCCGGCAGCGGTGA | 5-10-5 | 68.2 | 282 |
| 405920 | 1758 | 1777 | CGGAAGTTGCCGGCAGCGGT | 5-10-5 | 86.2 | 283 |
| 405921 | 1760 | 1779 | CCCGGAAGTTGCCGGCAGCG | 5-10-5 | 85.5 | 284 |
| 405922 | 1762 | 1781 | GTCCGGAAGTTGCCGGCAG | 5-10-5 | 86.0 | 285 |
| 405937 | 1820 | 1839 | GAGGCACCAATGATGTCCTC | 5-10-5 | 77.7 | 306 |
| 405938 | 1824 | 1843 | GCTGGAGGCACCAATGATGT | 5-10-5 | 75.5 | 307 |
| 405939 | 1826 | 1845 | TCGCTGGAGGCACCAATGAT | 5-10-5 | 70.6 | 308 |
| 405940 | 1828 | 1847 | AGTCGCTGGAGGCACCAATG | 5-10-5 | 84.4 | 309 |
| 405941 | 1830 | 1849 | GCAGTCGCTGGAGGCACCAA | 5-10-5 | 90.1 | 310 |
| 399804 | 1833 | 1852 | GCTGCAGTCGCTGGAGGCAC | 5-10-5 | 80.8 | 40 |
| 399960 | 1833 | 1852 | GCTGCAGTCGCTGGAGGCAC | 3-14-3 | 82.4 | 40 |
| 405942 | 1835 | 1854 | GTGCTGCAGTCGCTGGAGGC | 5-10-5 | 69.8 | 311 |
| 405943 | 1837 | 1856 | AGGTGCTGCAGTCGCTGGAG | 5-10-5 | 83.6 | 312 |
| 410737 | 1839 | 1858 | GCAGGTGCTGCAGTCGCTGG | 5-10-5 | 49.8 | 313 |

TABLE 19-continued

Antisense inhibition of PCSK9 in human cells (Hep3B) targeting SEQ ID NO: 3

| Isis No. | 5' Target Site to SEQ ID NO: 3 | 3' Target Site to SEQ ID NO: 3 | Sequence 5'-3' | Motif | % inhibition | SEQ ID NO: |
|---|---|---|---|---|---|---|
| 405944 | 1840 | 1859 | AGCAGGTGCTGCAGTCGCTG | 5-10-5 | 80.7 | 314 |
| 405945 | 1842 | 1861 | AAAGCAGGTGCTGCAGTCGC | 5-10-5 | 41.1 | 315 |
| 405946 | 1846 | 1865 | ACACAAAGCAGGTGCTGCAG | 5-10-5 | 70.4 | 316 |
| 405947 | 1848 | 1867 | TGACACAAAGCAGGTGCTGC | 5-10-5 | 72.5 | 317 |
| 410769 | 1858 | 1877 | TCCCACTCTGTGACACAAAG | 5-10-5 | 84.9 | 318 |
| 405948 | 1900 | 1919 | TCATGGCTGCAATGCCAGCC | 5-10-5 | 45.9 | 319 |
| 399806 | 1903 | 1922 | GCATCATGGCTGCAATGCCA | 5-10-5 | 82.8 | 42 |
| 399962 | 1903 | 1922 | GCATCATGGCTGCAATGCCA | 3-14-3 | 86.1 | 42 |
| 405949 | 1905 | 1924 | CAGCATCATGGCTGCAATGC | 5-10-5 | 84.9 | 320 |
| 405950 | 1907 | 1926 | GACAGCATCATGGCTGCAAT | 5-10-5 | 76.9 | 321 |
| 405951 | 1909 | 1928 | CAGACAGCATCATGGCTGCA | 5-10-5 | 75.4 | 322 |
| 405952 | 1913 | 1932 | TCGGCAGACAGCATCATGGC | 5-10-5 | 85.1 | 323 |
| 410738 | 1915 | 1934 | GCTCGGCAGACAGCATCATG | 5-10-5 | 68.4 | 324 |
| 405953 | 1917 | 1936 | CGGCTCGGCAGACAGCATCA | 5-10-5 | 93.6 | 325 |
| 405954 | 1919 | 1938 | TCCGGCTCGGCAGACAGCAT | 5-10-5 | 87.5 | 326 |
| 410770 | 1933 | 1952 | CGGCCAGGGTGAGCTCCGGC | 5-10-5 | 68.5 | 327 |
| 405955 | 1946 | 1965 | CTCTGCCTCAACTCGGCCAG | 5-10-5 | 94.2 | 328 |
| 405956 | 1948 | 1967 | GTCTCTGCCTCAACTCGGCC | 5-10-5 | 94.3 | 329 |
| 405958 | 1952 | 1971 | ATCAGTCTCTGCCTCAACTC | 5-10-5 | 80.3 | 331 |
| 405959 | 1954 | 1973 | GGATCAGTCTCTGCCTCAAC | 5-10-5 | 95.4 | 332 |
| 405960 | 1956 | 1975 | GTGGATCAGTCTCTGCCTCA | 5-10-5 | 90.1 | 333 |
| 405961 | 1958 | 1977 | AAGTGGATCAGTCTCTGCCT | 5-10-5 | 88.8 | 334 |
| 405962 | 1961 | 1980 | GAGAAGTGGATCAGTCTCTG | 5-10-5 | 56.1 | 335 |
| 410739 | 1963 | 1982 | CAGAGAAGTGGATCAGTCTC | 5-10-5 | NA | 336 |
| 405963 | 1965 | 1984 | GGCAGAGAAGTGGATCAGTC | 5-10-5 | 59.7 | 337 |
| 405964 | 1969 | 1988 | CTTTGGCAGAGAAGTGGATC | 5-10-5 | 45.3 | 338 |
| 405965 | 1974 | 1993 | GACATCTTTGGCAGAGAAGT | 5-10-5 | 55.9 | 339 |
| 405966 | 1976 | 1995 | ATGACATCTTTGGCAGAGAA | 5-10-5 | 51.3 | 340 |
| 405967 | 1980 | 1999 | ATTGATGACATCTTTGGCAG | 5-10-5 | 64.4 | 341 |
| 405968 | 1982 | 2001 | TCATTGATGACATCTTTGGC | 5-10-5 | 74.6 | 342 |
| 399967 | 1985 | 2004 | GCCTCATTGATGACATCTTT | 3-14-3 | 80.1 | 48 |
| 405969 | 1987 | 2006 | AGGCCTCATTGATGACATCT | 5-10-5 | 63.0 | 343 |
| 405970 | 1989 | 2008 | CCAGGCCTCATTGATGACAT | 5-10-5 | 66.8 | 344 |
| 410740 | 1991 | 2010 | AACCAGGCCTCATTGATGAC | 5-10-5 | 46.8 | 345 |
| 405885 | 1993 | 2012 | GGAACCAGGCCTCATTGATG | 5-10-5 | 73.4 | 346 |
| 410596 | 1995 | 2014 | AGGGAACCAGGCCTCATTGA | 3-14-3 | NA | 348 |

TABLE 19-continued

Antisense inhibition of PCSK9 in human cells (Hep3B) targeting SEQ ID NO: 3

| Isis No. | 5' Target Site to SEQ ID NO: 3 | 3' Target Site to SEQ ID NO: 3 | Sequence 5'-3' | Motif | % inhibition | SEQ ID NO: |
|---|---|---|---|---|---|---|
| 410672 | 1995 | 2014 | AGGGAACCAGGCCTCATTGA | 2-13-5 | NA | 348 |
| 405887 | 1995 | 2014 | AGGGAACCAGGCCTCATTGA | 5-10-5 | NA | 348 |
| 410597 | 1996 | 2015 | CAGGGAACCAGGCCTCATTG | 3-14-3 | NA | 349 |
| 405888 | 1996 | 2015 | CAGGGAACCAGGCCTCATTG | 5-10-5 | NA | 349 |
| 410673 | 1996 | 2015 | CAGGGAACCAGGCCTCATTG | 2-13-5 | NA | 349 |
| 410674 | 1997 | 2016 | TCAGGGAACCAGGCCTCATT | 2-13-5 | 60.7 | 49 |
| 399812 | 1997 | 2016 | TCAGGGAACCAGGCCTCATT | 5-10-5 | 68.7 | 49 |
| 399968 | 1997 | 2016 | TCAGGGAACCAGGCCTCATT | 3-14-3 | 84.5 | 49 |
| 410598 | 1998 | 2017 | CTCAGGGAACCAGGCCTCAT | 3-14-3 | 74.5 | 350 |
| 410675 | 1998 | 2017 | CTCAGGGAACCAGGCCTCAT | 2-13-5 | 76.9 | 350 |
| 405889 | 1998 | 2017 | CTCAGGGAACCAGGCCTCAT | 5-10-5 | 80.2 | 350 |
| 410599 | 1999 | 2018 | CCTCAGGGAACCAGGCCTCA | 3-14-3 | 70.6 | 351 |
| 410676 | 1999 | 2018 | CCTCAGGGAACCAGGCCTCA | 2-13-5 | 77.8 | 351 |
| 405890 | 1999 | 2018 | CCTCAGGGAACCAGGCCTCA | 5-10-5 | 87.7 | 351 |
| 410600 | 2000 | 2019 | TCCTCAGGGAACCAGGCCTC | 3-14-3 | 76.5 | 352 |
| 410677 | 2000 | 2019 | TCCTCAGGGAACCAGGCCTC | 2-13-5 | 88.4 | 352 |
| 405891 | 2000 | 2019 | TCCTCAGGGAACCAGGCCTC | 5-10-5 | 96.1 | 352 |
| 405892 | 2001 | 2020 | GTCCTCAGGGAACCAGGCCT | 5-10-5 | 71.4 | 353 |
| 410601 | 2001 | 2020 | GTCCTCAGGGAACCAGGCCT | 3-14-3 | 72.7 | 353 |
| 410678 | 2001 | 2020 | GTCCTCAGGGAACCAGGCCT | 2-13-5 | 75.0 | 353 |
| 395178 | 2002 | 2021 | GGTCCTCAGGGAACCAGGCC | 5-10-5 | 76.7 | 50 |
| 410679 | 2002 | 2021 | GGTCCTCAGGGAACCAGGCC | 2-13-5 | 77.6 | 50 |
| 399900 | 2002 | 2021 | GGTCCTCAGGGAACCAGGCC | 3-14-3 | 92.0 | 50 |
| 408653 | 2003 | 2022 | TGGTCCTCAGGGAACCAGGC | 5-10-5 | 42.5 | 354 |
| 410602 | 2003 | 2022 | TGGTCCTCAGGGAACCAGGC | 3-14-3 | 66.5 | 354 |
| 410680 | 2003 | 2022 | TGGTCCTCAGGGAACCAGGC | 2-13-5 | 71.6 | 354 |
| 410603 | 2004 | 2023 | CTGGTCCTCAGGGAACCAGG | 3-14-3 | 40.8 | 355 |
| 410681 | 2004 | 2023 | CTGGTCCTCAGGGAACCAGG | 2-13-5 | 44.4 | 355 |
| 405971 | 2004 | 2023 | CTGGTCCTCAGGGAACCAGG | 5-10-5 | 65.5 | 355 |
| 410540 | 2005 | 2024 | GCTGGTCCTCAGGGAACCAG | 5-10-5 | 50.9 | 356 |
| 410682 | 2005 | 2024 | GCTGGTCCTCAGGGAACCAG | 2-13-5 | 54.1 | 356 |
| 410604 | 2005 | 2024 | GCTGGTCCTCAGGGAACCAG | 3-14-3 | 62.5 | 356 |
| 405972 | 2006 | 2025 | CGCTGGTCCTCAGGGAACCA | 5-10-5 | 77.6 | 357 |
| 405973 | 2011 | 2030 | GTACCCGCTGGTCCTCAGGG | 5-10-5 | 83.8 | 358 |
| 405974 | 2013 | 2032 | CAGTACCCGCTGGTCCTCAG | 5-10-5 | 89.0 | 359 |
| 399813 | 2016 | 2035 | GGTCAGTACCCGCTGGTCCT | 5-10-5 | 72.4 | 51 |

TABLE 19-continued

Antisense inhibition of PCSK9 in human cells (Hep3B) targeting SEQ ID NO: 3

| Isis No. | 5' Target Site to SEQ ID NO: 3 | 3' Target Site to SEQ ID NO: 3 | Sequence 5'-3' | Motif | % inhibition | SEQ ID NO: |
|---|---|---|---|---|---|---|
| 399969 | 2016 | 2035 | GGTCAGTACCCGCTGGTCCT | 3-14-3 | 93.4 | 51 |
| 410771 | 2061 | 2080 | ACCTGCCCCATGGGTGCTGG | 5-10-5 | NA | 360 |
| 395181 | 2073 | 2092 | AAACAGCTGCCAACCTGCCC | 5-10-5 | 87.5 | 52 |
| 405975 | 2075 | 2094 | CAAAACAGCTGCCAACCTGC | 5-10-5 | 77.4 | 361 |
| 405976 | 2080 | 2099 | TCCTGCAAAACAGCTGCCAA | 5-10-5 | 81.2 | 362 |
| 405977 | 2082 | 2101 | AGTCCTGCAAAACAGCTGCC | 5-10-5 | 89.5 | 363 |
| 399992 | 2095 | 2114 | GTGCTGACCACACAGTCCTG | 3-14-3 | 92.6 | 130 |
| 405978 | 2105 | 2124 | GGCCCCGAGTGTGCTGACCA | 5-10-5 | 95.3 | 365 |
| 399904 | 2108 | 2127 | GTAGGCCCCGAGTGTGCTGA | 3-14-3 | 92.6 | 54 |
| 405979 | 2110 | 2129 | GTGTAGGCCCCGAGTGTGCT | 5-10-5 | 85.5 | 366 |
| 405980 | 2112 | 2131 | CCGTGTAGGCCCCGAGTGTG | 5-10-5 | 86.5 | 367 |
| 405981 | 2114 | 2133 | ATCCGTGTAGGCCCCGAGTG | 5-10-5 | 77.8 | 368 |
| 410741 | 2116 | 2135 | CCATCCGTGTAGGCCCCGAG | 5-10-5 | 78.4 | 369 |
| 405982 | 2118 | 2137 | GGCCATCCGTGTAGGCCCCG | 5-10-5 | 86.7 | 370 |
| 405983 | 2120 | 2139 | GTGGCCATCCGTGTAGGCCC | 5-10-5 | 73.1 | 371 |
| 405984 | 2168 | 2187 | CTGGAGCAGCTCAGCAGCTC | 5-10-5 | 83.4 | 372 |
| 405985 | 2170 | 2189 | AACTGGAGCAGCTCAGCAGC | 5-10-5 | 50.7 | 373 |
| 405986 | 2175 | 2194 | GGAGAAACTGGAGCAGCTCA | 5-10-5 | 75.6 | 374 |
| 405987 | 2177 | 2196 | CTGGAGAAACTGGAGCAGCT | 5-10-5 | 88.0 | 375 |
| 410776 | 2245 | 2264 | GTGCCAAGGTCCTCCACCTC | 5-10-5 | 77.3 | 408 |
| 410777 | 2265 | 2284 | TCAGCACAGGCGGCTTGTGG | 5-10-5 | 40.0 | 409 |
| 410778 | 2295 | 2314 | CCACGCACTGGTTGGGCTGA | 5-10-5 | 52.7 | 410 |
| 399908 | 2355 | 2374 | CTTTGCATTCCAGACCTGGG | 3-14-3 | 74.9 | 60 |
| 410713 | 2355 | 2374 | CTTTGCATTCCAGACCTGGG | 2-13-5 | 84.9 | 60 |
| 395186 | 2355 | 2374 | CTTTGCATTCCAGACCTGGG | 5-10-5 | 93.7 | 60 |
| 410714 | 2356 | 2375 | ACTTTGCATTCCAGACCTGG | 2-13-5 | 82.4 | 411 |
| 410633 | 2356 | 2375 | ACTTTGCATTCCAGACCTGG | 3-14-3 | 83.8 | 411 |
| 410562 | 2356 | 2375 | ACTTTGCATTCCAGACCTGG | 5-10-5 | 87.3 | 411 |
| 410715 | 2357 | 2376 | GACTTTGCATTCCAGACCTG | 2-13-5 | 80.5 | 412 |
| 410634 | 2357 | 2376 | GACTTTGCATTCCAGACCTG | 3-14-3 | 81.8 | 412 |
| 405996 | 2357 | 2376 | GACTTTGCATTCCAGACCTG | 5-10-5 | 91.0 | 412 |
| 410563 | 2358 | 2377 | TGACTTTGCATTCCAGACCT | 5-10-5 | 75.4 | 413 |
| 410635 | 2358 | 2377 | TGACTTTGCATTCCAGACCT | 3-14-3 | 75.9 | 413 |
| 410716 | 2358 | 2377 | TGACTTTGCATTCCAGACCT | 2-13-5 | 88.3 | 413 |
| 410636 | 2359 | 2378 | TTGACTTTGCATTCCAGACC | 3-14-3 | 61.3 | 414 |
| 410564 | 2359 | 2378 | TTGACTTTGCATTCCAGACC | 5-10-5 | 71.3 | 414 |

TABLE 19-continued

Antisense inhibition of PCSK9 in human cells (Hep3B) targeting SEQ ID NO: 3

| Isis No. | 5' Target Site to SEQ ID NO: 3 | 3' Target Site to SEQ ID NO: 3 | Sequence 5'-3' | Motif | % inhibition | SEQ ID NO: |
|---|---|---|---|---|---|---|
| 410717 | 2359 | 2378 | TTGACTTTGCATTCCAGACC | 2-13-5 | 76.7 | 414 |
| 410718 | 2360 | 2379 | CTTGACTTTGCATTCCAGAC | 2-13-5 | 55.8 | 61 |
| 399973 | 2360 | 2379 | CTTGACTTTGCATTCCAGAC | 3-14-3 | 82.1 | 61 |
| 399817 | 2360 | 2379 | CTTGACTTTGCATTCCAGAC | 5-10-5 | 93.6 | 61 |
| 405997 | 2362 | 2381 | TCCTTGACTTTGCATTCCAG | 5-10-5 | 95.6 | 415 |
| 410779 | 2375 | 2394 | CGGGATTCCATGCTCCTTGA | 5-10-5 | 79.7 | 416 |
| 410780 | 2405 | 2424 | GCAGGCCACGGTCACCTGCT | 5-10-5 | 60.9 | 417 |
| 410781 | 2442 | 2461 | GGAGGGCACTGCAGCCAGTC | 5-10-5 | 66.0 | 418 |
| 410719 | 2560 | 2579 | CAGATGGCAACGGCTGTCAC | 2-13-5 | 61.0 | 419 |
| 410637 | 2560 | 2579 | CAGATGGCAACGGCTGTCAC | 3-14-3 | 66.0 | 419 |
| 410565 | 2560 | 2579 | CAGATGGCAACGGCTGTCAC | 5-10-5 | 71.6 | 419 |
| 410638 | 2561 | 2580 | GCAGATGGCAACGGCTGTCA | 3-14-3 | 71.9 | 420 |
| 410720 | 2561 | 2580 | GCAGATGGCAACGGCTGTCA | 2-13-5 | 75.1 | 420 |
| 410566 | 2561 | 2580 | GCAGATGGCAACGGCTGTCA | 5-10-5 | 77.7 | 420 |
| 410639 | 2562 | 2581 | AGCAGATGGCAACGGCTGTC | 3-14-3 | 67.7 | 421 |
| 410721 | 2562 | 2581 | AGCAGATGGCAACGGCTGTC | 2-13-5 | 68.8 | 421 |
| 410567 | 2562 | 2581 | AGCAGATGGCAACGGCTGTC | 5-10-5 | 72.1 | 421 |
| 410568 | 2563 | 2582 | CAGCAGATGGCAACGGCTGT | 5-10-5 | 54.2 | 422 |
| 410640 | 2563 | 2582 | CAGCAGATGGCAACGGCTGT | 3-14-3 | 57.7 | 422 |
| 410722 | 2563 | 2582 | CAGCAGATGGCAACGGCTGT | 2-13-5 | 59.2 | 422 |
| 410569 | 2564 | 2583 | GCAGCAGATGGCAACGGCTG | 5-10-5 | 57.7 | 423 |
| 410641 | 2564 | 2583 | GCAGCAGATGGCAACGGCTG | 3-14-3 | 66.1 | 423 |
| 410723 | 2564 | 2583 | GCAGCAGATGGCAACGGCTG | 2-13-5 | 81.1 | 423 |
| 399909 | 2565 | 2584 | GGCAGCAGATGGCAACGGCT | 3-14-3 | 69.9 | 62 |
| 410724 | 2565 | 2584 | GGCAGCAGATGGCAACGGCT | 2-13-5 | 87.4 | 62 |
| 395187 | 2565 | 2584 | GGCAGCAGATGGCAACGGCT | 5-10-5 | 92.7 | 62 |
| 410642 | 2566 | 2585 | CGGCAGCAGATGGCAACGGC | 3-14-3 | 70.4 | 424 |
| 410725 | 2566 | 2585 | CGGCAGCAGATGGCAACGGC | 2-13-5 | 75.6 | 424 |
| 410570 | 2566 | 2585 | CGGCAGCAGATGGCAACGGC | 5-10-5 | 78.3 | 424 |
| 410571 | 2567 | 2586 | CCGGCAGCAGATGGCAACGG | 5-10-5 | 52.8 | 425 |
| 410643 | 2567 | 2586 | CCGGCAGCAGATGGCAACGG | 3-14-3 | 59.8 | 425 |
| 410726 | 2567 | 2586 | CCGGCAGCAGATGGCAACGG | 2-13-5 | 69.8 | 425 |
| 410644 | 2568 | 2587 | TCCGGCAGCAGATGGCAACG | 3-14-3 | 59.0 | 426 |
| 410727 | 2568 | 2587 | TCCGGCAGCAGATGGCAACG | 2-13-5 | 68.3 | 426 |
| 405998 | 2568 | 2587 | TCCGGCAGCAGATGGCAACG | 5-10-5 | 75.6 | 426 |
| 405988 | 2568 | 2587 | TCCGGCAGCAGATGGCAACG | 5-10-5 | 84.5 | 426 |

TABLE 19-continued

Antisense inhibition of PCSK9 in human cells (Hep3B) targeting SEQ ID NO: 3

| Isis No. | 5' Target Site to SEQ ID NO: 3 | 3' Target Site to SEQ ID NO: 3 | Sequence 5'-3' | Motif | % inhibition | SEQ ID NO: |
|---|---|---|---|---|---|---|
| 410572 | 2569 | 2588 | CTCCGGCAGCAGATGGCAAC | 5-10-5 | 40.9 | 427 |
| 410728 | 2569 | 2588 | CTCCGGCAGCAGATGGCAAC | 2-13-5 | 56.4 | 427 |
| 410645 | 2569 | 2588 | CTCCGGCAGCAGATGGCAAC | 3-14-3 | 70.2 | 427 |
| 410729 | 2570 | 2589 | GCTCCGGCAGCAGATGGCAA | 2-13-5 | 67.7 | 428 |
| 410573 | 2570 | 2589 | GCTCCGGCAGCAGATGGCAA | 5-10-5 | 71.8 | 428 |
| 410646 | 2570 | 2589 | GCTCCGGCAGCAGATGGCAA | 3-14-3 | 72.8 | 428 |
| 410782 | 2580 | 2599 | CCAGGTGCCGGCTCCGGCAG | 5-10-5 | 43.2 | 429 |
| 410783 | 2590 | 2609 | GAGGCCTGCGCCAGGTGCCG | 5-10-5 | 63.7 | 430 |
| 399819 | 2764 | 2783 | CCCACTCAAGGGCCAGGCCA | 5-10-5 | 93.4 | 65 |
| 399912 | 2852 | 2871 | ATGCCCCACAGTGAGGGAGG | 3-14-3 | 84.3 | 66 |
| 405893 | 3083 | 3102 | ATGAGGGCCATCAGCACCTT | 5-10-5 | 93.9 | 431 |
| 405894 | 3084 | 3103 | GATGAGGGCCATCAGCACCT | 5-10-5 | 93.9 | 432 |
| 405895 | 3085 | 3104 | AGATGAGGGCCATCAGCACC | 5-10-5 | 91.8 | 433 |
| 405896 | 3086 | 3105 | GAGATGAGGGCCATCAGCAC | 5-10-5 | 88.5 | 434 |
| 395194 | 3087 | 3106 | GGAGATGAGGGCCATCAGCA | 5-10-5 | 90.0 | 69 |
| 399916 | 3087 | 3106 | GGAGATGAGGGCCATCAGCA | 3-14-3 | 94.5 | 69 |
| 405897 | 3088 | 3107 | TGGAGATGAGGGCCATCAGC | 5-10-5 | 85.1 | 435 |
| 405898 | 3089 | 3108 | CTGGAGATGAGGGCCATCAG | 5-10-5 | 86.9 | 436 |
| 405899 | 3090 | 3109 | GCTGGAGATGAGGGCCATCA | 5-10-5 | 91.5 | 437 |
| 405900 | 3091 | 3110 | AGCTGGAGATGAGGGCCATC | 5-10-5 | 83.7 | 438 |
| 405901 | 3157 | 3176 | GCTAGATGCCATCCAGAAAG | 5-10-5 | 88.4 | 439 |
| 405902 | 3158 | 3177 | GGCTAGATGCCATCCAGAAA | 5-10-5 | 89.3 | 440 |
| 405903 | 3159 | 3178 | TGGCTAGATGCCATCCAGAA | 5-10-5 | 92.6 | 441 |
| 405904 | 3160 | 3179 | CTGGCTAGATGCCATCCAGA | 5-10-5 | 90.4 | 442 |
| 399821 | 3161 | 3180 | TCTGGCTAGATGCCATCCAG | 5-10-5 | 91.7 | 71 |
| 405905 | 3162 | 3181 | CTCTGGCTAGATGCCATCCA | 5-10-5 | 90.7 | 443 |
| 405906 | 3163 | 3182 | CCTCTGGCTAGATGCCATCC | 5-10-5 | 93.3 | 444 |
| 405907 | 3164 | 3183 | GCCTCTGGCTAGATGCCATC | 5-10-5 | 90.2 | 445 |
| 405908 | 3165 | 3184 | AGCCTCTGGCTAGATGCCAT | 5-10-5 | 83.3 | 446 |
| 399978 | 3243 | 3262 | AGCCTGGCATAGAGCAGAGT | 3-14-3 | 96.4 | 73 |

Antisense oligonucleotides that exhibited less than 30% inhibition of PCSK9 mRNA levels were marked with "NA".

Antisense oligonucleotides with the following ISIS Nos exhibited at least 80% inhibition of PCSK9 mRNA levels: 395163, 395165, 395166, 395168, 395181, 395186, 395187, 395194, 399798, 399801, 399804, 399806, 399817, 399819, 399821, 399887, 399888, 399891, 399900, 399904, 399912, 399916, 399935, 399936, 399954, 399960, 399962, 399967, 399968, 399969, 399973, 399978, 399992, 405869, 405870, 405871, 405872, 405873, 405874, 405875, 405876, 405877, 405878, 405879, 405880, 405881, 405882, 405883, 405884, 405889, 405890, 405891, 405893, 405894, 405895, 405896, 405897, 405898, 405899, 405900, 405901, 405902, 405903, 405904, 405905, 405906, 405907, 405908, 405909, 405910, 405911, 405913, 405914, 405915, 405916, 405920, 405921, 405922, 405940, 405941, 405943, 405944, 405949, 405952, 405953, 405954, 405955, 405956, 405958, 405959, 405960, 405961, 405973, 405974, 405976, 405977, 405978, 405979, 405980, 405982, 405984, 405987, 405988, 405996, 405997, 406026, 406028, 406029, 406030, 406031, 406032, 406033, 406035, 406036, 406038, 406039, 406040, 406041, 406042, 406043, 406044, 406045, 410562, 410583, 410589, 410590, 410591, 410592, 410593, 410595, 410633, 410634, 410658, 410664, 410666, 410667, 410668, 410671, 410677, 410713, 410714, 410715, 410716, 410723, 410724, 410754, 410757, 410759, 410760, and 410769. The target segments to which these antisense oligonucleotides are targeted are active target segments. The target regions to which these antisense oligonucleotides are targeted are active target regions.

ISIS Nos 395165, 395166, 395168, 395181, 395186, 395187, 395194, 399801, 399817, 399819, 399821, 399887, 399888, 399891, 399900, 399904, 399916, 399936, 399954, 399962, 399969, 399978, 399992, 405869, 405871, 405872, 405873, 405874, 405875, 405876, 405878, 405879, 405880, 405881, 405882, 405883, 405884, 405890, 405891, 405893, 405894, 405895, 405896, 405897, 405898, 405899, 405901, 405902, 405903, 405904, 405905, 405906, 405907, 405910, 405911, 405913, 405914, 405915, 405916, 405920, 405921, 405922, 405941, 405952, 405953, 405954, 405955, 405956, 405959, 405960, 405961, 405974, 405977, 405978, 405979, 405980, 405982, 405987, 405996, 405997, 406028, 406029, 406030, 406031, 406032, 406033, 406035, 406038, 406039, 406040, 406041, 406042, 406043, 406044, 406045, 410562, 410583, 410591, 410592, 410593, 410668, 410677, 410716, 410724, 410757, and 410760 each exhibited at least 85% inhibition of PCSK9 mRNA levels.

ISIS Nos 395165, 395166, 395168, 395186, 395187, 395194, 399801, 399817, 399819, 399821, 399887, 399888, 399891, 399900, 399904, 399916, 399954, 399969, 399978, 399992, 405873, 405874, 405875, 405876, 405878, 405879, 405880, 405881, 405882, 405883, 405884, 405891, 405893, 405894, 405895, 405899, 405903, 405904, 405905, 405906, 405907, 405910, 405913, 405914, 405916, 405941, 405953, 405955, 405956, 405959, 405960, 405978, 405996, 405997, 406028, 406029, 406030, 406033, 406035, 406039, 406040, 406041, 406042, 406043, 406044, 410592, 410668, and 410760 each exhibited at least 90% inhibition of PCSK9 mRNA levels.

ISIS Nos 395165, 395166, 399801, 399978, 405881, 405891, 405959, 405978, 405997, 406030, 406040, 406041, 406044, and 410760 each exhibited at least 95% inhibition of PCSK9 mRNA levels.

Example 4: Antisense Reduction of Human PCSK9 mRNA in HepG2 Cells: Dose Response Experiment Antisense oligonucleotides targeted to PCSK9 were tested at various doses in HepG2 cells. Cells were plated at densities of 10,000 cells per well and treated with nM concentrations of antisense oligonucleotide as indicated in Tables 20 and 21. After a treatment period of approximately 24 hours, RNA was isolated from the cells and PCSK9 mRNA levels were measured by quantitative real-time PCR, as described herein. Two different human PCSK9 primer probe sets were used to measure mRNA levels. Results with Primer Probe Set 2740 are shown in Table 20, and mRNA levels measured using primer probe set 2823 are shown in Table 21. Results are presented as percent PCSK9 mRNA levels relative to a control, as adjusted according to total RNA content measured by RIBOGREEN®. As illustrated in Tables 20 and 21, PCSK9 mRNA levels were reduced in a dose-dependent manner.

TABLE 20

Antisense Reduction of PCSK9 mRNA in HepG2 cells, Primer Probe Set 2740

| Isis No | 6.25 nM | 12.5 nM | 25.0 nM | 50.0 nM | 100.0 nM | 200.0 nM |
|---|---|---|---|---|---|---|
| 399819 | 93 | 113 | 84 | 71 | 26 | 12 |
| 395185 | 81 | 64 | 50 | 35 | 24 | 13 |
| 399916 | 65 | 56 | 41 | 18 | 20 | 25 |
| 399907 | 68 | 66 | 42 | 26 | 30 | 25 |
| 399954 | 71 | 63 | 38 | 22 | 16 | 15 |
| 395165 | 71 | 67 | 47 | 29 | 21 | 10 |
| 399936 | 65 | 51 | 31 | 20 | 30 | 28 |
| 399793 | 61 | 57 | 44 | 31 | 39 | 15 |
| 399969 | 57 | 54 | 40 | 27 | 25 | 19 |
| 395152 | 75 | 58 | 58 | 49 | 24 | 28 |

TABLE 21

Antisense Reduction of PCSK9 mRNA in HepG2 cells, Primer Probe Set 2823

| Isis No | 6.25 nM | 12.5 nM | 25.0 nM | 50.0 nM | 100.0 nM | 200.0 nM |
|---|---|---|---|---|---|---|
| 399819 | 80 | 264 | 87 | 85 | 34 | 15 |
| 395185 | 86 | 66 | 57 | 45 | 29 | 22 |
| 399916 | 75 | 47 | 45 | 20 | 30 | 45 |
| 399907 | 67 | 72 | 47 | 29 | 31 | 32 |
| 399954 | 59 | 50 | 35 | 17 | 22 | 27 |
| 395165 | 74 | 54 | 41 | 37 | 26 | 22 |
| 399936 | 62 | 41 | 33 | 32 | 28 | 42 |
| 399793 | 62 | 51 | 38 | 36 | 44 | 27 |
| 399969 | 73 | 40 | 58 | 28 | 29 | 35 |
| 395152 | 78 | 53 | 64 | 49 | 22 | 35 |

Example 5: Antisense Reduction of Human PCSK9 mRNA in Hep3B Cells: Dose Response Experiment Antisense oligonucleotides targeted to PCSK9 were tested at various doses in Hep3B cells. Cells were plated at densities of 4,500 cells per well and treated with nM concentrations of antisense oligonucleotide as indicated in Table 22. ISIS 141923 is not complementary to any known gene sequence and is used in this and the following experiments as a negative control. After a treatment period of approximately 24 hours, RNA was isolated from the cells and PCSK9 mRNA levels were measured by quantitative real-time PCR, as described herein. Two different human PCSK9 primer probe sets were used to measure mRNA levels. Results with Primer Probe Set 2740 are shown in Table 22. Results are presented as percent PCSK9 mRNA levels relative to a control, as adjusted according to total RNA content measured by RIBOGREEN®. As illustrated in Table 22, PCSK9 mRNA levels were reduced in a dose-dependent manner.

TABLE 22

Antisense Reduction of PCSK9 mRNA in Hep3B cells, Primer Probe Set 2740

| Isis No. | 2.78 nM | 8.33 nM | 25.0 nM | 75.0 nM |
|---|---|---|---|---|
| 399819 | 127.5 | 85.0 | 36.1 | 21.9 |
| 405891 | 133.7 | 111.4 | 40.2 | 27.2 |
| 406008 | 144.6 | 108.3 | 49.9 | 17.7 |
| 395186 | 124.4 | 106.4 | 42.2 | 30.7 |
| 395185 | 150.7 | 106.6 | 53.6 | 38.1 |
| 405994 | 141.9 | 101.2 | 49.3 | 30.8 |

TABLE 22-continued

Antisense Reduction of PCSK9 mRNA in
Hep3B cells, Primer Probe Set 2740

| Isis No. | 2.78 nM | 8.33 nM | 25.0 nM | 75.0 nM |
|---|---|---|---|---|
| 405988 | 148.1 | 117.4 | 47.8 | 25.2 |
| 406033 | 138.1 | 109.9 | 62.4 | 35.3 |
| 395187 | 133.0 | 115.6 | 59.9 | 31.6 |
| 405995 | 124.1 | 109.2 | 57.8 | 42.9 |
| 406023 | 130.0 | 103.5 | 67.1 | 28.0 |
| 399900 | 131.2 | 95.7 | 81.1 | 30.9 |
| 301012 | 121.2 | 100.1 | 63.8 | 49.6 |
| 395165 | 113.2 | 86.9 | 41.6 | 13.3 |
| 405879 | 124.6 | 88.8 | 44.1 | 13.1 |
| 405991 | 100.6 | 101.4 | 95.9 | 41.0 |
| 405923 | 130.4 | 115.0 | 68.9 | 35.1 |
| 395152 | 143.8 | 98.6 | 61.3 | 59.0 |
| 405881 | 100.7 | 77.4 | 50.2 | 4.5 |
| 141923 | 131.4 | 131.9 | 144.0 | 167.3 |

Example 6: Antisense Reduction of Human PCSK9 mRNA in HeLa Cells: Dose Response Experiment Antisense oligonucleotides targeted to PCSK9 were tested at various doses in HeLa cells. Cells were plated at densities of 5,000 cells per well and treated with nM concentrations of antisense oligonucleotide as indicated in Table 23. After a treatment period of approximately 24 hours, RNA was isolated from the cells and PCSK9 mRNA levels were measured by quantitative real-time PCR, as described herein. Two different human PCSK9 primer probe sets were used to measure mRNA levels. Results with Primer Probe Set 2740 are shown in Table 23. Results are presented as percent PCSK9 mRNA levels relative to a control, as adjusted according to total RNA content measured by RIBOGREEN®. As illustrated in Table 23, PCSK9 mRNA levels were reduced in a dose-dependent manner.

TABLE 23

Antisense Reduction of PCSK9 mRNA in
HeLa cells, Primer Probe Set 2740

| Isis No. | 2.963 nM | 8.8889 nM | 26.6667 nM | 80.0 nM |
|---|---|---|---|---|
| 399819 | 57 | 32 | 16 | 14 |
| 405891 | 57 | 46 | 17 | 18 |
| 406008 | 45 | 27 | 11 | 5.3 |
| 395186 | 40 | 28 | 11 | 6.6 |
| 395185 | 53 | 32 | 21 | 17 |
| 405994 | 48 | 34 | 20 | 13 |
| 405988 | 44 | 32 | 12 | 7.3 |
| 406033 | 61 | 42 | 25 | 12 |
| 395187 | 42 | 35 | 12 | 6.6 |
| 405995 | 54 | 39 | 21 | 15 |
| 406023 | 76 | 46 | 25 | 6.2 |
| 399900 | 85 | 48 | 23 | 6.4 |
| 301012 | 121 | 109 | 76 | 65 |
| 395165 | 61 | 30 | 10 | 2 |
| 405879 | 64 | 32 | 9.7 | 1 |
| 405991 | 64 | 35 | 24 | 10 |
| 405923 | 71 | 45 | 22 | 5 |
| 395152 | 73 | 34 | 13 | 3.1 |
| 405881 | 58 | 33 | 19 | 2.8 |
| 141923 | 122 | 118 | 131 | 140 |

Example 7: Antisense Reduction of Human PCSK9 mRNA in Primary Hepatocytes

Antisense oligonucleotides targeted to PCSK9 were tested for antisense inhibition of PCSK9 in human primary hepatocytes. Human primary hepatocytes were purchased from a commercial supplier, and cultured according to routine culture procedures. Cells were treated with 10, 25, 50, 150, or 300 nM of antisense oligonucleotide for a period of 24 hours, after which RNA was isolated and PCSK9 mRNA was measured by real-time PCR as described herein.

The antisense oligonucleotides tested in human primary hepatocytes were Isis 395152, 395155, 395165, 395185, 399819, 399821, 399916, 399954, 399978, and 399992. The antisense oligonucleotides inhibited PCSK9 in a dose-dependent manner in human primary hepatocytes.

Monkey primary hepatocytes were similarly treated with 10, 25, 50, 150, or 300 nM concentrations of antisense oligonucleotide targeted to PCSK9. The antisense oligonucleotides tested in monkey primary hepatocytes were Isis 395152, 395155, 395165, 395185, 399819, 399821, 399916, 399954, 399978, and 399992. Each of these antisense oligonucleotides is fully complementary to a monkey PCSK9 nucleic acid. The antisense oligonucleotides inhibited PCSK9 in a dose-dependent manner in monkey primary hepatocytes.

Example 8: Additional Antisense Reduction of Human PCSK9 mRNA in Primary Hepatocytes Antisense oligonucleotides targeted to PCSK9 were tested for antisense inhibition of PCSK9 in human primary hepatocytes. Human primary hepatocytes were purchased from a commercial supplier, and cultured according to routine culture procedures. Cells were treated with 10, 25, 50, 150, or 300 nM of antisense oligonucleotide for a period of 24 hours, after which RNA was isolated and PCSK9 mRNA was measured by real-time PCR as described herein.

The antisense oligonucleotides tested in human primary hepatocytes were Isis 395165, 395185, 395186, 395187, 405879, 405881, 405891, 405988, 405994, and 406008. The antisense oligonucleotides inhibited PCSK9 in a dose-dependent manner in human primary hepatocytes as shown in Table 24.

TABLE 24

Dose-dependent Reduction in Human PCSK9 mRNA
Expression in Human Primary Hepatocytes

| ISIS No. | 10 nM | 25 nM | 50 nM | 150 nM | 300 nM |
|---|---|---|---|---|---|
| 395165 | 76 | 48.7 | 22.5 | 20.2 | 16.2 |
| 395185 | 74.5 | 42.9 | 52.6 | 25.5 | 15.7 |
| 395186 | 123.8 | 58.3 | 34.4 | 21 | 19.9 |
| 395187 | 98.7 | 43.5 | 29.7 | 17.4 | 21.1 |
| 405879 | 119.2 | 176.6 | 64.9 | 48.4 | 47.7 |
| 405881 | 222.4 | 115.3 | 49.5 | 22.3 | 79.3 |
| 405891 | 169.9 | 138.7 | 73.9 | 86.9 | 48.7 |
| 405988 | 85.2 | 105.4 | 67.8 | 43.9 | 43.8 |
| 405994 | 95.7 | 83.3 | 43.5 | 24.6 | 10.5 |
| 406008 | 155 | 101.7 | 116 | 41.7 | 32.4 |

Example 9: Antisense Reduction of PCSK9 mRNA in Cyno Primary Hepatocytes

Antisense oligonucleotides targeted to PCSK9 were tested for antisense inhibition of PCSK9 in cyno primary hepatocytes. Cyno primary hepatocytes were purchased from a commercial supplier, and cultured according to routine culture procedures. Cells were treated with 10, 25, 50, 150, or 300 nM of antisense oligonucleotide for a period of 24 hours, after which RNA was isolated and PCSK9 mRNA was measured by real-time PCR as described herein.

The antisense oligonucleotides tested in cyno primary hepatocytes were Isis 395165, 395185, 395186, 395187, 405879, 405881, 405891, 405988, 405994, and 406008. The antisense oligonucleotides inhibited PCSK9 in a dose-dependent manner in cyno primary hepatocytes as shown in Table 25.

TABLE 25

Dose-dependent PCSK9 mRNA Inhibition in Cyno Primary Hepatocytes

| ISIS No. | 10 nM | 25 nM | 50 nM | 150 nM | 300 nM |
|---|---|---|---|---|---|
| 395165 | 36.3 | 29.9 | 14.9 | 8.6 | 3.2 |
| 395185 | 65.0 | 31.9 | 35.1 | 16.6 | 12.0 |
| 395186 | 65.8 | 42.3 | 21.6 | 23.3 | 16.7 |
| 395187 | 61.3 | 32.9 | 13.2 | 7.7 | 9.02 |
| 405879 | 24.3 | 21.9 | 7.7 | 7.1 | 3.0 |
| 405881 | 75.0 | 33.5 | 26.5 | 11.2 | 4.9 |
| 405891 | 52.4 | 24.8 | 11.2 | 10.8 | 6.7 |
| 405988 | 59.4 | 23.7 | 22.5 | 10.7 | 8.2 |
| 405994 | 64.8 | 52.7 | 22.2 | 7.9 | 6.5 |
| 406008 | 56.3 | 28.2 | 26.5 | 13.4 | 13.3 |

Example 10: Antisense Reduction of Mouse PCSK9 mRNA In Vitro

Antisense oligonucleotides were designed to target murine PCSK9, and were evaluated for their ability to reduce PCSK9 mRNA in primary mouse hepatocytes.

Primary mouse hepatocytes were treated with antisense oligonucleotides at doses of 50, 150, or 300 nM, for a period of 24 hours. RNA was isolated using QIAGEN® RNeasy isolation kits and subjected to quantitative real-time PCR using commercially available reagents (Invitrogen, Carlsbad, Calif.). PCSK9 mRNA levels were measured using a mouse PCSK9 primer probe set, and normalized to G3PDH mRNA levels and/or RIBOGREEN® levels.

ISIS 394814 (GAGCAACTTCGGAGGCAGC, SEQ ID NO: 456) was identified as a potent inhibitor of mouse PCSK9. PCSK9 mRNA levels ISIS 394814 yielded a 50% reduction in PCSK9 mRNA at a concentration of 25 nM (i.e., an IC50 of 25 nM) after a 24 hour incubation with primary mouse hepatocytes. No effect on cultured cell viability was observed.

Example 11: Antisense Reduction of PCSK9 mRNA in an Animal Model of Hyperlipidemia: High Fat Fed Mice Treatment C57BL/6 mice fed a high-fat diet are routinely employed as an animal model of hyperlipidemia, as well as an animal model of atherosclerosis. Accordingly, to evaluate the effects of PCSK9 antisense inhibition on serum lipid levels in vivo, ISIS 394814 was evaluated in C57BL/6 mice fed a high-fat diet. C57BL/6 mice 4-5 weeks of age were obtained from the Jackson Laboratory and maintained on a diet consisting of 60% fat. Treatment groups of 5 mice each were as follows: a group treated with ISIS 394814; a control group treated with saline; and control group treated with an oligonucleotide not complementary to any known gene sequence (ISIS 141923). Oligonucleotide or saline was administered intraperitoneally twice weekly, for a period of 6 weeks; oligonucleotide doses were 50 mg/kg. After the treatment period, whole blood was collected for analysis of serum parameters, and whole liver was collected for RNA analysis, protein analysis, and histological evaluation. Statistical analyses included a nonparametric, two-tailed t-test comparison of experimental samples (ISIS 394814) to control samples (saline or control oligonucleotide).

RNA Analysis

Liver RNA was isolated for real-time PCR analysis of PCSK9, LDL-receptor and apolipoprotein B mRNA levels. Treatment with ISIS 394814 resulted in a 92% reduction in PCSK9 mRNA levels, while no significant reduction in PCSK9 mRNA levels was observed in ISIS 141923-treated or saline-treated mice. Antisense inhibition of PCSK9 expression did not significantly affect liver LDL-receptor or liver apolipoprotein B mRNA levels.

Protein Analysis

Immunoblotting was performed to assess the effects of PCSK9 antisense inhibition on LDL-receptor protein and apolipoprotein B levels. Protein isolated from mouse liver was subjected to electrophoresis, transferred to a polyvinylidene-fluoride membrane, and subsequently probed with an anti-mouse LDL-receptor antibody and a scavenger receptor B1 (SR-B1) antibody. Mouse plasma was similarly subjected to electrophoresis and immunoblotting using an anti-mouse apolipoprotein B antibody. Secondary antibodies conjugated to peroxidase were used to detect primary antibodies. Protein bands were visualized using the ECL plus Western blot detection kit (Amersham Biosciences, UK) and quantified using ImageQuant™ analysis software (MolecularDynamics, Santa Clara, Calif.).

While LDL-receptor mRNA levels were not significantly affected, antisense inhibition of PCSK9 resulted in an approximate 2-fold increase in the level of hepatic LDL-receptor protein relative to 141923-treated controls. No changes in SR-B1 protein were observed. Furthermore, serum apoB-100 levels were significantly reduced by 50%, relative to 141923-treated controls. Serum apoB-48 levels were significantly increased by approximately 3-fold relative to 141923-treated controls. No significant changes in apoA-I protein were observed, relative to 141923-treated controls.

The mRNA levels of the RNA editing enzyme apobec-1 were also measured. Apobec-1 is responsible for the RNA editing that produces apoB-48 in murine liver and intestine. Human apobec-1 is expressed only in intestinal cells, thus these cells are the source of apoB-48 in humans. Antisense inhibition of PCSK9 resulted in an increase in murine hepatic apobec-1 mRNA levels by approximately 2.7 fold compared to saline-treated controls Serum Lipid Analysis Plasma concentrations of total cholesterol, LDL-C, HDL-C, free cholesterol, triglycerides, glucose, ketones, transaminases, and phospholipids were measured using an automated clinical chemistry analyzer (Hitachi Olympus AU400e, Melville, N.Y.). Serum lipoprotein and cholesterol profiling was performed as described by Crooke et al. (Lipid Res., 2005, 46, 872-884) using a Beckman System Gold 126 HPLC system, a 507e refrigerated autosampler, a 126 photodiode array detector (Beckman Instruments, Fullerton, Calif.), and a Superose 6 HR 10/30 column (Pfizer, Chicago, Ill.). HDL, LDL and VLDL fractions were measured at a wavelength of 505 nm and validated with a cholesterol calibration kit. (Sigma).

Administration of ISIS 394814 resulted in a 52% reduction in total cholesterol (saline, 183 mg/dL±18; ISIS 141923, 194 mg/dL±14; ISIS 394814, 87 mg/dL±19, p<0.005) and a 36% reduction in LDL-C (saline 22 mg/dL±4; ISIS 141923, 25 mg/dL±2; ISIS 394814, 14 mg/dL±2, p<0.005). Serum free cholesterol was reduced by 25% (saline 41 mg/dL±10; ISIS 141923, 58 mg/dL±3; ISIS 394814, 31 mg/dL±5, p<0.005) and phospholipids were reduced 54% (saline, 354 mg/dL±29; ISIS 141923, 383 mg/dL±21; ISIS 394814, 169 mg/dL±35, p<0.0001). HDL-C was also reduced by approximately 54% (saline, 183 mg/dL±18; ISIS 141923, 194 mg/dL±14; ISIS 394814, 87 mg/dL±19; p<0.0001). HPLC profiling confirmed the reduction of LDL and HDL lipid classes.

Liver Triglyceride Analysis

Liver triglyceride content was measured according to routine experimental procedures, for example, per procedures described by Desai et al., Diabetes, 2001, 50:2287-2295.

Antisense inhibition of PCSK9 for 6 weeks reduced liver triglyceride content by approximately 65% (p=0.01) relative to saline controls. No statistically significant changes in liver triglyceride content following 141923 treatment were observed.

Accordingly, one embodiment is a method of lowering LDL-C levels through the administration of an antisense oligonucleotide targeted to a PCSK9 nucleic acid. An additional embodiment includes a method of lowering total cholesterol through the administration of an antisense oligonucleotide targeted to a PCSK9 nucleic acid. An addition embodiment is lowering liver triglycerides by administering an antisense oligonucleotide targeted to a PCSK9 target nucleic acid.

Example 12: Antisense Reduction of PCSK9 mRNA in LDL-R Deficient/apoB-100 Animals LDL-receptor (LDL-R)-deficient/apoB-100 animals do not express the LDL-R gene, and express only the apoB-100 form of apoB. PCSK9 antisense oligonucleotide was administered to LDL-R deficient/apoB-100 mice, to evaluate the effects of antisense inhibition of PCSK9 in the absence of the LDL-R. Mice 4-5 weeks of age were maintained on a standard mouse diet. Treatment groups of 5 mice each were as follows: a group treated with ISIS 394814; a control group treated with saline; and control group treated with an oligonucleotide not complementary to any known gene sequence (ISIS 141923). Oligonucleotide or saline was administered intraperitoneally twice weekly, for a period of 6 weeks; oligonucleotide doses were 50 mg/kg (100 mg/kg/wk total). Real-time PCR of liver mRNA and serum analyses were performed as described for the C57Bl/6 study.

Antisense inhibition of PCSK9 reduced liver PCSK9 mRNA by approximately 90%, relative to saline controls. However, no reduction in serum cholesterol was observed. Liver triglyceride levels were unaffected by antisense inhibition of PCKS9 in these mice. An 80% increase in liver apobec1 mRNA levels was observed, relative to saline controls. These data suggest that a functioning LDL-R is required for cholesterol and liver triglyceride reduction via PCSK9 antisense inhibition.

Example 13: Antisense Reduction of PCSK9 mRNA in Mouse Primary Hepatocytes

Antisense oligonucleotides targeted to PCSK9 were tested for antisense inhibition of PCSK9 in mouse primary hepatocytes. Mouse primary hepatocytes were purchased from a commercial supplier, and cultured according to routine culture procedures. Cells were treated with 6.25, 12.5, 25, 50, 100, or 200 nM of antisense oligonucleotide for a period of 24 hours, after which RNA was isolated and PCSK9 mRNA was measured by real-time PCR as described herein.

The antisense oligonucleotides tested in human primary hepatocytes were Isis 395165, 395185, 395186, 395187, 405879, 405881, 405891, 405988, 405994, and 406008. The antisense oligonucleotides inhibited PCSK9 in a dose-dependent manner in human primary hepatocytes as shown in Table 26.

TABLE 26

Dose-Dependent Reduction PCSK9 mRNA in Mouse Primary Hepatocytes

| ISIS No | 6.25 nM | 12.5 nM | 25.0 nM | 50.0 nM | 100.0 nM | 200.0 nM |
| --- | --- | --- | --- | --- | --- | --- |
| 395165 | 95.2 | 94.9 | 81.7 | 66.3 | 57.5 | 29.9 |
| 395185 | 109.2 | 100 | 90.5 | 81.2 | 64.7 | 35.8 |
| 395186 | 101.9 | 91.5 | 77.8 | 59.1 | 39.5 | 13.7 |
| 395187 | 102.4 | 96.1 | 83.9 | 66.4 | 40 | 15.3 |
| 405879 | 107.3 | 97.5 | 87.8 | 76.6 | 63 | 43.1 |
| 405881 | 104.8 | 102.1 | 98.1 | 84.9 | 68.7 | 48.9 |
| 405891 | 104.9 | 103.3 | 101.5 | 88.9 | 79.6 | 49.5 |
| 405988 | 97.3 | 101.1 | 91.7 | 82.3 | 61.2 | 34.8 |
| 405994 | 110.2 | 101 | 111.6 | 94.4 | 80.1 | 57.7 |
| 406008 | 99.5 | 91.3 | 83.9 | 73.7 | 61.8 | 39.4 |
| 157700 | 97.8 | 98.3 | 96.2 | 94.3 | 83.2 | 76.4 |
| 141923 | 84.3 | 80 | 79.9 | 77.3 | 98.8 | 64.2 |

Example 14: Antisense Reduction of Human PCSK9 mRNA in Hep3B and HeLa Cells: Dose Response Experiment A subset of the antisense oligonucleotides that inhibited PCSK9 expression at high levels in the cell culture systems described above was selected for further screening. The group of selected antisense compounds is shown in Table 27. Table 27 shows the Isis number, nucleotide sequence, and percent inhibition obtained in Hep3B cells using the protocol disclosed in Example 3 (see Table 17) for the various antisense compounds.

TABLE 27

| Isis No. | Sequence 5'-3' | Motif | % inhibition | SEQ ID NO |
| --- | --- | --- | --- | --- |
| 405881 | CACCCTTGGCCACGCCGGCA | 5-10-5 | 98.3 | 250 |
| 399819 | CCCACTCAAGGGCCAGGCCA | 5-10-5 | 93.4 | 65 |
| 395165 | ACCCTTGGCCACGCCGGCAT | 5-10-5 | 96.7 | 28 |
| 405879 | CCTTGGCCACGCCGGCATCC | 5-10-5 | 94.1 | 248 |
| 406008 | CTTGGTGAGGTATCCCCGGC | 5-10-5 | 95.2 | 188 |
| 405891 | TCCTCAGGGAACCAGGCCTC | 5-10-5 | 96.1 | 352 |
| 395186 | CTTTGCATTCCAGACCTGGG | 5-10-5 | 93.7 | 60 |
| 405988 | GGCAGCACCTGGCAATGGCG | 5-10-5 | 95.9 | 381 |
| 405994 | GCAGTGGACACGGGTCCCCA | 5-10-5 | 95.2 | 400 |

TABLE 27-continued

| Isis No. | Sequence 5'-3' | Motif | % inhibition | SEQ ID NO |
|---|---|---|---|---|
| 406023 | TGGTATTCATCCGCCCGGTA | 5-10-5 | 92.5 | 212 |
| 395187 | GGCAGCAGATGGCAACGGCT | 5-10-5 | 92.7 | 62 |
| 395185 | CACGGGTCCCCATGCTGGCC | 5-10-5 | 92.7 | 59 |
| 406033 | CCTGCCAGGTGGGTGCCATG | 5-10-5 | 91.2 | 237 |
| 405923 | GGCATTGGTGGCCCCAACTG | 5-10-5 | 94.3 | 288 |
| 399900 | GGTCCTCAGGGAACCAGGCC | 3-14-3 | 92.0 | 50 |
| 405995 | TGGCAGTGGACACGGGTCCC | 5-10-5 | 92.4 | 402 |
| 405991 | GACACGGGTCCCCATGCTGG | 5-10-5 | 91.9 | 394 |
| 406005 | CGGGCAGTGCGCTCTGACTG | 5-10-5 | 83.4 | 180 |
| 399793 | CCTCGGAACGCAAGGCTAGC | 5-10-5 | 77.9 | 8 |
| 395152 | ACGCAAGGCTAGCACCAGCT | 5-10-5 | 93.3 | 7 |

The $IC_{50}$ of the various antisense compounds was determined using different cell culture systems. Antisense oligonucleotides targeted to PCSK9 were tested at various doses in Hep3B or HeLa cells, for example. Cells were plated at densities of 4,500 cells or 5,000 per well, respectively, and treated with of antisense oligonucleotides at various concentrations. After a treatment period of approximately 24 hours, RNA was isolated from the cells and PCSK9 mRNA levels were measured by quantitative real-time PCR, as described herein, relative to untreated control cells. Two different human PCSK9 primer probe sets were used to measure mRNA levels. Results with Primer Probe Set 2740 are shown in Table 28. PCSK9 mRNA levels were adjusted according to total RNA content as measured by RIBOGREEN®. Table 28 shows $IC_{50}$ values (nM) obtained from two experiments with Hep3B cells and from one experiment with HeLa cells.

TABLE 28

| | IC50 values | | | | |
|---|---|---|---|---|---|
| ISIS # | Hep3B IC$_{50}$ (nM) | Hep3B IC$_{50}$ (nM) | HeLa IC$_{50}$ (nM) | PCSK9 Target Sequence | SEQ ID NO |
| 405881 | 21 | 26 | 13 | CACCCTTGGCCACGCCGGCA | 250 |
| 399819 | 21 | 28 | 12 | CCCACTCAAGGGCCAGGCCA | 65 |
| 395165 | 23 | 28 | 13 | ACCCTTGGCCACGCCGGCAT | 28 |
| 405879 | 24 | 28 | 14 | CCTTGGCCACGCCGGCATCC | 248 |
| 406008 | 31 | 35 | 8 | CTTGGTGAGGTATCCCCGGC | 188 |
| 405891 | 32 | 38 | 14 | TCCTCAGGGAACCAGGCCTC | 352 |
| 395186 | 33 | 33 | 7 | CTTTGCATTCCAGACCTGGG | 60 |
| 405988 | 34 | 42 | 8 | GGCAGCACCTGGCAATGGCG | 381 |
| 405994 | 35 | 39 | 9 | GCAGTGGACACGGGTCCCCA | 400 |
| 406023 | 40 | 50 | 18 | TGGTATTCATCCGCCCGGTA | 212 |
| 395187 | 41 | 44 | 8 | GGCAGCAGATGGCAACGGCT | 62 |
| 395185 | 42 | 43 | 11 | CACGGGTCCCCATGCTGGCC | 59 |
| 406033 | 44 | 61 | 15 | CCTGCCAGGTGGGTGCCATG | 237 |
| 405923 | 47 | 41 | 20 | GGCATTGGTGGCCCCAACTG | 288 |
| 399900 | 48 | 44 | 21 | GGTCCTCAGGGAACCAGGCC | 50 |
| 405995 | 48 | 63 | 12 | TGGCAGTGGACACGGGTCCC | 402 |
| 405991 | 63 | 52 | 15 | GACACGGGTCCCCATGCTGG | 394 |
| 406005 | 63 | | | CGGGCAGTGCGCTCTGACTG | 180 |
| 399793 | >75 | | | CCTCGGAACGCAAGGCTAGC | 8 |
| 395152 | | 46 | 16 | ACGCAAGGCTAGCACCAGCT | 7 |

Several of the antisense compounds examined above were selected for further study. These antisense compounds exhibited at least about 93% inhibition of human PCSK9 mRNA expression in the Hep3B cell culture system, as shown in Tables 17-19, for example. As shown in Table 28, the selected antisense compounds also displayed $IC_{50}$ parameters of less than about 45 nM when tested with Hep3B cells and less than about 15 nM when tested with HeLa cells. The selected antisense compounds, listed in Table 29, are Isis 405881, Isis 395165, Isis 405879, Isis 406008, Isis 405891, Isis 395186, Isis 405988, Isis 405994, Isis 395187, and Isis 395185. Isis 405879, for example, showed superior results in both Hep3B and HeLa cells, with $IC_{50}$ values of about 26 nM and 14 nM, respectively.

Example 15: Dose-Dependent Antisense Reduction of PCSK9 mRNA in Human Primary Hepatocytes; Cynomolgus Monkey ("Cyno") Primary Hepatocytes; and Human HEK-293 Cells The selected antisense oligonucleotides were further tested for dose dependent antisense inhibition in human primary hepatocytes, cyno primary hepatocytes, and HEK-293 cells expressing human PCSK9. Cells were purchased from commercial suppliers and cultured according to routine culture procedures. Cells were treated with 10, 25, 50, 150, or 300 nM antisense oligonucleotide (i.e., a five-point dose response test) for a period of 24 hours, after which RNA was isolated. PCSK9 mRNA was measured by real-time PCR, as described herein.

Figure 2:
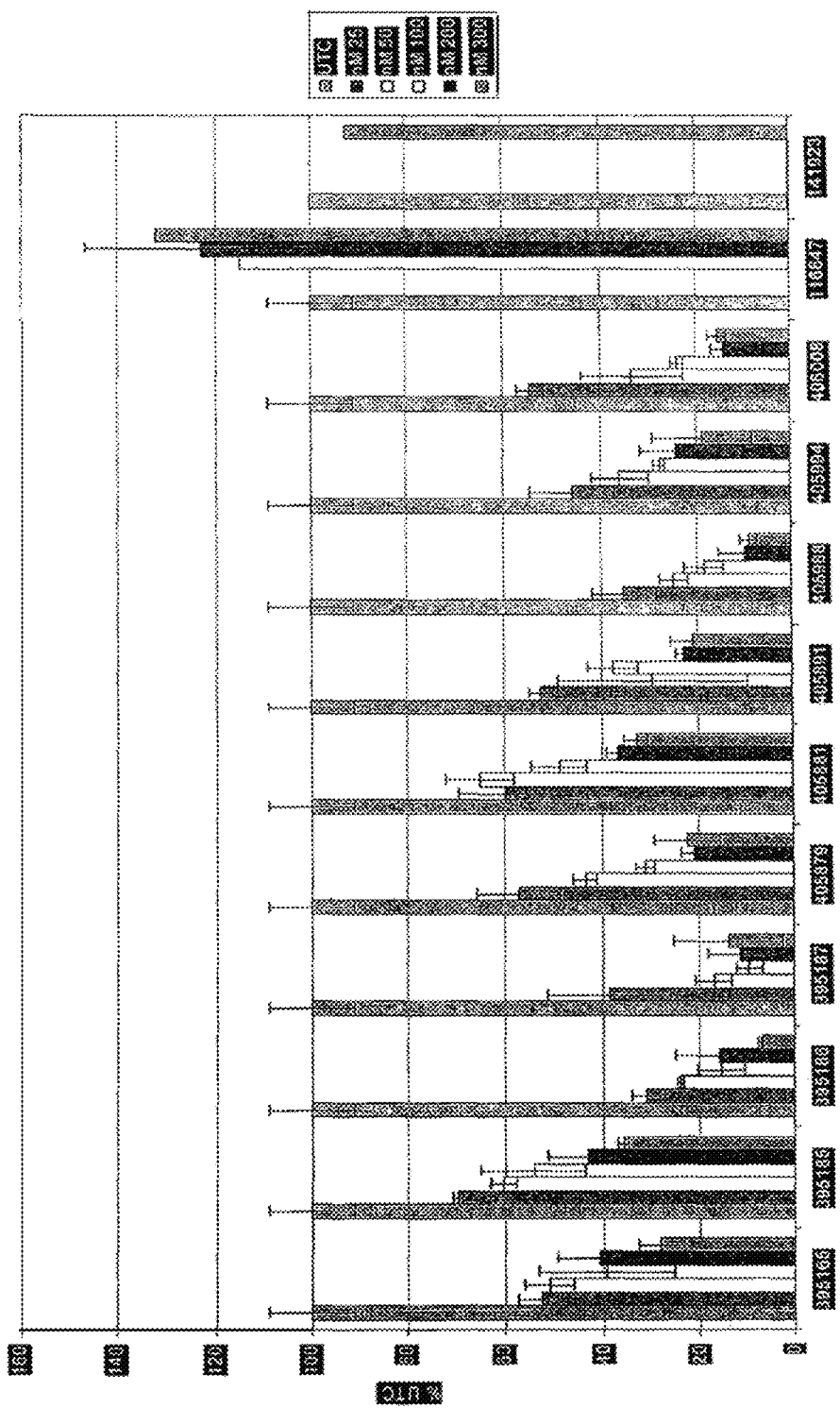
FIG. 2 depicts the results of a five-point dose response experiment with exemplary antisense compounds in HEK-293 cells. The antisense compounds are identified by Isis number. The bars from left to right represent PCSK9 expression in relative units at 0 nM, 25 nM, 50 nM, 100 nM, 200 nM, and 300 nM antisense oligonucleotides.
Figure 3:
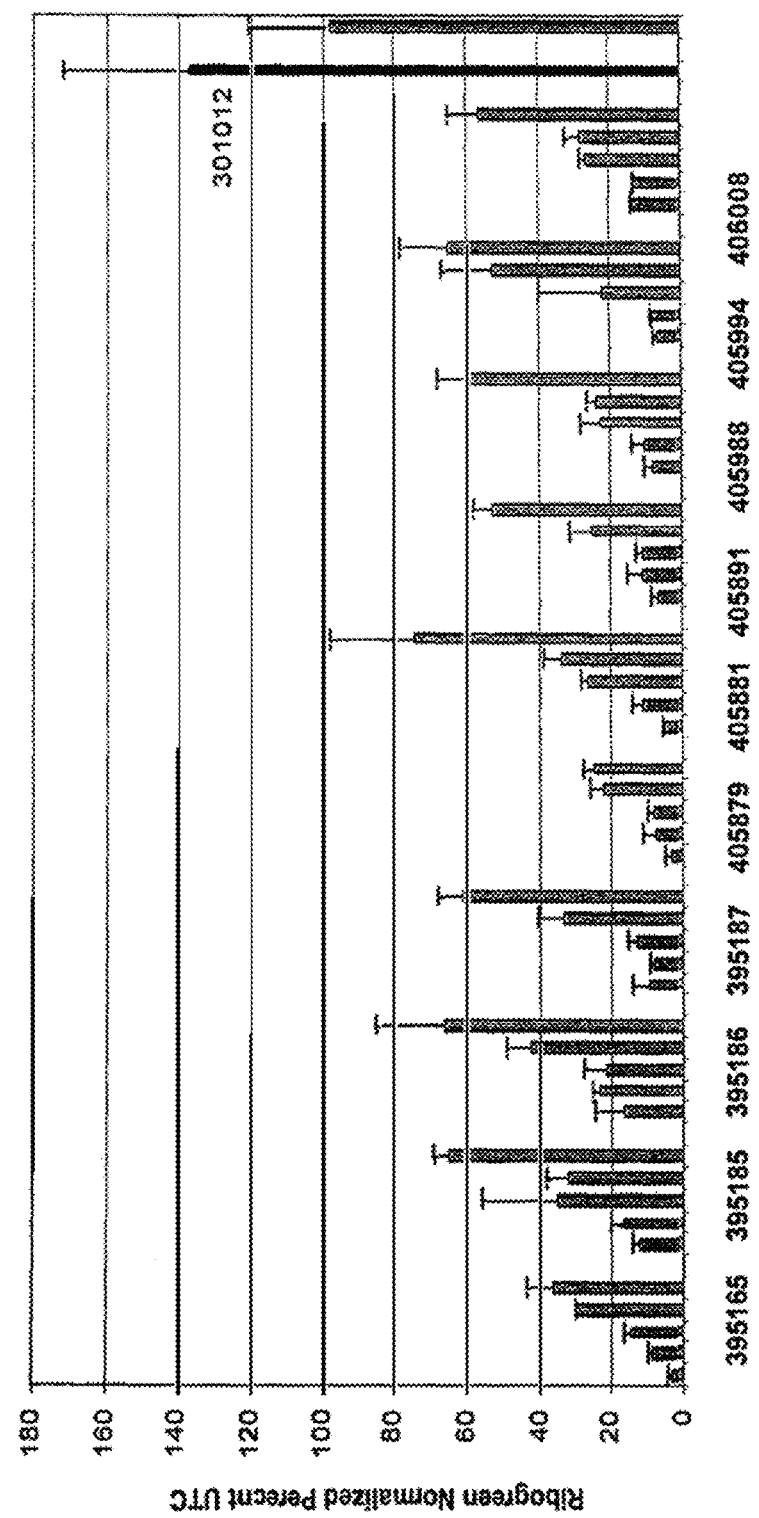
FIG. 3 depicts the results of a five-point dose response experiment with exemplary antisense compounds in cyno primary hepatocytes. The antisense compounds are identified by Isis number. The bars from left to right represent PCSK9 expression in relative units at 300 nM, 150 nM, 50 nM, nM, and 10 nM antisense oligonucleotides. Control values are shown in the rightmost two bars.

Results of the five-point dose response tests using HEK-293 cells are shown in FIG. 2. Results of the five-point dose response tests using cyno primary hepatocytes are shown in FIG. 3. The $IC_{50}$ results, expressed in nM units, for the five-point dose response test using human primary hepatocytes, cyno primary hepatocytes, HEK-293 cells, Hep3B cells, and HeLa cells are summarized in Table 29.

TABLE 29

IC$_{50}$ (nM) for Selected Antisense Compounds

| | Isis No. | | | | | | | | | |
|---|---|---|---|---|---|---|---|---|---|---|
| SEQ ID NO: | 395165 28 | 395185 59 | 395186 60 | 395187 62 | 405879 248 | 405881 250 | 405891 352 | 405988 381 | 405994 400 | 406008 188 |
| Human Primary Hepatocytes | 24 | 33 | 39 | 30 | ND | 50 | 297 | 166 | 56 | 163 |
| Cyno Primary Hepatocytes | 5 | 17 | 18 | 14 | 2 | 19 | 10 | 12 | 21 | 11 |
| HEK-293 | 40 | 116 | 6 | 11 | 35 | 86 | 21 | 11 | 17 | 27 |
| Hep3B | 28 | 43 | 33 | 44 | 28 | 26 | 38 | 42 | 39 | 35 |
| HeLa | 13 | 11 | 7 | 8 | 14 | 13 | 14 | 8 | 9 | 8 |

ISIS 405879 was tested at various doses in human primary hepatocytes. RNA was isolated from the cells and PCSK9 mRNA levels were measured by quantitative real-time PCR, as described herein. Human PCSK9 primer probe set 2740 was used to measure mRNA levels. Results are shown in Table 29.1.

TABLE 29.1

Dose-dependent Reduction in Human PCSK9 mRNA Expression in Human Primary Hepatocytes

| ISIS NO. | 300 nM | 200 nM | 150 nM | 100 nM | 50 nM | 25 nM | 10 nM |
|---|---|---|---|---|---|---|---|
| 405879 | 13 | 18 | 26 | 30 | 27 | 54 | 75 |

Isis 405879 has an IC$_{50}$ value of 29 nM in human primary hepatocytes. Overall Isis 405879 displays superior activity, particularly in cyno primary hepatocytes. Isis 405879 was thus further tested in the various cell models, and the results of the additional testing are shown in Table 30. In these experiments, Isis 405879 was administered to the cells using lipofectin transfection reagents. PCSK9 mRNA was assayed by PCR following 24 hr incubation after transfection. These results confirm that Isis 405879 potently inhibits PCSK9 mRNA expression at low concentrations.

TABLE 30

Isis 405879 activity in cell culture models

| | Hep3B Cells (human) | HepG2 Cells (human) | HeLa Cells (human) | Hepatocyte Transgenic Mouse (h-PCSK9) | Primary Hepatocyte (human) | Primary Hepatocyte (cyno) | Transgenic HEK293 cells (h-PCSK9) |
|---|---|---|---|---|---|---|---|
| Mean IC$_{50}$ (nM) | 17 | 5 | 14 | 140 | 22 | 7.4 | 18 |

These experiments confirm that the presently disclosed antisense oligonucleotides are capable of potently inhibiting PCSK9 mRNA expression in a variety of cell model systems, including a human primary cell line. Exemplary antisense compounds inhibit PCSK9 mRNA expression with IC$_{50}$ values in the nM range.

The transgenic PCSK9 cDNA construct expressed in mouse hepatocytes is thought to be rapidly exported to the cytoplasm, because it does not require post-transcriptional editing. The antisense oligonucleotides provided herein act by recruiting the RNase H enzyme, which is restricted to the nucleus. Therefore, inhibition by antisense oligonucleotides in this cell type is significantly diminished.

Example 16: In Vivo Testing Procedures 16.1. High Fat (HF)-Fed Hyperlipidemic Mouse Model Antisense compounds may be tested in a high fat-fed, hyperlipidemic mouse model to test efficacy of the antisense compounds in reducing PCSK9 mRNA expression, increasing LDL-R expression, reducing total cholesterol and LDL, and affecting other metrics of antisense compound efficacy. A representative hyperlipidemic mouse model is described in Graham et al., *J. Lipid Res.* (2007) 48: 763-767.

All animal experiments were conducted in accordance with Institutional American Association for the Accreditation of Laboratory Animal Care guidelines. C57BL/6 mice were obtained from Jackson Laboratory (http://www.jax.org). A majority of the mice were male, and studies were initiated when animals were 4-5 weeks of age. The mice were maintained on a 12 h light/12 h dark cycle and fed ad libitum. C57BL/6 mice were fed a diet consisting of 60% lard (Research Diets, New Brunswick, N.J.), whereas experimental Ldlr-deficient/apoB-100 mice were fed regular chow.

Antisense compounds were administered twice weekly (50 mg/kg) for 6 weeks by intraperitoneal injection (10 mg/mL dosing solution formulated in saline; saline control). After the treatment period, whole blood was collected for analysis of serum parameters, and whole liver was collected for RNA analysis, protein analysis, and histological evaluation.

16.2. H-ApoB/CETP Transgenic Mouse Model

A transgenic mouse model that expresses both human apolipoprotein (apo) B and human cholesteryl ester transfer protein (CETP) provides another useful animal model system to test the efficacy of the presently disclosed antisense compounds. The lipoprotein cholesterol distribution in the serum of a chow-fed h-apoB/CETP mouse resembles a human profile. Specifically, the percentages of total cholesterol within the HDL, LDL, and VLDL fractions of apoB/CETP animals are approximately 30%, 65%, and 5%, respectively, similar to the distribution of cholesterol in the plasma of normolipidemic humans. The h-apoB/CETP mouse model is described further in Grass et al., *J. Lipid Res.* (1995) 36: 1082-1091.

16.3. H-PCSK9 Transgenic Mouse Model

A transgenic mouse expressing human PCSK9 provides another useful animal model to study in vivo repression of PCSK9 mRNA by the present antisense compounds. H-PCSK9 transgenic mice overexpress human PCSK9 in liver and secrete large amounts of the protein into plasma, which increases plasma LDL-C concentrations to levels similar to those of LDLR-knockout mice. H-PCSK9 transgenic mice were constructed by inserting a cDNA encoding human PCSK9 into a pLiv-11 vector that contained the constitutive human apoE promoter and its hepatic control region, as described in Simonet et al., *J. Biol. Chem.* (1993) 268: 8221-8229. Transgenic mice were generated by injecting linearized pLiv-11-hPCSK9 into the fertilized eggs as described in Shimano et al., *J. Clin. Invest.* (1996) 98: 1575-1584. H-PCSK9 transgenic mice are further described in Lagace et al., *J. Clin. Invest.* (2006) 116: 2995-3005.

16.4. Mouse and Rat Models for In Vivo Tolerability, Half-Life and Tissue Distribution Mouse (CD1) and rat (Sprague-Dawley) models were used to test the in vivo tolerability of various antisense compounds. In the mouse CD1 model, antisense compounds were overdosed at 100 mg/kg/wk for six weeks. Possible proinflammatory effects and hepatotoxcity were assayed following administration of the antisense compounds. Serum levels of aspartate aminotransferase (AST), alanine aminotransferase (ALT), blood urea nitrogen (BUN), creatinine, albumin, and bilirubin were assayed. Weights of livers, kidneys, and spleens of animals were determined. Histopathologic screening was conducted to detect hepatocellular swelling, multifocal apoptosis, inflammatory cell infiltrates in the liver or lungs, or follicular hyperplasia. Additional studies were conducted in the rat model to screen for renal toxicity or high renal accumulation and proinflammatory effects. In these experiments, antisense compounds were administered at 60 or 100 mg/kg/wk for six weeks. In addition to the markers examined above, the urine protein/creatine ratio and proteinuria were assayed.

The half-life of administered antisense compounds also was examined in the target organ, i.e., liver, in the mouse model. For these experiments, antisense compounds were administered twice a week for two weeks at 50 mg/kg, and target organs were then harvested and assayed for the presence of the antisense compounds, as described below.

The distribution of administered antisense compounds in various organs also was examined in the rat model. Rats in these studies were administered 20 mg/kg antisense compounds twice weekly for three weeks. Livers and kidneys of test animals were then harvested and assayed for the presence of the antisense compounds, as described below.

16.5. Cynomolgus Monkey (*M. fascicularis*) Model

Potencies and pharmacodynamics of antisense compounds were compared in a cyno model to identify the compounds exhibiting the best combination of high potency and low renal accumulation, when given subcutaneously to animals for a 5-week period. In another study, dosing was conducted over a 13-week period. The cyno monkey is widely used in toxicity testing, and a substantial historic toxicology database is available for this model.

The PCSK9 target sequence for an antisense compound may differ in humans versus cyno monkey. As a result, an antisense compound for use in humans may not be fully complementary to a monkey PCSK9 nucleic acid. Antisense compounds having identical target sequences in the two species are preferred. Isis 405881 and Isis 395165 each have a one nucleotide mismatch compared to the cyno sequence, meaning that these antisense compounds are less preferred in the cyno model.

Cyno monkeys (Charles River BRF, Inc.) were approximately 26 to 32 months old and 2.5 to 4 kg in weight on the first day of dosing. Monkeys were offered water ad libitum and fed a daily ration of 12 biscuits approximately 2 hours post dose. Antisense compounds were administered subcutaneously at 3 doses every other day during the first week, then by weekly injections. A low dose of 15 mg/kg was used to assess the potency of the antisense compounds. A high dose of 8 subcutaneous injections of 30 mg/kg over 5 weeks or 13 weeks was used to assay renal accumulation and pharmacodynamics. Antisense compounds were administered at a concentration of 60 or 120 mg/mL, respectively, in a vehicle of sterile phosphate buffered saline. Plasma concentrations of antisense compounds were determined at each dose level to estimate systemic exposure in monkeys following subcutaneous administration and to assess whether systemic exposure was altered after repeat dosing.

To measure the host reaction to the administered antisense compounds, 2 mL blood samples were collected from the femoral vein of host individuals in tubes of appropriate size containing $K_2EDTA$. Plasma was obtained by centrifugation and samples were stored frozen. The analysis of the plasma samples included a determination of the level of plasma PCSK9 protein. To measure an effect on pharmacodynamic end points, LDL, HDL, and apoB levels also were analyzed. To determine whether the host individuals suffered side effects, blood samples were further analyzed for an effect on the hematological parameters listed in Table 31 and the serum chemistry parameters listed in Table 32:

TABLE 31

| Hematology markers | |
|---|---|
| erythrocyte count | red cell distribution width |
| hemoglobin | platelet count |
| hematocrit | mean platelet volume |
| mean corpuscular volume | absolute total and differential leukocyte counts |
| mean corpuscular hemoglobin concentration | evaluation of cell morphology |
| absolute reticulocyte count | |

TABLE 32

| Serum chemistry markers | |
|---|---|
| aspartate aminotransferase | triglycerides |
| alanine aminotransferase | glucose |
| gamma glutamyltransferase | urea nitrogen |
| alkaline phosphatase | creatinine |
| total bilirubin | calcium |
| total cholesterol | phosphorus |

TABLE 32-continued

Serum chemistry markers

| | |
|---|---|
| total protein | sodium |
| albumin | potassium |
| globulins | chloride |
| albumin/globulin ratio | |

Possible additional side effects were determined by screening individuals administered antisense compounds for gross changes in organs or microscopic changes in tissues. A limited necropsy conducted on all test animals included gross examination of various organs and tissues. Terminal body weights were recorded, and kidneys and spleen were weighed for all test animals. For microscopic evaluation, liver, kidney, spleen and injection sites from all animals were fixed in 10% neutral buffered formalin and were processed, embedded in paraffin, sectioned, and stained with hematoxylin and eosin.

Representative tissue samples of liver and kidney cortex from each scheduled-necropsy monkey from the high-dose and control groups were collected for ultrastructural examination using electron microscopy. Thin slices (2-4 mm in thickness) of liver and kidney cortex were cut and transferred to a piece of dental wax containing a small volume of McDowell-Trump fixative. Thin slices were further minced into approximately 1×1-2 mm cubes in McDowell-Trump fixative and analyzed by electron microscopy.

To evaluate PCSK9 mRNA levels, samples from liver (approximately 1 g) were homogenized using a Polytron tissue disruptor in 10 mL of RLT solution (Qiagen) and snap-frozen and stored at −70° C. or colder. Additionally, samples (approximately 500 mg each) from kidney were collected and snap-frozen for mRNA analysis.

Tissue samples from liver and kidney cortex were also analyzed for the presence of the administered antisense compounds. Antisense compounds present in the tissues can be detected and quantified using capillary gel electrophoresis (CGE), as described in Leeds et al, *Drug Metab Dispos.* (1998) 26: 670-675, for example. In this procedure, tissues are weighed, mixed with an internal standard (e.g., a 27-mer (T) oligonucleotide) in proteinase K digestion buffer (2.0 mg/ml proteinase K in 20 mM Tris-HCl, pH 8.0, 20 mM EDTA, 100 mM NaCl, 0.5% Nonidet P-40), and homogenized. Overnight incubation at 37° C. is followed by phenol/chloroform extraction. Tissue extracts are purified by sequential anion-exchange solid-phase extraction (SPE) followed by reverse-phase SPE, described in Leeds et al., *Anal Biochem* (1996) 235: 36-43. Samples are further desalted by membrane dialysis before analysis using gel-filled capillaries, as described in Leeds et al. (1996).

Capillary gel electrophoresis separations can be performed as described by Leeds et al. (1998), using a Beckman P/ACE capillary electrophoresis instrument (model 5010) with a 27-cm column (effective length, 20 cm) containing 12% polyacrylamide, with 8.3 M urea in 100 mM Tris-borate, pH 8.5, as the running buffer. Separation is achieved at 50° C. and 550 V/cm. Oligomers eluting from the column are detected by UV absorption at 260 nm. Quantification of antisense oligonucleotides is based on the tissue weight extracted and the initial T27 concentration.

Example 17: In Vivo Testing Results

17.1. Reducing PCSK9 mRNA In Vivo Using a Murine Antisense Compound Correlates with In Vivo Plasma LDL-C and Liver TG Reduction In vivo pharmacodynamic studies were performed with the murine antisense compound Isis 394816 to validate the pharmacodynamic endpoint of PCSK9 mRNA reduction. Isis 394816 has the sequence 5' GGTAAGGTGCGGTAAGTCCT 3' (SEQ ID NO: 462), which targets position 3100 (5') of the coding sequence of murine PCSK9 mRNA (NCBI Accession No. NM_153565.1; SEQ ID NO: 463). Isis 394816 has a 3-14-3 motif.

Figure 4:
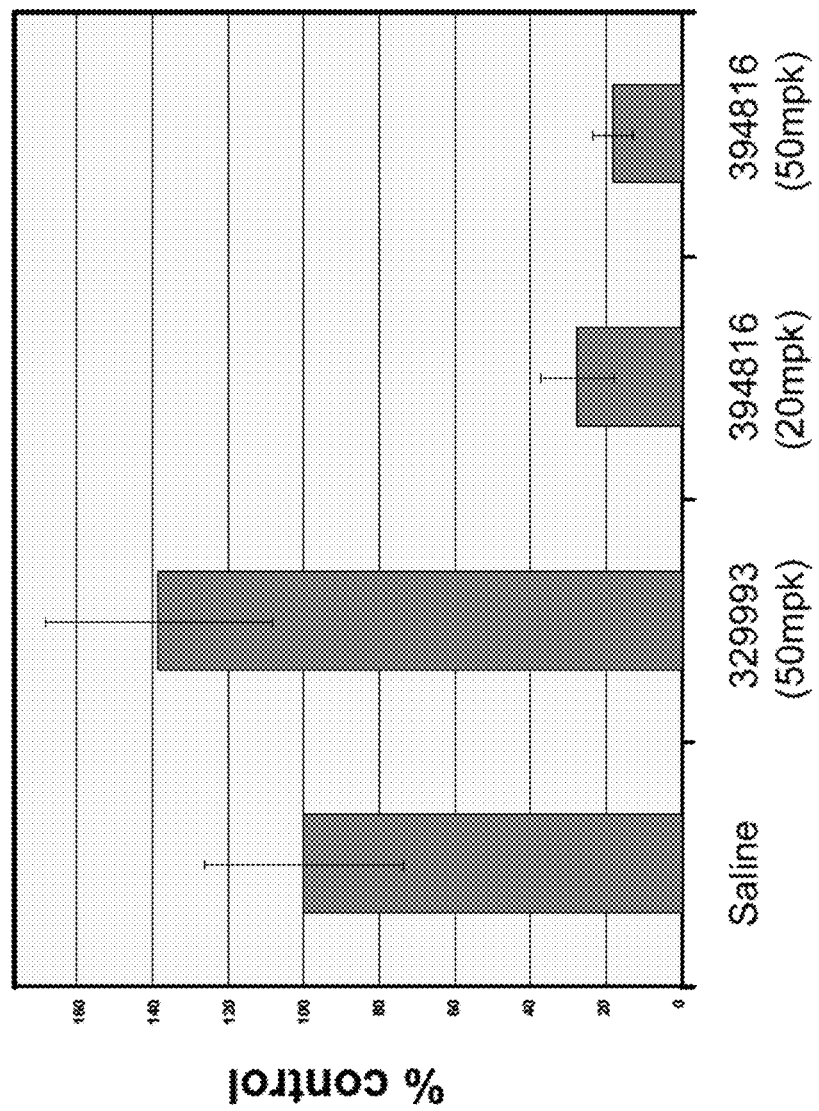
FIG. 4 depicts a reduction of murine PCSK9 mRNA expression (relative units) in the liver of h-apoB/CETP transgenic mice when administered Isis 394816. Isis 394816 was administered by intraperitoneal injection for 6 weeks at a dosing regimen of 20 mg/kg/wk or 50 mg/kg/wk. Isis 329993 was administered at 50 mg/kg/wk as a control.
Figure 5:
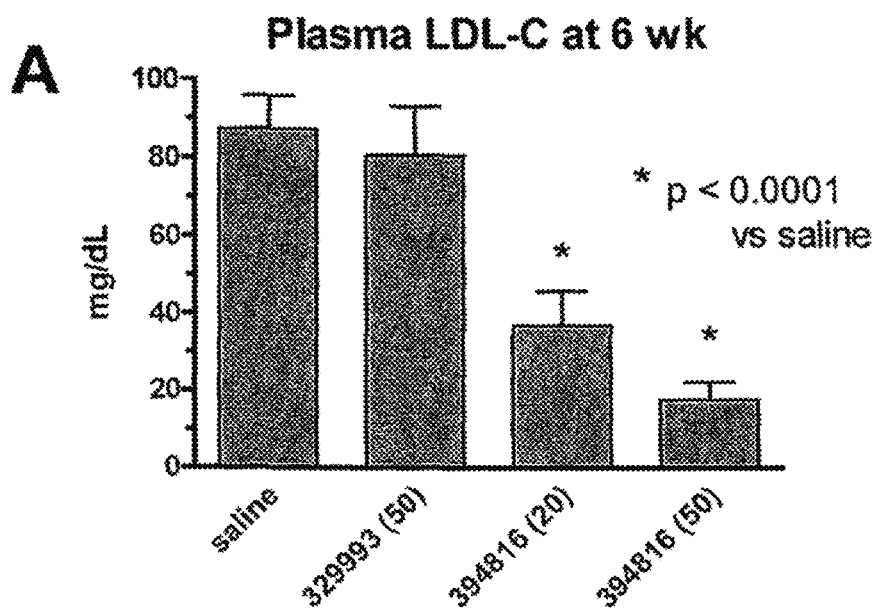
FIG. 5, Panel A, depicts inhibition of plasma LDL-C (mg/dL) in mice administered Isis 394816 at 20 mg/kg/wk or 50 mg/kg/wk.
Figure 5:
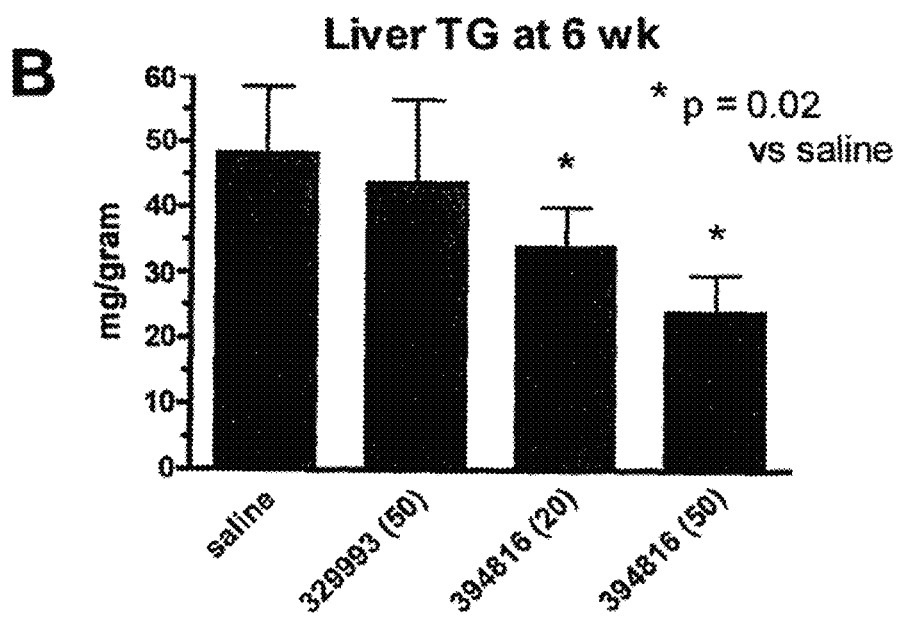

Isis 394816 was administered by intraperitoneal injection to an h-apoB/CETP transgenic mouse for 6 weeks at a dosing regimen of 20 mg/kg/wk or 50 mg/kg/wk. See Example 16.2. As shown in FIG. 4, Isis 394816 administered at either dose caused an approximate 80% reduction in PCSK9 mRNA expression in livers of test animals, compared to control animals. As shown in FIG. 5, panel A, Isis 394816 produced a significant ($p<0.0001$) decrease in the level of plasma LDL-C at the end of six weeks. Additionally, as shown in FIG. 5, panel B, Isis 394816 produced a significant ($p<0.02$) decrease in the level of liver TG at the end of six weeks.

Figure 6:
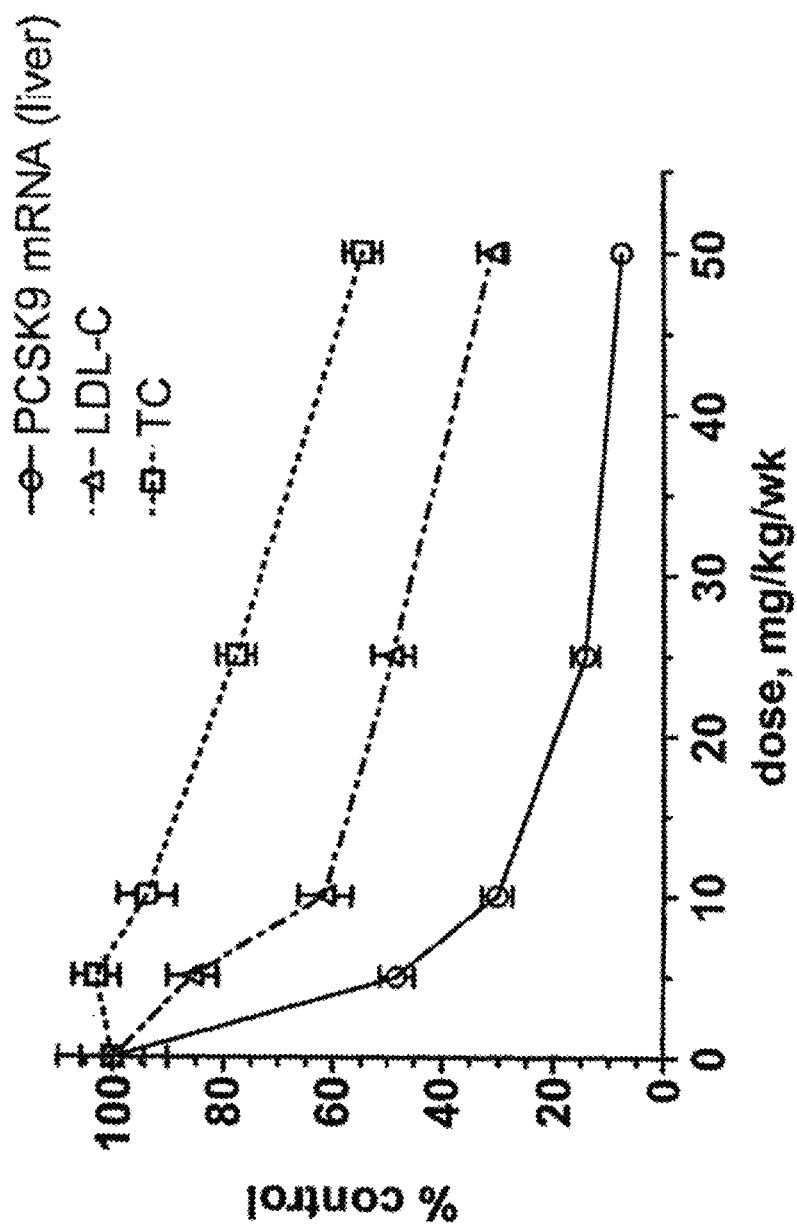
FIG. 6 depicts the dose-dependent inhibition (relative units) of liver PCSK9 mRNA, plasma LDL-C, and liver TG in response to the indicated doses of Isis 394816.
Figure 7:
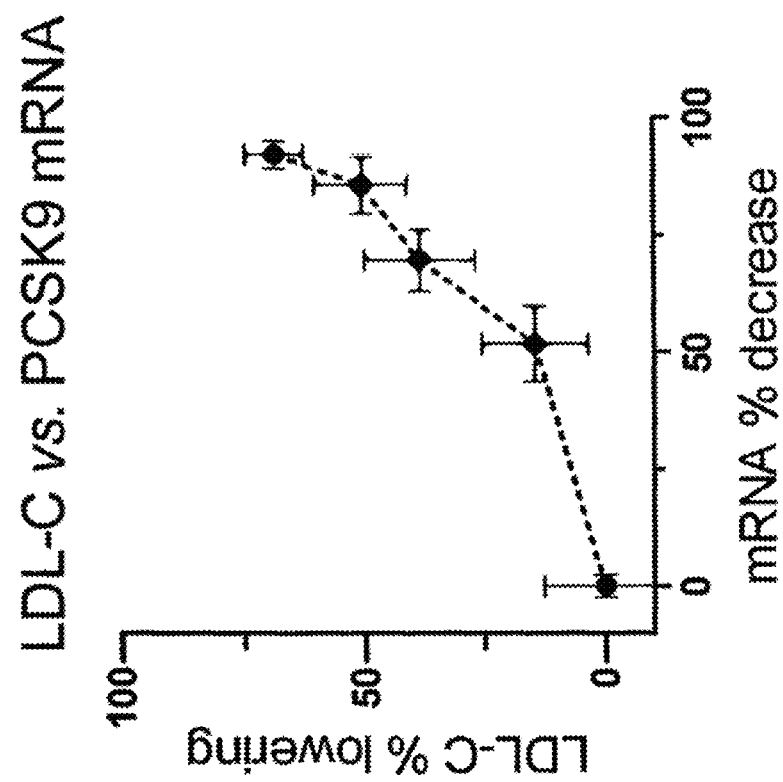
FIG. 7 depicts a correlation between LDL-C lowering and PCSK9 mRNA inhibition, using the data from FIG. 6.

Additionally, Isis 394816 reduced PCSK9 mRNA expression, plasma LDL-C, and liver TG in a dose dependent manner, as shown in FIG. 6. The potency of Isis 394816 was much higher in a hyperlipidemic mouse model (see Example 16.1.) than in a lean mouse model (data not shown). The reduction of plasma LDL-C positively correlated with the inhibition of PCSK9 mRNA levels in liver, shown in FIG. 7. These studies demonstrate that the reduction of liver PCSK9 mRNA correlates with the desired endpoint of reducing plasma LDL-C and liver TG. Accordingly, the reduction of liver PCSK9 mRNA provides a valid pharmacodynamic endpoint.

17.2. Differences in the Half-Life ($t_{1/2}$) of Antisense Compounds in Liver The half-lives of selected antisense compounds were assayed in mouse CD1 livers, according to the procedures set forth in Example 16.4. Half-lives varied among the tested antisense compounds, which again is attributable to differences in structural features of the antisense compounds, such as nucleotide sequences and/or motifs. For example, the half-life of Isis 405879 ($t_{1/2}$=27.7 days) was significantly higher than the half-life of Isis 395165 (20.4 days), although the target sequences of these two antisense compounds are shifted by only two nucleotides:

```
Isis 405879:
                                (SEQ ID NO: 248)
CCTTGGCCACGCCGGCATCC Isis 395165:
                                (SEQ ID NO: 28)
ACCCTTGGCCACGCCGGCAT
```

Half-life data for exemplary antisense compounds is summarized in Table 33. Isis 405879 displayed a particularly high half-life in liver.

TABLE 33

| Liver $t_{1/2}$ (days) | |
|---|---|
| Antisense Compound | Liver $t_{1/2}$ (d) |
| 395165 | 20.4 |
| 395185 | 20.2 |
| 395186 | 19.9 |
| 395187 | 13.7 |

TABLE 33-continued

| Liver $t_{1/2}$ (days) | |
| --- | --- |
| Antisense Compound | Liver $t_{1/2}$ (d) |
| 405879 | 27.7 |
| 405881 | 14.1 |
| 405891 | 17.1 |
| 405988 | 14.6 |
| 405994 | 20.2 |
| 406008 | 19.7 |

Figure 8:
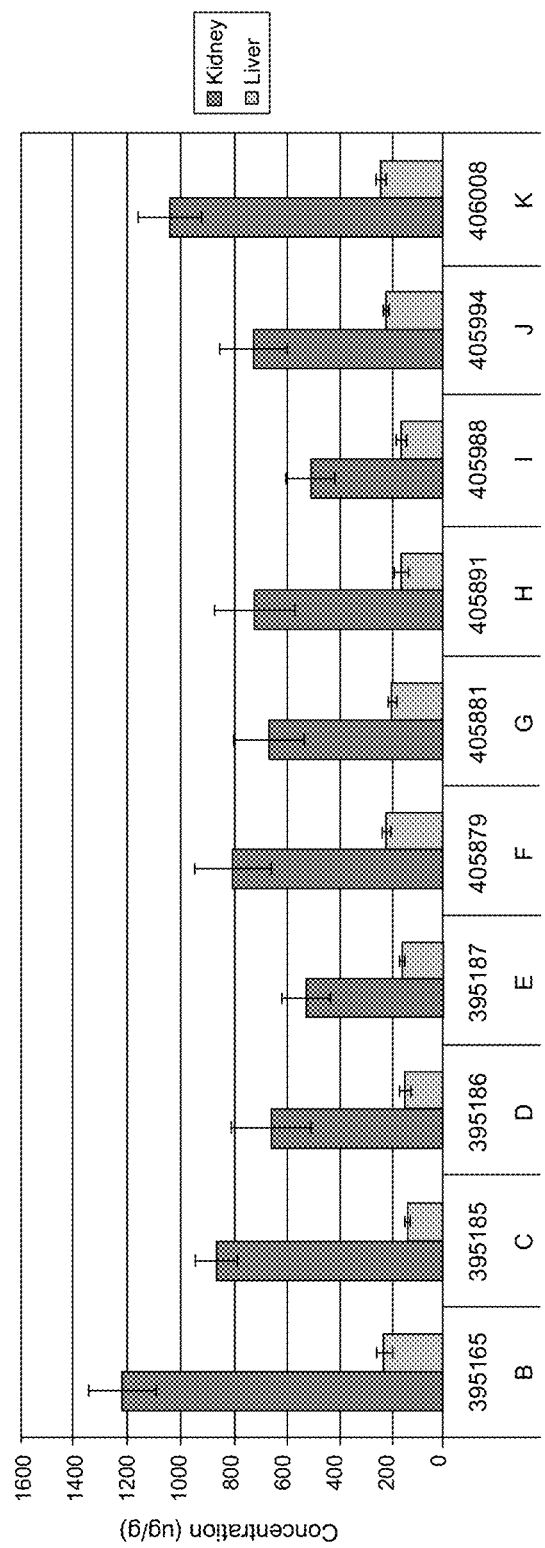
FIG. 8 depicts the accumulation of exemplary antisense compounds in rat tissues (μg/g tissue) following administration of antisense compounds. The antisense compounds are identified by Isis number. The bars from left to right represent antisense compound accumulation in kidney and liver.

17.3. Differences in the Liver and Kidney Distributions of Antisense Compounds The antisense compounds listed in Table 29 were administered to rats to determine the distribution of antisense compounds in liver and kidney. Accumulation of high levels of antisense compounds in the kidneys may cause adverse side effects. Antisense compounds were dosed and administered as described in Example 16.2. FIG. 8 shows the distribution of the antisense compounds shown in Table 29 in rat liver and kidneys. Isis 395185, Isis 395186, Isis 395187, Isis 405879, Isis 405881, Isis 405891, Isis 405988, and Isis 405994 show a particularly advantageous ratio of distribution between liver and kidney.

Figure 9:
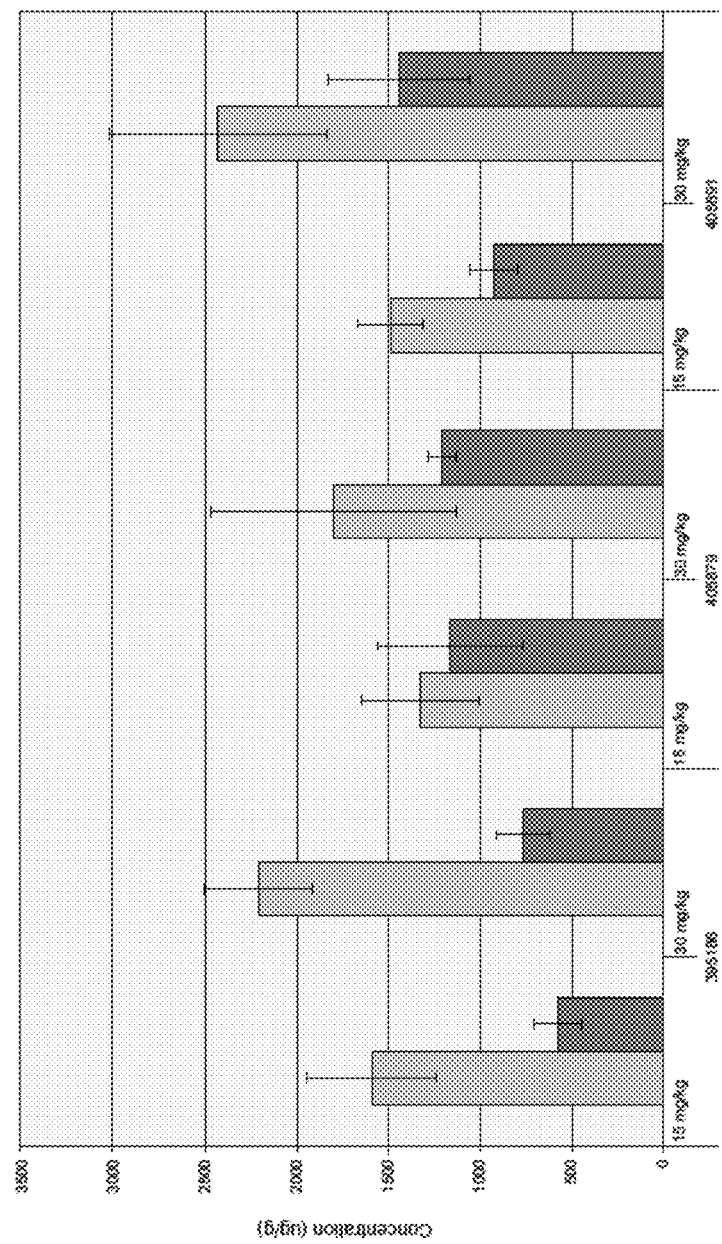
FIG. 9 depicts the accumulation of the identified antisense compounds in tissues (μg/g tissue) following administration to a cyno monkey. Accumulation at each dosing concentration (15 mg/kg and 30 mg/kg) is shown in cyno kidney (left side bar) and cyno liver (right side bar).

When tissue distribution was tested in a cyno model, further differences among antisense compounds were observed. Accumulation of Isis 395186, Isis 405879, and Isis 405891 in liver and kidney was examined after dosing each antisense compound at two concentrations. See Example 16.5. The results are shown in FIG. 9. Accumulation at each dosing concentration (15 mg/kg and 30 mg/kg) is shown for kidney (left side bar) and liver (right side bar). Isis 405879 advantageously accumulates at a high concentration in liver, even at a dose of 15 mg/kg, and accumulates at a low level in kidney. Specifically, Isis 405879 accumulated in kidneys at a concentration of 1300 µg/g (15 mg/kg dose) to 1800 µg/g (30 mg/kg dose). The average accumulation of antisense compounds in kidneys is 2500 µg/g (15 mg/kg dose) to 4000 µg/g (30 mg/kg dose). Variation in kidney and liver accumulation is attributable to structural differences, such as nucleotide sequences and/or motifs, between the antisense compounds.

17.4. Differences in Host Tolerance of Antisense Compounds

Rodent tolerability studies, conducted as described in Example 16.4, showed that antisense compounds were well tolerated. Following administration of the exemplary antisense compounds listing in Table 29, serum chemistry markers were normal, with some variably high ALT and AST levels observed for Isis 405988 and Isis 405994. Whole body weight and major organ weights in CD-1 mice also were not significantly affected by administration of the exemplary antisense compounds. Histological findings revealed differences between the various antisense compounds, but were consistent with the overall good tolerability for the antisense compounds. The results of the histological screens are shown in Table 34.

17.5. Results of the 5 wk Cyno Toxicology Study

Figure 25:
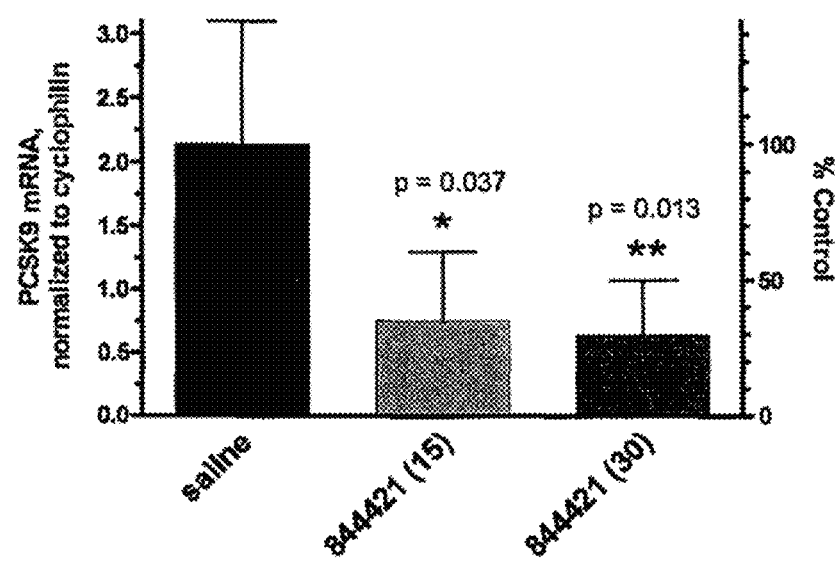
FIG. 25 depicts the Liver PCSK9 mRNA concentration in cyno monkeys after 13 weeks of treatment. The numbers in parentheses are administered doses in mg/kg.

The methods used to conduct the 5 wk cyno toxicology study are described in Example 16.5. Isis 405879 is referred to as BMS-844421 below and in the corresponding figures. The PCSK9 mRNA levels assayed by q-RT-PCR in the cyno liver tissue samples were decreased by BMS-844421 treatment by an average of 65% and 70% (average of males and females) versus saline controls at the low and high doses, respectively (FIG. 25). The effect was seen in both females and male monkeys, despite relatively high variability of mRNA level between animals. No dose-dependency was seen between the 2 doses. The data are mean+/−for male and female animals combined.

Figure 26:
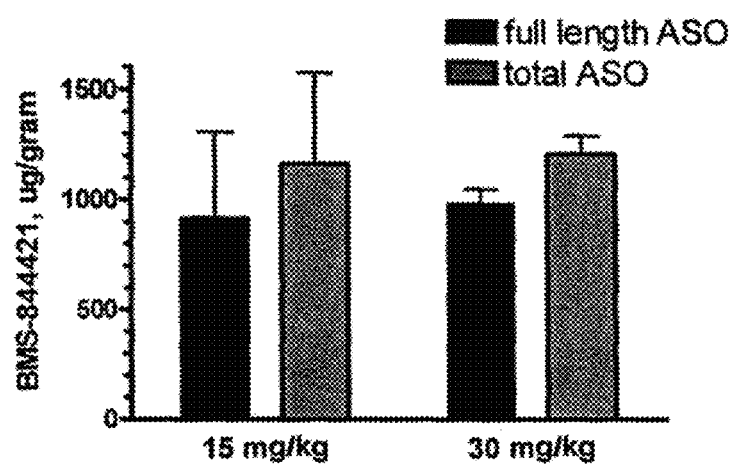
FIG. 26 depicts the concentration of BMS-844421 in the liver of cyno monkeys after 13 weeks of treatment.

The levels of BMS-844421 ASO were measured in liver at the end of the 5 wk study. As shown in FIG. 26, liver full-length BMS-844421 levels reached ~1 mg/gram tissue in both dose groups. This level is consistent with values from previous experiences with other liver-targeting ASOs. Most of the compound was detected as intact full-length BMS-844421. No dose-dependency was seen in the ASO liver accumulation data, in agreement with the lack of dose-dependent effects on liver PCSK9 target mRNA.

Figure 27:
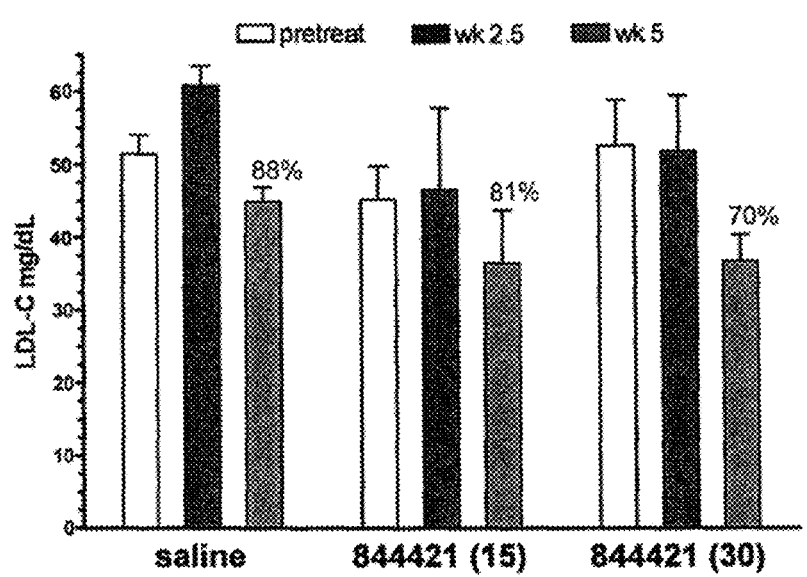
FIG. 27 depicts the average serum LDL-C levels in the cyno monkey study. The numbers in parentheses are administered doses in mg/kg.
Figures 28A, 28B:
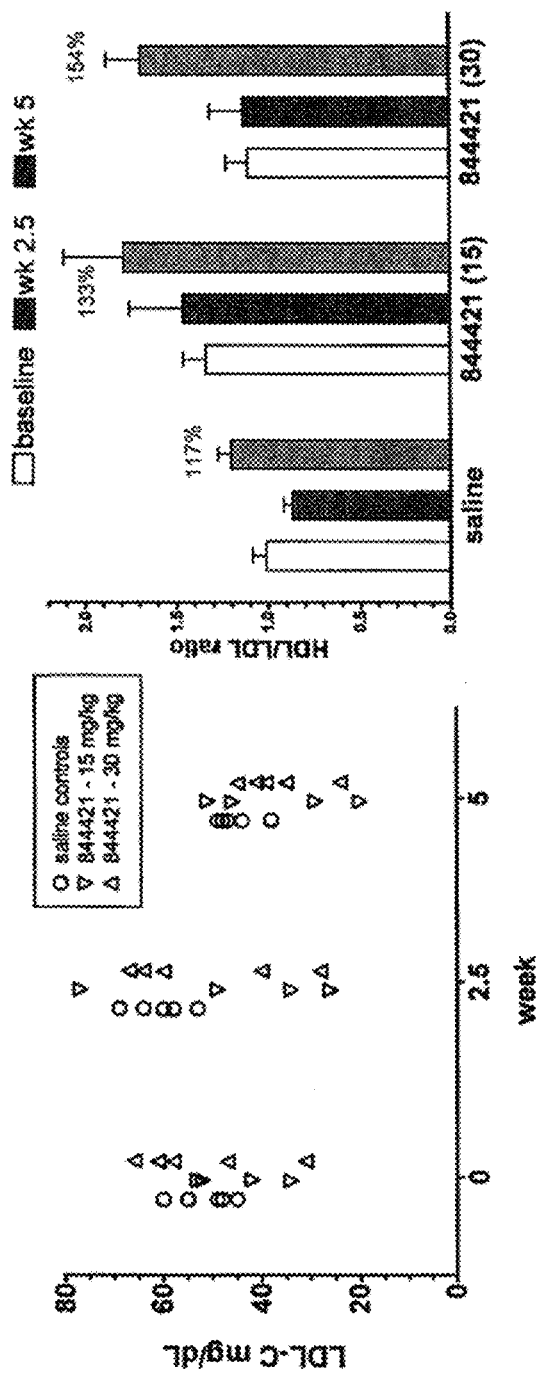
FIG. 28A depicts the pharmacodynamic responses in serum lipid assays for the cyno 2.5 and 5 wk ASO studies, as displayed in a scatterplot of individual animal data.
FIG. 28B depicts the average ratio of HDL/LDL in BMS-844421-treated cynos at 2.5 and 5 wk. The numbers in parentheses in FIG. 28B are administered doses in mg/kg.

Pharmacodynamic responses were assessed in serum lipid assays for the cyno 5 wk ASO study. As seen in FIG. 27, a modest trend (not statistically significant) toward lowering LDL-C was observed for BMS-844421 treated cyno monkeys at 2.5 and 5 wk of dosing. This trend at both time points for BMS-844421 relative to baseline was also seen in the scatterplot of individual animal data in FIG. 28A. HDL/LDL ratios were sometimes employed as a sensitive indicator of plasma lipid status. A chart of the average ratio of HDL/LDL in the cyno study showed a trend for increase in the ratio for BMS-844421 treated cynos at 2.5 and 5 wk (FIG. 28B).

Gene expression profiling by Affymetrix microarray was conducted on the RNA samples from this study. The analysis included liver RNA from animals administered vehicle alone, BMS-844421 at 15 mg/kg and 30 mg/kg and BMS-844419 and BMS-844423 at 30 mg/kg only. By microarray, there were significant (p<0.01) transcriptional changes in approximately 1 to 2% of genes with approximately 1% expected to change at this significance level by chance. For drug-dosed groups relative to control there were alterations in inflammation-, immune system-, and lipid homeostasis-related transcripts with statistically significant animal to animal variability. Other drug-related hepatic transcriptional changes common to multiple dose groups were associated with several or a few genes in various biological processes and are of unknown significance.

17.6. Results of the 13 wk Cyno Toxicology Study

Figure 29:
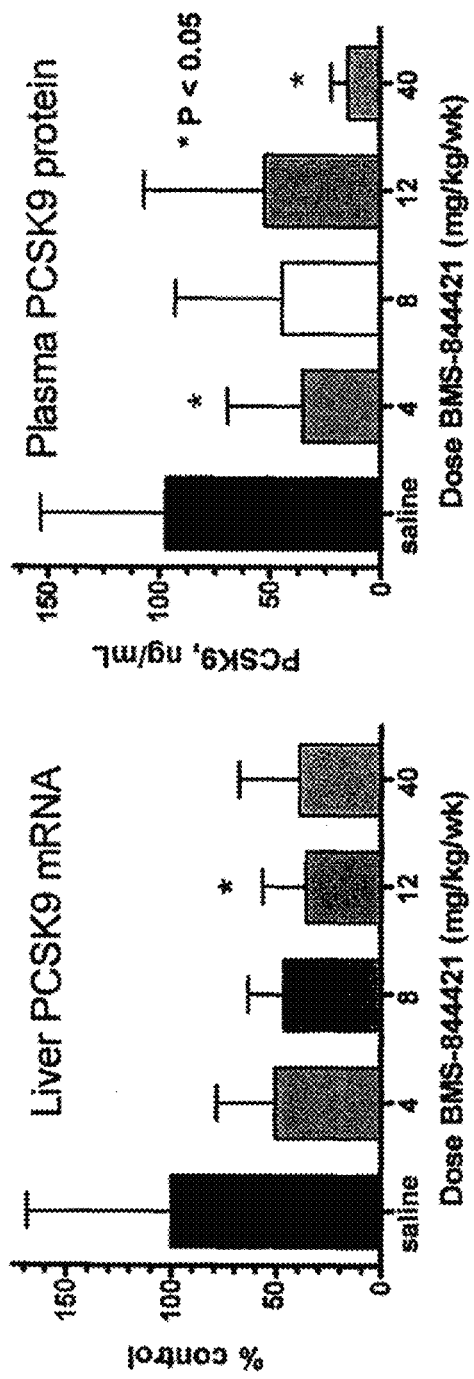
FIG. 29 depicts downregulation of PCSK9 target in cyno monkeys at 13 wk in the toxicology study of liver mRNA and plasma PCSK9.

An additional opportunity to monitor pharmacodynamic responses to BMS-844421 in monkeys was the 13 wk toxicology study, described in Example 16.5. Lean cyno monkeys with low LDL levels were again the subject for this study, as for the 5 wk cyno monkey study above. At 13 wks subcutaneous dosing at 4 different dose levels, BMS-844421 suppressed PCSK9 expression as measured by both liver PCSK9 mRNA and plasma PCSK9 protein levels. Despite the inter-animal variability in these values, it is apparent that BMS-844421 strongly suppressed both liver mRNA and plasma PCSK9 protein (FIG. 29). 40 mg/kg suppressed PCSK9 protein levels very robustly with less variation between animals (FIG. 29). No statistically significant differences were seen in plasma LDL-C or other lipid parameters in this study.

TABLE 34

Histological Findings in CD-I Mice

| Antisense compound | Liver | Kidney | Lung | Heart | Spleen | Lymph node | Intestine | Thyroid | Sternum | Skeletal Muscle |
|---|---|---|---|---|---|---|---|---|---|---|
| Saline | – | – | – | – | – | – | – | – | – | – |
| ISIS 395165 | +/++ | – | – | – | –/+ | –/+ | – | – | – | – |
| ISIS 395185 | + | – | – | – | –/+ | – | – | – | – | – |
| ISIS 395186 | – | – | – | – | – | – | – | – | – | – |
| ISIS 395187 | – | – | – | – | –/+ | – | – | – | – | – |
| ISIS 405879 | – | – | – | – | – | – | – | – | – | – |
| ISIS 405881 | inflam | – | inflam | – | –/+ | –/+ | – | – | – | – |
| ISIS 405891 | – | – | – | – | –/+ | –/+ | – | – | – | – |
| ISIS 405988 | – | – | – | – | – | – | – | – | – | – |
| ISIS 405994 | ++ | – | – | – | –/+ | – | – | – | – | – |
| ISIS 406008 | +/++ | – | – | – | – | – | – | – | – | – |

Normal: –
Minimal changes: –/+
Mild changes: +
Moderate changes: ++
Severe changes: +++

Microscopic evaluation of mouse organs from animals treated with 10 different human PCSK-9 antisense compounds revealed that all compounds generally were well tolerated, but that some antisense compounds were particularly well tolerated. The following results were seen in the various examined organs.

Liver: Mild (+) to moderate (++) liver injuries (cytoplasmic swelling to multifocal apoptosis) were seen in Isis 395165 (+/++), Isis 395185 (+), Isis 405988 (+/++), Isis 405994 (++), and Isis 406008 (+/++) treated livers. Mild inflammatory changes were seen in Isis 405881 treated livers.

Lung: No significant abnormality was seen in treated animals except for mild histiocytosis noticed in Isis 405881 treated animals.

Spleen: Mild follicular hyperplasia was seen in Isis 395165, Isis 395185, Isis 395187, Isis 405881, Isis 405891, and Isis 405994 treated spleens.

Lymph node: Minimal histiocytosis was observed in Isis 395165, Isis 405881 and Isis 405891 treated animals.

Heart: Minimal levels of macrophage infiltration were seen in Isis 395165, Isis 395186, Isis 405879, Isis 405881, Isis 405891, Isis 405988, and Isis 406008 treated hearts.

Kidney, Thyroid, small intestine, skeletal muscle and sternum: No abnormality was visualized.

Differences in the histological findings were seen even between Isis 395165 and Isis 405879. As noted above, the target sequences of these two antisense compounds are only shifted by two nucleotide positions. Nevertheless, Isis 405879 advantageously displays no adverse reactions, whereas Isis 395165 elicits a mild inflammatory response in liver, spleen, and lymph nodes. In summary, Isis 405879, Isis 395186, and Isis 405988 display superior tolerance, compared to the other antisense compounds tested in this study.

17.7. Differences in Achieving Pharmacodynamic Endpoints in the Cyno Model

Isis 395186 ("844419"), Isis 405879 ("844421"), and Isis 405891 ("844423") were selected for further study in the cyno model, using the procedures described in Example 16.6. As set forth above, these antisense compounds displayed high activity in cell culture models, were well tolerated, and displayed advantageous tissue distribution and half-life properties. Further, none of these antisense compounds targeted a PCSK9 sequence known to have differences in monkeys and humans. In addition, the target sequences in human PCSK9 were known not to contain SNPs having a wide distribution in the population.

Figure 10:
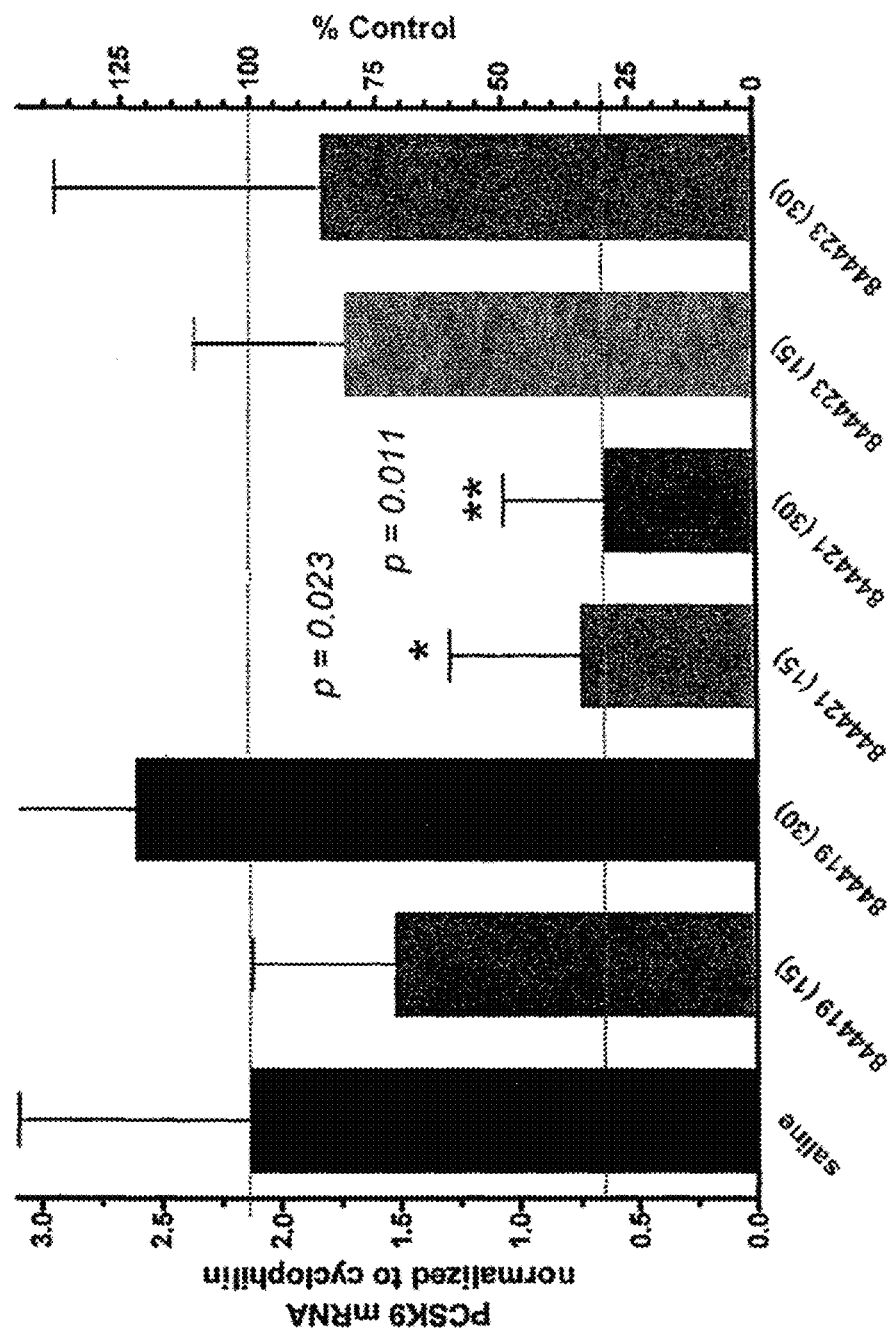
FIG. 10 depicts PCSK9 mRNA levels (relative units) following administration of the identified antisense compounds to a cyno monkey. Results are shown at each dosing concentration (15 mg/kg and 30 mg/kg).
Figure 11:
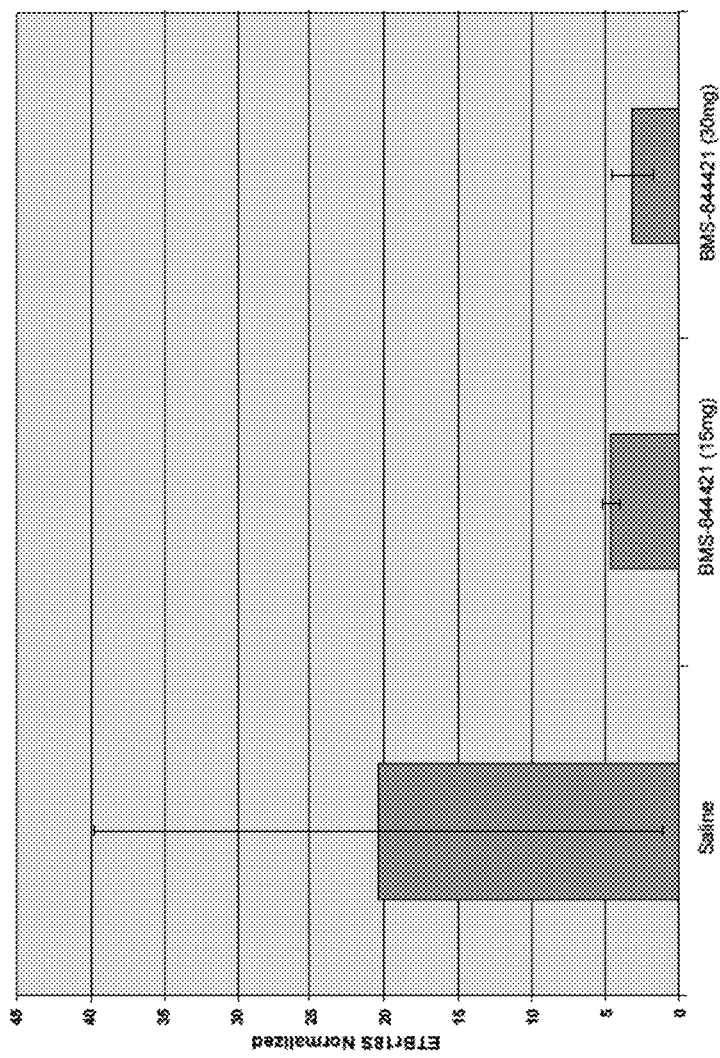
FIG. 11 depicts hepatic PCSK9 mRNA levels (relative units) detected by Northern analysis. Cyno monkeys were administered Isis 405879 ("BMS-844421") at a dose of 15 mg/kg or 30 mg/kg.

The antisense compounds were tested for their ability to reduce PCSK9 mRNA in cyno liver. See Example 16.6. The results of this experiment are shown in FIG. 10. Despite variability between the tested animals, Isis 405879 (labeled "844421") displayed a superior ability to reduce PCSK9 mRNA levels significantly. When administered at a low dose (15 mg/kg, shown in the left side bar), Isis 405879 significantly ($p<0.023$) reduced PCSK9 mRNA levels. When administered at a high dose (30 mg/kg, shown in the right side bar), Isis 405879 also significantly ($p<0.011$) inhibited PCSK9 mRNA expression. The results obtained with Isis 405879 were superior to those obtained with Isis 395186 (labeled "844419") and Isis 405891 (labeled "844423"). As shown in FIG. 11, Northern analysis of liver PCSK9 mRNA confirms that 15 mg/kg and 30 mg/kg Isis 405879 substantially reduces PCSK9 mRNA levels.

Figure 12:
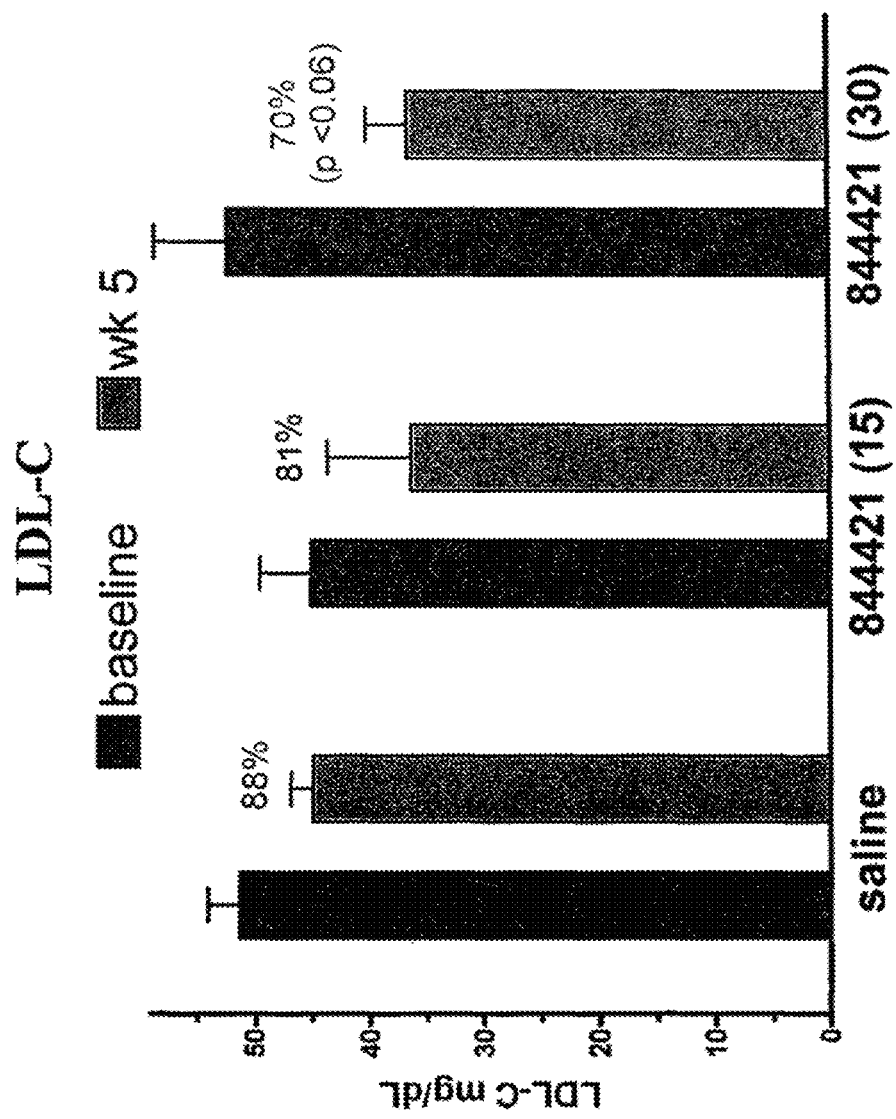
FIG. 12 depicts plasma LDL-C levels (mg/dL) following administration of Isis 405879 (labeled "BMS-844421") at a dose of 15 mg/kg or 30 mg/kg. Left side bars represent baseline levels of LDL-C in control animals; right side bars represent LDL-C following administration of antisense compounds.
Figure 13:
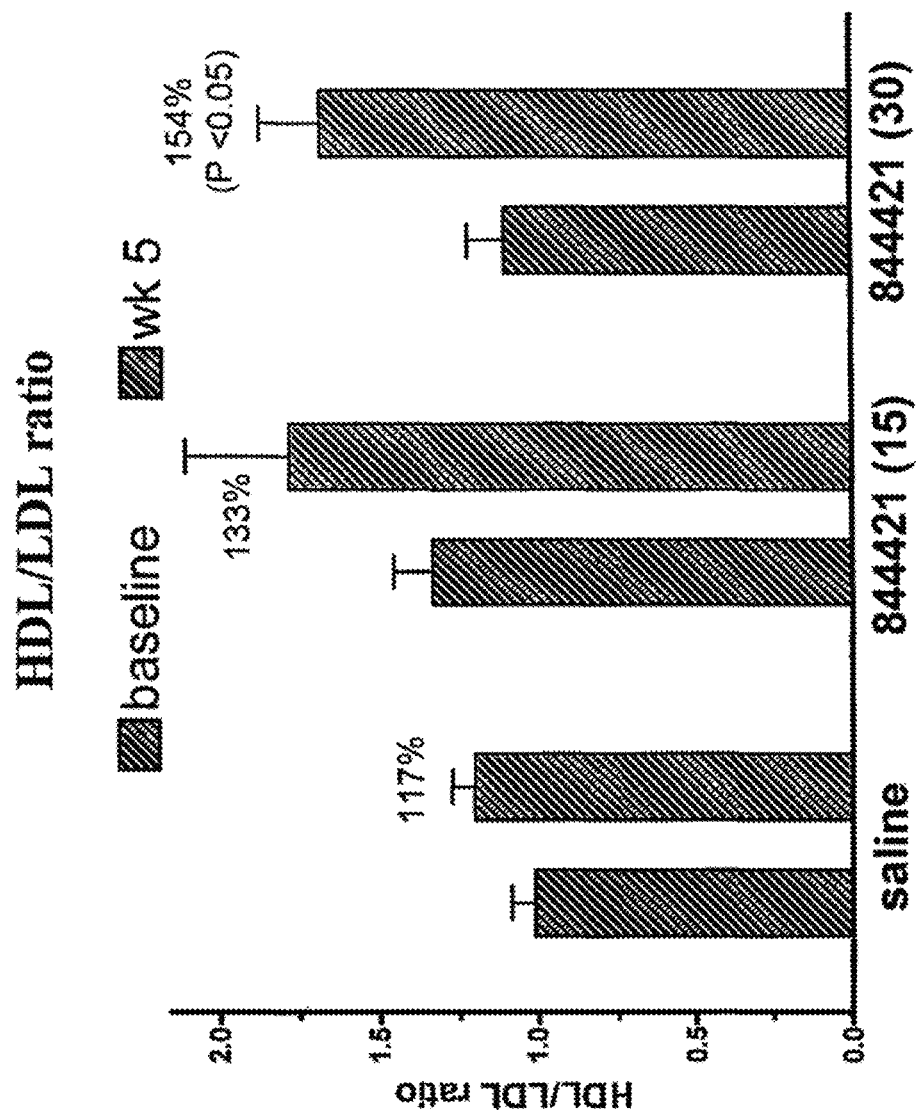
FIG. 13 depicts the ratio of plasma HDL/LDL following administration of Isis 405879 (labeled "BMS-844421") at a dose of 15 mg/kg or 30 mg/kg. Left side bars represent baseline HDL/LDL in control animals; right side bars represent HDL/LDL following administration of antisense compounds.

As described in Example 17.1, the reduction of PCSK9 mRNA is expected to correlate with a reduction in plasma LDL-C and liver TG. Consistent with this expectation, Isis 405879 produced a significant ($p<0.06$) decrease in cyno serum LDL-C after five weeks of administration at 30 mg/kg, as shown in FIG. 12. Isis 405879 additionally produced a significant ($p<0.05$) increase in the ratio of HDL to LDL following five weeks of administration at 30 mg/kg, as shown in FIG. 13.

Generally confirming earlier data obtained in rodents, Isis 405879 elicited no differences in serum chemistry, hematology, or organ weights, except for a slight increase in spleen weight. Histology revealed indicia of only mild inflammation. The advantageous distribution of Isis 405879 in liver and kidney in the cyno model is described above and shown in FIG. 9.

Example 18: Dose Response Study of Isis 405879 ("844421") in a Human PCSK9 Transgenic Mouse Model BMS-844421 is a human specific PCSK9 antisense oligonucleotide (ASO) designed to downregulate hepatic PCSK9 expression, increase LDL receptor activity, and promote clearance of LDL and reduction of plasma LDL-C levels in humans. A human genomic PCSK9 transgenic mouse model was recently established. This mouse line expresses hemizygous transgene in the presence of endogenous mouse PCSK9 (i.e., both genes are simultaneously expressed). It was found that the transgenic PCSK9 mice responded to chronic dosing with BMS-844421 and related human PCSK9 ASOs with decreased liver mRNA expression and decreased circulating human PCSK9 protein levels.

The present study examined the dose response to BMS-844421 in the hemizygous genomic transgenic mouse model on a normal chow diet. Experiments were conducted comparing the effects of BMS-844421 (human specific PCSK9 ASO) to those of ISIS 394816 (murine specific PCSK9 ASO) in this model alone and in combination. BMS-844421 exhibited dose-dependent suppression of liver target mRNA, reflected in dose-dependent decreases in plasma human PCSK9 levels. Both liver mRNA and plasma protein gave ED50 values of approximately 15 mg/kg (given twice weekly) for BMS-844421, while the suppression of plasma PCSK9 protein was greater than liver PCSK9 mRNA at each dose in this model. Trends for increased LDLR protein in liver total membrane fraction, and a feedback effect on liver HMGCoA reductase mRNA expression were observed, but no changes in plasma lipids were seen for BMS-844421 treated hemizygous mice. The combination of ISIS 394816+ BMS-844421 (each at 15 mg/kg) elicted a greater increase in liver LDLR protein than either ASO alone, consistent with the proposed mechanism of action and the dual expression of both human and murine PCSK9 in this model.

18.1. Materials and Methods

The sequences of BMS-844421 and other ASOs tested in this report are given in Table 35. The negative control ISIS 141923 is not complementary to any known gene. The design of the dose response study is described in the beginning of the Results section (section 18.2. below).

TABLE 35

Nucleotide sequences of ASOs

| ASO | Sequence | SEQ ID NO |
|---|---|---|
| BMS 844421, human PCSK9 specific* | 5'-CCTTGGCCACGCCGGCATCC-3' | 248 |
| ISIS 141923, non-targeting | 5'-CCTTCCCTGAAGGTTCCTCC-3' | 465 |
| ISIS 394816, murine PCSK9 specific | 5'-GGGCTCATAGCACATTATCC-3' | 466 |

*BMS-844421 is identical to ISIS 405879

Parameters evaluated at study termination included hepatic mRNA, hepatic LDLR protein levels, plasma concentrations of total cholesterol, LDL, HDL, triglycerides, transaminases, and organ and body weights. Whole liver was processed for RNA, and protein, and held for possible histological examination and hepatic triglyceride levels. Blood and liver samples were obtained 24 hr after the prior dose. Blood samples were obtained from tail vein or retro orbital plexus and EDTA, chilled on ice, and plasma samples were obtained by standard procedures. For mRNA assays, liver samples (30-50 mg each) were placed in eppendorf tubes containing 1000 uL of TRIzol (Invitrogen #15596-018) and homogenized using stainless steel beads on a Tissue Lyser instrument (Qiagen, Valencia, Calif.). Chloroform (200 µL) was added to each tube, the contents were mixed vigorously by hand and tubes were centrifuged at 12,000×g for 20 minutes at 4° C. About 300 µL of each supernatant was removed and placed in 1.5 mL microcentrifuge tubes. One volume of 70% EtOH was added, the mixtures were vortexed thoroughly and transferred to RNeasy Mini Spin Columns (QIAgen Cat. No. 74106). RNA was purified, treated with DNase and eluted into microcentrifuge tubes following QIAgen's manufacturer's instructions.

Plasma human PCSK9 levels were assayed using the human specific ELISA with mAb 4H5 as capture antibody.

18.2. Results

A dose-response study was run in human PCSK9 genomic transgenic mouse line 66 mice on a normal chow diet. Groups of 6 mice (3 males, 3 females) received the following treatments for 6 weeks. BMS-844421 was administered p.o. at 5, 10, 15, and 30 mg/kg per dose given twice weekly (on Tuesdays and Fridays) for 6 weeks. Controls received saline, and an additional group received the non-targeting negative control ASO ISIS 141923 (30 mg/kg twice weekly). The murine PCSK9 ASO ISIS 394816 was administered to another group at 15 mg/kg per dose. The final group received BMS-844421 (15 mg/kg) plus ISIS 394816 (15 mg/kg) combined.

Figure 14:
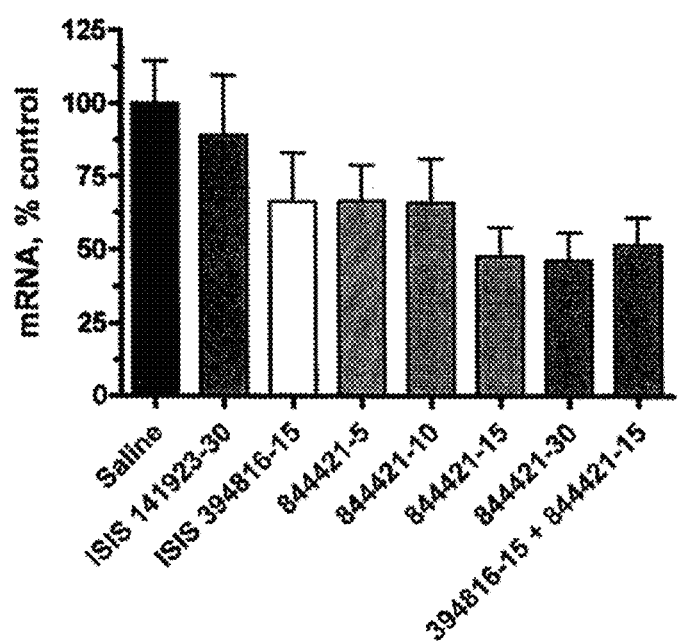
FIG. 14 depicts the effect of BMS-844421 and control ASOs on liver human PCSK9 mRNA in transgenic mice (6 wk).

Liver mRNA assayed by qRT-PCR showed that BMS-844421 decreased liver PCSK9 mRNA in a dose dependent manner, with greatest effect at the top dose studied (FIG. 14). The negative control ASO, ISIS 141923, had no significant effect on target mRNA, while the murine targeted ASO, ISIS 394816, decreased human PCSK9 mRNA by 33%, suggesting partial cross-hybridization to human PCSK9 mRNA.

Figure 15:
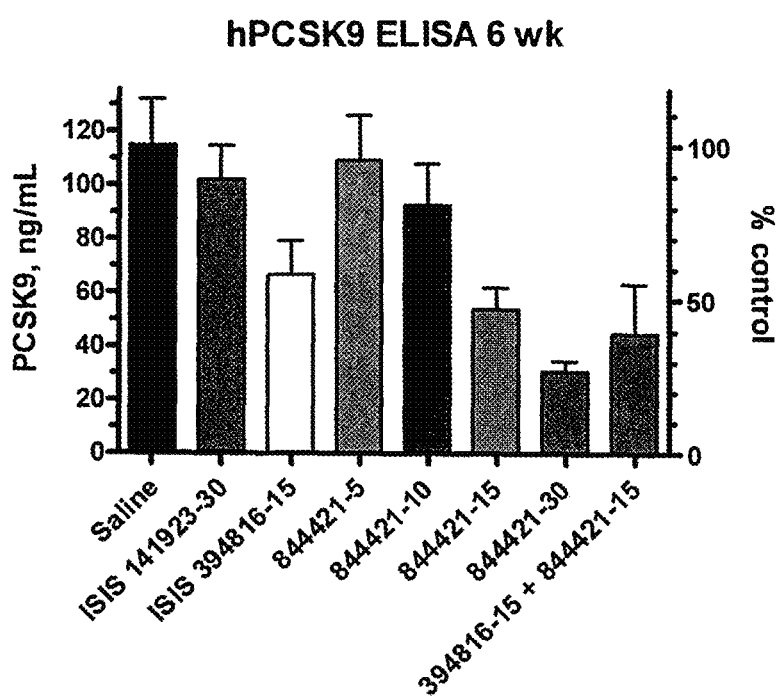
FIG. 15 depicts the effect of BMS-844421 and control ASOs on plasma levels of human PCSK9 protein in transgenic mice (6 wk).

The ASO effects on plasma human PCSK9 followed a similar pattern as mRNA, while the effects of the higher doses of BMS-844421 resulted in greater effects, up to 70% suppression at 30 mg/kg/dose (FIG. 15). ISIS 394816 suppressed approximately 30% (similar to mRNA effects), while ISIS 141923 had no significant effect.

Figures 16A, 16B, 16C:
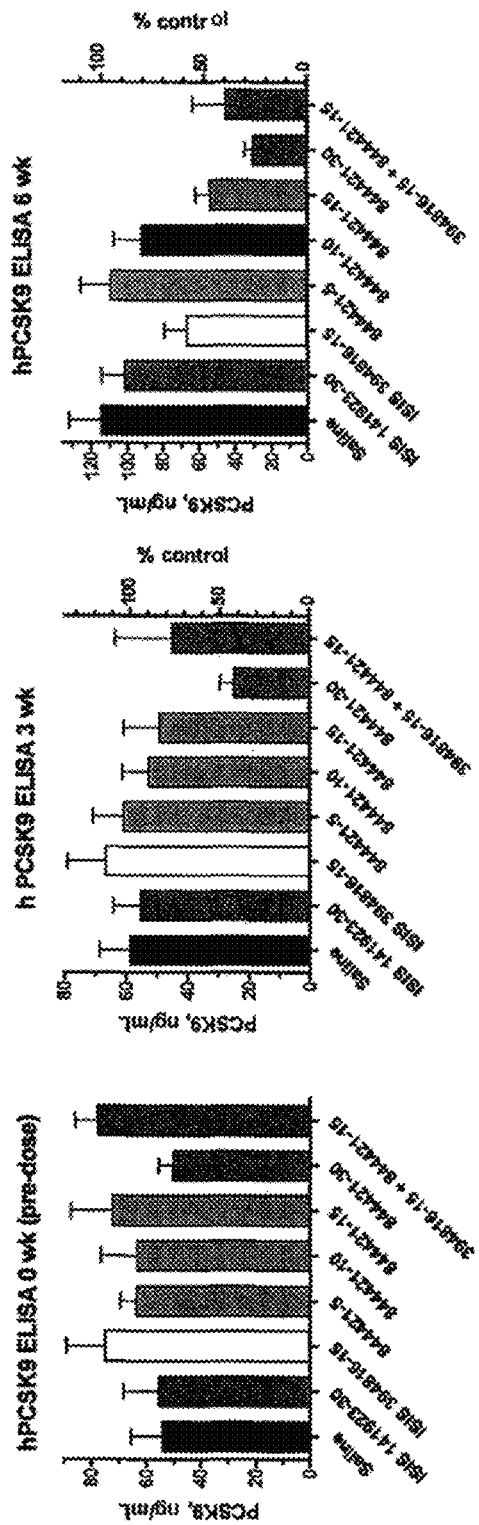
FIG. 16 depicts plasma hPCSK9 at baseline (FIG. 16A), 3 wk (FIG. 16B), and 6 wk (FIG. 16C) treatment.
Figure 17:
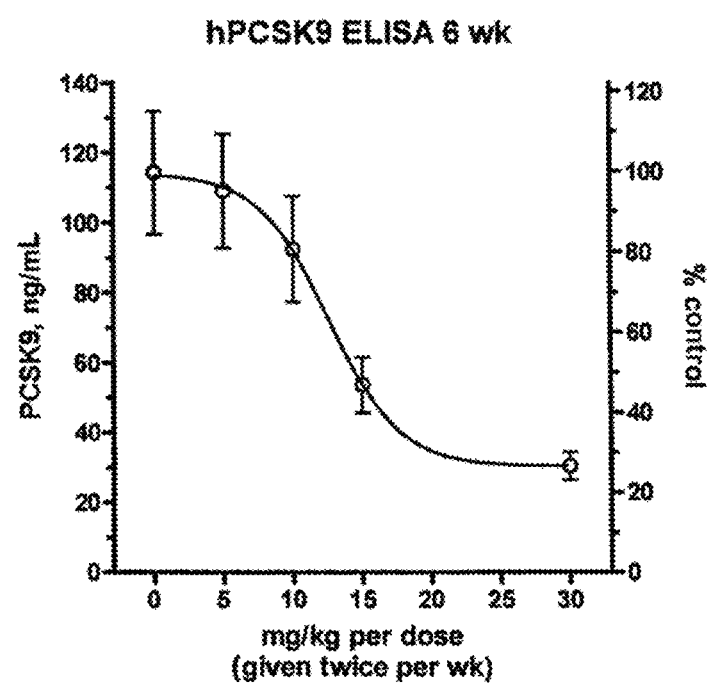
FIG. 17 depicts the BMS-844421 dose response for plasma hPCSK9 levels in transgenic mice at 6 weeks (wk).
Figure 18:
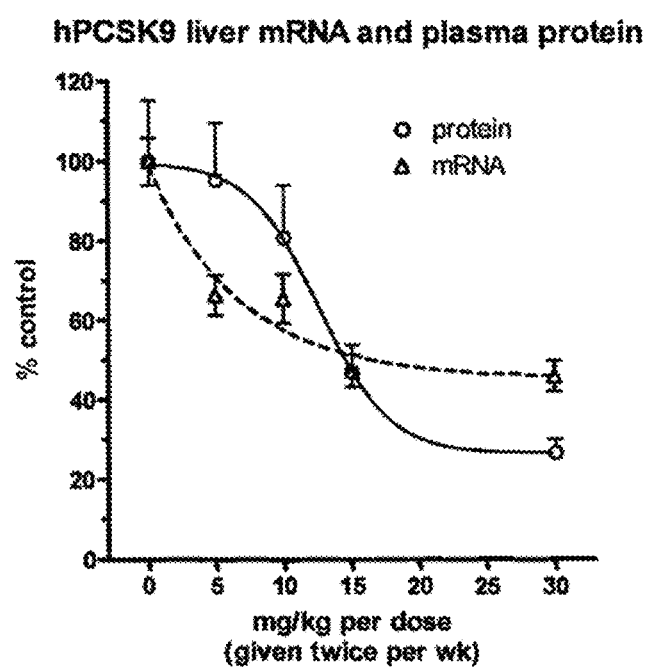
FIG. 18 depicts the BMS-844421 dose response for liver mRNA and plasma protein (hPCSK9).

Plasma human PCSK9 levels exhibited time dependent suppression with effects at 6 weeks, greater than at 3 wks for all doses of BMS-844421 (FIG. 16). At 3 wks dosing, only the highest dose of BMS-844421 showed significant suppression. As seen in FIG. 17, data for 6 wks treatment with BMS-844421 showed a sigmoidal dose-response curve, with ED50 approximately 15 mg/kg/dose (given twice weekly). Plotting the mRNA and protein data together showed that the two endpoints generally, though imperfectly, reflect each other, with protein showing greater sensitivity to suppression (FIG. 18).

Figure 19:
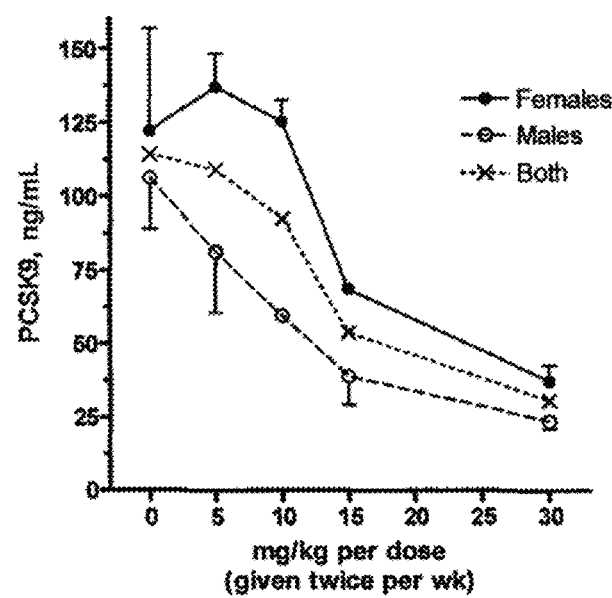
FIG. 19 depicts the dose response for plasma hPCSK9 in male and female transgenic mice.
Figure 20:
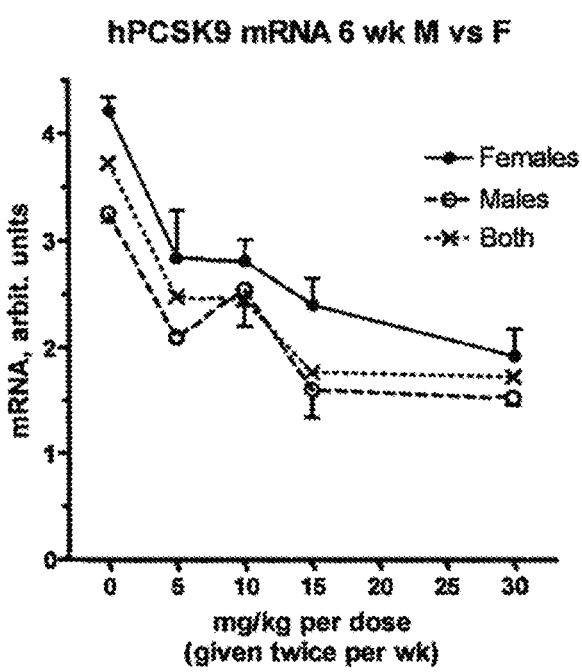
FIG. 20 depicts the dose response for liver hPCSK9 mRNA in male versus female transgenic mice.

Male transgenic mice responded more sensitively to BMS-844421 than the female transgenic mice in this study (FIG. 19). The data was not the result of different plasma baseline levels of human PCSK9 between males and females, which is human PCSK9=67+/−31 ng/mL in males and 60+/−27 ng/mL in females in the predosing samples. The difference in PCSK9 protein response for males vs. females was less apparent for liver target mRNA (FIG. 20).

Figure 21:
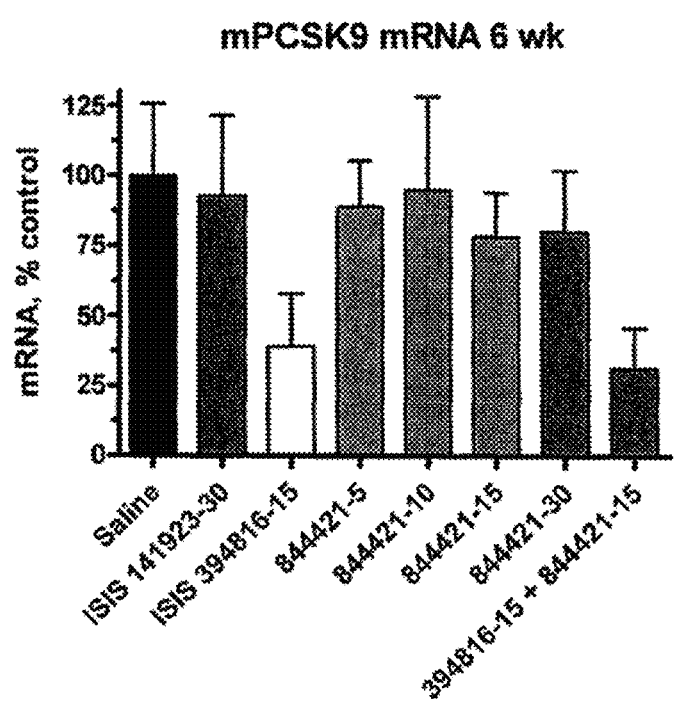
FIG. 21 depicts the effect of the ASOs on liver endogenous PCSK9 mRNA in the transgenic mouse after 6 weeks of administration. The numbers following the hyphens provide the mg ASO/kg body weight dose of each ASO. For example, "844421-30" is the data for BMS-84421 administered to test animals at 30 mg/kg.

Levels of endogenous mouse PCSK9 mRNA in liver were decreased by ISIS 394816 (and the combination of ISIS 394816 with BMS-844421), but were not decreased by BMS-844421 only (FIG. 21).

Figure 22:
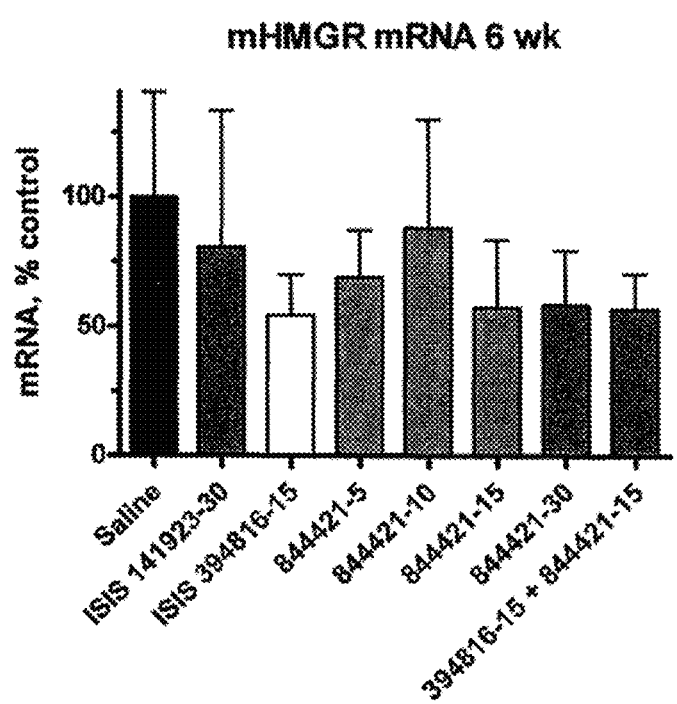
FIG. 22 depicts the effect of ASOs on liver endogenous HMGCoA reductase mRNA in the transgenic mouse after 6 weeks of administration.

A key cholesterol regulatory gene, HMGCoA reductase (HMGR), is known to respond to sterol feedback in the liver. An assay of endogenous mouse liver HMGR mRNA revealed 45% suppression of HMGR with BMS-844421 as well as ISIS 394816 (FIG. 22). These findings are consistent with downregulation of PCSK9 promoting higher levels of LDLR, in turn leading to increased cholesterol in the regulatory pool in liver cells, resulting in downregulation of HMGR. Similar, though quantitatively lesser effects, were also seen for the sterol pathway genes LDLR mRNA and for SREBP2 mRNA.

Figure 23:
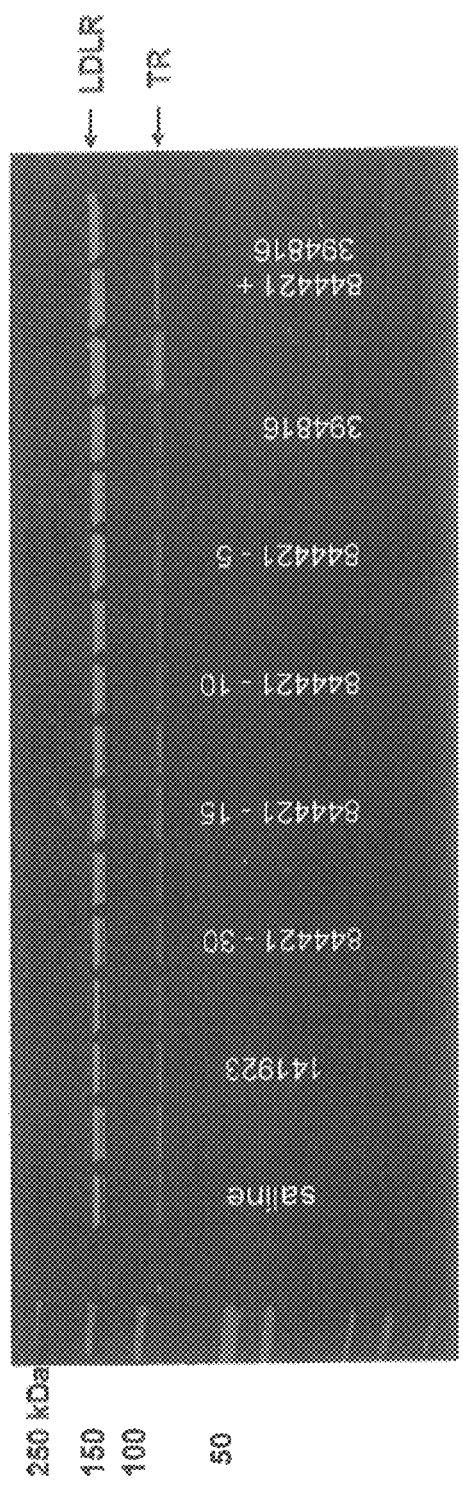
FIG. 23 depicts LDLR protein concentration following a 6 wk ASO treatment, as assayed by a Western blot.
Figure 24:
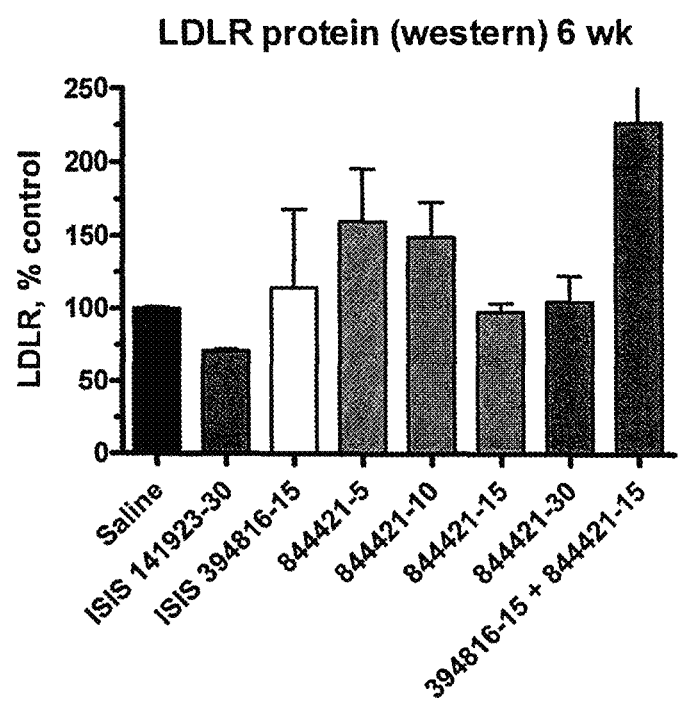
FIG. 24 depicts the quantification of the Western blot shown in FIG. 23. The LDLR band is normalized to a transferring receptor (TR) band, as observed using anti-LDLR and anti-TR antibodies, respectively.

LDLR protein levels were assayed in liver samples from the same study. Total hepatic membranes were prepared, and western blots of SDS-PAGE gels were assayed with anti-LDLR antibodies. As a control, transferrin receptor (TR) protein levels were measured with anti-TR antibodies. Liver samples from the ASO study were pooled from n=3 for the preparation of the membrane fraction. Pairs of pools for each group were assayed. Treatment with BMS-844421, and especially the combination of BMS-844421 with the murine ASO ISIS 394816, led to increases up to >2-fold in levels of LDLR protein, compared to the level of TR protein (FIG. 23 and FIG. 24).

The ELISA assay uses a monoclonal capture antibody and a polyclonal detector antibody developed against human recombinant PCSK9 produced in baculovirus. The recombinant human PCSK9 protein also serves as standard antigen for the ELISA assay. Cynomolgus monkey plasma PCSK9 was readily detectable using this assay. Human PCSK9 protein in plasma of human PCSK9 transgenic mouse lines was specifically detected with no cross-reactivity to murine PCSK9.

Despite these pharmacodynamic responses to BMS-844421, hemizygous transgenic mice did not exhibit changes in plasma LDL-C or total cholesterol following ASO treatment, including BMS-844421 (Table 36). However, normal chow fed mice have low levels of LDL-C (Table 36). It is plausible that these low LDL-C levels are not readily decreased by increases in LDLR protein. Another possible explanation is that the hemizygous expression of human PCSK9, i.e., the gene specifically targeted by BMS-844421, contributes only about ⅓ to ½ of the total murine+human PCSK9 in this hemizygous transgenic mouse model.

TABLE 36

Plasma lipids at 6 wk treatment with ASOs in transgenic mice

| Both Sexes | Triglycerides | Total Cholesterol | HDL | LDL |
|---|---|---|---|---|
| Saline | 72 ± 14 | 108 ± 8.2 | 57 ± 6.4 | 14 ± 1 |
| Missense | 64 ± 9.2 | 110 ± 8.6 | 57 ± 7.1 | 15 ± 1 |
| BMS-844421 (30 mg/kg) | 54 ± 8.6 | 129 ± 7.3 | 67 ± 4.6 | 18 ± 2 |
| BMS-844421 (15 mg/kg) | 54 ± 9.0 | 126 ± 9.2 | 65 ± 5.5 | 18 ± 1 |
| BMS-844421 (10 mg/kg) | 53 ± 9.4 | 118 ± 9.3 | 61 ± 6.9 | 17 ± 2 |
| BMS-844421 (5 mg/kg) | 56 ± 9.7 | 117 ± 8.5 | 61 ± 6.1 | 17 ± 1 |
| Mouse ASO I-394816 (15 mg/kg) | 50 ± 7.0 | 84.2 ± 2.9 | 45 ± 3.0 | 11 ± 2 |
| BMS-844421 + I-394816 (15 mg/kg each) | 55 ± 9.3 | 92 ± 5.3 | 48 ± 4.6 | 12 ± 2 |
| WT Littermates | 60 ± 8.1 | 111.7 ± 7.2 | 57 ± 5.3 | 15 ± 1 |

There were no changes in ALT or AST (not shown), suggesting that no liver abnormalities were present after 6 wks treatment.

18.3. Conclusions

The recently established human genomic PCSK9 transgenic mouse model responded to human PCSK9 ASO treatment with robust downregulation of human PCSK9 at both the mRNA and protein levels in liver. Plasma human PCSK9 was also decreased with the magnitude of decrease somewhat greater than liver mRNA suppression, suggesting that plasma PCSK9 levels are a good readout for suppression of the target mRNA. The ED50 for both endpoints was approximately 15 mg/kg (per dose given twice weekly). The transgenic mice did not exhibit significant changes in plasma LDL-C or total cholesterol following BMS-844421 or ISIS 394816 treatment, nor for the combination of the two ASOs. A trend for increasing liver LDLR protein was observed following treatment with BMS-844421, suggesting a functional effect consistent with the downregulation of PCSK9 mRNA and protein. Consistent with this was the downregulation of the sterol response gene HMGR in liver.

The limited pharmacodynamic responses in this model appear to be related both to the small LDL window in normal chow diet fed mice, and to the co-expression of the human PCSK9 gene with the endogenous murine PCSK9 gene. In the hemizygous mice, human PCSK9 appears to represent only about ⅓ of the total human+murine PCSK9 expressed. Consistent with this, in a previous study the murine specific PCSK9 ASO ISIS 394816 administered to human apoB-CETP double transgenic mice produced up to 90% suppression of liver PCSK9 mRNA and a corresponding decrease of up to 80% in plasma LDL-C levels.

What is claimed is:

1. A compound comprising a modified oligonucleotide targeting a PCSK9 nucleic acid and consisting of 15 to 30 linked nucleosides and having a nucleobase sequence comprising a portion which consists of at least 8 contiguous nucleobases complementary to an equal-length portion of 294-317, 406-440, 406-526, 410-436, 410-499, 446-526, 545-581, 591-619, 591-704, 591-743, 595-622, 600-626, 600-639, 600-670, 601-628, 602-628, 603-630, 611-636, 620-647, 638-665, 648-674, 657-684, 705-743, 782-810, 821-859, 835-859, 835-917, 835-942, 860-887, 860-899, 860-909, 860-917, 869-895, 878-905, 888-909, 923-952, 960-1034, 960-1173, 960-986, 967-991, 970-1023, 970-1064, 970-1117, 970-996, 977-1004, 985-1011, 989-1016, 992-1019, 997-1024, 997-1024, 998-1025, 999-1026, 1000-1027, 1001-1028, 1002-1029, 1003-1029, 1004-1029, 1005-1029, 1006-1029, 1007-1034, 1036-1061, 1045-1072, 1076-1096, 1088-1115, 1098-1123, 1200-1251, 1210-1237, 1219-1245, 1228-1251, 1273-1444, 1295-1316, 1318-1345, 1328-1354, 1337-1361, 1344-1371, 1354-1377, 1380-1406, 1389-1416, 1400-1426, 1409-1434, 1465-1491, 1465-1602, 1474-1499, 1482-1519, 1513-1540, 1523-1549, 1526-1602, 1526-1624, 1532-1558, 1541-1568, 1552-1579, 1560-1587, 1561-1589, 1564-1591, 1565-1592, 1566-1592, 1567-1592, 1570-1597, 1571-1599, 1605-1706, 1628-1706, 1640-1666, 1672-1698, 1681-1706, 1735-1761, 1735-1765, 1740-1765, 1849-1876, 1849-1879, 1850-1877, 1851-1877, 1852-1878, 1852-1879, 1853-1879, 1854-1879, 1905-1955, 1915-1942, 1916-1943, 1917-1944, 1918-1945, 1919-1946, 1920-1939, 1920-1947, 1921-1948, 1922-1949, 1923-1950, 1924-1951, 1925-1952, 1926-1952, 1927-1952, 1928-1955, 1962-2059, 2040-2126, 2100-2126, 2100-2139, 2100-2206, 2101-2126, 2305-2332, 2305-2354, 2306-2333, 2307-2334, 2308-2334, 2309-2334, 2310-2334, 2410-2434, 2504-2528, 2509-2528, 2582-2625, 2606-2668, 2828-2855, 2832-2851, 2900-2927, 2900-2929, 2902-2927, 2983-3007, 2983-3013, 3227-3252, 3227-3456, 3472-3496, or 3543-3569 of SEQ ID NO: 1, wherein the nucleobase sequence of the modified oligonucleotide is at least 95% complementary to SEQ ID NO: 1 over the entire length of the modified oligonucleotide; and wherein at least one at least one nucleoside comprises a modified sugar selected from a 2'-F, 2'-OMe and a 2'-O-methoxyethyl; and at least one internucleoside linkage is a phosphorothioate internucleoside linkage.

2. The compound of claim 1, wherein the modified oligonucleotide is 100% complementary to SEQ ID NO: 1.

3. A compound comprising a modified oligonucleotide targeting a PCSK9 nucleic acid and consisting of 15 to 30 linked nucleosides and having a nucleobase sequence comprising a portion of at least 8 contiguous nucleobases fully complementary to an equal length portion of nucleobases 294-317, 406-440, 406-526, 410-436, 410-499, 446-526, 545-581, 591-619, 591-704, 591-743, 595-622, 600-626, 600-639, 600-670, 601-628, 602-628, 603-630, 611-636, 620-647, 638-665, 648-674, 657-684, 705-743, 782-810, 821-859, 835-859, 835-917, 835-942, 860-887, 860-899, 860-909, 860-917, 869-895, 878-905, 888-909, 923-952, 960-1034, 960-1173, 960-986, 967-991, 970-1023, 970-1064, 970-1117, 970-996, 977-1004, 985-1011, 989-1016, 992-1019, 997-1024, 997-1024, 998-1025, 999-1026, 1000-1027, 1001-1028, 1002-1029, 1003-1029, 1004-1029, 1005-1029, 1006-1029, 1007-1034, 1036-1061, 1045-1072, 1076-1096, 1088-1115, 1098-1123, 1200-1251, 1210-1237, 1219-1245, 1228-1251, 1273-1444, 1295-1316, 1318-1345, 1328-1354, 1337-1361, 1344-1371, 1354-1377, 1380-1406, 1389-1416, 1400-1426, 1409-1434, 1465-1491, 1465-1602, 1474-1499, 1482-1519, 1513-1540, 1523-1549, 1526-1602, 1526-1624, 1532-1558, 1541-1568, 1552-1579, 1560-1587, 1561-1589, 1564-1591, 1565-1592, 1566-1592, 1567-1592, 1570-1597, 1571-1599, 1605-1706, 1628-1706, 1640-1666, 1672-1698, 1681-1706, 1735-1761, 1735-1765, 1740-1765, 1849-1876, 1849-1879, 1850-1877, 1851-1877, 1852-1878, 1852-1879, 1853-1879, 1854-1879, 1905-1955, 1915-1942, 1916-1943, 1917-1944, 1918-1945, 1919-1946, 1920-1939, 1920-1947, 1921-1948, 1922-1949, 1923-1950, 1924-1951, 1925-1952, 1926-1952, 1927-1952, 1928-1955, 1962-2059, 2040-2126, 2100-2126, 2100-2139, 2100-2206, 2101-2126, 2305-2332, 2305-2354, 2306-2333, 2307-2334, 2308-2334, 2309-2334, 2310-2334, 2410-2434, 2504-2528, 2509-2528, 2582-2625, 2606-2668, 2828-2855, 2832-2851, 2900-2927, 2900-2929, 2902-2927, 2983-3007, 2983-3013, 3227-3252, 3227-3456, 3472-3496, or 3543-3569 of SEQ ID NO: 1, wherein the nucleobase sequence of the modified oligonucleotide is at least 95% complementary to SEQ ID NO: 1 over the entire length of the modified oligonucleotide; and wherein at least one at least one nucleoside comprises a modified sugar selected from a 2'-F, 2'-OMe and a 2'-O-methoxyethyl; and at least one internucleoside linkage is a phosphorothioate internucleoside linkage.

4. The compound of claim 3, wherein the modified oligonucleotide is 100% complementary to SEQ ID NO: 1.

5. The compound of claim 1, consisting of a single-stranded modified oligonucleotide.

6. The compound of claim 1, wherein each internucleoside linkage is a phosphorothioate internucleoside linkage.

7. The compound of claim 1, wherein at least one nucleoside comprises a modified sugar which is a bicyclic sugar.

8. The compound of claim 7, wherein at least one modified sugar comprises a 2'-O-methoxyethyl.

9. The compound of claim 6, wherein at least one nucleoside comprises a modified nucleobase.

10. The compound of claim 9, wherein the modified nucleobase is a 5-methylcytosine.

11. The compound of claim 1, wherein the modified oligonucleotide comprises:

a gap segment consisting of linked deoxynucleosides;

a 5' wing segment consisting of linked nucleosides; and a 3' wing segment consisting of linked nucleosides;

wherein the gap segment is positioned between the 5' wing segment and the 3' wing segment; and wherein each nucleoside of each wing segment comprises a modified sugar.

12. The compound of claim 11, wherein the modified oligonucleotide comprises:

a gap segment consisting of ten linked deoxynucleosides;

a 5' wing segment consisting of five linked nucleosides; and a 3' wing segment consisting of five linked nucleosides;

wherein the gap segment is positioned between the 5' wing segment and the 3' wing segment, wherein each nucleoside of each wing segment comprises a 2'-O-methoxyethyl sugar; and wherein each internucleoside linkage is a phosphorothioate linkage.

* * * * *

SEQUENCE LISTING

```
<160> NUMBER OF SEQ ID NOS: 466

<210> SEQ ID NO 1
<211> LENGTH: 3636
<212> TYPE: DNA
<213> ORGANISM: Homo sapiens

<400> SEQUENCE: 1
cagcgacgtc gaggcgctca tggttgcagg cgggcgccgc cgttcagttc agggtctgag     60
cctggaggag tgagccaggc agtgagactg gctcgggcgg gccgggacgc gtcgttgcag    120
cagcggctcc cagctcccag ccaggattcc gcgcgcccct tcacgcgccc tgctcctgaa    180
```

```
cttcagctcc tgcacagtcc tccccaccgc aaggctcaag gcgccgccgg cgtggaccgc    240
gcacggcctc taggtctcct cgccaggaca gcaacctctc ccctggccct catgggcacc    300
gtcagctcca ggcggtcctg gtggccgctg ccactgctgc tgctgctgct gctgctcctg    360
ggtcccgcgg gcgcccgtgc gcaggaggac gaggacggcg actacgagga gctggtgcta    420
gccttgcgtt ccgaggagga cggcctggcc gaagcacccg agcacggaac cacagccacc    480
ttccaccgct gcgccaagga tccgtggagg ttgcctggca cctacgtggt ggtgctgaag    540
gaggagaccc acctctcgca gtcagagcgc actgcccgcc gcctgcaggc ccaggctgcc    600
cgccggggat acctcaccaa gatcctgcat gtcttccatg gccttcttcc tggcttcctg    660
gtgaagatga gtggcgacct gctggagctg gccttgaagt tgccccatgt cgactacatc    720
gaggaggact cctctgtctt tgcccagagc atccgtggaa cctggagcg gattacccct    780 ccacggtacc gggcggatga ataccagccc cccgacggag gcagcctggt ggaggtgtat    840
ctcctagaca ccagcataca gagtgaccac cgggaaatcg agggcagggt catggtcacc    900
gacttcgaga atgtgcccga ggaggacggg acccgcttcc acagacaggc cagcaagtgt    960
gacagtcatg gcacccacct ggcaggggtg gtcagcggcc gggatgccgg cgtggccaag   1020
ggtgccagca tgcgcagcct gcgcgtgctc aactgccaag ggaagggcac ggttagcggc   1080
accctcatag gcctggagtt tattcggaaa agccagctgg tccagcctgt ggggccactg   1140
gtggtgctgc tgcccctggc gggtgggtac agccgcgtcc tcaacgccgc ctgccagcgc   1200
ctggcgaggg ctggggtcgt gctggtcacc gctgccggca acttccggga cgatgcctgc   1260
ctctactccc cagcctcagc tcccgaggtc atcacagttg gggccaccaa tgcccaagac   1320
cagccggtga ccctggggac tttgggggacc aactttggcc gctgtgtgga cctctttgcc   1380
ccaggggagg acatcattgg tgcctccagc gactgcagca cctgctttgt gtcacagagt   1440
gggacatcac aggctgctgc ccacgtggct ggcattgcag ccatgatgct gtctgccgag   1500
ccggagctca ccctggccga gttgaggcag agactgatcc acttctctgc caaagatgtc   1560
atcaatgagg cctggttccc tgaggaccag cgggtactga cccccaacct ggtggccgcc   1620
ctgcccccca gcacccatgg ggcaggttgg cagctgtttt gcaggactgt atggtcagca   1680
cactcggggc ctacacggat ggccacagcc gtcgcccgct gcgccccaga tgaggagctg   1740
ctgagctgct ccagtttctc caggagtggg aagcggcggg gcgagcgcat ggaggcccaa   1800
gggggcaagc tggtctgccg ggcccacaac gcttttgggg gtgagggtgt ctacgccatt   1860
gccaggtgct gcctgctacc ccaggccaac tgcagcgtcc acacagctcc accagctgag   1920
gccagcatgg ggacccgtgt ccactgccac aacagggcc acgtcctcac aggctgcagc   1980
tcccactggg aggtggagga ccttggcacc cacaagccgc tgtgctgag gccacgaggt   2040 cagcccaacc agtgcgtggg ccacagggag gccagcatcc acgcttcctg ctgccatgcc   2100
ccaggtctgg aatgcaaagt caaggagcat ggaatcccgg cccctcagga gcaggtgacc   2160
gtggcctgcg aggagggctg gaccctgact ggctgcagtg ccctccctgg gacctcccac   2220
gtcctggggg cctacgccgt agacaacacg tgtgtagtca ggagccggga cgtcagcact   2280
acaggcagca ccagcgaagg ggccgtgaca gccgttgcca tctgctgccg gagccggcac   2340
ctggcgcagg cctcccagga gctccagtga cagccccatc ccaggatggg tgtctgggga   2400
gggtcaaggg ctgggctgaa gctttaaaat ggttccgact tgtccctctc tcagccctcc   2460
atggcctggc acgaggggat ggggatgctt ccgcctttcc ggggctgctg gcctggccct   2520
```

| | | | | |
|---|---|---|---|---|
| tgagtggggc | agcctccttg | cctggaactc | actcactctg | ggtgcctcct | ccccaggtgg | 2580 |
| aggtgccagg | aagctccctc | cctcactgtg | gggcatttca | ccattcaaac | aggtcgagct | 2640 |
| gtgctcgggt | gctgccagct | gctcccaatg | tgccgatgtc | cgtgggcaga | atgactttta | 2700 |
| ttgagctctt | gttccgtgcc | aggcattcaa | tcctcaggtc | tccaccaagg | aggcaggatt | 2760 |
| cttcccatgg | ataggggagg | gggcggtagg | ggctgcaggg | acaaacatcg | ttgggggtg | 2820 |
| agtgtgaaag | gtgctgatgg | ccctcatctc | cagctaactg | tggagaagcc | ctgggggct | 2880 |
| ccctgattaa | tggaggctta | gctttctgga | tggcatctag | ccagaggctg | agacaggtg | 2940 |
| cgcccctggt | ggtcacaggc | tgtgccttgg | tttcctgagc | cacctttact | ctgctctatg | 3000 |
| ccaggctgtg | ctagcaacac | ccaaaggtgg | cctgcgggga | gccatcacct | aggactgact | 3060 |
| cggcagtgtg | cagtggtgca | tgcactgtct | cagccaaccc | gctccactac | ccggcagggt | 3120 |
| acacattcgc | accctactt | cacagaggaa | gaaacctgga | accagagggg | gcgtgcctgc | 3180 |
| caagctcaca | cagcaggaac | tgagccagaa | acgcagattg | ggctggctct | gaagccaagc | 3240 |
| ctcttcttac | ttcacccggc | tgggctcctc | attttacgg | gtaacagtga | ggctgggaag | 3300 |
| gggaacacag | accaggaagc | tcggtgagtg | atggcagaac | gatgcctgca | ggcatggaac | 3360 |
| tttttccgtt | atcacccagg | cctgattcac | tggcctggcg | gagatgcttc | taaggcatgg | 3420 |
| tcggggaga | gggccaacaa | ctgtccctcc | ttgagcacca | gccccaccca | agcaagcaga | 3480 |
| catttatctt | ttgggtctgt | cctctctgtt | gccttttac | agccaacttt | tctagacctg | 3540 |
| ttttgctttt | gtaacttgaa | gatatttatt | ctgggttttg | tagcattttt | attaatatgg | 3600 |
| tgactttta | aaataaaaac | aaacaaacgt | tgtcct | | | 3636 |

<210> SEQ ID NO 2
<211> LENGTH: 29001
<212> TYPE: DNA
<213> ORGANISM: Homo sapiens

<400> SEQUENCE: 2

| | | | | | | |
|---|---|---|---|---|---|---|
| acgttttaaa | aaaacatttt | tcatgtaaat | ttaaaaaaat | tgaacattca | cacaaaaaga | 60 |
| tgcccctcc | cttgcaaaaa | agagtatgcc | cgttcaaaat | gttgaaatgt | acactcacag | 120 |
| caatggtggc | tgcagactcc | aagtttctga | ggttggagaa | ggtagccagg | gagcataaaa | 180 |
| gtgagttcta | tctactcatt | cagtctatga | ggggaaggca | atggctagaa | aagcattttg | 240 |
| agggacagta | aaagtggcat | ttttagaggg | aggaagcctt | gaggatgctt | gtgggtgaa | 300 |
| gggaaagaat | aactcaggaa | gaggcattta | gggataagag | gaggagagga | gatagtggag | 360 |
| gtaggtgatc | cctgcggagg | ccagattggg | gcaggggagt | gtcagctgag | tataagagga | 420 |
| tggtcccctc | tgccctgaag | gaggaaggca | ggaggggaaa | aggatgggtg | ttgacccaga | 480 |
| aagcacttgt | ggtggagggg | aggccccaga | agaggcttct | gacttaccct | gattgctggt | 540 |
| acctctcagg | ggagctggct | gcttatttgc | tggccaggt | gtgggggaac | ccatttgaga | 600 |
| agagggagaa | ggtgacacaa | ttcctttggg | caacttatgg | gaggggtaat | tggtgaggga | 660 |
| tgaaagccct | gccaagtggc | aggaggccca | gctgggctg | cccctcataa | gagtgcagtg | 720 |
| gaggatatgg | gatgagaagt | gactgcccct | ctggttccat | ctgtcgcaga | gcccagggtg | 780 |
| cttccttcct | ccccacctc | cctcagaaca | cacccactgc | atgctggaca | gcagcccct | 840 |
| tcctgggcct | ggggacatcc | atgtccctct | gtgcacaggc | ttcatcattc | tctgggtgca | 900 |
| cggtaacgac | cccggtaggt | gagaggccaa | ggtcccaaag | gggagcagca | gggaaagtta | 960 |
| gctcccatct | attcttgctc | caggggaggc | ctttgatgag | gaagctgcca | aaagcacatt | 1020 |

```
gcaaatacaa ttccaattac aggcaacagg aaggagaacc acctctgcca cctctgtcag   1080
caaaccatga gctcctactc tgtgctgcga tggcgggctc gatggggata actctgacct   1140
tacctcatgg agtcactgtc aacccactgg ttgcactgtc tttgtgcact ggctctctgg   1200
agtgaggtct ttgcaaacaa agtggaaaga gcatcaactt tggactccag cacctagatt   1260
cagagcaggc catttcactc ggaatctgct gtgcatctgc aagggaggat cataaattcg   1320
cctttgtttc ttcccagtat cgacagccct tccagaaaga gcaagcctca tgtcatgcca   1380
catgtacaat ctgaggccag gagctctctt tcccttttc atcctcctgc ctggtacaca   1440
ataggtgttt actggatgct tgtccagttg atttcttgaa catggtgtgt aaaaggaatc   1500
tttgcaaatt gaatcttctg gaaagctgag cttgtgccta ccatagaatt ctgaatgtac   1560
ctatatgacg tctttgcaaa cttaaaacct gaatctttgt agtataaatc ccttgaaatg   1620
catgtaggct ggacatcaaa agcaagcaat ctcttcaagg agcagctagt tggtaaggtc   1680
agtgtgcagg gtgcataaag ggcagaggcc ggaggggtc caggctaagt ttagaaggct   1740
gccaggttaa ggccagtgga aagaattcgg tgggcagcga ggagtccaca gtaggattga   1800
ttcagaagtc tcactggtca gcaggagaca aggtggaccc aggaaacact gaaaaggtgg   1860
gcccggcaga acttggagtc tggcatccca cgcagggtga gaggcgggag aggaggagcc   1920
cctagggcgc cggcctgcct tccagcccag ttaggatttg ggagtttttt cttccctctg   1980
cgcgtaatct gacgctgttt ggggagggcg aggccgaaac ctgatcctcc agtccggggg   2040
ttccgttaat gtttaatcag ataggatcgt ccgatgggc tctggtggcg tgatctgcgc   2100
gccccaggcg tcaagcaccc acaccctaga aggtttccgc agcgacgtcg aggcgctcat   2160
ggttgcaggc gggcgccgcc gttcagttca gggtctgagc ctggaggagt gagccaggca   2220
gtgagactgg ctcgggcggg ccgggacgcg tcgttgcagc agcggctccc agctcccagc   2280
caggattccg cgcgcccctt cacgcgccct gctcctgaac ttcagctcct gcacagtcct   2340
ccccaccgca aggctcaagg cgccgccggc gtggaccgcg cacggcctct aggtctcctc   2400
gccaggacag caacctctcc cctggccctc atgggcaccg tcagctccag gcggtcctgg   2460
tggccgctgc cactgctgct gctgctgctg ctgctcctgg gtcccgcggg cgcccgtgcg   2520
caggaggacg aggacggcga ctacgaggag ctggtgctag ccttgcgttc cgaggaggac   2580
ggcctggccg aagcacccga gcacggaacc acagccacct tccaccgctg cgccaaggtg   2640
cgggtgtagg gatgggaggc cggggcgaac ccgcagccgg gacggtgcgg tgctgtttcc   2700
tctcgggcct cagtttcccc ccatgtaaga gaggaagtgg agtgcaggtc gccgagggct   2760
cttcgcttgg cacgatcttg gggactgcag gcaaggcggc gggggaggac gggtagtggg   2820
gagcacggtg gagagcgggg acggccggct ctttggggac ttgctgggc gtgcggctgc   2880 gctattcagt gggaaggttc gcggggttgg gagacccgga ggccgaggaa gggcgagcag   2940
agcactgcca ggtatcctg cccagatttc ccagtttctg cctcgccgcg gcacaggtgg   3000
gtgaaggagt gaatgcctgg aacgtactgg gaactgcacc aggcacagag aaagcgggct   3060
tgccattata gtgggttccg atttggtttg gaaaacatgg gcagcggagg gtggagggcc   3120
tggagagaag gccctacccg agacaggggc ggggtgggaa ggacggcaga tgctgggagc   3180
acgaggcaat ttctttatga cacagaactc atgctctagt attccatctg tttcagccga   3240
agaaaagaac cagctgaagg ggcaggggag aaggggcgga ggtattctcg aggcccattg   3300
gcgtccttta ggactcaggc agggaagggc ccttggtgct ctggagccgg aggtggtgcg   3360
```

```
cctggtactg ggaccccgga gctgagcccg gcgcctcagc ccacctggct gtctgccgac    3420
cgtgtgcggg gcgagtttgc tcaacaactc tgccagcttc tggccctcag gctgtgggaa    3480
gcttcttccc ggggcgagac cactagcttt ttctaagtat taccagccca ggacttggct    3540
gaggttctgt gtccccagc ttggagtcag atgtggggtt gaatcttggc ttcctctcac    3600
tagctgtggt gcttgacaag tcacttatcc ttgagcctcc attgcctaat ctttaaaagg    3660
gaggtgacaa tcgtccctac ggctcagtgg cagcagatgg ggagatgaag ggaaagttct    3720
gttgaccatg agtgaactta caatgcaagc cccgggggga tcacttgcag ttttgtccct    3780
gtctgcagtg tgacctgttg gtgacattgt ctttgctcca aaccacagct cctggggcag    3840
aggggaaaat tctgccactc acagctgcct gcccacgctt ctgtctgagt gtgctgggtg    3900
gcaggatggc aagtccttac tcagctcagt atagccctct tccttgttcc ctgagccttt    3960
gactttctcg agggatgttg tggggttgtg gccaggataa gaaagggcat ttcaagttac    4020
cactgctcca aaacaactgt tctggaaata gtgagtaccc catcctgaga ggtgagtaag    4080
cagaggctgt atgaccacct gaaccaagcc cttgaggatg tttcttctct ggtggaagtt    4140
tggaacagga gcctcctcaa gttcattat tcattcatc aatggttatt ttgtgggaat     4200
cgaatttaga atgaaaatat ttttttggcaa gcagaaaata attttttagac caatccttt   4260 cttttagtca tgagaaactg aggcccagag agaggaggtc accccaggtg cattagaact    4320
gggtttccag aactgacact ccactgcaca gagtactctc ccaattcatt caatttttat    4380
ttagcggaag gcattttcag atgggtcttt gaagcattag taggagttca gcgatgatgg    4440
tgtcatgaga attttattct aggattagga ggtaccatga acaaagatac agagctggga    4500
aaaccagagg tggaagataa ggagcacatg tccacagttc ttttctttt tttttgaga    4560 tggagtttcg ctcttgttgc ccaggctgga gtgcaatggt gcagtctcag ctcactgcaa    4620
catctgtctc ccgggttcaa gtggttctcc tgcctcagcc tcccaagaag ctgggattac    4680
aggtacctgc caccacgccc ggctaatttt tgtatttta gtagagaagg ggtttcacca    4740
cgttggccag gctagtcgca aactcctgac ctcctcagtg gatccgagga ggtgatcctc    4800
ccgcctcagc ctcccaaagt gctcgaatta caggtgtgag ccaccacgcc tggcctccac    4860
agttctttat ccaccgtctg aaatgtaaaa tgttacgaaa accaaaagtt tttttgtga    4920 tttatttgat ggtagcacct gacgtgaact gacatgagat tatttttaat ttagttgtgt    4980
gaatatgcat attcatatat tttgctgcat agattacagt atgcagctcc agattcttcc    5040
aagcagactc tgattgccca ttactgcctt tctaaaatcc aaacaagttc tgaggttcaa    5100
aaccgttttg gccctaaggc tttgggtaaa ggggtggac tctgttctac tctgactgga    5160
gtccaagatg catatataca gagatatggg tgatggggct gcaaggtagg ttgaggtagg    5220
ggccaaggag gagcatggag tttggacttg attcatgagg ctgtggggag ccagtgaagg    5280
ttcttaagca ggtatgtctg cctgagagca gttggagcag acaagagcta aaaaccaaac    5340
aaatcaccat agatagtggc tgctataatt tgtttgtccc ctccaaatct catgtggaaa    5400
tttggtcctc agtgttggaa gtggggccta atgggaggtg tttgggtcat ggggaggaa    5460 cccctgtgaa aggcttggtg ccgtccttgt gataatgagt aagttctccc gctatgattt    5520 ccccttgaagg ctgattatta aaaagagctt ggcacctccc tctcttctct cttgcttctt   5580
ctcttgccat gtgattgatc tctgcacatg taggctcccc ttcaccttct gccatcagtg    5640
aaagcagctt aaggccctca ccagaagcag atgctggtgc catgcttcct ggagagcttg    5700
cagaatcatg agctgaataa atccctttttc cttgtaaatt actcaccttc aggtattcct   5760
```

```
ttatatagca acacaaaagg actaagacag tggccttgac ttttctctct ctttaagaag    5820
tgttgccttt gctcacttag tcatcccttc tgcctgcatt tgtagagcat ctggatggga    5880
gatttatata accgtcactc ttgactttcc cagcaggcct atgtcatagg tactgtggtc    5940
tctacaatac agcagaggta tctgaggctc cgagaggttg agtgacttgc tcatggctgc    6000
acaaccagta aatattggag ctggaattca ggtccacggt ttcctggctc caaagcccat    6060
gattttttcc ctcaatttat tctgactggg gcatggggga ggggtggcc tttgggcagg     6120 gccaccagga gcgaccaggc ccgtagagag ctgggtgcag gtacagagga aaacctgttg    6180
tcgagtgtgg cccgtagttc ccattttgc ctgaatggca catttgaaag tgttatataa     6240
ccatgtgaat aataatagtt ggcctatatg agttctttaa tttgcttttt ggtccgcatt    6300
tggtaacttc tttatcatct actatactct gttgtgtctc ttttgttgta atttgtaagt    6360
aggggtgaga taaagtacac ctagggtttg ctgggtttct tccatgtcat catgttcctc    6420
cttgcatggg gccaggatcc gtggaggttg cctggcacct acgtggtggt gctgaaggag    6480
gagacccacc tctcgcagtc agagcgcact gcccgccgcc tgcaggccca ggctgcccgc    6540
cggggatacc tcaccaagat cctgcatgtc ttccatggcc ttcttcctgg cttcctggtg    6600
aagatgagtg gcgacctgct ggagctggtg agccaccctt tttgggaatg gcacttcctg    6660
atagggctgg gccactgcat atacactggg gactgtgctt agtaggccca ttgctgaaaa    6720
tcagaagggg acagcaagta tgtattgagc acttatcggg taccaagcac agtaactact    6780
ggctttctgt atagaattcc ctttaagcct ggccatgccc cagtggtacg tctatcttca    6840
tttgaaagac gaggagactg aagttcagag gggaccacac agacagctag gggtagagcc    6900
tggatcaaac ccattggtct gcctgccagc cattcttgtg ccaatgcatc tgctgcctac    6960
ggaaacctgt agggacaagg ccctgggatg ttcagtggag cctgagtcat tttataaaaa    7020
agcatgactc tagggtccaa aattcctttg aagctgttgc tatccagagt gaagtccctt    7080
ctttaggaca gggtggccct cctccctcct ggatgtcaca tcttcggtgg aggggcagaa    7140
aggggactgg gtattctcct caccctggcc ctagtgcttc aaatcttaaa aaacgttttt    7200
tatttgtgct tctgcaccac cttctagccc acctcgtttc ctggcctcta acttgatgag    7260
agcgtgtgtc atttttcacac tgattctcca catggcaggc ggtgcttctt agcctcctgc    7320
agacagtgag gcccacggt cttgtccaag gtcacacagc gtgtaatggg cagggtcaga    7380
gtctggagtc tggacctggg tctcctagct gcactgcact gctgccccat gggttaatca    7440
gctcagcata ccgtggctga acagctacct cataccaagg cctgtggcgc catgacaggg    7500
attgacaggg tccctgcctt ggaaacccgt agtctaagta gaggagactg acaagtcaat    7560
gccttccatc agtctgctca acacacgttt accaagtgcc tactgtgtgc tgcagaggcg    7620
aagatgacac agctcaggcc tttcccttga gcttacagtt caggaggaga gactgaccag    7680
tgactgccag tacagttgac tatgggacaa tgtgctcagc cttggggaga gacgaagaag    7740
gtacccgtat agcaccagat gacaggcacg agcccacag gccagggcag ctgctcagag     7800
gagagtaggc caagcagaag gcaaacagaa ggctgcaggc atttgccatc gagagctgga    7860
cttcaaactg ggcatcatac cagcctgggt tcgagtcctg cccagcccct tattggctgt    7920 ctaacccctga gcaaatccct tcacctctct gagcctcatt cctctatctg taaaccagtt    7980
ataataattg gaacattcat ttaaggacta aatgaggtcg tgaagcattc agcagatgct    8040
aggtacggaa actcgctgaa gtgggggcag gttaagaagc ctctggggat acgaaggcat    8100
```

```
ccagggacta gttgtggcag gaggctgtta ccacttaggt ctgaagggta aggagaggga    8160
atagctttcc ctctgcccag ttggagccgg tggcatggag gagaggctgc ctgtggggaa    8220
tcacccgagg gttcaccgct gccatgcgca gggagtcagg aggtagggag ggagtggggc    8280
agatgcacac cattttttt tttttttgag actctgttgc ccagactgga gtgcagtggt     8340
gccatatctg cacctctgcc tcccgggttc aagctcactg caacctctgc ctcccgggtt    8400
caagcgattc tcctgcctca gcctcccgag tagctgggac tacaggtgtg tgccaccatg    8460
cctggctaat ttttgtattt ttaatagaga tggggtttca ccatgttggc caggctggtc    8520
tcgaactctc gacctcaggt gatccccac ctcggcctcc caaagtgctg ggattacagg     8580
cgtgagtcac cgctcccagc tgctgatgca ctcttgtcct tctaactcct gctagtgcct    8640
cccattggct gagcccaact ggaagctttg caagggagct ggtgctgcag tttgcactga    8700
gcaggctgga gaaggctgga gaatagacta ggggacaaac cgaattgcca gtgctgttat    8760
gtcatgattt aggcatggag tccagggcct gagcttcact ccatgtccat cctgcccaga    8820
gccttggcac agcctggctc ccagacaaga tgtcaagttc agaatccttc ctaaaaggaa    8880
tcctctatgc cagaccgtgt gcagggata tgggagtgct gggctcccag cctgatcaag     8940
gagcgagaaa actcaggctc ctagtctgtc ctccggggca ctagcaggga caaggtggga    9000
ggctgctggg ctgggatgtg gggacaggtt tgatcaggta aggccaggct gtggctgtgt    9060
ttgctgctgt ccaaatggct taagcagagt cccccggcct ctctggcttc tgcaggcctt    9120
gaagttgccc catgtcgact acatcgagga ggactcctct gtctttgccc agagcatccc    9180
gtggaacctg gagcggatta cccctccacg gtaccgggcg gatgaatacc agccccccgg    9240
taagacccc atctgtgccc tgccccaccc catctgagct gaatccattt gctctgccct      9300
ggcctggcct cctgctggt ggtttccact tctcgggggg cttgggact cagcacctcc      9360
actgacccct ttttttctgt cccatcccca tccctgcag cccccactgc ctgccttcct    9420
gttgccccac aaatgcaaaa gtcttgcctt aaatgatcct cttttccttc ttttctcttg    9480
ttttcctttt ctcaccattt ggaatggccc agcaggctgc acttaccttg aaggagggt     9540
tcatctgatg gtgactctac ctagggcccc caggcctcta taactcccag tgccctgcag    9600
actggaccag atcctttaat gggatagaca caaccctgtc tgggatgcct ctgcctacct    9660
tcctgttttg ctgctccacc tgcctccagc tccgttggc ttcctggggc tccctgcctg     9720
ggccactttg tgtcttccct ctaggccttt cttttccactg ttccctctgc ctggtgtggc   9780
ctggctatgg aagggaggga ggaggagcgg ccatggaaaa cggtctgcat tctagcaggg    9840
acttgcaggt ggcaattcag tcggggaaga ctctagatgc acctggcctg aggagagaat    9900
gaagggttct agttggactg tgttaagttt gaggtgccca tggtgtgagg tctgagctc     9960
agcgcagaga tgatgcaatg tggtgggtcc atgcaacatg gtgccaggac gcagagcttg    10020
gggtgaactc agctttcacc ccttaccggt tctcgtggga tcttgggaag ccactttctt    10080
ctatgagctt tgtcgttctt gtctgtaaaa tgggcacata accctgtccc tgtccttctc    10140
acaggttgct gtgagactcc aatgagttga aggatgtgca gatgcttttg gaagtgaaaa    10200
gttgggggc tactgtgtga ctttgcatac acccaaactg tgtgaccttg catatgtctg     10260
agttgctgcc attgcaacag atcagagctg gtgggctggg tgtggagaaa gggtttgtgt    10320
gggggacatc ctctggcaag ggtggcagca gcagaagtga ggggcctggt cggtcatgtg    10380
tgctgacccg gcctgggcag cctgtggcca gggaggagac agctcctctg taggaagagc    10440
ctgttccttt ccaaccaggt gagacctctt cagtggagcc ctggagcccc ctgtactcca    10500
```

```
catcagtgcc tcagggacct cccggagcag gctaatatca gagaccaaga gggacactgg    10560
cagaggatca cagagacccc agtccaggca gggactgaga agatcttgcc ccctaagtta    10620
gtttcctagc actgctgtga caaattacca cccctcggt tggaacaagt tgattctctg    10680
cagtcctgga ggccagaagc ctgaatcagt gtcggcagga ccactttctc ccgggggct    10740
ccagggagaa gcttctcttg cctcttccgt gtcccaacag cggcagcaca ccaatcccag    10800
cctctgtctt cacacagcct tctctgtgtc tctctcctct tcattgtctc ataaggacac    10860
ttgtcattgg atttagggcc cactggatcc tccaggatga tctcatgtgg ggaaccttaa    10920
ccacatctgc aaggaccctt tttccaaata aggtcacagc cacaggttgt gggggttagg    10980
atgtgagtgt atctctttgg cagccactgt tccctcctct cccttgggcc agaagcagac    11040
gtggggccct tcttccccca taggatgccc atggattgcc ccccttcccg cttccccga    11100
gtgtctgtgg gaggtggcag gaatggcagg caggggtgtg gaacccccttc tggagtcata    11160
tcaagggctt ggctggagga agtcctcctg gagctgttgg gctggcatgg ggcaggctgg    11220
ctgggcccag cagcagcttc ttcattcatg gggaggccac aagcatgggc cctagagctg    11280
gctgccgccc tcaaacccag accctgcact cttaactgtg tgaccttgca tacgtcactc    11340
accctctctg atcttcaggt tcctctgcaa aagggaggta atgataaccc tcactctggg    11400
gggctgtttg gagggttaaa tcagttattg ctgtagcatg catttctctg tcaggtattg    11460
agtgaggtgc tgtgatttta gccctgcatt tttcttttct taccattcaa taataacgtt    11520
ttgagcaccc actgtgcgcc aggcaccata ttaggtgctg gggatacaaa tgtgaatgaa    11580
atgaatgtgg tctcttcccc caacagtgta tccagaagat taatccattc cttaaacaaa    11640
tgctacttga cacagattag ttctggatag gctgagagct ctgaaggagt gcaggcagct    11700
gcgagcctgt gtatccagca gaaggatcag gaaaggattc ctggaggaag cgctgttcta    11760
gccaagacct acgggggcat tattaaccag gcaaagggga cggtgtccaa gcagtggaat    11820
gaacgtggat tgaagctgtg aggcaggagg gagtgtggcc tgtgcagaag ggaccgaggc    11880
tggtgagacc aggagggcct gggtggcctc caggtcagat gtgaaaggaa gaacttggcc    11940
acagtctgag cttctcaggc gtatggcagg gctgcctggt gagagggaat gagctccctg    12000
ctctggaggt atgcaagcag gactgggctc tcacctgcca gaggccacag agctttccag    12060
aggctggaag aggccactcc aaggcctctt tgccccgag agtggtggct cttcttgagg    12120
ccaccttgcc acgctgtcac agggaactag cagcccctgc ctcacccggg ggtttggaag    12180
atagagggag gcctaggaag ggccctgtgt ctcatccgag ctgggcccct ttccagcctc    12240
tcactggaag gaagcccaag gatgttcctg tggggctttt taccaggccc acctgccctc    12300
tgctggccat gcttgcagcc tcctgaccct gtcccagcag gacagtgggc tggtgtgagc    12360
gggcaggaac cgcctgcact tagaaggtgt ggggctgcct ccccgagctt ccatctgccg    12420
ctggggccac accccaggcc cagggatggg accccacagt ggtcacatca tcttgcagca    12480
gaacccaggt acagctcctg gagcagatgg tggtcccaag cacgggtggg accagaaagg    12540
actctcacct gggctaactc agctgcagcc tcagttccct cctcacacac gacgaggaac    12600
atggactgga agcctgccca gcaggccttc tgctcgatgt gcgttgtgtg gcttacgtcc    12660
agggagggaa gcagcctctg tgctgtcttc tagataagcc tgtattcccc gggctgtctg    12720
ccaatgtatc cagttgtccc gtcagcctgg aagctctgag ggaaaacctt gggctgcttc    12780
ctgagcacct gtatcccctg cagccagccc ggggcctctg ctaggagcag actgagcatg    12840
```

```
gcttatgggc ctggcaccat ctggcctctg cccaccttgc tggccttgtc ttgtgtctgc   12900
cccttcgaca ttccatagcc cagctcaata tctagtggtt cctctagggt ggcgagcact   12960
gtttggtctc cagatgtctt caggtcggag ctcacagcgc tctcagccac cccttcccag   13020
tgtagcaccg ggcacatggt agatgcctat tgatgagtga agctcctaa cacactcaga    13080 gagcaaggac tccgcctcat cccacagcct gggaggagag gcagactgcc aaggacctgc   13140
tcagcatgct acagaagaaa ccaaagtgcc cacgggactg atcagtggag cttcctgccg   13200
agactggagg ccttagggca gggtagatag tgtgtgtgca ggctgggac tcacagttcg     13260 gactgtgccc agacctacta gcatagtggg tgggtgggag gatgcgggac tgggggccga   13320
ccttgcctga aattcatgtg ggatctcaga gcagccactg aattgctctg tagggggcta   13380
aatagtggcc cccacagata cacacaccca gacagagcct gtgagccaga ccttatttgg   13440
agaaaaggtc tttgtagatg taattaagca tctcaagatg gcatcatctg gattatgcgg   13500
tgggctgtaa gtcctgtgat gtgtctttat gagagaaagg cagagggaga tttgacacac   13560
acaggagggg ccacgtggag acagaggtgg agattggaga aatgtggcca caagccaggg   13620
aacaccagca gccaccagaa gccggaagac gtgaggcagg gttcttccca gagccttcgc   13680
tgctgagtct gggaatttgt gaccgaagcc ataagaagtg ggtacacgcc ctgagcctcc   13740
cacacttgct cacctgtcct gagatgagaa tctctactct gcagcatatt tggaggatca   13800
ctgcgggggc cacagaggtg ctgttcagat ggcacttcag aagactcagg agaccctggg   13860
gcaggagcag tttgactgac agcccagagg gctgccctct gattccacct gaggccctgc   13920
ttttcctggc tgcaggggtt ccagggccag gccatttccg ctggcgcagg actctgctag   13980
cagcaacctg cctgaagtct tcctttggcc tggctgagag tttctgagac ctgcgctgga   14040
gcggaggtgc ttccttcctt gcttcctttc ttcctctctc ccttctccat ccagcaggct   14100
ggacctgcct ggcatctgtg agctctccct actttctcct ataccctaac ctttgtcctg   14160
catgggcgac tcccccagtg agtctcttgc agcttttacc ccagtgcctg cttcttggag   14220
aatccaaact gatccagtta gggatgataa agtgtagggt aggcgctcgg tgactgtttt   14280
ctctgaggtt gtgactcgtg tgaggcagaa gcagtccccg tgagccctcc tggtatcttg   14340
tggagtggag aacgcttgga cctggagcca ggaggcccag acatacatcc tgtccgagct   14400
gcagcttcct gtctctaaaa tgagccggcc agcgcaggtg ccagacatc actgttattc     14460 tcctttgagt cttttaaatct tgttgtcttt cttgcagact cggtgagctg tgaaaggcta   14520
taataggggc tttattttac actttgatac tatttttttga acattcatat tattgttaga   14580
tattgatatt catatgaagg agcaggatga cttgggtcct tcttggcagt agcattgcca   14640
gctgatggcc ttgacagtt acctgccctc tctaggcctc cctttccttg tctatgaaat    14700
acattataga ataggatgta gtgtgtgagg atttttttgga ggttaaacga gtgaatatat   14760
ttaaggcgct ttcaccagtg cctgggatgt gctctgtagt ttctgtgtgt taactataag   14820 gttgactta tgctcattcc ctcctctccc acaaatgtcg ccttggaaag acggaggcag    14880
cctggtggag gtgtatctcc tagacaccag catacagagt gaccaccggg aaatcgaggg   14940
cagggtcatg gtcaccgact tcgagaatgt gcccgaggag gacgggaccc gcttccacag   15000
acaggtaagc acggccgtct gatgggaggg ctgcctctgc ccatatcccc atcctggagg   15060
tgggtgggga ctgccacccc agagcgttgc agctgtactc ctgggttgca ccccccccag   15120
ctgtcactgt cccctccctg ccatcagttg tgggaagggc gttcatccat ccagccacct   15180
gctgatttgt tataggtgg agggggggtc tttctcatgt ggtccttgtg ttcgtcgagc    15240
```

```
aggccagcaa gtgtgacagt catggcaccc acctggcagg ggtggtcagc ggccgggatg   15300
ccggcgtggc caagggtgcc agcatgcgca gcctgcgcgt gctcaactgc caagggaagg   15360
gcacggttag cggcaccctc ataggtaagt gatggcccca gacgctggtc tctctccatc   15420
tggacctggc ctgggaggtg gcttgggctg ggcccaggga gagctaatgt ctcctaacca   15480
agaatgctgt ggcagcctct gccgcagagc cagagaacca gagtgccaag gctggcaggg   15540
ttcccagtgg ccacgagtgc agatgaagaa acccaggccc caagagggtc atgcaggtag   15600
cccagggagt tcagccttga ccctgggtca atgaccttc cacagttcca cactgctccc   15660
cttttaaaat ccggtgatgt ctttatgtct tttgttatgt tatcttcaat gtggagggac   15720
tcgaggtgat ctaagcaaac tttttctatc ttctgcttgc atacctctga gccagggga   15780 ctcactcact tgcatgactg ggccctgcag gtcacactgg ccaggcagat gtggtggagg   15840
aactggcaga ggactttttc tagactgtga ctacatttag tccacccagc ggcccccta   15900 tgaagtccag ttgagaacta ggactctggg ggccggtgga cagagaagag ggagggttct   15960
ctcccttact gacttccttc tgtggccaga cattgagcaa ggcctctgta cagcatgtcc   16020
tggggctggc cttgccgtag ctgctaaata gttgacgaaa ccagtccaga gaggggaggt   16080
gactgccagg gtcgcacagc tcaagctggg gaactcgctg ggaaaactgt cagctctggg   16140
cagcagcttg acttccactg taagcccag ccccagggt caaacactgg ctctggtgct   16200
ggcagaggca gcccactagc ctgtttcaaa ggctgagaag gcccaggagt ctgccctgtg   16260
ctccaccagt tctgccctga gactttccta cagagtacag gttttgatgt tcagttttaa   16320
aggcaagaat caataacctt ctgccccatc aggtgacccc ttgtgcctgt cccaccccctt  16380 tattgactga cctcggctca gtcaggtcag ttcctgaagg tcagtgtgtg gaggggaggc   16440 tgttcttcc cagaaaggcc ttccccaggc ctggtgctct ggcctctgga ggacttcctg   16500
gagaagtccc ttctttgggg tcccagtcag tgtatgggaa gcccttattg catgacctgg   16560
cacggggcag gggctcaaca gtcactattg ccttccttgc cactgccatt tcctcctctg   16620
taagcaggtg attgtgtgtc cagtctgagc acagagataa gcacacagca ggtgcttaat   16680
aactagcagc tgtaggctgg gcgcggtggc tcatgcctgt aatcccagca ctttgggagg   16740
ccgaggtggg cagatcacct gaggtcagga gttcgagacc agcctgttca acatggtgaa   16800
accccgtctc tactaaaaat acaaaaatta gccaggcatg gtggtgggtg tctgtatccc   16860
agctacttgg gaggctaagg caggagaatc gcttgaaccc aggaggtgga ggttgcagtg   16920
agctgagatc gtgccactgc aatccagcct gagtgataga gcgagattcc atctcaaaaa   16980
taaataagta aataactagc agctgtaaat gtggctgttg ttcttcacct ccacactcag   17040
tgccactcca ctccctccct ccgtggtgtg aggggcctca ctagctgtct cctaggagga   17100
gcatggctgt gagattccag ctccatcctt ggccacggct cctggagaca tcttagaggc   17160
caggatccag aaggctccca cacctcattt gacaggggag aagctgtcag ttccaggtcc   17220
ccttgcacat cagggccaga gctgcgttag gcctccagtc tccaggccac tgggccagag   17280
ctcacaggct ggcagagggt tagaactgtt actggtggct gggtgcagtg gctcacgcct   17340
gtaatcttag cactttggga gggcaaggcg ggaggatcat gaggtcagga catcgagacc   17400
atccttgcta acacggtgaa gccccgtctc tactaaaact acaaaaaatt agccgggcgt   17460
ggtggcaggc gcctgtagtc ccagctactc aggaggctga ggcaggagaa tggcgtgaac   17520
ccgggaggcg gagcttgcag tgagccgaga ttgcgccact gcactccagc ctgggcaata   17580
```

```
gagcgagact ccgtctggaa agaaaaaaaa aaaaagagc tgttactgtt gacagtagca   17640
tgaggtagac catggcctgc accaaaatgg gggagtggag tgccactgag gccagaagga   17700
accacaccct caagggtggg gagttatggt atgggggtc ctaggcatgg agtcttttaa    17760
ttctttagac aatcctggga gcaactgtcc ctgtttcaca gagggcgggg ccacacagct   17820
ggtgagtggg cagccaagac tctgttcaag tttgtgtggg tccaatactt gcggccacgg   17880
tggaggggca tctgagccag gcctcagaga gtggcggggg aagttgggtg gggaagtgtg   17940
cccttctcat tcctctgagg ctcatcctct tggtgcctct ctttcatgga aagggataat   18000
aaggttattg tgaggatccc ctgagttcgt atattcagac gcttagacag agccaggcac   18060
agagaagggc ccggggttgg ctagtttgat tgctggtgta attgctaata tcttccagtt   18120
tgtattggtc aaggttctgc agagaagcag aaccagtagg atgtatatat taagagtttc   18180
aagctcatgt gaccgtgcgg gctggcaagt ctgaaatccg cagggcaggc caggcaggct   18240
ggcaattcct gcagaatttg atgttgcaat actgagtcct aaggcagtcc tgggcagaa    18300 ttccttcttc cctgggaggc ctcagtctgt tctcttaagg ccttcaactg attaaatgag   18360
gcctgcccaa gttatagaga gtaacctgcc ttactccgtc ttctgattta aatgttagtc   18420
acatctaaaa aatattttcg cagcagcatt tccactggct tttgaccaaa catcaggcca   18480
caaagttgat ccccaaaatt aaccatcact ctgtgcctgt aagggagggg ctgggaaagg   18540
ggagcaggtc tccccaaggg gtgaccttgg ctttgttcct cccaggcctg gagtttattc   18600
ggaaaagcca gctggtccag cctgtggggc cactggtggt gctgctgccc ctggcgggtg   18660
ggtacagccg cgtcctcaac gccgcctgcc agcgcctggc gagggctggg gtcgtgctgg   18720
tcaccgctgc cggcaacttc cgggacgatg cctgcctcta ctccccagcc tcagctcccg   18780
aggtaggtgc tgggggctgct gccccaaggc gcgggtaggg ggcggagggc ggagggcgga   18840
gggagggcgg gcgggcaggc gggcttcttg tggcacgtgg gcttcttgtg gcacgttcct   18900
ggaggccgaa cccttctggc tttgaagga gtcgtcagag accccgcca tgcgggaggc    18960 tggggaggaa ggggctcgaa acctccatca tcgcagagtc tgaatagcag tggccccgcc   19020
atgcgcccac gtagcggcgc ctacgtagcc acgcccccac accccgtcct ggccactctc   19080
cctcctgaag gtcttctggt acccgccccc tccccatctc catccccagg ccctgcgtcc   19140
tctgcccaat actctttggg cctccctgtt gtccagctct ctccgcggct ccatgactga   19200
caacttgagc aaggctaatg tgaatgggag cggttgaggg ctcagacctc tcacccgagg   19260
aacatccaca gagtgtgccg catgcccggt gcagtgtggc tgcggggaca cagacacgga   19320
gcctcggccc tgaggagctg ggggcagtg accgtccctc ctctgaccca ccactcctcc    19380
agtgtcagga cactgcgggt atctagggga aggaatcttg ttccacttca agtctggaac   19440
ttcaagtctg tgtgtgtgcg tgcgcgcgcg cgcgttgggg gtgggggttg cagagcagat   19500
gcgtacctga cagcggtaac ctaggtcccc cctggcctat caaggcttcc ctggcggccg   19560
aatttaaagg catcaagcaa acaaagccca acacatctct gccttgtcct ctcagtttcc   19620
ccccgtggca cttagaacca cttgatacac cgaatagttt cctatctccc ccactaggat   19680
gtaaactcca caggggcatt gggaatgctg cctggctatg gtaggacag aggggagcac    19740 cagggcgggg caggggtgcc agagttctgc ctgggcagtc agattttcct taggagggga   19800
catttgagtg ggacccaaac aggtgtatag cagttgtcca gcccagctgg caaggcctga   19860
gtctgcctct gcaacccctc tctttgggctc ctttctctgc cacccacctc ctcacctttc   19920
caggtcatca cagttggggc caccaatgcc caagaccagc cggtgaccct ggggactttg   19980
```

```
gggaccaact ttggccgctg tgtggacctc tttgccccag gggaggacat cattggtgcc    20040
tccagcgact gcagcacctg ctttgtgtca cagagtggga catcacaggc tgctgcccac    20100
gtggctggta agtcaccacc ccactgcctc ggccaccgtg atgctaacag cccctttggc    20160
agtcagggtc tgtgccggga cctccagtgc caggctctgt gcaggggggac cagagatgaa    20220 gtaggcctga tggtgccttc aaggacactc agtctgatga gggaggcgag tgcacagagg    20280
aaacacgagg tcagggctgt attagaggga gcccagagga ggcacctgcc cagcccgagg    20340
gtcagagaag gcatcttgga ggagggacat ttgatcggga gcttgatgga tgaataggag    20400
ttcacctggc cgataagaca gcaactacca aggcttagag gtgtgagagg aggctgtctt    20460
acctcactga gtaaggactg caggcggctt accttcgaga agagagctta gtgtctgtgt    20520
gcacgtgtgt ttgtgtgtat gtgtgtgcgt gtgtgcactg gcaggagtcc cctgctgggg    20580
caggagggcc gggccatcac catctttcac cattcacccc tgcaccaggc attgcagcca    20640
tgatgctgtc tgccgagccg gagctcaccc tggccgagtt gaggcagaga ctgatccact    20700
tctctgccaa agatgtcatc aatgaggcct ggttccctga ggaccagcgg gtactgaccc    20760
ccaacctggt ggccgccctg ccccccagca cccatgggc aggtaagcag gatggcaggg    20820
tgggcaagtc caggctgggg cttgggaggt ctgtgtgacc ttgacagtct ctcccttctc    20880
ccttgtctgt gtaaggagga tgacgccacc ttaaatagga ttaaatgaga atggggctct    20940
gaaagggctg tgcaatattt tcataacgtg tttttataga gacagttgag tatgttcttt    21000
aagccctcct ctctcctacc atgaactaaa gatttctgtg gaggtcccct cactcccagc    21060
accccctcct catcccaggc ccttttttgca ggttggcagc tgtttttgcag gactgtatgg    21120 tcagcacact cggggcctac acggatggcc acagccgtcg cccgctgcgc cccagatgag    21180
gagctgctga gctgctccag tttctccagg agtgggaagc ggcggggcga gcgcatggag    21240
gtgactgtac ccctccttcg tgtgtgtgtg tgtgtgtgtg tgtgtgtgtg tgtgtgtgtg    21300
tgtgtgtgtg tcagtgctgg gccctcaggg accccccagca agcccctcca tcctccagac    21360
tccagctctt ctgtaagctt acagggctgg ccagaccagg agtgggggcac tcctcacttc    21420 acgcggctgg gggctgctgg agagagccac agcgggaagg gtttcctaga ggctgcagga    21480
cagtgctgga tggatttttca atgctcacct gggtgtgagc gtgcggcagg gccgcgtgag    21540
ggtcagcgat ctgctactct ggactcagcc atctctaggc ccctctcact caggtgctcc    21600
atggttctgg gagctgagaa atctcaaacc agcaaaaaag tggaattgat gttgatgcta    21660
caggatagtg cacagatgcc atctggttgc agcattttgg tggaagggca gtgcccagct    21720
aggagagtga ggaggggcag gcatttctgg cttgaggaga tggggtctta atgctcgtgt    21780
gagaggcaga gtgggtggag tggagctggc tggatccttg cttttggcctc ctggatttct    21840 ctctatctcc attttgaaac cactctgtgt ttggaagaac ttttgagtat tcagagctgc    21900
ccactggcag aacagtcttc cttgggcagg agtgagctcc ttgtcccag aaggctgggt    21960 ctggctggcc cctggcaggg acactgatga gggtgcttga gttgatcctg tctagtccct    22020
ttctgtgttt tcaaagccca ttctaaagca gattcccatt tccgtctttg actctaaggc    22080
ccaagggggc aagctggtct gccgggccca caacgctttt ggggtgagg gtgtctacgc    22140 cattgccagg tgctgcctgc tacccaggc caactgcagc gtccacacag ctccaccagc    22200
tgaggccagc atgggaccc gtgtccactg ccaccaacag ggccacgtcc tcacaggtag    22260
gaggctgggc ttgccctggg gtgaggaggg gtctctttct ccttatgcac ccactgcccg    22320
```

-continued

```
cgaggcttgg tcctcacaag tgtgatccat gagactcaag cctgacttgc agttccatac    22380
tctggttctg ccacttccat gccctttgag cctgggcagg tgaccttact tctcctcatc    22440
tcagcttcct cctccataag agggaaaaag gtattacctg cctcattgtg ttgcaaggag    22500
atgggcagca tctagggcac tggcctggag tatcgcaggt gctttgccta aggtggtgca    22560
gtccaggaga ggcagctcca gagagaggcc cccggctggg gctgaaagga gggcagacct    22620
cggtttgaat ttcaccctgc cgctctatag ctgtgtgact tgggcaaatt acttaacatc    22680
tctgtatgag gaaatgatga gtgctaagca cttagcttag tgccgggaca atataaattc    22740
tagctatcgt tactattgtt ttcatcaccc gttgctttaa aatccagcct ctggtatagg    22800
caactattga cgggctaccc tgtgtcgaaa acatgcccag gcaggtagca ggaagtcaca    22860 gatgggacc tcttgggca tcaagggatg gtgccctgag gctgagctgt tctggttggg    22920
tggagcatga gaggtctggg aagacagtgg gactccagcc tggaataaga ggctcagagt    22980
tgattctcgt ctgagcacgt ccaggggaac cactgagggt ttgggaacag gagagtgagg    23040
gtgagaacct ggttctgggc acagcaggct ggcatgtagg atggatgttc aggaaagatg    23100
agcatagtca ggtggctggt gcccttgtcc aggggagagg ctccgtcagg ttcaggggtc    23160
ctggcttgga gggaagtccg ccatgctcta atcacgctcc cctttggaag tgctcagccg    23220
atgagctcac aggcacatgt cagtttgaag tcatggaatc tgactccatg aagcgcacct    23280
caaagagcac cattttgcag ctaagggaac tgcaggctgg acatgctgag tggctgcccc    23340
gagcccttgc agctaggaca tagagaatgc tagtaaccac aaccctacca tgttcagagc    23400
acatgccagg ctccatgctg gggcttcgca cgtgtcatct tcacagtgtc cctgtgagta    23460
ggtgtggttt ctcttttccat cttacaaatg agtaaacaga gcctcagtgt agctaagtaa    23520
ccactatttt aggtttctta gccaatgggt gtgtctgact cctaagccca tggagggcat    23580
tctgaggtgg ttcagacaga ccccggctta cccttgaact tctgcctgct ggctgcatag    23640
ggaggggctg gggggagttt gagcatctca ggccatagag cccctgcctc actgtctcca    23700
tctctgggtg gaaagatggt gttttccctg agaaactaag gctcagagag gttgaatggc    23760
tctcccaagg tcacacagct ggtcagctgc agagttgaga acacaggagt cctggtgctc    23820
aggccagcat ctctttttt ctttgagttg tttctaggtt tcctagctct tgcctcagac    23880
cttaaagaga gagggtctga tggggatggg cactggagac ggagcatccc agcatttcac    23940
atctgagctg gctttcctct gccccaggct gcagctccca ctgggaggtg gaggaccttg    24000
gcacccacaa gccgcctgtg ctgaggccac gaggtcagcc caaccagtgc gtgggccaca    24060
gggaggccag catccacgct tcctgctgcc atgcccagg tctggaatgc aaagtcaagg    24120
agcatggaat cccggcccct caggagcagg tgaagaggcc cgtgaggccg ggtgggtggg    24180
gtgctgcgtg tctctcctgc acagcttttc tgtgtcagtt tgtgccacca ccataccgcc    24240
atgcatcagg gtggcggttt gccaggtaga tgctgtgggc agcttccgcc attgtgtgga    24300
cagcatgtat atgtgtctct gtgtggctgg gtctgttttt gcttttgtcc agatcagtaa    24360
ggtttgctac ctgggtaccc cactccactt ggagtagaat gtgcataaat atggcataaa    24420
gaaatgcaat atgcatgcat ttattgattg atctattttt ttctgagatg gggtcttgct    24480
gtgttgccca ggctggtctc aaattcctgg gctcaagcaa tcctctggtc tcagcctccc    24540
caagtgttgg gattataggc atgagccgct gcacctggcc tctctgatct atttaacaaa    24600
cctgctggga gggtctcagg gtcaggagca gcactgggct ctgaggacac agagctcact    24660
cagccgtgac ccagagggg tgcctgagct gcatgctgaa ggttgttagc atgaccagca    24720
```

```
aggcaagaaa aggccctgcc gagattagca aggcatgtgc caagccctgg aatgtgacag    24780
ccgggccttc tagaaacctg agtgtataac tctccttaaa agccagtagg agctcctcaa    24840
aaggcagccc taaggagtcc actcttaaat gaactcagag tcagttttaa aatgcaagtc    24900
tgtgttgatt ctggtctgga tggtgcattc ctcgagagca aaagacagtc ttggtcttgg    24960
atccacttgc cctgggtaca ctgagggctg ctaggttcca ggtgctcttc ctggcactgg    25020
ggagggatac aggcccaaga gacatgctgt tctccctcct ggagcatcta ttttagtgga    25080
ggaagacaga aaacaaacca ttaatataga gtactgaaaa gatgcgatgg agaaaactat    25140
agcaaggaag ggaatggggt gggagagagg tcaggagagg tctcgctgac aaggtggacg    25200
aaacaggcca tgaggcagag aacatgttcc aggcaaagca aaggccccca ggtggggatg    25260
tgcagggagt accaggaaac cagagaggtg ggaatagtta tgagatgggg ggtgcctcag    25320
aggggacagg gccaagtcag gtgagacctg agggtcacag tcagcagtga gctggggcca    25380
tgcaggggtc tggcctcaga ggagtgtggt ctggcctgga tctgaacctc tcactgtggc    25440
ctagctgctg agctgagaag agatgacaag gaccttgggc agaagcaggg agactggagg    25500
gaggcggtgg agggtccagg cgttggggcg ggctcaggc tggagtctga agggagcctg    25560
caggcctggt gggtggatgt gggtgggaga ggggaggat ggcaccaagg ctcgggcccc    25620
tggacagatg gagttgccat taagtgggat ggggcaggct atggggccat cagtttcaga    25680
gggatgagtt tggcactggc atggtaggca tctgtctatc tccacggccc tcaaaccagg    25740
catgaagcag gagctcacgt gtttggtcag ccatggtgca gaaccgcctg ggtgggaggt    25800
gcggggtggg agatacacgg ttgtgtccca aatgggctct gagccagcga gggccgtctg    25860
cactttggcc tcacagaagg atgtcggagg gagaaatgaa gtgtgggtgg gggtcccggg    25920
ccacgctaga catgtgcttt cttttcctcg ggctctggca ggtgaccgtg gcctgcgagg    25980
agggctggac cctgactggc tgcagtgccc tccctgggac ctcccacgtc ctgggggcct    26040
acgccgtaga caacacgtgt gtagtcagga gccgggacgt cagcactaca ggcagcacca    26100
gcgaaggggc cgtgacagcc gttgccatct gctgccggag ccggcacctg gcgcaggcct    26160
cccaggagct ccagtgacag ccccatccca ggatgggtgt ctggggaggg tcaagggctg    26220
gggctgagct ttaaaatggt tccgacttgt ccctctctca gccctccatg gcctggcacg    26280
aggggatggg gatgcttccg ccttttccggg gctgctggcc tggcccttga gtggggcagc    26340
ctccttgcct ggaactcact cactctgggt gcctcctccc caggtggagg tgccaggaag    26400
ctccctccct cactgtgggg catttcacca ttcaaacagg tcgagctgtg ctcgggtgct    26460
gccagctgct cccaatgtgc cgatgtccgt gggcagaatg acttttattg agctcttgtt    26520
ccgtgccagg cattcaatcc tcaggtctcc accaaggagg caggattctt cccatggata    26580
ggggaggggg cggtagggc tgcagggaca acatcgttg ggggtgagt gtgaaggtg    26640 ctgatggccc tcatctccag ctaactgtgg agaagcccct gggggctccc tgattaatgg    26700
aggcttagct ttctggatgg catctagcca gaggctggag acaggtgcgc cctggtggt    26760 cacaggctgt gccttggttt cctgagccac ctttactctg ctctatgcca ggctgtgcta    26820
gcaacaccca aggtggcct gcgggagcc atcctagg actgactcgg cagtgtgcag    26880
tggtgcatgc actgtctcag ccaacccgct ccactacccg gcagggtaca cattcgcacc    26940
cctacttcac agaggaagaa acctggaacc agaggggcg tgcctgccaa gctcacacag    27000
caggaactga gccagaaacg cagattgggc tggctctgaa gccaagcctc ttcttacttc    27060
```

| | |
|---|---:|
| acccggctgg gctcctcatt tttacgggta acagtgaggc tgggaagggg aacacagacc | 27120 |
| aggaagctcg gtgagtgatg cagaacgat gcctgcaggc atggaacttt ttccgttatc | 27180 |
| acccaggcct gattcactgg cctggcggag atgcttctaa ggcatggtcg ggggagaggg | 27240 |
| ccaacaactg tccctccttg agcaccagcc ccacccaagc aagcagacat ttatcttttg | 27300 |
| ggtctgtcct ctctgttgcc tttttacagc caacttttct agacctgttt tgcttttgta | 27360 |
| acttgaagat atttattctg ggttttgtag cattttttatt aatatggtga ctttttaaaa | 27420 |
| taaaaacaaa caaacgttgt cctaactctt gcatagactt gactgcctag ggtgatgcct | 27480 |
| tgcttatact aggaactggg taagtttgtt gaatagttga gtaagccaag tatttgatga | 27540 |
| gtacttttat cttgagtaca agtattgggc aagtactggt gatgtgaact tactccttgt | 27600 |
| gcctatccta ggaatgaaat gaatgtcttc ctgcagctcc cctgaccacc ctgcagtca | 27660 |
| aagtgcctcc tccttggtga caggtgccct acagcactct agatgctctg ttgtcctgac | 27720 |
| ctcccaatgc ccttttcatt cttttctccc cagtacctgg cacacagcct ggcccgagta | 27780 |
| tttacggaat aagttacagt gccagatgct tctgtaatga ccagtgcta agtccatggc | 27840 |
| tttttttcatg atttaaaatt cagaacagtc tcagattggg tgcaatggct cacacctgta | 27900 |
| atctcagtac tttgggaggc tgaggcagga ggattgcttg tgtttaggaa ttcaagaccc | 27960 |
| tgggcaacag tgagaccccg tctctataaa aaaatttaaa agattagcga ggtgtggtag | 28020 |
| cacatgcctg tggtcccggc tactcaggag gctgatatgg gaggcttgct tgagctggga | 28080 |
| ggctgagggt gcagtgagct gtaattacat catcactgca ctgcagcctg ggttacagag | 28140 |
| tgcataatga tcccattcaa tgtgggacct ccaggccctc cactctaagg ctggtgaata | 28200 |
| tagctgtctt aagcaagttc tctctctctc tagacagccc atgtcataag gaatctcagg | 28260 |
| caaaattcct cccagattac attttctgac aattcagtgt catatatgga aagcattcaa | 28320 |
| gagttgacag atggcaatgg cttgaacacc caactgtgtt atctctgccc gttggaacct | 28380 |
| aggcctgtgg tgcaaccta gactctctct ccttcccctc cacagaatca agtatcagct | 28440 |
| ggttagagat ccacaccctg acagctctgt gatgttggaa caacttggtt cttgcagagg | 28500 |
| gttagcaggt ggtcaccagg gatcggggag gaaggggtgt ggcttgcagg aaggcgaaaa | 28560 |
| tctggactag caaataggga aggggaccca tgtgagcaac gctggccact aggaatgaga | 28620 |
| ctgagacctg tgggatctag caagaagccc agtgtgacca cgacacgat ctatgctggg | 28680 |
| gaccacttgg gagagccaaa agctttggtg gagatgaatg gagaccatca acctaagttc | 28740 |
| agcatcctcc tctaagcttt gcagatgaat cctgaaatgg tcagcccctc cagagaaaag | 28800 |
| aacagcaaca ggctcagagg acccacagtc ccctttatta gtgtaaagta ctaagaggaa | 28860 |
| tcaacagcat ttagcaccag gcacaggctc gtgttccccc gcccactacg gctgtgttct | 28920 |
| gatatatgaa gaatggcggc aagactccaa ctctgttttt gaaaaattta ttttatactc | 28980 |
| ttagaagcta agaactttgc c | 29001 |

<210> SEQ ID NO 3
<211> LENGTH: 3891
<212> TYPE: DNA
<213> ORGANISM: Homo sapiens

<400> SEQUENCE: 3

| | |
|---|---:|
| ttatgagaga aaggcagagg gagatttgac acacacagga ggggccacgt ggagacagag | 60 |
| gtggagattg gagaaatgtg gccacaagcc agggaacacc agcagccacc agaagccgga | 120 |
| agacgtgagg cagggttctt cccagagcct tcgctgctga gtctgggaat tgttaccga | 180 |

```
agccataaga agtgggtaca cgccctgagc ctcccacact tgctcacctg tcctgagatg    240
agaatctcta ctctgcagca tatttggagg atcactgcgg gggccacaga ggtgctgttc    300
agatggcact tcagaagact caggagaccc tggggcagga gcagtttgac tgacagccca    360
gagggctgcc ctctgattcc acctgaggcc ctgcttttcc tggctgcagg ggttccaggg    420
ccaggccatt tccgctggcg caggactctg ctagcagcaa cctgcctgaa gtcttccttt    480
ggcctggctg agagtttctg agacctgcgc tggagcggag gtgcttcctt ccttgcttcc    540
tttcttcctc tctcccttct ccatccagca ggctggacct gcctggcatc tgtgagctct    600
ccctactttc tcctataccc taacctttgt cctgcatggg cgactccccc agtgagtctc    660
ttgcagcttt taccccagtg cctgcttctt ggagaatcca aactgatcca gttagggatg    720
ataaagtgta gggtaggtgc tcggtgactg ttttctctga ggttgtgact cgtgtgaggc    780
agaagcagtc cccgtgagcc ctcctggtat cttgtggagt ggagaacgct tggacctgga    840
gccaggaggc ccagacatac atcctgtccg agctgcagct tcctgtctct aaaatgagcc    900
ggccagcgca ggtggccaga catcactgtt attctccttt gagtctttaa atcttgttgt    960
ctttcttgca gactcggtga gctgtgaaag gctataatag gggctttatt ttacactttg   1020
atactatttt ttgaacattc atattattgt tagatattga tattcatatg aaggagcagg   1080
atgacttggg tccttcttgg cagtagcatt gccagctgat ggccttggac agttacctgc   1140
cctctctagg cctccctttc cttgtctatg aaatacatta tagaatagga tgtagtgtgt   1200
gaggattttt tggaggttaa acgagtgaat atatttaagg cgctttcacc agtggctggg   1260
atgtgctctg tagtttctgt gtgttaacta taaggttgac tttatgctca ttccctcctc   1320
tcccacaaat gtcaccttgg aaagacggag gcagcctggt ggaggtgtat ctcctagaca   1380
ccagcataca gagtgaccac cgggaaatcg agggcagggt catggtcacc gacttcgaga   1440
atgtgcccga ggaggacggg acccgcttcc acagacaggc cagcaagtgt gacagtcatg   1500
gcacccacct ggcaggggtg gtcagcggcc gggatgccgg cgtggccaag ggtgccagca   1560
tgcgcagcct gcgcgtgctc aactgccaag ggaagggcac ggttagcggc accctcatag   1620
gcctggagtt tattcggaaa agccagctgg tccagcctgt ggggccactg gtggtgctgc   1680 tgccctggc gggtgggtac agccgcgtcc tcaacgccgc ctgccagcgc ctggcgaggg   1740
ctggggtcgt gctggtcacc gctgccggca acttccggga cgatgcctgc ctctactccc   1800
cagcctcagc tcccgagggg aggacatcat tggtgcctcc agcgactgca gcacctgctt   1860
tgtgtcacag agtgggacat cacaggctgc tgcccacgtg gctggcattg cagccatgat   1920
gctgtctgcc gagccggagc tcaccctggc cgagttgagg cagagactga tccacttctc   1980
tgccaaagat gtcatcaatg aggcctggtt ccctgaggac cagcgggtac tgaccccaa    2040 cctggtggcc gccctgcccc ccagcaccca tggggcaggt tggcagctgt tttgcaggac   2100
tgtgtggtca gcacactcgg ggcctacacg gatggccaca gccatcgccc gctgcgcccc   2160
agatgaggag ctgctgagct gctccagttt ctccaggagt gggaagcggc ggggcgagcg   2220
catggaggct gcagctccca ctgggaggtg gaggaccttg gcacccacaa gccgcctgtg   2280
ctgaggccac gaggtcagcc caaccagtgc gtgggccaca gggaggccag catccacgct   2340
tcctgctgcc atgccccagg tctggaatgc aaagtcaagg agcatggaat cccggcccct   2400
caggagcagg tgaccgtggc ctgcgaggag ggctggaccc tgactggctg cagtgccctc   2460
cctgggacct cccacgtcct gggggcctac gccgtagaca acacgtgtgt agtcaggagc   2520
```

|                                                                   |      |
|-------------------------------------------------------------------|------|
| cgggacgtca gcactacagg cagcaccagc gaagaggccg tgacagccgt tgccatctgc | 2580 |
| tgccggagcc ggcacctggc gcaggcctcc caggagctcc agtgacagcc ccatcccagg | 2640 |
| atgggtgtct ggggagggtc aagggctggg gctgagcttt aaaatggttc cgacttgtcc | 2700 |
| ctctctcagc cctccatggc ctggcacgag gggatgggga tgcttccgcc tttccggggc | 2760 |
| tgctggcctg gcccttgagt ggggcagcct ccttgcctgg aactcactca ctctgggtgc | 2820 |
| ctcctcccca ggtggaggtg ccaggaagct ccctccctca ctgtggggca tttcaccatt | 2880 |
| caaacaggtc gagctgtgct cgggtgctgc cagctgctcc caatgtgccg atgtccgtgg | 2940 |
| gcagaatgac ttttattgag ctcttgttcc gtgccaggca ttcaatcctc aggtctccac | 3000 |
| caaggaggca ggattcttcc catggatagg ggaggggggcg gtaggggctg caggacaaa  | 3060 |
| catcgttggg gggtgagtgt gaaaggtgct gatggccctc atctccagct aactgtggag | 3120 |
| aagcccctgg gggctccctg attaatggag gcttagcttt ctggatggca tctagccaga | 3180 |
| ggctggagac aggtgtgccc ctggtggtca caggctgtgc cttggtttcc tgagccacct | 3240 |
| ttactctgct ctatgccagg ctgtgctagc aacacccaaa ggtggcctgc ggggagccat | 3300 |
| cacctaggac tgactcggca gtgtgcagtg gtgcatgcac tgtctcagcc aacccgctcc | 3360 |
| actacccggc agggtacaca ttcgcacccc tacttcacag aggaagaaac ctggaaccag | 3420 |
| aggggggcgtg cctgccaagc tcacacagca ggaactgagc cagaaacgca gattgggctg | 3480 |
| gctctgaagc caagcctctt cttacttcac ccggctgggc tcctcatttt tacgggtaac | 3540 |
| agtgaggctg ggaaggggaa cacagaccag gaagctcggt gagtgatggc agaacgatgc | 3600 |
| ctgcaggcat ggaactttt ccgttatcac ccaggcctga ttcactggcc tggcggagat  | 3660 |
| gcttctaagg catggtcggg ggagagggcc aacaactgtc cctccttgag caccagcccc | 3720 |
| acccaagcaa gcagacattt atcttttggg tctgtcctct ctgttgcctt tttacagcca | 3780 |
| acttttctag acctgttttg cttttgtaac ttgaagatat ttattctggg ttttgtagca | 3840 |
| tttttattaa tatggtgact ttttaaaata aaacaaaca aacgttgtcc t          | 3891 |

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 4
gcgcggaatc ctggctggga                                           20

<210> SEQ ID NO 5
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 5
gaggagacct agaggccgtg                                           20

<210> SEQ ID NO 6
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 6
aggaccgcct ggagctgacg                                              20

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 7
acgcaaggct agcaccagct                                              20

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 8
cctcggaacg caaggctagc                                              20

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 9
ccttggcgca gcggtggaag                                              20

<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 10
ggcgggcagt gcgctctgac                                              20

<210> SEQ ID NO 11
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 11
tggtgaggta tccccggcgg                                              20

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 12
ggatcttggt gaggtatccc                                              20

<210> SEQ ID NO 13
<211> LENGTH: 20
<212> TYPE: DNA

```
<213> ORGANISM: Artificial Sequence
<220> FEATURE:
<223> OTHER INFORMATION: Synthetic oligonucleotide

<400> SEQUENCE: 13
agacatgcag gatcttggtg                                              20

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 14
atggaagaca tgcaggatct                                              20

<210> SEQ ID NO 15
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 15
ttcaccagga agccaggaag                                              20

<210> SEQ ID NO 16
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 16
tcatcttcac caggaagcca                                              20

<210> SEQ ID NO 17
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 17
cctcgatgta gtcgacatgg                                              20

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 18
gtattcatcc gcccggtacc                                              20

<210> SEQ ID NO 19
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 19
ctggtgtcta ggagatacac                                              20
```

-continued

```
<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 20
gtatgctggt gtctaggaga                                                    20

<210> SEQ ID NO 21
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 21
gatttcccgg tggtcactct                                                    20

<210> SEQ ID NO 22
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 22
gccctcgatt tcccggtggt                                                    20

<210> SEQ ID NO 23
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 23
gtgaccatga ccctgccctc                                                    20

<210> SEQ ID NO 24
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 24
ctcgaagtcg gtgaccatga                                                    20

<210> SEQ ID NO 25
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 25
gtggaagcgg gtcccgtcct                                                    20

<210> SEQ ID NO 26
<211> LENGTH: 20
<212> TYPE: DNA
<213> ORGANISM: Artificial Sequence
<220> FEATURE:
```

<223> OTHER INFORMATION: Synthetic oligonucleotide

<400> SEQUENCE: 26
acccctgcca ggtgggtgcc                                               20

<210> SEQ ID NO 27
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 27
tgaccacccc tgccaggtgg                                               20

<210> SEQ ID NO 28
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 28
acccttggcc acgccggcat                                               20

<210> SEQ ID NO 29
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 29
ttggcagttg agcacgcgca                                               20

<210> SEQ ID NO 30
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 30
ttcccttggc agttgagcac                                               20

<210> SEQ ID NO 31
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 31
ccaggcctat gagggtgccg                                               20

<210> SEQ ID NO 32
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 32
gctggctttt ccgaataaac                                               20

```
<210> SEQ ID NO 33
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 33
gtgaccagca cgaccccagc                                               20

<210> SEQ ID NO 34
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 34
ccaaagtccc cagggtcacc                                               20

<210> SEQ ID NO 35
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 35
agttggtccc caaagtcccc                                               20

<210> SEQ ID NO 36
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 36
gccaaagttg gtccccaaag                                               20

<210> SEQ ID NO 37
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 37
gtccacacag cggccaaagt                                               20

<210> SEQ ID NO 38
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 38
ggcaaagagg tccacacagc                                               20

<210> SEQ ID NO 39
<211> LENGTH: 20
<212> TYPE: DNA
<213> ORGANISM: Artificial Sequence
<220> FEATURE:
<223> OTHER INFORMATION: Synthetic oligonucleotide
```

```
<400> SEQUENCE: 39
tggaggcacc aatgatgtcc                                                 20

<210> SEQ ID NO 40
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 40
gctgcagtcg ctggaggcac                                                 20

<210> SEQ ID NO 41
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 41
acaaagcagg tgctgcagtc                                                 20

<210> SEQ ID NO 42
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 42
gcatcatggc tgcaatgcca                                                 20

<210> SEQ ID NO 43
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 43
ggcagacagc atcatggctg                                                 20

<210> SEQ ID NO 44
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 44
gaagtggatc agtctctgcc                                                 20

<210> SEQ ID NO 45
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 45
ttggcagaga agtggatcag                                                 20

<210> SEQ ID NO 46
<211> LENGTH: 20
```

```
<212> TYPE: DNA
<213> ORGANISM: Artificial Sequence
<220> FEATURE:
<223> OTHER INFORMATION: Synthetic oligonucleotide

<400> SEQUENCE: 46
catctttggc agagaagtgg                                              20

<210> SEQ ID NO 47
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 47
tgatgacatc tttggcagag                                              20

<210> SEQ ID NO 48
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 48
gcctcattga tgacatcttt                                              20

<210> SEQ ID NO 49
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 49
tcagggaacc aggcctcatt                                              20

<210> SEQ ID NO 50
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 50
ggtcctcagg gaaccaggcc                                              20

<210> SEQ ID NO 51
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 51
ggtcagtacc cgctggtcct                                              20

<210> SEQ ID NO 52
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 52
```
aaacagctgc caacctgccc                                              20

<210> SEQ ID NO 53
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 53
ctgcaaaaca gctgccaacc                                              20

<210> SEQ ID NO 54
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 54
gtaggccccg agtgtgctga                                              20

<210> SEQ ID NO 55
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 55
agaaactgga gcagctcagc                                              20

<210> SEQ ID NO 56
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 56
tcctggagaa actggagcag                                              20

<210> SEQ ID NO 57
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 57
cgttgtgggc ccggcagacc                                              20

<210> SEQ ID NO 58
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 58
agcaggcagc acctggcaat                                              20

<210> SEQ ID NO 59
<211> LENGTH: 20
<212> TYPE: DNA
<213> ORGANISM: Artificial Sequence

```
<220> FEATURE:
<223> OTHER INFORMATION: Synthetic oligonucleotide

<400> SEQUENCE: 59
cacgggtccc catgctggcc                                                    20

<210> SEQ ID NO 60
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 60
ctttgcattc cagacctggg                                                    20

<210> SEQ ID NO 61
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 61
cttgactttg cattccagac                                                    20

<210> SEQ ID NO 62
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 62
ggcagcagat ggcaacggct                                                    20

<210> SEQ ID NO 63
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 63
aaccatttta aagctcagcc                                                    20

<210> SEQ ID NO 64
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 64
tcaagggcca ggccagcagc                                                    20

<210> SEQ ID NO 65
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 65
cccactcaag ggccaggcca                                                    20
```

<210> SEQ ID NO 66
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 66
atgccccaca gtgagggagg                                               20

<210> SEQ ID NO 67
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 67
aatggtgaaa tgccccacag                                               20

<210> SEQ ID NO 68
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 68
catgggaaga atcctgcctc                                               20

<210> SEQ ID NO 69
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 69
ggagatgagg gccatcagca                                               20

<210> SEQ ID NO 70
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 70
tagatgccat ccagaaagct                                               20

<210> SEQ ID NO 71
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 71
tctggctaga tgccatccag                                               20

<210> SEQ ID NO 72
<211> LENGTH: 20
<212> TYPE: DNA
<213> ORGANISM: Artificial Sequence
<220> FEATURE:
<223> OTHER INFORMATION: Synthetic oligonucleotide

```
<400> SEQUENCE: 72
ggcatagagc agagtaaagg                                              20

<210> SEQ ID NO 73
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 73
agcctggcat agagcagagt                                              20

<210> SEQ ID NO 74
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 74
aagtaagaag aggcttggct                                              20

<210> SEQ ID NO 75
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 75
gctcaaggag ggacagttgt                                              20

<210> SEQ ID NO 76
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 76
aaagataaat gtctgcttgc                                              20

<210> SEQ ID NO 77
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 77
acccaaaaga taaatgtctg                                              20

<210> SEQ ID NO 78
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 78
tcttcaagtt acaaaagcaa                                              20

<210> SEQ ID NO 79
```

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 79
aaatgcaggg ctaaaatcac                                           20

<210> SEQ ID NO 80
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 80
aacccagttc taatgcacct                                           20

<210> SEQ ID NO 81
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 81
aagcagggcc tcaggtggaa                                           20

<210> SEQ ID NO 82
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 82
aaggaaaggg aggcctagag                                           20

<210> SEQ ID NO 83
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 83
aaggaagact tcaggcaggt                                           20

<210> SEQ ID NO 84
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 84
aaggtcacac agttaagagt                                           20

<210> SEQ ID NO 85
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 85
```
acaaattccc agactcagca 20

<210> SEQ ID NO 86
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 86
acagcattct tggttaggag 20

<210> SEQ ID NO 87
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 87
acccgctggt cctcagggaa 20

<210> SEQ ID NO 88
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 88
actggataca ttggcagaca 20

<210> SEQ ID NO 89
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 89
agaaccatgg agcacctgag 20

<210> SEQ ID NO 90
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 90
agactaggag cctgagtttt 20

<210> SEQ ID NO 91
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 91
agactgatgg aaggcattga 20

<210> SEQ ID NO 92
<211> LENGTH: 20
<212> TYPE: DNA

```
<213> ORGANISM: Artificial Sequence
<220> FEATURE:
<223> OTHER INFORMATION: Synthetic oligonucleotide

<400> SEQUENCE: 92
agagacagga agctgcagct                                              20

<210> SEQ ID NO 93
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 93
agagaggagg gcttaaagaa                                              20

<210> SEQ ID NO 94
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 94
agcatggcac cagcatctgc                                              20

<210> SEQ ID NO 95
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 95
agctgccaac ctgcaaaaag                                              20

<210> SEQ ID NO 96
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 96
aggacccaag tcatcctgct                                              20

<210> SEQ ID NO 97
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 97
agtcaagctg ctgcccagag                                              20

<210> SEQ ID NO 98
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 98
agtgtaaaat aaagccccta                                              20
```

```
<210> SEQ ID NO 99
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 99
ataaatatct tcaagttaca                                                     20

<210> SEQ ID NO 100
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 100
atctcaggac aggtgagcaa                                                     20

<210> SEQ ID NO 101
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 101
atggctgcaa tgccagccac                                                     20

<210> SEQ ID NO 102
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 102
atgtgcagag atcaatcaca                                                     20

<210> SEQ ID NO 103
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 103
atttcataga caaggaaagg                                                     20

<210> SEQ ID NO 104
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 104
cacagtcctg caaaacagct                                                     20

<210> SEQ ID NO 105
<211> LENGTH: 20
<212> TYPE: DNA
<213> ORGANISM: Artificial Sequence
<220> FEATURE:
```

<223> OTHER INFORMATION: Synthetic oligonucleotide

<400> SEQUENCE: 105
cacattagcc ttgctcaagt                                               20

<210> SEQ ID NO 106
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 106
ccagtcagag tagaacagag                                               20

<210> SEQ ID NO 107
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 107
cccactataa tggcaagccc                                               20

<210> SEQ ID NO 108
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 108
cccagccctc tcaggaagtg                                               20

<210> SEQ ID NO 109
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 109 ccctgcaca gagcctggca                                                20

<210> SEQ ID NO 110
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 110
cctggaaccc ctgcagccag                                               20

<210> SEQ ID NO 111
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 111
ctagaggaac cactagatat                                               20

```
<210> SEQ ID NO 112
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 112
gaagaggctt ggcttcagag                                              20

<210> SEQ ID NO 113
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 113
gaataacagt gatgtctggc                                              20

<210> SEQ ID NO 114
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 114
gagaggttca gatccaggcc                                              20

<210> SEQ ID NO 115
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 115
gagtaaggca ggttactctc                                              20

<210> SEQ ID NO 116
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 116
gagtagagat tctcatctca                                              20

<210> SEQ ID NO 117
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 117
gagtcttctg aagtgccatc                                              20

<210> SEQ ID NO 118
<211> LENGTH: 20
<212> TYPE: DNA
<213> ORGANISM: Artificial Sequence
<220> FEATURE:
<223> OTHER INFORMATION: Synthetic oligonucleotide
```

<400> SEQUENCE: 118
gcaccatcca gaccagaatc                                               20

<210> SEQ ID NO 119
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 119
gcagggcggc caccaggttg                                               20

<210> SEQ ID NO 120
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 120
gctagttatt aagcacctgc                                               20

<210> SEQ ID NO 121
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 121
ggagcctaca tgtgcagaga                                               20

<210> SEQ ID NO 122
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 122
ggagggagct tcctggcacc                                               20

<210> SEQ ID NO 123
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 123
ggcactgccc ttccaccaaa                                               20

<210> SEQ ID NO 124
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 124
ggccatcagc tggcaatgct                                               20

<210> SEQ ID NO 125
<211> LENGTH: 20

```
<212> TYPE: DNA
<213> ORGANISM: Artificial Sequence
<220> FEATURE:
<223> OTHER INFORMATION: Synthetic oligonucleotide

<400> SEQUENCE: 125
ggcctgcaga agccagagag                                              20

<210> SEQ ID NO 126
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 126
ggtgcataag gagaaagaga                                              20

<210> SEQ ID NO 127
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 127
ggtggtaatt tgtcacagca                                              20

<210> SEQ ID NO 128
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 128
gtccccaaag tccccagggt                                              20

<210> SEQ ID NO 129
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 129
gtgccatctg aacagcacct                                              20

<210> SEQ ID NO 130
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 130
gtgctgacca cacagtcctg                                              20

<210> SEQ ID NO 131
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 131
```
gtgttgagca gactgatgga                                          20

<210> SEQ ID NO 132
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 132
taaaagctgc aagagactca                                          20

<210> SEQ ID NO 133
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 133
tagacaagga aagggaggcc                                          20

<210> SEQ ID NO 134
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 134
tagatgtgac taacatttaa                                          20

<210> SEQ ID NO 135
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 135
tagcacagcc tggcatagag                                          20

<210> SEQ ID NO 136
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 136
taggagaaag tagggagagc                                          20

<210> SEQ ID NO 137
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 137
tagggagagc tcacagatgc                                          20

<210> SEQ ID NO 138
<211> LENGTH: 20
<212> TYPE: DNA
<213> ORGANISM: Artificial Sequence

```
<220> FEATURE:
<223> OTHER INFORMATION: Synthetic oligonucleotide

<400> SEQUENCE: 138
tcacagctca ccgagtctgc                                                 20

<210> SEQ ID NO 139
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 139
tcagagaaaa cagtcaccga                                                 20

<210> SEQ ID NO 140
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 140
tcagccaggc caaaggaaga                                                 20

<210> SEQ ID NO 141
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 141
tcatggctgc aatgcctggt                                                 20

<210> SEQ ID NO 142
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 142
tcattttaga gacaggaagc                                                 20

<210> SEQ ID NO 143
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 143
tgaaaatcca tccagcactg                                                 20

<210> SEQ ID NO 144
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 144
tgacatccag gagggaggag                                                 20
```

<210> SEQ ID NO 145
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 145
tgacatcttg tctgggagcc                                           20

<210> SEQ ID NO 146
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 146
tgacatttgt gggagaggag                                           20

<210> SEQ ID NO 147
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 147
tgagttcatt taagagtgga                                           20

<210> SEQ ID NO 148
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 148
tggcagcaac tcagacatat                                           20

<210> SEQ ID NO 149
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 149
tgggcattgg tggccccaac                                           20

<210> SEQ ID NO 150
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 150
tgtgagctct ggcccagtgg                                           20

<210> SEQ ID NO 151
<211> LENGTH: 20
<212> TYPE: DNA
<213> ORGANISM: Artificial Sequence
<220> FEATURE:
<223> OTHER INFORMATION: Synthetic oligonucleotide

```
<400> SEQUENCE: 151
tgtgatgacc tggaaaggtg                                              20

<210> SEQ ID NO 152
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 152
ttcaggcagg ttgctgctag                                              20

<210> SEQ ID NO 153
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 153
ttgggagcag ctggcagcac                                              20

<210> SEQ ID NO 154
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 154 tttaaagct cagccccagc                                               20

<210> SEQ ID NO 155
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 155
cttatagtta acacacagaa                                              20

<210> SEQ ID NO 156
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 156
aagtcaacct tatagttaac                                              20

<210> SEQ ID NO 157
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 157
aggaacaaag ccaaggtcac                                              20

<210> SEQ ID NO 158
```

<210> SEQ ID NO 158
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 158
gtggtgactt accagccacg                                              20

<210> SEQ ID NO 159
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 159
gcctggagct gacggtgccc                                              20

<210> SEQ ID NO 160
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 160
gaccgcctgg agctgacggt                                              20

<210> SEQ ID NO 161
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 161
tccaaggtga catttgtggg                                              20

<210> SEQ ID NO 162
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 162
aaggctagca ccagctcctc                                              20

<210> SEQ ID NO 163
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 163
caaggctagc accagctcct                                              20

<210> SEQ ID NO 164
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 164

```
gcaaggctag caccagctcc                                               20

<210> SEQ ID NO 165
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 165
cgcaaggcta gcaccagctc                                               20

<210> SEQ ID NO 166
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 166
aacgcaaggc tagcaccagc                                               20

<210> SEQ ID NO 167
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 167
gaacgcaagg ctagcaccag                                               20

<210> SEQ ID NO 168
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 168
ggaacgcaag gctagcacca                                               20

<210> SEQ ID NO 169
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 169
cggaacgcaa ggctagcacc                                               20

<210> SEQ ID NO 170
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 170
tcctcctcgg aacgcaaggc                                               20

<210> SEQ ID NO 171
<211> LENGTH: 20
<212> TYPE: DNA
```

```
<213> ORGANISM: Artificial Sequence
<220> FEATURE:
<223> OTHER INFORMATION: Synthetic oligonucleotide

<400> SEQUENCE: 171
gtgctcgggt gcttcggcca                                              20

<210> SEQ ID NO 172
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 172
tggaaggtgg ctgtggttcc                                              20

<210> SEQ ID NO 173
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 173
atccttggcg cagcggtgga                                              20

<210> SEQ ID NO 174
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 174
ggatccttgg cgcagcggtg                                              20

<210> SEQ ID NO 175
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 175
ccacggatcc ttggcgcagc                                              20

<210> SEQ ID NO 176
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 176
cgtaggtgcc aggcaacctc                                              20

<210> SEQ ID NO 177
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 177
tgactgcgag aggtgggtct                                              20
```

<210> SEQ ID NO 178
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 178
cagtgcgctc tgactgcgag                                               20

<210> SEQ ID NO 179
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 179
ggcagtgcgc tctgactgcg                                               20

<210> SEQ ID NO 180
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 180
cgggcagtgc gctctgactg                                               20

<210> SEQ ID NO 181
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 181
cggcgggcag tgcgctctga                                               20

<210> SEQ ID NO 182
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 182
atccccggcg ggcagcctgg                                               20

<210> SEQ ID NO 183
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 183
aggtatcccc ggcgggcagc                                               20

<210> SEQ ID NO 184
<211> LENGTH: 20
<212> TYPE: DNA
<213> ORGANISM: Artificial Sequence
<220> FEATURE:

```
<223> OTHER INFORMATION: Synthetic oligonucleotide

<400> SEQUENCE: 184
tgaggtatcc ccggcgggca                                               20

<210> SEQ ID NO 185
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 185
gtgaggtatc cccggcgggc                                               20

<210> SEQ ID NO 186
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 186
ggtgaggtat ccccggcggg                                               20

<210> SEQ ID NO 187
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 187
ttggtgaggt atccccggcg                                               20

<210> SEQ ID NO 188
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 188
cttggtgagg tatccccggc                                               20

<210> SEQ ID NO 189
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 189
tcttggtgag gtatccccgg                                               20

<210> SEQ ID NO 190
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 190
atcttggtga ggtatccccg                                               20
```

```
<210> SEQ ID NO 191
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 191
gatcttggtg aggtatcccc                                              20

<210> SEQ ID NO 192
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 192
aggatcttgg tgaggtatcc                                              20

<210> SEQ ID NO 193
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 193
gcaggatctt ggtgaggtat                                              20

<210> SEQ ID NO 194
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 194
atgcaggatc ttggtgaggt                                              20

<210> SEQ ID NO 195
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 195
acatgcagga tcttggtgag                                              20

<210> SEQ ID NO 196
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 196
gaagacatgc aggatcttgg                                              20

<210> SEQ ID NO 197
<211> LENGTH: 20
<212> TYPE: DNA
<213> ORGANISM: Artificial Sequence
<220> FEATURE:
<223> OTHER INFORMATION: Synthetic oligonucleotide
```

<400> SEQUENCE: 197
agaaggccat ggaagacatg    20

<210> SEQ ID NO 198
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 198
gaagccagga agaaggccat    20

<210> SEQ ID NO 199
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 199
tcttcaccag gaagccagga    20

<210> SEQ ID NO 200
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 200
actcatcttc accaggaagc    20

<210> SEQ ID NO 201
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 201
ccactcatct tcaccaggaa    20

<210> SEQ ID NO 202
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 202
cgccactcat cttcaccagg    20

<210> SEQ ID NO 203
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 203
gtcgccactc atcttcacca    20

<210> SEQ ID NO 204
<211> LENGTH: 20

```
<212> TYPE: DNA
<213> ORGANISM: Artificial Sequence
<220> FEATURE:
<223> OTHER INFORMATION: Synthetic oligonucleotide

<400> SEQUENCE: 204
aggtcgccac tcatcttcac                                               20

<210> SEQ ID NO 205
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 205
gcaggtcgcc actcatcttc                                               20

<210> SEQ ID NO 206
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 206
cagcaggtcg ccactcatct                                               20

<210> SEQ ID NO 207
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 207
tccagcaggt cgccactcat                                               20

<210> SEQ ID NO 208
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 208
ggcaacttca aggccagctc                                               20

<210> SEQ ID NO 209
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 209
gcaaagacag aggagtcctc                                               20

<210> SEQ ID NO 210
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 210
```

```
ttcatccgcc cggtaccgtg                                              20

<210> SEQ ID NO 211
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 211
tattcatccg cccggtaccg                                              20

<210> SEQ ID NO 212
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 212
tggtattcat ccgcccggta                                              20

<210> SEQ ID NO 213
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 213
gctggtattc atccgcccgg                                              20

<210> SEQ ID NO 214
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 214
gggctggtat tcatccgccc                                              20

<210> SEQ ID NO 215
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 215
atacacctcc accaggctgc                                              20

<210> SEQ ID NO 216
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 216
gtgtctagga gatacacctc                                              20

<210> SEQ ID NO 217
<211> LENGTH: 20
<212> TYPE: DNA
<213> ORGANISM: Artificial Sequence
```

```
<220> FEATURE:
<223> OTHER INFORMATION: Synthetic oligonucleotide

<400> SEQUENCE: 217
tgctggtgtc taggagatac                                        20

<210> SEQ ID NO 218
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 218
tcgatttccc ggtggtcact                                        20

<210> SEQ ID NO 219
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 219
ctcgatttcc cggtggtcac                                        20

<210> SEQ ID NO 220
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 220
cctcgatttc ccggtggtca                                        20

<210> SEQ ID NO 221
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 221
ccctcgattt cccggtggtc                                        20

<210> SEQ ID NO 222
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 222
tgccctcgat ttcccggtgg                                        20

<210> SEQ ID NO 223
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 223
ctgccctcga tttcccggtg                                        20
```

<210> SEQ ID NO 224
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 224
cctgccctcg atttcccggt                                          20

<210> SEQ ID NO 225
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 225
ccctgccctc gatttcccgg                                          20

<210> SEQ ID NO 226
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 226
atgaccctgc cctcgatttc                                          20

<210> SEQ ID NO 227
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 227
ccatgaccct gccctcgatt                                          20

<210> SEQ ID NO 228
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 228
gaccatgacc ctgccctcga                                          20

<210> SEQ ID NO 229
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 229
cggtgaccat gaccctgccc                                          20

<210> SEQ ID NO 230
<211> LENGTH: 20
<212> TYPE: DNA
<213> ORGANISM: Artificial Sequence
<220> FEATURE:
<223> OTHER INFORMATION: Synthetic oligonucleotide

```
<400> SEQUENCE: 230
gtcggtgacc atgaccctgc                                        20

<210> SEQ ID NO 231
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 231
aagtcggtga ccatgaccct                                        20

<210> SEQ ID NO 232
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 232
cgaagtcggt gaccatgacc                                        20

<210> SEQ ID NO 233
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 233
ggcacattct cgaagtcggt                                        20

<210> SEQ ID NO 234
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 234
tggcctgtct gtggaagcgg                                        20

<210> SEQ ID NO 235
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 235
ggtgggtgcc atgactgtca                                        20

<210> SEQ ID NO 236
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 236
ccaggtgggt gccatgactg                                        20

<210> SEQ ID NO 237
```

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 237
cctgccaggt gggtgccatg                                               20

<210> SEQ ID NO 238
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 238
ccacccctgc caggtgggtg                                               20

<210> SEQ ID NO 239
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 239
gctgaccacc cctgccaggt                                               20

<210> SEQ ID NO 240
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 240
tcccggccgc tgaccacccc                                               20

<210> SEQ ID NO 241
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 241
ggcatcccgg ccgctgacca                                               20

<210> SEQ ID NO 242
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 242
gccggcatcc cggccgctga                                               20

<210> SEQ ID NO 243
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 243
```
gccacgccgg catcccggcc                                              20

<210> SEQ ID NO 244
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 244
ggccacgccg gcatcccggc                                              20

<210> SEQ ID NO 245
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 245
tggccacgcc ggcatcccgg                                              20

<210> SEQ ID NO 246
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 246
ttggccacgc cggcatcccg                                              20

<210> SEQ ID NO 247
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 247
cttggccacg ccggcatccc                                              20

<210> SEQ ID NO 248
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 248
ccttggccac gccggcatcc                                              20

<210> SEQ ID NO 249
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 249
cccttggcca cgccggcatc                                              20

<210> SEQ ID NO 250
<211> LENGTH: 20
<212> TYPE: DNA

```
<213> ORGANISM: Artificial Sequence
<220> FEATURE:
<223> OTHER INFORMATION: Synthetic oligonucleotide

<400> SEQUENCE: 250
cacccttggc cacgccggca                                               20

<210> SEQ ID NO 251
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 251
gcaccctggg ccacgccggc                                               20

<210> SEQ ID NO 252
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 252 ggcaccctg gccacgccgg                                                20

<210> SEQ ID NO 253
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 253
tggcaccctt ggccacgccg                                               20

<210> SEQ ID NO 254
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 254
ctggcaccct tggccacgcc                                               20

<210> SEQ ID NO 255
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 255
gctggcaccc ttggccacgc                                               20

<210> SEQ ID NO 256
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 256
cgcatgctgg caccctggc                                                20
```

<210> SEQ ID NO 257
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 257
cagttgagca cgcgcaggct                    20

<210> SEQ ID NO 258
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 258
ggcagttgag cacgcgcagg                    20

<210> SEQ ID NO 259
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 259
ccttggcagt tgagcacgcg                    20

<210> SEQ ID NO 260
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 260
ccttcccttg gcagttgagc                    20

<210> SEQ ID NO 261
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 261
gtgcccttcc cttggcagtt                    20

<210> SEQ ID NO 262
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 262
ccgtgccctt cccttggcag                    20

<210> SEQ ID NO 263
<211> LENGTH: 20
<212> TYPE: DNA
<213> ORGANISM: Artificial Sequence
<220> FEATURE:

<223> OTHER INFORMATION: Synthetic oligonucleotide

<400> SEQUENCE: 263
ggtgccgcta accgtgccct                                            20

<210> SEQ ID NO 264
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 264
caggcctatg agggtgccgc                                            20

<210> SEQ ID NO 265
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 265
ccgaataaac tccaggccta                                            20

<210> SEQ ID NO 266
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 266
tggcttttcc gaataaactc                                            20

<210> SEQ ID NO 267
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 267
cagctggctt ttccgaataa                                            20

<210> SEQ ID NO 268
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 268
accagctggc ttttccgaat                                            20

<210> SEQ ID NO 269
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 269
ggaccagctg gcttttccga                                            20

```
<210> SEQ ID NO 270
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 270
ggctggacca gctggctttt                                              20

<210> SEQ ID NO 271
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 271
gtggccccac aggctggacc                                              20

<210> SEQ ID NO 272
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 272
agcagcacca ccagtggccc                                              20

<210> SEQ ID NO 273
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 273
gctgtaccca cccgccaggg                                              20

<210> SEQ ID NO 274
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 274
cgaccccagc cctcgccagg                                              20

<210> SEQ ID NO 275
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 275
cggtgaccag cacgacccca                                              20

<210> SEQ ID NO 276
<211> LENGTH: 20
<212> TYPE: DNA
<213> ORGANISM: Artificial Sequence
<220> FEATURE:
<223> OTHER INFORMATION: Synthetic oligonucleotide
```

<400> SEQUENCE: 276
agcggtgacc agcacgaccc                                               20

<210> SEQ ID NO 277
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 277
gcagcggtga ccagcacgac                                               20

<210> SEQ ID NO 278
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 278
cggcagcggt gaccagcacg                                               20

<210> SEQ ID NO 279
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 279
ccggcagcgg tgaccagcac                                               20

<210> SEQ ID NO 280
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 280
ttgccggcag cggtgaccag                                               20

<210> SEQ ID NO 281
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 281
agttgccggc agcggtgacc                                               20

<210> SEQ ID NO 282
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 282
gaagttgccg gcagcggtga                                               20

<210> SEQ ID NO 283
<211> LENGTH: 20

```
<212> TYPE: DNA
<213> ORGANISM: Artificial Sequence
<220> FEATURE:
<223> OTHER INFORMATION: Synthetic oligonucleotide

<400> SEQUENCE: 283
cggaagttgc cggcagcggt                                               20

<210> SEQ ID NO 284
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 284
cccggaagtt gccggcagcg                                               20

<210> SEQ ID NO 285
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 285
gtcccggaag ttgccggcag                                               20

<210> SEQ ID NO 286
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 286
atgacctcgg gagctgaggc                                               20

<210> SEQ ID NO 287
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 287
cccaactgtg atgacctcgg                                               20

<210> SEQ ID NO 288
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 288
ggcattggtg gccccaactg                                               20

<210> SEQ ID NO 289
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 289
```
gctggtcttg ggcattggtg                                              20

<210> SEQ ID NO 290
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 290
cccagggtca ccggctggtc                                              20

<210> SEQ ID NO 291
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 291
tccccagggt caccggctgg                                              20

<210> SEQ ID NO 292
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 292
agtccccagg gtcaccggct                                              20

<210> SEQ ID NO 293
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 293
aaagtcccca gggtcaccgg                                              20

<210> SEQ ID NO 294
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 294
ccccaaagtc cccagggtca                                              20

<210> SEQ ID NO 295
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 295
ttggtcccca aagtccccag                                              20

<210> SEQ ID NO 296
<211> LENGTH: 20
<212> TYPE: DNA
<213> ORGANISM: Artificial Sequence

```
<220> FEATURE:
<223> OTHER INFORMATION: Synthetic oligonucleotide

<400> SEQUENCE: 296
aaagttggtc cccaaagtcc                                              20

<210> SEQ ID NO 297
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 297
cggccaaagt tggtccccaa                                              20

<210> SEQ ID NO 298
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 298
agcggccaaa gttggtcccc                                              20

<210> SEQ ID NO 299
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 299
acagcggcca aagttggtcc                                              20

<210> SEQ ID NO 300
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 300
acacagcggc caaagttggt                                              20

<210> SEQ ID NO 301
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 301
ccacacagcg gccaaagttg                                              20

<210> SEQ ID NO 302
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 302
aggtccacac agcggccaaa                                              20
```

<210> SEQ ID NO 303
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 303
agaggtccac acagcggcca                                              20

<210> SEQ ID NO 304
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 304
aaagaggtcc acacagcggc                                              20

<210> SEQ ID NO 305
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 305
caatgatgtc ctccctggg                                               20

<210> SEQ ID NO 306
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 306
gaggcaccaa tgatgtcctc                                              20

<210> SEQ ID NO 307
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 307
gctggaggca ccaatgatgt                                              20

<210> SEQ ID NO 308
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 308
tcgctggagg caccaatgat                                              20

<210> SEQ ID NO 309
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 309
agtcgctgga ggcaccaatg                                       20

<210> SEQ ID NO 310
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 310
gcagtcgctg gaggcaccaa                                       20

<210> SEQ ID NO 311
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 311
gtgctgcagt cgctggaggc                                       20

<210> SEQ ID NO 312
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 312
aggtgctgca gtcgctggag                                       20

<210> SEQ ID NO 313
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 313
gcaggtgctg cagtcgctgg                                       20

<210> SEQ ID NO 314
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 314
agcaggtgct gcagtcgctg                                       20

<210> SEQ ID NO 315
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 315
aaagcaggtg ctgcagtcgc                                       20

<210> SEQ ID NO 316

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 316
acacaaagca ggtgctgcag                                        20

<210> SEQ ID NO 317
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 317
tgacacaaag caggtgctgc                                        20

<210> SEQ ID NO 318
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 318
tcccactctg tgacacaaag                                        20

<210> SEQ ID NO 319
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 319
tcatggctgc aatgccagcc                                        20

<210> SEQ ID NO 320
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 320
cagcatcatg gctgcaatgc                                        20

<210> SEQ ID NO 321
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 321
gacagcatca tggctgcaat                                        20

<210> SEQ ID NO 322
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 322
```
cagacagcat catggctgca 20

<210> SEQ ID NO 323
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 323
tcggcagaca gcatcatggc 20

<210> SEQ ID NO 324
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 324
gctcggcaga cagcatcatg 20

<210> SEQ ID NO 325
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 325
cggctcggca gacagcatca 20

<210> SEQ ID NO 326
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 326
tccggctcgg cagacagcat 20

<210> SEQ ID NO 327
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 327
cggccagggt gagctccggc 20

<210> SEQ ID NO 328
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 328
ctctgcctca actcggccag 20

<210> SEQ ID NO 329
<211> LENGTH: 20
<212> TYPE: DNA

```
<213> ORGANISM: Artificial Sequence
<220> FEATURE:
<223> OTHER INFORMATION: Synthetic oligonucleotide

<400> SEQUENCE: 329
gtctctgcct caactcggcc                                                 20

<210> SEQ ID NO 330
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 330
cagtctctgc ctcaactcgg                                                 20

<210> SEQ ID NO 331
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 331
atcagtctct gcctcaactc                                                 20

<210> SEQ ID NO 332
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 332
ggatcagtct ctgcctcaac                                                 20

<210> SEQ ID NO 333
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 333
gtggatcagt ctctgcctca                                                 20

<210> SEQ ID NO 334
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 334
aagtggatca gtctctgcct                                                 20

<210> SEQ ID NO 335
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 335
gagaagtgga tcagtctctg                                                 20
```

<210> SEQ ID NO 336
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 336
cagagaagtg gatcagtctc                                                20

<210> SEQ ID NO 337
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 337
ggcagagaag tggatcagtc                                                20

<210> SEQ ID NO 338
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 338
ctttggcaga gaagtggatc                                                20

<210> SEQ ID NO 339
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 339
gacatctttg gcagagaagt                                                20

<210> SEQ ID NO 340
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 340
atgacatctt tggcagagaa                                                20

<210> SEQ ID NO 341
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 341
attgatgaca tctttggcag                                                20

<210> SEQ ID NO 342
<211> LENGTH: 20
<212> TYPE: DNA
<213> ORGANISM: Artificial Sequence
<220> FEATURE:

<223> OTHER INFORMATION: Synthetic oligonucleotide

<400> SEQUENCE: 342
tcattgatga catctttggc                                        20

<210> SEQ ID NO 343
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 343
aggcctcatt gatgacatct                                        20

<210> SEQ ID NO 344
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 344
ccaggcctca ttgatgacat                                        20

<210> SEQ ID NO 345
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 345
aaccaggcct cattgatgac                                        20

<210> SEQ ID NO 346
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 346
ggaaccaggc ctcattgatg                                        20

<210> SEQ ID NO 347
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 347
gggaaccagg cctcattgat                                        20

<210> SEQ ID NO 348
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 348
agggaaccag gcctcattga                                        20

```
<210> SEQ ID NO 349
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 349
cagggaacca ggcctcattg                                              20

<210> SEQ ID NO 350
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 350
ctcagggaac caggcctcat                                              20

<210> SEQ ID NO 351
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 351
cctcagggaa ccaggcctca                                              20

<210> SEQ ID NO 352
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 352
tcctcaggga accaggcctc                                              20

<210> SEQ ID NO 353
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 353
gtcctcaggg aaccaggcct                                              20

<210> SEQ ID NO 354
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 354
tggtcctcag ggaaccaggc                                              20

<210> SEQ ID NO 355
<211> LENGTH: 20
<212> TYPE: DNA
<213> ORGANISM: Artificial Sequence
<220> FEATURE:
<223> OTHER INFORMATION: Synthetic oligonucleotide
```

```
<400> SEQUENCE: 355
ctggtcctca gggaaccagg                                              20

<210> SEQ ID NO 356
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 356
gctggtcctc agggaaccag                                              20

<210> SEQ ID NO 357
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 357
cgctggtcct cagggaacca                                              20

<210> SEQ ID NO 358
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 358
gtacccgctg gtcctcaggg                                              20

<210> SEQ ID NO 359
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 359
cagtacccgc tggtcctcag                                              20

<210> SEQ ID NO 360
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 360
acctgcccca tgggtgctgg                                              20

<210> SEQ ID NO 361
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 361
caaaacagct gccaacctgc                                              20

<210> SEQ ID NO 362
<211> LENGTH: 20
```

```
<212> TYPE: DNA
<213> ORGANISM: Artificial Sequence
<220> FEATURE:
<223> OTHER INFORMATION: Synthetic oligonucleotide

<400> SEQUENCE: 362
tcctgcaaaa cagctgccaa                                                    20

<210> SEQ ID NO 363
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 363
agtcctgcaa aacagctgcc                                                    20

<210> SEQ ID NO 364
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 364
gctgaccata cagtcctgca                                                    20

<210> SEQ ID NO 365
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 365
ggccccgagt gtgctgacca                                                    20

<210> SEQ ID NO 366
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 366
gtgtaggccc cgagtgtgct                                                    20

<210> SEQ ID NO 367
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 367
ccgtgtaggc cccgagtgtg                                                    20

<210> SEQ ID NO 368
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 368
```
atccgtgtag gccccgagtg                                           20

<210> SEQ ID NO 369
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 369
ccatccgtgt aggccccgag                                           20

<210> SEQ ID NO 370
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 370
ggccatccgt gtaggccccg                                           20

<210> SEQ ID NO 371
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 371
gtggccatcc gtgtaggccc                                           20

<210> SEQ ID NO 372
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 372
ctggagcagc tcagcagctc                                           20

<210> SEQ ID NO 373
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 373
aactggagca gctcagcagc                                           20

<210> SEQ ID NO 374
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 374
ggagaaactg gagcagctca                                           20

<210> SEQ ID NO 375
<211> LENGTH: 20
<212> TYPE: DNA
<213> ORGANISM: Artificial Sequence

```
<220> FEATURE:
<223> OTHER INFORMATION: Synthetic oligonucleotide

<400> SEQUENCE: 375
ctggagaaac tggagcagct                                                 20

<210> SEQ ID NO 376
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 376
cacctggcaa tggcgtagac                                                 20

<210> SEQ ID NO 377
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 377
gcacctggca atggcgtaga                                                 20

<210> SEQ ID NO 378
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 378
agcacctggc aatggcgtag                                                 20

<210> SEQ ID NO 379
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 379
cagcacctgg caatggcgta                                                 20

<210> SEQ ID NO 380
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 380
gcagcacctg gcaatggcgt                                                 20

<210> SEQ ID NO 381
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 381
ggcagcacct ggcaatggcg                                                 20
```

<210> SEQ ID NO 382
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 382
aggcagcacc tggcaatggc                                             20

<210> SEQ ID NO 383
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 383
caggcagcac ctggcaatgg                                             20

<210> SEQ ID NO 384
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 384
gcaggcagca cctggcaatg                                             20

<210> SEQ ID NO 385
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 385
tagcaggcag cacctggcaa                                             20

<210> SEQ ID NO 386
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 386
gtagcaggca gcacctggca                                             20

<210> SEQ ID NO 387
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 387
tggcctcagc tggtggagct                                             20

<210> SEQ ID NO 388
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 388
gtccccatgc tggcctcagc							20

<210> SEQ ID NO 389
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 389
ggtccccatg ctggcctcag							20

<210> SEQ ID NO 390
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 390
gggtccccat gctggcctca							20

<210> SEQ ID NO 391
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 391
cgggtcccca tgctggcctc							20

<210> SEQ ID NO 392
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 392
acgggtcccc atgctggcct							20

<210> SEQ ID NO 393
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 393
acacgggtcc ccatgctggc							20

<210> SEQ ID NO 394
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 394
gacacgggtc cccatgctgg							20

<210> SEQ ID NO 395

-continued

<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 395
ggacacgggt ccccatgctg                                              20

<210> SEQ ID NO 396
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 396
tggacacggg tccccatgct                                              20

<210> SEQ ID NO 397
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 397
gtggacacgg gtccccatgc                                              20

<210> SEQ ID NO 398
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 398
agtggacacg ggtccccatg                                              20

<210> SEQ ID NO 399
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 399
cagtggacac gggtccccat                                              20

<210> SEQ ID NO 400
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 400
gcagtggaca cgggtcccca                                              20

<210> SEQ ID NO 401
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 401
ggcagtggac acgggtcccc 20

<210> SEQ ID NO 402
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 402
tggcagtgga cacgggtccc 20

<210> SEQ ID NO 403
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 403
gtggcagtgg acacgggtcc 20

<210> SEQ ID NO 404
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 404
ggtggcagtg gacacgggtc 20

<210> SEQ ID NO 405
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 405
tggtggcagt ggacacgggt 20

<210> SEQ ID NO 406
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 406
tgttggtggc agtggacacg 20

<210> SEQ ID NO 407
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 407
agctgcagcc tgtgaggacg 20

<210> SEQ ID NO 408
<211> LENGTH: 20
<212> TYPE: DNA

```
<213> ORGANISM: Artificial Sequence
<220> FEATURE:
<223> OTHER INFORMATION: Synthetic oligonucleotide

<400> SEQUENCE: 408
gtgccaaggt cctccacctc                                              20

<210> SEQ ID NO 409
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 409
tcagcacagg cggcttgtgg                                              20

<210> SEQ ID NO 410
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 410
ccacgcactg gttgggctga                                              20

<210> SEQ ID NO 411
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 411
actttgcatt ccagacctgg                                              20

<210> SEQ ID NO 412
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 412
gactttgcat tccagacctg                                              20

<210> SEQ ID NO 413
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 413
tgactttgca ttccagacct                                              20

<210> SEQ ID NO 414
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 414
ttgactttgc attccagacc                                              20
```

<210> SEQ ID NO 415
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 415
tccttgactt tgcattccag                                           20

<210> SEQ ID NO 416
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 416
cgggattcca tgctccttga                                           20

<210> SEQ ID NO 417
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 417
gcaggccacg gtcacctgct                                           20

<210> SEQ ID NO 418
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 418
ggagggcact gcagccagtc                                           20

<210> SEQ ID NO 419
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 419
cagatggcaa cggctgtcac                                           20

<210> SEQ ID NO 420
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 420
gcagatggca acggctgtca                                           20

<210> SEQ ID NO 421
<211> LENGTH: 20
<212> TYPE: DNA
<213> ORGANISM: Artificial Sequence
<220> FEATURE:

<223> OTHER INFORMATION: Synthetic oligonucleotide

<400> SEQUENCE: 421
agcagatggc aacggctgtc                                        20

<210> SEQ ID NO 422
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 422
cagcagatgg caacggctgt                                        20

<210> SEQ ID NO 423
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 423
gcagcagatg gcaacggctg                                        20

<210> SEQ ID NO 424
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 424
cggcagcaga tggcaacggc                                        20

<210> SEQ ID NO 425
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 425
ccggcagcag atggcaacgg                                        20

<210> SEQ ID NO 426
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 426
tccggcagca gatggcaacg                                        20

<210> SEQ ID NO 427
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 427
ctccggcagc agatggcaac                                        20

```
<210> SEQ ID NO 428
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 428
gctccggcag cagatggcaa                                             20

<210> SEQ ID NO 429
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 429
ccaggtgccg gctccggcag                                             20

<210> SEQ ID NO 430
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 430
gaggcctgcg ccaggtgccg                                             20

<210> SEQ ID NO 431
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 431
atgagggcca tcagcacctt                                             20

<210> SEQ ID NO 432
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 432
gatgagggcc atcagcacct                                             20

<210> SEQ ID NO 433
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 433
agatgagggc catcagcacc                                             20

<210> SEQ ID NO 434
<211> LENGTH: 20
<212> TYPE: DNA
<213> ORGANISM: Artificial Sequence
<220> FEATURE:
<223> OTHER INFORMATION: Synthetic oligonucleotide
```

```
<400> SEQUENCE: 434
gagatgaggg ccatcagcac                                                    20

<210> SEQ ID NO 435
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 435
tggagatgag ggccatcagc                                                    20

<210> SEQ ID NO 436
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 436
ctggagatga gggccatcag                                                    20

<210> SEQ ID NO 437
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 437
gctggagatg agggccatca                                                    20

<210> SEQ ID NO 438
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 438
agctggagat gagggccatc                                                    20

<210> SEQ ID NO 439
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 439
gctagatgcc atccagaaag                                                    20

<210> SEQ ID NO 440
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 440
ggctagatgc catccagaaa                                                    20

<210> SEQ ID NO 441
<211> LENGTH: 20
```

```
<212> TYPE: DNA
<213> ORGANISM: Artificial Sequence
<220> FEATURE:
<223> OTHER INFORMATION: Synthetic oligonucleotide

<400> SEQUENCE: 441
tggctagatg ccatccagaa                                               20

<210> SEQ ID NO 442
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 442
ctggctagat gccatccaga                                               20

<210> SEQ ID NO 443
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 443
ctctggctag atgccatcca                                               20

<210> SEQ ID NO 444
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 444
cctctggcta gatgccatcc                                               20

<210> SEQ ID NO 445
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 445
gcctctggct agatgccatc                                               20

<210> SEQ ID NO 446
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 446
agcctctggc tagatgccat                                               20

<210> SEQ ID NO 447
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 447
```

```
acccttggtc acgccggcat                                               20

<210> SEQ ID NO 448
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 448
ctgcccttcc accaaaatgc                                               20

<210> SEQ ID NO 449
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 449
actgcccttc caccaaaatg                                               20

<210> SEQ ID NO 450
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 450
cactgccctt ccaccaaaat                                               20

<210> SEQ ID NO 451
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 451
gcactgccct tccaccaaaa                                               20

<210> SEQ ID NO 452
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 452
gggcactgcc cttccaccaa                                               20

<210> SEQ ID NO 453
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 453
tgggcactgc ccttccacca                                               20

<210> SEQ ID NO 454
<211> LENGTH: 20
<212> TYPE: DNA
<213> ORGANISM: Artificial Sequence
```

<220> FEATURE:
<223> OTHER INFORMATION: Synthetic oligonucleotide

<400> SEQUENCE: 454
ctgggcactg cccttccacc                                                    20

<210> SEQ ID NO 455
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 455
gctgggcact gcccttccac                                                    20

<210> SEQ ID NO 456
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 456
gagcaacttc ggaggcagc                                                     19

<210> SEQ ID NO 457
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 457
gcctcagtct gcttcgcacc                                                    20

<210> SEQ ID NO 458
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 458
gcctatgagg gtgc                                                          14

<210> SEQ ID NO 459
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 459
tccaggccta tgag                                                          14

<210> SEQ ID NO 460
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 460
cagctcagca gctc                                                          14

<210> SEQ ID NO 461
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 461
ttaatcaggg agcc                                                            14

<210> SEQ ID NO 462
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 462
ggtaaggtgc ggtaagtcct                                                      20

<210> SEQ ID NO 463
<211> LENGTH: 3512
<212> TYPE: DNA
<213> ORGANISM: Mus musculus

<400> SEQUENCE: 463 tgggggattaa gagggggggaa tgtaacaggt tttgtcctca ctctgagcgt catttgacgc         60
cctttagtac cggggcccgt taatgtttaa tggcgtgatc tcccggcccc caggcgtcca         120
acgtggacgc gcaggctgcc ggtgggctcc ctgagccagt ccttggctcc ccagagacat         180
cgagtcccag gcgtccatgt ccttcccgag cacccactgc tctgcgtggc tgcggtggcc         240
gctgttgctg ctactgtgcc ccaccggcgc agagctgatg ctcgccctcc cgtcccagga         300
ggccaccgcc accttccgcc gttgctccaa tgtggtgctg atggaggaga cccagaggct         360
gacccgggct gcccgccggg gctatgtcat ccctggcttc ttggtgaaga tgagcagtga         420
tgtggagtac attgaggaag actcctttgt gcgaattatc ccagcatggc accagacaga         480
ggtggaggtg tatctcttag ataccagcat ggtcaccatc accgacttca acagcgtgcc         540
ggcgagcaag tgtgacagcc acggcaccca tggtgtggcc aagggcacca gcctgcacag         600
cacagtcagc ggcaccctca taggcctgga cccgtttgca gcccaattag tgtctgggga         660
gggcgaggcc tcagagagga tcttccgatg gtacccacac cccagaaggc cgttctctct         720
ctctttctga cacggcccgc agcccggag gccgcgcgca cctctcctcg gctgttgccg         780
ctgttgccgc tggtgcccag gacgaggatg ggatggcctg gctgatgagg ggaggcctgg         840
aggctgccag acagattgaa caaactgccc caaggttcta catatctttt cctgttgggc         900
ctggccctga cttcgcccag agcatcccat ggaagaccgc tccccgatg ccagggtgcc         960 catcgggaga ggaggaggat gggacacgct cctggcaggt gtggtcagcg cctgcgtgtg        1020
ctcaactgtc gtttattcgg aagagtcagc ctcggggcca ctcgtggttc tgctgcccct        1080
ggccggtggg tatagccgca tgcctgccgg cacctggcga ggactggggt ggtgctggtt        1140
gcagcagctg ggacgacgcc tgcctctact cccagcttc tgctccagag gtcatcacag        1200
gaatgcccag gaccagccag ttaccttggg gactttgggg actaattttg gatttggggt        1260
gaaacctgat gggctcgggg ttccaccttc ggctagagga ccaagtgccc cccgatggg        1320 cgctgctgct gagattatga ccgcacatgt gaacctacat accgcctgca atgacctctt        1380
agttgcccca ggaacctgga gaagcagcca ttgagggcag tccacagaca gccgggatgc        1440

-continued

```
aagggaaggg taatccagcc tcctcaacgc ggaacttccg tcggggccac gacgctgtgt    1500
ggatctcttt gccccggga aggacatcat cggagcgtcc agtgactgca gcacatgctt    1560
catgtcacag agtgggacct cacaggctgc tgcccacgtg gccggcattg tggctcggat    1620
gctgagccgg gagcccacac ttaccctggc cgagctgcgg cagaggctga tccacttctc    1680
taccaaagac gtcatcaaca tggcctggtt ccctgaggac cagcaggtgc tgaccccaa     1740
cctggtggcc acactgcccc ccagcaccca tgagacaggc gggcagctgc tctgtaggac    1800
ggtgtggtcg gcacactcgg ggcccactcg aacagctaca gctacagccc gctgtgcccc    1860
agaagaggag ctgctgagct gctccagctt ctccaggagc gggaggcgtc gtggtgattg    1920
gattgaggcc ataggaggcc agcaggtctg caaggccctc aatgcatttg ggggtgaggg    1980
tgtctatgcc gtcgcgagat gctgcctggt tccccgtgcc aactgcagca tccacaacac    2040
ccctgcagcc agagctggcc tggagaccca tgtccactgc caccagaagg accatgttct    2100
cacaggctgc agcttccatt gggaagtgga agaccttagt gtccggaggc agcctgcgct    2160
gaggtccaga cgtcagcctg ccagtgcgt tggccaccag gcggccagtg tctatgcttc     2220
ctgctgccat gccccagggc tggaatgcaa aatcaaggag catgggatct caggtccttc    2280
agagcaggtc actgtggcct gcgaagcagg atggaccctg actggatgca atgtgctccc    2340
tggggcatcc ctcactctgg gagcctacag cgtggacaac ctgtgtgtgg caagagtcca    2400
tgacactgcc agagcagaca ggaccagtgg agaagccaca gtagctgctg ccatctgctg    2460
ccggagccgg ccttcagcaa aggcctcctg ggttcagtga cagcctcagg cagggatggt    2520
gcttgaggct gggtgcagag atatgcctgc atggctctct tgtagccaaa ggtggggaga    2580
ttctgcgtgg gagaacttgg tgtctcaccc tgggtaccca ttcctggtgt atggaagcac    2640
ctccttcacg gtcaggggc ctgtgcttgg ctttctgcca tcagacatta agctgtagct     2700
ggctctggcc agctgctcca gtgtaccaga acctgaggat gctcgctgca aggcctcagt    2760
tctcaggcct tagggtgtat ttgtctttca ggaagatcat aatggacaga gatccttgga    2820
ggttcaaaga ccaagtacca gactggaaaa ttgagtctga aagccacaag gacagtcaac    2880
tcacagccag ctcacattgc agacaccatt ttgggctccc tgattaaatg cagatcagtt    2940
ctgcacacct ccaggggtgg atccagctgt aaggccatac ctatatcttc cagatgtcct    3000
catctgctgc agggctttgg ccctgctcag gataatgtgc tatgagccct catctgactc    3060
tcagtttgta ctggagaacc atacaggact taccgcacct taccccatcc actaccatgt    3120
gcactgactg gcctcatttt atgaaggaag agacaggacc agagaggcga tgtcacacag    3180
ccagtgatgt caggacataa attcagagtg gctggccctg aataatgcca ggctgggcag    3240
cgagaggaca ggctatggct tgctcctgga cctatactcc cttagcccca gtcccacaga    3300
tcaggtggag actggagtga cagagggcga ctgtaccaag gccacaccag ctgaccagca    3360
cacctctatc cttttgagct cttctgtctt tttatagtaa gcttcctcca cctgtgttgc    3420
ttttgtaact tgatatttat gcagggtttt gtagtttta ttatgtagtg acttttcaga     3480
ataaaagcag ctgatgtgac tgactgcatc cg                                   3512
```

<210> SEQ ID NO 464

<400> SEQUENCE: 464

000

```
<210> SEQ ID NO 465
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 465
ccttccctga aggttcctcc                                             20

<210> SEQ ID NO 466
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 466
gggctcatag cacattatcc                                             20
```